US006489476B1

(12) United States Patent
Dang et al.

(10) Patent No.: US 6,489,476 B1
(45) Date of Patent: *Dec. 3, 2002

(54) HETEROAROMATIC COMPOUNDS CONTAINING A PHOSPHONATE GROUP THAT ARE INHIBITORS OF FRUCTOSE-1,6-BISPHOSPHATASE

(75) Inventors: Qun Dang; Srinivas Rao Kasibhatla; K. Raja Reddy, all of San Diego; Mark D. Erion, Del Mar; M. Rami Reddy; Atul Agarwal, both of San Diego, all of CA (US)

(73) Assignee: Metabasis Therapeutics, Inc., San Diego, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/389,698

(22) Filed: Sep. 3, 1999

Related U.S. Application Data

(60) Provisional application No. 60/111,077, filed on Dec. 7, 1998, and provisional application No. 60/135,504, filed on Sep. 9, 1998.

(51) Int. Cl.[7] .............................. C07F 9/02; C07F 9/06; C07F 9/28; A61N 5/48; A61N 3/10

(52) U.S. Cl. .......................... 544/232; 546/22; 546/23; 548/112; 548/113; 548/119; 514/252.1; 514/256; 514/315; 514/359; 514/396

(58) Field of Search .............................. 544/232; 546/22; 546/23; 548/112, 113, 119; 514/252.1, 256, 315, 359, 396

(56) References Cited

U.S. PATENT DOCUMENTS

| | | |
|---|---|---|
| 3,551,422 A | 12/1970 | Tesoro et al. |
| 3,650,670 A | 3/1972 | Tesoro et al. |
| 4,046,841 A | 9/1977 | Foster et al. |
| 4,092,323 A | 5/1978 | Foster et al. |
| 4,939,130 A | 7/1990 | Jaeggi et al. |
| 5,116,919 A | 5/1992 | Buzinkai et al. |
| 5,142,000 A | 8/1992 | Wheland |
| 5,728,650 A | 3/1998 | Fisher et al. |
| 5,731,299 A | 3/1998 | Ebetino et al. |

FOREIGN PATENT DOCUMENTS

| | | |
|---|---|---|
| DE | 2 343 632 | 4/1974 |
| DE | 26 41 736 A1 | 3/1977 |
| DE | 40 29 444 A | 9/1989 |
| DE | 43 03 648 A1 | 8/1994 |
| DE | 195 01 843 A1 | 6/1996 |
| EP | 0 033 195 A1 | 8/1981 |
| EP | 0 100 718 B1 | 2/1984 |
| EP | 0 186 405 A2 | 2/1986 |
| EP | 0 230 068 A2 | 7/1987 |
| EP | 0 353 969 A1 | 2/1990 |
| EP | 0 354 322 | 2/1990 |
| EP | 0 427 799 | 9/1990 |
| EP | 0 243 173 B1 | 6/1991 |
| EP | 0 438 375 A2 | 7/1991 |
| EP | 0 407 344 A4 | 7/1992 |
| EP | 0 528 760 A1 | 2/1993 |
| EP | 0 559 079 A1 | 9/1993 |
| EP | 0 620 227 A1 | 10/1994 |
| EP | 0 636 630 A1 | 2/1995 |
| FR | 2 034 480 | 12/1970 |
| GB | 1343022 | 1/1974 |
| GB | 1 516 347 | 7/1978 |
| GB | 2271113 A | 4/1994 |
| JP | 6-306089 | 10/1988 |
| JP | 63-250290 | 10/1988 |
| JP | WO 97/24360 | 7/1997 |
| WO | WO 92/11269 A1 | 7/1992 |
| WO | WO 92/12985 A1 | 8/1992 |
| WO | WO 92/19629 A1 | 11/1992 |
| WO | WO 93/14081 | 7/1993 |
| WO | WO 93/15610 A1 | 8/1993 |
| WO | WO 94 07867 | 4/1994 |
| WO | WO 95/14385 A1 | 6/1995 |
| WO | WO 98/04528 | 2/1998 |
| WO | WO 98 39342 | 9/1998 |
| WO | 98 39343 | 9/1998 |
| WO | WO 98/39344 | 9/1998 |

OTHER PUBLICATIONS

Aboujaoude, et al., "Preparation Quasi Quantitative De Phosphonates β–Carbonyles Par L'emploi D'une Base Relais, Le Dipal," *Phosphorus and Sulfur* 25:57–61 (1985).

Arcoria, et al., "Reactions of Triethyl Phosphite with 2–Haloacetyl–furan, –thiophene, –pyrrole and –N–methlpyrrole (1)," *J. Het. Chem.*, 12:215–218 (1975).

(List continued on next page.)

*Primary Examiner*—Deborah C. Lambkin
(74) *Attorney, Agent, or Firm*—Brobeck, Phleger & Harrison, LLP

(57) ABSTRACT

FBPase inhibitors of the formula I and X

Formula I

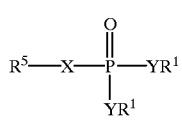

Formula X

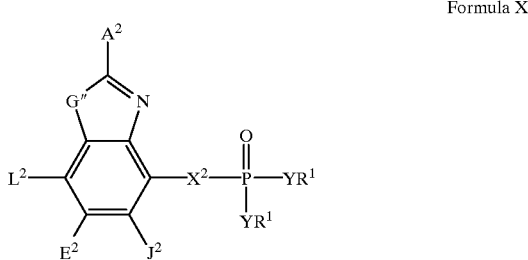

are useful in the treatment of diabetes and other conditions associated with elevated blood glucose or excess glycogen storage.

165 Claims, No Drawings

OTHER PUBLICATIONS

Baboulene, M., et al., "Reactivite Du Bromo–3 OXO–2 Propyl Phosphonate De Diethyle Dans La Reaction De Hantzsch," *Phosphorus and Sulfur*, 5:87–94 (1978).

Burke, et al., "Stereoselective Syntheses of the Rhizoxin C(1)–C(9) and C(12)–C(26) Subunits," *Tetrahedron Letters* 39:2239–2242 (1998).

Corsano, et al., A New Synthesis of Unsaturated Phosphonates (*) (**), *Gazzetta Chimica Italiana* 119:597–599 (1989).

Diziére and Phillippe Savignac, "A New Simple Method for the Synthesis of 1–Alkynylphosphonates using $(EtO)_2P(O)CCl_3$ as Precursor," *Tetrahedron Letters* 37(11):1783–1786 (1996).

Ebetino, et al., "A stereoselective process for the preparation of novel phosphonoalkylphosphinates," *Journal of Organometallic Chemistry* 529:135–142 (1997).

Flitsch, et al., "Reaktionen eins 1, 3–bisheterfunktionalisierten Propens mit Aldehyden," *Libgs, Ann Chem.*, (1985).

Franchetti, et al., "Acyclic Nucleotides Related to Clitocine: Synthesis and Anti–HIV Activity," *Nucleosides & Nucleotides* 14(3–5), 607–610 (1995).

Fujita, et al., "Organic Synthesis Utilizing Thiazolidine and The Related Heterocycles," *Heterocycles* 21(1):41–60 (1984).

Garuti, et al., "Synthesis and Biological Evaluation of Some New Phosphates," *Pharmazie* 47, 295–297 (1992).

Gloyna, et al., "Darstellung and H–NMR–spektroskopische Untersuchung von β–substituierten Athylen–phosphonsaure–diathylestern," *Journal f. prakt. Chemie. Band* 832–838 (1974).

Gohda, et al., "Teoretical Evidence of the Existence of a Diazafulvene Intermediate in the reaction Pathway of Imidazoleglycerol Phosphate Dehydratase: Desogn of Novel and Potent Heterocycle Structure for the Inhibitor on the Basis of the Electronic Structure–Activity Relationship Study," *Biochemica et Biophysica Acta*, 1385:107–114 (1998).

Kim, D., "Synthsis of Pyridylquinoline by a Modified Friedlander Synthesis for the Preparation of Stretonigrin Analogue," *Yakhak Hoeji*, 30(2):104–105 (1986).

Kolyamshin, O.A., "Phosphorus—Containing Small Rings. VII* Amino Phosphorus Esters with a 2, 2–Dichlorocycleopropyl Fragment," *Russian Journal of Gen. Chem.*, 63(1):29–33 (1993).

Maier, L., et al., "Organic Phosphorus Compounds 97.[1] Synthesis and Properties of 1–Amino–2–Aryl–and 2–Pyridyl–Ethylphosphonic Acids and Derivates," *Phosphorus, Sulfur and Silicone*, 62:15–27 (1991).

Maruszewska–Wieczorwska, et al., "Synthesis of 2–(Pyridyl)ethylphosphonic Acids and Esters," *Chemical Abstracts*, 23:1886–1889 (1958).

Menard, et al., "Synthesis and Preliminary Evaluatin of Chelating Resins Containing α–aminoalkylphosphonic Groups," *Reactive Polymers* 32:201–212 (1994).

Mikhailyuchenko, et al., "2–Chloro–1–(Diethoxyphosphinyl)Ethyl Isocyanate," *Institue of Organic Chemistry*, vol. 47: (10) 2011.

Mikityuk, et al., "C–Acylation of Diazomethane with (Diethoxy–phosphinyl)Acetyl Chloride," *UDC* 547.235:547.468.

Mori, et al., "Synthesis of Inhibitors of Imadazole Glycerol Phosphate Dehydratase," *J. Am Chem Soc.*, 117:4411–4412 (1995).

Morita, et al., "Synthesis and Antihypertensive Activities of 1, 4–Dihydrpyridine–5–phosphonate Derivatives," *Chem. Pharm Bull.*, 35:3898–3904 (1987).

O'Donnell, et al., "Preparation of an α–Aminophosphonate Cation Equivalent and its Reaction with Organoboranes," *Tetrahedron Letters* 35:6421–6424 (1994).

Ohler, et al., "(2,3–Epoxy–4–oxoalkyl) phosphonsaure–ester als Synthone fur Thiazole," *Chem. Ber.* 121:533–546 (1988).

Ohler, et al., "Syntese von Hetaryl–and Hetarylvinylphosphonsaureestern aus 2–Brom–1–oxoalkylphosphonaten and 4–Brom–3–oxo–1–alkenylphosphonaten," *Chem. Ber.* 117:3034–3047 (1984).

Palacios, et al., "A "One Pot"Synthesis of Polysustituted Pyridines from Metallated Alkylphosphonates, Nitriles and α, β–Unsaturated Ketones," *Tetrahedron Letters* 37(26): 4577–4580 (1996).

Palacios, et al., "A New and Efficient Strategy for the Preparation of 1, 5, 2–Diazaphosphorines from Primary β–Enaminophosphonates," *Tetrahedron Lett.*, 3091–3104 (1999).

Palacios, et al., "A Simple and Efficient Strategy for the Prepartion of 5–Phyosphorylated Imidazol.–2–ones from Primary β–Enaminophosphonates," *Tetrahedron* 54:2281–2288 (1998).

Reznick, V.S., et al., "Synthesis and Properties of Pyrimidinylalkylphosphonic Acids. 6. Reaction of Some Hydroxypyrimidines with Dibutyl 3–Chlorophosphonate," *Chem. Abs.*, 79:380 (1973).

Reznick, V.S., et al., "Synthesis and Properties of Pyrimidinylalkylphosphonic Acids." 8. Interaction of Some Hydroxypyrimidines With Formadehyde and Some Phosphorus (III) Derivatives, *Organometallics*, 83:52 (1975).

Rizzi, et al., "PPN–type nitrones: preparation and use of a new series of β–phosphorylated spin–trapping agents," *J. Chem. Soc. Perkin Trans.* 2 2513 (1997).

Scarlato, et al., "Synthesis of Trans–4–Alkenyl Oxazoles," *Tetrahedron Letters*, 32(13): 1609–1612 (1991).

Smith, et al., "Synthesis and Biological Activity of Novel Cephalosporins Containing a (Z)–Vinyl Dimethylphosphonate Group," 48(1): 73–82 (1995).

Szczepaniak, et al., "Phosphoroorganic Complexones, PartVII*. N–(Picolylamino)Isopropylphosphonic Acids," *Polish J. of Chem.*, 52:721–726 (1978).

Waschbusch, et al., "A New Route to α–Flourovinylphosphonates Utilizing Peterson Olefination Methodology," *Tetrahedron* 52(45): 14199–14216 (1996).

Waschbusch, et al., "A useful magnesium reagent for the prepartion of 1, 1–difluoro–2–hydroxyphosphonates from diethyl bromodifluoromethylphosphonate via a metal–halogen exchange reaction," *Journal of Organometallic Chemistry* 529:267–278 (1997).

Yokoo, et al., "Synthesis, Antibacterial Activity and Oral Absorption of New 3–[(Z)–2–Methoxycarbonylvinylthio] –7β–[(Z)–2–(2–Aminothiazol–4–yl)–2–(Oxyimino)Acetimino] Cephalosporins," *J. of Antibiotics*, 45:(6) 932–939 (1992).

Yoshino et al., "Organic Phosphorus Compounds. 2. Synthesis and Coronary Vasodilator Activity of (Benzothiazolylbenzyl)phosphonate Derivatives," *J./ Med. Chem.* 32:1528–1532 (1989).

Zbiral, et al., "Ein Neuartiger Zugang zu Heteroarylmenthyl–, Heteroarylethylphosphonsaure–estern und deren freien Sauren," *Communications*, 735–739 (1998).

US 6,489,476 B1

HETEROAROMATIC COMPOUNDS CONTAINING A PHOSPHONATE GROUP THAT ARE INHIBITORS OF FRUCTOSE-1,6-BISPHOSPHATASE

RELATED APPLICATION

This application is a continuation-in-part of Provisional Application Serial Nos. 60/135,504, filed Sep. 9, 1998 and 60/111,077, filed Dec. 7, 1998 and are incorporated by reference in its entirety.

FIELD OF THE INVENTION

This invention relates to novel heteroaromatic compounds that possess a phosphonate group that are inhibitors of Fructose-1,6-bisphosphatase. The invention also relates to the preparation and use of these compounds in the treatment of diabetes, and other diseases where the inhibition of gluconeogenesis, control of blood glucose levels, reduction in glycogen storage, or reduction in insulin levels is beneficial.

BACKGROUND AND INTRODUCTION TO THE INVENTION

The following description of the background of the invention is provided to aid in understanding the invention, but is not admitted to be, or to describe, prior art to the invention. All cited publications are incorporated by reference in their entirety.

Diabetes mellitus (or diabetes) is one of the most prevalent diseases in the world today. Diabetic patients have been divided into two classes, namely type I or insulin-dependent diabetes mellitus and type II or non-insulin dependent diabetes mellitus (NIDDM). NIDDM accounts for approximately 90% of all diabetics and is estimated to affect 12–14 million adults in the U.S. alone (6.6% of the population). NIDDM is characterized by both fasting hyperglycemia and exaggerated postprandial increases in plasma glucose levels. NIDDM is associated with a variety of long-term complications, including microvascular diseases such as retinopathy, nephropathy and neuropathy, and macrovascular diseases such as coronary heart disease. Numerous studies in animal models demonstrate a causal relationship between long term hyperglycemia and complications. Results from the Diabetes Control and Complications Trial (DCCT) and the Stockholm Prospective Study demonstrate this relationship for the first time in man by showing that insulin-dependent diabetics with tighter glycemic control are at substantially lower risk for the development and progression of these complications. Tighter control is also expected to benefit NIDDM patients.

Current therapies used to treat NIDDM patients entail both controlling lifestyle risk factors and pharmaceutical intervention. First-line therapy for NIDDM is typically a tightly-controlled regimen of diet and exercise since an overwhelming number of NIDDM patients are overweight or obese (67%) and since weight loss can improve insulin secretion, insulin sensitivity and lead to normoglycemia. Normalization of blood glucose occurs in less than 30% of these patients due to poor compliance and poor response. Patients with hyperglycemia not controlled by diet alone are subsequently treated with oral hypoglycemics or insulin. Until recently, the sulfonylureas were the only class of oral hypoglycemic agents available for NIDDM. Treatment with sulfonylureas leads to effective blood glucose lowering in only 70% of patients and only 40% after 10 years of therapy. Patients that fail to respond to diet and sulfonylureas are subsequently treated with daily insulin injections to gain adequate glycemic control.

Although the sulfonylureas represent a major therapy for NIDDM patients, four factors limit their overall success. First, as mentioned above, a large segment of the NIDDM population do not respond adequately to sulfonylurea therapy (i.e. primary failures) or become resistant (i.e. secondary failures). This is particularly true in NIDDM patients with advanced NIDDM since these patients have severely impaired insulin secretion. Second, sulfonylurea therapy is associated with an increased risk of severe hypoglycemic episodes. Third, chronic hyperinsulinemia has been associated with increased cardiovascular disease although this relationship is considered controversial and unproven. Last, sulfonylureas are associated with weight gain, which leads to worsening of peripheral insulin sensitivity and thereby can accelerate the progression of the disease.

Results from the U.K. Diabetes Prospective Study also showed that patients undergoing maximal therapy of a sulfonylurea, metformin, or a combination of the two, were unable to maintain normal fasting glycemia over the six year period of the study. U.K. Prospective Diabetes Study 16. *Diabetes*, 44:1249–158 (1995). These results further illustrate the great need for alternative therapies.

Gluconeogenesis from pyruvate and other 3-carbon precursors is a highly regulated biosynthetic pathway requiring eleven enzymes. Seven enzymes catalyze reversible reactions and are common to both gluconeogenesis and glycolysis. Four enzymes catalyze reactions unique to gluconeogenesis, namely pyruvate carboxylase, phosphoenolpyruvate carboxykinase, fructose-1,6-bisphosphatase and glucose-6-phosphatase. Overall flux through the pathway is controlled by the specific activities of these enzymes, the enzymes that catalyzed the corresponding steps in the glycolytic direction, and by substrate availability. Dietary factors (glucose, fat) and hormones (insulin, glucagon, glucocorticoids, epinephrine) coordinatively regulate enzyme activities in the gluconeogenesis and glycolysis pathways through gene expression and post-translational mechanisms.

Of the four enzymes specific to gluconeogenesis, fructose-1,6-bisphosphatase (hereinafter "FBPase") is the most suitable target for a gluconeogenesis inhibitor based on efficacy and safety considerations. Studies indicate that nature uses the FBPase/PFK cycle as a major control point (metabolic switch) responsible for determining whether metabolic flux proceeds in the direction of glycolysis or gluconeogenesis. Claus, et al., *Mechanisms of Insulin Action*, Belfrage, P. editor, pp.305–321, Elsevier Science 1992; Regen, et al. *J. Theor. Biol.*, 111:635–658 (1984); Pilkis, et al. *Annu. Rev. Biochem*, 57:755–783 (1988). FBPase is inhibited by fructose-2,6-bisphosphate in the cell. Fructose-2,6-bisphosphate binds to the substrate site of the enzyme. AMP binds to an allosteric site on the enzyme.

Synthetic inhibitors of FBPase have also been reported. McNiel reported that fructose-2,6-bisphosphate analogs inhibit FBPase by binding to the substrate site. *J. Am. Chem. Soc.*, 106:7851–7853 (1984); U.S. Pat. No. 4,968,790 (1984). These compounds, however, were relatively weak and did not inhibit glucose production in hepatocytes presumably due to poor cell penetration.

Gruber reported that some nucleosides can lower blood glucose in the whole animal through inhibition of FBPase. These compounds exert their activity by first undergoing phosphorylation to the corresponding monophosphate. EP 0 427 799 B1.

Gruber et al. U.S. Pat. No. 5,658,889 described the use of inhibitors of the AMP site of FBPase to treat diabetes. WO 98/39344, WO/39343, and WO 98/39342 describe specific inhibitors of FBPase to treat diabetes.

SUMMARY OF THE INVENTION

The present invention is directed towards novel heteroaromatic compounds containing a phosphonate group and are potent FBPase inhibitors. In another aspect, the present invention is directed to the preparation of this type of compound and to the in vitro and in vivo FBPase inhibitory activity of these compounds. Another aspect of the present invention is directed to the clinical use of these FBPase inhibitors as a method of treatment or prevention of diseases responsive to inhibition of gluconeogenesis and in diseases responsive to lowered blood glucose levels.

The compounds are also useful in treating or preventing excess glycogen storage diseases and diseases such as cardiovascular diseases including atherosclerosis, myocardial ischemic injury, and diseases such as metabolic disorders such as hypercholesterolemia, hyperlipidemia which are exacerbated by hyperinsulinema and hyperglycemia.

The invention also comprises the novel compounds and methods of using them as specified below in formulae I and X. Also included in the scope of the present invention are prodrugs of the compounds of formulae I and X.

Formula I

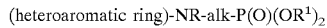

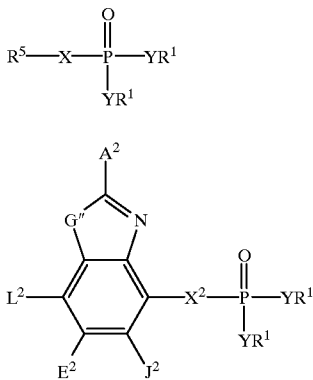

Formula X

Since these compounds may have asymmetric centers, the present invention is directed not only to racemic mixtures of these compounds, but also to individual stereoisomers. The present invention also includes pharmaceutically acceptable and/or useful salts of the compounds of formulae I and X, including acid addition salts. The present inventions also encompass prodrugs of compounds of formulae I and X.

Definitions

In accordance with the present invention and as used herein, the following terms are defined with the following meanings, unless explicitly stated otherwise.

X and $X^2$ group nomenclature as used herein in formulae I and X describes the group attached to the phosphonate and ends with the group attached to the heteroaromatic ring. For example, when X is alkylamino, the following structure is intended:

(heteroaromatic ring)-NR-alk-P(O)(OR$^1$)$_2$

Likewise, A, B, C, D, E, A", B", C", D", E", $A^2$, $L^2$, $E^2$, and $J^2$ groups and other substituents of the heteroaromatic ring are described in such a way that the term ends with the group attached to the heteroaromatic ring. Generally, substituents are named such that the term ends with the group at the point of attachment.

The term "aryl" refers to aromatic groups which have 5–14 ring atoms and at least one ring having a conjugated pi electron system and includes carbocyclic aryl, heterocyclic aryl and biaryl groups, all of which may be optionally substituted. Suitable aryl groups include phenyl and furan-2,5-diyl.

Carbocyclic aryl groups are groups wherein the ring atoms on the aromatic ring are carbon atoms. Carbocyclic aryl groups include monocyclic carbocyclic aryl groups and polycyclic or fused compounds such as optionally substituted naphthyl groups.

Heterocyclic aryl or heteroaryl groups are groups having from 1 to 4 heteroatoms as ring atoms in the aromatic ring and the remainder of the ring atoms being carbon atoms. Suitable heteroatoms include oxygen, sulfur, nitrogen, and selendum. Suitable heteroaryl groups include furanyl, thienyl, pyridyl, pyrrolyl, N-lower alkyl pyrrolyl, pyridyl-N-oxide, pyrimidyl, pyrazinyl, imidazolyl, and the like, all optionally substituted.

The term "annulation" or "annulated" refers to the formation of an additional cyclic moiety onto an existing aryl or heteroaryl group. The newly formed ring may be carbocyclic or heterocyclic, saturated or unsaturated, and contains 2–9 new atoms of which 0–3 may be heteroatoms taken from the group of N, O, and S. The annulation may incorporate atoms from the X group as part of the newly formed ring. For example, the phrase "together $L^2$ and $E^2$ form an annulated cyclic group," includes

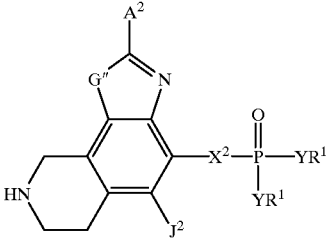

The term "biaryl" represents aryl groups containing more than one aromatic ring including both fused ring systems and aryl groups substituted with other aryl groups. Such groups may be optionally substituted. Suitable biaryl groups include naphthyl and biphenyl.

The term "alicyclic" means compounds which combine the properties of aliphatic and cyclic compounds. Such cyclic compounds include but are not limited to, aromatic, cycloalkyl and bridged cycloalkyl compounds. The cyclic compound includes heterocycles. Cyclohexenylethyl and cyclohexylethyl are suitable alicyclic groups. Such groups may be optionally substituted.

The term "optionally substituted" or "substituted" includes groups substituted by one to four substituents, independently selected from lower alkyl, lower aryl, lower aralkyl, lower alicyclic, hydroxy, lower alkoxy, lower aryloxy, perhaloalkoxy, aralkoxy, heteroaryl, heteroaryloxy, heteroarylalkyl, heteroaralkoxy, azido, amino, guanidino, amidino, halo, lower alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, aralkylamino, phosphono, sulfonyl, -carboxamidoalkylaryl, -carboxamidoaryl, hydroxyalkyl, haloalkyl, alkylaminoalkylcarboxy-, aminocarboxamidoalkyl-, cyano, lower alkoxyalkyl, lower perhaloalkyl, and arylalkyloxyalkyl. "Substituted aryl" and "substituted heteroaryl" preferably refers to aryl and heteroaryl groups substituted with 1–3 substituents. Preferably these substituents are selected from the group consisting of lower alkyl, lower alkoxy, lower perhaloalkyl, halo, hydroxy, and amino. "Substituted" when describing an $R^5$ group does not include annulation.

The term "aralkyl" refers to an alkyl group substituted with an aryl group. Suitable aralkyl groups include benzyl, picolyl, and the like, and may be optionally substituted. The term "-aralkyl-" refers to a divalent group -aryl-alkylene-. "Heteroarylalkyl" refers to an alkylene group substituted with a heteroaryl group.

The term "-alkylaryl-" refers to the group -alk-aryl- where "alk" is an alkylene group. "Lower -alkylaryl-" refers to such groups where alkylene is lower alkylene.

The term "lower" referred to herein in connection with organic radicals or compounds respectively defines such as with up to and including 10, preferably up to and including 6, and advantageously one to four carbon atoms. Such groups may be straight chain, branched, or cyclic.

The terms "arylamino" (a), and "aralkylamino" (b), respectively, refer to the group —NRR' wherein respectively, (a) R is aryl and R' is hydrogen, alkyl, aralkyl or aryl, and (b) R is aralkyl and R' is hydrogen or aralkyl, aryl, alkyl.

The term "acyl" refers to —C(O)R where R is alkyl and aryl.

The term "carboxy esters" refers to —C(O)OR where R is alkyl, aryl, aralkyl, and alicyclic, all optionally substituted.

The term "carboxyl" refers to —C(O)OH.

The term "oxo" refers to =O in an alkyl group.

The term "amino" refers to —NRR' where R and R' are independently selected from hydrogen, alkyl, aryl, aralkyl and alicyclic, all except H are optionally substituted; and R and $R^1$ can form a cyclic ring system.

The term "carbonylamino" and "-carbonylamino-" refers to RCONR— and —CONR—, respectively, where each R is independently hydrogen or alkyl.

The term "halogen" or "halo" refers to —F, —Cl, —Br and —I.

The term "-oxyalkylamino-" refers to —O-alk-NR—, where "alk" is an alkylene group and R is H or alkyl.

The term "-alkylaminoalkylcarboxy-" refers to the group -alk-NR-alk-C(O)—O— where "alk" is an alkylene group, and R is a H or lower alkyl.

The term "-alkylaminocarbonyl-" refers to the group -alk-NR—C(O)— where "alk" is an alkylene group, and R is a H or lower alkyl.

The term "-oxyalkyl-" refers to the group —O-alk- where "alk" is an alkylene group.

The term "-alkylcarboxyalkyl-" refers to the group -alk-C(O)—O-alk- where each alk is independently an alkylene group.

The term "alkyl" refers to saturated aliphatic groups including straight-chain, branched chain and cyclic groups. Alkyl groups may be optionally substituted. Suitable alkyl groups include methyl, isopropyl, and cyclopropyl.

The term "cyclic alkyl" or "cycloalkyl" refers to alkyl groups that are cyclic. Suitable cyclic groups include norbornyl and cyclopropyl. Such groups may be substituted.

The term "heterocyclic" and "heterocyclic alkyl" refer to cyclic groups of 3 to 10 atoms, more preferably 3 to 6 atoms, containing at least one heteroatom, preferably 1 to 3 heteroaroms. Suitable heteroatoms include oxygen, sulfur, and nitrogen. Heterocyclic groups may be attached through a nitrogen or through a carbon atom in the ring. Suitable heterocyclic groups include pyrrolidinyl, morpholino, morpholinoethyl, and pyridyl.

The term "phosphono" refers to —$PO_3R_2$, where R is selected from the group consisting of —H, alkyl, aryl, aralkyl, and alicyclic.

The term "sulphonyl" or "sulfonyl" refers to —$SO_3R$, where R is H, alkyl, aryl, aralkyl, and alicyclic.

The term "alkenyl" refers to unsaturated groups which contain at least one carbon—carbon double bond and includes straight-chain, branched-chain and cyclic groups. Alkenyl groups may be optionally substituted. Suitable alkenyl groups include allyl. "1-alkenyl" refers to alkenyl groups where the double bond is between the first and second carbon atom. If the 1-alkenyl group is attached to another group, e.g. it is a W substituent attached to the cyclic phosph(oramid)ate, it is attached at the first carbon.

The term "alkynyl" refers to unsaturated groups which contain at least one carbon—carbon triple bond and includes straight-chain, branched-chain and cyclic groups. Alkynyl groups may be optionally substituted. Suitable alkynyl groups include ethynyl. "1-alkynyl" refers to alkynyl groups where the triple bond is between the first and second carbon atom. If the 1-alkynyl group is attached to another group, e.g. it is a W substituent attached to the cyclic phosph (oramid)ate, it is attached at the first carbon.

The term "alkylene" refers to a divalent straight chain, branched chain or cyclic saturated aliphatic group.

The term "-cycloalkylene-$COOR^3$" refers to a divalent cyclic alkyl group or heterocyclic group containing 4 to 6 atoms in the ring, with 0–1 heteroatoms selected from O, N, and S. The cyclic alkyl or heterocyclic group is substituted with —$COOR^3$.

The term "acyloxy" refers to the ester group —O—C(O) R, where R is H, alkyl, alkenyl, alkynyl, aryl, aralkyl, or alicyclic.

The term "aminoalkyl-" refers to the group $NR_2$-alk- wherein "alk" is an alkylene group and R is selected from H, alkyl, aryl, aralkyl, and alicyclic.

The term "-alkyl(hydroxy)-" refers to an —OH off the alkyl chain. When this term is an X group, the —OH is at the position a to the phosphorus atom.

The term "alkylaminoalkyl-" refers to the group alkyl-NR-alk- wherein each "alk" is an independently selected alkylene, and R is H or lower alkyl. "Lower alkylaminoalkyl-" refers to groups where each alkylene group is lower alkylene.

The term "arylaminoalkyl-" refers to the group aryl-NR-alk- wherein "alk" is an alkylene group and R is H, alkyl, aryl, aralkyl, and alicyclic. In "lower arylaminoalkyl-", the alkylene group is lower alkylene.

The term "alkylaminoaryl-" refers to the group alkyl-NR-aryl- wherein "aryl" is a divalent group and R is H, alkyl, aralkyl, and alicyclic. In "lower alkylaminoaryl-", the alkylene group is lower alkyl.

The term "alkyloxyaryl-" refers to an aryl group substituted with an alkyloxy group. In "lower alkyloxyaryl-", the alkyl group is lower alkyl.

The term "aryloxyalkyl-" refers to an alkyl group substituted with an aryloxy group.

The term "aralkyloxyalkyl-" refers to the group aryl-alk-O-alk- wherein "alk" is an alkylene group. "Lower aralkyloxyalkyl-" refers to such groups where the alkylene groups are lower alkylene.

The term "-alkoxy-" or "-alkyloxy-" refers to the group -alk-O- wherein "alk" is an alkylene group. The term "alkoxy-" refers to the group alkyl-O—.

The term "-alkoxyalkyl-" or "-alkyloxyalkyl-" refer to the group -alk-O-alk- wherein each "alk" is an independently selected alkylene group. In "lower -alkoxyalkyl-", each alkylene is lower alkylene.

The terms "alkylthio-" and "-alkylthio-" refer to the groups alkyl-S—, and -alk-S—, respectively, wherein "alk" is alkylene group.

The term "-alkylthioalkyl-" refers to the group -alk-S-alk- wherein each "alk" is an independently selected alkylene group. In "lower -alkylthioalkyl-" each alkylene is lower alkylene.

The term "alkoxycarbonyloxy-" refers to alkyl-O—C(O)—O—.

The term "aryloxycarbonyloxy-" refers to aryl-O—C(O)—O—.

The term "alkylthiocarbonyloxy-" refers to alkyl-S—C(O)—O—.

The term "-alkoxycarbonylamino-" refers to -alk-O—C(O)—NR$^1$—, where "alk" is alkylene and R$^1$ includes —H, alkyl, aryl, alicyclic, and aralkyl.

The term "-alkylaminocarbonylamino-" refers to -alk-NR$^1$—C(O)—NR$^1$—, where "alk" is alkylene and R$^1$ is independently selected from H, alkyl, aryl, aralkyl, and alicyclic.

The terms "amido" or "carboxamido" refer to NR$_2$—C(O)— and RC(O)—NR$^1$—, where R and R$^1$ include H, alkyl, aryl, aralkyl, and alicyclic. The term does not include urea, —NR—C(O)—NR—.

The terms "carboxamidoalkylaryl" and "carboxamidoaryl" refers to an aryl-alk-NR$^1$—C(O)—, and an —NR$^1$—C(O)-alk-, respectively, where "ar" is aryl, and "alk" is alkylene, R' and R include H, alkyl, aryl, aralkyl, and aliyclic.

The term "-alkylcarboxamido-" or "-alkylcarbonylamino-" refers to the group -alk-C(O)N(R)— wherein "alk" is an alkylene group and R is H or lower alkyl.

The term "-alkylaminocarbonyl-" refers to the group -alk-NR—C(O)— wherein "alk" is an alkylene group and R is H or lower alkyl.

The term "aminocarboxamidoalkyl-" refers to the group NR$_2$—C(O)—N(R)-alk- wherein R is an alkyl group or H and "alk" is an alkylene group. "Lower aminocarboxamidoalkyl-" refers to such groups wherein "alk" is lower alkylene.

The term "thiocarbonate" refers to —O—C(S)—O— either in a chain or in a cyclic group.

The term "hydroxyalkyl" refers to an alkyl group substituted with one —OH.

The term "haloalkyl" refers to an alkyl group substituted with one halo, selected from the group I, Cl, Br, F.

The term "cyano" refers to —C—N.

The term "nitro" refers to —NO$_2$.

The term "acylalkyl" refers to an alkyl-C(O)-alk-, where "alk" is alkylene.

The term "heteroarylalkyl" refers to an alkyl group substituted with a heteroaryl group.

The term "-1,1-dihaloalkyl-" refers to an X group where the 1 position and therefore halogens are a to the phosphorus atom.

The term "perhalo" refers to groups wherein every C—H bond has been replaced with a C-halo bond on an aliphatic or aryl group. Suitable perhaloalkyl groups include —CF$_3$ and —CFCl$_2$.

The term "guanidino" refers to both —NR—C(NR)—NR$_2$ as well as —N═C(NR$_2$)$_2$ where each R group is independently selected from the group of —H, alkyl, alkenyl, alkynyl, aryl, and alicyclic, all except —H are optionally substituted.

The term "amidino" refers to —C(NR)—NR$_2$ where each R group is independently selected from the group of —H, alkyl, alkenyl, alkynyl, aryl, and alicyclic, all except —H are optionally substituted.

The term "pharmaceutically acceptable salt" includes salts of compounds of formula I and its prodrugs derived from the combination of a compound of this invention and an organic or inorganic acid or base. Suitable acids include HCl.

The term "prodrug" as used herein refers to any compound that when administered to a biological system generates the "drug" substance (a biologically active compound) as a result of spontaneous chemical reaction(s), enzyme catalyzed chemical reaction(s), and/or metabolic chemical reaction(s). Standard prodrugs are formed using groups attached to functionality, e.g. HO—, HS—, HOOC—, R$_2$N—, associated with the FBPase inhibitor, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Standard prodrugs of phosphonic acids are also included and may be represented by R$^1$ in formulae I and X. The groups illustrated are exemplary, not exhaustive, and one skilled in the art could prepare other known varieties of prodrugs. Such prodrugs of the compounds of formulae I and X, fall within the scope of the present invention. Prodrugs must undergo some form of a chemical transformation to produce the compound that is biologically active or is a precursor of the biologically active compound. In some cases, the prodrug is biologically active usually less than the drug itself, and serves to imprive efficacy or safety through improved oral bioavailability, pharmacodynamic half-life, etc.

The term "prodrug ester" as employed herein includes, but is not limited to, the following groups and combinations of these groups:

[1] Acyloxyalkyl esters which are well described in the literature (Farquhar et al., *J. Pharm. Sci.* 72, 324–325 (1983)) and are represented by formula A

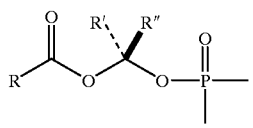

Formula A wherein

R, R', and R" are independently H, alkyl, aryl, alkylaryl, and alicyclic; (see WO 90/08155; WO 90/10636).

[2] Other acyloxyalkyl esters are possible in which an alicyclic ring is formed such as shown in formula B. These esters have been shown to generate phosphorus-containing nucleotides inside cells through a postulated sequence of reactions beginning with deesterification and followed by a series of elimination reactions (e.g. Freed et al., *Biochem. Pharm.* 38: 3193–3198 (1989)).

Formula B

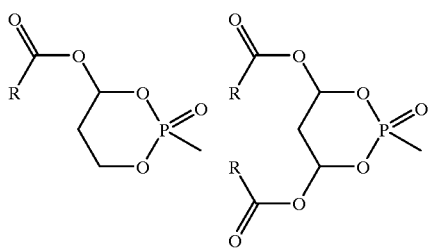

Formula D

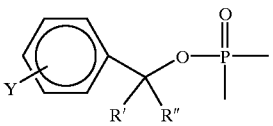

wherein

X and Y are independently H, alkyl, aryl, alkylaryl, alkoxy, acyloxy, hydroxy, cyano, nitro, perhaloalkyl, halo, or alkyloxycarbonyl; and R' and R" are independently H, alkyl, aryl, alkylaryl, halogen, and alicyclic.

[6] Thio-containing phosphonate proesters have been described that are useful in the delivery of FBPase inhibitors to hepatocytes. These proesters contain a protected thioethyl moiety as shown in formula E. One or more of the oxygens of the phosphonate can be esterified. Since the mechanism that results in de-esterification requires the generation of a free thiolate, a variety of thiol protecting groups are possible. For example, the disulfide is reduced by a reductase-mediated process (Puech et al., *Antiviral Res.*, 22: 155–174 (1993)). Thioesters will also generate free thiolates after esterase-mediated hydrolysis. Benzaria, et al., *J. Med. Chem.*, 39:4958 (1996). Cyclic analogs are also possible and were shown to liberate phosphonate in isolated rat hepatocytes. The cyclic disulfide shown below has not been previously described and is novel.

wherein

R is —H, alkyl, aryl, alkylaryl, alkoxy, aryloxy, alkylthio, arylthio, alkylamino, arylamino, cycloalkyl, or alicyclic.

[3] Another class of these double esters known as alkyloxycarbonyloxymethyl esters, as shown in formula A, where R is alkoxy, aryloxy, alkylthio, arylthio, alkylamino, and arylamino; R', and R" are independently H, alkyl, aryl, alkylaryl, and alicyclic, have been studied in the area of -lactam antibiotics (Tatsuo Nishimura et al. *J. Antibiotics*, 1987, 40(1), 81–90; for a review see Ferres, H., *Drugs of Today*, 1983,19, 499.). More recently Cathy, M. S., et al. (Abstract from AAPS Western Regional Meeting, April, 1997) showed that these alkyloxycarbonyloxymethyl ester prodrugs on (9-[(R)-2-phosphonomethoxy)propyl]adenine (PMPA) are bioavailable up to 30% in dogs.

[4] Aryl esters have also been used as phosphonate prodrugs (e.g. Erion, DeLambert et al., *J. Med. Chem.* 37: 498, 1994; Serafinowska et al., *J. Med. Chem.* 38: 1372, 1995). Phenyl as well as mono and poly-substituted phenyl proesters have generated the parent phosphonic acid in studies conducted in animals and in man (Formula C). Another approach has been described where Y is a carboxylic ester ortho to the phosphate. Khamnei and Torrence, *J. Med. Chem.*; 39:4109–4115 (1996).

Formula E

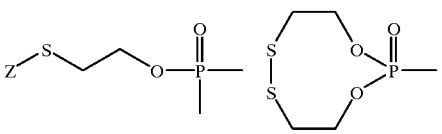

wherein

Z is alkylcarbonyl, alkoxycarbonyl, arylcarbonyl, aryloxycarbonyl, or alkylthio.

Other examples of suitable prodrugs include proester classes exemplified by Biller and Magnin (U.S. Pat. No. 5,157,027); Serafinowska et al. (*J. Med. Chem.* 38, 1372 (1995)); Starrett et al. (*J. Med. Chem.* 37, 1857 (1994)); Martin et al. *J. Pharm. Sci.* 76, 180 (1987); Alexander et al., *Collect. Czech. Chem. Commun*, 59, 1853 (1994)); and EPO patent application 0 632 048 A1. Some of the structural classes described are optionally substituted, including fused lactones attached at the omega position (formulae E-1 and E-2) and optionally substituted 2-oxo-1,3-dioxolenes attached through a methylene to the phosphorus oxygen (formula E-3) such as:

Formula C

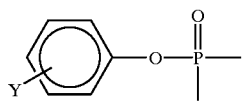

wherein

Y is H, alkyl, aryl, alkylaryl, alkoxy, acyloxy, halogen, amino, alkoxycarbonyl, hydroxy, cyano, and alicyclic.

[5] Benzyl esters have also been reported to generate the parent phosphonic acid. In some cases, using substituents at the para-position can accelerate the hydrolysis. Benzyl analogs with 4-acyloxy or 4-alkyloxy group [Formula D, X=H, OR or O(CO)R or O(CO)OR] can generate the 4-hydroxy compound more readily through the action of enzymes, e.g. oxidases, esterases, etc. Examples of this class of prodrugs are described in Mitchell et al., *J. Chem. Soc. Perkin Trans.* I 2345 (1992); Brook, et al. WO 91/19721.

E-1

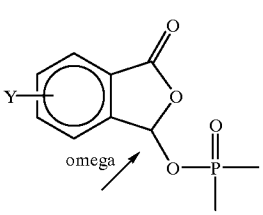

3-phthalidyl

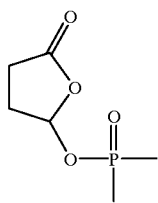

2-oxotetrahydrofuran-5-yl

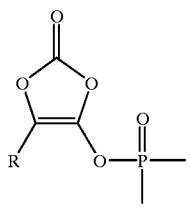

2-oxo-4,5-
didehydro-1,3-
dioxolanemethyl wherein

R is —H, alkyl, cycloalkyl, or alicyclic; and wherein

Y is —H, alkyl, aryl, alkylaryl, cyano, alkoxy, acyloxy, halogen, amino, alicyclic, and alkoxycarbonyl.

The prodrugs of Formula E-3 are an example of "optionally substituted alicyclic where the cyclic moiety contains a carbonate or thiocarbonate."

[7] Propyl phosphonate proesters can also be used to deliver FBPase inhibitors into hepatocytes. These proesters may contain a hydroxyl and hydroxyl group derivatives at the 3-position of the propyl group as shown in formula F. The R and X groups can form a cyclic ring system as shown in formula F. One or more of the oxygens of the phosphonate can stefied.

Formula F

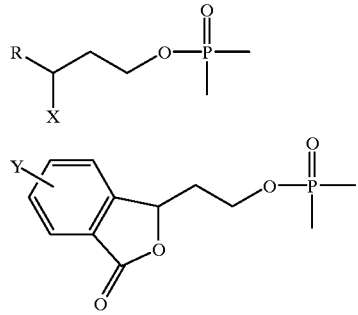

wherein

R is alkyl, aryl, heteroaryl;

X is hydrogen, alkylcarbonyloxy, alkyloxycarbonyloxy; and

Y is alkyl, aryl, heteroaryl, alkoxy, alkylamino, alkylthio, halogen, hydrogen, hydroxy, acyloxy, amino.

[8] Phosphoramidate derivatives have been explored as phosphate prodrugs (e.g. McGuigan et al., *J. Med. Chem.*, 1999, 42: 393 and references cited therein) as shown in Formula G.

Formula G

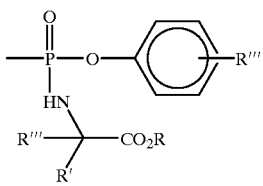

Cyclic phosphoramidates have also been studied as phosphonate prodrugs because of their speculated higher stability compared to non-cyclic phosphoramidates (e.g. Starrett et al., *J. Med. Chem.*, 1994, 37: 1857.

Another type of nucleotide prodrug was reported as the combination of S-acyl-2-thioethyl ester and phosphoramidate (Egron et al., *Nucleosides & Nucleotides*, 1999, 18, 981) as shown in Formula H.

Formula H

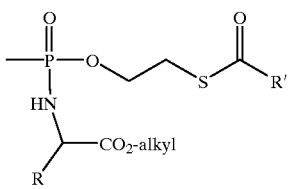

Other prodrugs are possible based on literature reports such as substituted ethyls for example, bis(trichloroethyl) esters as disclosed by McGuigan, et al. *Bioorg Med. Chem. Lett.*, 3:1207–1210 (1993), and the phenyl and benzyl combined nucleotide esters reported by Meier, C. et al. *Bioorg. Med. Chem. Lett.*, 7:99–104 (1997).

The structure

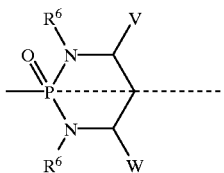

has a plane of symmetry running through the phosphorus-oxygen double bond when $R^6=R^6$, $V=W$, $W'=H$, and V and W are either both pointing up or both pointing down. The same is true of structures where each —NR$^6$ is replaced with —O—.

The term "cyclic 1',3'-propane ester", "cyclic 1,3-propane ester", "cyclic 1',3'-prop anyl ester", and "cyclic 1,3-propanyl ester" refers to the following:

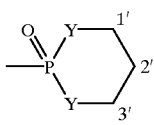

The phrase "together V and Z are connected via an additional 3–5 atoms to form a cyclic group containing 5–7 atoms, optionally containing 1 heteroatom, substituted with hydroxy, acyloxy, alkoxycarbonyloxy, or aryloxycarbonyloxy attached to a carbon atom that is three atoms from both Y groups attached to the phosphorus" includes the following:

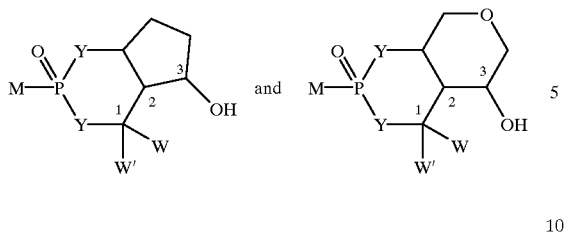

The structure shown above (left) has an additional 3 carbon atoms that forms a five member cyclic group. Such cyclic groups must possess the listed substitution to be oxidized.

The phrase "together V and Z are connected via an additional 3–5 atoms to form a cyclic group, optionally containing one heteroatom, that is fused to an aryl group attached at the beta and gamma position to the Y attached to the phosphorus" includes the following:

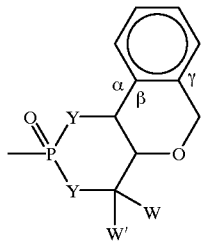

The phrase "together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxy carbonyloxy, attached to one of said additional carbon atoms that is three atoms from a Y attached to the phosphorus" includes the following:

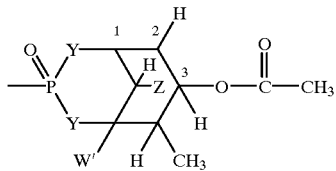

The structure above has an acyloxy substituent that is three carbon atoms from a Y, and an optional substituent, —CH$_3$, on the new 6-membered ring. There has to be at least one hydrogen at each of the following positions: the carbon attached to Z; both carbons alpha to the carbon labelled "3"; and the carbon attached to "OC(O)CH$_3$" above.

The phrase "together W and W' are connected via an additional 2–5 atoms to form a cyclic group, optionally containing 0–2 heteroatoms, and V must be aryl, substituted aryl, heteroaryl, or substituted heteroaryl" includes the following:

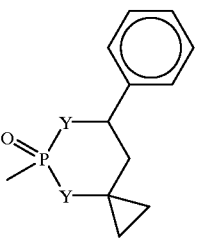

The structure above has V=aryl, and a spiro-fused cyclopropyl group for W and W'.

The term "cyclic phosph(oramid)ate" refers to

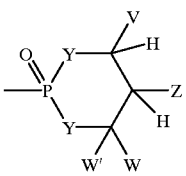

where Y is independently —O— or —NR$^6$—. The carbon attached to V must have a C—H bond. The carbon attached to Z must also have a C—H bond.

The term "liver" refers to liver and to like tissues and cells that contain the CYP3A4 isozyme or any other P450 isozyme found to oxidize the phosph(oramid)ate esters of the invention. Based on Example F, we have found that prodrugs of formula VI and VIII are selectively oxidized by the cytochrome P450 isoenzyme CYP3A4. According to DeWaziers et al (J. Pharm. Exp. Ther., 253, 387–394 (1990)), CYP3A4 is located in humans in the following tissues (determined by immunoblotting and enzyme measurements):

| Tissues | % of liver activity |
|---|---|
| Liver | 100 |
| Duodenum | 50 |
| jejunum | 30 |
| ileum | 10 |
| colon | <5 (only P450 isoenzyme found) |
| stomach | <5 |
| esophagus | <5 |
| kidney | not detectable |

Thus, "liver" more preferably refers to the liver, duodenum, jejunum, ileum, colon, stomach, and esophagus. Most preferably, liver refers to the liver organ.

The term "enhancing" refers to increasing or improving a specific property.

The term "liver specificity" refers to the ratio:

$$\frac{[\text{drug or a drug metabolite in liver tissue}]}{[\text{drug or a drug metabolite in blood or another tissue}]}$$

as measured in animals treated with the drug or a prodrug. The ratio can be determined by measuring tissue levels at a specific time or may represent an AUC based on values measured at three or more time points.

The term "increased or enhanced liver specificity" refers to an increase in the liver specificity ratio in animals treated with the prodrug relative to animals treated with the parent drug.

The term "enhanced oral bioavailability" refers to an increase of at least 50% of the absorption of the dose of the parent drug or prodrug(not of this invention) from the gastrointestinal tract. More preferably it is at least 100%. Measurement of oral bioavailability usually refers to measurements of the prodrug, drug, or drug metabolite in blood, tissues, or urine following oral administration compared to measurements following systemic administration.

The term "parent drug" refers to any compound which delivers the same biologically active compound. The parent drug form is $R^5$—X—P(O)(OH)$_2$ and standard prodrugs, such as esters.

The term "drug metabolite" refers to any compound produced in vivo or in vitro from the parent drug, which can include the biologically active drug.

The term "pharmacodynamic half-life" refers to the time after administration of the drug or prodrug to observe a diminution of one half of the measured pharmacological response. Pharmacodynamic half-life is enhanced when the half-life is increased by preferably at least 50%.

The term "pharmacokinetic half-life" refers to the time after administration of the drug or prodrug to observe a dimunition of one half of the drug concentration in plasma or tissues.

The term "therapeutic index" refers to the ratio of the dose of a drug or prodrug that produces a therapeutically beneficial response relative to the dose that produces an undesired response such as death, an elevation of markers that are indicative of toxicity, and/or pharmacological side effects.

The term "sustained delivery" refers to an increase in the period in which there is adequate blood levels of the biologically active drug to have a therapeutic effect.

The term "bypassing drug resistance" refers to the loss or partial loss of therapeutic effectiveness of a drug (drug resistance) due to changes in the biochemical pathways and cellular activities important for producing and maintaining the biologically active form of the drug at the desired site in the body and to the ability of an agent to bypass this resistance through the use of alternative pathways and cellular activities.

The term "biologically active drug or agent" refers to the chemical entity that produces a biological effect. Thus, active drugs or agents include compounds which as $R^5$—X—P(O)(OH)$_2$ are biologically active.

The term "therapeutically effective amount" refers to an amount that has any beneficial effect in treating a disease or condition.

Preferred Compounds of Formula I

Suitable alkyl groups include groups having from 1 to about 20 carbon atoms. Suitable aryl groups include groups having from 1 to about 20 carbon atoms. Suitable aralkyl groups include groups having from 2 to about 21 carbon atoms. Suitable acyloxy groups include groups having from 1 to about 20 carbon atoms. Suitable alkylene groups include groups having from 1 to about 20 carbon atoms. Suitable alicyclic groups include groups having 3 to about 20 carbon atoms. Suitable heteroaryl groups include groups having from 1 to about 20 carbon atoms and from 1 to 4 heteroatoms, preferably independently selected from nitrogen, oxygen, phosphorous, and sulfur. Suitable heteroalicyclic groups include groups having from 2 to about twenty carbon atoms and from 1 to 5 heteroatoms, preferably independently selected from nitrogen, oxygen, phosphorous, and sulfur.

In the method claims, preferred are the following compounds of formula (I):

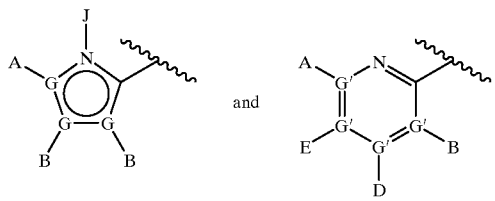

wherein:
each G is independently selected from the group consisting of C, N, O, S and Se, and wherein only one G may be O, S, or Se;

each G' is independently selected from the group consisting of C and N and wherein no more than two G' groups are N;

A is selected from the group consisting of —H, —NR$^4$$_2$, —CONR$^4$$_2$, —CO$_2$R$^3$, halo, —S(O)R$^3$, —SO$_2$R$^3$, alkyl, alkenyl, alkynyl, perhaloalkyl, haloalkyl, aryl, —CH$_2$OH, —CH$_2$NR$^4$$_2$, —CH$_2$CN, —CN, —C(S)NH$_2$, —OR$^3$, —SR$^3$, —N$_3$, —NHC(S)NR$^4$$_2$, —NHAc, and null;

each B and D are independently selected from the group consisting of —H, alkyl, alkenyl, alkynyl, aryl, alicyclic, aralkyl, alkoxyalkyl, —C(O)R$^{11}$, —C(O)SR$^3$, —SO$_2$R$^{11}$, —S(O)R$^3$, —CN, —NR$^9$$_2$, —OR$^3$, —SR$^3$, perhaloalkyl, halo, —NO$_2$, and null, all except —H, —CN, perhaloalkyl, —NO$_2$, and halo are optionally substituted;

E is selected from the group consisting of —H, alkyl, alkenyl, alkynyl, aryl, alicyclic, alkoxyalkyl, —C(O)OR$^3$, —CONR$^4$$_2$, —CN, —NR$^9$$_2$, —NO$_2$, —OR$^3$, —SR$^3$, perhaloalkyl, halo, and null, all except —H, —CN, perhaloalkyl, and halo are optionally substituted;

J is selected from the group consisting of —H and null;

X is an optionally substituted linking group that links $R^5$ to the phosphorus atom via 2–4 atoms, including 0–1 heteroatoms selected from N, O, and S, except that if X is urea or carbamate there is 2 heteroatoms, measured by the shortest path between $R^5$ and the phosphorus atom, and wherein the atom attached to the phosphorus is a carbon atom, and wherein there is no N in the linking group unless it is connected directly to a carbonyl or in the ring of a heterocycle; and wherein X is not a 2 carbon atom -alkyl- or -alkenyl- group; with the proviso that X is not substituted with —COOR$^2$, —SO$_3$R$^1$, or —PO$_3$R$^1$$_2$;

Y is independently selected from the group consisting of —O—, and —NR$^6$—;

when Y is —O—, then R$^1$ attached to —O— is independently selected from the group consisting of —H, alkyl, optionally substituted aryl, optionally substituted alicyclic where the cyclic moiety contains a carbonate or thiocarbonate, optionally substituted -alkylaryl, —C(R$^2$)$_2$OC(O)NR$^2$$_2$, —NR$^2$—C(O)—R$^3$, —C(R$^2$)$_2$—OC(O)R$^3$, —C(R$^2$)$_2$—O—C(O)OR$^3$, —C(R$^2$)$_2$OC(O)SR$^3$, -alkyl-S—C(O)R$^3$, -alkyl-S—S-alkylhydroxy, and -alkyl-S—S—S-alkylhydroxy, when Y is —NR$^6$—, then R$^1$ attached to —NR$^6$— is independently selected from the group consisting of —H, [C(R$^2$)$_2$]$_q$—COOR$^3$, —C(R$^4$)$_2$COOR$^3$, —[C(R$^2$)$_2$]$_q$—C(O)SR, and -cycloalkylene-COOR$^3$;

or when either Y is independently selected from —O— and —NR$^6$—, then together R$^1$ and R$^1$ are -alkyl-S—

S-alkyl- to form a cyclic group, or together R¹ and R¹ are

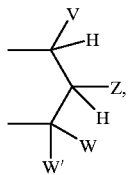

wherein
V, W, and W' are independently selected from the group consisting of —H, alkyl, aralkyl, alicyclic, aryl, substituted aryl, heteroaryl, substituted heteroaryl, 1-alkenyl, and 1-alkynyl; or
together V and Z are connected via an additional 3–5 atoms to form a cyclic group containing 5–7 atoms, optionally 1 heteroatom, substituted with hydroxy, acyloxy, alkoxycarbonyloxy, or aryloxycarbonyloxy attached to a carbon atom that is three atoms from both Y groups attached to the phosphorus; or
together V and Z are connected via an additional 3–5 atoms to form a cyclic group, optionally containing 1 heteroatom, that is fused to an aryl group at the beta and gamma position to the Y attached to the phosphorus;
together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;
together Z and W are connected via an additional 3–5 atoms to form a cyclic group, optionally containing one heteroatom, and V must be aryl, substituted aryl, heteroaryl, or substituted heteroaryl;
together W and W' are connected via an additional 2–5 atoms to form a cyclic group, optionally containing 0–2 heteroatoms, and V must be aryl, substituted aryl, heteroaryl, or substituted heteroaryl;
Z is selected from the group consisting of —CHR²OH, —CHR²OC(O)R³, —CHR²OC(S)R³, —CHR²OC(S) OR³, —CHR²OC(O)SR³, —CHR²OCO₂R³, —OR², —SR², —CHR²N₃, —CH₂aryl, —CH(aryl)OH, —CH(CH=CR²₂)OH, —CH(C≡CR²)OH, —R², —N²₂, —OCOR³, —OCO₂R³, —SCOR³, —SCO₂R³, —NHCOR², —NHCO₂R³, —CH₂NHaryl, —(CH₂)$_p$—OR², and —(CH₂)$_p$—SR²;
p is an integer 2 or 3;
q is an integer 1 or 2;
with the provisos that:
a) V, Z, W, W' are not all —H; and
b) when Z is —R², then at least one of V, W, and W' is not —H, alkyl, aralkyl, or alicyclic;
R² is selected from the group consisting of R³ and —H;
R³ is selected from the group consisting of alkyl, aryl, alicyclic, and aralkyl;
each R⁴ is independently selected from the group consisting of —H, and alkyl, or together R⁴ and R⁴ form a cyclic alkyl group;
R⁶ is selected from the group consisting of —H, lower alkyl, acyloxyalkyl, alkoxycarbonyloxyalkyl, and lower acyl;
each R⁹ is independently selected from the group consisting of —H, alkyl, aralkyl, and alicyclic, or together R⁹ and R⁹ form a cyclic alkyl group;
R¹¹ is selected from the group consisting of alkyl, aryl, —NR²₂, and —OR²; and with the provisos that:
1) when G' is N, then the respective A, B, D, or E is null;
2) at least one of A and B, or A, B, D, and E is not selected from the group consisting of —H or null;
3) when R⁵ is a six-membered ring, then X is not any 2 atom linker, an optionally substituted -alkyl-, an optionally substituted -alkenyl-, an optionally substituted -alkyloxy-, or an optionally substituted -alkylthio-;
4) when G is N, then the respective A or B is not halogen or a group directly bonded to G via a heteroatom;
5) R¹ is not unsubstituted C1–C10 alkyl;
6) when X is not an -aryl- group, then R¹ is not substituted with two or more aryl groups;

and pharmaceutically acceptable prodrugs and salts thereof.

In the methods of using such compounds, preferred R⁵ groups include pyrrolyl, imidazolyl, oxazolyl, thiazolyl, isothiazolyl, 1,2,4-thiadiazolyl, pyrazolyl, isoxazolyl, 1,2,3-oxadiazolyl, 1,2,4-oxadiazolyl, 1,2,5-oxadiazolyl, 1,3,4-oxadiazolyl, 1,2,4-thiadiazolyl, 1,3,4-thiadiazolyl, 1,2,3-triazolyl, 1,2,4-triazolyl, 1,2,3,4-tetrazolyl, pyridinyl, pyrimidinyl, pyrazinyl, pyridazinyl, 1,3,5-triazinyl, 1,2,4-triazinyl, and 1,3-selenazolyl, all of which contain at least one substituent.

More preferred are compounds where R⁵ is:

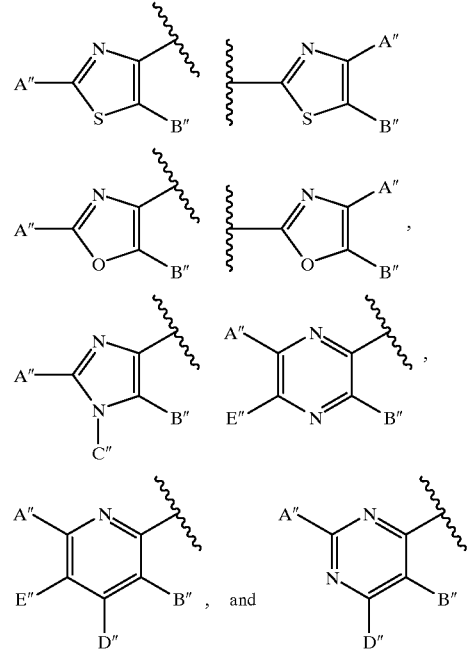

wherein
A" is selected from the group consisting of —H, —NR⁴₂, —CONR⁴₂, —CO₂R³, halo, C1–C6 alkyl, C2–C6 alkenyl, C2–C6 alkynyl, C1–C6 perhaloalkyl, C1–C6 haloalkyl, aryl, —CH₂OH, —CH₂NR⁴₂, —CH₂CN, —CN, —C(S)NH₂, —OR³, —SR³, —N₃, —NHC(S)NR⁴₂, and —NHAc;

B" and D" are independently selected from the group consisting of —H, alkyl, alkenyl, alkynyl, aryl, alicyclic, aralkyl, alkoxyalkyl, —C(O)R$^{11}$, —C(O)SR$^3$, —SO$_2$R$^{11}$, —S(O)R$^3$, —CN, —NR$^9$$_2$, —OR$^3$, —SR$^3$, perhaloalkyl, and halo, all except —H, —CN, perhaloalkyl, and halo are optionally substituted;

E" is selected from the group consisting of —H, C1–C6 alkyl, C2–C6 alkenyl, C2–C6 alkynyl, aryl, C4–C6 alicyclic, alkoxyalkyl, —C(O)OR, —CONR$^4$$_2$, —CN, —NR$^9$$_2$, —OR$^3$, —SR$^3$, C1–C6 perhaloalkyl, and halo, all except —H, —CN, perhaloalkyl, and halo are optionally substituted; and C" is selected from the group consisting of —H, alkyl, alkylalkenyl, alkylalkynyl, aryl, alicyclic, aralkyl, aryloxyalkyl, and alkoxyalkyl, all optionally substituted;

R$^4$ is selected from the group consisting of —H and C1–C2 alkyl.

Particularly preferred are such compounds where R$^5$ is:

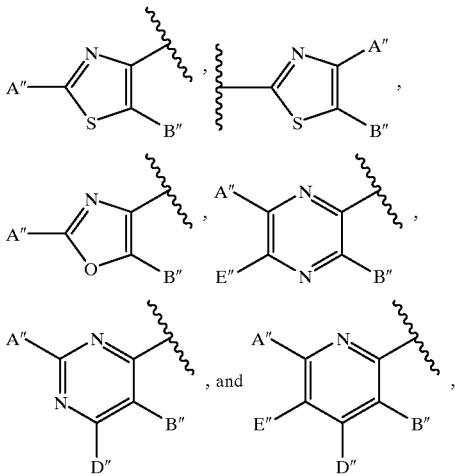

wherein
A" is selected from the group consisting of —H, —NR$^4$$_2$, —CONR$^4$$_2$, —CO$_2$R$^3$, halo, C1–C6 alkyl, C2–C6 alkenyl, C2–C6 alkynyl, C1–C6 perhaloalkyl, C1–C6 haloalkyl, aryl, —CH$_2$OH, —CH$_2$NR$^4$$_2$, —CH$_2$CN, —CN, —C(S)NH$_2$, —OR$^3$, —SR$^3$, —N$_3$, —NHC(S)NR$^4$$_2$, and —NHAc;

B" and D" are independently selected from the group consisting of —H, alkyl, alkenyl, alkynyl, aryl, alicyclic, aralkyl, alkoxyalkyl, —C(O)R$^{11}$, —C(O)SR$^3$, —SO$_2$R$^{11}$, —S(O)R$^3$, —CN, —NR$^9$$_2$, —OR$^3$, —SR$^3$, perhaloalkyl, and halo, all except —H, —CN, perhaloalkyl, and halo are optionally substituted;

E" is selected from the group consisting of —H, C1–C6 alkyl, C2–C6 alkenyl, C2–C6 alkynyl, C4–C6 alicyclic, alkoxyalkyl, —C(O)OR$^3$, —CONR$^4$$_2$, —CN, —NR$^9$$_2$, —OR$^3$, —SR$^3$, C1–C6 perhaloalkyl, and halo, all except H, —CN, perhaloalkyl, and halo are optionally substituted; and each R$^4$ is independently selected from the group consisting of —H and C 1–C2 alkyl.

In the methods, preferred X groups include -alkyl (hydroxy)-, -alkyl-, -alkynyl-, —aryl-, -carbonylalkyl-, -1,1-dihaloalkyl-, -alkoxyalkyl-, -alkyloxy-, -alkylthioalkyl-, —alkylthio-, -alkylaminocarbonyl-, -alkylcarbonylamino-, -alicyclic-, -aralkyl-, -alkylaryl-, —alkoxycarbonyl-, -carbonyloxyalkyl-, -alkoxycarbonylamino-, —alkylaminocarbonylamino-, -alkylamino-, and -alkenyl-, all optionally substituted.

In the compound and method claims, preferred are novel compounds of formula (I):

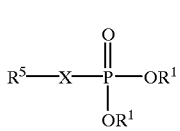

(I)

wherein R$^5$ is selected from the group consisting of:

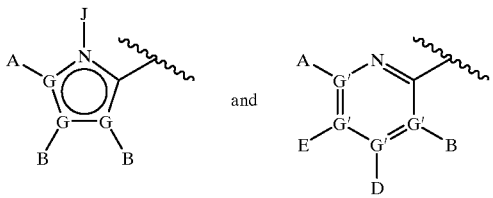

wherein:
each G is independently selected from the group consisting of C, N, O, S, and Se, and wherein only one G may be O, S, or Se, and at most one G is N;

each G' is independently selected from the group consisting of C and N and wherein no more than two G' groups are N;

A is selected from the group consisting of —H, —NR$^4$$_2$, —CONR$^4$$_2$, —CO$_2$R$^3$, halo, —S(O)R$^3$, —SO$_2$R$^3$, alkyl, alkenyl, alkynyl, perhaloalkyl, haloalkyl, aryl, —CH$_2$OH, —CH$_2$NR$^4$$_2$, —CH$_2$CN, —CN, —C(S)NH$_2$, —OR$^3$, —SR$^3$, —N$_3$, —NHC(S)NR$^4$$_2$, —NHAc, and null;

each B and D are independently selected from the group consisting of —H, alkyl, alkenyl, alkynyl, aryl, alicyclic, aralkyl, alkoxyalkyl, —C(O)R$^{11}$, —C(O)SR$^3$, —SO$_2$R$^{11}$, —S(O)R$^3$, —CN, —NR$^9$$_2$, —OR$^3$, —SR$^3$, perhaloalkyl, halo, —NO$_2$, and null, all except —H, —CN, perhaloalkyl, —NO$_2$, and halo are optionally substituted;

E is selected from the group consisting of —H, alkyl, alkenyl, alkynyl, aryl, alicyclic, alkoxyalkyl, —C(O)OR$^3$, —CONR$^4$$_2$, —CN, —NR$^9$$_2$, —NO$_2$, —OR$^3$, —SR$^3$, perhaloalkyl, halo, and null, all except —H, —CN, perhaloalkyl, and halo are optionally substituted;

J is selected from the group consisting of —H and null;

X is an optionally substituted linking group that links R$^5$ to the phosphorus atom via 2–4 atoms, including 0–1 heteroatoms selected from N, O, and S, except that if X is urea or carbamate there is 2 heteroatoms, measured by the shortest path between R$^5$ and the phosphorus atom, and wherein the atom attached to the phosphorus is a carbon atom, and wherein there is no N in the linking group unless it is connected directly to a carbonyl or in the ring of a heterocycle; and wherein X is not a 2 carbon atom -alkyl- or -alkenyl- group; with the proviso that X is not substituted with —COOR$^2$, —SO$_3$R$^1$, or —PO$_3$R$^1$$_2$;

Y is independently selected from the group consisting of —O—, and —NR$^6$—;

when Y is —O—, then R$^1$ attached to —O— is independently selected from the group consisting of —H, alkyl, optionally substituted aryl, optionally substituted alicyclic where the cyclic moiety contains a carbonate or thiocarbonate, optionally substituted -alkylaryl, —C(R²)₂OC(O)NR²₂, —NR²—C(O)—R³, —C(R²)₂—OC(O)R³, —C(R²)₂—O—C(O)OR³, —C(R²)₂OC(O)SR³, -alkyl-S—C(O)R³, -alkyl-S—S-alkylhydroxy, and -alkyl-S—S—S-alkylhydroxy, when Y is —NR⁶—, then R¹ attached to —NR⁶— is independently selected from the group consisting of —H, —[C(R²)₂]_q—COOR³, —C(R⁴)₂COOR³, —[C(R²)₂]_q—C(O)SR, and -cycloalkylene-COOR³;

or when either Y is independently selected from —O— and —NR⁶—, then together R¹ and R¹ are -alkyl-S—S-alkyl- to form a cyclic group, or together R¹ and R¹ are

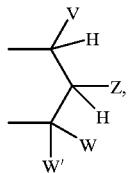

wherein
V, W, and W' are independently selected from the group consisting of —H, alky, aralkyl, alicyclic, aryl, substituted aryl, heteroaryl, substituted heteroaryl, 1-alkenyl, and 1-alkynyl; or together V and Z are connected via an additional 3–5 atoms to form a cyclic group containing 5–7 atoms, optionally 1 heteroatom, substituted with hydroxy, acyloxy, alkoxycarbonyloxy, or aryloxycarbonyloxy attached to a carbon atom that is three atoms from both Y groups attached to the phosphorus; or together V and Z are connected via an additional 3–5 atoms to form a cyclic group, optionally containing 1 heteroatom, that is fused to an aryl group at the beta and gamma position to the Y attached to the phosphorus;

together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, optionally containing one heteroatom, and V must be aryl, substituted aryl, heteroaryl, or substituted heteroaryl;

together W and W' are connected via an additional 2–5 atoms to form a cyclic group, optionally containing 0–2 heteroatoms, and V must be aryl, substituted aryl, heteroaryl, or substituted heteroaryl;

Z is selected from the group consisting of —CHR²OH, —CHR²OC(O)R³, —CHR²OC(S)R³, —CHR²OC(S)OR³, —CHR²OC(O)SR³, —CHR²OCO₂R³, —OR², —SR², —CHR²N₃, —CH₂aryl, —CH(aryl)OH, —CH(CH=CR²₂)OH, —CH(C≡CR²)OH, —R², —NR²₂, —OCOR³, —OCO₂R³, —SCOR³, —SCO₂R³, —NHCOR², —NHCO₂R³, —CH₂NHaryl, —(CH₂)_p—OR², and —(CH₂)_p—SR²;

p is an integer 2 or 3;
q is an integer 1 or 2;
with the provisos that:
  a) V, Z, W, W' are not all —H; and
  b) when Z is —R², then at least one of V, W, and W' is not —H, alkyl, aralkyl, or alicyclic;

R² is selected from the group consisting of R³ and —H;

R³ is selected from the group consisting of alkyl, aryl, alicyclic, and aralkyl;

each R⁴ is independently selected from the group consisting of —H, and alkyl, or together R⁴ and R⁴ form a cyclic alkyl group;

R⁶ is selected from the group consisting of —H, lower alkyl, acyloxyalkyl, alkoxycarbonyloxyalkyl, and lower acyl;

each R⁹ is independently selected from the group consisting of —H, alkyl, aralkyl, and alicyclic, or together R⁹ and R⁹ form a cyclic alkyl group;

R¹¹ is selected from the group consisting of alkyl, aryl, —NR²₂, and —OR²; and with the provisos that:
  1) when G' is N, then the respective A, B, D, or E is null;
  2) at least one of A and B, or A, B, D, and E is not selected from the group consisting of —H or null;
  3) when R⁵ is a six-membered ring, then X is not any 2 atom linker, an optionally substituted -alkyl-, an optionally substituted -alkenyl-, an optionally substituted -alkyloxy-, or an optionally substituted -alkylthio-;
  4) when G is N, then the respective A or B is not halogen or a group directly bonded to G via a heteroatom;
  5) R¹ is not unsubstituted C1–C10 alkyl;
  6) when X is not an -aryl- group, then R⁵ is not substituted with two or more aryl groups;

and pharmaceutically acceptable prodrugs and salts thereof.

Preferred R⁵ groups include pyrrolyl, imidazolyl, oxazolyl, thiazolyl, isothiazolyl, 1,2,4-thiadiazolyl, pyrazolyl, isoxazolyl, 1,2,3-oxadiazolyl, 1,2,4-oxadiazolyl, 1,2,5-oxadiazolyl, 1,3,4-oxadiazolyl, 1,2,4-thiadiazolyl, 1,3,4-thiadiazolyl, pyridinyl, pyrimidinyl, pyrazinyl, pyridazinyl, 1,3,5-triazinyl, 1,2,4-triazinyl, and 1,3-selenazolyl, all of which contain at least one substituent.

In one aspect, preferred are compounds of formula I where:

A is selected from the group consisting of —H, —NR⁴₂, —CONR⁴₂, —CO₂R³, halo, C1–C6 alkyl, C2–C6 alkenyl, C2–C6 alkynyl, C1–C6 perhaloalkyl, C1–C6 haloalkyl, aryl, —CH₂OH, —CH₂NR⁴₂, —CH₂CN, —CN, —C(S)NH₂, —OR⁴, —SR⁴, —N₃, —NHC(S)NR⁴₂, —NHAc, and null;

each B and D are independently selected from the group consisting of —H, alkyl, alkenyl, alkynyl, aryl, alicyclic, aralkyl, alkoxyalkyl, —C(O)R¹¹, —C(O)SR³, —SO₂R¹¹, —S(O)R³, —CN, —NR²₂, —OR³, —SR³, perhaloalkyl, halo, and null, all except —H, —CN, perhaloalkyl, and halo are optionally substituted;

E is selected from the group consisting of —H, C1–C6 alkyl, C2–C6 alkenyl, C2–C6 alkynyl, aryl, C4–C6 alicyclic, alkoxyalkyl, —C(O)OR³, —CONR⁴₂, —CN, —NR⁹₂, —OR³, —SR³, C1–C6 perhaloalkyl, halo, and null, all except —H, —CN, perhaloalkyl, and halo are optionally substituted; and each R⁴ is independently selected from the group consisting of —H, and C1–C2 alkyl.

In another preferred aspect, R⁵ is:

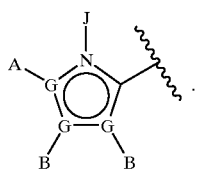

In another preferred aspect, R⁵ is:

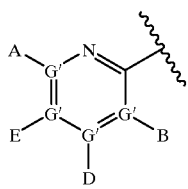

In another preferred aspect, R⁵ is selected from the group consisting of:

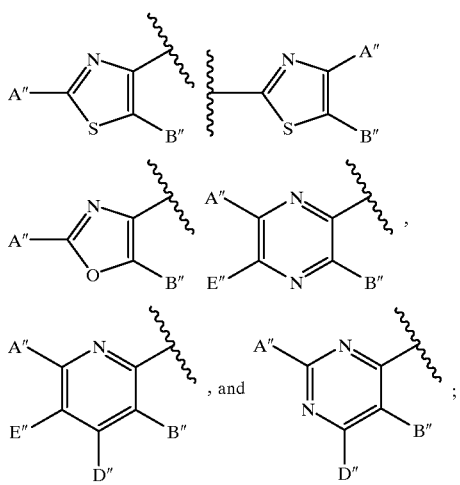

wherein
- A'' is selected from the group consisting of —H, —NR⁴₂, —CONR⁴₂, —CO₂R³, halo, C1–C6 alkyl, C2–C6 alkenyl, C2–C6 alkynyl, C1–C6 perhaloalkyl, C1–C6 haloalkyl, aryl, —CH₂OH, —CH₂NR⁴₂, —CH₂CN, —CN, —C(S)NH₂, —OR³, —SR³, —N₃, —NHC(S)NR⁴₂, and —NHAc;
- B'' and D'' are independently selected from the group consisting of —H, alkyl, alkenyl, alkynyl, aryl, alicyclic, aralkyl, alkoxyalkyl, —C(O)R¹¹, —C(O)SR³, —SO₂R¹¹, —S(O)R³, —CN, —NR⁹₂, —OR³, —SR³, perhaloalkyl, and halo, all except —H, —CN, perhaloalkyl, and halo are optionally substituted;
- E'' is selected from the group consisting of —H, C1–C6 alkyl, C2–C6 alkenyl, C2–C6 alkynyl, C4–C6 alicyclic, alkoxyalkyl, —C(O)OR³, —CONR⁴₂, —CN, —NR⁹₂, —OR³, —SR³, C1–C6 perhaloalkyl, and halo, all except H, —CN, perhaloalkyl, and halo are optionally substituted; and
- each R⁴ is independently selected from the group consisting of —H and C1–C2 alkyl.

More preferred are such where Rs is selected from the group consisting of:

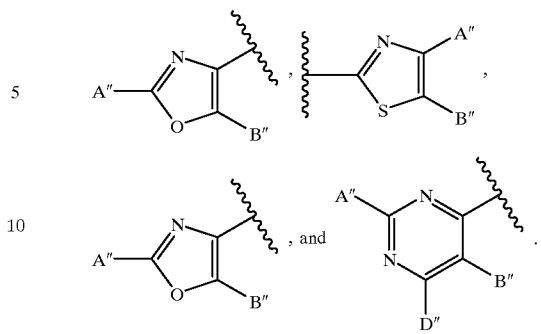

Also more preferred are such where R⁵ is selected from the group consisting of:

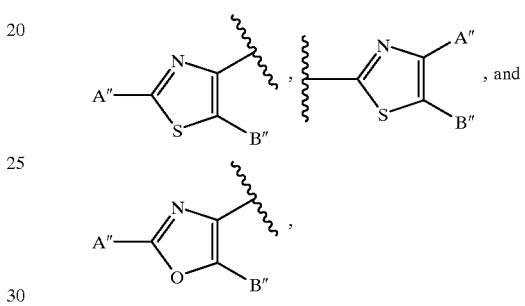

Also more preferred are such where R⁵ is selected from the group consisting of:

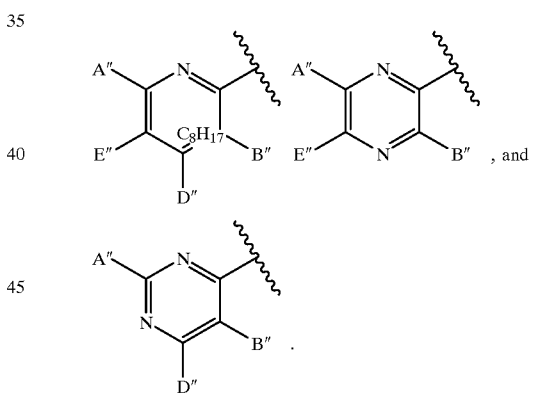

Preferred X groups include -alkyl(hydroxy)-, -alkyl-, -alkynyl-, -aryl-, —carbonylalkyl-, -1,1-dihaloalkyl-, -alkoxyalkyl-, -alkyloxy-, -alkylthioalkyl-, -alkylthio-, —alkylaminocarbonyl-, -alkylcarbonylamino-, -alicyclic-, -aralkyl-, -alkylaryl-, —alkoxycarbonyl-, -carbonyloxyalkyl-, -alkoxycarbonylamino-, and -alkylaminocarbonylamino-, all optionally substituted.

More preferred X groups include -heteroaryl-, -alkylcarbonylamino-, -alkylaminocarbonyl-, -alkoxycarbonyl-, and -alkoxyalkyl-.

Particularly preferred X groups include -heteroaryl-, and -alkoxycarbonyl-. Especially preferred are furan-3,5-diyl, -methylaminocarbonyl-, and methyloxycarbonyl-.

Also particularly preferred are compounds where X is as shown in formulae II, III, or IV

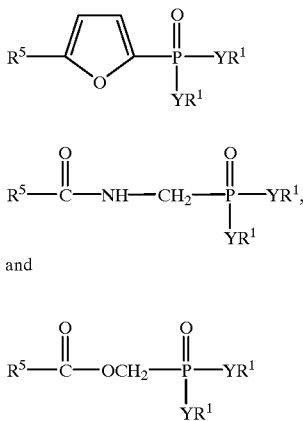

Especially preferred are compounds where X is as shown in formulae II and IV.

Preferred A groups include —H, —NR$^4_2$, —CONR$^4_2$, —CO$_2$R$^3$, halo, C1–C6 alkyl, C2–C6 alkenyl, C2–C6 alkynyl, C1–C6 perhaloalkyl, C1–C6 haloalkyl, aryl, —CH$_2$OH, —CH$_2$NR$^4_2$, —CH$_2$CN, —CN, —C(S)NH$_2$, —OR$^3$, —SR$^3$, —N$_3$, —NHC(S)NR$^4_2$, null, and —NHAc. More preferred A groups include —NH$_2$, —CONH$_2$, halo, —CH$_3$, —CF$_3$, —CH$_2$-halo, —CN, —OCH$_3$, —SCH$_3$, null, and —H. Especially preferred A groups include —NH$_2$, —Cl, —Br, null, and —CH$_3$.

Preferred A" groups include —H, —NR$^4_2$, —CONR$^4_2$, —CO$_2$R$^3$, halo, C1–C6 alkyl, C2–C6 alkenyl, C2–C6 alkynyl, C1–C6 perhaloalkyl, C1–C6 haloalkyl, aryl, —CH$_2$OH, —CH$_2$NR$^4_2$, —CH$_2$CN, —CN, —C(S)NH$_2$, —OR$^3$, —SR$^3$, —N$_3$, —NHC(S)NR$^4_2$, and —NHAc. More preferred A" groups include —NH$_2$, —CONH$_2$, halo, —CH$_3$, —CF$_3$, —CH$_2$-halo, —CN, —OCH$_3$, —SCH$_3$, and —H. Especially preferred A" groups include —NH$_2$, —Cl, —Br, and —CH$_3$.

Preferred B groups include —H, alkyl, alkenyl, alkynyl, aryl, alicyclic, aralkyl, alkoxyalkyl, —C(O)R$^{11}$, —C(O)SR$^3$, —SO$_2$R$^{11}$, —S(O)R$^3$, —CN, —NR$^9_2$, —OR$^3$, —SR$^3$, perhaloalkyl, halo, and null, all except —H, —CN, perhaloalkyl, null, and halo are optionally substituted. More preferred B groups include —H, —C(O)R$^{11}$, —C(O)SR$^3$, alkyl, aryl, alicyclic, halo, —NR$^9_2$, —OR$^3$, null and —SR$^3$. Especially preferred B groups include —H, —C(O)OR$^3$, —C(O)SR$^3$, C1–C6 alkyl, alicyclic, halo, heteroaryl, null, and —SR$^3$.

Preferred B" groups include —H, alkyl, alkenyl, alkynyl, aryl, alicyclic, aralkyl, alkoxyalkyl, —C(O)R$^{11}$, —C(O)SR$^3$, —SO$_2$R$^{11}$, —S(O)R$^3$, —CN, —NR$^9_2$, —OR$^3$, —SR$^3$, perhaloalkyl, and halo, all except —H, —CN, perhaloalkyl, and halo are optionally substituted. More preferred B" groups include —H, —C(O)R$^{11}$, —C(O)SR$^3$, alkyl, aryl, alicyclic, halo, —NR$^9_2$, —OR$^3$, and —SR$^3$. Especially preferred B" groups include —H, —C(O)OR$^3$, —C(O)SR$^3$, C1–C6 alkyl, alicyclic, halo, heteroaryl, and —SR$^3$.

Preferred D groups include —H, alkyl, alkenyl, alkynyl, aryl, alicyclic, aralkyl, alkoxyalkyl, —C(O)R$^{11}$, —C(O)SR$^3$, —SO$_2$R$^{11}$, —S(O)R$^3$, —CN, NR$^2_2$, —OR$^3$, —SR$^3$, perhaloalkyl, halo, and null, all except —H, —CN, perhaloalkyl, null, and halo are optionally substituted. More preferred D groups include —H, —C(O)R$^{11}$, alkyl, —C(O)SR$^3$, aryl, alicyclic, halo, —NR$^9_2$, null and —SR$^3$. Especially preferred D groups include —H, —C(O)OR$^3$, lower alkyl, alicyclic, null, and halo.

Preferred D" groups include —H, alkyl, alkenyl, alkynyl, aryl, alicyclic, aralkyl, alkoxyalkyl, —C(O)R$^{11}$, —C(O)SR$^3$, —SO$_2$R$^{11}$, —S(O)R$^3$, —CN, —NR$^2_2$, —OR$^3$, —SR$^3$, perhaloalkyl, and halo, all except —H, —CN, perhaloalkyl, and halo are optionally substituted. More preferred D" groups include —H, —C(O)R$^{11}$, —C(O)SR$^3$, alkyl, aryl, alicyclic, halo, —NR$^9_2$, and —SR$^3$. Especially preferred D" groups include —H, —C(O)OR$^3$, lower alkyl, alicyclic, and halo.

Preferred E groups include —H, C1–C6 alkyl, C2–C6 alkenyl, C2–C6 alkynyl, aryl, C4–C6 alicyclic, alkoxyalkyl, —C(O)OR$^3$, —CONR$^4_2$, —CN, —NR$^9_2$, —OR$^3$, —SR$^3$, C1–C6 perhaloalky, halo, and null, all except —H, —CN, perhaloalkyl, null, and halo are optionally substituted. More preferred E groups include —H, C1–C6 alkyl, lower alicyclic, halogen, —CN, —C(O)OR$^3$, —SR$^3$, —CONR$^4_2$, and null. Especially preferred E groups include —H, —Br, —Cl, and null.

Preferred E" groups include —H, C1–C6 alkyl, C2–C6 alkenyl, C2–C6 alkynyl, aryl, C4–C6 alicyclic, alkoxyalkyl, —C(O)OR$^3$, —CONR$^4_2$, —CN, —NR$^9_2$, —OR$^3$, —SR$^3$, C1–C6 perhaloalky, and halo, all except —H, —CN, perhaloalkyl, and halo are optionally substituted. More preferred E" groups include —H, C1–C6 alkyl, lower alicyclic, halogen, —CN, —C(O)OR$^3$, —SR$^3$, and —CONR$^4_2$. Especially preferred E" groups include —H, —Br, and —Cl.

In one preferred aspect,

A" is selected from the group consisting of —NH$_2$, —CONH$_2$, halo, —CH$_3$, —CF$_3$, —CH$_2$-halo, —CN, —OCH$_3$, —SCH$_3$, and —H;

B" is selected from the group consisting of —H, —C(O)R$^{11}$, —C(O)SR$^3$, alkyl, aryl, alicyclic, halo, —CN, —SR$^3$, OR$^3$ and —NR$^9_2$;

D" is selected from the group consisting of —H, —C(O)R$^{11}$, —C(O)SR$^3$, —NR$^9_2$, alkyl, aryl, alicyclic, halo, and —SR$^3$;

E" is selected from the group consisting of —H, C1–C6 alkyl, lower alicyclic, halo, —CN, —C(O)OR$^3$, and —SR$^3$.

X is selected from the group consisting of -alkyl (hydroxy)-, -alkyl-, -alkynyl-, —aryl-, -carbonylalkyl-, -1,1-dihaloalkyl-, -alkoxyalkyl-, -alkyloxy-, -alkylthioalkyl-, —alkylthio-, -alkylaminocarbonyl-, -alkylcarbonylamino-, -alicyclic-, -aralkyl-, -alkylaryl-, —alkoxycarbonyl-, -carbonyloxyalkyl-, -alkoxycarbonylamino-, and -alkylaminocarbonylamino-, all optionally substituted;

when both Y groups are —O—, then R$^1$ is independently selected from the group consisting of optionally substituted aryl, optionally substituted benzyl, —C(R$^2$)$_2$OC(O)R$^3$, —C(R$^2$)$_2$OC(O)OR$^3$, and —H; or when one Y is —O—, then R$^1$ attached to —O— is optionally substituted aryl; and the other Y is —NR$^6$—, then R$^1$ attached to —NR$^6$— is selected from the group consisting of —C(R$^4$)$_2$COOR$^3$, and —C(R$^2$)$_2$COOR$^3$; or when Y is —O— or —NR$^6$—, then together R$^1$ and R$^1$ are

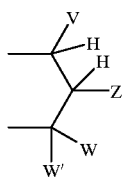

wherein
- V, W, and W' are independently selected from the group consisting of —H, alkyl, aralkyl, alicyclic, aryl, substituted aryl, heteroaryl, substituted heteroaryl, 1-alkenyl, and 1-alkynyl, or
- together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;
- together Z and W are connected via an additional 3–5 atoms to form a cyclic group, optionally containing one heteroatom, and V must be aryl, substituted aryl, heteroaryl, or substituted heteroaryl;
- together W and W' are connected via an additional 2–5 atoms to form a cyclic group, optionally containing 0–2 heteroatoms, and V must be aryl, substituted aryl, heteroaryl, or substituted heteroaryl;
- Z is selected from the group consisting of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —R$^2$, —NHCOR$^2$, —NHCO$_2$R$^3$, —(CH$_2$)$_p$—OR$^2$, and —(CH$_2$)$_p$—SR$^2$;
- p is an integer 2 or 3;
- with the provisos that:
  - a) V, Z, W, W' are not all —H;
  - b) when Z is —R$^2$, then at least one of V, W, and W' is not —H, alkyl, aralkyl, or alicyclic; and
  - c) both Y groups are not —NR$^6$—;
- R$^2$ is selected from the group consisting of R$^3$ and —H;
- R$^3$ is selected from the group consisting of alkyl, aryl, alicyclic, and aralkyl;
- R$^6$ is selected from the group consisting of —H, and lower alkyl.

In one particularly preferred aspect, R$^5$ is

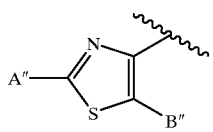

X is selected from the group consisting of methylenoxycarbonyl, and furan-2,5-diyl; at least one Y group is —O—; and pharmaceutically acceptable salts and prodrugs thereof. More preferred are such compounds wherein when Y is —O—, then R$^1$ attached to —O— is independently selected from the group consisting of —H, optionally substituted phenyl, —CH$_2$OC(O)-tBu, —CH$_2$OC(O)Et and —CH$_2$OC(O)-iPr;

when Y is —NR$^6$—, then R$^1$ is attached to —NR$^6$— independently selected from the group consisting of —C(R$^2$)$_2$COOR$^3$, —C(R$^4$)$_2$COOR$^3$, or when Y is —O— or —NR$^6$—, and at least one Y is —O—, then together R$^1$ and R$^1$ are

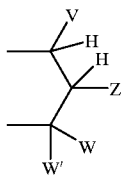

wherein
- V is selected from the group consisting of optionally substituted aryl, and optionally substituted heteroaryl; and Z, W', and W are H; and
- R$^6$ is selected from the group consisting of —H, and lower alkyl.

The following such compounds and their salts are most preferred:
1) A" is —NH$_2$, X is furan-2,5-diyl, and B" is —CH$_2$—CH(CH$_3$)$_2$;
2) A" is —NH$_2$, X is furan-2,5-diyl, and B" is —COOEt;
3) A" is —NH$_2$, X is furan-2,5-diyl, and B" is —SCH$_3$;
4) A" is —NH$_2$, X is furan-2,5-diyl, and B" is —SCH$_2$CH$_2$SCH$_3$;
5) A" is —NH$_2$, X is methyleneoxycarbonyl, and B" is —CH(CH$_3$)$_2$.

In another particularly preferred aspect, R$^5$ is

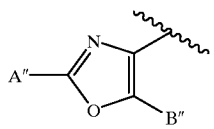

X is furan-2,5-diyl, and methyleneoxycarbonyl, and A" is —NH$_2$; at least one Y group is —O—; and pharmaceutically acceptable salts and prodrugs thereof. Especially preferred are such compounds wherein when Y is —O—, then each R$^1$ is independently selected from the group consisting of —H, optionally substituted phenyl, —CH$_2$OC(O)-tBu, —CH$_2$OC(O)Et, and —CH$_2$OC(O)-iPr;

or when Y is —NR$^6$—, then each R$^1$ is independently selected from the group consisting of —C(R$^2$)$_2$C(O)OR$^3$, and —C(R$^4$)$_2$COOR$^3$;

or when Y is independently selected from —O— and —NR$^6$—, then together R$^1$ and R$^1$ are

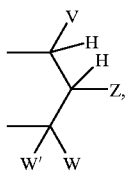

wherein
- V selected from the group consisting of optionally substituted aryl and optionally substituted heteroaryl; and Z, W', and W are H. Also especially preferred are such compounds wherein B" is —SCH$_2$CH$_2$CH$_3$.

In another particularly preferred aspect, R⁵ is

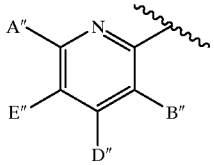

A″ is —NH₂, E″ and D″ are —H, B″ is n-propyl and cyclopropyl, X is furan-2,5-diyl and methyleneoxycarbonyl; at least one Y group is —O—; and pharmaceutically acceptable salts and prodrugs thereof. Especially preferred are such compounds wherein R¹ is selected from the group consisting of —H, optionally substituted phenyl —CH₂OC(O)-tBu, —CH₂OC(O)Et, and —CH₂OC(O)-iPr, or when Y is —NR⁶—, then each R¹ is independently selected from the group consisting of —C(R²)₂C(O)OR³, and —C(R⁴)₂COOR³;

or when either Y is independently selected from —O— and —NR⁶—, and at least one Y is —O—, then together R¹ and R¹ are

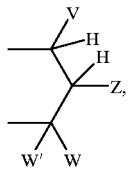

wherein

V is selected from the group consisting of optionally substituted aryl and optionally substituted heteroaryl; and Z, W', and W are H.

In another particularly preferred aspect, R⁵ is

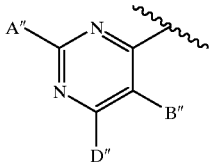

A″ is —NH₂, D″ is —H, B″ is n-propyl and cyclopropyl, X is furan-2,5-diyl and methyleneoxycarbonyl; at least one Y group is —O—; and pharmaceutically acceptable salts and prodrugs thereof. Especially preferred are such compounds wherein when Y is —O— then R¹ is selected from the group consisting of —H, optionally substituted phenyl, —CH₂OC(O)-tBu, —CH₂OC(O)Et, and —CH₂OC(O)-iPr;

or when one Y is —O— and its corresponding R¹ is -phenyl while the other Y is —NH— and its corresponding R¹ is —CH(Me)C(O)OEt, or when at least one Y group is —O—, then together R¹ and R¹ are

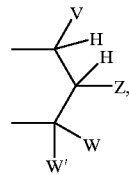

wherein

V is selected from the group consisting of optionally substituted aryl and optionally substituted heteroaryl; and Z, W', and W are H.

Preferred are compounds of formula (X):

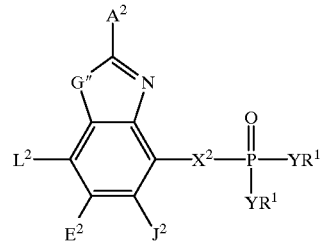

(X)

wherein:

G″ is selected from the group consisting of —O— and —S—;

A², L², E², and J² are selected from the group consisting of —NR⁴₂, —NO₂, —H, —OR², —SR², —C(O)NR⁴₂, halo, —COR¹¹, —SO₂R³, guanidinyl, amidinyl, aryl, aralkyl, alkyoxyalkyl, —SCN, —NHSO₂R⁹, —SO₂NR⁴₂, —CN, —S(O)R³, perhaloacyl, perhaloalkyl, perhaloalkoxy, C1–C5 alkyl, C2–C5 alkenyl, C2–C5 alkynyl, and lower alicyclic, or together L² and E² or E² and J² form an annulated cyclic group;

X² is an optionally substituted linking group that links R⁵ to the phosphorus atom via 1–3 atoms, including 0–1 heteroatoms, selected from N, O, and S, and wherein in the atom attached to the phosphorus is a carbon atom;

with the proviso that X² is not substituted with —COOR², —SO₃R¹, or —PO₃R¹₂;

Y is independently selected from the group consisting of —O—, and —NR⁶—;

when Y is —O—, then R¹ attached to —O— is independently selected from the group consisting of —H, alkyl, optionally substituted aryl, optionally substituted alicyclic where the cyclic moiety contains a carbonate or thiocarbonate, optionally substituted -alkylaryl, —C(R²)₂OC(O)NR²₂, —NR²—C(O)—R³, —C(R²)₂—OC(O)R³, —C(R²)₂—O—C(O)OR³, —C(R²)₂OC(O)SR³, -alkyl-S—C(O)R³, -alkyl-S—S-alkylhydroxy, and -alkyl-S—S—S-alkylhydroxy, when Y is —NR⁶—, then R¹ attached to —NR⁶— is independently selected from the group consisting of —H, —[C(R²)₂]_q—COOR³, —C(R⁴)₂COOR³, [C(R²)₂]_q—C(O)SR, and -cycloalkylene-COOR³;

or when either Y is independently selected from —O— and —NR⁶—, then together R¹ and R¹ are -alkyl-S—S-alkyl- to form a cyclic group, or together R¹ and R¹ are

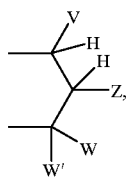

wherein
- V, W, and W' are independently selected from the group consisting of —H, alkyl, aralkyl, alicyclic, aryl, substituted aryl, heteroaryl, substituted heteroaryl, 1-alkenyl, and 1-alkynyl; or
- together V and Z are connected via an additional 3–5 atoms to form a cyclic group containing 5–7 atoms, optionally 1 heteroatom, substituted with hydroxy, acyloxy, alkoxycarbonyloxy, or aryloxycarbonyloxy attached to a carbon atom that is three atoms from both Y groups attached to the phosphorus; or
- together V and Z are connected via an additional 3–5 atoms to form a cyclic group, optionally containing 1 heteroatom, that is fused to an aryl group at the beta and gamma position to the Y attached to the phosphorus;
- together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;
- together Z and W are connected via an additional 3–5 atoms to form a cyclic group, optionally containing one heteroatom, and V must be aryl, substituted aryl, heteroaryl, or substituted heteroaryl;
- together W and W' are connected via an additional 2–5 atoms to form a cyclic group, optionally containing 0–2 heteroatoms, and V must be aryl, substituted aryl, heteroaryl, or substituted heteroaryl;
- Z is selected from the group consisting of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=CR$^2$$_2$)OH, —CH(C≡CR$^2$)OH, —R$^2$, —NR$^2$$_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^2$, and —(CH$_2$)$_p$—SR$^2$;
- p is an integer 2 or 3;
- q is an integer 1 or 2;
- with the provisos that:
  - a) V, Z, W, W' are not all —H; and
  - b) when Z is —R$^2$, then at least one of V, W, and W' is not —H, alkyl, aralkyl, or alicyclic;
- R$^2$ is selected from the group consisting of R$^3$ and —H;
- R$^3$ is selected from the group consisting of alkyl, aryl, alicyclic, and aralkyl;
- each R$^4$ is independently selected from the group consisting of —H, alkyl, or together R$^4$ and R$^4$ form a cyclic alkyl;
- R$^6$ is selected from the group consisting of —H, lower alkyl, acyloxyalkyl, alkoxycarbonyloxyalkyl, and lower acyl;
- each R$^9$ is independently selected from the group consisting of —H, alkyl, aralkyl, and alicyclic, or together R$^9$ and R$^9$ form a cyclic alkyl group;

R$^{11}$ is selected from the group consisting of alkyl, aryl, —NR$^2$$_2$, and —OR$^2$; and pharmaceutically acceptable prodrugs and salts thereof The preferred G" group is —S—.

Preferred A$^2$, L$^2$, E$^2$, and J$^2$ groups include —H, —NR$^4$$_2$, —S—CN, halogen, —OR$^3$, hydroxy, -alkyl(OH), aryl, alkyloxycarbonyl, —SR$^3$, lower perhaloalkyl, and C1–C5 alkyl, or together L$^2$ and E$^2$ form an annulated cyclic group. More preferred A$^2$, E$^2$, E$^2$ and J$^2$ groups include —H, —NR$^4$$_2$, —S≡CN, halogen, lower alkoxy, hydroxy, lower alkyl(hydroxy), lower aryl, and C1–C5 alkyl, or together L$^2$ and E$^2$ form an annulated cyclic group. Particularly preferred J$^2$ groups are —H, and lower alkyl. Particularly preferred A$^2$ groups include —NH$_2$, —H, halo, and C1–C5 alkyl.

Particularly preferred compounds include those where L$^2$ and E$^2$ are independently selected from the group consisting of —H, —S—C≡N, lower alkoxy, C1–C5 alkyl, lower alkyl(hydroxy), lower aryl, and halogen or together L$^2$ and E$^2$ form an annulated cyclic group containing an additional 4 carbon atoms.

Preferred X$^2$ groups include -alkyl-, -alkenyl-, -alkynyl-, -alkylene-NR$^4$—, —alkylene-O—, alkylene-S—, —C(O)-alkylene-, and -alkylene-C(O)—. More preferred X$^2$ groups include -alkylene-O—, alkylene-S—, and -alkyl-. Especially preferred X$^2$ groups include -methyleneoxy-.

In one aspect, preferred are compounds of formula X wherein A$^2$ is selected from the group consisting of —H, —NH$_2$, —CH$_3$, Cl, and Br;
- L$^2$ is —H, lower alkyl, halogen, lower alkyloxy, hydroxy, -alkenylene-OH, or together with E$^2$ forms a cyclic group including aryl, cyclic alkyl, heteroaryls, heterocyclic alkyl;
- E$^2$ is selected from the groups consisting of H, lower alkyl, halogen, SCN, lower alkyloxycarbonyl, lower alkyloxy, or together with L$^2$ forms a cyclic group including aryl, cyclic alkyl, heteroaryl, or heterocyclic alkyl;
- J$^2$ is selected from the groups consisting of H, halogen, and lower alkyl;
- G" is —S—;
- X$^2$ is —CH$_2$O—; and
- at least one Y group is —O—; and pharmaceutically acceptable salts and prodrugs thereof. Also particularly preferred are such compounds where A$^2$ is NH$_2$, G" is —S—, L$^2$ is Et, E$^2$ is SCN, and J$^2$ is H. More preferred are such compounds wherein one Y is —O— and its corresponding R$^1$ is optionally substituted phenyl, while the other Y is —NH—, and its corresponding R$^1$ is —C(R$^2$)$_2$—COOR$^3$. When R$^1$ is —CHR$^3$COOR$^3$, then the corresponding —NR$^6$—*CHR$^3$COOR$^3$, preferably has L stereochemistry.

Also more preferred are such compounds wherein one Y is —O—, and its corresponding R$^1$ is -phenyl, while the other Y is —NH— and its corresponding R$^1$ is —CH(Me)CO$_2$Et.

In compounds of formula I and X, preferably both Y groups are —O—; or one Y is —O— and one Y is —NR$^6$—. When only one Y is —NR$^6$—, preferably the Y closest to W and W' is —O—. Most preferred are prodrugs where both Y groups are —O—;

In another particularly preferred aspect, both Y groups are —O—, and R$^1$ and R$^1$ together are

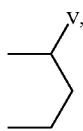

and V is phenyl substituted with 1–3 halogens. Especially preferred are such 3-bromo-4-fluorophenyl, 3-chlorophenyl, 3-bromophenyl, and 3,5-dichlorophenyl.

In another particularly preferred aspect, one Y is —O— and its corresponding $R^1$ is phenyl, or phenyl substituted with 1–2 substituents selected from —NHC(O)CH$_3$, —F, —Cl, —Br, —C(O)OCH$_2$CH$_3$, and —CH$_3$; while the other Y is —NR$^6$— and its corresponding $R^1$ is —C(R$^2$)COOR$^3$; each $R^2$ is independently selected from —H, —CH$_3$, and —CH$_2$CH$_3$. More preferred $R^6$ is —H, and $R^1$ attached to —NH— is —CH(Me)CO$_2$Et.

In general, preferred substituents, V, Z, W, and W' of formulae I and X are chosen such that they exhibit one or more of the following properties:

(1) enhance the oxidation reaction since this reaction is likely to be the rate determining step and therefore must compete with drug elimination processes.

(2) enhance stability in aqueous solution and in the presence of other non-p450 enzymes;

(3) enhance cell penetration, e.g. substituents are not charged or of high molecular weight since both properties can limit oral bioavailability as well as cell penetration;

(4) promote the β-elimination reaction following the initial oxidation by producing ring-opened products that have one or more of the following properties:
   a) fail to recyclize;
   b) undergo limited covalent hydration;
   c) promote β-elimination by assisting in the proton abstraction;
   d) impede addition reactions that form stable adducts, e.g. thiols to the initial hydroxylated product or nucleophilic addition to the carbonyl generated after ring opening; and
   e) limit metabolism of reaction intermediates (e.g. ring-opened ketone);

(5) lead to a non-toxic and non-mutagenic by-product with one or more of the following characteristics. Both properties can be minimized by using substituents that limit Michael additions, reactions, e.g.
   a) electron donating Z groups that decrease double bond polarization;
   b) W groups that sterically block nucleophilic addition to β-carbon;
   c) Z groups that eliminate the double bond after the elimination reaction either through retautomerization (enol-→keto) or hydrolysis (e.g. enamine);
   d) V groups that contain groups that add to the α,β-unsaturated ketone to form a ring;
   e) Z groups that form a stable ring via Michael addition to double bond; and
   f) groups that enhance detoxification of the by-product by one or more of the following characteristics:
      (i) confine to liver; and
      (ii) make susceptible to detoxification reactions (e.g. ketone reduction); and (6) capable of generating a pharmacologically active product.

In another aspect, it is preferred when Y is —O—, then $R^1$ attached to —O— is independently selected from the group consisting of —H, optionally substituted aryl, optionally substituted alicyclic where the cyclic moiety contains a carbonate or thiocarbonate, optionally substituted -alkylaryl, —C(R$^2$)$_2$OC(O)R$^3$, —C(R$^2$)$_2$—O—C(O)OR$^3$, —C(R$^2$)$_2$OC(O)SR$^3$, -alkyl-S—C(O)R$^3$, and -alkyl-S—S-alkylhydroxy;

when Y is —NR$^1$—, then $R^1$ attached to —NR$^6$— is independently selected from the group consisting of —H, —[C(R$^2$)$_2$]$_q$—COOR$^3$, —[C(R$^2$)$_2$]$_q$—C(O)SR$^3$, —C(R$^4$)$_2$COOR$^3$, and -cycloalkylene-COOR$^3$;

or when either Y is independently selected from —O— and —NR$^6$—, then together $R^1$ and $R^1$ are

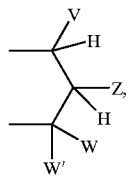

wherein

V, W, and W' are independently selected from the group consisting of —H, alkyl, aralkyl, alicyclic, aryl, substituted aryl, heteroaryl, substituted heteroaryl, 1-alkenyl, and 1-alkynyl, or together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, optionally containing one heteroatom, and V must be aryl, substituted aryl, heteroaryl, or substituted heteroaryl;

together W and W' are connected via an additional 2–5 atoms to form a cyclic group, optionally containing 0–2 heteroatoms, and V must be aryl, substituted aryl, heteroaryl, or substituted heteroaryl;

Z is selected from the group consisting of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —R$^2$, —NHCOR$^2$, —NHCO$_2$R$^3$, —(CH$_2$)$_p$—OR$^2$, and —(CH$_2$)$_p$—SR$^2$;

p is an integer 2 or 3;

q is an integer 1 or 2;

with the provisos that:
  a) V, Z, W, W' are not all —H;
  b) when Z is —R$^2$, then at least one of V, W, and W' is not —H, alkyl, aralkyl, or alicyclic; and
  c) both Y groups are not —NR$^6$—;

$R^2$ is selected from the group consisting of $R^3$ and —H;

$R^3$ is selected from the group consisting of alkyl, aryl, alicyclic, and aralkyl;

$R^6$ is selected from the group consisting of —H, and lower alkyl.

More preferred are such compounds wherein when both Y groups are —O—, then $R^1$ is independently selected from the group consisting of optionally substituted aryl, optionally substituted benzyl, —C(R$^2$)$_2$OC(O)R$^3$, —C(R$^2$)$_2$OC(O)OR$^3$, and —H; and when Y is —NR$^6$—, then the $R^1$ attached to said —NR$^6$— group is selected from the group consisting of —C(R⁴)₂—COOR³, and —C(R²)₂COOR³; and the other Y group is —O— and then R¹ attached to said —O— is selected from the group consisting of optionally substituted aryl, —C(R²)₂OC(O)R³, and —C(R²)₂OC(O)OR³.

In another aspect, when one Y is —O—, then its corresponding R¹ is phenyl, and the other Y is —NH—, and its corresponding R¹ is —CH₂CO₂Et.

In another preferred aspect, when one Y is —O—, its corresponding R¹ is phenyl, and the other Y is —NH— and its corresponding R¹ is —C(Me)₂CO₂Et.

In another preferred aspect, when one Y is —O—, its corresponding R¹ is 4-NHC(O)CH₃-phenyl, and the other Y is —NH—, and its corresponding R¹ is —CH₂COOEt.

In another preferred aspect, when one Y is —O—, its corresponding R¹ is 2-CO₂Et-phenyl, and the other Y is —NH— and its corresponding R¹ is —CH₂CO₂Et.

In another preferred aspect, when one Y is —O—, then its corresponding R¹ is 2-CH₃-phenyl, and the other Y is —NH, and its corresponding, R1 is —CH₂CO₂Et.

In another aspect, preferred are compounds wherein both Y groups are —O—, and R¹ is aryl, or —C(R²)₂-aryl.

Also preferred are compounds wherein both Y groups are O—, and at least one R¹ is selected from the group consisting of —C(R²)₂—OC(O)R³, and —C(R²)₂—C(O)OR³.

In another aspect, preferred are compounds wherein both Y groups are —O— and at least one R¹ is -alkyl-S—S-alkylhydroxyl, -alkyl-S—C(O)R³, and -alkyl-S—S—S-alkylhydroxy, or together R¹ and R¹ are -alkyl-S—S-alkyl- to form a cyclic group.

In one aspect, particularly preferred are compounds wherein both Y groups are —O—, and R¹ is H.

In another aspect, particularly preferred are compounds where both Y groups are —O—, and R=is —CH₂OC(O)OEt.

More preferred are compounds wherein at least one Y is —O—, and together R¹ and R¹ are

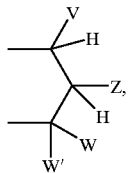

wherein

V, W, and W' are independently selected from the group consisting of —H, alkyl, aralkyl, alicyclic, aryl, substituted aryl, heteroaryl, substituted heteroaryl, 1-alkenyl, and 1-alkynyl, or together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, optionally containing one heteroatom, and V must be aryl, substituted aryl, heteroaryl, or substituted heteroaryl;

together W and W' are connected via an additional 2–5 atoms to form a cyclic group, optionally containing 0–2 heteroatoms, and V must be aryl, substituted aryl, heteroaryl, or substituted heteroaryl;

Z is selected from the group consisting of —CHR²OH, —CHR²OC(O)R³, —CHR²OC(S)R³, —CHR²OC(S)OR³, —CHR²OC(O)SR³, —CHR²OCO₂R³, —OR², —SR², —R², —NHCOR², —NHCO₂R³, —(CH₂)ₚ—OR², and —(CH₂)ₚ—SR²;

p is an integer 2 or 3;

with the provisos that:
a) V, Z, W, W' are not all —H;
b) when Z is —R², then at least one of V, W, and W' is not —H, alkyl, aralkyl, or alicyclic; and
c) both Y groups are not —NR⁶—;

R² is selected from the group consisting of R³ and —H;

R³ is selected from the group consisting of alkyl, aryl, alicyclic, and aralkyl;

R⁶ is selected from the group consisting of —H, and lower alkyl.

In an other aspect, more preferred are compounds wherein one Y is —O—, and R¹ is optionally substituted aryl; and the other Y is —NR⁶—, where R¹ on said —NR⁶— is selected from the group consisting of —C(R⁴)₂COOR³, and —C(R²)₂C(O)OR³. Particularly preferred are such compounds where R¹ attached to —O— is -phenyl, and R1 to —NH— is —CH(Me)CO₂Et, and —NH*CH(Me)CO₂Et is in the L configuration.

Especially preferred are such compounds where R¹ attached to —O— is selected from the group consisting of phenyl and phenyl substituted with 1–2 substituents selected from the group consisting of —NHAc, —F, —Cl, —Br, —COOEt, and —CH₃; and R¹ attached to —NR⁶, is —C(R²)₂COOR³ where R² and R³ independently is —H, —CH₃, and -Et. Of such compounds, when R¹ attached to —O— is phenyl substituted with —NHAc or —COOEt, then preferably any —NHAc is at the 4-position, and any —COOEt is at the 2-position. More preferred are such compounds where the substituents on the substituted phenyl is 4-NHC(O)CH₃, —Cl, —Br, 2-C(O)OCH₃CH₃, or —CH₃.

More preferred V groups of formula VI are aryl, substituted aryl, heteroaryl, and substituted heteoaryl. Preferably Y is —O—. Particularly preferred aryl and substituted aryl groups include phenyl, and phenyl substituted with 1–3 halogens. Especially preferred are 3,5-dichlorophenyl, 3-bromo-4-fluorophenyl, 3-chlorophenyl, and 3-bromophenyl.

It is also especially preferred when V is selected from the group consisting of monocyclic heteroaryl and monocyclic substituted heteroaryl containing at least one nitrogen atom. Most preferred is when such heteroaryl and substituted heteroaryl is 4-pyridyl, and 3-bromopyridyl, respectively.

It is also preferred when together V and Z are connected via an additional 3–5 atoms to form a cyclic group, optionally containing 1 heteroatom, that is fused to an aryl group at the beta and gamma positions to the Y attached to phosphorus. In such compounds preferably said aryl group is an optionally substituted monocyclic aryl group and the connection between Z and the gamma position of the aryl group is selected from the group consisting of O, CH₂, CH₂CH₂, OCH₂ or CH₂O.

In another aspect, it is preferred when together V and W are connected via an additional 3 carbon atoms to form an optionally substituted cyclic group containing 6 carbon atoms and monosubstituted with one substituent selected from the group consisting of hydroxy, acyloxy, alkosycarbonyloxy, alkylthiocarbonyloxy, and aryloxycarbonyloxy attached to one of said additional carbon atoms that is three atoms from a Y attached to the phosphorus. In such compounds, it is more preferred when together V and W form a cyclic group selected from the group consisting of —$CH_2$—$CH(OH)$—$CH_2$—, $CH_2CH(OCOR^3)$—$CH_2$—, and —$CH_2CH(OCO_2R^3)$—$CH_2$—.

Another preferred V group is 1-alkene. Oxidation by p450 enzymes is known to occur at benzylic and allylic carbons.

In one aspect, a preferred V group is —H, when Z is selected from the group consisting of —$CHR^2OH$, —$CHR^2OCOR^3$, and —$CHR^2OCO_2R^3$.

In another aspect, when V is aryl, substituted aryl, heteroaryl, or substituted heteroaryl, preferred Z groups include —$OR^2$, —$SR^2$, —$CHR^2N_3$, —$R^2$, —$NR^2_2$, —$OCOR^2$, —$OCO_2R^3$, —$SCOR^3$, —$SCO_2R^3$, —$NHCOR^2$, —$NHCO_2R^3$, —$CH_2NHaryl$, —$(CH_2)_p$—$OR^2$, and —$(CH_2)_p$—$SR^2$. More preferred Z groups include —$OR^2$, —$R^2$, —$OCOR^2$, —$OCO_2R^3$, —$CH_3$, —$NHCOR^2$, —$NHCO_2R^3$, —$(CH_2)_p$—$OR^2$, and, —$(CH_2)_p$—$SR^2$. Most preferred Z groups include —$OR^2$, —H, —$OCOR^2$, —$OCO_2R^3$, and —$NHCOR^2$.

Preferred W and W' groups include H, $R^3$, aryl, substituted aryl, heteroaryl, and substituted aryl. Preferably, W and W' are the same group. More preferred is when W and W' are H.

In one aspect, prodrugs of formula VI are preferred:

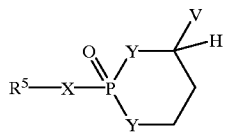

VI wherein

V is selected from the group consisting of aryl, substituted aryl, heteroaryl, and substituted heteroaryl, 1-alkenyl, and 1-alkynyl. More preferred V groups of formula VI are aryl, substituted, heteroaryl, and substituted heteoaryl. Preferably Y is —O—. Particularly preferred aryl and substituted aryl groups include phenyl and substituted phenyl. Particularly preferred heteroaryl groups include monocyclic substiutted and unsubstituted heteroaryl groups. Especially preferred are 4-pyridyl and 3-bromopyridyl.

In one aspect, the compounds of formula VI preferably have a group Z which is H, alkyl, alicyclic, hydroxy, alkoxy,

or NHCOR. Preferred are such groups in which Z decreases the propensity of the byproduct, vinyl aryl ketone to undergo Michael additions. Preferred Z groups are groups that donate electrons to the vinyl group which is a known strategy for decreasing the propensity of α,β-unsaturated carbonyl compounds to undergo a Michael addition. For example, a methyl group in a similar position on acrylamide results in no mutagenic activity whereas the unsubstituted vinyl analog is highly mutagenic. Other groups could serve a similar function, e.g. Z=OR, NHAc, etc. Other groups may also prevent the Michael addition especially groups that result in removal of the double bond altogether such as Z=OH, —OC(O)R, —$OCO_2R$, and $NH_2$, which will rapidly undergo retautomerization after the elimination reaction. Certain W and W' groups are also advantageous in this role since the group(s) impede the addition reaction to the β-carbon or destabilize the product. Another preferred Z group is one that contains a nucleophilic group capable of adding to the α,β-unsaturated double bond after the elimination reaction i.e. $(CH_2)_pSH$ or $(CH_2)_nOH$ where p is 2 or 3. Yet another preferred group is a group attached to V which is capable of adding to the α,β-unsaturated double bond after the elimination reaction:

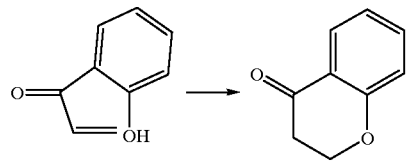

In another aspect, prodrugs of formula VII are preferred:

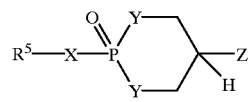

VII wherein

Z is selected from the group consisting of:
—$CHR^2H$, —$CHR^2OCOR^3$, —$CHR^2OC(S)R^3$, —$CHR^2OCO_2R^3$, —$CHR^2OC(O)SR^3$, and —$CHR^2OC(S)OR^3$. Preferably Y is —O—. More preferred groups include —$CHR^2OH$, —$CHR^2OC(O)R^3$, and —$CHR^2OCO_2R^3$.

In another aspect, prodrugs of formula VIII are preferred:

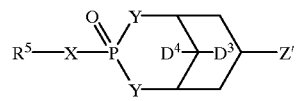

VIII wherein

Z' is selected from the group consisting of —OH, —OC(O)$R^3$, —$OCO_2R^3$, and —OC(O)$SR^3$;

$D^4$ and $D^3$ are independently selected from the group consisting of —H, alkyl, $OR^2$, —OH, and —OC(O)$R^3$; with the proviso that at least one of $D^4$ and $D^3$ are —H. Preferably Y is —O—.

In one preferred embodiment, W' and Z are —H, W and V are both the same aryl, substituted aryl, heteroaryl, or substituted heteroaryl such that the phosphonate prodrug moiety:

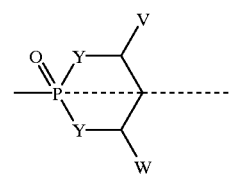

has a plane of symmetry. Preferably Y is —O—.

In another preferred embodiment, W and W' are H, V is selected from the group consisting of aryl, substituted aryl, heteroaryl, substituted heteroaryl, and Z is selected from the group consisting of —H, OR', and —NHCOR². More preferred are such compounds where Z is —H.

Preferably, oral bioavailability is at least 5%. More preferably, oral bioavailability is at least 10%.

p450 oxidation can be sensitive to stereochemistry which might either be at phosphorus or at the carbon bearing the aromatic group. The prodrugs of the present invention have two isomeric forms around the phosphorus. Preferred is the stereochemistry that enables both oxidation and the elimination reaction. Preferred is the cis-stereochemistry.

The preferred compounds of formula VIII utilize a Z' group that is capable of undergoing an oxidative reaction that yields an unstable intermediate which via elimination reactions breaks down to the corresponding $R^5$—X—$PO_3^{2-}$, $R^5$—X—P(O)(NHR$^6$)$_2$, or $R^5$—X—P(O)(O$^{-})(NHR^6)$. Especially preferred Z' groups is OH. Groups $D^4$ and $D^3$ are preferably hydrogen, alkyl, and —OR$^2$, —OC(O)R$^3$, but at least one of $D^4$ or $D^3$ must be H.

In the following examples of preferred compounds, the following prodrugs are preferred:

Acyloxyalkyl esters;
Alkoxycarbonyloxyalkyl esters;
Aryl esters;
Benzyl and substituted benzyl esters;
Disulfide containing esters;
Substituted (1,3-dioxolen-2-one)methyl esters;
Substituted 3-phthalidyl esters;
Cyclic-[5-hydroxycyclohexan-1,3-diyl] diesters and hydroxy protected forms;
Cyclic-[2-hydroxymethylpropan-1,3-diyl] diesters and hydroxy protected forms;
Cyclic-(1-arylpropan-1,3-diyl);
Monoaryl ester N-substituted mono phosphoramidates;
Bis Omega substituted lactone esters; and all mixed esters resulted from possible combinations of above esters;

More preferred are the following:
Bis-pivaloyloxymethyl esters;
Bis-isobutyryloxymethyl esters;
Cyclic-[1-(3-chlorophenyl)propan-1,3-diyl] diesters;
Cyclic-[1-(3,5-dichlorophenyl)propan-1,3-diyl] diester;
Cyclic-[1-(3-bromo-4-fluorophenyl)propan-1,3-diyl] diester;
Cyclic-[2-hydroxymethylpropan-1,3-diyl] diester;
Cyclic-[2-acetoxymethylpropan-1,3-diyl] diester;
Cyclic-[2-methyloxycarbonyloxymethylpropan-1,3-diyl] diester;
Cyclic-[1-phenylpropan-1,3-diyl] diesters;
Cyclic-[1-(2-pyridyl)propan-1,3-diyl)] diesters;
Cyclic-[1-(3-pyridyl)propan-1,3-diyl] diesters;
Cyclic-[1-(4-pyridyl)propan-1,3-diyl] diesters;
Cyclic-[5-hydroxycyclohexan-1,3-diyl] diesters and hydroxy protected forms;
Bis-benzoylthiomethyl esters;
Bis-benzoylthioethyl esters;
Bis-benzoyloxymethyl esters;
Bis-p-fluorobenzoyloxymethyl esters;
Bis-6-chloronicotinoyloxymethyl esters;
Bis-5-bromonicotinoyloxymethyl esters;
Bis-thiophenecarbonyloxymethyl esters;
Bis-2-furoyloxymethyl esters;
Bis-3-furoyloxymethyl esters;
Diphenyl esters;
Bis-(4-methoxyphenyl) esters;
Bis-(2-methoxyphenyl) esters;
Bis-(2-ethoxyphenyl) esters;
Mono-(2-ethoxyphenyl) esters;
Bis-(4-acetamidophenyl) esters;
Bis-(4-acetoxyphenyl) esters;
Bis-(4-hydroxyphenyl) esters;
Bis-(2-acetoxyphenyl) esters;
Bis-(3-acetoxyphenyl) esters;
Bis-(4-morpholinophenyl) esters;
Bis-[4-(1-triazolophenyl) esters;
Bis-(3-N,N-dimethylaninophenyl) esters;
Bis-(1,2,3,4-tetrahydronapthalen-2-yl) esters;
Bis-(3-chloro-4-methoxy)benzyl esters;
Bis-(3-bromo-4-methoxy)benzyl esters;
Bis-(3-cyano-4-methoxy)benzyl esters;
Bis-(3-chloro-4-acetoxy)benzyl esters;
Bis-(3-bromo-4-acetoxy)benzyl esters;
Bis-(3-cyano-4-acetoxy)benzyl esters;
Bis-(4-chloro)benzyl esters;
Bis-(4-acetoxy)benzyl esters;
Bis-(3,5-dimethoxy-4-acetoxy)benzyl esters;
Bis-(3-methyl-4-acetoxy)benzyl esters;
Bis-(benzyl)esters;
Bis-(3-methoxy-4-acetoxy)benzyl esters;
Bis-(6'-hydroxy-3',4'-dithia)hexyl esters;
Bis-(6'-acetoxy-3',4'-dithia)hexyl esters;
(3,4-dithiahexan-1,6-diyl) esters;
Bis-(5-methyl-1,3-dioxolen-2-one-4-yl)methyl esters;
Bis-(5-ethyl-1,3-dioxolen-2-one-4-yl)methyl esters;
Bis-(5-tert-butyl-1,3-dioxolen-2-one-4-yl)methyl esters;
Bis-3-(5,6,7-trimethoxy)phthalidyl esters;
Bis-(cyclohexyloxycarbonyloxymethyl) esters;
Bis-(isopropyloxycarbonyloxymethyl) esters;
Bis-(ethyloxycarbonyloxymethyl) esters;
Bis-(methyloxycarbonyloxymethyl) esters;
Bis-(isopropythiocarbonyloxymethyl) esters;
Bis-(phenyloxycarbonyloxymethyl) esters;
Bis-(benzyloxycarbonyloxymethyl) esters;
Bis-(phenylthiocarbonyloxymethyl) esters;
Bis-(p-methoxyphenoxycarbonyloxymethyl) esters;
Bis-(m-methoxyphenoxycarbonyloxymethyl) esters;
Bis-(o-methoxyphenoxycarbonyloxymethyl) esters;
Bis-(o-methylphenoxycarbonyloxymethyl) esters;
Bis-(-chlorophenoxycarbonyloxymethyl) esters;
Bis-(1,4-biphenoxycarbonyloxymethyl) esters;
Bis-[(2-phthalimidoethyl)oxycarbonyloxymethyl]esters;
Bis-(N-phenyl-N-methylcarbamoyloxymethyl) esters;
Bis-(2,2,2-trichloroethyl) esters;
Bis-(2-bromoethyl) esters;
Bis-(2-iodoethyl) esters;
Bis-(2-azidoethyl) esters;
Bis-(2-acetoxyethyl) esters;
Bis-(2-aminoethyl) esters;
Bis-(2-N,N-dimethylaminoethyl) esters;
Bis-(2-aminoethyl) esters;
Bis-(methoxycarbonylmethyl) esters;
Bis-(2-aminoethyl) esters;
Bis-[N,N-di(2-hydroxyethyl)]carbamoylmethylesters;
Bis-(2-aminoethyl) esters;

Bis-(2-methyl-5-thiazolomethyl) esters;
Bis-(bis-2-hydroxyethylcarbamoylmethyl) esters.
O-phenyl-[-(1-ethoxycarbonyl)ethyl]phosphoramidates (—P(O)(OPh)N(H)—CH(Me)CO$_2$Et)
O-phenyl-[N-(1-methoxycarbonyl)ethyl] phosphoramidates (—P(O)(OPh)(N(H)—CH(Me)CO$_2$Me)
O-(3-chlorophenyl)-[N -(1-ethoxycarbonyl)ethyl] phosphoramidates (—P(O)(OPh-3-Cl)(NH—CH(Me)CO$_2$Et)
O-(2-chlorophenyl)-[N-(1-ethoxycarbonyl)ethyl] phosphoramidates (—P(O)(OPh-2-Cl)(NH—CH(Me)CO$_2$Et)
O-(4-chlorophenyl)-[N-(1-ethoxycarbonyl)ethyl] phosphoramidates (—P(O)(OPh-4-Cl)(NH—CH(Me)CO$_2$Et)
O-(4-acetamidophenyl)-[N-(1-ethoxycarbonyl)ethyl] phosphoramidates (—P(O)(OPh-4—NHAc)(NH—CH(Me)CO$_2$Et)
O-(2-ethoxycarbonylphenyl)-[N-(1-ethoxycarbonyl)ethyl]phosphoramidates (—P(O)(OPh-2-CO$_2$Et)(NH—CH(Me)CO$_2$Et)
O-phenyl-[N-(1-ethoxycarbonyl-1-methyl)ethyl] phosphoramidates (—P(O)(OPh)(NH—C(Me)$_2$CO$_2$Et)
O-phenyl-[N-(1-methoxycarbonyl-1-methyl)ethyl] phosphoramidates (—P(O)(OPh)(NH—C(Me)$_2$CO$_2$Me)
O-(3-chlorophenyl)-[N-(1-ethoxycarbonyl-1-methyl)ethyl]phosphoramidates (—P(O)(OPh-3-Cl)(NH—C(Me)$_2$CO$_2$Et)
O-(2-chlorophenyl)-[N-(1-ethoxycarbonyl-1-methyl)ethyl]phosphoramidates (—P(O)(OPh-2-Cl)(NH—C(Me)$_2$CO$_2$Et)
O-(4-chlorophenyl)-[N-(1-ethoxycarbonyl-1-methyl)ethyl]phosphoramidates (—P(O)(OPh-4-Cl)(NH—C(Me)$_2$CO$_2$Et)
O-(4-acetamidophenyl)-[N-(1-ethoxycarbonyl-1-methyl)ethyl]phosphoramidates (—P(O)(OPh-4-NHAc)(NH—C(Me)$_2$CO$_2$Et)
O-(2-ethoxycarbonylphenyl)-[N-(1-ethoxycarbonyl-1-methyl)ethyl]phosphoramidates (—P(O)(OPh-2-CO$_2$Et)(NH—C(Me)$_2$CO$_2$Et)
O-phenyl-[N-(ethoxycarbonyl)methyl]phosphoramidates (—P(O)(OPh)(NH—CH$_2$CO$_2$Et)
O-phenyl-[N-(methoxycarbonyl)methyl] phosphoramidates (—P(O)(OPh)(NH—CH$_2$CO$_2$Me)
O-(3-chlorophenyl)-[N-(ethoxycarbonyl)methyl] phosphoramidates (—P(O)(OPh-3-Cl)(NH—CH$_2$CO$_2$Et)
O-(2-chlorophenyl)-[N-(ethoxycarbonyl)methyl] phosphoramidates (—P(O)(OPh-2-Cl)(NH—CH$_2$CO$_2$Et)
O-(4-chlorophenyl)-[N-(ethoxycarbonyl)methyl] phosphoramidates (—P(O)(OPh-4-Cl)(NH—CH$_2$CO$_2$Et)
O-(4-acetamidophenyl)-[N-(ethoxycarbonyl)methyl] phosphoramidates (—P(O)(OPh-4-NHAc)(NH—CH$_2$CO$_2$Et)
O-(2-ethoxycarbonylphenyl)-[N-(ethoxycarbonyl) methyl]phosphoramidates (—P(O)(OPh-2-CO$_2$Et)(NH—CH$_2$CO$_2$Et)

Most preferred are the following:
Bis-pivaloyloxymethyl esters;
Bis-isobutyryloxymethyl esters;
Cyclic-[1-(3-chlorophenyl)propan-1,3-diyl] diesters;
Cyclic-[1-3,5-dichlorophenyl)propan-1,3-diyl] diester;
Cyclic-[1-(3-bromo-4-fluorophenyl)propan-1,3-diyl] diester;
Cyclic-(2-hydroxymethylpropan-1,3-diyl) ester;
Cyclic-(2-acetoxymethylpropan-1,3-diyl) ester;
Cyclic-(2-methyloxycarbonyloxymethylpropan-1,3-diyl) ester;
Cyclic-(2-cyclohexylcarbonyloxymethylpropan-1,3-diyl) ester;
Cyclic-[phenylpropan-1,3-diyl] diesters;
Cyclic-[1-(2-pyridyl)propan-1,3-diyl)] diesters;
Cyclic-[1-(3-pyridyl)propan-1,3-diyl] diesters;
Cyclic-[1-(4-pyridyl)propan-1,3-diyl] diesters;
Cyclic-[5-hydroxycyclohexan-1,3-diyl] diesters and hydroxy protected forms;
Bis-benzoylthiomethyl esters;
Bis-benzoylthioethylesters;
Bis-benzoyloxymethyl esters;
Bis-p-fluorobenzoyloxymethyl esters;
Bis-6-chloronicotinoyloxymethyl esters;
Bis-5-bromonicotinoyloxymethyl esters;
Bis-thiophenecarbonyloxymethyl esters;
Bis-2-furoyloxyethyl esters;
Bis-3-furoyloxymethyl esters;
Diphenyl esters;
Bis-(2-methylphenyl) esters;
Bis-(2-methoxyphenyl) esters;
Bis-(2-ethoxyphenyl) esters;
Bis-(4-methoxyphenyl) esters;
Bis-(3-bromo-4-methoxybenzyl) esters;
Bis-(4-acetoxybenzyl) esters;
Bis-(3,5-dimethoxy-4-acetoxybenzyl) esters;
Bis-(3-methyl-4-acetoxybenzyl) esters;
Bis-(3-methoxy-4-acetoxybenzyl) esters;
Bis-(3-chloro-4-acetoxybenzyl) esters;
Bis-(cyclohexyloxycarbonyloxymethyl) esters;
Bis-(isopropyloxycarbonyloxymethyl) esters;
Bis-(ethyloxycarbonyloxymethyl) esters;
Bis-(methyloxycarbonyloxymethyl) esters;
Bis-(isopropylthiocarbonyloxymethyl) esters;
Bis-(phenyloxycarbonyloxymethyl) esters;
Bis-(benzyloxycarbonyloxymethyl) esters;
Bis-(phenylthiocarbonyloxymethyl) esters;
Bis-p-methoxyphenoxycarbonyloxymethyl) esters;
Bis-(m-methoxyphenoxycarbonyloxymethyl) esters;
Bis-(o-methoxyphenoxycarbonyloxymethyl) esters;
Bis-(o-methylphenoxycarbonyloxymethyl) esters;
Bis-(p-chlorophenoxycarbonyloxymethyl) esters;
Bis-(1,4-biphenoxycarbonyloxymethyl) esters;
Bis-[(2-phthalimidoethyl)oxycarbonyloxymethyl]esters;
Bis-(6-hydroxy-3,4-dithia)hexyl esters;
Cyclic-(3,4-dithiahexan-1,6-diyl) esters;
Bis-(2-bromoethyl) esters;

Bis-(2-aminoethyl) esters;
Bis-(2-N,N-dianinoetlyl) esters;
O-phenyl-[N-(1-ethoxycarbonyl)ethyl]phosphoramidates (—P(O)(OPh)(NH—*CH(Me)CO₂Et)
O-phenyl-[N-(1-methoxycarbonyl)ethyl] phosphoramidates (—P(O)(OPh)(NH—*CH(Me)CO₂Me)
O-(3-chlorophenyl)-[N-(1-ethoxycarbonyl)ethyl] phosphoramidates (—P(O)(OPh-3-Cl)(NH—*CH(Me)CO₂Et)
O-(2-chlorophenyl)-[N-(1-ethoxycarbonyl)ethyl] phosphoramidates (—P(O)(OPh-2-Cl)(NH—*CH(Me)CO₂Et)
O-(4-chlorophenyl)-[N-(1-ethoxycarbonyl)ethyl] phosphoramidates (—P(O)(OPh-4-Cl)(NH—*CH(Me)CO₂Et)
O-(4-acetamidophenyl)-[N-(1-ethoxycarbonyl)ethyl] phosphoramidates (—P(O)(OPh-4-NHAc)(NH—*CH(Me)CO₂Et)
O-(2-ethoxycarbonylphenyl)-[N-(1-ethoxycarbonyl)ethyl]phosphoramidates (—P(O)(OPh-2-CO₂Et)(NH—*CH(Me)CO₂Et)
O-phenyl-[N-(1-ethoxycarbonyl-1-methyl)ethyl] phosphoramidates (—P(O)(OPh)(NH—C(Me)₂CO₂Et)
O-phenyl-[N-(1-methoxycarbonyl-1-methyl)ethyl] phosphoramidates (—P(O)(OPh)(NH—C(Me)₂CO₂Me)
O-(3-chlorophenyl)-[N-(1-ethoxycarbonyl-1-methyl)ethyl]phosphoramidates (—P(O)(OPh-3-Cl)(NH—C(Me)₂CO₂Et)
O-(2-chlorophenyl)-[N-(1-ethoxycarbonyl-1-methyl)ethyl]phosphoramidates (—P(O)(OPh-2-Cl)(NH—C(Me)₂CO₂Et)
O-(4-chlorophenyl)-[N-(1-ethoxycarbonyl-1-methyl)ethyl]phosphoramidates (—P(O)(OPh-4-Cl)(NH—C(Me)₂CO₂Et)
O-(4-acetamidophenyl)-[N-(1-ethoxycarbonyl-1-methyl)ethyl]phosphoramidates (—P(O)(OPh-4-NHAc)(NH—C(Me)₂CO₂Et)
O-(2-ethoxycarbonylphenyl)-[N-(1-ethoxycarbonyl-1-methyl)ethyl]phosphoramidates (—P(O)(OPh-2-CO₂Et)(NH—C(Me)₂CO₂Et)

In the above prodrugs an asterisk (*) on a carbon refers to the L-configuration.

O-phenyl-[N-(ethoxycarbonyl)methyl]phosphoramidates (—P(O)(OPh)(NH—CH₂CO₂Et)
O-phenyl-[N-(methoxycarbonyl)methyl] phosphoramidates (—P(O)(OPh)(NH—CH₂CO₂Me)
O-(3-chlorophenyl)[N-((ethoxycarbonyl)methyl] phosphoramidates (—P(O)(OPh-3-Cl)(NH—CH₂CO₂Et)
O-(2-chlorophenyl)-[N-(ethoxycarbonyl)methyl] phosphoramidates (—P(O)(OPh-2-Cl)(NH—CH₂CO₂Et)
O-(4-chlorophenyl)-[N-(ethoxycarbonyl)methyl] phosphoramidates (—P(O)(OPh-4-Cl)(NH—CH₂CO₂Et)
O-(4-acetamidophenyl)-[N-(ethoxycarbonyl)methyl] phosphoramidates (—P(O)(OPh-4-NHAc)(NH—CH₂CO₂Et)
O-(2-ethoxycarbonylphenyl)-[N-(ethoxycarbonyl) methyl]phosphoramidates (—P(O)(OPh-2-CO₂Et)(NH—CH₂CO₂Et)

The following compounds of formula I wherein R⁵ is a thiazolyl, or an oxazolyl, or a selenazolyl, or a pyrazolyl, or an imidazolyl or an isoxazolyl or a 1,2,4-triazolyl, or a 1,2,4-thiadiazolyl, or a 1,2,4-oxadiazolyl, and pharmaceutically acceptable salts and prodrugs thereof are preferred. These preferred compounds are shown in structures (i)–(iv), below:

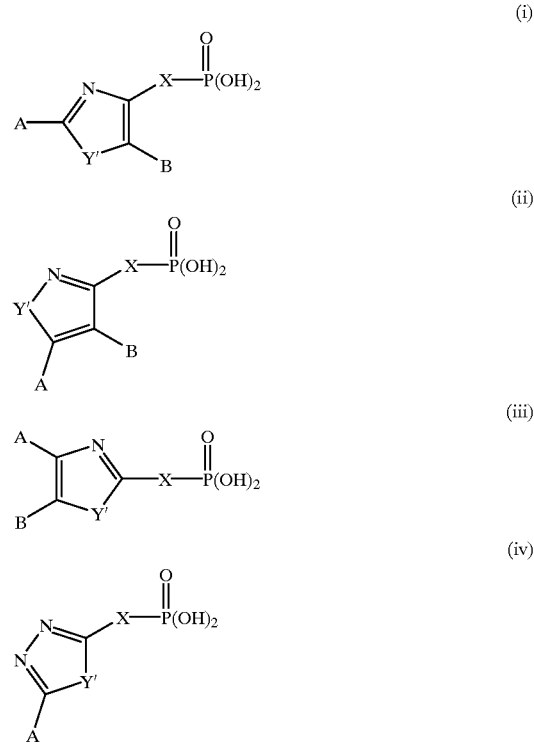

The preferred compounds are listed in Table 1 by designated numbers assigned to A, B, X and Y' moieties in the above formulae i–iv according to the following convention: A.B.X.Y'. For each moiety, structures are assigned to a number shown in the following tables for A, B, X, and Y'. The following terms are used: Pr-c is cyclopropyl, Pr-n is n-propyl, Pr-i is isopropyl, Bu-n is n-butyl, Bu-I is isobutyl, Bu-c is cyclobutyl, Bu-s is sec-butyl, Bu-t is tert-butyl and hexyl-c is cyclohexyl.

Variable A is selected from seven different substituents.
The A groups are assigned the following numbers:

TABLE A

| | 1 | 2 | 3 | 4 | 5 | 6 | 7 |
|---|---|---|---|---|---|---|---|
| A = | H | NH₂ | Br | Cl | F | Me | CF₃ |

Variable B is divided into four Groups, each listing nine different substituents.
The Group 1 substituents for variable B are assigned the following numbers:

| | 1 | 2 | 3 | 4 | 5 | 6 | 7 | 8 | 9 |
|---|---|---|---|---|---|---|---|---|---|
| B = | H | Me | Et | Pr-n | Pr-i | Pr-c | Br | Cl | I |

The Group 2 substituents for variable B are assigned the following numbers:

|   | 1 | 2 | 3 | 4 | 5 | 6 | 7 | 8 | 9 |
|---|---|---|---|---|---|---|---|---|---|
| B = | F | CN | CH$_2$Pr-c | CH$_2$OMe | neopentyl | C(O)OMe | OEt | SMe | C(O)SMe |

The Group 3 substituents for variable B are assigned the following numbers:

|   | 1 | 2 | 3 | 4 | 5 | 6 | 7 | 8 | 9 |
|---|---|---|---|---|---|---|---|---|---|
| B = | SEt | 4-pyridyl | Bu-c | C(O)OEt | NMe$_2$ | SPr-n | CF$_3$ | Bu-n | Bu-i |

The Group 4 substituents for variable B are assigned the following numbers:

|   | 1 | 2 | 3 | 4 | 5 | 6 | 7 | 8 | 9 |
|---|---|---|---|---|---|---|---|---|---|
| B = | SPr-c | OPr-i | OPr-c | SPr-i | 2-furanyl | 2-thienyl | OMe | CH$_2$SMe | Bn |

Variable X is selected from nine different substituents.
The X groups are assigned the following numbers:

TABLE X

|   | 1 | 2 | 3 | 4 | 5 | 6 | 7 | 8 | 9 |
|---|---|---|---|---|---|---|---|---|---|
| X = | Furan-2,5-diyl | Pyridin-2,6-diyl | Oxazol-2,5-diyl | C(O)—OCH$_2$ | C(O)—NHCH$_2$ | C(O)—SCH$_2$ | C(O)—N(Me)CH$_2$ | NHC(O)—CH$_2$ | CH$_2$O CH$_2$ |

The direction of X groups is defined as going from the heterocycle to the phosphorus atom as shown in formula (i), (ii), (iii) and (iv).

Variable Y' is selected from six different substituents.

The Y' groups are assigned the following numbers:

TABLE Y

|   | 1 | 2 | 3 | 4 | 5 | 6 |
|---|---|---|---|---|---|---|
| Y' = | S | O | Se | NH | NMe | NEt |

TABLE 1

| | | | | | | | | | |
|---|---|---|---|---|---|---|---|---|---|
| 1.1.1.1 | 1.1.1.2 | 1.1.1.3 | 1.1.1.4 | 1.1.1.5 | 1.1.1.6 | 1.1.2.1 | 1.1.2.2 | 1.1.2.3 | 1.1.2.4 |
| 1.1.2.5 | 1.1.2.6 | 1.1.3.1 | 1.1.3.2 | 1.1.3.3 | 1.1.3.4 | 1.1.3.5 | 1.1.3.6 | 1.1.4.1 | 1.1.4.2 |
| 1.1.4.3 | 1.1.4.4 | 1.1.4.5 | 1.1.4.6 | 1.1.5.1 | 1.1.5.2 | 1.1.5.3 | 1.1.5.4 | 1.1.5.5 | 1.1.5.6 |
| 1.1.6.1 | 1.1.6.2 | 1.1.6.3 | 1.1.6.4 | 1.1.6.5 | 1.1.6.6 | 1.1.7.1 | 1.1.7.2 | 1.1.7.3 | 1.1.7.4 |
| 1.1.7.5 | 1.1.7.6 | 1.1.8.1 | 1.1.8.2 | 1.1.8.3 | 1.1.8.4 | 1.1.8.5 | 1.1.8.6 | 1.1.9.1 | 1.1.9.2 |
| 1.1.9.3 | 1.1.9.4 | 1.1.9.5 | 1.1.9.6 | 1.2.1.1 | 1.2.1.2 | 1.2.1.3 | 1.2.1.4 | 1.2.1.5 | 1.2.1.6 |
| 1.2.2.1 | 1.2.2.2 | 1.2.2.3 | 1.2.2.4 | 1.2.2.5 | 1.2.2.6 | 1.2.3.1 | 1.2.3.2 | 1.2.3.3 | 1.2.3.4 |
| 1.2.3.5 | 1.2.3.6 | 1.2.4.1 | 1.2.4.2 | 1.2.4.3 | 1.2.4.4 | 1.2.4.5 | 1.2.4.6 | 1.2.5.1 | 1.2.5.2 |
| 1.2.5.3 | 1.2.5.4 | 1.2.5.5 | 1.2.5.6 | 1.2.6.1 | 1.2.6.2 | 1.2.6.3 | 1.2.6.4 | 1.2.6.5 | 1.2.6.6 |
| 1.2.7.1 | 1.2.7.2 | 1.2.7.3 | 1.2.7.4 | 1.2.7.5 | 1.2.7.6 | 1.2.8.1 | 1.2.8.2 | 1.2.9.3 | 1.2.8.4 |
| 1.2.8.5 | 1.2.8.6 | 1.2.9.1 | 1.2.9.2 | 1.2.9.3 | 1.2.9.4 | 1.2.9.5 | 1.2.9.6 | 1.3.1.1 | 1.3.1.2 |
| 1.3.1.3 | 1.3.1.4 | 1.3.1.5 | 1.3.1.6 | 1.3.2.1 | 1.3.2.2 | 1.3.2.3 | 1.3.2.4 | 1.3.2.5 | 1.3.2.6 |
| 1.3.3.1 | 1.3.3.2 | 1.3.3.3 | 1.3.3.4 | 1.3.3.5 | 1.3.3.6 | 1.3.4.1 | 1.3.4.2 | 1.3.4.3 | 1.3.4.4 |
| 1.3.4.5 | 1.3.4.6 | 1.3.5.1 | 1.3.5.2 | 1.3.5.3 | 1.3.5.4 | 1.3.5.5 | 1.3.5.6 | 1.3.6.1 | 1.3.6.2 |
| 1.3.6.3 | 1.3.6.4 | 1.3.6.5 | 1.3.6.6 | 1.3.7.1 | 1.3.7.2 | 1.3.7.3 | 1.3.7.4 | 1.3.7.5 | 1.3.7.6 |
| 1.3.8.1 | 1.3.8.2 | 1.3.8.3 | 1.3.8.4 | 1.3.8.5 | 1.3.8.6 | 1.3.9.1 | 1.3.9.2 | 1.3.9.3 | 1.3.9.4 |
| 1.3.9.5 | 1.3.9.6 | 1.4.1.1 | 1.4.1.2 | 1.4.1.3 | 1.4.1.4 | 1.4.1.5 | 1.4.1.6 | 1.4.2.1 | 1.4.2.2 |
| 1.4.2.3 | 1.4.2.4 | 1.4.2.5 | 1.4.2.6 | 1.4.3.1 | 1.4.3.2 | 1.4.3.3 | 1.4.3.4 | 1.4.3.5 | 1.4.3.6 |

TABLE 1-continued

| | | | | | | | | | |
|---|---|---|---|---|---|---|---|---|---|
| 1.4.4.1 | 1.4.4.2 | 1.4.4.3 | 1.4.4.4 | 1.4.4.5 | 1.4.4.6 | 1.4.5.1 | 1.4.5.2 | 1.4.5.3 | 1.4.5.4 |
| 1.4.5.5 | 1.4.5.6 | 1.4.6.1 | 1.4.6.2 | 1.4.6.3 | 1.4.6.4 | 1.4.6.5 | 1.4.6.6 | 1.4.7.1 | 1.4.7.2 |
| 1.4.7.3 | 1.4.7.4 | 1.4.7.5 | 1.4.7.6 | 1.4.8.1 | 1.4.8.2 | 1.4.8.3 | 1.4.8.4 | 1.4.8.5 | 1.4.8.6 |
| 1.4.9.1 | 1.4.9.2 | 1.4.9.3 | 1.4.9.4 | 1.4.9.5 | 1.4.9.6 | 1.5.1.1 | 1.5.1.2 | 1.5.1.3 | 1.5.1.4 |
| 1.5.1.5 | 1.5.1.6 | 1.5.2.1 | 1.5.2.2 | 1.5.2.3 | 1.5.2.4 | 1.5.2.5 | 1.5.2.6 | 1.5.3.1 | 1.5.3.2 |
| 1.5.3.3 | 1.5.3.4 | 1.5.3.5 | 1.5.3.6 | 1.5.4.1 | 1.5.4.2 | 1.5.4.3 | 1.5.4.4 | 1.5.4.5 | 1.5.4.6 |
| 1.5.5.1 | 1.5.5.2 | 1.5.5.3 | 1.5.5.4 | 1.5.5.5 | 1.5.5.6 | 1.5.6.1 | 1.5.6.2 | 1.5.6.3 | 1.5.6.4 |
| 1.5.6.5 | 1.5.6.6 | 1.5.7.1 | 1.5.7.2 | 1.5.7.3 | 1.5.7.4 | 1.5.7.5 | 1.5.7.6 | 1.5.8.1 | 1.5.8.2 |
| 1.5.8.3 | 1.5.8.4 | 1.5.8.5 | 1.5.8.6 | 1.5.9.1 | 1.5.9.2 | 1.5.9.3 | 1.5.9.4 | 1.5.9.5 | 1.5.9.6 |
| 1.6.1.1 | 1.6.1.2 | 1.6.1.3 | 1.6.1.4 | 1.6.1.5 | 1.6.1.6 | 1.6.2.1 | 1.6.2.2 | 1.6.2.3 | 1.6.2.4 |
| 1.6.2.5 | 1.6.2.6 | 1.6.3.1 | 1.6.3.2 | 1.6.3.3 | 1.6.3.4 | 1.6.3.5 | 1.6.3.6 | 1.6.4.1 | 1.6.4.2 |
| 1.6.4.3 | 1.6.4.4 | 1.6.4.5 | 1.6.4.6 | 1.6.5.1 | 1.6.5.2 | 1.6.5.3 | 1.6.5.4 | 1.6.5.5 | 1.6.5.6 |
| 1.6.6.1 | 1.6.6.2 | 1.6.6.3 | 1.6.6.4 | 1.6.6.5 | 1.6.6.6 | 1.6.7.1 | 1.6.7.2 | 1.6.7.3 | 1.67.4 |
| 1.6.7.5 | 1.6.7.6 | 1.6.8.1 | 1.6.8.2 | 1.6.8.3 | 1.6.8.4 | 1.6.8.5 | 1.6.8.6 | 1.6.9.1 | 1.6.9.2 |
| 1.6.9.3 | 1.6.9.4 | 1.6.9.5 | 1.6.9.6 | 1.7.1.1 | 1.7.1.2 | 1.7.1.3 | 1.7.1.4 | 1.7.1.5 | 1.7.1.6 |
| 1.7.2.1 | 1.7.2.2 | 1.7.2.3 | 1.7.2.4 | 1.7.2.5 | 1.7.2.6 | 1.7.3.1 | 1.7.3.2 | 1.7.3.3 | 1.7.3.4 |
| 1.7.3.5 | 1.7.3.6 | 1.7.4.1 | 1.7.4.2 | 1.7.4.3 | 1.7.4.4 | 1.7.4.5 | 1.7.4.6 | 1.7.5.1 | 1.7.5.2 |
| 1.7.5.3 | 1.7.5.4 | 1.7.5.5 | 1.7.5.6 | 1.7.6.1 | 1.7.6.2 | 1.7.6.3 | 1.7.6.4 | 1.7.6.5 | 1.7.6.6 |
| 1.7.7.1 | 1.7.7.2 | 1.7.7.3 | 1.7.7.4 | 1.7.7.5 | 1.7.7.6 | 1.7.8.1 | 1.7.8.2 | 1.7.8.3 | 1.7.8.4 |
| 1.7.8.5 | 1.7.8.6 | 1.7.9.1 | 1.7.9.2 | 1.7.9.3 | 1.7.9.4 | 1.7.9.5 | 1.7.9.6 | 1.8.1.1 | 1.8.1.2 |
| 1.8.1.3 | 1.8.1.4 | 1.8.1.5 | 1.8.1.6 | 1.8.2.1 | 1.8.2.2 | 1.8.2.3 | 1.8.2.4 | 1.8.2.5 | 1.8.2.6 |
| 1.8.3.1 | 1.8.3.2 | 1.8.3.3 | 1.8.3.4 | 1.8.3.5 | 1.8.3.6 | 1.8.4.1 | 1.8.4.2 | 1.8.4.3 | 1.8.4.4 |
| 1.8.4.5 | 1.8.4.6 | 1.8.5.1 | 1.8.5.2 | 1.8.5.3 | 1.8.5.4 | 1.8.5.5 | 1.8.5.6 | 1.8.6.1 | 1.8.6.2 |
| 1.8.6.3 | 1.8.6.4 | 1.8.6.5 | 1.8.6.6 | 1.8.7.1 | 1.8.7.2 | 1.8.7.3 | 1.8.7.4 | 1.8.7.5 | 1.8.7.6 |
| 1.8.8.1 | 1.8.8.2 | 1.8.8.3 | 1.8.8.4 | 1.8.8.5 | 1.8.8.6 | 1.8.9.1 | 1.8.9.2 | 1.8.9.3 | 1.8.9.4 |
| 1.8.9.5 | 1.8.9.6 | 1.9.1.1 | 1.9.1.2 | 1.9.1.3 | 1.9.1.4 | 1.9.1.5 | 1.9.1.6 | 1.9.2.1 | 1.9.2.2 |
| 1.9.2.3 | 1.9.2.4 | 1.9.2.5 | 1.9.2.6 | 1.9.3.1 | 1.9.3.2 | 1.9.3.3 | 1.9.3.4 | 1.9.3.5 | 1.9.3.6 |
| 1.9.4.1 | 1.9.4.2 | 1.9.4.3 | 1.9.4.4 | 1.9.4.5 | 1.9.4.6 | 1.9.5.1 | 1.9.5.2 | 1.9.5.3 | 1.9.5.4 |
| 1.9.5.5 | 1.9.5.6 | 1.9.6.1 | 1.9.6.2 | 1.9.6.3 | 1.9.6.4 | 1.9.6.5 | 1.9.6.6 | 1.9.7.1 | 1.9.7.2 |
| 1.9.7.3 | 1.9.7.4 | 1.9.7.5 | 1.9.7.6 | 1.9.8.1 | 1.9.8.2 | 1.9.8.3 | 1.9.8.4 | 1.9.8.5 | 1.9.8.6 |
| 1.9.9.1 | 1.9.9.2 | 1.9.9.3 | 1.9.9.4 | 1.9.9.5 | 1.9.9.6 | 2.1.1.1 | 2.1.1.2 | 2.1.1.3 | 2.1.1.4 |
| 2.1.1.5 | 2.1.1.6 | 2.1.2.1 | 2.1.2.2 | 2.1.2.3 | 2.1.2.4 | 2.1.2.5 | 2.1.2.6 | 2.1.3.1 | 2.1.3.2 |
| 2.1.3.3 | 2.1.3.4 | 2.1.3.5 | 2.1.3.6 | 2.1.4.1 | 2.1.4.2 | 2.1.4.3 | 2.1.4.4 | 2.1.4.5 | 2.1.4.6 |
| 2.1.5.1 | 2.1.5.2 | 2.1.5.3 | 2.1.5.4 | 2.1.5.5 | 2.1.5.6 | 2.1.6.1 | 2.1.6.2 | 2.1.6.3 | 2.1.6.4 |
| 2.1.6.5 | 2.1.6.6 | 2.1.7.1 | 2.1.7.2 | 2.1.7.3 | 2.1.7.4 | 2.1.7.5 | 2.1.7.6 | 2.1.8.1 | 2.1.8.2 |
| 2.1.8.3 | 2.1.8.4 | 2.1.8.5 | 2.1.8.6 | 2.1.9.1 | 2.1.9.2 | 2.1.9.3 | 2.1.9.4 | 2.1.9.5 | 2.1.9.6 |
| 2.2.1.1 | 2.2.1.2 | 2.2.1.3 | 2.2.1.4 | 2.2.1.5 | 2.2.1.6 | 2.2.2.1 | 2.2.2.2 | 2.2.2.3 | 2.2.2.4 |
| 2.2.2.5 | 2.2.2.6 | 2.2.3.1 | 2.2.3.2 | 2.2.3.3 | 2.2.3.4 | 2.2.3.5 | 2.2.3.6 | 2.2.4.1 | 2.2.4.2 |
| 2.2.4.3 | 2.2.4.4 | 2.2.4.5 | 2.2.4.6 | 2.2.5.1 | 2.2.5.2 | 2.2.5.3 | 2.2.5.4 | 2.2.5.5 | 2.2.5.6 |
| 2.2.6.1 | 2.2.6.2 | 2.2.6.3 | 2.2.6.4 | 2.2.6.5 | 2.2.6.6 | 2.2.7.1 | 2.2.7.2 | 2.2.7.3 | 2.2.7.4 |
| 2.2.7.5 | 2.2.7.6 | 2.2.8.1 | 2.2.8.2 | 2.2.8.3 | 2.2.8.4 | 2.2.8.5 | 2.2.8.6 | 2.2.9.1 | 2.2.9.2 |
| 2.2.9.3 | 2.2.9.4 | 2.2.9.5 | 2.2.9.6 | 2.3.1.1 | 2.3.1.2 | 2.3.1.3 | 2.3.1.4 | 2.3.1.5 | 2.3.1.6 |
| 2.3.2.1 | 2.3.2.2 | 2.3.2.3 | 2.3.2.4 | 2.3.2.5 | 2.3.2.6 | 2.3.3.1 | 2.3.3.2 | 2.3.3.3 | 2.3.3.4 |
| 2.3.3.5 | 2.3.3.6 | 2.3.4.1 | 2.3.4.2 | 2.3.4.3 | 2.3.4.4 | 2.3.4.5 | 2.3.4.6 | 2.3.5.1 | 2.3.5.2 |
| 2.3.5.3 | 2.3.5.4 | 2.3.5.5 | 2.3.5.6 | 2.3.6.1 | 2.3.6.2 | 2.3.6.3 | 2.3.6.4 | 2.3.6.5 | 2.3.6.6 |
| 2.3.7.1 | 2.3.7.2 | 2.3.7.3 | 2.3.7.4 | 2.3.7.5 | 2.3.7.6 | 2.3.8.1 | 2.3.8.2 | 2.3.8.3 | 2.3.8.4 |
| 2.3.8.5 | 2.3.8.6 | 2.3.9.1 | 2.3.9.2 | 2.3.9.3 | 2.3.9.4 | 2.3.9.5 | 2.3.9.6 | 2.4.1.1 | 2.4.1.2 |
| 2.4.1.3 | 2.4.1.4 | 2.4.1.5 | 2.4.1.6 | 2.4.2.1 | 2.4.2.2 | 2.4.2.3 | 2.4.2.4 | 2.4.2.5 | 2.4.2.6 |
| 2.4.3.1 | 2.4.3.2 | 2.4.3.3 | 2.4.3.4 | 2.4.3.5 | 2.4.3.6 | 2.4.4.1 | 2.4.4.2 | 2.4.4.3 | 2.4.4.4 |
| 2.4.4.5 | 2.4.4.6 | 2.4.5.1 | 2.4.5.2 | 2.4.5.3 | 2.4.5.4 | 2.4.5.5 | 2.4.5.6 | 2.4.6.1 | 2.4.6.2 |
| 2.4.6.3 | 2.4.6.4 | 2.4.6.5 | 2.4.6.6 | 2.4.7.1 | 2.4.7.2 | 2.4.7.3 | 2.4.7.4 | 2.4.7.5 | 2.4.7.6 |
| 2.4.8.1 | 2.4.8.2 | 2.4.8.3 | 2.4.8.4 | 2.4.8.5 | 2.4.8.6 | 2.4.9.1 | 2.4.9.2 | 2.4.9.3 | 2.4.9.4 |
| 2.4.9.5 | 2.4.9.6 | 2.5.1.1 | 2.5.1.2 | 2.5.1.3 | 2.5.1.4 | 2.5.1.5 | 2.5.1.6 | 2.5.2.1 | 2.5.2.2 |
| 2.5.2.3 | 2.5.2.4 | 2.5.2.5 | 2.5.2.6 | 2.5.3.1 | 2.5.3.2 | 2.5.3.3 | 2.5.3.4 | 2.5.3.5 | 2.5.3.6 |
| 2.5.4.1 | 2.5.4.2 | 2.5.4.3 | 2.5.4.4 | 2.5.4.5 | 2.5.4.6 | 2.5.5.1 | 2.5.5.2 | 2.5.5.3 | 2.5.5.4 |
| 2.5.5.5 | 2.5.5.6 | 2.5.6.1 | 2.5.6.2 | 2.5.6.3 | 2.5.6.4 | 2.5.6.5 | 2.5.6.6 | 2.5.7.1 | 2.5.7.2 |
| 2.5.7.3 | 2.5.7.4 | 2.5.7.5 | 2.5.7.6 | 2.5.8.1 | 2.5.8.2 | 2.5.8.3 | 2.5.8.4 | 2.5.8.5 | 2.5.8.6 |
| 2.5.9.1 | 2.5.9.2 | 2.5.9.3 | 2.5.9.4 | 2.5.9.5 | 2.5.9.6 | 2.6.1.1 | 2.6.1.2 | 2.6.1.3 | 2.6.1.4 |
| 2.6.1.5 | 2.6.1.6 | 2.6.2.1 | 2.6.2.2 | 2.6.2.3 | 2.6.2.4 | 2.6.2.5 | 2.6.2.6 | 2.6.3.1 | 2.6.3.2 |
| 2.6.3.3 | 2.6.3.4 | 2.6.3.5 | 2.6.3.6 | 2.6.4.1 | 2.6.4.2 | 2.6.4.3 | 2.6.4.4 | 2.6.4.5 | 2.6.4.6 |
| 2.6.5.1 | 2.6.5.2 | 2.6.5.3 | 2.6.5.4 | 2.6.5.5 | 2.6.5.6 | 2.6.6.1 | 2.6.6.2 | 2.6.6.3 | 2.6.6.4 |
| 2.6.6.5 | 2.6.6.6 | 2.6.7.1 | 2.6.7.2 | 2.6.7.3 | 2.6.7.4 | 2.6.7.5 | 2.6.7.6 | 2.6.8.1 | 2.6.8.2 |
| 2.6.8.3 | 2.6.8.4 | 2.6.8.5 | 2.6.8.6 | 2.6.9.1 | 2.6.9.2 | 2.6.9.3 | 2.6.9.4 | 2.6.9.5 | 2.6.9.6 |
| 2.7.1.1 | 2.7.1.2 | 2.7.1.3 | 2.7.1.4 | 2.7.1.5 | 2.7.1.6 | 2.7.2.1 | 2.7.2.2 | 2.7.2.3 | 2.7.2.4 |
| 2.7.2.5 | 2.7.2.6 | 2.7.3.1 | 2.7.3.2 | 2.7.3.3 | 2.7.3.4 | 2.7.3.5 | 2.7.3.6 | 2.7.4.1 | 2.7.4.2 |
| 2.7.4.3 | 2.7.4.4 | 2.7.4.5 | 2.7.4.6 | 2.7.5.1 | 2.7.5.2 | 2.7.5.3 | 2.7.5.4 | 2.7.5.5 | 2.7.5.6 |
| 2.7.6.1 | 2.7.6.2 | 2.7.6.3 | 2.7.6.4 | 2.7.6.5 | 2.7.6.6 | 2.7.7.1 | 2.7.7.2 | 2.7.7.3 | 2.7.7.4 |
| 2.7.7.5 | 2.7.7.6 | 2.7.8.1 | 2.7.8.2 | 2.7.8.3 | 2.7.8.4 | 2.7.8.5 | 2.7.8.6 | 2.7.9.1 | 2.7.9.2 |
| 2.7.9.3 | 2.7.9.4 | 2.7.9.5 | 2.7.9.6 | 2.8.1.1 | 2.8.1.2 | 2.8.1.3 | 2.8.1.4 | 2.8.1.5 | 2.8.1.6 |
| 2.8.2.1 | 2.8.2.2 | 2.8.2.3 | 2.8.2.4 | 2.8.2.5 | 2.8.2.6 | 2.8.3.1 | 2.8.3.2 | 2.8.3.3 | 2.8.3.4 |
| 2.8.3.5 | 2.8.3.6 | 2.8.4.1 | 2.8.4.2 | 2.8.4.3 | 2.8.4.4 | 2.8.4.5 | 2.8.4.6 | 2.8.5.1 | 2.8.5.2 |
| 2.8.5.3 | 2.8.5.4 | 2.8.5.5 | 2.8.5.6 | 2.8.6.1 | 2.8.6.2 | 2.8.6.3 | 2.8.6.4 | 2.8.6.5 | 2.8.6.6 |
| 2.8.7.1 | 2.8.7.2 | 2.8.7.3 | 2.8.7.4 | 2.8.7.5 | 2.8.7.6 | 2.8.8.1 | 2.8.8.2 | 2.8.8.3 | 2.8.8.4 |
| 2.8.8.5 | 2.8.8.6 | 2.8.9.1 | 2.8.9.2 | 2.8.9.3 | 2.8.9.4 | 2.8.9.5 | 2.8.9.6 | 2.9.1.1 | 2.9.1.2 |
| 2.9.1.3 | 2.9.1.4 | 2.9.1.5 | 2.9.1.6 | 2.9.2.1 | 2.9.2.2 | 2.9.2.3 | 2.9.2.4 | 2.9.2.5 | 2.9.2.6 |
| 2.9.3.1 | 2.9.3.2 | 2.9.3.3 | 2.9.3.4 | 2.9.3.5 | 2.9.3.6 | 2.9.4.1 | 2.9.4.2 | 2.9.4.3 | 2.9.4.4 |
| 2.9.4.5 | 2.9.4.6 | 2.9.5.1 | 2.9.5.2 | 2.9.5.3 | 2.9.5.4 | 2.9.5.5 | 2.9.5.6 | 2.9.6.1 | 2.9.6.2 |
| 2.9.6.3 | 2.9.6.4 | 2.9.6.5 | 2.9.6.6 | 2.9.7.1 | 2.9.7.2 | 2.9.7.3 | 2.9.7.4 | 2.9.7.5 | 2.9.7.6 |
| 2.9.8.1 | 2.9.8.2 | 2.9.8.3 | 2.9.8.4 | 2.9.8.5 | 2.9.8.6 | 2.9.9.1 | 2.9.9.2 | 2.9.9.3 | 2.9.9.4 |

TABLE 1-continued

| | | | | | | | | |
|---|---|---|---|---|---|---|---|---|
| 2.9.9.5 | 2.9.9.6 | 3.1.1.1 | 3.1.1.2 | 3.1.1.3 | 3.1.1.4 | 3.1.1.5 | 3.1.1.6 | 3.1.2.1 | 3.1.2.2 |
| 3.1.2.3 | 3.1.2.4 | 3.1.2.5 | 3.1.2.6 | 3.1.3.1 | 3.1.3.2 | 3.1.3.3 | 3.1.3.4 | 3.1.3.5 | 3.1.3.6 |
| 3.1.4.1 | 3.1.4.2 | 3.1.4.3 | 3.1.4.4 | 3.1.4.5 | 3.1.4.6 | 3.1.5.1 | 3.1.5.2 | 3.1.5.3 | 3.1.5.4 |
| 3.1.5.5 | 3.1.5.6 | 3.1.6.1 | 3.1.6.2 | 3.1.6.3 | 3.1.6.4 | 3.1.6.5 | 3.1.6.6 | 3.1.7.1 | 3.1.7.2 |
| 3.1.7.3 | 3.1.7.4 | 3.1.7.5 | 3.1.7.6 | 3.1.8.1 | 3.1.8.2 | 3.1.8.3 | 3.1.8.4 | 3.1.8.5 | 3.1.8.6 |
| 3.1.9.1 | 3.1.9.2 | 3.1.9.3 | 3.1.9.4 | 3.1.9.5 | 3.1.9.6 | 3.2.1.1 | 3.2.1.2 | 3.2.1.3 | 3.2.1.4 |
| 3.2.1.5 | 3.2.1.6 | 3.2.2.1 | 3.2.2.2 | 3.2.2.3 | 3.2.2.4 | 3.2.2.5 | 3.2.2.6 | 3.2.3.1 | 3.2.3.2 |
| 3.2.3.3 | 3.2.3.4 | 3.2.3.5 | 3.2.3.6 | 3.2.4.1 | 3.2.4.2 | 3.2.4.3 | 3.2.4.4 | 3.2.4.5 | 3.2.4.6 |
| 3.2.5.1 | 3.2.5.2 | 3.2.5.3 | 3.2.5.4 | 3.2.5.5 | 3.2.5.6 | 3.2.6.1 | 3.2.6.2 | 3.2.6.3 | 3.2.6.4 |
| 3.2.6.5 | 3.2.6.6 | 3.2.7.1 | 3.2.7.2 | 3.2.7.3 | 3.2.7.4 | 3.2.7.5 | 3.2.7.6 | 3.2.8.1 | 3.2.8.2 |
| 3.2.8.3 | 3.2.8.4 | 3.2.8.5 | 3.2.8.6 | 3.2.9.1 | 3.2.9.2 | 3.2.9.3 | 3.2.9.4 | 3.2.9.5 | 3.2.9.6 |
| 3.3.1.1 | 3.3.1.2 | 3.3.1.3 | 3.3.1.4 | 3.3.1.5 | 3.3.1.6 | 3.3.2.1 | 3.3.2.2 | 3.3.2.3 | 3.3.2.4 |
| 3.3.2.5 | 3.3.2.6 | 3.3.3.1 | 3.3.3.2 | 3.3.3.3 | 3.3.3.4 | 3.3.3.5 | 3.3.3.6 | 3.3.4.1 | 3.3.4.2 |
| 3.3.4.3 | 3.3.4.4 | 3.3.4.5 | 3.3.4.6 | 3.3.5.1 | 3.3.5.2 | 3.3.5.3 | 3.3.5.4 | 3.3.5.5 | 3.3.5.6 |
| 3.3.6.1 | 3.3.6.2 | 3.3.6.3 | 3.3.6.4 | 3.3.6.5 | 3.3.6.6 | 3.3.7.1 | 3.3.7.2 | 3.3.7.3 | 3.3.7.4 |
| 3.3.7.5 | 3.3.7.6 | 3.3.8.1 | 3.3.8.2 | 3.3.8.3 | 3.3.8.4 | 3.3.8.5 | 3.3.8.6 | 3.3.9.1 | 3.3.9.2 |
| 3.3.9.3 | 3.3.9.4 | 3.3.9.5 | 3.3.9.6 | 3.4.1.1 | 3.4.1.2 | 3.4.1.3 | 3.4.1.4 | 3.4.1.5 | 3.4.1.6 |
| 3.4.2.1 | 3.4.2.2 | 3.4.2.3 | 3.4.2.4 | 3.4.2.5 | 3.4.2.6 | 3.4.3.1 | 3.4.3.2 | 3.4.3.3 | 3.4.3.4 |
| 3.4.3.5 | 3.4.3.6 | 3.4.4.1 | 3.4.4.2 | 3.4.4.3 | 3.4.4.4 | 3.4.4.5 | 3.4.4.6 | 3.4.5.1 | 3.4.5.2 |
| 3.4.5.3 | 3.4.5.4 | 3.4.5.5 | 3.4.5.6 | 3.4.6.1 | 3.4.6.2 | 3.4.6.3 | 3.4.6.4 | 3.4.6.5 | 3.4.6.6 |
| 3.4.7.1 | 3.4.7.2 | 3.4.7.3 | 3.4.7.4 | 3.4.7.5 | 3.4.7.6 | 3.4.8.1 | 3.4.8.2 | 3.4.8.3 | 3.4.8.4 |
| 3.4.8.5 | 3.4.8.6 | 3.4.9.1 | 3.4.9.2 | 3.4.93 | 3.4.9.4 | 3.4.9.5 | 3.4.9.6 | 3.5.1.1 | 3.5.1.2 |
| 3.5.1.3 | 3.5.1.4 | 3.5.1.5 | 3.5.1.6 | 3.5.2.1 | 3.5.2.2 | 3.5.2.3 | 3.5.2.4 | 3.5.2.5 | 3.5.2.6 |
| 3.5.3.1 | 3.5.3.2 | 3.5.3.3 | 3.5.3.4 | 3.5.3.5 | 3.5.3.6 | 3.5.4.1 | 3.5.4.2 | 3.5.4.3 | 3.5.4.4 |
| 3.5.4.5 | 3.5.4.6 | 3.5.5.1 | 3.5.5.2 | 3.5.5.3 | 3.5.5.4 | 3.5.5.5 | 3.5.5.6 | 3.5.6.1 | 3.5.6.2 |
| 3.5.6.3 | 3.5.6.4 | 3.5.6.5 | 3.5.6.6 | 3.5.7.1 | 3.5.7.2 | 3.5.7.3 | 3.5.7.4 | 3.5.7.5 | 3.5.7.6 |
| 3.5.8.1 | 3.5.8.2 | 3.5.8.3 | 3.5.8.4 | 3.5.8.5 | 3.5.8.6 | 3.5.9.1 | 3.5.9.2 | 3.5.9.3 | 3.5.9.4 |
| 3.5.9.5 | 3.5.9.6 | 3.6.1.1 | 3.6.1.2 | 3.6.1.3 | 3.6.1.4 | 3.6.1.5 | 3.6.1.6 | 3.6.2.1 | 3.6.2.2 |
| 3.6.2.3 | 3.6.2.4 | 3.6.2.5 | 3.6.2.6 | 3.6.3.1 | 3.6.3.2 | 3.6.3.3 | 3.6.3.4 | 3.6.3.5 | 3.6.3.6 |
| 3.6.4.1 | 3.6.4.2 | 3.6.4.3 | 3.6.4.4 | 3.6.4.5 | 3.6.4.6 | 3.6.5.1 | 3.6.5.2 | 3.6.5.3 | 3.6.5.4 |
| 3.6.5.5 | 3.6.5.6 | 3.6.6.1 | 3.6.6.2 | 3.6.6.3 | 3.6.6.4 | 3.6.6.5 | 3.6.6.6 | 3.6.7.1 | 3.6.7.2 |
| 3.6.7.3 | 3.6.7.4 | 3.6.7.5 | 3.6.7.6 | 3.6.8.1 | 3.6.8.2 | 3.6.8.3 | 3.6.8.4 | 3.6.8.5 | 3.6.8.6 |
| 3.6.9.1 | 3.6.9.2 | 3.6.9.3 | 3.6.9.4 | 3.6.9.5 | 3.6.9.6 | 3.7.1.1 | 3.7.1.2 | 3.7.1.3 | 3.7.1.4 |
| 3.7.1.5 | 3.7.1.6 | 3.7.2.1 | 3.7.2.2 | 3.7.2.3 | 3.7.2.4 | 3.7.2.5 | 3.7.2.6 | 3.7.3.1 | 3.7.3.2 |
| 3.7.3.3 | 3.7.3.4 | 3.7.3.5 | 3.7.3.6 | 3.7.4.1 | 3.7.4.2 | 3.7.4.3 | 3.7.4.4 | 3.7.4.5 | 3.7.4.6 |
| 3.7.5.1 | 3.7.5.2 | 3.7.5.3 | 3.7.5.4 | 3.7.5.5 | 3.7.5.6 | 3.7.6.1 | 3.7.6.2 | 3.7.6.3 | 3.7.6.4 |
| 3.7.6.5 | 3.7.6.6 | 3.7.7.1 | 3.7.7.2 | 3.7.7.3 | 3.7.7.4 | 3.7.7.5 | 3.7.7.6 | 3.7.8.1 | 3.7.8.2 |
| 3.7.8.3 | 3.7.8.4 | 3.7.8.5 | 3.7.8.6 | 3.7.9.1 | 3.7.9.2 | 3.7.9.3 | 3.7.9.4 | 3.7.9.5 | 3.7.9.6 |
| 3.8.1.1 | 3.8.1.2 | 3.8.1.3 | 3.8.1.4 | 3.8.1.5 | 3.8.1.6 | 3.8.2.1 | 3.8.2.2 | 3.8.2.3 | 3.8.2.4 |
| 3.8.2.5 | 3.8.2.6 | 3.8.3.1 | 3.8.3.2 | 3.8.3.3 | 3.8.3.4 | 3.8.3.5 | 3.8.3.6 | 3.8.4.1 | 3.8.4.2 |
| 3.8.4.3 | 3.8.4.4 | 3.8.4.5 | 3.8.4.6 | 3.8.5.1 | 3.8.5.2 | 3.8.5.3 | 3.8.5.4 | 3.8.5.5 | 3.8.5.6 |
| 3.8.6.1 | 3.8.6.2 | 3.8.6.3 | 3.8.6.4 | 3.8.6.5 | 3.8.6.6 | 3.8.7.1 | 3.8.7.2 | 3.8.7.3 | 3.8.7.4 |
| 3.8.7.5 | 3.8.7.6 | 3.8.8.1 | 3.8.8.2 | 3.8.8.3 | 3.8.8.4 | 3.8.8.5 | 3.8.8.6 | 3.8.9.1 | 3.8.9.2 |
| 3.8.9.3 | 3.8.9.4 | 3.8.9.5 | 3.8.9.6 | 3.9.1.1 | 3.9.1.2 | 3.9.1.3 | 3.9.1.4 | 3.9.1.5 | 3.9.1.6 |
| 3.9.2.1 | 3.9.2.2 | 3.9.2.3 | 3.9.2.4 | 3.9.2.5 | 3.9.2.6 | 3.9.3.1 | 3.9.3.2 | 3.9.3.3 | 3.9.3.4 |
| 3.9.3.5 | 3.9.3.6 | 3.9.4.1 | 3.9.4.2 | 3.9.4.3 | 3.9.4.4 | 3.9.4.5 | 3.9.4.6 | 3.9.5.1 | 3.9.5.2 |
| 3.9.5.3 | 3.9.5.4 | 3.9.5.5 | 3.9.5.6 | 3.9.6.1 | 3.9.6.2 | 3.9.6.3 | 3.9.6.4 | 3.9.6.5 | 3.9.6.6 |
| 3.9.7.1 | 3.9.7.2 | 3.9.7.3 | 3.9.7.4 | 3.9.7.5 | 3.9.7.6 | 3.9.8.1 | 3.9.8.2 | 3.9.8.3 | 3.9.8.4 |
| 3.9.8.5 | 3.9.8.6 | 3.9.9.1 | 3.9.9.2 | 3.9.9.3 | 3.9.9.4 | 3.9.9.5 | 3.9.9.6 | 4.1.1.1 | 4.1.1.2 |
| 4.1.1.3 | 4.1.1.4 | 4.1.1.5 | 4.1.1.6 | 4.1.2.1 | 4.1.2.2 | 4.1.2.3 | 4.1.2.4 | 4.1.2.5 | 4.1.2.6 |
| 4.1.3.1 | 4.1.3.2 | 4.1.3.3 | 4.1.3.4 | 4.1.3.5 | 4.1.3.6 | 4.1.4.1 | 4.1.4.2 | 4.1.4.3 | 4.1.4.4 |
| 4.1.4.5 | 4.1.4.6 | 4.1.5.1 | 4.1.5.2 | 4.1.5.3 | 4.1.5.4 | 4.1.5.5 | 4.1.5.6 | 4.1.6.1 | 4.1.6.2 |
| 4.1.6.3 | 4.1.6.4 | 4.1.6.5 | 4.1.6.6 | 4.1.7.1 | 4.1.7.2 | 4.1.7.3 | 4.1.7.4 | 4.1.7.5 | 4.1.7.6 |
| 4.1.8.1 | 4.1.8.2 | 4.1.8.3 | 4.1.8.4 | 4.1.8.5 | 4.1.8.6 | 4.1.9.1 | 4.1.9.2 | 4.1.9.3 | 4.1.9.4 |
| 4.1.9.5 | 4.1.9.6 | 4.2.1.1 | 4.2.1.2 | 4.2.1.3 | 4.2.1.4 | 4.2.1.5 | 4.2.1.6 | 4.2.2.1 | 4.2.2.2 |
| 4.2.2.3 | 4.2.2.4 | 4.2.2.5 | 4.2.2.6 | 4.2.3.1 | 4.2.3.2 | 4.2.3.3 | 4.2.3.4 | 4.2.3.5 | 4.2.3.6 |
| 4.2.4.1 | 4.2.4.2 | 4.2.4.3 | 4.2.4.4 | 4.2.4.5 | 4.2.4.6 | 4.2.5.1 | 4.2.5.2 | 4.2.5.3 | 4.2.5.4 |
| 4.2.5.5 | 4.2.5.6 | 4.2.6.1 | 4.2.6.2 | 4.2.6.3 | 4.2.6.4 | 4.2.6.5 | 4.2.6.6 | 4.2.7.1 | 4.2.7.2 |
| 4.2.7.3 | 4.2.7.4 | 4.2.7.5 | 4.2.7.6 | 4.2.8.1 | 4.2.8.2 | 4.2.8.3 | 4.2.8.4 | 4.2.8.5 | 4.2.8.6 |
| 4.2.9.1 | 4.2.9.2 | 4.2.9.3 | 4.2.9.4 | 4.2.9.5 | 4.2.9.6 | 4.3.1.1 | 4.3.1.2 | 4.3.1.3 | 4.3.1.4 |
| 4.3.1.5 | 4.3.1.6 | 4.3.2.1 | 4.3.2.2 | 4.3.2.3 | 4.3.2.4 | 4.3.2.5 | 4.3.2.6 | 4.3.3.1 | 4.3.3.2 |
| 4.3.3.3 | 4.3.3.4 | 4.3.3.5 | 4.3.3.6 | 4.3.4.1 | 4.3.4.2 | 4.3.4.3 | 4.3.4.4 | 4.3.4.5 | 4.3.4.6 |
| 4.3.5.1 | 4.3.5.2 | 4.3.5.3 | 4.3.5.4 | 4.3.5.5 | 4.3.5.6 | 4.3.6.1 | 4.3.6.2 | 4.3.6.3 | 4.3.6.4 |
| 4.3.6.5 | 4.3.6.6 | 4.3.7.1 | 4.3.7.2 | 4.3.7.3 | 4.3.7.4 | 4.3.7.5 | 4.3.7.6 | 4.3.8.1 | 4.3.8.2 |
| 4.3.8.3 | 4.3.8.4 | 4.3.8.5 | 4.3.8.6 | 4.3.9.1 | 4.3.9.2 | 4.3.9.3 | 4.3.9.4 | 4.3.9.5 | 4.3.9.6 |
| 4.4.1.1 | 4.4.1.2 | 4.4.1.3 | 4.4.1.4 | 4.4.1.5 | 4.4.1.6 | 4.4.2.1 | 4.4.2.2 | 4.4.2.3 | 4.4.2.4 |
| 4.4.2.5 | 4.4.2.6 | 4.4.3.1 | 4.4.3.2 | 4.4.3.3 | 4.4.3.4 | 4.4.3.5 | 4.4.3.6 | 4.4.4.1 | 4.4.4.2 |
| 4.4.4.3 | 4.4.4.4 | 4.4.4.5 | 4.4.4.6 | 4.4.5.1 | 4.4.5.2 | 4.4.5.3 | 4.4.5.4 | 4.4.5.5 | 4.4.5.6 |
| 4.4.6.1 | 4.4.6.2 | 4.4.6.3 | 4.4.6.4 | 4.4.6.5 | 4.4.6.6 | 4.4.7.1 | 4.4.7.2 | 4.4.7.3 | 4.4.7.4 |
| 4.4.7.5 | 4.4.7.6 | 4.4.8.1 | 4.4.8.2 | 4.4.8.3 | 4.4.8.4 | 4.4.8.5 | 4.4.8.6 | 4.4.9.1 | 4.4.9.2 |
| 4.4.9.3 | 4.4.9.4 | 4.4.9.5 | 4.4.9.6 | 4.5.1.1 | 4.5.1.2 | 4.5.1.3 | 4.5.1.4 | 4.5.1.5 | 4.5.1.6 |
| 4.5.2.1 | 4.5.2.2 | 4.5.2.3 | 4.5.2.4 | 4.5.2.5 | 4.5.2.6 | 4.5.3.1 | 4.5.3.2 | 4.5.3.3 | 4.5.3.4 |
| 4.5.3.5 | 4.5.3.6 | 4.5.4.1 | 4.5.4.2 | 4.5.4.3 | 4.5.4.4 | 4.5.4.5 | 4.5.4.6 | 4.5.5.1 | 4.5.5.2 |
| 4.5.5.3 | 4.5.5.4 | 4.5.5.5 | 4.5.5.6 | 4.5.6.1 | 4.5.6.2 | 4.5.6.3 | 4.5.6.4 | 4.5.6.5 | 4.5.6.6 |
| 4.5.7.1 | 4.5.7.2 | 4.5.7.3 | 4.5.7.4 | 4.5.7.5 | 4.5.7.6 | 4.5.8.1 | 4.5.8.2 | 4.5.8.3 | 4.5.8.4 |
| 4.5.8.5 | 4.5.8.6 | 4.5.9.1 | 4.5.9.2 | 4.5.9.3 | 4.5.9.4 | 4.5.9.5 | 4.5.9.6 | 4.6.1.1 | 4.6.1.2 |
| 4.6.1.3 | 4.6.1.4 | 4.6.1.5 | 4.6.1.6 | 4.6.2.1 | 4.6.2.2 | 4.6.2.3 | 4.6.2.4 | 4.6.2.5 | 4.6.2.6 |
| 4.6.3.1 | 4.6.3.2 | 4.6.3.3 | 4.6.3.4 | 4.6.3.5 | 4.6.3.6 | 4.6.4.1 | 4.6.4.2 | 4.6.4.3 | 4.6.4.4 |
| 4.6.4.5 | 4.6.4.6 | 4.6.5.1 | 4.6.5.2 | 4.6.5.3 | 4.6.5.4 | 4.6.5.5 | 4.6.5.6 | 4.6.6.1 | 4.6.6.2 |

TABLE 1-continued

| | | | | | | | | | |
|---|---|---|---|---|---|---|---|---|---|
| 4.6.6.3 | 4.6.6.4 | 4.6.6.5 | 4.6.6.6 | 4.6.7.1 | 4.6.7.2 | 4.6.7.3 | 4.6.7.4 | 4.6.7.5 | 4.6.7.6 |
| 4.6.8.1 | 4.6.8.2 | 4.6.8.3 | 4.6.8.4 | 4.6.8.5 | 4.6.8.6 | 4.6.9.1 | 4.6.9.2 | 4.6.9.3 | 4.6.9.4 |
| 4.6.9.5 | 4.6.9.6 | 4.7.1.1 | 4.7.1.2 | 4.7.1.3 | 4.7.1.4 | 4.7.1.5 | 4.7.1.6 | 4.7.2.1 | 4.7.2.2 |
| 4.7.2.3 | 4.7.2.4 | 4.7.2.5 | 4.7.2.6 | 4.7.3.1 | 4.7.3.2 | 4.7.3.3 | 4.7.3.4 | 4.7.3.5 | 4.7.3.6 |
| 4.7.4.1 | 4.7.4.2 | 4.7.4.3 | 4.7.4.4 | 4.7.4.5 | 4.7.4.6 | 4.7.5.1 | 4.7.5.2 | 4.7.5.3 | 4.7.5.4 |
| 4.7.5.5 | 4.7.5.6 | 4.7.6.1 | 4.7.6.2 | 4.7.6.3 | 4.7.6.4 | 4.7.6.5 | 4.7.6.6 | 4.7.7.1 | 4.7.7.2 |
| 4.7.7.3 | 4.7.7.4 | 4.7.7.5 | 4.7.7.6 | 4.7.8.1 | 4.7.8.2 | 4.7.8.3 | 4.7.8.4 | 4.7.8.5 | 4.7.8.6 |
| 4.7.9.1 | 4.7.9.2 | 4.7.9.3 | 4.7.9.4 | 4.7.9.5 | 4.7.9.6 | 4.8.1.1 | 4.8.1.2 | 4.8.1.3 | 4.8.1.4 |
| 4.8.1.5 | 4.8.1.6 | 4.8.2.1 | 4.8.2.2 | 4.8.2.3 | 4.8.2.4 | 4.8.2.5 | 4.8.2.6 | 4.8.3.1 | 4.8.3.2 |
| 4.8.3.3 | 4.8.3.4 | 4.8.3.5 | 4.8.3.6 | 4.8.4.1 | 4.8.4.2 | 4.8.4.3 | 4.8.4.4 | 4.8.4.5 | 4.8.4.6 |
| 4.8.5.1 | 4.8.5.2 | 4.8.5.3 | 4.8.5.4 | 4.8.5.5 | 4.8.5.6 | 4.8.6.1 | 4.8.6.2 | 4.8.6.3 | 4.8.6.4 |
| 4.8.6.5 | 4.8.6.6 | 4.8.7.1 | 4.8.7.2 | 4.8.7.3 | 4.8.7.4 | 4.8.7.5 | 4.8.7.6 | 4.8.8.1 | 4.8.8.2 |
| 4.8.8.3 | 4.8.8.4 | 4.8.8.5 | 4.8.8.6 | 4.8.9.1 | 4.8.9.2 | 4.8.9.3 | 4.8.9.4 | 4.8.9.5 | 4.8.9.6 |
| 4.9.1.1 | 4.9.1.2 | 4.9.1.3 | 4.9.1.4 | 4.9.1.5 | 4.9.1.6 | 4.9.2.1 | 4.9.2.2 | 4.9.2.3 | 4.9.2.4 |
| 4.9.2.5 | 4.9.2.6 | 4.9.3.1 | 4.9.3.2 | 4.9.3.3 | 4.9.3.4 | 4.9.3.5 | 4.9.3.6 | 4.9.4.1 | 4.9.4.2 |
| 4.9.4.3 | 4.9.4.4 | 4.9.4.5 | 4.9.4.6 | 4.9.5.1 | 4.9.5.2 | 4.9.5.3 | 4.9.5.4 | 4.9.5.5 | 4.9.5.6 |
| 4.9.6.1 | 4.9.6.2 | 4.9.6.3 | 4.9.6.4 | 4.9.6.5 | 4.9.6.6 | 4.9.7.1 | 4.9.7.2 | 4.9.7.3 | 4.9.7.4 |
| 4.9.7.5 | 4.9.7.6 | 4.9.8.1 | 4.9.8.2 | 4.9.8.3 | 4.9.8.4 | 4.9.8.5 | 4.9.8.6 | 4.9.9.1 | 4.9.9.2 |
| 4.9.9.3 | 4.9.9.4 | 4.9.9.5 | 4.9.9.6 | 5.1.1.1 | 5.1.1.2 | 5.1.1.3 | 5.1.1.4 | 5.1.1.5 | 5.1.1.6 |
| 5.1.2.1 | 5.1.2.2 | 5.1.2.3 | 5.1.2.4 | 5.1.2.5 | 5.1.2.6 | 5.1.3.1 | 5.1.3.2 | 5.1.3.3 | 5.1.3.4 |
| 5.1.3.5 | 5.1.3.6 | 5.1.4.1 | 5.1.4.2 | 5.1.4.3 | 5.1.4.4 | 5.1.4.5 | 5.1.4.6 | 5.1.5.1 | 5.1.5.2 |
| 5.1.5.3 | 5.1.5.4 | 5.1.5.5 | 5.1.5.6 | 5.1.6.1 | 5.1.6.2 | 5.1.6.3 | 5.1.6.4 | 5.1.6.5 | 5.1.6.6 |
| 5.1.7.1 | 5.1.7.2 | 5.1.7.3 | 5.1.7.4 | 5.1.7.5 | 5.1.7.6 | 5.1.8.1 | 5.1.8.2 | 5.1.8.3 | 5.1.8.4 |
| 5.1.8.5 | 5.1.8.6 | 5.1.9.1 | 5.1.9.2 | 5.1.9.3 | 5.1.9.4 | 5.1.9.5 | 5.1.9.6 | 5.2.1.1 | 5.2.1.2 |
| 5.2.1.3 | 5.2.1.4 | 5.2.1.5 | 5.2.1.6 | 5.2.2.1 | 5.2.2.2 | 5.2.2.3 | 5.2.2.4 | 5.2.2.5 | 5.2.2.6 |
| 5.2.3.1 | 5.2.3.2 | 5.2.3.3 | 5.2.3.4 | 5.2.3.5 | 5.2.3.6 | 5.2.4.1 | 5.2.4.2 | 5.2.4.3 | 5.2.4.4 |
| 5.2.4.5 | 5.2.4.6 | 5.2.5.1 | 5.2.5.2 | 5.2.5.3 | 5.2.5.4 | 5.2.5.5 | 5.2.5.6 | 5.2.6.1 | 5.2.6.2 |
| 5.2.6.3 | 5.2.6.4 | 5.2.6.5 | 5.2.6.6 | 5.2.7.1 | 5.2.7.2 | 5.2.7.3 | 5.2.7.4 | 5.2.7.5 | 5.2.7.6 |
| 5.2.8.1 | 5.2.8.2 | 5.2.8.3 | 5.2.8.4 | 5.2.8.5 | 5.2.8.6 | 5.2.9.1 | 5.2.9.2 | 5.2.9.3 | 5.2.9.4 |
| 5.2.9.5 | 5.2.9.6 | 5.3.1.1 | 5.3.1.2 | 5.3.1.3 | 5.3.1.4 | 5.3.1.5 | 5.3.1.6 | 5.3.2.1 | 5.3.2.2 |
| 5.3.2.3 | 5.3.2.4 | 5.3.2.5 | 5.3.2.6 | 5.3.3.1 | 5.3.3.2 | 5.3.3.3 | 5.3.3.4 | 5.3.3.5 | 5.3.3.6 |
| 5.3.4.1 | 5.3.4.2 | 5.3.4.3 | 5.3.4.4 | 5.3.4.5 | 5.3.4.6 | 5.3.5.1 | 5.3.5.2 | 5.3.5.3 | 5.3.5.4 |
| 5.3.5.5 | 5.3.5.6 | 5.3.6.1 | 5.3.6.2 | 5.3.6.3 | 5.3.6.4 | 5.3.6.5 | 5.3.6.6 | 5.3.7.1 | 5.3.7.2 |
| 5.3.7.3 | 5.3.7.4 | 5.3.7.5 | 5.3.7.6 | 5.3.8.1 | 5.3.8.2 | 5.3.8.3 | 5.3.8.4 | 5.3.8.5 | 5.3.8.6 |
| 5.3.9.1 | 5.3.9.2 | 5.3.9.3 | 5.3.9.4 | 5.3.9.5 | 5.3.9.6 | 5.4.1.1 | 5.4.1.2 | 5.4.1.3 | 5.4.1.4 |
| 5.4.1.5 | 5.4.1.6 | 5.4.2.1 | 5.4.2.2 | 5.4.2.3 | 5.4.2.4 | 5.4.2.5 | 5.4.2.6 | 5.4.3.1 | 5.4.3.2 |
| 5.4.3.3 | 5.4.3.4 | 5.4.3.5 | 5.4.3.6 | 5.4.4.1 | 5.4.4.2 | 5.4.4.3 | 5.4.4.4 | 5.4.4.5 | 5.4.4.6 |
| 5.4.5.1 | 5.4.5.2 | 5.4.5.3 | 5.4.5.4 | 5.4.5.5 | 5.4.5.6 | 5.4.6.1 | 5.4.6.2 | 5.4.6.3 | 5.4.6.4 |
| 5.4.6.5 | 5.4.6.6 | 5.4.7.1 | 5.4.7.2 | 5.4.7.3 | 5.4.7.4 | 5.4.7.5 | 5.4.7.6 | 5.4.8.1 | 5.4.8.2 |
| 5.4.8.3 | 5.4.8.4 | 5.4.8.5 | 5.4.8.6 | 5.4.9.1 | 5.4.9.2 | 5.4.9.3 | 5.4.9.4 | 5.4.9.5 | 5.4.9.6 |
| 5.5.1.1 | 5.5.1.2 | 5.5.1.3 | 5.5.1.4 | 5.5.1.5 | 5.5.1.6 | 5.5.2.1 | 5.5.2.2 | 5.5.2.3 | 5.5.2.4 |
| 5.5.2.5 | 5.5.2.6 | 5.5.3.1 | 5.5.3.2 | 5.5.3.3 | 5.5.3.4 | 5.5.3.5 | 5.5.3.6 | 5.5.4.1 | 5.5.4.2 |
| 5.5.4.3 | 5.5.4.4 | 5.5.4.5 | 5.5.4.6 | 5.5.5.1 | 5.5.5.2 | 5.5.5.3 | 5.5.5.4 | 5.5.5.5 | 5.5.5.6 |
| 5.5.6.1 | 5.5.6.2 | 5.5.6.3 | 5.5.6.4 | 5.5.6.5 | 5.5.6.6 | 5.5.7.1 | 5.5.7.2 | 5.5.7.3 | 5.5.7.4 |
| 5.5.7.5 | 5.5.7.6 | 5.5.8.1 | 5.5.8.2 | 5.5.8.3 | 5.5.8.4 | 5.5.8.5 | 5.5.8.6 | 5.5.9.1 | 5.5.9.2 |
| 5.5.9.3 | 5.5.9.4 | 5.5.9.5 | 5.5.9.6 | 5.6.1.1 | 5.6.1.2 | 5.6.1.3 | 5.6.1.4 | 5.6.1.5 | 5.6.1.6 |
| 5.6.2.1 | 5.6.2.2 | 5.6.2.3 | 5.6.2.4 | 5.6.2.5 | 5.6.2.6 | 5.6.3.1 | 5.6.3.2 | 5.6.3.3 | 5.6.3.4 |
| 5.6.3.5 | 5.6.3.6 | 5.6.4.1 | 5.6.4.2 | 5.6.4.3 | 5.6.4.4 | 5.6.4.5 | 5.6.4.6 | 5.6.5.1 | 5.6.5.2 |
| 5.6.5.3 | 5.6.5.4 | 5.6.5.5 | 5.6.5.6 | 5.6.6.1 | 5.6.6.2 | 5.6.6.3 | 5.6.6.4 | 5.6.6.5 | 5.6.6.6 |
| 5.6.7.1 | 5.6.7.2 | 5.6.7.3 | 5.6.7.4 | 5.6.7.5 | 5.6.7.6 | 5.6.8.1 | 5.6.8.2 | 5.6.8.3 | 5.6.8.4 |
| 5.6.8.5 | 5.6.8.6 | 5.6.9.1 | 5.6.9.2 | 5.6.9.3 | 5.6.9.4 | 5.6.9.5 | 5.6.9.6 | 5.7.1.1 | 5.7.1.2 |
| 5.7.1.3 | 5.7.1.4 | 5.7.1.5 | 5.7.1.6 | 5.7.2.1 | 5.7.2.2 | 5.7.2.3 | 5.7.2.4 | 5.7.2.5 | 5.7.2.6 |
| 5.7.3.1 | 5.7.3.2 | 5.7.3.3 | 5.7.3.4 | 5.7.3.5 | 5.7.3.6 | 5.7.4.1 | 5.7.4.2 | 5.7.4.3 | 5.7.4.4 |
| 5.7.4.5 | 5.7.4.6 | 5.7.5.1 | 5.7.5.2 | 5.7.5.3 | 5.7.5.4 | 5.7.5.5 | 5.7.5.6 | 5.7.6.1 | 5.7.6.2 |
| 5.7.6.3 | 5.7.6.4 | 5.7.6.5 | 5.7.6.6 | 5.7.7.1 | 5.7.7.2 | 5.7.7.3 | 5.7.7.4 | 5.7.7.5 | 5.7.7.6 |
| 5.7.8.1 | 5.7.8.2 | 5.7.8.3 | 5.7.8.4 | 5.7.8.5 | 5.7.8.6 | 5.7.9.1 | 5.7.9.2 | 5.7.9.3 | 5.7.9.4 |
| 5.7.9.5 | 5.7.9.6 | 5.8.1.1 | 5.8.1.2 | 5.8.1.3 | 5.8.1.4 | 5.8.1.5 | 5.8.1.6 | 5.8.2.1 | 5.8.2.2 |
| 5.8.2.3 | 5.8.2.4 | 5.8.2.5 | 5.8.2.6 | 5.8.3.1 | 5.8.3.2 | 5.8.3.3 | 5.8.3.4 | 5.8.3.5 | 5.8.3.6 |
| 5.8.4.1 | 5.8.4.2 | 5.8.4.3 | 5.8.4.4 | 5.8.4.5 | 5.8.4.6 | 5.8.5.1 | 5.8.5.2 | 5.8.5.3 | 5.8.5.4 |
| 5.8.5.5 | 5.8.5.6 | 5.8.6.1 | 5.8.6.2 | 5.8.6.3 | 5.8.6.4 | 5.8.6.5 | 5.8.6.6 | 5.8.7.1 | 5.8.7.2 |
| 5.8.7.3 | 5.8.7.4 | 5.8.7.5 | 5.8.7.6 | 5.8.8.1 | 5.8.8.2 | 5.8.8.3 | 5.8.8.4 | 5.8.8.5 | 5.8.8.6 |
| 5.8.9.1 | 5.8.9.2 | 5.8.9.3 | 5.8.9.4 | 5.8.9.5 | 5.8.9.6 | 5.9.1.1 | 5.9.1.2 | 5.9.1.3 | 5.9.1.4 |
| 5.9.1.5 | 5.9.1.6 | 5.9.2.1 | 5.9.2.2 | 5.9.2.3 | 5.9.2.4 | 5.9.2.5 | 5.9.2.6 | 5.9.3.1 | 5.9.3.2 |
| 5.9.3.3 | 5.9.3.4 | 5.9.3.5 | 5.9.3.6 | 5.9.4.1 | 5.9.4.2 | 5.9.4.3 | 5.9.4.4 | 5.9.4.5 | 5.9.4.6 |
| 5.9.5.1 | 5.9.5.2 | 5.9.5.3 | 5.9.5.4 | 5.9.5.5 | 5.9.5.6 | 5.9.6.1 | 5.9.6.2 | 5.9.6.3 | 5.9.6.4 |
| 5.9.6.5 | 5.9.6.6 | 5.9.7.1 | 5.9.7.2 | 5.9.7.3 | 5.9.7.4 | 5.9.7.5 | 5.9.7.6 | 5.9.8.1 | 5.9.8.2 |
| 5.9.8.3 | 5.9.8.4 | 5.9.8.5 | 5.9.8.6 | 5.9.9.1 | 5.9.9.2 | 5.9.9.3 | 5.9.9.4 | 5.9.9.5 | 5.9.9.6 |
| 6.1.1.1 | 6.1.1.2 | 6.1.1.3 | 6.1.1.4 | 6.1.1.5 | 6.1.1.6 | 6.1.2.1 | 6.1.2.2 | 6.1.2.3 | 6.1.2.4 |
| 6.1.2.5 | 6.1.2.6 | 6.1.3.1 | 6.1.3.2 | 6.1.3.3 | 6.1.3.4 | 6.1.3.5 | 6.1.3.6 | 6.1.4.1 | 6.1.4.2 |
| 6.1.4.3 | 6.1.4.4 | 6.1.4.5 | 6.1.4.6 | 6.1.5.1 | 6.1.5.2 | 6.1.5.3 | 6.1.5.4 | 6.1.5.5 | 6.1.5.6 |
| 6.1.6.1 | 6.1.6.2 | 6.1.6.3 | 6.1.6.4 | 6.1.6.5 | 6.1.6.6 | 6.1.7.1 | 6.1.7.2 | 6.1.7.3 | 6.1.7.4 |
| 6.1.7.5 | 6.1.7.6 | 6.1.8.1 | 6.1.8.2 | 6.1.8.3 | 6.1.8.4 | 6.1.8.5 | 6.1.8.6 | 6.1.9.1 | 6.1.9.2 |
| 6.1.9.3 | 6.1.9.4 | 6.1.9.5 | 6.1.9.6 | 6.2.1.1 | 6.2.1.2 | 6.2.1.3 | 6.2.1.4 | 6.2.1.5 | 6.2.1.6 |
| 6.2.2.1 | 6.2.2.2 | 6.2.2.3 | 6.2.2.4 | 6.2.2.5 | 6.2.2.6 | 6.2.3.1 | 6.2.3.2 | 6.2.3.3 | 6.2.3.4 |
| 6.2.3.5 | 6.2.3.6 | 6.2.4.1 | 6.2.4.2 | 6.2.4.3 | 6.2.4.4 | 6.2.4.5 | 6.2.4.6 | 6.2.5.1 | 6.2.5.2 |
| 6.2.5.3 | 6.2.5.4 | 6.2.5.5 | 6.2.5.6 | 6.2.6.1 | 6.2.6.2 | 6.2.6.3 | 6.2.6.4 | 6.2.6.5 | 6.2.6.6 |
| 6.2.7.1 | 6.2.7.2 | 6.2.7.3 | 6.2.7.4 | 6.2.7.5 | 6.2.7.6 | 6.2.8.1 | 6.2.8.2 | 6.2.8.3 | 6.2.8.4 |
| 6.2.8.5 | 6.2.8.6 | 6.2.9.1 | 6.2.9.2 | 6.2.9.3 | 6.2.9.4 | 6.2.9.5 | 6.2.9.6 | 6.3.1.1 | 6.3.1.2 |
| 6.3.1.3 | 6.3.1.4 | 6.3.1.5 | 6.3.1.6 | 6.3.2.1 | 6.3.2.2 | 6.3.2.3 | 6.3.2.4 | 6.3.2.5 | 6.3.2.6 |

TABLE 1-continued

| | | | | | | | | | |
|---|---|---|---|---|---|---|---|---|---|
| 6.3.3.1 | 6.3.3.2 | 6.3.3.3 | 6.3.3.4 | 6.3.3.5 | 6.3.3.6 | 6.3.4.1 | 6.3.4.2 | 6.3.4.3 | 6.3.4.4 |
| 6.3.4.5 | 6.3.4.6 | 6.3.5.1 | 6.3.5.2 | 6.3.5.3 | 6.3.5.4 | 6.3.5.5 | 6.3.5.6 | 6.3.6.1 | 6.3.6.2 |
| 6.3.6.3 | 6.3.6.4 | 6.3.6.5 | 6.3.6.6 | 6.3.7.1 | 6.3.7.2 | 6.3.7.3 | 6.3.7.4 | 6.3.7.5 | 6.3.7.6 |
| 6.3.8.1 | 6.3.8.2 | 6.3.8.3 | 6.3.8.4 | 6.3.8.5 | 6.3.8.6 | 6.3.9.1 | 6.3.9.2 | 6.3.9.3 | 6.3.9.4 |
| 6.3.9.5 | 6.3.9.6 | 6.4.1.1 | 6.4.1.2 | 6.4.1.3 | 6.4.1.4 | 6.4.1.5 | 6.4.1.6 | 6.4.2.1 | 6.4.2.2 |
| 6.4.2.3 | 6.4.2.4 | 6.4.2.5 | 6.4.2.6 | 6.4.3.1 | 6.4.3.2 | 6.4.3.3 | 6.4.3.4 | 6.4.3.5 | 6.4.3.6 |
| 6.4.4.1 | 6.4.4.2 | 6.4.4.3 | 6.4.4.4 | 6.4.4.5 | 6.4.4.6 | 6.4.5.1 | 6.4.5.2 | 6.4.5.3 | 6.4.5.4 |
| 6.4.5.5 | 6.4.5.6 | 6.4.6.1 | 6.4.6.2 | 6.4.6.3 | 6.4.6.4 | 6.4.6.5 | 6.4.6.6 | 6.4.7.1 | 6.4.7.2 |
| 6.4.7.3 | 6.4.7.4 | 6.4.7.5 | 6.4.7.6 | 6.4.8.1 | 6.4.8.2 | 6.4.8.3 | 6.4.8.4 | 6.4.8.5 | 6.4.8.6 |
| 6.4.9.1 | 6.4.9.2 | 6.4.9.3 | 6.4.9.4 | 6.4.9.5 | 6.4.9.6 | 6.5.1.1 | 6.5.1.2 | 6.5.1.3 | 6.5.1.4 |
| 6.5.1.5 | 6.5.1.6 | 6.5.2.1 | 6.5.2.2 | 6.5.2.3 | 6.5.2.4 | 6.5.2.5 | 6.5.2.6 | 6.5.3.1 | 6.5.3.2 |
| 6.5.3.3 | 6.5.3.4 | 6.5.3.5 | 6.5.3.6 | 6.5.4.1 | 6.5.4.2 | 6.5.4.3 | 6.5.4.4 | 6.5.4.5 | 6.5.4.6 |
| 6.5.5.1 | 6.5.5.2 | 6.5.5.3 | 6.5.5.4 | 6.5.5.5 | 6.5.5.6 | 6.5.6.1 | 6.5.6.2 | 6.5.6.3 | 6.5.6.4 |
| 6.5.6.5 | 6.5.6.6 | 6.5.7.1 | 6.5.7.2 | 6.5.7.3 | 6.5.7.4 | 6.5.7.5 | 6.5.7.6 | 6.5.8.1 | 6.5.8.2 |
| 6.5.8.3 | 6.5.8.4 | 6.5.8.5 | 6.5.8.6 | 6.5.9.1 | 6.5.9.2 | 6.5.9.3 | 6.5.9.4 | 6.5.9.5 | 6.5.9.6 |
| 6.6.1.1 | 6.6.1.2 | 6.6.1.3 | 6.6.1.4 | 6.6.1.5 | 6.6.1.6 | 6.6.2.1 | 6.6.2.2 | 6.6.2.3 | 6.6.2.4 |
| 6.6.2.5 | 6.6.2.6 | 6.6.3.1 | 6.6.3.2 | 6.6.3.3 | 6.6.3.4 | 6.6.3.5 | 6.6.3.6 | 6.6.4.1 | 6.6.4.2 |
| 6.6.4.3 | 6.6.4.4 | 6.6.4.5 | 6.6.4.6 | 6.6.5.1 | 6.6.5.2 | 6.6.5.3 | 6.6.5.4 | 6.6.5.5 | 6.6.5.6 |
| 6.6.6.1 | 6.6.6.2 | 6.6.6.3 | 6.6.6.4 | 6.6.6.5 | 6.6.6.6 | 6.6.7.1 | 6.6.7.2 | 6.6.7.3 | 6.6.7.4 |
| 6.6.7.5 | 6.6.7.6 | 6.6.8.1 | 6.6.8.2 | 6.6.8.3 | 6.6.8.4 | 6.6.8.5 | 6.6.8.6 | 6.6.9.1 | 6.6.9.2 |
| 6.6.9.3 | 6.6.9.4 | 6.6.9.5 | 6.6.9.6 | 6.7.1.1 | 6.7.1.2 | 6.7.1.3 | 6.7.1.4 | 6.7.1.5 | 6.7.1.6 |
| 6.7.2.1 | 6.7.2.2 | 6.7.2.3 | 6.7.2.4 | 6.7.2.5 | 6.7.2.6 | 6.7.3.1 | 6.7.3.2 | 6.7.3.3 | 6.7.3.4 |
| 6.7.3.5 | 6.7.3.6 | 6.7.4.1 | 6.7.4.2 | 6.7.4.3 | 6.7.4.4 | 6.7.4.5 | 6.7.4.6 | 6.7.5.1 | 6.7.5.2 |
| 6.7.5.3 | 6.7.5.4 | 6.7.5.5 | 6.7.5.6 | 6.7.6.1 | 6.7.6.2 | 6.7.6.3 | 6.7.6.4 | 6.7.6.5 | 6.7.6.6 |
| 6.7.7.1 | 6.7.7.2 | 6.7.7.3 | 6.7.7.4 | 6.7.7.5 | 6.7.7.6 | 6.7.8.1 | 6.7.8.2 | 6.7.8.3 | 6.7.8.4 |
| 6.7.8.5 | 6.7.8.6 | 6.7.9.1 | 6.7.9.2 | 6.7.9.3 | 6.7.9.4 | 6.7.9.5 | 6.7.9.6 | 6.8.1.1 | 6.8.1.2 |
| 6.8.1.3 | 6.8.1.4 | 6.8.1.5 | 6.8.1.6 | 6.8.2.1 | 6.8.2.2 | 6.8.2.3 | 6.8.2.4 | 6.8.2.5 | 6.8.2.6 |
| 6.8.3.1 | 6.8.3.2 | 6.8.3.3 | 6.8.3.4 | 6.8.3.5 | 6.8.3.6 | 6.8.4.1 | 6.8.4.2 | 6.8.4.3 | 6.8.4.4 |
| 6.8.4.5 | 6.8.4.6 | 6.8.5.1 | 6.8.5.2 | 6.8.5.3 | 6.8.5.4 | 6.8.5.5 | 6.8.5.6 | 6.8.6.1 | 6.8.6.2 |
| 6.8.6.3 | 6.8.6.4 | 6.8.6.5 | 6.8.6.6 | 6.8.7.1 | 6.8.7.2 | 6.8.7.3 | 6.8.7.4 | 6.8.7.5 | 6.8.7.6 |
| 6.8.8.1 | 6.8.8.2 | 6.8.8.3 | 6.8.8.4 | 6.8.8.5 | 6.8.8.6 | 6.8.9.1 | 6.8.9.2 | 6.8.9.3 | 6.8.9.4 |
| 6.8.9.5 | 6.8.9.6 | 6.9.1.1 | 6.9.1.2 | 6.9.1.3 | 6.9.1.4 | 6.9.1.5 | 6.9.1.6 | 6.9.2.1 | 6.9.2.2 |
| 6.9.2.3 | 6.9.2.4 | 6.9.2.5 | 6.9.2.6 | 6.9.3.1 | 6.9.3.2 | 6.9.3.3 | 6.9.3.4 | 6.9.3.5 | 6.9.3.6 |
| 6.9.4.1 | 6.9.4.2 | 6.9.4.3 | 6.9.4.4 | 6.9.4.5 | 6.9.4.6 | 6.9.5.1 | 6.9.5.2 | 6.9.5.3 | 6.9.5.4 |
| 6.9.5.5 | 6.9.5.6 | 6.9.6.1 | 6.9.6.2 | 6.9.6.3 | 6.9.6.4 | 6.9.6.5 | 6.9.6.6 | 6.9.7.1 | 6.9.7.2 |
| 6.9.7.3 | 6.9.7.4 | 6.9.7.5 | 6.9.7.6 | 6.9.8.1 | 6.9.8.2 | 6.9.8.3 | 6.9.8.4 | 6.9.8.5 | 6.9.8.6 |
| 6.9.9.1 | 6.9.9.2 | 6.9.9.3 | 6.9.9.4 | 6.9.9.5 | 6.9.9.6 | 7.1.1.1 | 7.1.1.2 | 7.1.1.3 | 7.1.1.4 |
| 7.1.1.5 | 7.1.1.6 | 7.1.2.1 | 7.1.2.2 | 7.1.2.3 | 7.1.2.4 | 7.1.2.5 | 7.1.2.6 | 7.1.3.1 | 7.1.3.2 |
| 7.1.3.3 | 7.1.3.4 | 7.1.3.5 | 7.1.3.6 | 7.1.4.1 | 7.1.4.2 | 7.1.4.3 | 7.1.4.4 | 7.1.4.5 | 7.1.4.6 |
| 7.1.5.1 | 7.1.5.2 | 7.1.5.3 | 7.1.5.4 | 7.1.5.5 | 7.1.5.6 | 7.1.6.1 | 7.1.6.2 | 7.1.6.3 | 7.1.6.4 |
| 7.1.6.5 | 7.1.6.6 | 7.1.7.1 | 7.1.7.2 | 7.1.7.3 | 7.1.7.4 | 7.1.7.5 | 7.1.7.6 | 7.1.8.1 | 7.1.8.2 |
| 7.1.8.3 | 7.1.8.4 | 7.1.8.5 | 7.1.8.6 | 7.1.9.1 | 7.1.9.2 | 7.1.9.3 | 7.1.9.4 | 7.1.9.5 | 7.1.9.6 |
| 7.2.1.1 | 7.2.1.2 | 7.2.1.3 | 7.2.1.4 | 7.2.1.5 | 7.2.1.6 | 7.2.2.1 | 7.2.2.2 | 7.2.2.3 | 7.2.2.4 |
| 7.2.2.5 | 7.2.2.6 | 7.2.3.1 | 7.2.3.2 | 7.2.3.3 | 7.2.3.4 | 7.2.3.5 | 7.2.3.6 | 7.2.4.1 | 7.2.4.2 |
| 7.2.4.3 | 7.2.4.4 | 7.2.4.5 | 7.2.4.6 | 7.2.5.1 | 7.2.5.2 | 7.2.5.3 | 7.2.5.4 | 7.2.5.5 | 7.2.5.6 |
| 7.2.6.1 | 7.2.6.2 | 7.2.6.3 | 7.2.6.4 | 7.2.6.5 | 7.2.6.6 | 7.2.7.1 | 7.2.7.2 | 7.2.7.3 | 7.2.7.4 |
| 7.2.7.5 | 7.2.7.6 | 7.2.8.1 | 7.2.8.2 | 7.2.8.3 | 7.2.8.4 | 7.2.8.5 | 7.2.8.6 | 7.2.9.1 | 7.2.9.2 |
| 7.2.9.3 | 7.2.9.4 | 7.2.9.5 | 7.2.9.6 | 7.3.1.1 | 7.3.1.2 | 7.3.1.3 | 7.3.1.4 | 7.3.1.5 | 7.3.1.6 |
| 7.3.2.1 | 7.3.2.2 | 7.3.2.3 | 7.3.2.4 | 7.3.2.5 | 7.3.2.6 | 7.3.3.1 | 7.3.3.2 | 7.3.3.3 | 7.3.3.4 |
| 7.3.3.5 | 7.3.3.6 | 7.3.4.1 | 7.3.4.2 | 7.3.4.3 | 7.3.4.4 | 7.3.4.5 | 7.3.4.6 | 7.3.5.1 | 7.3.5.2 |
| 7.3.5.3 | 7.3.5.4 | 7.3.5.5 | 7.3.5.6 | 7.3.6.1 | 7.3.6.2 | 7.3.6.3 | 7.3.6.4 | 7.3.6.5 | 7.3.6.6 |
| 7.3.7.1 | 7.3.7.2 | 7.3.7.3 | 7.3.7.4 | 7.3.7.5 | 7.3.7.6 | 7.3.8.1 | 7.3.8.2 | 7.3.8.3 | 7.3.8.4 |
| 7.3.8.5 | 7.3.8.6 | 7.3.9.1 | 7.3.9.2 | 7.3.9.3 | 7.3.9.4 | 7.3.9.5 | 7.3.9.6 | 7.4.1.1 | 7.4.1.2 |
| 7.4.1.3 | 7.4.1.4 | 7.4.1.5 | 7.4.1.6 | 7.4.2.1 | 7.4.2.2 | 7.4.2.3 | 7.4.2.4 | 7.4.2.5 | 7.4.2.6 |
| 7.4.3.1 | 7.4.3.2 | 7.4.3.3 | 7.4.3.4 | 7.4.3.5 | 7.4.3.6 | 7.4.4.1 | 7.4.4.2 | 7.4.4.3 | 7.4.4.4 |
| 7.4.4.5 | 7.4.4.6 | 7.4.5.1 | 7.4.5.2 | 7.4.5.3 | 7.4.5.4 | 7.4.5.5 | 7.4.5.6 | 7.4.6.1 | 7.4.6.2 |
| 7.4.6.3 | 7.4.6.4 | 7.4.6.5 | 7.4.6.6 | 7.4.7.1 | 7.4.7.2 | 7.4.7.3 | 7.4.7.4 | 7.4.7.5 | 7.4.7.6 |
| 7.4.8.1 | 7.4.8.2 | 7.4.8.3 | 7.4.8.4 | 7.4.8.5 | 7.4.8.6 | 7.4.9.1 | 7.4.9.2 | 7.4.9.3 | 7.4.9.4 |
| 7.4.9.5 | 7.4.9.6 | 7.5.1.1 | 7.5.1.2 | 7.5.1.3 | 7.5.1.4 | 7.5.1.5 | 7.5.1.6 | 7.5.2.1 | 7.5.2.2 |
| 7.5.2.3 | 7.5.2.4 | 7.5.2.5 | 7.5.2.6 | 7.5.3.1 | 7.5.3.2 | 7.5.3.3 | 7.5.3.4 | 7.5.3.5 | 7.5.3.6 |
| 7.5.4.1 | 7.5.4.2 | 7.5.4.3 | 7.5.4.4 | 7.5.4.5 | 7.5.4.6 | 7.5.5.1 | 7.5.5.2 | 7.5.5.3 | 7.5.5.4 |
| 7.5.5.5 | 7.5.5.6 | 7.5.6.1 | 7.5.6.2 | 7.5.6.3 | 7.5.6.4 | 7.5.6.5 | 7.5.6.6 | 7.5.7.1 | 7.5.7.2 |
| 7.5.7.3 | 7.5.7.4 | 7.5.7.5 | 7.5.7.6 | 7.5.8.1 | 7.5.8.2 | 7.5.8.3 | 7.5.8.4 | 7.5.8.5 | 7.5.8.6 |
| 7.5.9.1 | 7.5.9.2 | 7.5.9.3 | 7.5.9.4 | 7.5.9.5 | 7.5.9.6 | 7.6.1.1 | 7.6.1.2 | 7.6.1.3 | 7.6.1.4 |
| 7.6.1.5 | 7.6.1.6 | 7.6.2.1 | 7.6.2.2 | 7.6.2.3 | 7.6.2.4 | 7.6.2.5 | 7.6.2.6 | 7.6.3.1 | 7.6.3.2 |
| 7.6.3.3 | 7.6.3.4 | 7.6.3.5 | 7.6.3.6 | 7.6.4.1 | 7.6.4.2 | 7.6.4.3 | 7.6.4.4 | 7.6.4.5 | 7.6.4.6 |
| 7.6.5.1 | 7.6.5.2 | 7.6.5.3 | 7.6.5.4 | 7.6.5.5 | 7.6.5.6 | 7.6.6.1 | 7.6.6.2 | 7.6.6.3 | 7.6.6.4 |
| 7.6.6.5 | 7.6.6.6 | 7.6.7.1 | 7.6.7.2 | 7.6.7.3 | 7.6.7.4 | 7.6.7.5 | 7.6.7.6 | 7.6.8.1 | 7.6.8.2 |
| 7.6.8.3 | 7.6.8.4 | 7.6.8.5 | 7.6.8.6 | 7.6.9.1 | 7.6.9.2 | 7.6.9.3 | 7.6.9.4 | 7.6.9.5 | 7.6.9.6 |
| 7.7.1.1 | 7.7.1.2 | 7.7.1.3 | 7.7.1.4 | 7.7.1.5 | 7.7.1.6 | 7.7.2.1 | 7.7.2.2 | 7.7.2.3 | 7.7.2.4 |
| 7.7.2.5 | 7.7.2.6 | 7.7.3.1 | 7.7.3.2 | 7.7.3.3 | 7.7.3.4 | 7.7.3.5 | 7.7.3.6 | 7.7.4.1 | 7.7.4.2 |
| 7.7.4.3 | 7.7.4.4 | 7.7.4.5 | 7.7.4.6 | 7.7.5.1 | 7.7.5.2 | 7.7.5.3 | 7.7.5.4 | 7.7.5.5 | 7.7.5.6 |
| 7.7.6.1 | 7.7.6.2 | 7.7.6.3 | 7.7.6.4 | 7.7.6.5 | 7.7.6.6 | 7.7.7.1 | 7.7.7.2 | 7.7.7.3 | 7.7.7.4 |
| 7.7.7.5 | 7.7.7.6 | 7.7.8.1 | 7.7.8.2 | 7.7.8.3 | 7.7.8.4 | 7.7.8.5 | 7.7.8.6 | 7.7.9.1 | 7.7.9.2 |
| 7.7.9.3 | 7.7.9.4 | 7.7.9.5 | 7.7.9.6 | 7.8.1.1 | 7.8.1.2 | 7.8.1.3 | 7.8.1.4 | 7.8.1.5 | 7.8.1.6 |
| 7.8.2.1 | 7.8.2.2 | 7.8.2.3 | 7.8.2.4 | 7.8.2.5 | 7.8.2.6 | 7.8.3.1 | 7.8.3.2 | 7.8.3.3 | 7.8.3.4 |
| 7.8.3.5 | 7.8.3.6 | 7.8.4.1 | 7.8.4.2 | 7.8.4.3 | 7.8.4.4 | 7.8.4.5 | 7.8.4.6 | 7.8.5.1 | 7.8.5.2 |
| 7.8.5.3 | 7.8.5.4 | 7.8.5.5 | 7.8.5.6 | 7.8.6.1 | 7.8.6.2 | 7.8.6.3 | 7.8.6.4 | 7.8.6.5 | 7.8.6.6 |
| 7.8.7.1 | 7.8.7.2 | 7.8.7.3 | 7.8.7.4 | 7.8.7.5 | 7.8.7.6 | 7.8.8.1 | 7.8.8.2 | 7.8.8.3 | 7.8.8.4 |

TABLE 1-continued

| | | | | | | | | | |
|---|---|---|---|---|---|---|---|---|---|
| 7.8.8.5 | 7.8.8.6 | 7.8.9.1 | 7.8.9.2 | 7.8.9.3 | 7.8.9.4 | 7.8.9.5 | 7.8.9.6 | 7.9.1.1 | 7.9.1.2 |
| 7.9.1.3 | 7.9.1.4 | 7.9.1.5 | 7.9.1.6 | 7.9.2.1 | 7.9.2.2 | 7.9.2.3 | 7.9.2.4 | 7.9.2.5 | 7.9.2.6 |
| 7.9.3.1 | 7.9.3.2 | 7.9.3.3 | 7.9.3.4 | 7.9.3.5 | 7.9.3.6 | 7.9.4.1 | 7.9.4.2 | 7.9.4.3 | 7.9.4.4 |
| 7.9.4.5 | 7.9.4.6 | 7.9.5.1 | 7.9.5.2 | 7.9.5.3 | 7.9.5.4 | 7.9.5.5 | 7.9.5.6 | 7.9.6.1 | 7.9.6.2 |
| 7.9.6.3 | 7.9.6.4 | 7.9.6.5 | 7.9.6.6 | 7.9.7.1 | 7.9.7.2 | 7.9.7.3 | 7.9.7.4 | 7.9.7.5 | 7.9.7.6 |
| 7.9.8.1 | 7.9.8.2 | 7.9.8.3 | 7.9.8.4 | 7.9.8.5 | 7.9.8.6 | 7.9.9.1 | 7.9.9.2 | 7.9.9.3 | 7.9.9.4 |
| 7.9.9.5 | 7.9.9.6 | | | | | | | | |

Therefore, compounds named in Table 1 of formula (i) having —S— as Y' are compounds with a thiazolyl as $R^5$ in formula I. For example, using Group 1 for variable B, the compound named 2.6.1.1 specifies —$NH_2$ as A, -Pr-c as B, furan-2,5-diyl as X and —S— as Y', and this compound is 2-amino-5-cyclopropyl-4-[2-(5-phosphono)furanyl]thiazole prepared in Example 3 as compound 3.27. Analogously, compounds named in Table 1 of formula (i) having —O— as Y' are compounds with an oxazolyl as $R^5$ in formula I. For example, using group 1 for variable B, the compound named 2.4.1.2 in Table 1 of formula (i) has the structure of 2-amino-5-propyl-4-[2-(phosphono)furanyl]oxazole prepared in Example 10 as compound 10.2. Similarly, compounds named in Table 1 of formula (i) having —Se— as Y' are compounds with a selenazolyl as $R^5$ in formula I. Thus, using Group 1 for variable B, the compound named 2.3.1.3 in Table 1 of formula (i) has the structure of 2-amino-5-ethyl-4-[2-(5-phosphono)furanyl]selenazole prepared in Example 3 as compound 3.72.

Likewise, using Group 2 for variable B, the compound named in Table 1 of formula (i) as 2.8.1.1 is 2-amino-5-methylthio-4-[2-(5-phosphono)furanyl]thiazole prepared in Example 3 as compound 3.26. Using Group 3 for variable B, the compound named in Table 1 of formula (i) as 2.9.1.1 is 2-amino-5-isobutyl-4-[2-(5-phosphono)furanyl]thiazole prepared in Example 3 as compound 3.1.

Using Group 4 for variable B, the compound named in Table 1 of formula (i) as 2.6.1.1 is 2-amino-5-(2-thienyl)-4-[2-(5-phosphono)furanyl]thiazole prepared in Example 6 a compound 6.3.

Some of the exemplary embodiments of the compounds named in Table 1 using Groups 1–4 for variable B in the compounds of formulae (i), (ii), (iii) and (iv) are listed in Table 2.

TABLE 2

| Compound number. as A.B.X.Y | Synthetic Example No. | formula | A | compound groups where B is selected | B | X* | Y |
|---|---|---|---|---|---|---|---|
| 2.1.1.1 | 3.13 | (i) | NH2 | 1 | H | furan-2,5-diyl | S |
| 2.2.1.1 | 3.16 | (i) | NH2 | 1 | Me | furan-2,5-diyl | S |
| 2.3.1.1 | 3.21 | (i) | NH2 | 1 | Et | furan-2,5-diyl | S |
| 2.4.1.1 | 3.24 | (i) | NH2 | 1 | Pr-n | furan-2,5-diyl | S |
| 2.5.1.1 | 3.2 | (i) | NH2 | 1 | Pr-i | furan-2,5-diyl | S |
| 2.6.1.1 | 3.27 | (i) | NH2 | 1 | Pr-c | furan-2,5-diyl | S |
| 2.9.1.1 | 3.1 | (i) | NH2 | 1 | Bu-i | furan-2,5-diyl | S |
| 2.5.1.1 | 6.2 | (i) | NH2 | 4 | 2-furanyl | furan-2,5-diyl | S |
| 2.3.1.1 | 3.30 | (i) | NH2 | 3 | Bu-c | furan-2,5-diyl | S |
| 2.6.1.1 | 6.3 | (i) | NH2 | 4 | 2-thienyl | furan-2,5-diyl | S |
| 2.8.1.1 | 4.2 | (i) | NH2 | 1 | Cl | furan-2,5-diyl | S |
| 2.7.1.1 | 4.1 | (i) | NH2 | 1 | Br | furan-2,5-diyl | S |
| 2.9.1.1 | 4.3 | (i) | NH2 | 1 | I | furan-2,5-diyl | S |
| 2.8.1.1 | 3.26 | (i) | NH2 | 2 | SMe | furan-2,5-diyl | S |
| 2.1.1.1 | 3.59 | (i) | NH2 | 3 | SEt | furan-2,5-diyl | S |
| 2.6.1.1 | 3.58 | (i) | NH2 | 3 | SPr-n | furan-2,5-diyl | S |
| 2.4.1.1 | 3.55 | (i) | NH2 | 4 | SPr-i | furan-2,5-diyl | S |
| 2.9.1.1 | 3.36 | (i) | NH2 | 4 | Bn | furan-2,5-diyl | S |
| 2.6.1.1 | 3.33 | (i) | NH2 | 2 | C(O)OMe | furan-2,5-diyl | S |
| 2.4.1.1 | 3.25 | (i) | NH2 | 3 | C(O)OEt | furan-2,5-diyl | S |
| 1.1.1.1 | 3.3 | (i) | H | 1 | H | furan-2,5-diyl | S |
| 1.9.1.1 | 3.7 | (i) | H | 3 | Bu-i | furan-2,5-diyl | S |
| 6.8.1.1 | 3.50 | (i) | Me | 2 | SMe | furan-2,5-diyl | S |
| 4.9.1.1 | 5.2 | (i) | Cl | 3 | Bu-i | furan-2,5-diyl | S |
| 3.7.1.1 | 4.4 | (i) | Br | 1 | Br | furan-2,5-diyl | S |
| 3.9.1.1 | 5.1 | (i) | Br | 3 | Bu-i | furan-2,5-diyl | S |
| 6.6.1.1 | 3.42 | (i) | Me | 1 | Pr-c | furan-2,5-diyl | S |
| 6.1.1.1 | 3.4 | (i) | Me | 1 | H | furan-2,5-diyl | S |
| 6.2.1.1 | 3.17 | (i) | Me | 1 | Me | furan-2,5-diyl | S |
| 6.7.1.1 | 4.5 | (i) | Me | 1 | Br | furan-2,5-diyl | S |
| 6.9.1.1 | 3.2 | (i) | Me | 3 | Bu-i | furan-2,5-diyl | S |
| 6.3.1.1 | 3.41 | (i) | Me | 1 | Et | furan-2,5-diyl | S |
| 6.4.1.1 | 3.43 | (i) | Me | 3 | C(O)OEt | furan-2,5-diyl | S |
| 1.4.1.1 | 3.65 | (i) | H | 3 | C(O)OEt | furan-2,5-diyl | S |
| 6.1.9.1 | 8.1 | (i) | Me | 1 | H | CH2OCH2 | S |
| 6.7.9.1 | 8.2 | (i) | Me | 1 | Br | CH2OCH2 | S |
| 2.9.4.1 | 18.16 | (i) | NH2 | 4 | Bn | C(O)OCH2 | S |
| 2.1.9.1 | 8.3 | (i) | NH2 | 1 | H | CH2OCH2 | S |

TABLE 2-continued

| Compound number. as A.B.X.Y | Synthetic Example No. | formula | A | compound groups where B is selected | B | X* | Y |
|---|---|---|---|---|---|---|---|
| 2.2.4.1 | 18.27 | (i) | NH2 | 1 | Me | C(O)OCH2 | S |
| 2.1.4.1 | 18.37 | (i) | NH2 | 1 | H | C(O)OCH2 | S |
| 2.3.4.1 | 18.3 | (i) | NH2 | 1 | Et | C(O)OCH2 | S |
| 2.5.4.1 | 18.20 | (i) | NH2 | 1 | Pr-i | C(O)OCH2 | S |
| 2.5.5.1 | 18.19 | (i) | NH2 | 1 | Pr-i | C(O)NHCH2 | S |
| 2.3.5.1 | 18.18 | (i) | NH2 | 1 | Et | C(O)NHCH2 | S |
| 2.2.5.1 | 18.24 | (i) | NH2 | 1 | Me | C(O)NHCH2 | S |
| 2.1.5.1 | 18.6 | (i) | NH2 | 1 | H | C(O)NHCH2 | S |
| 2.1.4.1 | 18.1 | (i) | NH2 | 1 | H | C(O)OCH2 | S |
| 2.7.5.1 | 18.11 | (i) | NH2 | 1 | Br | C(O)NHCH2 | S |
| 2.7.4.1 | 18.2 | (i) | NH2 | 1 | Br | C(O)OCH2 | S |
| 2.6.4.1 | 18.15 | (i) | NH2 | 4 | 2-thienyl | C(O)OCH2 | S |
| 2.6.5.1 | 18.12 | (i) | NH2 | 4 | 2-thienyl | C(O)NHCH2 | S |
| 2.1.2.1 | 3.67 | (i) | NH2 | 1 | H | pyridin-2,6-diyl | S |
| 6.2.8.1 | 18.7 | (iii) | Me | 1 | Me | NHC(O)CH2 | S |
| 2.1.1.2 | 10.5 | (i) | NH2 | 1 | H | furan-2,5-diyl | O |
| 2.2.1.2 | 10.4 | (i) | NH2 | 1 | Me | furan-2,5-diyl | O |
| 2.3.1.2 | 10.3 | (i) | NH2 | 1 | Et | furan-2,5-diyl | O |
| 2.4.1.2 | 10.2 | (i) | NH2 | 1 | Pr-n | furan-2,5-diyl | O |
| 2.8.1.2 | 10.12 | (i) | NH2 | 3 | Bu-n | furan-2,5-diyl | O |
| 2.9.1.2 | 10.1 | (i) | NH2 | 3 | Bu-i | furan-2,5-diyl | O |
| 2.6.1.2 | 10.37 | (i) | NH2 | 2 | C(O)OMe | furan-2,5-diyl | O |
| 2.1.4.2 | 18.22 | (i) | NH2 | 1 | H | C(O)OCH2 | O |
| 2.5.4.2 | 18.30 | (i) | NH2 | 1 | Pr-i | C(O)OCH2 | O |
| 2.2.4.2 | 18.33 | (i) | NH2 | 1 | Me | C(O)OCH2 | O |
| 2.8.4.2 | 18.38 | (i) | NH2 | 3 | Bu-n | C(O)OCH2 | O |
| 2.4.4.2 | 18.40 | (i) | NH2 | 1 | Pr-n | C(O)OCH2 | O |
| 2.9.1.2 | 10.8 | (i) | NH2 | 4 | Bn | furan-2,5-diyl | O |
| 2.8.1.2 | 10.34 | (i) | NH2 | 2 | SMe | furan-2,5-diyl | O |
| 2.1.1.2 | 10.42 | (i) | NH2 | 3 | SEt | furan-2,5-diyl | O |
| 2.6.1.2 | 10.43 | (i) | NH2 | 3 | SPr-n | furan-2,5-diyl | O |
| 2.4.1.2 | 10.40 | (i) | NH2 | 4 | SPr-i | furan-2,5-diyl | O |
| 2.4.1.2 | 10.27 | (i) | NH2 | 3 | C(O)OEt | furan-2,5-diyl | O |
| 1.9.1.2 | 10.11 | (i) | NH2 | 3 | Bu-i | furan-2,5-diyl | O |
| 6.9.1.2 | 10.19 | (i) | Me | 2 | Bu-i | furan-2,5-diyl | O |
| 7.1.1.4 | 10.22 | (i) | CF3 | 1 | H | furan-2,5-diyl | NH |
| 6.9.1.4 | 10.21 | (i) | Me | 3 | Bu-i | furan-2,5-diyl | NH |
| 6.9.1.5 | 11.2 | (i) | Me | 3 | Bu-i | furan-2,5-diyl | NMe |
| 6.4.1.4 | 10.2 | (i) | Me | 1 | Pr-n | furan-2,5-diyl | NH |
| 6.9.1.5 | 11.2 | (i) | Me | 3 | Bu-i | furan-2,5-diyl | NMe |
| 6.2.1.4 | 10.34 | (iii) | Me | 1 | Me | furan-2,5-diyl | NH |
| 2.4.1.2 | 26.4 | (ii) | NH2 | 3 | C(O)OEt | furan-2,5-diyl | O |
| 1.9.1.5 | 25.2 | (ii) | H | 3 | Bu-i | furan-2,5-diyl | NMe |
| 1.9.1.4 | 25.1 | (ii) | H | 3 | Bu-i | furan-2,5-diyl | H |
| 1.7.8.1 | | (iii) | H | 1 | Br | NHC(O)CH2 | S |
| 1.1.8.1 | | (iii) | H | 1 | H | NHC(O)CH2 | S |

*The direction of X groups is defined as going from R5 to the phosphorus atom.

The following compounds of formula I wherein $R^5$ is a pyridinyl, or a pyrimidinyl, or a pyrazinyl or a pyridazinyl, and pharmaceutically acceptable salts and prodrugs thereof are preferred. These preferred compounds are shown in structures (v)–(ix), below:

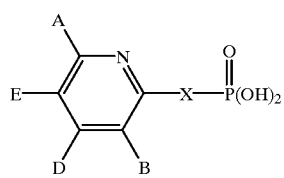

(v)

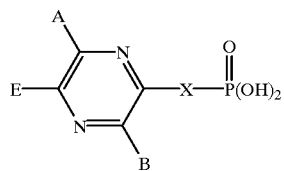

(vi)

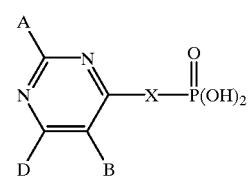

(vii)

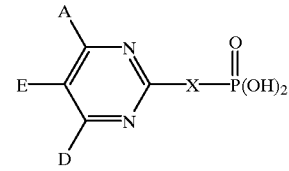

(viii)

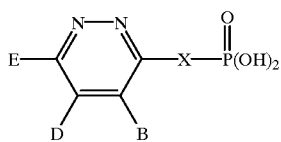

The preferred compounds of formula (v)–(ix) are listed in Table 3 by designated numbers assigned to A, B, X, D and E in the above formulae (v)–(ix) according to the following convention: A.B.X.D.E. For compounds of formula (vi) D is null and designated with number 0, for compounds of formula (vii) E is null and designated with number 0, and for compounds of formula (viii) B is null and designated with number 0. For example, all compounds named in Table 3 of formula (vi) are assigned as A.B.X.0.E, all compounds named in Table 3 of formula (vii) are assigned as A.B.X.D.0, all compounds named in Table 3 of formula (viii) are assigned as A.0.X.D.E, and all compounds named in Table 3 of formula (ix) are assigned as 0.B.X.D.E. For each moiety, structures are assigned to a number shown in the following tables for A, B, X, D, and E.

Variable A is selected from eight different sub stituents.

The A groups are assigned the following numbers:

TABLE A

| 1 | 2 | 3 | 4 | 5 | 6 | 7 | 8 |
|---|---|---|---|---|---|---|---|
| A = H | $NH_2$ | Br | Cl | F | Me | $CF_3$ | $C(O)NH_2$ |

Variable B is divided into four Groups, each listing eight different substituents.

The Group 1 substituents for variable B are assigned the following numbers:

TABLE B

| 1 | 2 | 3 | 4 | 5 | 6 | 7 | 8 |
|---|---|---|---|---|---|---|---|
| B = H | Me | Et | Pr-n | Pr-i | Pr-c | Br | Cl |

The Group 2 substituents for variable B are assigned the following numbers:

| 1 | 2 | 3 | 4 | 5 | 6 | 7 | 8 |
|---|---|---|---|---|---|---|---|
| B = F | CN | $CH_2$Pr-c | Bu-i | C(O)SMe | C(O)OMe | OEt | SMe |

The Group 3 substituents for variable B are assigned the following numbers:

| 1 | 2 | 3 | 4 | 5 | 6 | 7 | 8 |
|---|---|---|---|---|---|---|---|
| B = SEt | 4-pyridyl | Bu-c | C(O)OEt | $NMe_2$ | SPr-n | $CF_3$ | OPr-n |

The Group 4 substituents for variable B are assigned the following numbers:

| 1 | 2 | 3 | 4 | 5 | 6 | 7 | 8 |
|---|---|---|---|---|---|---|---|
| B = SPr-c | OPr-i | OPr-c | SPr-i | 2-furanyl | 2-thienyl | OMe | Bn |

Variable X is divided into two Groups, each listing four different substituents.

The Group 1 substituents for variable X are assigned with the following numbers:

TABLE X

| 1 | 2 | 3 | 4 |
|---|---|---|---|
| X = Furan-2,5-diyl | Pyridin-2,6-diyl | $C(O)NHCH_2$ | $C(O)OCH_2$ |

The direction of X groups is defined as going from the heterocycle to the phosphorus atom as shown in formula (v), (vi), (vii), (viii) and (ix).

The Group 2 substituents for variable X are assigned the following numbers:

| 1 | 2 | 3 | 4 |
|---|---|---|---|
| X = $NHC(O)CH_2$ | $C(O)N(Me)CH_2$ | Ethyn-1,2-diyl | $CH_2O\ CH_2$ |

Variable D is divided into two groups, each listing eight different substituents.

The D groups are assigned the following numbers:

TABLE D

| 1 | 2 | 3 | 4 | 5 | 6 | 7 | 8 |
|---|---|---|---|---|---|---|---|
| D = H | Me | Et | C(O)OEt | SMe | Pr-c | Br | Cl |

The Group 2 substituents for variable D are assigned the following numbers:

|   | 1 | 2 | 3  | 4       | 5       | 6       | 7   | 8    |
|---|---|---|----|---------|---------|---------|-----|------|
| D = | F | I | CN | CH$_2$Pr-c | CH$_2$OMe | C(O)NH$_2$ | OMe | CF$_3$ |

Variable E is divided into three Groups, each listing four different substituents.

The Group 1 substituents for variable E are assigned the following numbers:

TABLE E

|   | 1 | 2  | 3  | 4    |
|---|---|----|----|------|
| E = | H | Me | Et | Pr-n |

The Group 2 substituents for variable E are assigned the following numbers:

|   | 1  | 2  | 3 | 4  |
|---|----|----|---|----|
| E = | Br | Cl | F | CN |

The Group 3 substituents for variable E are assigned the following numbers:

|   | 1      | 2    | 3   | 4   |
|---|--------|------|-----|-----|
| E = | C(O)OMe | Pr-c | SMe | OMe |

TABLE 3

| | | | | | | | |
|---|---|---|---|---|---|---|---|
| 1.1.1.1.1 | 1.1.1.1.2 | 1.1.1.1.3 | 1.1.1.1.4 | 1.1.1.2.1 | 1.1.1.2.2 | 1.1.1.2.3 | 1.1.1.2.4 |
| 1.1.1.3.1 | 1.1.1.3.2 | 1.1.1.3.3 | 1.1.1.3.4 | 1.1.1.4.1 | 1.1.1.4.2 | 1.1.1.4.3 | 1.1.1.4.4 |
| 1.1.1.5.1 | 1.1.1.5.2 | 1.1.1.5.3 | 1.1.1.5.4 | 1.1.1.6.1 | 1.1.1.6.2 | 1.1.1.6.3 | 1.1.1.6.4 |
| 1.1.1.7.1 | 1.1.1.7.2 | 1.1.1.7.3 | 1.1.1.7.4 | 1.1.1.8.1 | 1.1.1.8.2 | 1.1.1.8.3 | 1.1.1.8.4 |
| 1.1.2.1.1 | 1.1.2.1.2 | 1.1.2.1.3 | 1.1.2.1.4 | 1.1.2.2.1 | 1.1.2.2.2 | 1.1.2.2.3 | 1.1.2.2.4 |
| 1.1.2.3.1 | 1.1.2.3.2 | 1.1.2.3.3 | 1.1.2.3.4 | 1.1.2.4.1 | 1.1.2.4.2 | 1.1.2.4.3 | 1.1.2.4.4 |
| 1.1.2.5.1 | 1.1.2.5.2 | 1.1.2.5.3 | 1.1.2.5.4 | 1.1.2.6.1 | 1.1.2.6.2 | 1.1.2.6.3 | 1.1.2.6.4 |
| 1.1.2.7.1 | 1.1.2.7.2 | 1.1.2.7.3 | 1.1.2.7.4 | 1.1.2.8.1 | 1.1.2.8.2 | 1.1.2.8.3 | 1.1.2.8.4 |
| 1.1.3.1.1 | 1.1.3.1.2 | 1.1.3.1.3 | 1.1.3.1.4 | 1.1.3.2.1 | 1.1.3.2.2 | 1.1.3.2.3 | 1.1.3.2.4 |
| 1.1.3.3.1 | 1.1.3.3.2 | 1.1.3.3.3 | 1.1.3.3.4 | 1.1.3.4.1 | 1.1.3.4.2 | 1.1.3.4.3 | 1.1.3.4.4 |
| 1.1.3.5.1 | 1.1.3.5.2 | 1.1.3.5.3 | 1.1.3.5.4 | 1.1.3.6.1 | 1.1.3.6.2 | 1.1.3.6.3 | 1.1.3.6.4 |
| 1.1.3.7.1 | 1.1.3.7.2 | 1.1.3.7.3 | 1.1.3.7.4 | 1.1.3.8.1 | 1.1.3.8.2 | 1.1.3.8.3 | 1.1.3.8.4 |
| 1.1.4.1.1 | 1.1.4.1.2 | 1.1.4.1.3 | 1.1.4.1.4 | 1.1.4.2.1 | 1.1.4.2.2 | 1.1.4.2.3 | 1.1.4.2.4 |
| 1.1.4.3.1 | 1.1.4.3.2 | 1.1.4.3.3 | 1.1.4.3.4 | 1.1.4.4.1 | 1.1.4.4.2 | 1.1.4.4.3 | 1.1.4.4.4 |
| 1.1.4.5.1 | 1.1.4.5.2 | 1.1.4.5.3 | 1.1.4.5.4 | 1.1.4.6.1 | 1.1.4.6.2 | 1.1.4.6.3 | 1.1.4.6.4 |
| 1.1.4.7.1 | 1.1.4.7.2 | 1.1.4.7.3 | 1.1.4.7.4 | 1.1.4.8.1 | 1.1.4.8.2 | 1.1.4.8.3 | 1.1.4.8.4 |
| 1.2.1.1.1 | 1.2.1.1.2 | 1.2.1.1.3 | 1.2.1.1.4 | 1.2.1.2.1 | 1.2.1.2.2 | 1.2.1.2.3 | 1.2.1.2.4 |
| 1.2.1.3.1 | 1.2.1.3.2 | 1.2.1.3.3 | 1.2.1.3.4 | 1.2.1.4.1 | 1.2.1.4.2 | 1.2.1.4.3 | 1.2.1.4.4 |
| 1.2.1.5.1 | 1.2.1.5.2 | 1.2.1.5.3 | 1.2.1.5.4 | 1.2.1.6.1 | 1.2.1.6.2 | 1.2.1.6.3 | 1.2.1.6.4 |
| 1.2.1.7.1 | 1.2.1.7.2 | 1.2.1.7.3 | 1.2.1.7.4 | 1.2.1.8.1 | 1.2.1.8.2 | 1.2.1.8.3 | 1.2.1.8.4 |
| 1.2.2.1.1 | 1.2.2.1.2 | 1.2.2.1.3 | 1.2.2.1.4 | 1.2.2.2.1 | 1.2.2.2.2 | 1.2.2.2.3 | 1.2.2.2.4 |
| 1.2.2.3.1 | 1.2.2.3.2 | 1.2.2.3.3 | 1.2.2.3.4 | 1.2.2.4.1 | 1.2.2.4.2 | 1.2.2.4.3 | 1.2.2.4.4 |
| 1.2.2.5.1 | 1.2.2.5.2 | 1.2.2.5.3 | 1.2.2.5.4 | 1.2.2.6.1 | 1.2.2.6.2 | 1.2.2.6.3 | 1.2.2.6.4 |
| 1.2.2.7.1 | 1.2.2.7.2 | 1.2.2.7.3 | 1.2.2.7.4 | 1.2.2.8.1 | 1.2.2.8.2 | 1.2.2.8.3 | 1.2.2.8.4 |
| 1.2.3.1.1 | 1.2.3.1.2 | 1.2.3.1.3 | 1.2.3.1.4 | 1.2.3.2.1 | 1.2.3.2.2 | 1.2.3.2.3 | 1.2.3.2.4 |
| 1.2.3.3.1 | 1.2.3.3.2 | 1.2.3.3.3 | 1.2.3.3.4 | 1.2.3.4.1 | 1.2.3.4.2 | 1.2.3.4.3 | 1.2.3.4.4 |
| 1.2.3.5.1 | 1.2.3.5.2 | 1.2.3.5.3 | 1.2.3.5.4 | 1.2.3.6.1 | 1.2.3.6.2 | 1.2.3.6.3 | 1.2.3.6.4 |
| 1.2.3.7.1 | 1.2.3.7.2 | 1.2.3.7.3 | 1.2.3.7.4 | 1.2.3.8.1 | 1.2.3.8.2 | 1.2.3.8.3 | 1.2.3.8.4 |
| 1.2.4.1.1 | 1.2.4.1.2 | 1.2.4.1.3 | 1.2.4.1.4 | 1.2.4.2.1 | 1.2.4.2.2 | 1.2.4.2.3 | 1.2.4.2.4 |
| 1.2.4.3.1 | 1.2.4.3.2 | 1.2.4.3.3 | 1.2.4.3.4 | 1.2.4.4.1 | 1.2.4.4.2 | 1.2.4.4.3 | 1.2.4.4.4 |
| 1.2.4.5.1 | 1.2.4.5.2 | 1.2.4.5.3 | 1.2.4.5.4 | 1.2.4.6.1 | 1.2.4.6.2 | 1.2.4.6.3 | 1.2.4.6.4 |
| 1.2.4.7.1 | 1.2.4.7.2 | 1.2.4.7.3 | 1.2.4.7.4 | 1.2.4.8.1 | 1.2.4.8.2 | 1.2.4.8.3 | 1.2.4.8.4 |
| 1.3.1.1.1 | 1.3.1.1.2 | 1.3.1.1.3 | 1.3.1.1.4 | 1.3.1.2.1 | 1.3.1.2.2 | 1.3.1.2.3 | 1.3.1.2.4 |
| 1.3.1.3.1 | 1.3.1.3.2 | 1.3.1.3.3 | 1.3.1.3.4 | 1.3.1.4.1 | 1.3.1.4.2 | 1.3.1.4.3 | 1.3.1.4.4 |
| 1.3.1.5.1 | 1.3.1.5.2 | 1.3.1.5.3 | 1.3.1.5.4 | 1.3.1.6.1 | 1.3.1.6.2 | 1.3.1.6.3 | 1.3.1.6.4 |
| 1.3.1.7.1 | 1.3.1.7.2 | 1.3.1.7.3 | 1.3.1.7.4 | 1.3.1.8.1 | 1.3.1.8.2 | 1.3.1.8.3 | 1.3.1.8.4 |
| 1.3.2.1.1 | 1.3.2.1.2 | 1.3.2.1.3 | 1.3.2.1.4 | 1.3.2.2.1 | 1.3.2.2.2 | 1.3.2.2.3 | 1.3.2.2.4 |
| 1.3.2.3.1 | 1.3.2.3.2 | 1.3.2.3.3 | 1.3.2.3.4 | 1.3.2.4.1 | 1.3.2.4.2 | 1.3.2.4.3 | 1.3.2.4.4 |
| 1.3.2.5.1 | 1.3.2.5.2 | 1.3.2.5.3 | 1.3.2.5.4 | 1.3.2.6.1 | 1.3.2.6.2 | 1.3.2.6.3 | 1.3.2.6.4 |
| 1.3.2.7.1 | 1.3.2.7.2 | 1.3.2.7.3 | 1.3.2.7.4 | 1.3.2.8.1 | 1.3.2.8.2 | 1.3.2.8.3 | 1.3.2.8.4 |
| 1.3.3.1.1 | 1.3.3.1.2 | 1.3.3.1.3 | 1.3.3.1.4 | 1.3.3.2.1 | 1.3.3.2.2 | 1.3.3.2.3 | 1.3.3.2.4 |
| 1.3.3.3.1 | 1.3.3.3.2 | 1.3.3.3.3 | 1.3.3.3.4 | 1.3.3.4.1 | 1.3.3.4.2 | 1.3.3.4.3 | 1.3.3.4.4 |
| 1.3.3.5.1 | 1.3.3.5.2 | 1.3.3.5.3 | 1.3.3.5.4 | 1.3.3.6.1 | 1.3.3.6.2 | 1.3.3.6.3 | 1.3.3.6.4 |
| 1.3.3.7.1 | 1.3.3.7.2 | 1.3.3.7.3 | 1.3.3.7.4 | 1.3.3.8.1 | 1.3.3.8.2 | 1.3.3.8.3 | 1.3.3.8.4 |
| 1.3.4.1.1 | 1.3.4.1.2 | 1.3.4.1.3 | 1.3.4.1.4 | 1.3.4.2.1 | 1.3.4.2.2 | 1.3.4.2.3 | 1.3.4.2.4 |
| 1.3.4.3.1 | 1.3.4.3.2 | 1.3.4.3.3 | 1.3.4.3.4 | 1.3.4.4.1 | 1.3.4.4.2 | 1.3.4.4.3 | 1.3.4.4.4 |
| 1.3.4.5.1 | 1.3.4.5.2 | 1.3.4.5.3 | 1.3.4.5.4 | 1.3.4.6.1 | 1.3.4.6.2 | 1.3.4.6.3 | 1.3.4.6.4 |
| 1.3.4.7.1 | 1.3.4.7.2 | 1.3.4.7.3 | 1.3.4.7.4 | 1.3.4.8.1 | 1.3.4.8.2 | 1.3.4.8.3 | 1.3.4.8.4 |
| 1.4.1.1.1 | 1.4.1.1.2 | 1.4.1.1.3 | 1.4.1.1.4 | 1.4.1.2.1 | 1.4.1.2.2 | 1.4.1.2.3 | 1.4.1.2.4 |

TABLE 3-continued

| | | | | | | | |
|---|---|---|---|---|---|---|---|
| 1.4.1.3.1 | 1.4.1.3.2 | 1.4.1.3.3 | 1.4.1.3.4 | 1.4.1.4.1 | 1.4.1.4.2 | 1.4.1.4.3 | 1.4.1.4.4 |
| 1.4.1.5.1 | 1.4.1.5.2 | 1.4.1.5.3 | 1.4.1.5.4 | 1.4.1.6.1 | 1.4.1.6.2 | 1.4.1.6.3 | 1.4.1.6.4 |
| 1.4.1.7.1 | 1.4.1.7.2 | 1.4.1.7.3 | 1.4.1.7.4 | 1.4.1.8.1 | 1.4.1.8.2 | 1.4.1.8.3 | 1.4..1.8.4 |
| 1.4.2.1.1 | 1.4.2.1.2 | 1.4.2.1.3 | 1.4.2.1.4 | 1.4.2.2.1 | 1.4.2.2.2 | 1.4.2.2.3 | 1.4.2.2.4 |
| 1.4.2.3.1 | 1.4.2.3.2 | 1.4.2.3.3 | 1.4.2.3.4 | 1.4.2.4.1 | 1.4.2.4.2 | 1.4.2.4.3 | 1.4.2.4.4 |
| 1.4.2.5.1 | 1.4.2.5.2 | 1.4.2.5.3 | 1.4.2.5.4 | 1.4.2.6.1 | 1.4.2.6.2 | 1.4.2.6.3 | 1.4.2.6.4 |
| 1.4.2.7.1 | 1.4.2.7.2 | 1.4.2.7.3 | 1.4.2.7.4 | 1.4.2.8.1 | 1.4.2.8.2 | 1.4.2.8.3 | 1.4.2.8.4 |
| 1.4.3.1.1 | 1.4.3.1.2 | 1.4.3.1.3 | 1.4.3.1.4 | 1.4.3.2.1 | 1.4.3.2.2 | 1.4.3.2.3 | 1.4.3.2.4 |
| 1.4.3.3.1 | 1.4.3.3.2 | 1.4.3.3.3 | 1.4.3.3.4 | 1.4.3.4.1 | 1.4.3.4.2 | 1.4.3.4.3 | 1.4.3.4.4 |
| 1.4.3.5.1 | 1.4.3.5.2 | 1.4.3.5.3 | 1.4.3.5.4 | 1.4.3.6.1 | 1.4.3.6.2 | 1.4.3.6.3 | 1.4.3.6.4 |
| 1.4.3.7.1 | 1.4.3.7.2 | 1.4.3.7.3 | 1.4.3.7.4 | 1.4.3.8.1 | 1.4.3.8.2 | 1.4.3.8.3 | 1.4.3.8.4 |
| 1.4.4.1.1 | 1.4.4.1.2 | 1.4.4.1.3 | 1.4.4.1.4 | 1.4.4.2.1 | 1.4.4.2.2 | 1.4.4.2.3 | 1.4.4.2.4 |
| 1.4.4.3.1 | 1.4.4.3.2 | 1.4.4.3.3 | 1.4.4.3.4 | 1.4.4.4.1 | 1.4.4.4.2 | 1.4.4.4.3 | 1.4.4.4.4 |
| 1.4.4.5.1 | 1.4.4.5.2 | 1.4.4.5.3 | 1.4.4.5.4 | 1.4.4.6.1 | 1.4.4.6.2 | 1.4.4.6.3 | 1.4.4.6.4 |
| 1.4.4.7.1 | 1.4.4.7.2 | 1.4.4.7.3 | 1.4.4.7.4 | 1.4.4.8.1 | 1.4.4.8.2 | 1.4.4.8.3 | 1.4.4.8.4 |
| 1.5.1.1.1 | 1.5.1.1.2 | 1.5.1.1.3 | 1.5.1.1.4 | 1.5.1.2.1 | 1.5.1.2.2 | 1.5.1.2.3 | 1.5.1.2.4 |
| 1.5.1.3.1 | 1.5.1.3.2 | 1.5.1.3.3 | 1.5.1.3.4 | 1.5.1.4.1 | 1.5.1.4.2 | 1.5.1.4.3 | 1.5.1.4.4 |
| 1.5.1.5.1 | 1.5.1.5.2 | 1.5.1.5.3 | 1.5.1.5.4 | 1.5.1.6.1 | 1.5.1.6.2 | 1.5.1.6.3 | 1.5.1.6.4 |
| 1.5.1.7.1 | 1.5.1.7.2 | 1.5.1.7.3 | 1.5.1.7.4 | 1.5.1.8.1 | 1.5.1.8.2 | 1.5.1.8.3 | 1.5.1.8.4 |
| 1.5.2.1.1 | 1.5.2.1.2 | 1.5.2.1.3 | 1.5.2.1.4 | 1.5.2.2.1 | 1.5.2.2.2 | 1.5.2.2.3 | 1.5.2.2.4 |
| 1.5.2.3.1 | 1.5.2.3.2 | 1.5.2.3.3 | 1.5.2.3.4 | 1.5.2.4.1 | 1.5.2.4.2 | 1.5.2.4.3 | 1.5.2.4.4 |
| 1.5.2.5.1 | 1.5.2.5.2 | 1.5.2.5.3 | 1.5.2.5.4 | 1.5.2.6.1 | 1.5.2.6.2 | 1.5.2.6.3 | 1.5.2.6.4 |
| 1.5.2.7.1 | 1.5.2.7.2 | 1.5.2.7.3 | 1.5.2.7.4 | 1.5.2.8.1 | 1.5.2.8.2 | 1.5.2.8.3 | 1.5.2.8.4 |
| 1.5.3.1.1 | 1.5.3.1.2 | 1.5.3.1.3 | 1.5.3.1.4 | 1.5.3.2.1 | 1.5.3.2.2 | 1.5.3.2.3 | 1.5.3.2.4 |
| 1.5.3.3.1 | 1.5.3.3.2 | 1.5.3.3.3 | 1.5.3.3.4 | 1.5.3.4.1 | 1.5.3.4.2 | 1.5.3.4.3 | 1.5.3.4.4 |
| 1.5.3.5.1 | 1.5.3.5.2 | 1.5.3.5.3 | 1.5.3.5.4 | 1.5.3.6.1 | 1.5.3.6.2 | 1.5.3.6.3 | 1.5.3.6.4 |
| 1.5.3.7.1 | 1.5.3.7.2 | 1.5.3.7.3 | 1.5.3.7.4 | 1.5.3.8.1 | 1.5.3.8.2 | 1.5.3.8.3 | 1.5.3.8.4 |
| 1.5.4.1.1 | 1.5.4.1.2 | 1.5.4.1.3 | 1.5.4.1.4 | 1.5.4.2.1 | 1.5.4.2.2 | 1.5.4.2.3 | 1.5.4.2.4 |
| 1.5.4.3.1 | 1.5.4.3.2 | 1.5.4.3.3 | 1.5.4.3.4 | 1.5.4.4.1 | 1.5.4.4.2 | 1.5.4.4.3 | 1.5.4.4.4 |
| 1.5.4.5.1 | 1.5.4.5.2 | 1.5.4.5.3 | 1.5.4.5.4 | 1.5.4.6.1 | 1.5.4.6.2 | 1.5.4.6.3 | 1.5.4.6.4 |
| 1.5.4.7.1 | 1.5.4.7.2 | 1.5.4.7.3 | 1.5.4.7.4 | 1.5.4.8.1 | 1.5.4.8.2 | 1.5.4.8.3 | 1.5.4.8.4 |
| 1.6.1.1.1 | 1.6.1.1.2 | 1.6.1.1.3 | 1.6.1.1.4 | 1.64.2.1 | 1.6.1.2.2 | 1.6.1.2.3 | 1.6.1.2.4 |
| 1.6.1.3.1 | 1.6.1.3.2 | 1.6.1.3.3 | 1.6.1.3.4 | 1.6.1.4.1 | 1.6.1.4.2 | 1.6.1.4.3 | 1.6.1.4.4 |
| 1.6.1.5.1 | 1.6.1.5.2 | 1.6.1.5.3 | 1.6.1.5.4 | 1.6.1.6.1 | 1.6.1.6.2 | 1.6.1.6.3 | 1.6.1.6.4 |
| 1.6.1.7.1 | 1.6.1.7.2 | 1.6.1.7.3 | 1.6.1.7.4 | 1.6.1.8.1 | 1.6.1.8.2 | 1.6.1.8.3 | 1.6.1.8.4 |
| 1.6.2.1.1 | 1.6.2.1.2 | 1.6.2.1.3 | 1.6.2.1.4 | 1.6.2.2.1 | 1.6.2.2.2 | 1.6.2.2.3 | 1.6.2.2.4 |
| 1.6.2.3.1 | 1.6.2.3.2 | 1.6.2.3.3 | 1.6.2.3.4 | 1.6.2.4.1 | 1.6.2.4.2 | 1.6.2.4.3 | 1.6.2.4.4 |
| 1.6.2.5.1 | 1.6.2.5.2 | 1.6.2.5.3 | 1.6.2.5.4 | 1.6.2.6.1 | 1.6.2.6.2 | 1.6.2.6.3 | 1.6.2.6.4 |
| 1.6.2.7.1 | 1.6.2.7.2 | 1.6.2.7.3 | 1.6.2.7.4 | 1.6.2.8.1 | 1.6.2.8.2 | 1.6.2.8.3 | 1.6.2.8.4 |
| 1.6.3.1.1 | 1.6.3.1.2 | 1.6.3.1.3 | 1.6.3.1.4 | 1.6.3.2.1 | 1.6.3.2.2 | 1.6.3.2.3 | 1.6.3.2.4 |
| 1.6.3.3.1 | 1.6.3.3.2 | 1.6.3.3.3 | 1.6.3.3.4 | 1.6.3.4.1 | 1.6.3.4.2 | 1.6.3.4.3 | 1.6.3.4.4 |
| 1.6.3.5.1 | 1.6.3.5.2 | 1.6.3.5.3 | 1.6.3.5.4 | 1.6.3.6.1 | 1.6.3.6.2 | 1.6.3.6.3 | 1.6.3.6.4 |
| 1.6.3.7.1 | 1.6.3.7.2 | 1.6.3.7.3 | 1.6.3.7.4 | 1.6.3.8.1 | 1.6.3.8.2 | 1.6.3.8.3 | 1.6.3.8.4 |
| 1.6.4.1.1 | 1.6.4.1.2 | 1.6.4.1.3 | 1.6.4.1.4 | 1.6.4.2.1 | 1.6.4.2.2 | 1.6.4.2.3 | 16.4.2.4 |
| 1.6.4.3.1 | 1.6.4.3.2 | 1.6.4.3.3 | 1.6.4.3.4 | 1.6.4.4.1 | 1.6.4.4.2 | 1.6.4.4.3 | 1.6.4.4.4 |
| 1.6.4.5.1 | 1.6.4.5.2 | 1.6.4.5.3 | 1.6.4.5.4 | 1.6.4.6.1 | 1.6.4.6.2 | 1.6.4.6.3 | 1.6.4.6.4 |
| 1.6.4.7.1 | 1.6.4.7.2 | 1.6.4.7.3 | 1.6.4.7.4 | 1.6.4.8.1 | 1.6.4.8.2 | 1.6.4.8.3 | 1.6.4.8.4 |
| 1.7.1.1.1 | 1.7.1.1.2 | 1.7.1.1.3 | 1.7.1.1.4 | 1.7.1.2.1 | 1.7.1.2.2 | 1.7.1.2.3 | 1.7.1.2.4 |
| 1.7.1.3.1 | 1.7.1.3.2 | 1.7.1.3.3 | 1.7.1.3.4 | 1.7.1.4.1 | 1.7.1.4.2 | 1.7.1.4.3 | 1.7.1.4.4 |
| 1.7.1.5.1 | 1.7.1.5.2 | 1.7.1.5.3 | 1.7.1.5.4 | 1.7.1.6.1 | 1.7.1.6.2 | 1.7.1.6.3 | 1.7.1.6.4 |
| 1.7.1.7.1 | 1.7.1.7.2 | 1.7.1.7.3 | 1.7.1.7.4 | 1.7.1.8.1 | 1.7.1.8.2 | 1.7.1.8.3 | 1.7.1.8.4 |
| 1.7.2.1.1 | 1.7.2.1.2 | 1.7.2.1.3 | 1.7.2.1.4 | 1.7.2.2.1 | 1.7.2.2.2 | 1.7.2.2.3 | 1.7.2.2.4 |
| 1.7.2.3.1 | 1.7.2.3.2 | 1.7.2.3.3 | 1.7.2.3.4 | 1.7.2.4.1 | 1.7.2.4.2 | 1.7.2.4.3 | 1.7.2.4.4 |
| 1.7.2.5.1 | 1.7.2.5.2 | 4.7.2.5.3 | 1.7.2.5.4 | 1.7.2.6.1 | 1.7.2.6.2 | 1.7.2.6.3 | 1.7.2.6.4 |
| 1.7.2.7.1 | 1.7.2.7.2 | 1.7.2.7.3 | 1.7.2.7.4 | 1.7.2.8.1 | 1.7.2.8.2 | 1.7.2.8.3 | 1.7.2.8.4 |
| 1.7.3.1.1 | 1.7.3.1.2 | 1.7.3.1.3 | 1.7.3.1.4 | 1.7.3.2.1 | 1.7.3.2.2 | 1.7.3.2.3 | 1.7.3.2.4 |
| 1.7.3.3.1 | 1.7.3.3.2 | 1.7.3.3.3 | 1.7.3.3.4 | 1.7.3.4.1 | 1.7.3.4.2 | 1.7.3.4.3 | 1.7.3.4.4 |
| 1.7.3.5.1 | 1.7.3.5.2 | 1.7.3.5.3 | 1.7.3.5.4 | 1.7.3.6.1 | 1.7.3.6.2 | 1.7.3.6.3 | 1.7.3.6.4 |
| 1.7.3.7.1 | 1.7.3.7.2 | 1.7.3.7.3 | 1.7.3.7.4 | 1.7.3.8.1 | 1.7.3.8.2 | 1.7.3.8.3 | 1..7.3.8.4 |
| 1.7.4.1.1 | 1.7.4.1.2 | 1.7.4.1.3 | 1.7.4.1.4 | 1.7.4.2.1 | 1.7.4.2.2 | 1.7.4.2.3 | 1.7.4.2.4 |
| 1.7.4.3.1 | 1.7.4.3.2 | 1.7.4.3.3 | 1.7.4.3.4 | 1.7.4.4.1 | 1.7.4.4.2 | 1.7.4.4.3 | 1.7.4.4.4 |
| 1.7.4.5.1 | 1.7.4.5.2 | 1.7.4.5.3 | 1.7.4.5.4 | 1.7.4.6.1 | 1.7.4.6.2 | 1.7.4.6.3 | 1.7.4.6.4 |
| 1.7.4.7.1 | 1.7.4.7.2 | 1.7.4.7.3 | 1.7.4.7.4 | 1.7.4.8.1 | 1.7.4.8.2 | 1.7.4.8.3 | 1.7.4.8.4 |
| 1.8.1.1.1 | 1.8.1.1.2 | 1.8.1.1.3 | 1.8.1.1.4 | 1.8.1.2.1 | 1.8.1.2.2 | 1.8.1.2.3 | 1.8.1.2.4 |
| 1.8.1.3.1 | 1.8.1.3.2 | 1.8.1.3.3 | 1.8.1.3.4 | 1.8.1.4.1 | 1.8.1.4.2 | 1.8.1.4.3 | 1.8.1.4.4 |
| 1.8.1.5.1 | 1.8.1.5.2 | 1.8.1.5.3 | 1.8.1.5.4 | 1.8.1.6.1 | 1.8.1.6.2 | 1.8.1.6.3 | 1.8.1.6.4 |
| 1.8.1.7.1 | 1.8.1.7.2 | 1.8.1.7.3 | 1.8.1.7.4 | 1.8.1.8.1 | 1.8.1.8.2 | 1.8.1.8.3 | 1.8.1.8.4 |
| 1.8.2.1.1 | 1.8.2.1.2 | 1.8.2.1.3 | 1.8.2.1.4 | 1.8.2.2.1 | 1.8.2.2.2 | 1.8.2.2.3 | 1.8.2.2.4 |
| 1.8.2.3.1 | 1.8.2.3.2 | 1.8.2.3.3 | 1.8.2.3.4 | 1.8.2.4.1 | 1.8.2.4.2 | 1.8.2.4.3 | 1.8.2.4.4 |
| 1.8.2.5.1 | 1.8.2.5.2 | 1.8.2.5.3 | 1.8.2.5.4 | 1.8.2.6.1 | 1.8.2.6.2 | 1.8.2.6.3 | 1.8.2.6.4 |
| 1.8.2.7.1 | 1.8.2.7.2 | 1.8.2.7.3 | 1.8.2.7.4 | 1.8.2.8.1 | 1.8.2.8.2 | 1.8.2.8.3 | 1.8.2.8.4 |
| 1.8.3.1.1 | 1.8.3.1.2 | 1.8.3.1.3 | 1.8.3.1.4 | 1.8.3.2.1 | 1.8.3.2.2 | 1.8.3.2.3 | 1.8.3.2.4 |
| 1.8.3.3.1 | 1.8.3.3.2 | 1.8.3.3.3 | 1.8.3.3.4 | 1.8.3.4.1 | 1.8.3.4.2 | 1.8.3.4.3 | 1.8.3.4.4 |
| 1.8.3.5.1 | 1.8.3.5.2 | 1.8.3.5.3 | 1.8.3.5.4 | 1.8.3.6.1 | 1.8.3.6.2 | 1.8.3.6.3 | 1.8.3.6.4 |
| 1.8.3.7.1 | 1.8.3.7.2 | 1.8.3.7.3 | 1.8.3.7.4 | 1.8.3.8.1 | 1.8.3.8.2 | 1.8.3.8.3 | 1.8.3.8.4 |
| 1.8.4.1.1 | 1.8.4.1.2 | 1.8.4.1.3 | 1.8.4.1.4 | 1.8.4.2.1 | 1.8.4.2.2 | 1.8.4.2.3 | 1.8.4.2.4 |
| 1.8.4.3.1 | 1.8.4.3.2 | 1.8.4.3.3 | 1.8.4.3.4 | 1.8.4.4.1 | 1.8.4.4.2 | 1.8.4.4.3 | 1.8.4.4.4 |
| 1.8.4.5.1 | 1.8.4.5.2 | 1.8.4.5.3 | 1.8.4.5.4 | 1.8.4.6.1 | 1.8.4.6.2 | 1.8.4.6.3 | 1.8.4.6.4 |
| 1.8.4.7.1 | 1.8.4.7.2 | 1.8.4.7.3 | 1.8.4.7.4 | 1.8.4.8.1 | 1.8.4.8.2 | 1.8.4.8.3 | 1.8.4.8.4 |

TABLE 3-continued

| | | | | | | | |
|---|---|---|---|---|---|---|---|
| 2.1.1.1.1 | 2.1.1.1.2 | 2.1.1.1.3 | 2.1.1.1.4 | 2.1.1.2.1 | 2.1.1.2.2 | 2.1.1.2.3 | 2.1.1.2.4 |
| 2.1.1.3.1 | 2.1.1.3.2 | 2.1.1.3.3 | 2.1.1.3.4 | 2.1.1.4.1 | 2.1.1.4.2 | 2.1.1.4.3 | 2.1.1.4.4 |
| 2.1.1.5.1 | 2.1.1.5.2 | 2.1.1.5.3 | 2.1.1.5.4 | 2.1.1.6.1 | 2.1.1.6.2 | 2.1.1.6.3 | 2.1.1.6.4 |
| 2.1.1.7.1 | 2.1.1.7.2 | 2.1.1.7.3 | 2.1.1.7.4 | 2.1.1.8.1 | 2.1.1.8.2 | 2.1.1.8.3 | 2.1.1.8.4 |
| 2.1.2.1.1 | 2.1.2.1.2 | 2.1.2.1.3 | 2.1.2.1.4 | 2.1.2.2.1 | 2.1.2.2.2 | 2.1.2.2.3 | 2.1.2.2.4 |
| 2.1.2.3.1 | 2.1.2.3.2 | 2.1.2.3.3 | 2.1.2.3.4 | 2.1.2.4.1 | 2.1.2.4.2 | 2.1.2.4.3 | 2.1.2.4.4 |
| 2.1.2.5.1 | 2.1.2.5.2 | 2.1.2.5.3 | 2.1.2.5.4 | 2.1.2.6.1 | 2.1.2.6.2 | 2.1.2.6.3 | 2.1.2.6.4 |
| 2.1.2.7.1 | 2.1.2.7.2 | 2.1.2.7.3 | 2.1.2.7.4 | 2.1.2.8.1 | 2.1.2.8.2 | 2.1.2.8.3 | 2.1.2.8.4 |
| 2.1.3.1.1 | 2.1.3.1.2 | 2.1.3.1.3 | 2.1.3.1.4 | 2.1.3.2.1 | 2.1.3.2.2 | 2.1.3.2.3 | 2.1.3.2.4 |
| 2.1.3.3.1 | 2.1.3.3.2 | 2.1.3.3.3 | 2.1.3.3.4 | 2.1.3.4.1 | 2.1.3.4.2 | 2.1.3.4.3 | 2.1.3.4.4 |
| 2.1.3.5.1 | 2.1.3.5.2 | 2.1.3.5.3 | 2.1.3.5.4 | 2.1.3.6.1 | 2.1.3.6.2 | 2.1.3.6.3 | 2.1.3.6.4 |
| 2.1.3.7.1 | 2.1.3.7.2 | 2.1.3.7.3 | 2.1.3.7.4 | 2.1.3.8.1 | 2.1.3.8.2 | 2.1.3.8.3 | 2.1.3.8.4 |
| 2.1.4.1.1 | 2.1.4.1.2 | 2.1.4.1.3 | 2.1.4.1.4 | 2.1.4.2.1 | 2.1.4.2.2 | 2.1.4.2.3 | 2.1.4.2.4 |
| 2.1.4.3.1 | 2.1.4.3.2 | 2.1.4.3.3 | 2.1.4.3.4 | 2.1.4.4.1 | 2.1.4.4.2 | 2.1.4.4.3 | 2.1.4.4.4 |
| 2.1.4.5.1 | 2.1.4.5.2 | 2.1.4.5.3 | 2.1.4.5.4 | 2.1.4.6.1 | 2.1.4.6.2 | 2.1.4.6.3 | 2.1.4.6.4 |
| 2.1.4.7.1 | 2.1.4.7.2 | 2.1.4.7.3 | 2.1.4.7.4 | 2.1.4.8.1 | 2.1.4.8.2 | 2.1.4.8.3 | 2.1.4.8.4 |
| 2.2.1.1.1 | 2.2.1.1.2 | 2.2.1.1.3 | 2.2.1.1.4 | 2.2.1.2.1 | 2.2.1.2.2 | 2.2.1.2.3 | 2.2.1.2.4 |
| 2.2.1.3.1 | 2.2.1.3.2 | 2.2.1.3.3 | 2.2.1.3.4 | 2.2.1.4.1 | 2.2.1.4.2 | 2.2.1.4.3 | 2.2.1.4.4 |
| 2.2.1.5.1 | 2.2.1.5.2 | 2.2.1.5.3 | 2.2.1.5.4 | 2.2.1.6.1 | 2.2.1.6.2 | 2.2.1.6.3 | 2.2.1.6.4 |
| 2.2.1.7.1 | 2.2.1.7.2 | 2.2.1.7.3 | 2.2.1.7.4 | 2.2.1.8.1 | 2.2.1.8.2 | 2.2.1..8.3 | 2.2.1.8.4 |
| 2.2.2.1.1 | 2.2.2.1.2 | 2.2.2.1.3 | 2.2.2.1.4 | 2.2.2.2.1 | 2.2.2.2.2 | 2.2.2.2.3 | 2.2.2.2.4 |
| 2.2.2.3.1 | 2.2.2.3.2 | 2.2.2.3.3 | 2.2.2.3.4 | 2.2.2.4.1 | 2.2.2.4.2 | 2.2.2.4.3 | 2.2.2.4.4 |
| 2.2.2.5.1 | 2.2.2.5.2 | 2.2.2.5.3 | 2.2.2.5.4 | 2.2.2.6.1 | 2.2.2.6.2 | 2.2.2.6.3 | 2.2.2.6.4 |
| 2.2.2.7.1 | 2.2.2.7.2 | 2.2.2.7.3 | 2.2.2.7.4 | 2.2.2.8.1 | 2.2.2.8.2 | 2.2.2.8.3 | 2.2.2.8.4 |
| 2.2.3.1.1 | 2.2.3.1.2 | 2.2.3.1.3 | 2.2.3.1.4 | 2.2.3.2.1 | 2.2.3.2.2 | 2.2.3.2.3 | 2.2.3.2.4 |
| 2.2.3.3.1 | 2.2.3.3.2 | 2.2.3.3.3 | 2.2.3.3.4 | 2.2.3.4.1 | 2.2.3.4.2 | 2.2.3.4.3 | 2.2.3.4.4 |
| 2:2.3.5.1 | 2.2.3.5.2 | 2.2.3.5.3 | 2.2.3.5.4 | 2.2.3.6.1 | 2.2.3.6.2 | 2.2.3.6.3 | 2.2.3.6.4 |
| 2.2.3.7.1 | 2.2.3.7.2 | 2.2.3.7.3 | 2.2.3.7.4 | 2.2.3.8.1 | 2.2.3.8.2 | 2.2.3.8.3 | 2.2.3.8.4 |
| 2.2.4.1.1 | 2.2.4.1.2 | 2.2.4.1.3 | 2.2.4.1.4 | 2.2.4.2.1 | 2.2.4.2.2 | 2.2.4.2.3 | 2.2.4.2.4 |
| 2.2.4.3.1 | 2.2.4.3.2 | 2.2.4.3.3 | 2.2.4.3.4 | 2.2.4.4.1 | 2.2.4.4.2 | 2.2.4.4.3 | 2.2.4.4.4 |
| 2.2.4.5.1 | 2.2.4.5.2 | 2.2.4.5.3 | 2.2.4.5.4 | 2.2.4.6.1 | 2.2.4.6.2 | 2.2.4.6.3 | 2.2.4.6.4 |
| 2.2.4.7.1 | 2.2.4.7.2 | 2.2.4.7.3 | 2.2.4.7.4 | 2.2.4.8.1 | 2.2.4.8.2 | 2.2.4.8.3 | 2.2.4.8.4 |
| 2.3.1.1.1 | 2.3.1.1.2 | 2.3.1.1.3 | 2.3.1.1.4 | 2.3.1.2.1 | 2.3.1.2.2 | 2.3.1.2.3 | 2.3.1.2.4 |
| 2.3.1.3.1 | 2.3.1.3.2 | 2.3.1.3.3 | 2.3.1.3.4 | 2.3.1.4.1 | 2.3.1.4.2 | 2.3.1.4.3 | 2.3.1.4.4 |
| 2.3.1.5.1 | 2.3.1.5.2 | 2.3.1.5.3 | 2.3.1.5.4 | 2.3.1.6.1 | 2.3.1.6.2 | 2.3.1.6.3 | 2.3.1.6.4 |
| 2.3.1.7.1 | 2.3.1.7.2 | 2.3.1.7.3 | 2.3.1.7.4 | 2.3.1.8.1 | 2.3.1.8.2 | 2.3.1.8.3 | 2.3.1.8.4 |
| 2.3.2.1.1 | 2.3.2.1.2 | 2.3.2.1.3 | 2.3.2.1.4 | 2.3.2.2.1 | 2.3.2.2.2 | 2.3.2.2.3 | 2.3.2.2.4 |
| 2.3.2.3.1 | 2.3.2.3.2 | 2.3.2.3.3 | 2.3.2.3.4 | 2.3.2.4.1 | 2.3.2.4.2 | 2.3.2.4.3 | 2.3.2.4.4 |
| 2.3.2.5.1 | 2.3.2.5.2 | 2.3.2.5.3 | 2.3.2.5.4 | 2.3.2.6.1 | 2.3.2.6.2 | 2.3.2.6.3 | 2.3.2.6.4 |
| 2.3.2.7.1 | 2.3.2.7.2 | 2.3.2.7.3 | 2.3.2.7.4 | 2.3.2.8.1 | 2.3.2.8.2 | 2.3.2.8.3 | 2.3.2.8.4 |
| 2.3.3.1.1 | 2:3.3.1.2 | 2.3.3.1.3 | 2.3.3.1.4 | 2.3.3.2.1 | 2.3.3.2.2 | 2.3.3.2.3 | 2.3.3.2.4 |
| 2.3.3.3.1 | 2.3.3.3.2 | 2.3.3.3.3 | 2.3.3.3.4 | 2.3.3.4.1 | 2.3.3.4.2 | 2.3.3.4.3 | 2.3.3.4.4 |
| 2.3.3.5.1 | 2.3.3.5.2 | 2.3.3.5.3 | 2.3.3.5.4 | 2.3.3.6.1 | 2.3.3.6.2 | 2.3.3.6.3 | 2.3.3.6.4 |
| 2.3.3.7.1 | 2.3.3.7.2 | 2.3.3.7.3 | 2.3.3.7.4 | 2.3.3.8.1 | 2.3.3.8.2 | 2.3.3.8.3 | 2.3.3.8.4 |
| 2.3.4.1.1 | 2.3.4.1.2 | 2.3.4.1.3 | 2.3.4.1.4 | 2.3.4.2.1 | 2.3.4.2.2 | 2.3.4.2.3 | 2.3.4.2.4 |
| 2.3.4.3.1 | 2.3.4.3.2 | 2.3.4.3.3 | 2.3.4.3.4 | 2.3.4.4.1 | 2.3.4.4.2 | 2.3.4.4.3 | 2.3.4.4.4 |
| 2.3.4.5.1 | 2.3.4.5.2 | 2.3.4.5.3 | 2.3.4.5.4 | 2.3.4.6.1 | 2.3.4.6.2 | 2.3.4.6.3 | 2.3.4.6.4 |
| 2.3.4.7.1 | 2.3.4.7.2 | 2.3.4.7.3 | 2.3.4.7.4 | 2.3.4.8.1 | 2.3.4.8.2 | 2.3.4.8.3 | 2.3.4.8.4 |
| 2.4.1.1.1 | 2.4.1.1.2 | 2.4.1.1.3 | 2.4.1.1.4 | 2.4.1.2.1 | 2.4.1.2.2 | 2.4.1.2.3 | 2.4.1.2.4 |
| 2.4.1.3.1 | 2.4.1.3.2 | 2.4.1.3.3 | 2.4.1.3.4 | 2.4.1.4.1 | 2.4.1.4.2 | 2.4.1.4.3 | 2.4.1.4.4 |
| 2.4.1.5.1 | 2.4.1.5.2 | 2.4.1.5.3 | 2.4.1.5.4 | 2.4.1.6.1 | 2.4.1.6.2 | 2.4.1.6.3 | 2.4.1.6.4 |
| 2.4.1.7.1 | 2.4.1.7.2 | 2.4.1.7.3 | 2.4.1.7.4 | 2.4.1.8.1 | 2.4.1.8.2 | 2.4.1.8.3 | 2.4.1.8.4 |
| 2.4.2.1.1 | 2.4.2.1.2 | 2.4.2.1.3 | 2.4.2.1.4 | 2.4.2.2.1 | 2.4.2.2.2 | 2.4.2.2.3 | 2.4.2.2.4 |
| 2.4.2.3.1 | 2.4.2.3.2 | 2.4.2.3.3 | 2.4.2.3.4 | 2.4.2.4.1 | 2.4.2.4.2 | 2.4.2.4.3 | 2.4.2.4.4 |
| 2.4.2.5.1 | 2.4.2.5.2 | 2.4.2.5.3 | 2.4.2.5.4 | 2.4.2.6.1 | 2.4.2.6.2 | 2.4.2.6.3 | 2.4.2.6.4 |
| 2.4.2.7.1 | 2.4.2.7.2 | 2.4.2.7.3 | 2.4.2.7.4 | 2.4.2.8.1 | 2.4.2.8.2 | 2.4.2.8.3 | 2.4.2.8.4 |
| 2.4.3.1.1 | 2.4.3.1.2 | 2.4.3.1.3 | 2.4.3.1.4 | 2.4.3.2.1 | 2.4.3.2.2 | 2.4.3.2.3 | 2.4.3.2.4 |
| 2.4.3.3.1 | 2.4.3.3.2 | 2.4.3.3.3 | 2.4.3.3.4 | 2.4.3.4.1 | 2.4.3.4.2 | 2.4.3.4.3 | 2.4.3.4.4 |
| 2.4.3.5.1 | 2.4.3.5.2 | 2.4.3.5.3 | 2.4.3.5.4 | 2.4.3.6.1 | 2.4.3.6.2 | 2.4.3.6.3 | 2.4.3.6.4 |
| 2.4.3.7.1 | 2.4.3.7.2 | 2.4.3.7.3 | 2.4.3.7.4 | 2.4.3.8.1 | 2.4.3.8.2 | 2.4.3.8.3 | 2.4.3.8.4 |
| 2.4.4.1.1 | 2.4.4.1.2 | 2.4.4.1.3 | 2.4.4.1.4 | 2.4.4.2.1 | 2.4.4.2.2 | 2.4.4.2.3 | 2.4.4.2.4 |
| 2.4.4.3.1 | 2.4.4.3.2 | 2.4.4.3.3 | 2.4.4.3.4 | 2.4.4.4.1 | 2.4.4.4.2 | 2.4.4.4.3 | 2.4.4.4.4 |
| 2.4.4.5.1 | 2.4.4.5.2 | 2.4.4.5.3 | 2.4.4.5.4 | 2.4.4.6.1 | 2.4.4.6.2 | 2.4.4.6.3 | 2.4.4.6.4 |
| 2.4.4.7.1 | 2.4.4.7.2 | 2.4.4.7.3 | 2.4.4.7.4 | 2.4.4.8.1 | 2.4.4.8.2 | 2.4.4.8.3 | 2.4.4.8.4 |
| 2.5.1.1.1 | 2.5.1.1.2 | 2.5.1.1.3 | 2.5.1.1.4 | 2.5.1.2.1 | 2.5.1.2.2 | 2.5.1.2.3 | 2.5.1.2.4 |
| 2.5.1.3.1 | 2.5.1.3.2 | 2.5.1.3.3 | 2.5.1.3.4 | 2.5.1.4.1 | 2.5.1.4.2 | 2.5.1.4.3 | 2.5.1.4.4 |
| 2.5.1.5.1 | 2.5.1.5.2 | 2.5.1.5.3 | 2.5.1.5.4 | 2.5.1.6.1 | 2.5.1.6.2 | 2.5.1.6.3 | 2.5.1.6.4 |
| 2.5.1.7.1 | 2.5.1.7.2 | 2.5.1.7.3 | 2.5.1.7.4 | 2.5.1.8.1 | 2.5.1.8.2 | 2.5.1.8.3 | 2.5.1.8.4 |
| 2.5.2.1.1 | 2.5.2.1.2 | 2.5.2.1.3 | 2.5.2.1.4 | 2.5.2.2.1 | 2.5.2.2.2 | 2.5.2.2.3 | 2.5.2.2.4 |
| 2.5.2.3.1 | 2.5.2.3.2 | 2.5.2.3.3 | 2.5.2.3.4 | 2.5.2.4.1 | 2.5.2.4.2 | 2.5.2.4.3 | 2.5.2.4.4 |
| 2.5.2.5.1 | 2.5.2.5.2 | 2.5.2.5.3 | 2.5.2.5.4 | 2.5.2.6.1 | 2.5.2.6.2 | 2.5.2.6.3 | 2.5.2.6.4 |
| 2.5.2.7.1 | 2.5.2.7.2 | 2.5.2.7.3 | 2.5.2.7.4 | 2.5.2.8.1 | 2.5.2.8.2 | 2.5.2.8.3 | 2.5.2.8.4 |
| 2.5.3.1.1 | 2.5.3.1.2 | 2.5.3.1.3 | 2.5.3.1.4 | 2.5.3.2.1 | 2.5.3.2.2 | 2.5.3.2.3 | 2.5.3.2.4 |
| 2.5.3.3.1 | 2.5.3.3.2 | 2.5.3.3.3 | 2.5.3.3.4 | 2.5.3.4.1 | 2.5.3.4.2 | 2.5.3.4.3 | 2.5.3.4.4 |
| 2.5.3.5.1 | 2.5.3.5.2 | 2.5.3.5.3 | 2.5.3.5.4 | 2.5.3.6.1 | 2.5.3.6.2 | 2.5.3.6.3 | 2.5.3.6.4 |
| 2.5.3.7.1 | 2.5.3.7.2 | 2.5.3.7.3 | 2.5.3.7.4 | 2.5.3.8.1 | 2.5.3.8.2 | 2.5.3.8.3 | 2.5.3.8.4 |
| 2.5.4.1.1 | 2.5.4.1.2 | .2.5.4.1.3 | 2.5.4.1.4 | 2.5.4.2.1 | 2.5.4.2.2 | 2.5.4.2.3 | 2.5.4.2.4 |
| 2.5.4.3.1 | 2.5.4.3.2 | 2.5.4.3.3 | 2.5.4.3.4 | 2.5.4.4.1 | 2.5.4.4.2 | 2.5.4.4.3 | 2.5.4.4.4 |
| 2.5.4.5.1 | 2.5.4.5.2 | 2.5.4.5.3 | 2.5.4.5.4 | 2.5.4.6.1 | 2.5.4.6.2 | 2.5.4.6.3 | 2.5.4.6.4 |

TABLE 3-continued

| | | | | | | | |
|---|---|---|---|---|---|---|---|
| 2.5.4.7.1 | 2.5.4.7.2 | 2.5.4.7.3 | 2.5.4.7.4 | 2.5.4.8.1 | 2.5.4.8.2 | 2.5.4.8.3 | 2.5.4.8.4 |
| 2.6.1.1.1 | 2.6.1.1.2 | 2.6.1.1.3 | 2.6.1.1.4 | 2.6.1.2.1 | 2.6.1.2.2 | 2.6.1.2.3 | 2.6.1.2.4 |
| 2.6.1.3.1 | 2.6.1.3.2 | 2.6.1.3.3 | 2.6.1.3.4 | 2.6.1.4.1 | 2.6.1.4.2 | 2.6.1.4.3 | 2.6.1.4.4 |
| 2.6.1.5.1 | 2.6.1.5.2 | 2.6.1.5.3 | 2.6.1.5.4 | 2.6.1.6.1 | 2.6.1.6.2 | 2.6.1.6.3 | 2.6.1.6.4 |
| 2.6.1.7.1 | 2.6.1.7.2 | 2.6.1.7.3 | 2.6.1.7.4 | 2.6.1.8.1 | 2.6.1.8.2 | 2.6.1.8.3 | 2.6.1.8.4 |
| 2.6.2.1.1 | 2.6.2.1.2 | 2.6.2.1.3 | 2.6.2.1.4 | 2.6.2.2.1 | 2.6.2.2.2 | 2.6.2.2.3 | 2.6.2.2.4 |
| 2.6.2.3.1 | 2.6.2.3.2 | 2.6.2.3.3 | 2.6.2.3.4 | 2.6.2.4.1 | 2.6.2.4.2 | 2.6.2.4.3 | 2.6.2.4.4 |
| 2.6.2.5.1 | 2.6.2.5.2 | 2.6.2.5.3 | 2.6.2.5.4 | 2.6.2.6.1 | 2.6.2.6.2 | 2.6.2.6.3 | 2.6.2.6.4 |
| 2.6.2.7.1 | 2.6.2.7.2 | 2.6.2.7.3 | 2.6.2.7.4 | 2.6.2.8.1 | 2.6.2.8.2 | 2.6.2.8.3 | 2.6.2.8.4 |
| 2.6.3.1.1 | 2.6.3.1.2 | 2.6.3.1.3 | 2.6.3.1.4 | 2.6.3.2.1 | 2.6.3.2.2 | 2.6.3.2.3 | 2.6.3.2.4 |
| 2.6.3.3.1 | 2.6.3.3.2 | 2.6.3.3.3 | 2.6.3.3.4 | 2.6.3.4.1 | 2.6.3.4.2 | 2.6.3.4.3 | 2.6.3.4.4 |
| 2.6.3.5.1 | 2.6.3.5.2 | 2.6.3.5.3 | 2.6.3.5.4 | 2.6.3.6.1 | 2.6.3.6.2 | 2.6.3.6.3 | 2.6.3.6.4 |
| 2.6.3.7.1 | 2.6.3.7.2 | 2.6.3.7.3 | 2.6.3.7.4 | 2.6.3.8.1 | 2.6.3.8.2 | 2.6.3.8.3 | 2.6.3.8.4 |
| 2.6.4.1.1 | 2.6.4.1.2 | 2.6.4.1.3 | 2.6.4.1.4 | 2.6.4.2.1 | 2..6.4.2.2 | 2.6.4.2.3 | 2.6.4.2.4 |
| 2.6.4.3.1 | 2.6.4.3.2 | 2.6.4.3.3 | 2.6.4.3.4 | 2.6.4.4.1 | 2.6.4.4.2 | 2.6.4.4.3 | 2.6.4.4.4 |
| 2.6.4.5.1 | 2.6.4.5.2 | 2.6.4.5.3 | 2.6.4.5.4 | 2.6.4.6.1 | 2.6.4.6.2 | 2.6.4.6.3 | 2.6.4.6.4 |
| 2.6.4.7.1 | 2.6.4.7.2 | 2.6.4.7.3 | 2.6.4.7.4 | 2.6.4.8.1 | 2.6.4.8.2 | 2.6.4.8.3 | 2.6.4.8.4 |
| 2.7.1.1.1 | 2.7.1.1.2 | 2.7.1.1.3 | 2.7.1.1.4 | 2.7.1.2.1 | 2.7.1.2.2 | 2.7.1.2.3 | 2.7.1.2.4 |
| 2.7.1.3.1 | 2.7.1.3.2 | 2.7.1.3.3 | 2.7.1.3.4 | 2.7.1.4.1 | 2.7.1.4.2 | 2.7.1.4.3 | 2.7.1.4.4 |
| 2.7.1.5.1 | 2.7.1.5.2 | 2.7.1.5.3 | 2.7.1.5.4 | 2.7.1.6.1 | 2.7.1.6.2 | 2.7.1.6.3 | 2.7.1.6.4 |
| 2.7.1.7.1 | 2.7.1.7.2 | 2.7.1.7.3 | 2.7.1.7.4 | 2.7.1.8.1 | 2.7.1.8.2 | 2.7.1.8.3 | 2.7.1.8.4 |
| 2.7.2.1.1 | 2.7.2.1.2 | 2.7.2.1.3 | 2.7.2.1.4 | 2.7.2.2.1 | 2.7.2.2.2 | 2.7.2.2.3 | 2.7.2.2.4 |
| 2.7.2.3.1 | 2.7.2.3.2 | 2.7.2.3.3 | 2.7.2.3.4 | 2 7.2.4.1 | 2.7.2.4.2 | 2.7.2.4.3 | 2.7.2.4.4 |
| 2.7.2.5.1 | 2.7.2.5.2 | 2.7.2.5.3 | 2.7.2.5.4 | 2.7.2.6.1 | 2.7.2.6.2 | 2.7.2.6.3 | 2.7.2.6.4 |
| 2.7.2.7.1 | 2.7.2.7.2 | 2.7.2.7.3 | 2.7.2.7.4 | 2.7.2.8.1 | 2.7.2.8.2 | 2.7.2.8.3 | 2.7.2.8.4 |
| 2.7.3.1.1 | 2.7.3.1.2 | 2.7.3.1.3 | 2.7.3.1.4 | 2.7.3.2.1 | 2.7.3.2.2 | 2.7.3.2.3 | 2.7.3.2.4 |
| 2.7.3.3.1 | 2.7.3.3.2 | 2.7.3.3.3 | 2.7.3.3.4 | 2.7.3.4.1 | 2.7.3.4.2 | 2.7.3.4.3 | 2.7.3.4.4 |
| 2.7.3.5.1 | 2.7.3.5.2 | 2.7.3.5.3 | 2.7.3.5.4 | 2.7.3.6.1 | 2.7.3.6.2 | 2.7.3.6.3 | 2.7.3.6.4 |
| 2.7.3.7.1 | 2.7.3.7.2 | 2.7.3.7.3 | 2.7.3.7.4 | 2.7.3.8.1 | 2.7.3.8.2 | 2.7.3.8.3 | 2.7.3.8.4 |
| 2.7.4.1.1 | 2.7.4.1.2 | 2.7.4.1.3 | 2.7.4.1.4 | 2.7.4.2.1 | 2.7.4.2.2 | 2.7.4.2.3 | 2.7.4.2.4 |
| 2.7.4.3.1 | 2.7.4.3.2 | 2.7.4.3.3 | 2.7.4.3.4 | 2.7.4.4.1 | 2.7.4.4.2 | 2.7.4.4.3 | 2.7.4.4.4 |
| 2.7.4.5.1 | 2.7.4.5.2 | 2.7.4.5.3 | 2.7.4.5.4 | 2.7.4.6.1 | 2.7.4.6.2 | 2.7.4.6.3 | 2.7.4.6.4 |
| 2.7.4.7.1 | 2.7.4.7.2 | 2.7.4.7.3 | 2.7.4.7.4 | 2.7.4.8.1 | 2.7.4.8.2 | 2.7.4.8.3 | 2.7.4.8.4 |
| 2.8.1.1.1 | 2.8.1.1.2 | 2.8.1.1.3 | 2.8.1.1.4 | 2.8.1.2.1 | 2.8.1.2.2 | 2.8.1.2.3 | 2.8.1.2.4 |
| 2.8.1.3.1 | 2.8.1.3.2 | 2.8.1.3.3 | 2.8.1.3.4 | 2.8.1.4.1 | 2.8.1.4.2 | 2.8.1.4.3 | 2.8.1.4.4 |
| 2.8.1.5.1 | 2.8.1.5.2 | 2.8.1.5.3 | 2.8.1.5.4 | 2.8.1.6.1 | 2.8.1.6.2 | 2.8.1.6.3 | 2.8.1.6.4 |
| 2.8.1.7.1 | 2.8.1.7.2 | 2.8.1.7.3 | 2.8.1.7.4 | 2.8.1.8.1 | 2.8.1.8.2 | 2.8.1.8.3 | 2.8.1.8.4 |
| 2.8.2.1.1 | 2.8.2.1.2 | 2.8.2.1.3 | 2.8.2.1.4 | 2.8.2.2.1 | 2.8.2.2.2 | 2.8.2.2.3 | 2.8.2.2.4 |
| 2.8.2.3.1 | 2.8.2.3.2 | 2.8.2.3.3 | 2.8.2.3.4 | 2.8.2.4.1 | 2.8.2.4.2 | 2.8.2.4.3 | 2.8.2.4.4 |
| 2.8.2.5.1 | 2.8.2.5.2 | 2.8.2.5.3 | 2.8.2.5.4 | 2.8.2.6.1 | 2.8.2.6.2 | 2.8.2.6.3 | 2.8.2.6.4 |
| 2.8.2.7.1 | 2.8.2.7.2 | 2.8.2.7.3 | 2.8.2.7.4 | 2.8.2.8.1 | 2.8.2.8.2 | 2.8.2.8.3 | 2.8.2.8.4 |
| 2.8.3.1.1 | 2.8.3.1.2 | 2.8.3.1.3 | 2.8.3.1.4 | 2.8.3.2.1 | 2.8.3.2.2 | 2.8.3.2.3 | 2.8.3.2.4 |
| 2.8.3.3.1 | 2.8.3.3.2 | 2.8.3.3.3 | 2.8.3.3.4 | 2.8.3.4.1 | 2.8.3.4.2 | 2.8.3.4.3 | 2.8.3.4.4 |
| 2.8.3.5.1 | 2.8.3.5.2 | 2.8.3.5.3 | 2.8.3.5.4 | 2.8.3.6.1 | 2.8.3.6.2 | 2.8.3.6.3 | 2.8.3.6.4 |
| 2.8.3.7.1 | 2.8.3.7.2 | 2.8.3.7.3 | 2.8.3.7.4 | 2.8.3.8.1 | 2.8.3.8.2 | 2.8.3.8.3 | 2.8.3.8.4 |
| 2.8.4.1.1 | 2.8.4.1.2 | 2.8.4.1.3 | 2.8.4.1.4 | 2.8.4.2.1 | 2.8.4.2.2 | 2.8.4.2.3 | 2.8.4.2.4 |
| 2.8.4.3.1 | 2.8.4.3.2 | 2.8.4.3.3 | 2.8.4.3.4 | 2.8.4.4.1 | 2.8.4.4.2 | 2.8.4.4.3 | 2.8.4.4.4 |
| 2.8.4.5.1 | 2.8.4.5.2 | 2.8.4.5.3 | 2.8.4.5.4 | 2.8.4.6.1 | 2.8.4.6.2 | 2.8.4.6.3 | 2.8.4.6.4 |
| 2.8.4.7.1 | 2.8.4.7.2 | 2.8.4.7.3 | 2.8.4.7.4 | 2.8.4.8.1 | 2.8.4.8.2 | 2.8.4.8.3 | 2.8.4.8.4 |
| 3.1.1.1.1 | 3.1.1.1.2 | 3.1.1.1.3 | 3.1.1.1.4 | 3.1.1.2.1 | 3.1.1.2.2 | 3.1.1.2.3 | 3.1.1.2.4 |
| 3.1.1.3.1 | 3.1.1.3.2 | 3.1.1.3.3 | 3.1.1.3.4 | 3.1.1.4.1 | 3.1.1.4.2 | 3.1.1.4.3 | 3.1.1.4.4 |
| 3.1.1.5.1 | 3.1.1.5.2 | 3.1.1.5.3 | 3.1.1.5.4 | 3.1.1.6.1 | 3.1.1.6.2 | 3.1.1.6.3 | 3.1.1.6.4 |
| 3.1.1.7.1 | 3.1.1.7.2 | 3.1.1.7.3 | 3.1.1.7.4 | 3.1.1.8.1 | 3.1.1.8.2 | 3.1.1.8.3 | 3.1.1.8.4 |
| 3.1.2.1.1 | 3.1.2.1.2 | 3.1.2.1.3 | 3.1.2.1.4 | 3.1.2.2.1 | 3.1.2.2.2 | 3.1.2.2.3 | 3.1.2.2.4 |
| 3.1.2.3.1 | 3.1.2.3.2 | 3.1.2.3.3 | 3.1.2.3.4 | 3.1.2.4.1 | 3.1.2.4.2 | 3.1.2.4.3 | 3.1.2.4.4 |
| 3.1.2.5.1 | 3.1.2.5.2 | 3.1.2.5.3 | 3.1.2.5.4 | 3.1.2.6.1 | 3.1.2.6.2 | 3.1.2.6.3 | 3.1.2.6.4 |
| 3.1.2.7.1 | 3.1.2.7.2 | 3.1.2.7.3 | 3.1.2.7.4 | 3.1.2.8.1 | 3.1.2.8.2 | 3.1.2.8.3 | 3.1.2.8.4 |
| 3.1.3.1.1 | 3.1.3.1.2 | 3.1.3.1.3 | 3.1.3.1.4 | 3.1.3.2.1 | 3.1.3.2.2 | 3.1.3.2.3 | 3.1.3.2.4 |
| 3.1.3.3.1 | 3.1.3.3.2 | 3.1.3.3.3 | 3.1.3.3.4 | 3.1.3.4.1 | 3.1.3.4.2 | 3.1.3.4.3 | 3.1.3.4.4 |
| 3.1.3.5.1 | 3.1.3.5.2 | 3.1.3.5.3 | 3.1.3.5.4 | 3.1.3.6.1 | 3.1.3.6.2 | 3.1.3.6.3 | 3.1.3.6.4 |
| 3.1.3.7.1 | 3.1.3.7.2 | 3.1.3.7.3 | 3.1.3.7.4 | 3.1.3.8.1 | 3.1.3.8.2 | 3.1.3.8.3 | 3.1.3.8.4 |
| 3.1.4.1.1 | 3.1.4.1.2 | 3.1.4.1.3 | 3.1.4.1.4 | 3.1.4.2.1 | 3.1.4.2.2 | 3.1.4.2.3 | 3.1.4.2.4 |
| 3.1.4.3.1 | 3.1.4.3.2 | 3.1.4.3.3 | 3.1.4.3.4 | 3.1.4.4.1 | 3.1.4.4.2 | 3.1.4.4.3 | 3.1.4.4.4 |
| 3.1.4.5.1 | 3.1.4.5.2 | 3.1.4.5.3 | 3.1.4.5.4 | 3.1.4.6.1 | 3.1.4.6.2 | 3.1.4.6.3 | 3.1.4.6.4 |
| 3.1.4.7.1 | 3.1.4.7.2 | 3.1.4.7.3 | 3.1.4.7.4 | 3.1.4.8.1 | 3.1.4.8.2 | 3.1.4.8.3 | 3.1.4.8.4 |
| 3.2.1.1.1 | 3.2.1.1.2 | 3.2.1.1.3 | 3.2.1.1.4 | 3.2.1.2.1 | 3.2.1.2.2 | 3.2.1.2.3 | 3.2.1.2.4 |
| 3.2.1.3.1 | 3.2.1.3.2 | 3.2.1.3.3 | 3.2.1.3.4 | 3.2.1.4.1 | 3.2.1.4.2 | 3.2.1.4.3 | 3.2.1.4.4 |
| 3.2.1.5.1 | 3.2.1.5.2 | 3.2.1.5.3 | 3.2.1.5.4 | 3.2.1.6.1 | 3.2.1.6.2 | 3.2.1.6.3 | 3.2.1.6.4 |
| 3.2.1.7.1 | 3.2.1.7.2 | 3.2.1.7.3 | 3.2.1.7.4 | 3.2.1.8.1 | 3.2.1.8.2 | 3.2.1.8.3 | 3.2.1.8.4 |
| 3.2.2.1.1 | 3.2.2.1.2 | 3.2.2.1.3 | 3.2.2.1.4 | 3.2.2.2.1 | 3.2.2.2.2 | 3.2.2.2.3 | 3.2.2.2.4 |
| 3.2.2.3.1 | 3.Z.2.3.2 | 3.2.2.3.3 | 3.2.2.3.4 | 3.2.2.4.1 | 3.2.2.4.2 | 3.2.2.4.3 | 3.2.2.4.4 |
| 3.2.2.5.1 | 3.2.2.5.2 | 3.2.2.5.3 | 3.2.2.5.4 | 3.2.2.6.1 | 3.2.2.6.2 | 3.2.2.6.3 | 3.2.2.6.4 |
| 3.2.2.7.1 | 3.2.2.7.2 | 3.2.2.7.3 | 3.2.2.7.4 | 3.2.2.8.1 | 3.2.2.8.2 | 3.2.2.8.3 | 3.2.2.8.4 |
| 3.2.3.1.1 | 3.2.3.1.2 | 3.2.3.1.3 | 3.2.3.1.4 | 3.2.3.2.1 | 3.2.3.2.2 | 3.2.3.2.3 | 3.2.3.2.4 |
| 3.2.3.3.1 | 3.2.3.3.2 | 3.2.3.3.3 | 3.2.3.3.4 | 3.2.3.4.1 | 3.2.3.4.2 | 3.2.3.4.3 | 3.2.3.4.4 |
| 3.2.3.5.1 | 3.2.3.5.2 | 3.2.3.5.3 | 3.2.3.5.4 | 3.2.3.6.1 | 3.2.3.6.2 | 3.2.3.6.3 | 3.2.3.6.4 |
| 3.2.3.7.1 | 3.2.3.7.2 | 3.2.3.7.3 | 3.2.3.7.4 | 3.2.3.8.1 | 3.2.3.8.2 | 3.2.3.8.3 | 3.2.3.8.4 |
| 3.2.4.1.1 | 3.2.4.1.2 | 3.2.4.1.3 | 3.2.4.1.4 | 3.2.4.2.1 | 3.2.4.2.2 | 3.2.4.2.3 | 3.2.4.2.4 |
| 3.2.4.3.1 | 3.2.4.3.2 | 3.2.4.3.3 | 3.2.4.3.4 | 3.2.4.4.1 | 3.2.4.4.2 | 3.2.4.4.3 | 3.2.4.4.4 |

TABLE 3-continued

| | | | | | | | |
|---|---|---|---|---|---|---|---|
| 3.2.4.5.1 | 3.2.4.5.2 | 3.2.4.5.3 | 3.2.4.5.4 | 3.2.4.6.1 | 3.2.4.6.2 | 3.2.4.6.3 | 3.2.4.6.4 |
| 3.2.4.7.1 | 3.2.4.7.2 | 3.2.4.7.3 | 3.2.4.7.4 | 3.2.4.8.1 | 3.2.4.8.2 | 3.2.4.8.3 | 3.2.4.8.4 |
| 3.3.1.1.1 | 3.3.1.1.2 | 3.3.1.1.3 | 3.3.1.1.4 | 3.3.1.2.1 | 3.3.1.2.2 | 3.3.1.2.3 | 3.3.1.2.4 |
| 3.3.1.3.1 | 3.3.1.3.2 | 3.3.1.3.3 | 3.3.1.3.4 | 3.3.1.4.1 | 3.3.1.4.2 | 3.3.1.4.3 | 3.3.1.4.4 |
| 3.3.1.5.1 | 3.3.1.5.2 | 3.3.1.5.3 | 3.3.1.5.4 | 3.3.1.6.1 | 3.3.1.6.2 | 3.3.1.6.3 | 3.3.1.6.4 |
| 3.3.1.7.1 | 3.3.1.7.2 | 3.3.1.7.3 | 3.3.1.7.4 | 3.3.1.8.1 | 3.3.1.8.2 | 3.3.1.8.3 | 3.3.1.8.4 |
| 3.3.2.1.1 | 3.3.2.1.2 | 3.3.2.1.3 | 3.3.2.1.4 | 3.3.2.2.1 | 3.3.2.2.2 | 3.3.2.2.3 | 3.3.2.2.4 |
| 3.3.2.3.1 | 3.3.2.3.2 | 3.3.2.3.3 | 3.3.2.3.4 | 3.3.2.4.1 | 3.3.2.4.2 | 3.3.2.4.3 | 3.3.2.4.4 |
| 3.3.2.5.1 | 3.3.2.5.2 | 3.3.2.5.3 | 3.3.2.5.4 | 3.3.2.6.1 | 3.3.2.6.2 | 3.3.2.6.3 | 3.3.2.6.4 |
| 3.3.2.7.1 | 323.2.7.2 | 3.3.2.7.3 | 3.3.2.7.4 | 3.3.2.8.1 | 3.3.2.8.2 | 3.3.2.8.3 | 3.3.2.8.4 |
| 3.3.3.1.1 | 3.3.3.1.2 | 3.3.3.1.3 | 3.3.3.1.4 | 3.3.3.2.1 | 3.3.3.2.2 | 3.3.3.2.3 | 3.3.3.2.4 |
| 3.3.3.3.1 | 3.3.3.3.2 | 3.3.3.3.3 | 3.3.3.3.4 | 3.3.3.4.1 | 3.3.3.4.2 | 3.3.3.4.3 | 3.3.3.4.4 |
| 3.3.3.5.1 | 3.3.3.5.2 | 3.3.3.5.3 | 3.3.3.5.4 | 3.3.3.6.1 | 3.3.3.6.2 | 3.3.3.6.3 | 3.3.3.6.4 |
| 3.3.3.7.1 | 3.3.3.7.2 | 3.3.3.7.3 | 3.3.3.7.4 | 3.3.3.8.1 | 3.3.3.8.2 | 3.3.3.8.3 | 3.3.3.8.4 |
| 3.3.4.1.1 | 3.3.4.1.2 | 3.3.4.1.3 | 3.3.4.1.4 | 3.3.4.2.1 | 3.3.4.2.2 | 3.3.4.2.3 | 3.3.4.2.4 |
| 3.3.4.3.1 | 3.3.4.3.2 | 3.3.4.3.3 | 3.3.4.3.4 | 3.3.4.4.1 | 3.3.4.4.2 | 3.3.4.4.3 | 3.3.4.4.4 |
| 3.3.4.5.1 | 3.3.4.5.2 | 3.3.4.5.3 | 3.3.4.5.4 | 3.3.4.6.1 | 3.3.4.6.2 | 3.3.4.6.3 | 3.3.4.6.4 |
| 3.3.4.7.1 | 3.3.4.7.2 | 3.3.4.7.3 | 3.3.4.7.4 | 3.3.4.8.1 | 3.3.4.8.2 | 3.3.4.8.3 | 3.3.4.8.4 |
| 3.4.1.1.1 | 3.4.1.1.2 | 3.4.1.1.3 | 3.4.1.1.4 | 3.4.1.2.1 | 3.4.1.2.2 | 3.4.1.2.3 | 3.4.1.2.4 |
| 3.4.1.3.1 | 3.4.1.3.2 | 3.4.1.3.3 | 3.4.1.3.4 | 3.4.1.4.1 | 3.4.1.4.2 | 3.4.1.4.3 | 3.4.1.4.4 |
| 3.4.1.5.1 | 3.4.1.5.2 | 3.4.1.5.3 | 3.4.1.5.4 | 3.4.1.6.1 | 3.4.1.6.2 | 3.4.1.6.3 | 3.4.1.6.4 |
| 3.4.1.7.1 | 3.4.1.7.2 | 3.4.1.7.3 | 3.4.1.7.4 | 3.4.1.8.1 | 3.4.1.8.2 | 3.4.1.8.3 | 3.4.1.8.4 |
| 3.4.2.1.1 | 3.4.2.1.2 | 3.4.2.1.3 | 3.4.2.1.4 | 3.4.2.2.1 | 3.4.2.2.2 | 3.4.2.2.3 | 3.4.2.2.4 |
| 3.4.2.3.1 | 3.4.2.3.2 | 3.4.2.3.3 | 3.4.2.3.4 | 3.4.2.4.1 | 3.4.2.4.2 | 3.4.2.4.3 | 3.4.2.4.4 |
| 3.4.2.5.1 | 3.4.2.5.2 | 3.4.2.5.3 | 3.4.2.5.4 | 3.4.2.6.1 | 3.4.2.6.2 | 3.4.2.6.3 | 3.4.2.6.4 |
| 3.4.2.7.1 | 3.4.2.7.2 | 3.4.2.7.3 | 3.4.2.7.4 | 3.4.2.8.1 | 3.4.2.8.2 | 3.4.2.8.3 | 3.4.2.8.4 |
| 3.4.3.1.1 | 3.4.3.1.2 | 3.4.3.1.3 | 3.4.3.1.4 | 3.4.3.2.1 | 3.4.3.2.2 | 3.4.3.2.3 | 3.4.3.2.4 |
| 3.4.3.3.1 | 3.4.3.3.2 | 3.4.3.3.3 | 3.4.3.3.4 | 3.4.3.4.1 | 3.4.3.4.2 | 3.4.3.4.3 | 3.4.3.4.4 |
| 3.4.3.5.1 | 3.4.3.5.2 | 3.4.3.5.3 | 3.4.3.5.4 | 3.4.3.6.1 | 3.4.3.6.2 | 3.4.3.6.3 | 3.4.3.6.4 |
| 3.4.3.7.1 | 3.4.3.7.2 | 3.4.3.7.3 | 3.4.3.7.4 | 3.4.3.8.1 | 3.4.3.8.2 | 3.4.3.8.3 | 3.4.3.8.4 |
| 3.4.4.1.1 | 3.4.4.1.2 | 3.4.4.1.3 | 3.4.4.1.4 | 3.4.4.2.1 | 3.4.4.2.2 | 3.4.4.2.3 | 3.4.4.2.4 |
| 3.4.4.3.1 | 3.4.4.3.2 | 3.4.4.3.3 | 3.4.4.3.4 | 3.4.4.4.1 | 3.4.4.4.2 | 3.4.4.4.3 | 3.4.4.4.4 |
| 3.4.4.5.1 | 3.4.4.5.2 | 3.4.4.5.3 | 3.4.4.5.4 | 3.4.4.6.1 | 3.4.4.6.2 | 3.4.4.6.3 | 3.4.4.6.4 |
| 3.4.4.7.1 | 3.4.4.7.2 | 3.4.4.7.3 | 3.4.4.7.4 | 3.4.4.8.1 | 3.4.4.8.2 | 3.4.4.8.3 | 3.4.4.8.4 |
| 3.5.1.1.1 | 3.5.1.1.2 | 3.5.1.1.3 | 3.5.1.1.4 | 3.5.1.2.1 | 3.5.1.2.2 | 3..5.1.2.3 | 3.5.1.2.4 |
| 3.5.1.3.1 | 3.5.1.3.2 | 3.5.1.3.3 | 3.5.1.3.4 | 3.5.1.4.1 | 3.5.1.4.2 | 3.5.1.4.3 | 3.5.1.4.4 |
| 3.5.1.5.1 | 3.5.1.5.2 | 3.5.1.5.3 | 3.5.1.5.4 | 3.5.1.6.1 | 3.5.1.6.2 | 3.5.1.6.3 | 3.5.1.6.4 |
| 3.5.1.7.1 | 3.5.1.7.2 | 3.5.1.7.3 | 3.5.1.7.4 | 3.5.1.8.1 | 3.5.1.8.2 | 3.5.1.8.3 | 3.5.1.8.4 |
| 3.5.2.1.1 | 3.5.2.1.2 | 3.5.2.1.3 | 3.5.2.1.4 | 3.5.2.2.1 | 3.5.2.2.2 | 3.5.2.2.3 | 3.5.2.2.4 |
| 3.5.2.3.1 | 3.5.2.3.2 | 3.5.2.3.3 | 3.5.2.3.4 | 3.5.2.4.1 | 3.5.2.4.2 | 3.5.2.4.3 | 3.5.2.4.4 |
| 3.5.2.5.1 | 3.5.2.5.2 | 3.5.2.5.3 | 3.5.2.5.4 | 3.5.2.6.1 | 3.5.2.6.2 | 3.5.2.6.3 | 3.5.2.6.4 |
| 3.5.2.7.1 | 3.5.2.7.2 | 3.5.2.7.3 | 3.5.2.7.4 | 3.5.2.8.1 | 3.5.2.8.2 | 3.5.2.8.3 | 3.5.2.8.4 |
| 3.5.3.1.1 | 3.5.3.1.2 | 3.5.3.1.3 | 3.5.3.1.4 | 3.5.3.2.1 | 3.5.3.2.2 | 3.5.3.2.3 | 3.5.3.2.4 |
| 3.5.3.3.1 | 3.5.3.3.2 | 3.5.3.3.3 | 3.5.3.3.4 | 3.5.3.4.1 | 3.5.3.4.2 | 3.5.3.4.3 | 3.5.3.4.4 |
| 3.5.3.5.1 | 3.5.3.5.2 | 3.5.3.5.3 | 3.5.3.5.4 | 3.5.3.6.1 | 3.5.3.6.2 | 3.5.3.6.3 | 3.5.3.6.4 |
| 3.5.3.7.1 | 3.5.3.7.2 | 3.5.3.7.3 | 3.5.3.7.4 | 3.5.3.8.1 | 3.5.3.8.2 | 3.5.3.8.3 | 3.5.3.8.4 |
| 3.5.4.1.1 | 3.5.4.1.2 | 3.5.4.1.3 | 3.5.4.1.4 | 3.5.4.2.1 | 3.5.4.2.2 | 3.5.4.2.3 | 3.5.4.2.4 |
| 3.5.4.3.1 | 3.5.4.3.2 | 3.5.4.3.3 | 3.5.4.3.4 | 3.5.4.4.1 | 3.5.4.4.2 | 3.5.4.4.3 | 3.5.4.4.4 |
| 3.5.4.5.1 | 3.5.4.5.2 | 3.5.4.5.3 | 3.5.4.5.4 | 3.5.4.6.1 | 3.5.4.6.2 | 3.5.4.6.3 | 3.5.4.6.4 |
| 3.5.4.7.1 | 3.5.4.7.2 | 3.5.4.7.3 | 3.5.4.7.4 | 3.5.4.8.1 | 3.5.4.8.2 | 3.5.4.8.3 | 3.5.4.8.4 |
| 3.6.1.1.1 | 3.6.1.1.2 | 3.6.1.1.3 | 3.6.1.1.4 | 3.6.1.2.1 | 3.6.1.2.2 | 3.6.1.2.3 | 3.6.1.2.4 |
| 3.6.1.3.1 | 3.6.1.3.2 | 3.6.1.3.3 | 3.6.1.3.4 | 3.6.1.4.1 | 3.6.1.4.2 | 3.6.1.4.3 | 3.6.1.4.4 |
| 3.6.1.5.1 | 3.6.1.5.2 | 3.6.1.5.3 | 3.6.1.5.4 | 3.6.1.6.1 | 3.6.1.6.2 | 3.6.1.6.3 | 3.6.1.6.4 |
| 3.6.1.7.1 | 3.6.1.7.2 | 3.6.1.7.3 | 3.6.1.7.4 | 3.6.1.8.1 | 3.6.1.8.2 | 3.6.1.8.3 | 3.6.1.8.4 |
| 3.6.2.1.1 | 3.6.2.1.2 | 3.6.2.1.3 | 3.6.2.1.4 | 3.6.2.2.1 | 3.6.2.2.2 | 3.6.2.2.3 | 3.6.2.2.4 |
| 3.6.2.3.1 | 3.6.2.3.2 | 3.6.2.3.3 | 3.6.2.3.4 | 3.6.2.4.1 | 3.6.2.4.2 | 3.6.2.4.3 | 3.6.2.4.4 |
| 3.6.2.5.1 | 3.6.2.5.2 | 3.6.2.5.3 | 3.6.2.5.4 | 3.6.2.6.1 | 3.6.2.6.2 | 3.6.2.6.3 | 3.6.2.6.4 |
| 3.6.2.7.1 | 3.6.2.7.2 | 3.6.2.7.3 | 3.6.2.7.4 | 3.6.2.8.1 | 3.6.2.8.2 | 3.6.2.8.3 | 3.6.2.8.4 |
| 3.6.3.1.1 | 3.6.3.1.2 | 3.6.3.1.3 | 3.6.3.1.4 | 3.6.3.2.1 | 3.6.3.2.2 | 3.6.3.2.3 | 3.6.3.2.4 |
| 3.6.3.3.1 | 3.6.3.3.2 | 3.6.3.3.3 | 3.6.3.3.4 | 3.6.3.4.1 | 3.6.3.4.2 | 3.6.3.4.3 | 3.6.3.4.4 |
| 3.6.3.5.1 | 3.6.3.5.2 | 3.6.3.5.3 | 3.6.3.5.4 | 3.6.3.6.1 | 3.6.3.6.2 | 3.6.3.6.3 | 3.6.3.6.4 |
| 3.6.3.7.1 | 3.6.3.7.2 | 3.6.3.7.3 | 3.6.3.7.4 | 3.6.3.8.1 | 3.6.3.8.2 | 3.6.3.8.3 | 3.6.3.8.4 |
| 3.6.4.1.1 | 3.6.4.1.2 | 3.6.4.1.3 | 3.6.4.1.4 | 3.6.4.2.1 | 3.6.4.2.2 | 3.6.4.2.3 | 3.6.4.2.4 |
| 3.6.4.3.1 | 3.6.4.3.2 | 3.6.4.3.3 | 3.6.4.3.4 | 3.6.4.4.1 | 3.6.4.4.2 | 3.6.4.4.3 | 3.6.4.4.4 |
| 3.6.4.5.1 | 3.6.4.5.2 | 3.6.4.5.3 | 3.6.4.5.4 | 3.6.4.6.1 | 3.6.4.6.2 | 3.6.4.6.3 | 3.6.4.6.4 |
| 3.6.4.7.1 | 3.6.4.7.2 | 3.6.4.7.3 | 3.6.4.7.4 | 3.6.4.8.1 | 3.6.4.8.2 | 3.6.4.8.3 | 3.6.4.8.4 |
| 3.7.1.1.1 | 3.7.1.1.2 | 3.7.1.1.3 | 3.7.1.1.4 | 3.7.1.2.1 | 3.7.1.2.2 | 3.7.1.2.3 | 3.7.1.2.4 |
| 3.7.1.3.1 | 3.7.1.3.2 | 3.7.1.3.3 | 3.7.1.3.4 | 3.7.1.4.1 | 3.7.1.4.2 | 3.7.1.4.3 | 3.7.1.4.4 |
| 3.7.1.5.1 | 3.7.1.5.2 | 3.7.1.5.3 | 3.7.1.5.4 | 3.7.1.6.1 | 3.7.1.6.2 | 3.7.1.6.3 | 3.7.1.6.4 |
| 3.7.1.7.1 | 3.7.1.7.2 | 3.7.1.7.3 | 3.7.1.7.4 | 3.7.1.8.1 | 3.7.1.8.2 | 3.7.1.8.3 | 3.7.1.8.4 |
| 3.7.2.1.1 | 3.7.2.1.2 | 3.7.2.1.3 | 3.7.2.1.4 | 3.7.2.2.1 | 3.7.2.2.2 | 3.7.2.2.3 | 3.7.2.2.4 |
| 3.7.2.3.1 | 3.7.2.3.2 | 3.7.2.3.3 | 3.7.2.3.4 | 3.7.2.4.1 | 3.7.2.4.2 | 3.7.2.4.3 | 3.7.2.4.4 |
| 3.7.2.5.1 | 3.7.2.5.2 | 3.7.2.5.3 | 3.7.2.5.4 | 3.7.2.6.1 | 3.7.2.6.2 | 3.7.2.6.3 | 3.7.2.6.4 |
| 3.7.2.7.1 | 3.7.2.7.2 | 3.7.2.7.3 | 3.7.2.7.4 | 3.7.2.8.1 | 3.7.2.8.2 | 3.7.2.8.3 | 3.7.2.8.4 |
| 3.7.3.1.1 | 3.7.3.1.2 | 3.7.3.1.3 | 3.7.3.1.4 | 3.7.3.2.1 | 3.7.3.2.2 | 3.7.3.2.3 | 3.7.3.2.4 |
| 3.7.3.3.1 | 3.7.3.3.2 | 3.7.3.3.3 | 3.7.3.3.4 | 3.7.3.4.1 | 3.7.3.4.2 | 3.7.3.4.3 | 3.7.3.4.4 |
| 3.7.3.5.1 | 3.7.3.5.2 | 3.7.3.5.3 | 3.7.3.5.4 | 3.7.3.6.1 | 3.7.3.6.2 | 3.7.3.6.3 | 3.7.3.6.4 |
| 3.7.3.7.1 | 3.7.3.7.2 | 3.7.3.7.3 | 3.7.3.7.4 | 3.7.3.8.1 | 3.7.3.8.2 | 3.7.3.8.3 | 3.7.3.8.4 |
| 3.7.4.1.1 | 3.7.4.1.2 | 3.7.4.1.3 | 3.7.4.1.4 | 3.7.4.2.1 | 3.7.4.2.2 | 3.7.4.2.3 | 3.7.4.2.4 |

TABLE 3-continued

| | | | | | | | |
|---|---|---|---|---|---|---|---|
| 3.7.4.3.1 | 3.7.4.3.2 | 3.7.4.3.3 | 3.7.4.3.4 | 3.7.4.4.1 | 3.7.4.4.2 | 3.7.4.4.3 | 3.7.4.4.4 |
| 3.7.4.5.1 | 3.7.4.5.2 | 3.7.4.5.3 | 3.7.4.5.4 | 3.7.4.6.1 | 3.7.4.6.2 | 3.7.4.6.3 | 3.7.4.6.4 |
| 3.7.4.7.1 | 3.7.4.7.2 | 3.7.4.7.3 | 3.7.4.7.4 | 3.7.4.8.1 | 3.7.4.8.2 | 3.7.4.8.3 | 3.7.4.8.4 |
| 3.8.1.1.1 | 3.8.1.1.2 | 3.8.1.1.3 | 3.8.1.1.4 | 3.8.1.2.1 | 3.8.1.2.2 | 3.8.1.2.3 | 3.8.1.2.4 |
| 3.8.1.3.1 | 3.8.1.3.2 | 3.8.1.3.3 | 3.8.1.3.4 | 3.8.1.4.1 | 3.8.1.4.2 | 3.8.1.4.3 | 3.8.1.4.4 |
| 3.8.1.5.1 | 3.8.1.5.2 | 3.8.1.5.3 | 3.8.1.5.4 | 3.8.1.6.1 | 3.8.1.6.2 | 3.8.1.6.3 | 3.8.1.6.4 |
| 3.8.1.7.1 | 3.8.1.7.2 | 3.8.1.7.3 | 3.8.1.7.4 | 3.8.1.8.1 | 3.8.1.8.2 | 3.8.1.8.3 | 3.8.1.8.4 |
| 3.8.2.1.1 | 3.8.2.1.2 | 3.8.2.1.3 | 3.8.2.1.4 | 3.8.2.2.1 | 3.8.2.2.2 | 3.8.2.2.3 | 3.8.2.2.4 |
| 3.8.2.3.1 | 3.8.2.3.2 | 3.8.2.3.3 | 3.8.2.3.4 | 3.8.2.4.1 | 3.8.2.4.2 | 3.8.2.4.3 | 3.8.2.4.4 |
| 3.8.2.5.1 | 3.8.2.5.2 | 3.8.2.5.3 | 3.8.2.5.4 | 3.8.2.6.1 | 3.8.2.6.2 | 3.8.2.6.3 | 3.8.2.6.4 |
| 3.8.2.7.1 | 3.8.2.7.2 | 3.8.2.7.3 | 3.8.2.7.4 | 3.8.2.8.1 | 3.8.2.8.2 | 3.8.2.8.3 | 3.8.2.8.4 |
| 3.8.3.1.1 | 3.8.3.1.2 | 3.8.3.1.3 | 3.8.3.1.4 | 3.8.3.2.1 | 3.8.3.2.2 | 3.8.3.2.3 | 3.8.3.2.4 |
| 3.8.3.3.1 | 3.8.3.3.2 | 3.8.3.3.3 | 3.8.3.3.4 | 3.8.3.4.1 | 3.8.3.4.2 | 3.8.3.4.3 | 3.8.3.4.4 |
| 3.8.3.5.1 | 3.8.3.5.2 | 3.8.3.5.3 | 3.8.3.5.4 | 3.8.3.6.1 | 3.8.3.6.2 | 3.8.3.6.3 | 3.8.3.6.4 |
| 3.8.3.7.1 | 3.8.3.7.2 | 3.8.3.7.3 | 3.8.3.7.4 | 3.8.3.8.1 | 3.8.3.8.2 | 3.8.3.8.3 | 3.8.3.8.4 |
| 3.8.4.1.1 | 3.8.4.1.2 | 3.8.4.1.3 | 3.8.4.1.4 | 3.8.4.2.1 | 3.8.4.2.2 | 3.8.4.2.3 | 3.8.4.2.4 |
| 3.8.4.3.1 | 3.8.4.3.2 | 3.8.4.3.3 | 3.8.4.3.4 | 3.8.4.4.1 | 3.8.4.4.2 | 3.8.4.4.3 | 3.8.4.4.4 |
| 3.8.4.5.1 | 3.8.4.5.2 | 3.8.4.5.3 | 3.8.4.5.4 | 3.8.4.6.1 | 3.8.4.6.2 | 3.8.4.6.3 | 3.8.4.6.4 |
| 3.8.4.7.1 | 3.8.4.7.2 | 3.8.4.7.3 | 3.8.4.7.4 | 3.8.4.8.1 | 3.8.4.8.2 | 3.8.4.8.3 | 3.8.4.8.4 |
| 4.1.1.1.1 | 4.1.1.1.2 | 4.1.1.1.3 | 4.1.1.1.4 | 4.1.1.2.1 | 4.1.1.2.2 | 4.1.1.2.3 | 4.1.1.2.4 |
| 4.1.1.3.1 | 4.1.1.3.2 | 4.1.1.3.3 | 4.1.1.3.4 | 4.1.1.4.1 | 4.1.1.4.2 | 4.1.1.4.3 | 4.1.1.4.4 |
| 4.1.1.5.1 | 4.1.1.5.2 | 4.1.1.5.3 | 4.1.1.5.4 | 4.1.1.6.1 | 4.1.1.6.2 | 4.1.1.6.3 | 4.1.1.6.4 |
| 4.1.1.7.1 | 4.1.1.7.2 | 4.1.1.7.3 | 4.1.1.7.4 | 4.1.1.8.1 | 4.1.1.8.2 | 4.1.1.8.3 | 4.1.1.8.4 |
| 4.1.2.1.1 | 4.1.2.1.2 | 4.1.2.1.3 | 4.1.2.1.4 | 4.1.2.2.1 | 4.1.2.2.2 | 4.1.2.2.3 | 4.1.2.2.4 |
| 4.1.2.3.1 | 4.1.2.3.2 | 4.1.2.3.3 | 4.1.2.3.4 | 4.1.2.4.1 | 4.1.2.4.2 | 4.1.2.4.3 | 4.1.2.4.4 |
| 4.1.2.5.1 | 4.1.2.5.2 | 4.1.2.5.3 | 4.1.2.5.4 | 4.1.2.6.1 | 4.1.2.6.2 | 4.1.2.6.3 | 4.1.2.6.4 |
| 4.1.2.7.1 | 4.1.2.7.2 | 4.1.2.7.3 | 4.1.2.7.4 | 4.1.2.8.1 | 4.1.2.8.2 | 4.1.2.8.3 | 4.1.2.8.4 |
| 4.1.3.1.1 | 4.1.3.1.2 | 4.1.3.1.3 | 4.1.3.1.4 | 4.1.3.2.1 | 4.1.3.2.2 | 4.1.3.2.3 | 4.1.3.2.4 |
| 4.1.3.3.1 | 4.1.3.3.2 | 4.1.3.3.3 | 4.1.3.3.4 | 4.1.3.4.1 | 4.1.3.4.2 | 4.1.3.4.3 | 4.1.3.4.4 |
| 4.1.3.5.1 | 4.1.3.5.2 | 4.1.3.5.3 | 4.1.3.5.4 | 4.1.3.6.1 | 4.1.3.6.2 | 4.1.3.6.3 | 4.1.3.6.4 |
| 4.1.3.7.1 | 4.1.3.7.2 | 4.1.3.7.3 | 4.1.3.7.4 | 4.1.3.8.1 | 4.1.3.8.2 | 4.1.3.8.3 | 4.1.3.8.4 |
| 4.1.4.1.1 | 4.1.4.1.2 | 4.1.4.1.3 | 4.1.4.1.4 | 4.1.4.2.1 | 4.1.4.2.2 | 4.1.4.2.3 | 4.1.4.2.4 |
| 4.1.4.3.1 | 4.1.4.3.2 | 4.1.4.3.3 | 4.1.4.3.4 | 4.1.4.4.1 | 4.1.4.4.2 | 4.1.4.4.3 | 4.1.4.4.4 |
| 4.1.4.5.1 | 4.1.4.5.2 | 4.1.4.5.3 | 4.1.4.5.4 | 4.1.4.6.1 | 4.1.4.6.2 | 4.1.4.6.3 | 4.1.4.6.4 |
| 4.1.4.7.1 | 4.1.4.7.2 | 4.1.4.7.3 | 4.1.4.7.4 | 4.1.4.8.1 | 4.1.4.8.2 | 4.1.4.8.3 | 4.1.4.8.4 |
| 4.2.1.1.1 | 4.2.1.1.2 | 4.2.1.1.3 | 4.2.1.1.4 | 4.2.1.2.1 | 4.2.1.2.2 | 4.2.1.2.3 | 4.2.1.2.4 |
| 4.2.1.3.1 | 4.2.1.3.2 | 4.2.1.3.3 | 4.2.1.3.4 | 4.2.1.4.1 | 4.2.1.4.2 | 4.2.1.4.3 | 4.2.1.4.4 |
| 4.2.1.5.1 | 4.2.1.5.2 | 4.2.1.5.3 | 4.2.1.5.4 | 4.2.1.6.1 | 4.2.1.6.2 | 4.2.1.6.3 | 4.2.1.6.4 |
| 4.2.1.7.1 | 4.2.1.7.2 | 4.2.1.7.3 | 4.2.1.7.4 | 4.2.1.8.1 | 4.2.1.8.2 | 4.2.1.8.3 | 4.2.1.8.4 |
| 4.2.2.1.1 | 4.2.2.1.2 | 4.2.2.1.3 | 4.2.2.1.4 | 4.2.2.2.1 | 4.2.2.2.2 | 4.2.2.2.3 | 4.2.2.2.4 |
| 4.2.2.3.1 | 4.2.2.3.2 | 4.2.2.3.3 | 4.2.2.3.4 | 4.2.2.4.1 | 4.2.2.4.2 | 4.2.2.4.3 | 4.2.2.4.4 |
| 4.2.2.5.1 | 4.2.2.5.2 | 4.2.2.5.3 | 4.2.2.5.4 | 4.2.2.6.1 | 4.2.2.6.2 | 4.2.2.6.3 | 4.2.2.6.4 |
| 4.2.2.7.1 | 4.2.2.7.2 | 4.2.2.7.3 | 4.2.2.7.4 | 4.2.2.8.1 | 4.2.2.8.2 | 4.2.2.8.3 | 4.2.2.8.4 |
| 4.2.3.1.1 | 4.2.3.1.2 | 4.2.3.1.3 | 4.2.3.1.4 | 4.2.3.2.1 | 4.2.3.2.2 | 4.2.3.2.3 | 4.2.3.2.4 |
| 4.2.3.3.1 | 4.2.3.3.2 | 4.2.3.3.3 | 4.2.3.3.4 | 4.2.3.4.1 | 4.2.3.4.2 | 4.2.3.4.3 | 4.2.3.4.4 |
| 4.2.3.5.1 | 4.2.3.5.2 | 4.2.3.5.3 | 4.2.3.5.4 | 4.2.3.6.1 | 4.2.3.6.2 | 4.2.3.6.3 | 4.2.3.6.4 |
| 4.2.3.7.1 | 4.2.3.7.2 | 4.2.3.7.3 | 4.2.3.7.4 | 4.2.3.8.1 | 4.2.3.8.2 | 4.2.3.8.3 | 4.2.3.8.4 |
| 4.2.4.1.1 | 4.2.4.1.2 | 4.2.4.1.3 | 4.2.4.1.4 | 4.2.4.2.1 | 4.2.4.2.2 | 4.2.4.2.3 | 4.2.4.2.4 |
| 4.2.4.3.1 | 4.2.4.3.2 | 4.2.4.3.3 | 4.2.4.3.4 | 4.2.4.4.1 | 4.2.4.4.2 | 4.2.4.4.3 | 4.2.4.4.4 |
| 4.2.4.5.1 | 4.2.4.5.2 | 4.2.4.5.3 | 4.2.4.5.4 | 4.2.4.6.1 | 4.2.4.6.2 | 4.2.4.6.3 | 4.2.4.6.4 |
| 4.2.4.7.1 | 4.2.4.7.2 | 4.2.4.7.3 | 4.2.4.7.4 | 4.2.4.8.1 | 4.2.4.8.2 | 4.2.4.8.3 | 4.2.4.8.4 |
| 4.3.1.1.1 | 4.3.1.1.2 | 4.3.1.1.3 | 4.3.1.1.4 | 4.3.1.2.1 | 4.3.1.2.2 | 4.3.1.2.3 | 4.3.1.2.4 |
| 4.3.1.3.1 | 4.3.1.3.2 | 4.3.1.3.3 | 4.3.1.3.4 | 4.3.1.4.1 | 4.3.1.4.2 | 4.3.1.4.3 | 4.3.1.4.4 |
| 4.3.1.5.1 | 4.3.1.5.2 | 4.3.1.5.3 | 4.3.1.5.4 | 4.3.1.6.1 | 4.3.1.6.2 | 4.3.1.6.3 | 4.3.1.6.4 |
| 4.3.1.7.1 | 4.3.1.7.2 | 4.3.1.7.3 | 4.3.1.7.4 | 4.3.1.8.1 | 4.3.1.8.2 | 4.3.1.8.3 | 4.3.1.8.4 |
| 4.3.2.1.1 | 4.3.2.1.2 | 4.3.2.1.3 | 4.3.2.1.4 | 4.3.2.2.1 | 4.3.2.2.2 | 4.3.2.2.3 | 4.3.2.2.4 |
| 4.3.2.3.1 | 4.3.2.3.2 | 4.3.2.3.3 | 4.3.2.3.4 | 4.3.2.4.1 | 4.3.2.4.2 | 4.3.2.4.3 | 4.3.2.4.4 |
| 4.3.2.5.1 | 4.3.2.5.2 | 4.3.2.5.3 | 4.3.2.5.4 | 4.3.2.6.1 | 4.3.2.6.2 | 4.3.2.6.3 | 4.3.2.6.4 |
| 4.3.2.7.1 | 4.3.2.7.2 | 4.3.2.7.3 | 4.3.2.7.4 | 4.3.2.8.1 | 4.3.2.8.2 | 4.3.2.8.3 | 4.3.2.8.4 |
| 4.3.3.1.1 | 4.3.3.1.2 | 4.3.3.1.3 | 4.3.3.1.4 | 4.3.3.2.1 | 4.3.3.2.2 | 4.3.3.2.3 | 4.3.3.2.4 |
| 4.3.3.3.1 | 4.3.3.3.2 | 4.3.3.3.3 | 4.3.3.3.4 | 4.3.3.4.1 | 4.3.3.4.2 | 4.3.3.4.3 | 4.3.3.4.4 |
| 4.3.3.5.1 | 4.3.3.5.2 | 4.3.3.5.3 | 4.3.3.5.4 | 4.3.3.6.1 | 4.3.3.6.2 | 4.3.3.6.3 | 4.3.3.6.4 |
| 4.3.3.7.1 | 4.3.3.7.2 | 4.3.3.7.3 | 4.3.3.7.4 | 4.3.3.8.1 | 4.3.3.8.2 | 4.3.3.8.3 | 4.3.3.8.4 |
| 4.3.4.1.1 | 4.3.4.1.2 | 4.3.4.1.3 | 4.3.4.1.4 | 4.3.4.2.1 | 4.3.4.2.2 | 4.3.4.2.3 | 4.3.4.2.4 |
| 4.3.4.3.1 | 4.3.4.3.2 | 4.3.4.3.3 | 4.3.4.3.4 | 4.3.4.4.1 | 4.3.4.4.2 | 4.3.4.4.3 | 4.3.4.4.4 |
| 4.3.4.5.1 | 4.3.4.5.2 | 4.3.4.5.3 | 4.3.4.5.4 | 4.3.4.6.1 | 4.3.4.6.2 | 4.3.4.6.3 | 4.3.4.6.4 |
| 4.3.4.7.1 | 4.3.4.7.2 | 4.3.4.7.3 | 4.3.4.7.4 | 4.3.4.8.1 | 4.3.4.8.2 | 4.3.4.8.3 | 4.3.4.8.4 |
| 4.4.1.1.1 | 4.4.1.1.2 | 4.4.1.1.3 | 4.4.1.1.4 | 4.4.1.2.1 | 4.4.1.2.2 | 4.4.1.2.3 | 4.4.1.2.4 |
| 4.4.1.3.1 | 4.4.1.3.2 | 4.4.1.3.3 | 4.4.1.3.4 | 4.4.1.4.1 | 4.4.1.4.2 | 4.4.1.4.3 | 4.4.1.4.4 |
| 4.4.1.5.1 | 4.4.1.5.2 | 4.4.1.5.3 | 4.4.1.5.4 | 4.4.1.6.1 | 4.4.1.6.2 | 4.4.1.6.3 | 4.4.1.6.4 |
| 4.4.1.7.1 | 4.4.1.7.2 | 4.4.1.7.3 | 4.4.1.7.4 | 4.4.1.8.1 | 4.4.1.8.2 | 4.4.1.8.3 | 4.4.1.8.4 |
| 4.4.2.1.1 | 4.4.2.1.2 | 4.4.2.1.3 | 4.4.2.1.4 | 4.4.2.2.1 | 4.4.2.2.2 | 4.4.2.2.3 | 4.4.2.2.4 |
| 4.4.2.3.1 | 4.4.2.3.2 | 4.4.2.3.3 | 4.4.2.3.4 | 4.4.2.4.1 | 4.4.2.4.2 | 4.4.2.4.3 | 4.4.2.4.4 |
| 4.4.2.5.1 | 4.4.2.5.2 | 4.4.2.5.3 | 4.4.2.5.4 | 4.4.2.6.1 | 4.4.2.6.2 | 4.4.2.6.3 | 4.4.2.6.4 |
| 4.4.2.7.1 | 4.4.2.7.2 | 4.4.2.7.3 | 4.4.2.7.4 | 4.4.2.8.1 | 4.4.2.8.2 | 4.4.2.8.3 | 4.4.2.8.4 |
| 4.4.3.1.1 | 4.4.3.1.2 | 4.4.3.1.3 | 4.4.3.1.4 | 4.4.3.2.1 | 4.4.3.2.2 | 4.4.3.2.3 | 4.4.3.2.4 |
| 4.4.3.3.1 | 4.4.3.3.2 | 4.4.3.3.3 | 4.4.3.3.4 | 4.4.3.4.1 | 4.4.3.4.2 | 4.4.3.4.3 | 4.4.3.4.4 |
| 4.4.3.5.1 | 4.4.3.5.2 | 4.4.3.5.3 | 4.4.3.5.4 | 4.4.3.6.1 | 4.4.3.6.2 | 4.4.3.6.3 | 4.4.3.6.4 |
| 4.4.3.7.1 | 4.4.3.7.2 | 4.4.3.7.3 | 4.4.3.7.4 | 4.4.3.8.1 | 4.4.3.8.2 | 4.4.3.8.3 | 4.4.3.8.4 |

TABLE 3-continued

| | | | | | | | |
|---|---|---|---|---|---|---|---|
| 4.4.4.1.1 | 4.4.4.1.2 | 4.4.4.1.3 | 4.4.4.1.4 | 4.4.4.2.1 | 4.4.4.2.2 | 4.4.4.2.3 | 4.4.4.2.4 |
| 4.4.4.3.1 | 4.4.4.3.2 | 4.4.4.3.3 | 4.4.4.3.4 | 4.4.4.4.1 | 4.4.4.4.2 | 4.4.4.4.3 | 4.4.4.4.4 |
| 4.4.4.5.1 | 4.4.4.5.2 | 4.4.4.5.3 | 4.4.4.5.4 | 4.4.4.6.1 | 4.4.4.6.2 | 4.4.4.6.3 | 4.4.4.6.4 |
| 4.4.4.7.1 | 4.4.4.7.2 | 4.4.4.7.3 | 4.4.4.7.4 | 4.4.4.8.1 | 4.4.4.8.2 | 4.4.4.8.3 | 4.4.4.8.4 |
| 4.5.1.1.1 | 4.5.1.1.2 | 4.5.1.1.3 | 4.5.1.1.4 | 4.5.1.2.1 | 4.5.1.2.2 | 4.5.1.2.3 | 4.5.1.2.4 |
| 4.5.1.3.1 | 4.5.1.3.2 | 4.5.1.3.3 | 4.5.1.3.4 | 4.5.1.4.1 | 4.5.1.4.2 | 4.5.1.4.3 | 4.5.1.4.4 |
| 4.5.1.5.1 | 4.5.1.5.2 | 4.5.1.5.3 | 4.5.1.5.4 | 4.5.1.6.1 | 4.5.1.6.2 | 4.5.1.6.3 | 4.5.1.6.4 |
| 4.5.1.7.1 | 4.5.1.7.2 | 4.5.1.7.3 | 4.5.1.7.4 | 4.5.1.8.1 | 4.5.1.8.2 | 4.5.1.8.3 | 4.5.1.8.4 |
| 4.5.2.1.1 | 4.5.2.1.2 | 4.5.2.1.3 | 4.5.2.1.4 | 4.5.2.2.1 | 4.5.2.2.2 | 4.5.2.2.3 | 4.5.2.2.4 |
| 4.5.2.3.1 | 4.5.2.3.2 | 4.5.2.3.3 | 4.5.2.3.4 | 4.5.2.4.1 | 4.5.2.4.2 | 4.5.2.4.3 | 4.5.2.4.4 |
| 4.5.2.5.1 | 4.5.2.5.2 | 4.5.2.5.3 | 4.5.2.5.4 | 4.5.2.6.1 | 4.5.2.6.2 | 4.5.2.6.3 | 4.5.2.6.4 |
| 4.5.2.7.1 | 4.5.2.7.2 | 4.5.2.7.3 | 4.5.2.7.4 | 4.5.2.8.1 | 4.5.2.8.2 | 4.5.2.8.3 | 4.5.2.8.4 |
| 4.5.3.1.1 | 4.5.3.1.2 | 4.5.3.1.3 | 4.5.3.1.4 | 4.5.3.2.1 | 4.5.3.2.2 | 4.5.3.2.3 | 4.5.3.2.4 |
| 4.5.3.3.1 | 4.5.3.3.2 | 4.5.3.3.3 | 4.5.3.3.4 | 4.5.3.4.1 | 4.5.3.4.2 | 4.5.3.4.3 | 4.5.3.4.4 |
| 4.5.3.5.1 | 4.5.3.5.2 | 4.5.3.5.3 | 4.5.3.5.4 | 4.5.3.6.1 | 4.5.3.6.2 | 4.5.3.6.3 | 4.5.3.6.4 |
| 4.5.3.7.1 | 4.5.3.7.2 | 4.5.3.7.3 | 4.5.3.7.4 | 4.5.3.8.1 | 4.5.3.8.2 | 4.5.3.8.3 | 4.5.3.8.4 |
| 4.5.4.1.1 | 4.5.4.1.2 | 4.5.4.1.3 | 4.5.4.1.4 | 4.5.4.2.1 | 4.5.4.2.2 | 4.5.4.2.3 | 4.5.4.2.4 |
| 4.5.4.3.1 | 4.5.4.3.2 | 4.5.4.3.3 | 4.5.4.3.4 | 4.5.4.4.1 | 4.5.4.4.2 | 4.5.4.4.3 | 4.5.4.4.4 |
| 4.5.4.5.1 | 4.5.4.5.2 | 4.5.4.5.3 | 4.5.4.5.4 | 4.5.4.6.1 | 4.5.4.6.2 | 4.5.4.6.3 | 4.5.4.6.4 |
| 4.5.4.7.1 | 4.5.4.7.2 | 4.5.4.7.3 | 4.5.4.7.4 | 4.5.4.8.1 | 4.5.4.8.2 | 4.5.4.8.3 | 4.5.4.8.4 |
| 4.6.1.1.1 | 4.6.1.1.2 | 4.6.1.1.3 | 4.6.1.1.4 | 4.6.1.2.1 | 4.6.1.2.2 | 4.6.1.2.3 | 4.6.1.2.4 |
| 4.6.1.3.1 | 4.6.1.3.2 | 4.6.1.3.3 | 4.6.1.3.4 | 4.6.1.4.1 | 4.6.1.4.2 | 4.6.1.4.3 | 4.6.1.4.4 |
| 4.6.1.5.1 | 4.6.1.5.2 | 4.6.1.5.3 | 4.6.1.5.4 | 4.6.1.6.1 | 4.6.1.6.2 | 4.6.1.6.3 | 4.6.1.6.4 |
| 4.6.1.7.1 | 4.6.1.7.2 | 4.6.1.7.3 | 4.6.1.7.4 | 4.6.1.8.1 | 4.6.1.8.2 | 4.6.1.8.3 | 4.6.1.8.4 |
| 4.6.2.1.1 | 4.6.2.1.2 | 4.6.2.1.3 | 4.6.2.1.4 | 4.6.2.2.1 | 4.6.2.2.2 | 4.6.2.2.3 | 4.6.2.2.4 |
| 4.6.2.3.1 | 4.6.2.3.2 | 4.6.2.3.3 | 4.6.2.3.4 | 4.6.2.4.1 | 4.6.2.4.2 | 4.6.2.4.3 | 4.6.2.4.4 |
| 4.6.2.5.1 | 4.6.2.5.2 | 4.6.2.5.3 | 4.6.2.5.4 | 4.6.2.6.1 | 4.6.2.6.2 | 4.6.2.6.3 | 4.6.2.6.4 |
| 4.6.2.7.1 | 4.6.2.7.2 | 4.6.2.7.3 | 4.6.2.7.4 | 4.6.2.8.1 | 4.6.2.8.2 | 4.6.2.8.3 | 4.6.2.8.4 |
| 4.6.3.1.1 | 4.6.3.1.2 | 4.6.3.1.3 | 4.6.3.1.4 | 4.6.3.2.1 | 4.6.3.2.2 | 4.6.3.2.3 | 4.6.3.2.4 |
| 4.6.3.3.1 | 4.6.3.3.2 | 4.6.3.3.3 | 4.6.3.3.4 | 4.6.3.4.1 | 4.6.3.4.2 | 4.6.3.4.3 | 4.6.3.4.4 |
| 4.6.3.5.1 | 4.6.3.5.2 | 4.6.3.5.3 | 4.6.3.5.4 | 4.6.3.6.1 | 4.6.3.6.2 | 4.6.3.6.3 | 4.6.3.6.4 |
| 4.6.3.7.1 | 4.6.3.7.2 | 4.6.3.7.3 | 4.6.3.7.4 | 4.6.3.8.1 | 4.6.3.8.2 | 4.6.3.8.3 | 4.6.3.8.4 |
| 4.6.4.1.1 | 4.6.4.1.2 | 4.6.4.1.3 | 4.6.4.1.4 | 4.6.4.2.1 | 4.6.4.2.2 | 4.6.4.2.3 | 4.6.4.2.4 |
| 4.6.4.3.1 | 4.6.4.3.2 | 4.6.4.3.3 | 4.6.4.3.4 | 4.6.4.4.1 | 4.6.4.4.2 | 4.6.4.4.3 | 4.6.4.4.4 |
| 4.6.4.5.1 | 4.6.4.5.2 | 4.6.4.5.3 | 4.6.4.5.4 | 4.6.4.6.1 | 4.6.4.6.2 | 4.6.4.6.3 | 4.6.4.6.4 |
| 4.6.4.7.1 | 4.6.4.7.2 | 4.6.4.7.3 | 4.6.4.7.4 | 4.6.4.8.1 | 4.6.4.8.2 | 4.6.4.8.3 | 4.6.4.8.4 |
| 4.7.1.1.1 | 4.7.1.1.2 | 4.7.1.1.3 | 4.7.1.1.4 | 4.7.1.2.1 | 4.7.1.2.2 | 4.7.1.2.3 | 4.7.1.2.4 |
| 4.7.1.3.1 | 4.7.1.3.2 | 4.7.1.3.3 | 4.7.1.3.4 | 4.7.1.4.1 | 4.7.1.4.2 | 4.7.1.4.3 | 4.7.1.4.4 |
| 4.7.1.5.1 | 4.7.1.5.2 | 4.7.1.5.3 | 4.7.1.5.4 | 4.7.1.6.1 | 4.7.1.6.2 | 4.7.1.6.3 | 4.7.1.6.4 |
| 4.7.1.7.1 | 4.7.1.7.2 | 4.7.1.7.3 | 4.7.1.7.4 | 4.7.1.8.1 | 4.7.1.8.2 | 4.7.1.8.3 | 4.7.1.8.4 |
| 4.7.2.1.1 | 4.7.2.1.2 | 4.7.2.1.3 | 4.7.2.1.4 | 4.7.2.2.1 | 4.7.2.2.2 | 4.7.2.2.3 | 4.7.2.2.4 |
| 4.7.2.3.1 | 4.7.2.3.2 | 4.7.2.3.3 | 4.7.2.3.4 | 4.7.2.4.1 | 4.7.2.4.2 | 4.7.2.4.3 | 4.7.2.4.4 |
| 4.7.2.5.1 | 4.7.2.5.2 | 4.7.2.5.3 | 4.7.2.5.4 | 4.7.2.6.1 | 4.7.2.6.2 | 4.7.2.6.3 | 4.7.2.6.4 |
| 4.7.2.7.1 | 4.7.2.7.2 | 4.7.2.7.3 | 4.7.2.7.4 | 4.7.2.8.1 | 4.7.2.8.2 | 4.7.2.8.3 | 4.7.2.8.4 |
| 4.7.3.1.1 | 4.7.3.1.2 | 4.7.3.1.3 | 4.7.3.1.4 | 4.7.3.2.1 | 4.7.3.2.2 | 4.7.3.2.3 | 4.7.3.2.4 |
| 4.7.3.3.1 | 4.7.3.3.2 | 4.7.3.3.3 | 4.7.3.3.4 | 4.7.3.4.1 | 4.7.3.4.2 | 4.7.3.4.3 | 4.7.3.4.4 |
| 4.7.3.5.1 | 4.7.3.5.2 | 4.7.3.5.3 | 4.7.3.5.4 | 4.7.3.6.1 | 4.7.3.6.2 | 4.7.3.6.3 | 4.7.3.6.4 |
| 4.7.3.7.1 | 4.7.3.7.2 | 4.7.3.7.3 | 4.7.3.7.4 | 4.7.3.8.1 | 4.7.3.8.2 | 4.7.3.8.3 | 4.7.3.8.4 |
| 4.7.4.1.1 | 4.7.4.1.2 | 4.7.4.1.3 | 4.7.4.1.4 | 4.7.4.2.1 | 4.7.4.2.2 | 4.7.4.2.3 | 4.7.4.2.4 |
| 4.7.4.3.1 | 4.7.4.3.2 | 4.7.4.3.3 | 4.7.4.3.4 | 4.7.4.4.1 | 4.7.4.4.2 | 4.7.4.4.3 | 4.7.4.4.4 |
| 4.7.4.5.1 | 4.7.4.5.2 | 4.7.4.5.3 | 4.7.4.5.4 | 4.7.4.6.1 | 4.7.4.6.2 | 4.7.4.6.3 | 4.7.4.6.4 |
| 4.7.4.7.1 | 4.7.4.7.2 | 4.7.4.7.3 | 4.7.4.7.4 | 4.7.4.8.1 | 4.7.4.8.2 | 4.7.4.8.3 | 4.7.4.8.4 |
| 4.8.1.1.1 | 4.8.1.1.2 | 4.8.1.1.3 | 4.8.1.1.4 | 4.8.1.2.1 | 4.8.1.2.2 | 4.8.1.2.3 | 4.8.1.2.4 |
| 4.8.1.3.1 | 4.8.1.3.2 | 4.8.1.3.3 | 4.8.1.3.4 | 4.8.1.4.1 | 4.8.1.4.2 | 4.8.1.4.3 | 4.8.1.4.4 |
| 4.8.1.5.1 | 4.8.1.5.2 | 4.8.1.5.3 | 4.8.1.5.4 | 4.8.1.6.1 | 4.8.1.6.2 | 4.8.1.6.3 | 4.8.1.6.4 |
| 4.8.1.7.1 | 4.8.1.7.2 | 4.8.1.7.3 | 4.8.1.7.4 | 4.8.1.8.1 | 4.8.1.8.2 | 4.8.1.8.3 | 4.8.1.8.4 |
| 4.8.2.1.1 | 4.8.2.1.2 | 4.8.2.1.3 | 4.8.2.1.4 | 4.8.2.2.1 | 4.8.2.2.2 | 4.8.2.2.3 | 4.8.2.2.4 |
| 4.8.2.3.1 | 4.8.2.3.2 | 4.8.2.3.3 | 4.8.2.3.4 | 4.8.2.4.1 | 4.8.2.4.2 | 4.8.2.4.3 | 4.8.2.4.4 |
| 4.8.2.5.1 | 4.8.2.5.2 | 4.8.2.5.3 | 4.8.2.5.4 | 4.8.2.6.1 | 4.8.2.6.2 | 4.8.2.6.3 | 4.8.2.6.4 |
| 4.8.2.7.1 | 4.8.2.7.2 | 4.8.2.7.3 | 4.8.2.7.4 | 4.8.2.8.1 | 4.8.2.8.2 | 4.8.2.8.3 | 4.8.2.8.4 |
| 4.8.3.1.1 | 4.8.3.1.2 | 4.8.3.1.3 | 4.8.3.1.4 | 4.8.3.2.1 | 4.8.3.2.2 | 4.8.3.2.3 | 4.8.3.2.4 |
| 4.8.3.3.1 | 4.8.3.3.2 | 4.8.3.3.3 | 4.8.3.3.4 | 4.8.3.4.1 | 4.8.3.4.2 | 4.8.3.4.3 | 4.8.3.4.4 |
| 4.8.3.5.1 | 4.8.3.5.2 | 4.8.3.5.3 | 4.8.3.5.4 | 4.8.3.6.1 | 4.8.3.6.2 | 4.8.3.6.3 | 4.8.3.6.4 |
| 4.8.3.7.1 | 4.8.3.7.2 | 4.8.3.7.3 | 4.8.3.7.4 | 4.8.3.8.1 | 4.8.3.8.2 | 4.8.3.8.3 | 4.8.3.8.4 |
| 4.8.4.1.1 | 4.8.4.1.2 | 4.8.4.1.3 | 4.8.4.1.4 | 4.8.4.2.1 | 4.8.4.2.2 | 4.8.4.2.3 | 4.8.4.2.4 |
| 4.8.4.3.1 | 4.8.4.3.2 | 4.8.4.3.3 | 4.8.4.3.4 | 4.8.4.4.1 | 4.8.4.4.2 | 4.8.4.4.3 | 4.8.4.4.4 |
| 4.8.4.5.1 | 4.8.4.5.2 | 4.8.4.5.3 | 4.8.4.5.4 | 4.8.4.6.1 | 4.8.4.6.2 | 4.8.4.6.3 | 4.8.4.6.4 |
| 4.8.4.7.1 | 4.8.4.7.2 | 4.8.4.7.3 | 4.8.4.7.4 | 4.8.4.8.1 | 4.8.4.8.2 | 4.8.4.8.3 | 4.8.4.8.4 |
| 5.1.1.1.1 | 5.1.1.1.2 | 5.1.1.1.3 | 5.1.1.1.4 | 5.1.1.2.1 | 5.1.1.2.2 | 5.1.1.2.3 | 5.1.1.2.4 |
| 5.1.1.3.1 | 5.1.1.3.2 | 5.1.1.3.3 | 5.1.1.3.4 | 5.1.1.4.1 | 5.1.1.4.2 | 5.1.1.4.3 | 5.1.1.4.4 |
| 5.1.1.5.1 | 5.1.1.5.2 | 5.1.1.5.3 | 5.1.1.5.4 | 5.1.1.6.1 | 5.1.1.6.2 | 5.1.1.6.3 | 5.1.1.6.4 |
| 5.1.1.7.1 | 5.1.1.7.2 | 5.1.1.7.3 | 5.1.1.7.4 | 5.1.1.8.1 | 5.1.1.8.2 | 5.1.1.8.3 | 5.1.1.8.4 |
| 5.1.2.1.1 | 5.1.2.1.2 | 5.1.2.1.3 | 5.1.2.1.4 | 5.1.2.2.1 | 5.1.2.2.2 | 5.1.2.2.3 | 5.1.2.2.4 |
| 5.1.2.3.1 | 5.1.2.3.2 | 5.1.2.3.3 | 5.1.2.3.4 | 5.1.2.4.1 | 5.1.2.4.2 | 5.1.2.4.3 | 5.1.2.4.4 |
| 5.1.2.5.1 | 5.1.2.5.2 | 5.1.2.5.3 | 5.1.2.5.4 | 5.1.2.6.1 | 5.1.2.6.2 | 5.1.2.6.3 | 5.1.2.6.4 |
| 5.1.2.7.1 | 5.1.2.7.2 | 5.1.2.7.3 | 5.1.2.7.4 | 5.1.2.8.1 | 5.1.2.8.2 | 5.1.2.8.3 | 5.1.2.8.4 |
| 5.1.3.1.1 | 5.1.3.1.2 | 5.1.3.1.3 | 5.1.3.1.4 | 5.1.3.2.1 | 5.1.3.2.2 | 5.1.3.2.3 | 5.1.3.2.4 |
| 5.1.3.3.1 | 5.1.3.3.2 | 5.1.3.3.3 | 5.1.3.3.4 | 5.1.3.4.1 | 5.1.3.4.2 | 5.1.3.4.3 | 5.1.3.4.4 |
| 5.1.3.5.1 | 5.1.3.5.2 | 5.1.3.5.3 | 5.1.3.5.4 | 5.1.3.6.1 | 5.1.3.6.2 | 5.1.3.6.3 | 5.1.3.6.4 |

TABLE 3-continued

| | | | | | | | |
|---|---|---|---|---|---|---|---|
| 5.1.3.7.1 | 5.1.3.7.2 | 5.1.3.7.3 | 5.1.3.7.4 | 5.1.3.8.1 | 5.1.3.8.2 | 5.1.3.8.3 | 5.1.3.8.4 |
| 5.1.4.1.1 | 5.1.4.1.2 | 5.1.4.1.3 | 5.1.4.1.4 | 5.1.4.2.1 | 5.1.4.2.2 | 5.1.4.2.3 | 5.1.4.2.4 |
| 5.1.4.3.1 | 5.1.4.3.2 | 5.1.4.3.3 | 5.1.4.3.4 | 5.1.4.4.1 | 5.1.4.4.2 | 5.1.4.4.3 | 5.1.4.4.4 |
| 5.1.4.5.1 | 5.1.4.5.2 | 5.1.4.5.3 | 5.1.4.5.4 | 5.1.4.6.1 | 5.1.4.6.2 | 5.1.4.6.3 | 5.1.4.6.4 |
| 5.1.4.7.1 | 5.1.4.7.2 | 5.1.4.7.3 | 5.1.4.7.4 | 5.1.4.8.1 | 5.1.4.8.2 | 5.1.4.8.3 | 5.1.4.8.4 |
| 5.2.1.1.1 | 5.2.1.1.2 | 5.2.1.1.3 | 5.2.1.1.4 | 5.2.1.2.1 | 5.2.1.2.2 | 5.2.1.2.3 | 5.2.1.2.4 |
| 5.2.1.3.1 | 5.2.1.3.2 | 5.2.1.3.3 | 5.2.1.3.4 | 5.2.1.4.1 | 5.2.1.4.2 | 5.2.1.4.3 | 5.2.1.4.4 |
| 5.2.1.5.1 | 5.2.1.5.2 | 5.2.1.5.3 | 5.2.1.5.4 | 5.2.1.6.1 | 5.2.1.6.2 | 5.2.1.6.3 | 5.2.1.6.4 |
| 5.2.1.7.1 | 5.2.1.7.2 | 5.2.1.7.3 | 5.2.1.7.4 | 5.2.1.8.1 | 5.2.1.8.2 | 5.2.1.8.3 | 5.2.1.8.4 |
| 5.2.2.1.1 | 5.2.2.1.2 | 5.2.2.1.3 | 5.2.2.1.4 | 5.2.2.2.1 | 5.2.2.2.2 | 5.2.2.2.3 | 5.2.2.2.4 |
| 5.2.2.3.1 | 5.2.2.3.2 | 5.2.2.3.3 | 5.2.2.3.4 | 5.2.2.4.1 | 5.2.2.4.2 | 5.2.2.4.3 | 5.2.2.4.4 |
| 5.2.2.5.1 | 5.2.2.5.2 | 5.2.2.5.3 | 5.2.2.5.4 | 5.2.2.6.1 | 5.2.2.6.2 | 5.2.2.6.3 | 5.2.2.6.4 |
| 5.2.2.7.1 | 5.2.2.7.2 | 5.2.2.7.3 | 5.2.2.7.4 | 5.2.2.8.1 | 5.2.2.8.2 | 5.2.2.8.3 | 5.2.2.8.4 |
| 5.2.3.1.1 | 5.2.3.1.2 | 5.2.3.1.3 | 5.2.3.1.4 | 5.2.3.2.1 | 5.2.3.2.2 | 5.2.3.2.3 | 5.2.3.2.4 |
| 5.2.3.3.1 | 5.2.3.3.2 | 5.2.3.3.3 | 5.2.3.3.4 | 5.2.3.4.1 | 5.2.3.4.2 | 5.2.3.4.3 | 5.2.3.4.4 |
| 5.2.3.5.1 | 5.2.3.5.2 | 5.2.3.5.3 | 5.2.3.5.4 | 5.2.3.6.1 | 5.2.3.6.2 | 5.2.3.6.3 | 5.2.3.6.4 |
| 5.2.3.7.1 | 5.2.3.7.2 | 5.2.3.7.3 | 5.2.3.7.4 | 5.2.3.8.1 | 5.2.3.8.2 | 5.2.3.8.3 | 5.2.3.8.4 |
| 5.2.4.1.1 | 5.2.4.1.2 | 5.2.4.1.3 | 5.2.4.1.4 | 5.2.4.2.1 | 5.2.4.2.2 | 5.2.4.2.3 | 5.2.4.2.4 |
| 5.2.4.3.1 | 5.2.4.3.2 | 5.2.4.3.3 | 5.2.4.3.4 | 5.2.4.4.1 | 5.2.4.4.2 | 5.2.4.4.3 | 5.2.4.4.4 |
| 5.2.4.5.1 | 5.2.4.5.2 | 5.2.4.5.3 | 5.2.4.5.4 | 5.2.4.6.1 | 5.2.4.6.2 | 5.2.4.6.3 | 5.2.4.6.4 |
| 5.2.4.7.1 | 5.2.4.7.2 | 5.2.4.7.3 | 5.2.4.7.4 | 5.2.4.8.1 | 5.2.4.8.2 | 5.2.4.8.3 | 5.2.4.8.4 |
| 5.3.1.1.1 | 5.3.1.1.2 | 5.3.1.1.3 | 5.3.1.1.4 | 5.3.1.2.1 | 5.3.1.2.2 | 5.3.1.2.3 | 5.3.1.2.4 |
| 5.3.1.3.1 | 5.3.1.3.2 | 5.3.1.3.3 | 5.3.1.3.4 | 5.3.1.4.1 | 5.3.1.4.2 | 5.3.1.4.3 | 5.3.1.4.4 |
| 5.3.1.5.1 | 5.3.1.5.2 | 5.3.1.5.3 | 5.3.1.5.4 | 5.3.1.6.1 | 5.3.1.6.2 | 5.3.1.6.3 | 5.3.1.6.4 |
| 5.3.1.7.1 | 5.3.1.7.2 | 5.3.1.7.3 | 5.3.1.7.4 | 5.3.1.8.1 | 5.3.1.8.2 | 5.3.1.8.3 | 5.3.1.8.4 |
| 5.3.2.1.1 | 5.3.2.1.2 | 5.3.2.1.3 | 5.3.2.1.4 | 5.3.2.2.1 | 5.3.2.2.2 | 5.3.2.2.3 | 5.3.2.2.4 |
| 5.3.2.3.1 | 5.3.2.3.2 | 5.3.2.3.3 | 5.3.2.3.4 | 5.3.2.4.1 | 5.3.2.4.2 | 5.3.2.4.3 | 5.3.2.4.4 |
| 5.3.2.5.1 | 5.3.2.5.2 | 5.3.2.5.3 | 5.3.2.5.4 | 5.3.2.6.1 | 5.3.2.6.2 | 5.3.2.6.3 | 5.3.2.6.4 |
| 5.3.2.7.1 | 5.3.2.7.2 | 5.3.2.7.3 | 5.3.2.7.4 | 5.3.2.8.1 | 5.3.2.8.2 | 5.3.2.8.3 | 5.3.2.8.4 |
| 5.3.3.1.1 | 5.3.3.1.2 | 5.3.3.1.3 | 5.3.3.1.4 | 5.3.3.2.1 | 5.3.3.2.2 | 5.3.3.2.3 | 5.3.3.2.4 |
| 5.3.3.3.1 | 5.3.3.3.2 | 5.3.3.3.3 | 5.3.3.3.4 | 5.3.3.4.1 | 5.3.3.4.2 | 5.3.3.4.3 | 5.3.3.4.4 |
| 5.3.3.5.1 | 5.3.3.5.2 | 5.3.3.5.3 | 5.3.3.5.4 | 5.3.3.6.1 | 5.3.3.6.2 | 5.3.3.6.3 | 5.3.3.6.4 |
| 5.3.3.7.1 | 5.3.3.7.2 | 5.3.3.7.3 | 5.3.3.7.4 | 5.3.3.8.1 | 5.3.3.8.2 | 5.3.3.8.3 | 5.3.3.8.4 |
| 5.3.4.1.1 | 5.3.4.1.2 | 5.3.4.1.3 | 5.3.4.1.4 | 5.3.4.2.1 | 5.3.4.2.2 | 5.3.4.2.3 | 5.3.4.2.4 |
| 5.3.4.3.1 | 5.3.4.3.2 | 5.3.4.3.3 | 5.3.4.3.4 | 5.3.4.4.1 | 5.3.4.4.2 | 5.3.4.4.3 | 5.3.4.4.4 |
| 5.3.4.5.1 | 5.3.4.5.2 | 5.3.4.5.3 | 5.3.4.5.4 | 5.3.4.6.1 | 5.3.4.6.2 | 5.3.4.6.3 | 5.3.4.6.4 |
| 5.3.4.7.1 | 5.3.4.7.2 | 5.3.4.7.3 | 5.3.4.7.4 | 5.3.4.8.1 | 5.3.4.8.2 | 5.3.4.8.3 | 5.3.4.8.4 |
| 5.4.1.1.1 | 5.4.1.1.2 | 5.4.1.1.3 | 5.4.1.1.4 | 5.4.1.2.1 | 5.4.1.2.2 | 5.4.1.2.3 | 5.4.1.2.4 |
| 5.4.1.3.1 | 5.4.1.3.2 | 5.4.1.3.3 | 5.4.1.3.4 | 5.4.1.4.1 | 5.4.1.4.2 | 5.4.1.4.3 | 5.4.1.4.4 |
| 5.4.1.5.1 | 5.4.1.5.2 | 5.4.1.5.3 | 5.4.1.5.4 | 5.4.1.6.1 | 5.4.1.6.2 | 5.4.1.6.3 | 5.4.1.6.4 |
| 5.4.1.7.1 | 5.4.1.7.2 | 5.4.1.7.3 | 5.4.1.7.4 | 5.4.1.8.1 | 5.4.1.8.2 | 5.4.1.8.3 | 5.4.1.8.4 |
| 5.4.2.1.1 | 5.4.2.1.2 | 5.4.2.1.3 | 5.4.2.1.4 | 5.4.2.2.1 | 5.4.2.2.2 | 5.4.2.2.3 | 5.4.2.2.4 |
| 5.4.2.3.1 | 5.4.2.3.2 | 5.4.2.3.3 | 5.4.2.3.4 | 5.4.2.4.1 | 5.4.2.4.2 | 5.4.2.4.3 | 5.4.2.4.4 |
| 5.4.2.5.1 | 5.4.2.5.2 | 5.4.2.5.3 | 5.4.2.5.4 | 5.4.2.6.1 | 5.4.2.6.2 | 5.4.2.6.3 | 5.4.2.6.4 |
| 5.4.2.7.1 | 5.4.2.7.2 | 5.4.2.7.3 | 5.4.2.7.4 | 5.4.2.8.1 | 5.4.2.8.2 | 5.4.2.8.3 | 5.4.2.8.4 |
| 5.4.3.1.1 | 5.4.3.1.2 | 5.4.3.1.3 | 5.4.3.1.4 | 5.4.3.2.1 | 5.4.3.2.2 | 5.4.3.2.3 | 5.4.3.2.4 |
| 5.4.3.3.1 | 5.4.3.3.2 | 5.4.3.3.3 | 5.4.3.3.4 | 5.4.3.4.1 | 5.4.3.4.2 | 5.4.3.4.3 | 5.4.3.4.4 |
| 5.4.3.5.1 | 5.4.3.5.2 | 5.4.3.5.3 | 5.4.3.5.4 | 5.4.3.6.1 | 5.4.3.6.2 | 5.4.3.6.3 | 5.4.3.6.4 |
| 5.4.3.7.1 | 5.4.3.7.2 | 5.4.3.7.3 | 5.4.3.7.4 | 5.4.3.8.1 | 5.4.3.8.2 | 5.4.3.8.3 | 5.4.3.8.4 |
| 5.4.4.1.1 | 5.4.4.1.2 | 5.4.4.1.3 | 5.4.4.1.4 | 5.4.4.2.1 | 5.4.4.2.2 | 5.4.4.2.3 | 5.4.4.2.4 |
| 5.4.4.3.1 | 5.4.4.3.2 | 5.4.4.3.3 | 5.4.4.3.4 | 5.4.4.4.1 | 5.4.4.4.2 | 5.4.4.4.3 | 5.4.4.4.4 |
| 5.4.4.5.1 | 5.4.4.5.2 | 5.4.4.5.3 | 5.4.4.5.4 | 5.4.4.6.1 | 5.4.4.6.2 | 5.4.4.6.3 | 5.4.4.6.4 |
| 5.4.4.7.1 | 5.4.4.7.2 | 5.4.4.7.3 | 5.4.4.7.4 | 5.4.4.8.1 | 5.4.4.8.2 | 5.4.4.8.3 | 5.4.4.8.4 |
| 5.5.1.1.1 | 5.5.1.1.2 | 5.5.1.1.3 | 5.5.1.1.4 | 5.5.1.2.1 | 5.5.1.2.2 | 5.5.1.2.3 | 5.5.1.2.4 |
| 5.5.1.3.1 | 5.5.1.3.2 | 5.5.1.3.3 | 5.5.1.3.4 | 5.5.1.4.1 | 5.5.1.4.2 | 5.5.1.4.3 | 5.5.1.4.4 |
| 5.5.1.5.1 | 5.5.1.5.2 | 5.5.1.5.3 | 5.5.1.5.4 | 5.5.1.6.1 | 5.5.1.6.2 | 5.5.1.6.3 | 5.5.1.6.4 |
| 5.5.1.7.1 | 5.5.1.7.2 | 5.5.1.7.3 | 5.5.1.7.4 | 5.5.1.8.1 | 5.5.1.8.2 | 5.5.1.8.3 | 5.5.1.8.4 |
| 5.5.2.1.1 | 5.5.2.1.2 | 5.5.2.1.3 | 5.5.2.1.4 | 5.5.2.2.1 | 5.5.2.2.2 | 5.5.2.2.3 | 5.5.2.2.4 |
| 5.5.2.3.1 | 5.5.2.3.2 | 5.5.2.3.3 | 5.5.2.3.4 | 5.5.2.4.1 | 5.5.2.4.2 | 5.5.2.4.3 | 5.5.2.4.4 |
| 5.5.2.5.1 | 5.5.2.5.2 | 5.5.2.5.3 | 5.5.2.5.4 | 5.5.2.6.1 | 5.5.2.6.2 | 5.5.2.6.3 | 5.5.2.6.4 |
| 5.5.2.7.1 | 5.5.2.7.2 | 5.5.2.7.3 | 5.5.2.7.4 | 5.5.2.8.1 | 5.5.2.8.2 | 5.5.2.8.3 | 5.5.2.8.4 |
| 5.5.3.1.1 | 5.5.3.1.2 | 5.5.3.1.3 | 5.5.3.1.4 | 5.5.3.2.1 | 5.5.3.2.2 | 5.5.3.2.3 | 5.5.3.2.4 |
| 5.5.3.3.1 | 5.5.3.3.2 | 5.5.3.3.3 | 5.5.3.3.4 | 5.5.3.4.1 | 5.5.3.4.2 | 5.5.3.4.3 | 5.5.3.4.4 |
| 5.5.3.5.1 | 5.5.3.5.2 | 5.5.3.5.3 | 5.5.3.5.4 | 5.5.3.6.1 | 5.5.3.6.2 | 5.5.3.6.3 | 5.5.3.6.4 |
| 5.5.3.7.1 | 5.5.3.7.2 | 5.5.3.7.3 | 5.5.3.7.4 | 5.5.3.8.1 | 15.3.8.2 | 5.5.3.8.3 | 5.5.3.8.4 |
| 5.5.4.1.1 | 5.5.4.1.2 | 5.5.4.1.3 | 5.5.4.1.4 | 5.5.4.2.1 | 5.5.4.2.2 | 5.5.4.2.3 | 5.5.4.2.4 |
| 5.5.4.3.1 | 5.5.4.3.2 | 5.5.4.3.3 | 5.5.4.3.4 | 5.5.4.4.1 | 5.5.4.4.2 | 5.5.4.4.3 | 5.5.4.4.4 |
| 5.5.4.5.1 | 5.5.4.5.2 | 5.5.4.5.3 | 5.5.4.5.4 | 5.5.4.6.1 | 5.5.4.6.2 | 5.5.4.6.3 | 5.5.4.6.4 |
| 5.5.4.7.1 | 5.5.4.7.2 | 5.5.4.7.3 | 5.5.4.7.4 | 5.5.4.8.1 | 5.5.4.8.2 | 5.5.4.8.3 | 5.5.4.8.4 |
| 5.6.1.1.1 | 5.6.1.1.2 | 5.6.1.1.3 | 5.6.1.1.4 | 5.6.1.2.1 | 5.6.1.2.2 | 5.6.1.2.3 | 5.6.1.2.4 |
| 5.6.1.3.1 | 5.6.1.3.2 | 5.6.1.3.3 | 5.6.1.3.4 | 5.6.1.4.1 | 5.6.1.4.2 | 5.6.1.4.3 | 5.6.1.4.4 |
| 5.6.1.5.1 | 5.6.1.5.2 | 5.6.1.5.3 | 5.6.1.5.4 | 5.6.1.6.1 | 5.6.1.6.2 | 5.6.1.6.3 | 5.6.1.6.4 |
| 5.6.1.7.1 | 5.6.1.7.2 | 5.6.1.7.3 | 5.6.1.7.4 | 5.6.1.8.1 | 5.6.1.8.2 | 5.6.1.8.3 | 5.6.1.8.4 |
| 5.6.2.1.1 | 5.6.2.1.2 | 5.6.2.1.3 | 5.6.2.1.4 | 5.6.2.2.1 | 5.6.2.2.2 | 5.6.2.2.3 | 5.6.2.2.4 |
| 5.6.2.3.1 | 5.6.2.3.2 | 5.6.2.3.3 | 5.6.2.3.4 | 5.6.2.4.1 | 5.6.2.4.2 | 5.6.2.4.3 | 5.6.2.4.4 |
| 5.6.2.5.1 | 5.6.2.5.2 | 5.6.2.5.3 | 5.6.2.5.4 | 5.6.2.6.1 | 5.6.2.6.2 | 5.6.2.6.3 | 5.6.2.6.4 |
| 5.6.2.7.1 | 5.6.2.7.2 | 5.6.2.7.3 | 5.6.2.7.4 | 5.6.2.8.1 | 5.6.2.8.2 | 5.6.2.8.3 | 5.6.2.8.4 |
| 5.6.3.1.1 | 5.6.3.1.2 | 5.6.3.1.3 | 5.6.3.1.4 | 5.6.3.2.1 | 5.6.3.2.2 | 5.6.3.2.3 | 5.6.3.2.4 |
| 5.6.3.3.1 | 5.6.3.3.2 | 5.6.3.3.3 | 5.6.3.3.4 | 5.6.3.4.1 | 5.6.3.4.2 | 5.6.3.4.3 | 5.6.3.4.4 |

TABLE 3-continued

| | | | | | | | |
|---|---|---|---|---|---|---|---|
| 5.6.3.5.1 | 5.6.3.5.2 | 5.6.3.5.3 | 5.6.3.5.4 | 5.6.3.6.1 | 5.6.3.6.2 | 5.6.3.6.3 | 5.6.3.6.4 |
| 5.6.3.7.1 | 5.6.3.7.2 | 5.6.3.7.3 | 5.6.3.7.4 | 5.6.3.8.1 | 5.6.3.8.2 | 5.6.3.8.3 | 5.6.3.8.4 |
| 5.6.4.1.1 | 5.6.4.1.2 | 5.6.4.1.3 | 5.6.4.1.4 | 5.6.4.2.1 | 5.6.4.2.2 | 5.6.4.2.3 | 5.6.4.2.4 |
| 5.6.4.3.1 | 5.6.4.3.2 | 5.6.4.3.3 | 5.6.4.3.4 | 5.6.4.4.1 | 5.6.4.4.2 | 5.6.4.4.3 | 5.6.4.4.4 |
| 5.6.4.5.1 | 5.6.4.5.2 | 5.6.4.5.3 | 5.6.4.5.4 | 5.6.4.6.1 | 5.6.4.6.2 | 5.6.4.6.3 | 5.6.4.6.4 |
| 5.6.4.7.1 | 5.6.4.7.2 | 5.6.4.7.3 | 5.6.4.7.4 | 5.6.4.8.1 | 5.6.4.8.2 | 5.6.4.8.3 | 5.6.4.8.4 |
| 5.7.1.1.1 | 5.7.1.1.2 | 5.7.1.1.3 | 5.7.1.1.4 | 5.7.1.2.1 | 5.7.1.2.2 | 5.7.1.2.3 | 5.7.1.2.4 |
| 5.7.1.3.1 | 5.7.1.3.2 | 5.7.1.3.3 | 5.7.1.3.4 | 5.7.1.4.1 | 5.7.1.4.2 | 5.7.1.4.3 | 5.7.1.4.4 |
| 5.7.1.5.1 | 5.7.1.5.2 | 5.7.1.5.3 | 5.7.1.5.4 | 5.7.1.6.1 | 5.7.1.6.2 | 5.7.1.6.3 | 5.7.1.6.4 |
| 5.7.1.7.1 | 5.7.1.7.2 | 5.7.1.7.3 | 5.7.1.7.4 | 5.7.1.8.1 | 5.7.1.8.2 | 5.7.1.8.3 | 5.7.1.8.4 |
| 5.7.2.1.1 | 5.7.2.1.2 | 5.7.2.1.3 | 5.7.2.1.4 | 5.7.2.2.1 | 5.7.2.2.2 | 5.7.2.2.3 | 5.7.2.2.4 |
| 5.7.2.3.1 | 5.7.2.3.2 | 5.7.2.3.3 | 5.7.2.3.4 | 5.7.2.4.1 | 5.7.2.4.2 | 5.7.2.4.3 | 5.7.2.4.4 |
| 5.7.2.5.1 | 5.7.2.5.2 | 5.7.2.5.3 | 5.7.2.5.4 | 5.7.2.6.1 | 5.7.2.6.2 | 5.7.2.6.3 | 5.7.2.6.4 |
| 5.7.2.7.1 | 5.7.2.7.2 | 5.7.2.7.3 | 5.7.2.7.4 | 5.7.2.8.1 | 5.7.2.8.2 | 5.7.2.8.3 | 5.7.2.8.4 |
| 5.7.3.1.1 | 5.7.3.1.2 | 5.7.3.1.3 | 5.7.3.1.4 | 5.7.3.2.1 | 5.7.3.2.2 | 5.7.3.2.3 | 5.7.3.2.4 |
| 5.7.3.3.1 | 5.7.3.3.2 | 5.7.3.3.3 | 5.7.3.3.4 | 5.7.3.4.1 | 5.7.3.4.2 | 5.7.3.4.3 | 5.7.3.4.4 |
| 5.7.3.5.1 | 5.7.3.5.2 | 5.7.3.5.3 | 5.7.3.5.4 | 5.7.3.6.1 | 5.7.3.6.2 | 5.7.3.6.3 | 5.7.3.6.4 |
| 5.7.3.7.1 | 5.7.3.7.2 | 5.7.3.7.3 | 5.7.3.7.4 | 5.7.3.8.1 | 5.7.3.8.2 | 5.7.3.8.3 | 5.7.3.8.4 |
| 5.7.4.1.1 | 5.7.4.1.2 | 5.7.4.1.3 | 5.7.4.1.4 | 5.7.4.2.1 | 5.7.4.2.2 | 5.7.4.2.3 | 5.7.4.2.4 |
| 5.7.4.3.1 | 5.7.4.3.2 | 5.7.4.3.3 | 5.7.4.3.4 | 5.7.4.4.1 | 5.7.4.4.2 | 5.7.4.4.3 | 5.7.4.4.4 |
| 5.7.4.5.1 | 5.7.4.5.2 | 5.7.4.5.3 | 5.7.4.5.4 | 5.7.4.6.1 | 5.7.4.6.2 | 5.7.4.6.3 | 5.7.4.6.4 |
| 5.7.4.7.1 | 5.7.4.7.2 | 5.7.4.7.3 | 5.7.4.7.4 | 5.7.4.8.1 | 5.7.4.8.2 | 5.7.4.8.3 | 5.7.4.8.4 |
| 5.8.1.1.1 | 5.8.1.1.2 | 5.8.1.1.3 | 5.8.1.1.4 | 5.8.1.2.1 | 5.8.1.2.2 | 5.8.1.2.3 | 5.8.1.2.4 |
| 5.8.1.3.1 | 5.8.1.3.2 | 5.8.1.3.3 | 5.8.1.3.4 | 5.8.1.4.1 | 5.8.1.4.2 | 5.8.1.4.3 | 5.8.1.4.4 |
| 5.8.1.5.1 | 5.8.1.5.2 | 5.8.1.5.3 | 5.8.1.5.4 | 5.8.1.6.1 | 5.8.1.6.2 | 5.8.1.6.3 | 5.8.1.6.4 |
| 5.8.1.7.1 | 5.8.1.7.2 | 5.8.1.7.3 | 5.8.1.7.4 | 5.8.1.8.1 | 5.8.1.8.2 | 5.8.1.8.3 | 5.8.1.8.4 |
| 5.8.2.1.1 | 5.8.2.1.2 | 5.8.2.1.3 | 5.8.2.1.4 | 5.8.2.2.1 | 5.8.2.2.2 | 5.8.2.2.3 | 5.8.2.2.4 |
| 5.8.2.3.1 | 5.8.2.3.2 | 5.8.2.3.3 | 5.8.2.3.4 | 5.8.2.4.1 | 5.8.2.4.2 | 5.8.2.4.3 | 5.8.2.4.4 |
| 5.8.2.5.1 | 5.8.2.5.2 | 5.8.2.5.3 | 5.8.2.5.4 | 5.8.2.6.1 | 5.8.2.6.2 | 5.8.2.6.3 | 5.8.2.6.4 |
| 5.8.2.7.1 | 5.8.2.7.2 | 5.8.2.7.3 | 5.8.2.7.4 | 5.8.2.8.1 | 5.8.2.8.2 | 5.8.2.8.3 | 5.8.2.8.4 |
| 5.8.3.1.1 | 5.8.3.1.2 | 5.8.3.1.3 | 5.8.3.1.4 | 5.8.3.2.1 | 5.8.3.2.2 | 5.8.3.2.3 | 5.8.3.2.4 |
| 5.8.3.3.1 | 5.8.3.3.2 | 5.8.3.3.3 | 5.8.3.3.4 | 5.8.3.4.1 | 5.8.3.4.2 | 5.8.3.4.3 | 5.8.3.4.4 |
| 5.8.3.5.1 | 5.8.3.5.2 | 5.8.3.5.3 | 5.8.3.5.4 | 5.8.3.6.1 | 5.8.3.6.2 | 5.8.3.6.3 | 5.8.3.6.4 |
| 5.8.3.7.1 | 5.8.3.7.2 | 5.8.3.7.3 | 5.8.3.7.4 | 5.8.3.8.1 | 5.8.3.8.2 | 5.8.3.8.3 | 5.8.3.8.4 |
| 5.8.4.1.1 | 5.8.4.1.2 | 5.8.4.1.3 | 5.8.4.1.4 | 5.8.4.2.1 | 5.8.4.2.2 | 5.8.4.2.3 | 5.8.4.2.4 |
| 5.8.4.3.1 | 5.8.4.3.2 | 5.8.4.3.3 | 5.8.4.3.4 | 5.8.4.4.1 | 5.8.4.4.2 | 5.8.4.4.3 | 5.8.4.4.4 |
| 5.8.4.5.1 | 5.8.4.5.2 | 5.8.4.5.3 | 5.8.4.5.4 | 5.8.4.6.1 | 5.8.4.6.2 | 5.8.4.6.3 | 5.8.4.6.4 |
| 5.8.4.7.1 | 5.8.4.7.2 | 5.8.4.7.3 | 5.8.4.7.4 | 5.8.4.8.1 | 5.8.4.8.2 | 5.8.4.8.3 | 5.8.4.8.4 |
| 6.1.1.1.1 | 6.1.1.1.2 | 6.1.1.1.3 | 6.1.1.1.4 | 6.1.1.2.1 | 6.1.1.2.2 | 6.1.1.2.3 | 6.1.1.2.4 |
| 6.1.1.3.1 | 6.1.1.3.2 | 6.1.1.3.3 | 6.1.1.3.4 | 6.1.1.4.1 | 6.1.1.4.2 | 6.1.1.4.3 | 6.1.1.4.4 |
| 6.1.1.5.1 | 6.1.1.5.2 | 6.1.1.5.3 | 6.1.1.5.4 | 6.1.1.6.1 | 6.1.1.6.2 | 6.1.1.6.3 | 6.1.1.6.4 |
| 6.1.1.7.1 | 6.1.1.7.2 | 6.1.1.7.3 | 6.1.1.7.4 | 6.1.1.8.1 | 6.1.1.8.2 | 6.1.1.8.3 | 6.1.1.8.4 |
| 6.1.2.1.1 | 6.1.2.1.2 | 6.1.2.1.3 | 6.1.2.1.4 | 6.1.2.2.1 | 6.1.2.2.2 | 6.1.2.2.3 | 6.1.2.2.4 |
| 6.1.2.3.1 | 6.1.2.3.2 | 6.1.2.3.3 | 6.1.2.3.4 | 6.1.2.4.1 | 6.1.2.4.2 | 6.1.2.4.3 | 6.1.2.4.4 |
| 6.1.2.5.1 | 6.1.2.5.2 | 6.1.2.5.3 | 6.1.2.5.4 | 6.1.2.6.1 | 6.1.2.6.2 | 6.1.2.6.3 | 6.1.2.6.4 |
| 6.1.2.7.1 | 6.1.2.7.2 | 6.1.2.7.3 | 6.1.2.7.4 | 6.1.2.8.1 | 6.1.2.8.2 | 6.1.2.8.3 | 6.1.2.8.4 |
| 6.1.3.1.1 | 6.1.3.1.2 | 6.1.3.1.3 | 6.1.3.1.4 | 6.1.3.2.1 | 6.1.3.2.2 | 6.1.3.2.3 | 6.1.3.2.4 |
| 6.1.3.3.1 | 6.1.3.3.2 | 6.1.3.3.3 | 6.1.3.3.4 | 6.1.3.4.1 | 6.1.3.4.2 | 6.1.3.4.3 | 6.1.3.4.4 |
| 6.1.3.5.1 | 6.1.3.5.2 | 6.1.3.5.3 | 6.1.3.5.4 | 6.1.3.6.1 | 6.1.3.6.2 | 6.1.3.6.3 | 6.1.3.6.4 |
| 6.1.3.7.1 | 6.1.3.7.2 | 6.1.3.7.3 | 6.1.3.7.4 | 6.1.3.8.1 | 6.1.3.8.2 | 6.1.3.8.3 | 6.1.3.8.4 |
| 6.1.4.1.1 | 6.1.4.1.2 | 6.1.4.1.3 | 6.1.4.1.4 | 6.1.4.2.1 | 6.1.4.2.2 | 6.1.4.2.3 | 6.1.4.2.4 |
| 6.1.4.3.1 | 6.1.4.3.2 | 6.1.4.3.3 | 6.1.4.3.4 | 6.1.4.4.1 | 6.1.4.4.2 | 6.1.4.4.3 | 6.1.4.4.4 |
| 6.1.4.5.1 | 6.1.4.5.2 | 6.1.4.5.3 | 6.1.4.5.4 | 6.1.4.6.1 | 6.1.4.6.2 | 6.1.4.6.3 | 6.1.4.6.4 |
| 6.1.4.7.1 | 6.1.4.7.2 | 6.1.4.7.3 | 6.1.4.7.4 | 6.1.4.8.1 | 6.1.4.8.2 | 6.1.4.8.3 | 6.4.4.8.4 |
| 6.2.1.1.1 | 6.2.1.1.2 | 6.2.1.1.3 | 6.2.1.1.4 | 6.2.1.2.1 | 6.2.1.2.2 | 6.2.1.2.3 | 6.2.1.2.4 |
| 6.2.1.3.1 | 6.2.1.3.2 | 6.2.1.3.3 | 6.2.1.3.4 | 6.2.1.4.1 | 6.2.1.4.2 | 6.2.1.4.3 | 6.2.1.4.4 |
| 6.2.1.5.1 | 6.2.1.5.2 | 6.2.1.5.3 | 6.2.1.5.4 | 6.2.1.6.1 | 6.2.1.6.2 | 6.2.1.6.3 | 6.2.1.6.4 |
| 6.2.1.7.1 | 6.2.1.7.2 | 6.2.1.7.3 | 6.2.1.7.4 | 6.2.1.8.1 | 6.2.1.8.2 | 6.2.1.8.3 | 6.2.1.8.4 |
| 6.2.2.1.1 | 6.2.2.1.2 | 6.2.2.1.3 | 6.2.2.1.4 | 6.2.2.2.1 | 6.2.2.2.2 | 6.2.2.2.3 | 6.2.2.2.4 |
| 6.2.2.3.1 | 6.2.2.3.2 | 6.2.2.3.3 | 6.2.2.3.4 | 6.2.2.4.1 | 6.2.2.4.2 | 6.2.2.4.3 | 6.2.2.4.4 |
| 6.2.2.5.1 | 6.2.2.5.2 | 6.2.2.5.3 | 6.2.2.5.4 | 6.2.2.6.1 | 6.2.2.6.2 | 6.2.2.6.3 | 6.2.2.6.4 |
| 6.2.2.7.1 | 6.2.2.7.2 | 6.2.2.7.3 | 6.2.2.7.4 | 6.2.2.8.1 | 6.2.2.8.2 | 6.2.2.8.3 | 6.2.2.8.4 |
| 6.2.3.1.1 | 6.2.3.1.2 | 6.2.3.1.3 | 6.2.3.1.4 | 6.2.3.2.1 | 6.2.3.2.2 | 6.2.3.2.3 | 6.2.3.2.4 |
| 6.2.3.3.1 | 6.2.3.3.2 | 6.2.3.3.3 | 6.2.3.3.4 | 6.2.3.4.1 | 6.2.3.4.2 | 6.2.3.4.3 | 6.2.3.4.4 |
| 6.2.3.5.1 | 6.2.3.5.2 | 6.2.3.5.3 | 6.2.3.5.4 | 6.2.3.6.1 | 6.2.3.6.2 | 6.2.3.6.3 | 6.2.3.6.4 |
| 6.2.3.7.1 | 6.2.3.7.2 | 6.2.3.7.3 | 6.2.3.7.4 | 6.2.3.8.1 | 6.2.3.8.2 | 6.2.3.8.3 | 6.2.3.8.4 |
| 6.2.4.1.1 | 6.2.4.1.2 | 6.2.4.1.3 | 6.2.4.1.4 | 6.2.4.2.1 | 6.2.4.2.2 | 6.2.4.2.3 | 6.2.4.2.4 |
| 6.2.4.3.1 | 6.2.4.3.2 | 6.2.4.3.3 | 6.2.4.3.4 | 6.2.4.4.1 | 6.2.4.4.2 | 6.2.4.4.3 | 6.2.4.4.4 |
| 6.2.4.5.1 | 6.2.4.5.2 | 6.2.4.5.3 | 6.2.4.5.4 | 6.2.4.6.1 | 6.2.4.6.2 | 6.2.4.6.3 | 6.2.4.6.4 |
| 6.2.4.7.1 | 6.2.4.7.2 | 6.2.4.7.3 | 6.2.4.7.4 | 6.2.4.8.1 | 6..2.4.8.2 | 6.2.4.8.3 | 6.2.4.8.4 |
| 6.3.1.1.1 | 6.3.1.1.2 | 6.3.1.1.3 | 6.3.1.1.4 | 6.3.1.2.1 | 6.3.1.2.2 | 6.3.1.2.3 | 6.3.1.2.4 |
| 6.3.1.3.1 | 6.3.1.3.2 | 6.3.1.3.3 | 6.3.1.3.4 | 6.3.1.4.1 | 6.3.1.4.2 | 6.3.1.4.3 | 6.3.1.4.4 |
| 6.3.1.5.1 | 6.3.1.5.2 | 6.3.1.5.3 | 6.3.1.5.4 | 6.3.1.6.1 | 6.3.1.6.2 | 6.3.1.6.3 | 6.3.1.6.4 |
| 6.3.1.7.1 | 6.3.1.7.2 | 6.3.1.7.3 | 6.3.1.7.4 | 6.3.1.8.1 | 6.3.1.8.2 | 6.3.1.8.3 | 6.3.1.8.4 |
| 6.3.2.1.1 | 6.3.2.1.2 | 6.3.2.1.3 | 6.3.2.1.4 | 6.3.2.2.1 | 6.3.2.2.2 | 6.3.2.2.3 | 6.3.2.2.4 |
| 6.3.2.3.1 | 6.3.2.3.2 | 6.3.2.3.3 | 6.3.2.3.4 | 6.3.2.4.1 | 6.3.2.4.2 | 6.3.2.4.3 | 6.3.2.4.4 |
| 6.3.2.5.1 | 6.3.2.5.2 | 6.3.2.5.3 | 6.3.2.5.4 | 6.3.2.6.1 | 6.3.2.6.2 | 6.3.2.6.3 | 6.3.2.6.4 |
| 6.3.2.7.1 | 6.3.2.7.2 | 6.3.2.7.3 | 6.3.2.7.4 | 6.3.2.8.1 | 6.3.2.8.2 | 6.3.2.8.3 | 6.3.2.8.4 |
| 6.3.3.1.1 | 6.3.3.1.2 | 6.3.3.1.3 | 6.3.3.1.4 | 6.3.3.2.1 | 6.3.3.2.2 | 6.3.3.2.3 | 6.3.3.2.4 |

TABLE 3-continued

| | | | | | | | |
|---|---|---|---|---|---|---|---|
| 6.3.3.3.1 | 6.3.3.3.2 | 6.3.3.3.3 | 6.3.3.3.4 | 6.3.3.4.1 | 6.3.3.4.2 | 6.3.3.4.3 | 6.3.3.4.4 |
| 6.3.3.5.1 | 6.3.3.5.2 | 6.3.3.5.3 | 6.3.3.5.4 | 6.3.3.6.1 | 6.3.3.6.2 | 6.3.3.6.3 | 6.3.3.6.4 |
| 6.3.3.7.1 | 6.3.3.7.2 | 6.3.3.7.3 | 6.3.3.7.4 | 6.3.3.8.1 | 6.3.3.8.2 | 6.3.3.8.3 | 6.3.3.8.4 |
| 6.3.4.1.1 | 6.3.4.1.2 | 6.3.4.1.3 | 6.3.4.1.4 | 6.3.4.2.1 | 6.3.4.2.2 | 6.3.4.2.3 | 6.3.4.2.4 |
| 6.3.4.3.1 | 6.3.4.3.2 | 6.3.4.3.3 | 6.3.4.3.4 | 6.3.4.4.1 | 6.3.4.4.2 | 6.3.4.4.3 | 6.3.4.4.4 |
| 6.3.4.5.1 | 6.3.4.5.2 | 6.3.4.5.3 | 6.3.4.5.4 | 6.3.4.6.1 | 6.3.4.6.2 | 6.3.4.6.3 | 6.3.4.6.4 |
| 6.3.4.7.1 | 6.3.4.7.2 | 6.3.4.7.3 | 6.3.4.7.4 | 6.3.4.8.1 | 6.3.4.8.2 | 6.3.4.8.3 | 6.3.4.8.4 |
| 6.4.1.1.1 | 6.4.1.1.2 | 6.4.1.1.3 | 6.4.1.1.4 | 6.4.1.2.1 | 6.4.1.2.2 | 6.4.1.2.3 | 6.4.1.2.4 |
| 6.4.1.3.1 | 6.4.1.3.2 | 6.4.1.3.3 | 6.4.1.3.4 | 6.4.1.4.1 | 6.4.1.4.2 | 6.4.1.4.3 | 6.4.1.4.4 |
| 6.4.1.5.1 | 6.4.1.5.2 | 6.4.1.5.3 | 6.4.1.5.4 | 6.4.1.6.1 | 6.4.1.6.2 | 6.4.1.6.3 | 6.4.1.6.4 |
| 6.4.1.7.1 | 6.4.1.7.2 | 6.4.1.7.3 | 6.4.1.7.4 | 6.4.1.8.1 | 6.4.1.8.2 | 6.4.1.8.3 | 6.4.1.8.4 |
| 6.4.2.1.1 | 6.4.2.1.2 | 6.4.2.1.3 | 6.4.2.1.4 | 6.4.2.2.1 | 6.4.2.2.2 | 6.4.2.2.3 | 6.4.2.2.4 |
| 6.4.2.3.1 | 6.4.2.3.2 | 6.4.2.3.3 | 6.4.2.3.4 | 6.4.2.4.1 | 6.4.2.4.2 | 6.4.2.4.3 | 6.4.2.4.4 |
| 6.4.2.5.1 | 6.4.2.5.2 | 6.4.2.5.3 | 6.4.2.5.4 | 6.4.2.6.1 | 6.4.2.6.2 | 6.4.2.6.3 | 6.4.2.6.4 |
| 6.4.2.7.1 | 6.4.2.7.2 | 6.4.2.7.3 | 6.4.2.7.4 | 6.4.2.8.1 | 6.4.2.8.2 | 6.4.2.8.3 | 6.4.2.8.4 |
| 6.4.3.1.1 | 6.4.3.1.2 | 6.4.3.1.3 | 6.4.3.1.4 | 6.4.3.2.1 | 6.4.3.2.2 | 6.4.3.2.3 | 6.4.3.2.4 |
| 6.4.3.3.1 | 6.4.3.3.2 | 6.4.3.3.3 | 6.4.3.3.4 | 6.4.3.4.1 | 6.4.3.4.2 | 6.4.3.4.3 | 6.4.3.4.4 |
| 6.4.3.5.1 | 6.4.3.5.2 | 6.4.3.5.3 | 6.4.3.5.4 | 6.4.3.6.1 | 6.4.3.6.2 | 6.4.3.6.3 | 6.4.3.6.4 |
| 6.4.3.7.1 | 6.4.3.7.2 | 6.4.3.7.3 | 6.4.3.7.4 | 6.4.3.8.1 | 6.4.3.8.2 | 6.4.3.8.3 | 6.4.3.8.4 |
| 6.4.4.1.1 | 6.4.4.1.2 | 6.4.4.1.3 | 6.4.4.1.4 | 6.4.4.2.1 | 6.4.4.2.2 | 6.4.4.2.3 | 6.4.4.2.4 |
| 6.4.4.3.1 | 6.4.4.3.2 | 6.4.4.3.3 | 6.4.4.3.4 | 6.4.4.4.1 | 6.4.4.4.2 | 6.4.4.4.3 | 6.4.4.4.4 |
| 6.4.4.5.1 | 6.4.4.5.2 | 6.4.4.5.3 | 6.4.4.5.4 | 6.4.4.6.1 | 6.4.4.6.2 | 6.4.4.6.3 | 6.4.4.6.4 |
| 6.4.4.7.1 | 6.4.4.7.2 | 6.4.4.7.3 | 6.4.4.7.4 | 6.4.4.8.1 | 6.4.4.8.2 | 6.4.4.8.3 | 6.4.4.8.4 |
| 6.5.1.1.1 | 6.5.1.1.2 | 6.5.1.1.3 | 6.5.1.1.4 | 6.5.1.2.1 | 6.5.1.2.2 | 6.5.1.2.3 | 6.5.1.2.4 |
| 6.5.1.3.1 | 6.5.1.3.2 | 6.5.1.3.3 | 6.5.1.3.4 | 6.5.1.4.1 | 6.5.1.4.2 | 6.5.1.4.3 | 6.5.1.4.4 |
| 6.5.1.5.1 | 6.5.1.5.2 | 6.5.1.5.3 | 6.5.1.5.4 | 6.5.1.6.1 | 6.5.1.6.2 | 6.5.1.6.3 | 6.5.1.6.4 |
| 6.5.1.7.1 | 6.5.1.7.2 | 6.5.1.7.3 | 6.5.1.7.4 | 6.5.1.8.1 | 6.5.1.8.2 | 6.5.1.8.3 | 6.5.1.8.4 |
| 6.5.2.1.1 | 6.5.2.1.2 | 6.5.2.1.3 | 6.5.2.1.4 | 6.5.2.2.1 | 6.5.2.2.2 | 6.5.2.2.3 | 6.5.2.2.4 |
| 6.5.2.3.1 | 6.5.2.3.2 | 6.5.2.3.3 | 6.5.2.3.4 | 6.5.2.4.1 | 6.5.2.4.2 | 6.5.2.4.3 | 6.5.2.4.4 |
| 6.5.2.5.1 | 6.5.2.5.2 | 6.5.2.5.3 | 6.5.2.5.4 | 6.5.2.6.1 | 6.5.2.6.2 | 6.5.2.6.3 | 6.5.2.6.4 |
| 6.5.2.7.1 | 6.5.2.7.2 | 6.5.2.7.3 | 6.5.2.7.4 | 6.5.2.8.1 | 6.52.8.2 | 6.5.2.8.3 | 6.5.2.8.4 |
| 6.5.3.1.1 | 6.5.3.1.2 | 6.5.3.1.3 | 6.5.3.1.4 | 6.5.3.2.1 | 6.5.3.2.2 | 6.5.3.2.3 | 6.5.3.2.4 |
| 6.5.3.3.1 | 6.5.3.3.2 | 6.5.3.3.3 | 6.5.3.3.4 | 6.5.3.4.1 | 6.5.3.4.2 | 6.5.3.4.3 | 6.5.3.4.4 |
| 6.5.3.5.1 | 6.5.3.5.2 | 6.5.3.5.3 | 6.5.3.5.4 | 6.5.3.6.1 | 6.5.3.6.2 | 6.5.3.6.3 | 6.5.3.6.4 |
| 6.5.3.7.1 | 6.5.3.7.2 | 6.5.3.7.3 | 6.5.3.7.4 | 6.5.3.8.1 | 6.5.3.8.2 | 6.5.3.8.3 | 6.5.3.8.4 |
| 6.5.4.1.1 | 6.5.4.1.2 | 6.5.4.1.3 | 6.5.4.1.4 | 6.5.4.2.1 | 6.5.4.2.2 | 6.5.4.2.3 | 6.5.4.2.4 |
| 6.5.4.3.1 | 6.5.4.3.2 | 6.5.4.3.3 | 6.5.4.3.4 | 6.5.4.4.1 | 6.5.4.4.2 | 6.5.4.4.3 | 6.5.4.4.4 |
| 6.5.4.5.1 | 6.5.4.5.2 | 6.5.4.5.3 | 6.5.4.5.4 | 6.5.4.6.1 | 6.5.4.6.2 | 6.5.4.6.3 | 6.5.4.6.4 |
| 6.5.4.7.1 | 6.5.4.7.2 | 6.5.4.7.3 | 6.5.4.7.4 | 6.5.4.8.1 | 6.5.4.8.2 | 6.5.4.8.3 | 6.5.4.8.4 |
| 6.6.1.1.1 | 6.6.1.1.2 | 6.6.1.1.3 | 6.6.1.1.4 | 6.6.1.2.1 | 6.6.1.2.2 | 6.6.1.2.3 | 6.6.1.2.4 |
| 6.6.1.3.1 | 6.6.1.3.2 | 6.6.1.3.3 | 6.6.1.3.4 | 6.6.1.4.1 | 6.6.1.4.2 | 6.6.1.4.3 | 6.6.1.4.4 |
| 6.6.1.5.1 | 6.6.1.5.2 | 6.6.1.5.3 | 6.6.1.5.4 | 6.6.1.6.1 | 6.6.1.6.2 | 6.6.1.6.3 | 6.6.1.6.4 |
| 6.6.1.7.1 | 6.6.1.7.2 | 6.6.1.7.3 | 6.6.1.7.4 | 6.6.1.8.1 | 6.6.1.8.2 | 6.6.1.8.3 | 6.6.1.8.4 |
| 6.6.2.1.1 | 6.6.2.1.2 | 6.6.2.1.3 | 6.6.2.1.4 | 6.6.2.2.1 | 6.6.2.2.2 | 6.6.2.2.3 | 6.6.2.2.4 |
| 6.6.2.3.1 | 6.6.2.3.2 | 6.6.2.3.3 | 6.6.2.3.4 | 6.6.2.4.1 | 6.6.2.4.2 | 6.6.2.4.3 | 6.6.2.4.4 |
| 6.6.2.5.1 | 6.6.2.5.2 | 6.6.2.5.3 | 6.6.2.5.4 | 6.6.2.6.1 | 6.6.2.6.2 | 6.6.2.6.3 | 6.6.2.6.4 |
| 6.6.2.7.1 | 6.6.2.7.2 | 6.6.2.7.3 | 6.6.2.7.4 | 6.6.2.8.1 | 6.6.2.8.2 | 6.6.2.8.3 | 6.6.2.8.4 |
| 6.6.3.1.1 | 6.6.3.1.2 | 6.6.3.1.3 | 6.6.3.1.4 | 6.6.3.2.1 | 6.6.3.2.2 | 6.6.3.2.3 | 6.6.3.2.4 |
| 6.6.3.3.1 | 6.6.3.3.2 | 6.6.3.3.3 | 6.6.3.3.4 | 6.6.3.4.1 | 6.6.3.4.2 | 6.6.3.4.3 | 6.6.3.4.4 |
| 6.6.3.5.1 | 6.6.3.5.2 | 6.6.3.5.3 | 6.6.3.5.4 | 6.6.3.6.1 | 6.6.3.6.2 | 6.6.3.6.3 | 6.6.3.6.4 |
| 6.6.3.7.1 | 6.6.3.7.2 | 6.6.3.7.3 | 6.6.3.7.4 | 6.6.3.8.1 | 6.6.3.8.2 | 6.6.3.8.3 | 6.6.3.8.4 |
| 6.6.4.1.1 | 6.6.4.1.2 | 6.6.4.1.3 | 6.6.4.1.4 | 6.6.4.2.1 | 6.6.4.2.2 | 6.6.4.2.3 | 6.6.4.2.4 |
| 6.6.4.3.1 | 6.6.4.3.2 | 6.6.4.3.3 | 6.6.4.3.4 | 6.6.4.4.1 | 6.6.4.4.2 | 6.6.4.4.3 | 6.6.4.4.4 |
| 6.6.4.5.1 | 6.6.4.5.2 | 6.6.4.5.3 | 6.6.4.5.4 | 6.6.4.6.1 | 6.6.4.6.2 | 6.6.4.6.3 | 6.6.4.6.4 |
| 6.6.4.7.1 | 6.6.4.7.2 | 6.6.4.7.3 | 6.6.4.7.4 | 6.6.4.8.1 | 6.6.4.8.2 | 6.6.4.8.3 | 6.6.4.8.4 |
| 6.7.1.1.1 | 6.7.1.1.2 | 6.7.1.1.3 | 6.7.1.1.4 | 6.7.1.2.1 | 6.7.1.2.2 | 6.7.1.2.3 | 6.7.1.2.4 |
| 6.7.1.3.1 | 6.7.1.3.2 | 6.7.1.3.3 | 6.7.1.3.4 | 6.7.1.4.1 | 6.7.1.4.2 | 6.7.1.4.3 | 6.7.1.4.4 |
| 6.7.1.5.1 | 6.7.1.5.2 | 6.7.1.5.3 | 6.7.1.5.4 | 6.7.1.6.1 | 6.7.1.6.2 | 6.7.1.6.3 | 6.7.1.6.4 |
| 6.7.1.7.1 | 6.7.1.7.2 | 6.7.1.7.3 | 6.7.1.7.4 | 6.7.1.8.1 | 6.7.1.8.2 | 6.7.1.8.3 | 6.7.1.8.4 |
| 6.7.2.1.1 | 6.7.2.1.2 | 6.7.2.1.3 | 6.7.2.1.4 | 6.7.2.2.1 | 6.7.2.2.2 | 6.7.2.2.3 | 6.7.2.2.4 |
| 6.7.2.3.1 | 6.7.2.3.2 | 6.7.2.3.3 | 6.7.2.3.4 | 6.7.2.4.1 | 6.7.2.4.2 | 6.7.2.4.3 | 6.7.2.4.4 |
| 6.7.2.5.1 | 6.7.2.5.2 | 6.7.2.5.3 | 6.7.2.5.4 | 6.7.2.6.1 | 6.7.2.6.2 | 6.7.2.6.3 | 6.7.2.6.4 |
| 6.7.2.7.1 | 6.7.2.7.2 | 6.7.2.7.3 | 6.7.2.7.4 | 6.7.2.8.1 | 6.7.2.8.2 | 6.7.2.8.3 | 6.7.2.8.4 |
| 6.7.3.1.1 | 6.7.3.1.2 | 6.7.3.1.3 | 6.7.3.1.4 | 6.7.3.2.1 | 6.7.3.2.2 | 6.7.3.2.3 | 6.7.3.2.4 |
| 6.7.3.3.1 | 6.7.3.3.2 | 6.7.3.3.3 | 6.7.3.3.4 | 6.7.3.4.1 | 6.7.3.4.2 | 6.7.3.4.3 | 6.7.3.4.4 |
| 6.7.3.5.1 | 6.7.3.5.2 | 6.7.3.5.3 | 6.7.3.5.4 | 6.7.3.6.1 | 6.7.3.6.2 | 6.7.3.6.3 | 6.7.3.6.4 |
| 6.7.3.7.1 | 6.7.3.7.2 | 6.7.3.7.3 | 6.7.3.7.4 | 6.7.3.8.1 | 6.7.3.8.2 | 6.7.3.8.3 | 6.7.3.8.4 |
| 6.7.4.1.1 | 6.7.4.1.2 | 6.7.4.1.3 | 6.7.4.1.4 | 6.7.4.2.1 | 6.7.4.2.2 | 6.7.4.2.3 | 6.7.4.2.4 |
| 6.7.4.3.1 | 6.7.4.3.2 | 6.7.4.3.3 | 6.7.4.3.4 | 6.7.4.4.1 | 6.7.4.4.2 | 6.7.4.4.3 | 6.7.4.4.4 |
| 6.7.4.5.1 | 6.7.4.5.2 | 6.7.4.5.3 | 6.7.4.5.4 | 6.7.4.6.1 | 6.7.4.6.2 | 6.7.4.6.3 | 6.7.4.6.4 |
| 6.7.4.7.1 | 6.7.4.7.2 | 6.7.4.7.3 | 6.7.4.7.4 | 6.7.4.8.1 | 6.7.4.8.2 | 6.7.4.8.3 | 6.7.4.8.4 |
| 6.8.1.1.1 | 6.8.1.1.2 | 6.8.1.1.3 | 6.8.1.1.4 | 6.8.1.2.1 | 6.8.1.2.2 | 6.8.1.2.3 | 6.8.1.2.4 |
| 6.8.1.3.1 | 6.8.1.3.2 | 6.8.1.3.3 | 6.8.1.3.4 | 6.8.1.4.1 | 6.8.1.4.2 | 6.8.1.4.3 | 6.8.1.4.4 |
| 6.8.1.5.1 | 6.8.1.5.2 | 6.8.1.5.3 | 6.8.1.5.4 | 6.8.1.6.1 | 6.8.1.6.2 | 6.8.1.6.3 | 6.8.1.6.4 |
| 6.8.1.7.1 | 6.8.1.7.2 | 6.8.1.7.3 | 6.8.1.7.4 | 6.8.1.8.1 | 6.8.1.8.2 | 6.8.1.8.3 | 6.8.1.8.4 |
| 6.8.2.1.1 | 6.8.2.1.2 | 6.8.2.1.3 | 6.8.2.1.4 | 6.8.2.2.1 | 6.8.2.2.2 | 6.8.2.2.3 | 6.8.2.2.4 |
| 6.8.2.3.1 | 6.8.2.3.2 | 6.8.2.3.3 | 6.8.2.3.4 | 6.8.2.4.1 | 6.8.2.4.2 | 6.8.2.4.3 | 6.8.2.4.4 |
| 6.8.2.5.1 | 6.8.2.5.2 | 6.8.2.5.3 | 6.8.2.5.4 | 6.8.2.6.1 | 6.8.2.6.2 | 6.8.2.6.3 | 6.8.2.6.4 |
| 6.8.2.7.1 | 6.8.2.7.2 | 6.8.2.7.3 | 6.8.2.7.4 | 6.8.2.8.1 | 6.8.2.8.2 | 6.8.2.8.3 | 6.8.2.8.4 |

TABLE 3-continued

| | | | | | | | |
|---|---|---|---|---|---|---|---|
| 6.8.3.1.1 | 6.8.3.1.2 | 6.8.3.1.3 | 6.8.3.1.4 | 6.8.3.2.1 | 6.8.3.2.2 | 6.8.3.2.3 | 6.8.3.2.4 |
| 6.8.3.3.1 | 6.8.3.3.2 | 6.8.3.3.3 | 6.8.3.3.4 | 6.8.3.4.1 | 6.8.3.4.2 | 6.8.3.4.3 | 6.8.3.4.4 |
| 6.8.3.5.1 | 6.8.3.5.2 | 6.8.3.5.3 | 6.8.3.5.4 | 6.8.3.6.1 | 6.8.3.6.2 | 6.8.3.6.3 | 6.8.3.6.4 |
| 6.8.3.7.1 | 6.8.3.7.2 | 6.8.3.7.3 | 6.8.3.7.4 | 6.8.3.8.1 | 6.8.3.8.2 | 6.8.3.8.3 | 6.8.3.8.4 |
| 6.8.4.1.1 | 6.8.4.1.2 | 6.8.4.1.3 | 6.8.4.1.4 | 6.8.4.21 | 6.8.4.2.2 | 6.8.4.2.3 | 6.8.4.2.4 |
| 6.8.4.3.1 | 6.8.4.3.2 | 6.8.4.3.3 | 6.8.4.3.4 | 6.8.4.4.1 | 6.8.4.4.2 | 6.8.4.4.3 | 6.8.4.4.4 |
| 6.8.4.5.1 | 6.8.4.5.2 | 6.8.4.5.3 | 6.8.4.5.4 | 6.8.4.6.1 | 6.8.4.6.2 | 6.8.4.6.3 | 6.8.4.6.4 |
| 6.8.4.7.1 | 6.8.4.7.2 | 6.8.4.7.3 | 6.8.4.7.4 | 6.8.4.8.1 | 6.8.4.8.2 | 6.8.4.8.3 | 6.8.4.8.4 |
| 7.1.1.1.1 | 7.1.1.1.2 | 7.1.1.1.3 | 7.1.1.1.4 | 7.1.1.2.1 | 7.1.1.2.2 | 7.1.1.2.3 | 7.1.1.2.4 |
| 7.1.1.3.1 | 7.1.1.3.2 | 7.1.1.3.3 | 7.1.1.3.4 | 7.1.1.4.1 | 7.1.1.4.2 | 7.1.1.4.3 | 7.1.1.4.4 |
| 7.1.1.5.1 | 7.1.1.5.2 | 7.1.1.5.3 | 7.1.1.5.4 | 7.1.1.6.1 | 7.1.1.6.2 | 7.1.1.6.3 | 7.1.1.6.4 |
| 7.1.1.7.1 | 7.1.1.7.2 | 7.1.1.7.3 | 7.1.1.7.4 | 7.1.1.8.1 | 7.1.1.8.2 | 7.1.1.8.3 | 7.1.1.8.4 |
| 7.1.2.1.1 | 7.1.2.1.2 | 7.1.2.1.3 | 7.1.2.1.4 | 7.1.2.2.1 | 7.1.2.2.2 | 7.1.2.2.3 | 7.1.2.2.4 |
| 7.1.2.3.1 | 7.1.2.3.2 | 7.1.2.3.3 | 7.1.2.3.4 | 7.1.2.4.1 | 7.1.2.4.2 | 7.1.2.4.3 | 7.1.2.4.4 |
| 7.1.2.5.1 | 7.1.2.5.2 | 7.1.2.5.3 | 7.1.2.5.4 | 7.1.2.6.1 | 7.1.2.6.2 | 7.1.2.6.3 | 7.1.2.6.4 |
| 7.1.2.7.1 | 7.1.2.7.2 | 7.1.2.7.3 | 7.1.2.7.4 | 7.1.2.8.1 | 7.1.2.8.2 | 7.1.2.8.3 | 7.1.2.8.4 |
| 7.1.3.1.1 | 7.1.3.1.2 | 7.1.3.1.3 | 7.1.3.1.4 | 7.1.3.2.1 | 7.1.3.2.2 | 7.1.3.2.3 | 7.1.3.2.4 |
| 7.1.3.3.1 | 7.1.3.3.2 | 7.1.3.3.3 | 7.1.3.3.4 | 7.1.3.4.1 | 7.1.3.4.2 | 7.1.3.4.3 | 7.1.3.4.4 |
| 7.1.3.5.1 | 7.1.3.5.2 | 7.1.3.5.3 | 7.1.3.5.4 | 7.1.3.6.1 | 7.1.3.6.2 | 7.1.3.6.3 | 7.1.3.6.4 |
| 7.1.3.7.1 | 7.1.3.7.2 | 7.1.3.7.3 | 7.1.3.7.4 | 7.1.3.8.1 | 7.1.3.8.2 | 7.1.3.8.3 | 7.1.3.8.4 |
| 7.1.4.1.1 | 7.1.4.1.2 | 7.1.4.1.3 | 7.1.4.1.4 | 7.1.4.2.1 | 7.1.4.2.2 | 7.1.4.2.3 | 7.1.4.2.4 |
| 7.1.4.3.1 | 7.1.4.3.2 | 7.1.4.3.3 | 7.1.4.3.4 | 7.1.4.4.1 | 7.1.4.4.2 | 7.1.4.4.3 | 7.1.4.4.4 |
| 7.1.4.5.1 | 7.1.4.5.2 | 7.1.4.5.3 | 7.1.4.5.4 | 7.1.4.6.1 | 7.1.4.6.2 | 7.1.4.6.3 | 7.1.4.6.4 |
| 7.1.4.7.1 | 7.1.4.7.2 | 7.1.4.7.3 | 7.1.4.7.4 | 7.1.4.8.1 | 7.1.4.8.1 | 7.1.4.8.3 | 7.1.4.8.4 |
| 7.2.1.1.1 | 7.2.1.1.2 | 7.2.1.1.3 | 7.2.1.1.4 | 7.2.1.2.1 | 7.2.1.2.2 | 7.2.1.2.3 | 7.2.1.2.4 |
| 7.2.1.3.1 | 7.2.1.3.2 | 7.2.1.3.3 | 7.2.1.3.4 | 7.2.1.4.1 | 7.2.1.4.2 | 7.2.1.4.3 | 7.2.1.4.4 |
| 7.2.1.5.1 | 7.2.1.5.2 | 7.2.1.5.3 | 7.2.1.5.4 | 7.2.1.6.1 | 7.2.1.6.2 | 7.2.1.6.3 | 7.2.1.6.4 |
| 7.2.1.7.1 | 7.2.1.7.2 | 7.2.1.7.3 | 7.2.1.7.4 | 7.2.1.8.1 | 7.2.1.8.2 | 7.2.1.8.3 | 7.2.1.8.4 |
| 7.2.2.1.1 | 7.2.2.1.2 | 7.2.2.1.3 | 7.2.2.1.4 | 7.2.2.2.1 | 7.2.2.2.2 | 7.2.2.2.3 | 7.2.2.2.4 |
| 7.2.2.3.1 | 7.2.2.3.2 | 7.2.2.3.3 | 7.2.2.3.4 | 7.2.2.4.1 | 7.2.2.4.2 | 7.2.2.4.3 | 7.2.2.4.4 |
| 7.2.2.5.1 | 7.2.2.5.2 | 7.2.2.5.3 | 7.2.2.5.4 | 7.2.2.6.1 | 7.2.2.6.2 | 7.2.2.6.3 | 7.2.2.6.4 |
| 7.2.2.7.1 | 7.2.2.7.2 | 7.2.2.7.3 | 7.2.2.7.4 | 7.2.2.8.1 | 7.2.2.8.2 | 7.2.2.8.3 | 7.2.2.8.4 |
| 7.2.3.1.1 | 7.2.3.1.2 | 7.2.3.1.3 | 7.2.3.1.4 | 7.2.3.2.1 | 7.2.3.2.2 | 7.2.3.2.3 | 7.2.3.2.4 |
| 7.2.3.3.1 | 7.2.3.3.2 | 7.2.3.3.3 | 7.2.3.3.4 | 7.2.3.4.1 | 7.2.3.4.2 | 7.2.3.4.3 | 7.2.3.4.4 |
| 7.2.3.5.1 | 7.2.3.5.2 | 7.2.3.5.3 | 7.2.3.5.4 | 7.2.3.6.1 | 7.2.3.6.2 | 7.2.3.6.3 | 7.2.3.6.4 |
| 7.2.3.7.1 | 7.2.3.7.2 | 7.2.3.7.3 | 7.2.3.7.4 | 7.2.3.8.1 | 7.2.3.8.2 | 7.2.3.8.3 | 7.2.3.8.4 |
| 7.2.4.1.1 | 7.2.4.1.2 | 7.2.4.1.3 | 7.2.4.1.4 | 7.2.4.2.1 | 7.2.4.2.2 | 7.2.4.2.3 | 7.2.4.2.4 |
| 7.2.4.3.1 | 7.2.4.3.2 | 7.2.4.3.3 | 7.2.4.3.4 | 7.2.4.4.1 | 7.2.4.4.2 | 7.2.4.4.3 | 7.2.4.4.4 |
| 7.2.4.5.1 | 7.2.4.5.2 | 7.2.4.5.3 | 7.2.4.5.4 | 7.2.4.6.1 | 7.2.4.6.2 | 7.2.4.6.3 | 7.2.4.6.4 |
| 7.2.4.7.1 | 7.2.4.7.2 | 7.2.4.7.3 | 7.2.4.7.4 | 7.2.4.8.1 | 7.2.4.8.2 | 7.2.4.8.3 | 7.2.4.8.4 |
| 7.3.1.1.1 | 7.3.1.1.2 | 7.3.1.1.3 | 7.3.1.1.4 | 7.3.1.2.1 | 7.3.1.2.2 | 7.3.1.2.3 | 7.3.1.2.4 |
| 7.3.1.3.1 | 7.3.1.3.2 | 7.3.1.3.3 | 7.3.1.3.4 | 7.3.1.4.1 | 7.3.1.4.2 | 7.3.1.4.3 | 7.3.1.4.4 |
| 7.3.1.5.1 | 7.3.1.5.2 | 7.3.1.5.3 | 7.3.1.5.4 | 7.3.1.6.1 | 7.3.1.6.2 | 7.3.1.6.3 | 7.3.1.6.4 |
| 7.3.1.7.1 | 7.3.1.7.2 | 7.3.1.7.3 | 7.3.1.7.4 | 7.3.1.8.1 | 7.3.1.8.2 | 7.3.1.8.3 | 7.3.1.8.4 |
| 7.3.2.1.1 | 7.3.2.1.2 | 7.3.2.1.3 | 7.3.2.1.4 | 7.3.2.2.1 | 7.3.2.2.2 | 7.3.2.2.3 | 7.3.2.2.4 |
| 7.3.2.3.1 | 7.3.2.3.2 | 7.3.2.3.3 | 7.3.2.3.4 | 7.3.2.4.1 | 7.3.2.4.2 | 7.3.2.4.3 | 7.3.2.4.4 |
| 7.3.2.5.1 | 7.3.2.5.2 | 7.3.2.5.3 | 7.3.2.5.4 | 7.3.2.6.1 | 7.3.2.6.2 | 7.3.2.6.3 | 7.3.2.6.4 |
| 7.3.2.7.1 | 7.3.2.7.2 | 7.3.2.7.3 | 7.3.Z.7.4 | 7.3.2.8.1 | 7.3.2.8.2 | 7.3.2.8.3 | 7.3.2.8.4 |
| 7.3.3.1.1 | 7.3.3.1.2 | 7.3.3.1.3 | 7.3.3.1.4 | 7.3.3.2.1 | 7.3.3.2.2 | 7.3.3.2.3 | 7.3.3.2.4 |
| 7.3.3.3.1 | 7.3.3.3.2 | 7.3.3.3.3 | 7.3.3.3.4 | 7.3.3.4.1 | 7.3.3.4.2 | 7.3.3.4.3 | 7.3.3.4.4 |
| 7.3.3.5.1 | 7.3.3.5.2 | 7.3.3.5.3 | 7.3.3.5.4 | 7.3.3.6.1 | 7.3.3.6.2 | 7.3.3.6.3 | 7.3.3.6.4 |
| 7.3.3.7.1 | 7.3.3.7.2 | 7.3.3.7.3 | 7.3.3.7.4 | 7.3.3.8.1 | 7.3.3.8.2 | 7.3.3.8.3 | 7.3.3.8.4 |
| 7.3.4.1.1 | 7.3.4.1.2 | 7.3.4.1.3 | 7.3.4.1.4 | 7.3.4.2.1 | 7.3.4.2.2 | 7.3.4.2.3 | 7.3.4.2.4 |
| 7.3.4.3.1 | 7.3.4.3.2 | 7.3.4.3.3 | 7.3.4.3.4 | 7.3.4.4.1 | 7.3.4.4.2 | 7.3.4.4.3 | 7.3.4.4.4 |
| 7.3.4.5.1 | 7.3.4.5.2 | 7.3.4.5.3 | 7.3.4.5.4 | 7.3.4.6.1 | 7.3.4.6.2 | 7.3.4.6.3 | 7.3.4.6.4 |
| 7.3.4.7.1 | 7.3.4.7.2 | 7.3.4.7.3 | 7.3.4.7.4 | 7.3.4.8.1 | 7.3.4.8.2 | 7.3.4.8.3 | 7.3.4.8.4 |
| 7.4.1.1.1 | 7.4.1.1.2 | 7.4.1.1.3 | 7.4.1.1.4 | 7.4.1.2.1 | 7.4.1.2.2 | 7.4.1.2.3 | 7.4.1.2.4 |
| 7.4.1.3.1 | 7.4.1.3.2 | 7.4.1.3.3 | 7.4.1.3.4 | 7.4.1.4.1 | 7.4.1.4.2 | 7.4.1.4.3 | 7.4.1.4.4 |
| 7.4.1.5.1 | 7.4.1.5.2 | 7.4.1.5.3 | 7.4.1.5.4 | 7.4.1.6.1 | 7.4.1.6.2 | 7.4.1.6.3 | 7.4.1.6.4 |
| 7.4.1.7.1 | 7.4.1.7.2 | 7.4.1.7.3 | 7.4.1.7.4 | 7.4.1.8.1 | 7.4.1.8.2 | 7.4.1.8.3 | 7.4.1.8.4 |
| 7.4.2.1.1 | 7.4.2.1.2 | 7.4.2.1.3 | 7.4.2.1.4 | 7.4.2.2.1 | 7.4.2.2.2 | 7.4.2.2.3 | 7.4.2.2.4 |
| 7.4.2.3.1 | 7.4.2.3.2 | 7.4.2.3.3 | 7.4.2.3.4 | 7.4.2.4.1 | 7.4.2.4.2 | 7.4.2.4.3 | 7.4.2.4.4 |
| 7.4.2.5.1 | 7.4.2.5.2 | 7.4.2.5.3 | 7.4.2.5.4 | 7.4.2.6.1 | 7.4.2.6.2 | 7.4.2.6.3 | 7.4.2.6.4 |
| 7.4.2.7.1 | 7.4.2.7.2 | 7.4.2.7.3 | 7.4.2.7.4 | 7.4.2.8.1 | 7.4.2.8.2 | 7.4.2.8.3 | 7.4.2.8.4 |
| 7.4.3.1.1 | 7.4.3.1.2 | 7.4.3.1.3 | 7.4.3.1.4 | 7.4.3.2.1 | 7.4.3.2.2 | 7.4.3.2.3 | 7.4.3.2.4 |
| 7.4.3.3.1 | 7.4.3.3.2 | 7.4.3.3.3 | 7.4.3.3.4 | 7.4.3.4.1 | 7.4.3.4.2 | 7.4.3.4.3 | 7.4.3.4.4 |
| 7.4.3.5.1 | 7.4.3.5.2 | 7.4.3.5.3 | 7.4.3.5.4 | 7.4.3.6.1 | 7.4.3.6.2 | 7.4.3.6.3 | 7.4.3.6.4 |
| 7.4.3.7.1 | 7.4.3.7.2 | 7.4.3.7.3 | 7.4.3.7.4 | 7.4.3.8.1 | 7.4.3.8.2 | 7.4.3.8.3 | 7.4.3.8.4 |
| 7.4.4.1.1 | 7.4.4.1.2 | 7.4.4.1.3 | 7.4.4.1.4 | 7.4.4.2.1 | 7.4.4.2.2 | 7.4.4.2.3 | 7.4.4.2.4 |
| 7.4.4.3.1 | 7.4.4.3.2 | 7.4.4.3.3 | 7.4.4.3.4 | 7.4.4.4.1 | 7.4.4.4.2 | 7.4.4.4.3 | 7.4.4.4.4 |
| 7.4.4.5.1 | 7.4.4.5.2 | 7.4.4.5.3 | 7.4.4.5.4 | 7.4.4.6.1 | 7.4.4.6.2 | 7.4.4.6.3 | 7.4.4.6.4 |
| 7.4.4.7.1 | 7.4.4.7.2 | 7.4.4.7.3 | 7.4.4.7.4 | 7.4.4.8.1 | 7.4.4.8.2 | 7.4.4.8.3 | 7.4.4.8.4 |
| 7.5.1.1.1 | 7.5.1.1.2 | 7.5.1.1.3 | 7.5.1.1.4 | 7.5.1.2.1 | 7.5.1.2.2 | 7.5.1.2.3 | 7.5.1.2.4 |
| 7.5.1.3.1 | 7.5.1.3.2 | 7.5.1.3.3 | 7.5.1.3.4 | 7.5.1.4.1 | 7.5.1.4.2 | 7.5.1.4.3 | 7.5.1.4.4 |
| 7.5.1.5.1 | 7.5.1.5.2 | 7.5.1.5.3 | 7.5.1.5.4 | 7.5.1.6.1 | 7.5.1.6.2 | 7.5.1.6.3 | 7.5.1.6.4 |
| 7.5.1.7.1 | 7.5.1.7.2 | 7.5.1.7.3 | 7.5.1.7.4 | 7.5.1.8.1 | 7.5.1.8.2 | 7.5.1.8.3 | 7.5.1.8.4 |
| 7.5.2.1.1 | 7.5.2.1.2 | 7.5.2.1.3 | 7.5.2.1.4 | 7.5.2.2.1 | 7.5.2.2.2 | 7.5.2.2.3 | 7.5.2.2.4 |
| 7.5.2.3.1 | 7.5.2.3.2 | 7.5.2.3.3 | 7.5.2.3.4 | 7.5.2.4.1 | 7.5.2.4.2 | 7.5.2.4.3 | 7.5.2.4.4 |
| 7.5.2.5.1 | 7.5.2.5.2 | 7.5.2.5.3 | 7.5.2.5.4 | 7.5.2.6.1 | 7.5.2.6.2 | 7.5.2.6.3 | 7.5.2.6.4 |

TABLE 3-continued

| | | | | | | |
|---|---|---|---|---|---|---|
| 7.5.2.7.1 | 7.5.2.7.2 | 7.5.2.7.3 | 7.5.2.7.4 | 7.5.2.8.1 | 7.5.2.8.2 | 7.5.2.8.3 | 7.5.2.8.4 |
| 7.5.3.1.1 | 7.5.3.1.2 | 7.5.3.1.3 | 7.5.3.1.4 | 7.5.3.2.1 | 7.5.3.2.2 | 7.5.3.2.3 | 7.5.3.2.4 |
| 7.5.3.3.1 | 7.5.3.3.2 | 7.5.3.3.3 | 7.5.3.3.4 | 7.5.3.4.1 | 7.5.3.4.2 | 7.5.3.4.3 | 7.5.3.4.4 |
| 7.5.3.5.1 | 7.5.3.5.2 | 7.5.3.5.3 | 7.5.3.5.4 | 7.5.3.6.1 | 7.5.3.6.2 | 7.5.3.6.3 | 7.5.3.6.4 |
| 7.5.3.7.1 | 7.5.3.7.2 | 7.5.3.7.3 | 7.5.3.7.4 | 7.5.3.8.1 | 7.5.3.8.2 | 7.5.3.8.3 | 7.5.3.8.4 |
| 7.5.4.1.1 | 7.5.4.1.2 | 7.5.4.1.3 | 7.5.4.1.4 | 7.5.4.2.1 | 7.5.4.2.2 | 7.5.4.2.3 | 7.5.4.2.4 |
| 7.5.4.3.1 | 7.5.4.3.2 | 7.5.4.3.3 | 7.5.4.3.4 | 7.5.4.4.1 | 7.5.4.4.2 | 7.5.4.4.3 | 7.5.4.4.4 |
| 7.5.4.5.1 | 7.5.4.5.2 | 7.5.4.5.3 | 7.5.4.5.4 | 7.5.4.6.1 | 7.5.4.6.2 | 7.5.4.6.3 | 7.5.4.6.4 |
| 7.5.4.7.1 | 7.5.4.7.2 | 7.5.4.7.3 | 7.5.4.7.4 | 7.5.4.8.1 | 7.5.4.8.2 | 7.5.4.8.3 | 7.5.4.8.4 |
| 7.6.1.1.1 | 7.6.1.1.2 | 7.6.1.1.3 | 7.6.1.1.4 | 7.6.1.2.1 | 7.6.1.2.2 | 7.6.1.2.3 | 7.6.1.2.4 |
| 7.6.1.3.1 | 7.6.1.3.2 | 7.6.1.3.3 | 7.6.1.3.4 | 7.6.1.4.1 | 7.6.1.4.2 | 7.6.1.4.3 | 7.6.1.4.4 |
| 7.6.1.5.1 | 7.6.1.5.2 | 7.6.1.5.3 | 7.6.1.5.4 | 7.6.1.6.1 | 7.6.1.6.2 | 7.6.1.6.3 | 7.6.1.6.4 |
| 7.6.1.7.1 | 7.6.1.7.2 | 7.6.1.7.3 | 7.6.1.7.4 | 7.6.1.8.1 | 7.6.1.8.2 | 7.6.1.8.3 | 7.6.1.8.4 |
| 7.6.2.1.1 | 7.6.2.1.2 | 7.6.2.1.3 | 7.6.2.1.4 | 7.6.2.2.1 | 7.6.2.2.2 | 7.6.2.2.3 | 7.6.2.2.4 |
| 7.6.2.3.1 | 7.6.2.3.2 | 7.6.2.3.3 | 7.6.2.3.4 | 7.6.2.4.1 | 7.6.2.4.2 | 7.6.2.4.3 | 7.6.2.4.4 |
| 7.6.2.5.1 | 7.6.2.5.2 | 7.6.2.5.3 | 7.6.2.5.4 | 7.6.2.6.1 | 7.6.2.6.2 | 7.6.2.6.3 | 7.6.2.6.4 |
| 7.6.2.7.1 | 7.6.2.7.2 | 7.6.2.7.3 | 7.6.2.7.4 | 7.6.2.8.1 | 7.6.2.8.2 | 7.6.2.8.3 | 7.6.2.8.4 |
| 7.6.3.1.1 | 7.6.3.1.2 | 7.6.3.1.3 | 7.6.3.1.4 | 7.6.3.2.1 | 7.6.3.2.2 | 7.6.3.2.3 | 7.6.3.2.4 |
| 7.6.3.3.1 | 7.6.3.3.2 | 7.6.3.3.3 | 7.6.3.3.4 | 7.6.3.4.1 | 7.6.3.4.2 | 7.6.3.4.3 | 7.6.3.4.4 |
| 7.6.3.5.1 | 7.6.3.5.2 | 7.6.3.5.3 | 7.6.3.5.4 | 7.6.3.6.1 | 7.6.3.6.2 | 7.6.3.6.3 | 7.6.3.6.4 |
| 7.6.3.7.1 | 7.6.3.7.2 | 7.6.3.7.3 | 7.6.3.7.4 | 7.6.3.8.1 | 7.6.3.8.2 | 7.6.3.8.3 | 7.6.3.8.4 |
| 7.6.4.1.1 | 7.6.4.1.2 | 7.6.4.1.3 | 7.6.4.1.4 | 7.6.4.2.1 | 7.6.4.2.2 | 7.6.4.2.3 | 7.6.4.2.4 |
| 7.6.4.3.1 | 7.6.4.3.2 | 7.6.4.3.3 | 7.6.4.3.4 | 7.6.4.4.1 | 7.6.4.4.2 | 7.6.4.4.3 | 7.6.4.4.4 |
| 7.6.4.5.1 | 7.6.4.5.2 | 7.6.4.5.3 | 7.6.4.5.4 | 7.6.4.6.1 | 7.6.4.6.2 | 7.6.4.6.3 | 7.6.4.6.4 |
| 7.6.4.7.1 | 7.6.4.7.2 | 7.6.4.7.3 | 7.6.4.7.4 | 7.6.4.8.1 | 7.6.4.8.2 | 7.6.4.8.3 | 7.6.4.8.4 |
| 7.7.1.1.1 | 7.7.1.1.2 | 7.7.1.1.3 | 7.7.1.1.4 | 7.7.1.2.1 | 7.7.1.2.2 | 7.7.1.2.3 | 7.7.1.2.4 |
| 7.7.1.3.1 | 7.7.1.3.2 | 7.7.1.3.3 | 7.7.1.3.4 | 7.7.1.4.1 | 7.7.1.4.2 | 7.7.1.4.3 | 7.7.1.4.4 |
| 7.7.1.5.1 | 7.7.1.5.2 | 7.7.1.5.3 | 7.7.1.5.4 | 7.7.1.6.1 | 7.7.1.6.2 | 7.7.1.6.3 | 7.7.1.6.4 |
| 7.7.1.7.1 | 7.7.1.7.2 | 7.7.1.7.3 | 7.7.1.7.4 | 7.7.1.8.1 | 7.7.1.8.2 | 7.7.1.8.3 | 7.7.1.8.4 |
| 7.7.2.1.1 | 7.7.2.1.2 | 7.7.2.1.3 | 7.7.2.1.4 | 7.7.2.2.1 | 7.7.2.2.2 | 7.7.2.2.3 | 7.7.2.2.4 |
| 7.7.2.3.1 | 7.7.2.3.2 | 7.7.2.3.3 | 7.7.2.3.4 | 7.7.2.4.1 | 7.7.2.4.2 | 7.7.2.4.3 | 7.7.2.4.4 |
| 7.7.2.5.1 | 7.7.2.5.2 | 7.7.2.5.3 | 7.7.2.5.4 | 1.7.2.6.1 | 7.7.2.6.2 | 7.7.2.6.3 | 7.7.2.6.4 |
| 7.7.2.7.1 | 7.7.2.7.2 | 7.7.2.7.3 | 7.7.2.7.4 | 7.7.2.8.1 | 7.7.2.8.2 | 7.7.2.8.3 | 7.7.2.8.4 |
| 7.7.3.1.1 | 7.7.3.1.2 | 7.7.3.1.3 | 7.7.3.1.4 | 7.7.3.2.1 | 7.7.3.2.2 | 7.7.3.2.3 | 7.7.3.2.4 |
| 7.7.3.3.1 | 7.7.3.3.2 | 7.7.3.3.3 | 7.7.3.3.4 | 7.7.3.4.1 | 7.7.3.4.2 | 7.7.3.4.3 | 7.7.3.4.4 |
| 7.7.3.5.1 | 7.7.3.5.2 | 7.7.3.5.3 | 7.7.3.5.4 | 7.7.3.6.1 | 7.7.3.6.2 | 7.7.3.6.3 | 7.7.3.6.4 |
| 7.7.3.7.1 | 7.7.3.7.2 | 7.7.3.7.3 | 7.7.3.7.4 | 7.7.3.8.1 | 7.7.3.8.2 | 7.7.3.8.3 | 7.7.3.8.4 |
| 7.7.4.1.1 | 7.7.4.1.2 | 7.7.4.1.3 | 7.7.4.1.4 | 7.7.4.2.1 | 7.7.4.2.2 | 7.7.4.2.3 | 7.7.4.2.4 |
| 7.7.4.3.1 | 7.7.4.3.2 | 7.7.4.3.3 | 7.7.4.3.4 | 7.7.4.4.1 | 7.7.4.4.2 | 7.7.4.4.3 | 7.7.4.4.4 |
| 7.7.4.5.1 | 7.7.4.5.2 | 7.7.4.5.3 | 7.7.4.5.4 | 7.7.4.6.1 | 7.7.4.6.2 | 7.7.4.6.3 | 7.7.4.6.4 |
| 7.7.4.7.1 | 7.7.4.7.2 | 7.7.4.7.3 | 7.7.4.7.4 | 7.7.4.8.1 | 7.7.4.8.2 | 7.7.4.8.3 | 7.7.4.8.4 |
| 7.8.1.1.1 | 7.8.1.1.2 | 7.8.1.1.3 | 7.8.1.1.4 | 7.8.1.2.1 | 7.8.1.2.2 | 7.8.1.2.3 | 7.8.1.2.4 |
| 7.8.1.3.1 | 7.8.1.3.2 | 7.8.1.3.3 | 7.8.1.3.4 | 7.8.1.4.1 | 7.8.1.4.2 | 7.8.1.4.3 | 7.8.1.4.4 |
| 7.8.1.5.1 | 7.8.1.5.2 | 7.8.1.5.3 | 7.8.1.5.4 | 7.8.1.6.1 | 7.8.1.6.2 | 7.8.1.6.3 | 7.8.1.6.4 |
| 7.8.1.7.1 | 7.8.1.7.2 | 7.8.1.7.3 | 7.8:1.7.4 | 7.8.1.8.1 | 7.8.1.8.2 | 7.8.1.8.3 | 7.8.1.8.4 |
| 7.8.2.1.1 | 7.8.2.1.2 | 7.8.2.1.3 | 7.8.2.1.4 | 7.8.2.2.1 | 7.8.2.2.2 | 7.8.2.2.3 | 7.8.2.2.4 |
| 7.8.2.3.1 | 7.8.2.3.2 | 7.8.2.3.3 | 7.8.2.3.4 | 7.8.2.4.1 | 7.8.2.4.2 | 7.8.2.4.3 | 7.8.2.4.4 |
| 7.8.2.5.1 | 7.8.2.5.2 | 7.8.2.5.3 | 7.8.2.5.4 | 7.8.2.6.1 | 7.8.2.6.2 | 7.8.2.6.3 | 7.8.2.6.4 |
| 7.8.2.7.1 | 7.8.2.7.2 | 7.8.2.7.3 | 7.8.2.7.4 | 7.8.2.8.1 | 7.8.2.8.2 | 7.8.2.8.3 | 7.8.2.8.4 |
| 7.8.3.1.1 | 7.8.3.1.2 | 7.8.3.1.3 | 7.8.3.1.4 | 7.8.3.2.1 | 7.8.3.2.2 | 7.8.3.2.3 | 7.8.3.2.4 |
| 7.8.3.3.1 | 7.8.3.3.2 | 7.8.3.3.3 | 7.8.3.3.4 | 7.8.3.4.1 | 7.8.3.4.2 | 7.8.3.4.3 | 7.8.3.4.4 |
| 7.8.3.5.1 | 7.8.3.5.2 | 7.8.3.5.3 | 7.8.3.5.4 | 7.8.3.6.1 | 7.8.3.6.2 | 7.8.3.6.3 | 7.8.3.6.4 |
| 7.8.3.7.1 | 7.8.3.7.2 | 7.8.3.7.3 | 7.8.3.7.4 | 7.8.3.8.1 | 7.8.3.8.2 | 7.8.3.8.3 | 7.8.3.8.4 |
| 7.8.4.1.1 | 7.8.4.1.2 | 7.8.4.1.3 | 7.8.4.1.4 | 7.8.4.2.1 | 7.8.4.2.2 | 7.8.4.2.3 | 7.8.4.2.4 |
| 7.8.4.3.1 | 7.8.4.3.2 | 7.8.4.3.3 | 7.8.4.3.4 | 7.8.4.4.1 | 7.8.4.4.2 | 7.8.4.4.3 | 7.8.4.4.4 |
| 7.8.4.5.1 | 7.8.4.5.2 | 7.8.4.5.3 | 7.8.4.5.4 | 7.8.4.6.1 | 7.8.4.6.2 | 7.8.4.6.3 | 7.8.4.6.4 |
| 7.8.4.7.1 | 7.8.4.7.2 | 7.8.4.7.3 | 7.8.4.7.4 | 7.8.4.8.1 | 7.8.4.8.2 | 7.8.4.8.3 | 7.8.4.8.4 |
| 8.1.1.1.1 | 8.1.1.1.2 | 8.1.1.1.3 | 8.1.1.1.4 | 8.1.1.2.1 | 8.1.1.2.2 | 8.1.1.2.3 | 8.1.1.2.4 |
| 8.1.1.3.1 | 8.1.1.3.2 | 8.1.1.3.3 | 8.1.1.3.4 | 8.1.1.4.1 | 8.1.1.4.2 | 8.1.1.4.3 | 8.1.1.4.4 |
| 8.1.1.5.1 | 8.1.1.5.2 | 8.1.1.5.3 | 8.1.1.5.4 | 8.1.1.6.1 | 8.1.1.6.2 | 8.1.1.6.3 | 8.1.1.6.4 |
| 8.1.1.7.1 | 8.1.1.7.2 | 8.1.1.7.3 | 8.1.1.7.4 | 8.1.1.8.1 | 8.1.1.8.2 | 8.1.1.8.3 | 8.1.1.8.4 |
| 8.1.2.1.1 | 8.1.2.1.2 | 8.1.2.1.3 | 8.1.2.1.4 | 8.1.2.2.1 | 8.1.2.2.2 | 8.1.2.2.3 | 8.1.2.2.4 |
| 8.1.2.3.1 | 8.1.2.3.2 | 8.1.2.3.3 | 8.1.2.3.4 | 8.1.2.4.1 | 8.1.2.4.2 | 8.1.2.4.3 | 8.1.2.4.4 |
| 8.1.2.5.1 | 8.1.2.5.2 | 8.1.2.5.3 | 8.1.2.5.4 | 8.1.2.6.1 | 8.1.2.6.2 | 8.1.2.6.3 | 8.1.2.6.4 |
| 8.1.2.7.1 | 8.1.2.7.2 | 8.1.2.7.3 | 8.1.2.7.4 | 8.1.2.8.1 | 8.1.2.8.2 | 8.1.2.8.3 | 8.1.2.8.4 |
| 8.1.3.1.1 | 8.1.3.1.2 | 8.1.3.1.3 | 8.1.3.1.4 | 8.1.3.2.1 | 8.1.3.2.2 | 8.1.3.2.3 | 8.1.3.2.4 |
| 8.1.3.3.1 | 8.1.3.3.2 | 8.1.3.3.3 | 8.1.3.3.4 | 8.1.3.4.1 | 8.1.3.4.2 | 8.1.3.4.3 | 8.1.3.4.4 |
| 8.1.3.5.1 | 8.1.3.5.2 | 8.1.3.5.3 | 8.1.3.5.4 | 8.1.3.6.1 | 8.1.3.6.2 | 8.1.3.6.3 | 8.1.3.6.4 |
| 8.1.3.7.1 | 8.1.3.7.2 | 8.1.3.7.3 | 8.1.3.7.4 | 8.1.3.8.1 | 8.1.3.8.2 | 8.1.3.8.3 | 8.1.3.8.4 |
| 8.1.4.1.1 | 8.1.4.1.2 | 8.1.4.1.3 | 8.1.4.1.4 | 8.1.4.2.1 | 8.1.4.2.2 | 8.1.4.2.3 | 8.1.4.2.4 |
| 8.1.4.3.1 | 8.1.4.3.2 | 8.1.4.3.3 | 8.1.4.3.4 | 8.1.4.4.1 | 8.1.4.4.2 | 8.1.4.4.3 | 8.1.4.4.4 |
| 8.1.4.5.1 | 8.1.4.5.2 | 8.1.4.5.3 | 8.1.4.5.4 | 8.1.4.6.1 | 8.1.4.6.2 | 8.1.4.6.3 | 8.1.4.6.4 |
| 8.1.4.7.1 | 8.1.4.7.2 | 8.1.4.7.3 | 8.1.4.7.4 | 8.1.4.8.1 | 8.1.4.8.2 | 8.1.4.8.3 | 8.1.4.8.4 |
| 8.2.1.1.1 | 8.2.1.1.2 | 8.2.1.1.3 | 8.2.1.1.4 | 8.2.1.2.1 | 8.2.1.2.2 | 8.2.1.2.3 | 8.2.1.2.4 |
| 8.2.1.3.1 | 8.2.1.3.2 | 8.2.1.3.3 | 8.2.1.3.4 | 8.2.1.4.1 | 8.2.1.4.2 | 8.2.1.4.3 | 8.2.1.4.4 |
| 8.2.1.5.1 | 8.2.1.5.2 | 8.2.1.5.3 | 8.2.1.5.4 | 8.2.1.6.1 | 8.2.1.6.2 | 8.2.1.6.3 | 8.2.1.6.4 |
| 8.2.1.7.1 | 8.2.1.7.2 | 8.2.1.7.3 | 8.2.1.7.4 | 8.2.1.8.1 | 8.2.1.8.2 | 8.2.1.8.3 | 8.2.1.8.4 |
| 8.2.2.1.1 | 8.2.2.1.2 | 8.2.2.1.3 | 8.2.2.1.4 | 8.2.2.2.1 | 8.2.2.2.2 | 8.2.2.2.3 | 8.2.2.2.4 |
| 8.2.2.3.1 | 8.2.2.3.2 | 8.2.2.3.3 | 8.2.2.3.4 | 8.2.2.4.1 | 8.2.2.4.2 | 8.2.2.4.3 | 8.2.2.4.4 |

TABLE 3-continued

| | | | | | | | |
|---|---|---|---|---|---|---|---|
| 8.2.2.5.1 | 8.2.2.5.2 | 8.2.2.5.3 | 8.2.2.5.4 | 8.2.2.6.1 | 8.2.2.6.2 | 8.2.2.6.3 | 8.2.2.6.4 |
| 8.2.2.7.1 | 8.2.2.7.2 | 8.2.2.7.3 | 8.2.2.7.4 | 8.2.2.8.1 | 8.2.2.8.2 | 8.2.2.8.3 | 8.2.2.8.4 |
| 8.2.3.1.1 | 8.2.3.1.2 | 8.2.3.1.3 | 8.2.3.1.4 | 8.2.3.2.1 | 8.2.3.2.2 | 8.2.3.2.3 | 8.2.3.2.4 |
| 8.2.3.3.1 | 8.2.3.3.2 | 8.2.3.3.3 | 8.2.3.3.4 | 8.2.3.4.1 | 8.2.3.4.2 | 8.2.3.4.3 | 8.2.3.4.4 |
| 8.2.3.5.1 | 8.2.3.5.2 | 8.2.3.5.3 | 8.2.3.5.4 | 8.2.3.6.1 | 8.2.3.6.2 | 8.2.3.6.3 | 8.2.3.6.4 |
| 8.2.3.7.1 | 8.2.3.7.2 | 8.2.3.7.3 | 8.2.3.7.4 | 8.2.3.8.1 | 8.2.3.8.2 | 8.2.3.8.3 | 8.2.3.8.4 |
| 8.2.4.1.1 | 8.2.4.1.2 | 8.2.4.1.3 | 8.2.4.1.4 | 8.2.4.2.1 | 8.2.4.2.2 | 8.2.4.2.3 | 8.2.4.2.4 |
| 8.2.4.3.1 | 8.2.4.3.2 | 8.2.4.3.3 | 8.2.4.3.4 | 8.2.4.4.1 | 8.2.4.4.2 | 8.2.4.4.3 | 8.2.4.4.4 |
| 8.2.4.5.1 | 8.2.4.5.2 | 8.2.4.5.3 | 8.2.4.5.4 | 8.2.4.6.1 | 8.2.4.6.2 | 8.2.4.6.3 | 8.2.4.6.4 |
| 8.2.4.7.1 | 8.2.4.7.2 | 8.2.4.7.3 | 8.2.4.7.4 | 8.2.4.8.1 | 8.2.4.8.2 | 8.2.4.8.3 | 8.2.4.8.4 |
| 8.3.1.1.1 | 8.3.1.1.2 | 8.3.1.1.3 | 8.3.1.1.4 | 8.3.1.2.1 | 8.3.1.2.2 | 8.3.1.2.3 | 8.3.1.2.4 |
| 8.3.1.3.1 | 8.3.1.3.2 | 8.3.1.3.3 | 8.3.1.3.4 | 8.3.1.4.1 | 8.3.1.4.2 | 8.3.1.4.3 | 8.3.1.4.4 |
| 8.3.1.5.1 | 8.3.1.5.2 | 8.3.1.5.3 | 8.3.1.5.4 | 8.3.1.6.1 | 8.3.1.6.2 | 8.3.1.6.3 | 8.3.1.6.4 |
| 8.3.1.7.1 | 8.3.1.7.2 | 8.3.1.7.3 | 8.3.1.7.4 | 8.3.1.8.1 | 8.3.1.8.2 | 8.3.1.8.3 | 8.3.1.8.4 |
| 8.3.2.1.1 | 8.3.2.1.2 | 8.3..2.1.3 | 8.3.2.1.4 | 8.3.2.2.1 | 8.3.2.2.2 | 8.3.2.2.3 | 8.3.2.2.4 |
| 8.3.2.3.1 | 8.3.2.3.2 | 8.3.2.3.3 | 8.3.2.3.4 | 8.3.2.4.1 | 8.3.2.4.2 | 8.3.2.4.3 | 8.3.2.4.4 |
| 8.3.2.5.1 | 8.3.2.5.2 | 8.3.2.5.3 | 8.3.2.5.4 | 8.3.2.6.1 | 8.3.2.6.2 | 8.3.2.6.3 | 8.3.2.6.4 |
| 8.3.2.7.1 | 8.3.2.7.2 | 8.3.2.7.3 | 8.3.2.7.4 | 8.3.2.8.1 | 8.3.2.8.2 | 8.3.2.8.3 | 8.3.2.8.4 |
| 8.3.3.1.1 | 8.3.3.1.2 | 8.3.3.1.3 | 8.3.3.1.4 | 8.3.3.2.1 | 8.3.3.2.2 | 8.3.3.2.3 | 8.3.3.2.4 |
| 8.3.3.3.1 | 8.3.3.3.2 | 8.3.3.3.3 | 8.3.3.3.4 | 8.3.3.4.1 | 8.3.3.4.2 | 8.3.3.4.3 | 8.3.3.4.4 |
| 8.3.3.5.1 | 8.3.3.5.2 | 8.3.3.5.3 | 8.3.3.5.4 | 8.3.3.6.1 | 8.3.3.6.2 | 8.3.3.6.3 | 8.3.3.6.4 |
| 8.3.3.7.1 | 8.3.3.7.2 | 8.3.3.7.3 | 8.3.3.7.4 | 8.3.3.8.1 | 8.3.3.8.2 | 8.3.3.8.3 | 8.3.3.8.4 |
| 8.3.4.1.1 | 8.3.4.1.2 | 8.3.4.1.3 | 8.3.4.1.4 | 8.3.4.2.1 | 8.3.4.2.2 | 8.3.4.2.3 | 8.3.4.2.4 |
| 8.3.4.3.1 | 8.3.4.3.2 | 8.3.4.3.3 | 8.3.4.3.4 | 8.3.4.4.1 | 8.3.4.4.2 | 8.3.4.4.3 | 8.3.4.4.4 |
| 8.3.4.5.1 | 8.3.4.5.2 | 8.3.4.5.3 | 8.3.4.5.4 | 8.3.4.6.1 | 8.3.4.6.2 | 8.3.4.6.3 | 8.3.4.6.4 |
| 8.3.4.7.1 | 8.3.4.7.2 | 8.3.4.7.3 | 8.3.4.7.4 | 8.3.4.8.1 | 8.3.4.8.2 | 8.3.4.8.3 | 8.3.4.8.4 |
| 8.4.1.1.1 | 8.4.1.1.2 | 8.4.1.1.3 | 8.4.1.1.4 | 8.4.1.2.1 | 8.4.1.2.2 | 8.4.1.2.3 | 8.4.1.2.4 |
| 8.4.1.3.1 | 8.4.1.3.2 | 8.4.1.3.3 | 8.4.1.3.4 | 8.4.1.4.1 | 8.4.1.4.2 | 8.4.1.4.3 | 8.4.1.4.4 |
| 8.4.1.5.1 | 8.4.1.5.2 | 8.4.1.5.3 | 8.4.1.5.4 | 8.4.1.6.1 | 8.4.1.6.2 | 8.4.1.6.3 | 8.4.1.6.4 |
| 8.4.1.7.1 | 8.4.1.7.2 | 8.4.1.7.3 | 8.4.1.7.4 | 8.4.1.8.1 | 8.4.1.8.2 | 8.4.1.8.3 | 8.4.1.8.4 |
| 8.4.2.1.1 | 8.4.2.1.2 | 8.4.2.1.3 | 8.4.2.1.4 | 8.4.2.2.1 | 8.4.2.2.2 | 8.4.2.2.3 | 8.4.2.2.4 |
| 8.4.2.3.1 | 8.4.2.3.2 | 8.4.2.3.3 | 8.4.2.3.4 | 8.4.2.4.1 | 8.4.2.4.2 | 8.4.2.4.3 | 8.4.2.4.4 |
| 8.4.2.5.1 | 8.4.2.5.2 | 8.4.2.5.3 | 8.4.2.5.4 | 8.4.2.6.1 | 8.4.2.6.2 | 8.4.2.6.3 | 8.4.2.6.4 |
| 8.4.2.7.1 | 8.4.2.7.2 | 8.4.2.7.3 | 8.4.2.7.4 | 8.4.2.8.1 | 8.4.2.8.2 | 8.4.2.8.3 | 8.4.2.8.4 |
| 8.4.3.1.1 | 8.4.3.1.2 | 8.4.3.1.3 | 8.4.3.1.4 | 8.4.3.2.1 | 8.4.3.2.2 | 8.4.3.2.3 | 8.4.3.2.4 |
| 8.4.3.3.1 | 8.4.3.3.2 | 8.4.3.3.3 | 8.4.3.3.4 | 8.4.3.4.1 | 8.4.3.4.2 | 8.4.3.4.3 | 8.4.3.4.4 |
| 8.4.3.5.1 | 8.4.3.5.2 | 8.4.3.5.3 | 8.4.3.5.4 | 8.4.3.6.1 | 8.4.3.6.2 | 8.4.3.6.3 | 8.4.3.6.4 |
| 8.4.3.7.1 | 8.4.3.7.2 | 8.4.3.7.3 | 8.4.3.7.4 | 8.4.3.8.1 | 8.4.3.8.2 | 8.4.3.8.3 | 8.4.3.8.4 |
| 8.4.4.1.1 | 8.4.4.1.2 | 8.4.4.1.3 | 8.4.4.1.4 | 8.4.4.2.1 | 8.4.4.2.2 | 8.4.4.2.3 | 8.4.4.2.4 |
| 8.4.4.3.1 | 8.4.4.3.2 | 8.4.4.3.3 | 8.4.4.3.4 | 8.4.4.4.1 | 8.4.4.4.2 | 8.4.4.4.3 | 8.4.4.4.4 |
| 8.4.4.5.1 | 8.4.4.5.2 | 8.4.4.5.3 | 8.4.4.5.4 | 8.4.4.6.1 | 8.4.4.6.2 | 8.4.4.6.3 | 8.4.4.6.4 |
| 8.4.4.7.1 | 8.4.4.7.2 | 8.4.4.7.3 | 8.4.4.7.4 | 8.4.4.8.1 | 8.4.4.8.2 | 8.4.4.8.3 | 8.4.4.8.4 |
| 8.5.1.1.1 | 8.5.1.1.2 | 8.5.1.1.3 | 8.5.1.1.4 | 8.5.1.2.1 | 8.5.1.2.2 | 8.5.1.2.3 | 8.5.1.2.4 |
| 8.5.1.3.1 | 8.5.1.3.2 | 8.5.1.3.3 | 8.5.1.3.4 | 8.5.1.4.1 | 8.5.1.4.2 | 8.5.1.4.3 | 8.5.1.4.4 |
| 8.5.1.5.1 | 8.5.1.5.2 | 8.5.1.5.3 | 8.5.1.5.4 | 8.5.1.6.1 | 8.5.1.6.2 | 8.5.1.6.3 | 8.5.1.6.4 |
| 8.5.1.7.1 | 8.5.1.7.2 | 8.5.1.7.3 | 8.5.1.7.4 | 8.5.1.8.1 | 8.5.1.8.2 | 8.5.1.8.3 | 8.5.1.8.4 |
| 8.5.2.1.1 | 8.5.2.1.2 | 8.5.2.1.3 | 8.5.2.1.4 | 8.5.2.2.1 | 8.5.2.2.2 | 8.5.2.2.3 | 8.5.2.2.4 |
| 8.5.2.3.1 | 8.5.2.3.2 | 8.5.2.3.3 | 8.5.2.3.4 | 8.5.2.4.1 | 8.5.2.4.2 | 8.5.2.4.3 | 8.5.2.4.4 |
| 8.5.2.5.1 | 8.5.2.5.2 | 8.5.2.5.3 | 8.5.2.5.4 | 8.5.2.6.1 | 8.5.2.6.2 | 8.5.2.6.3 | 8.5.2.6.4 |
| 8.5.2.7.1 | 8.5.2.7.2 | 8.5.2.7.3 | 8.5.2.7.4 | 8.5.2.8.1 | 8.5.2.8.2 | 8.5.2.8.3 | 8.5.2.8.4 |
| 8.5.3.1.1 | 8.5.3.1.2 | 8.5.3.1.3 | 8.5.3.1.4 | 8.5.3.2.1 | 8.5.3.2.2 | 8.5.3.2.3 | 8.5.3.2.4 |
| 8.5.3.3.1 | 8.5.3.3.2 | 8.5.3.3.3 | 8.5.3.3.4 | 8.5.3.4.1 | 8.5.3.4.2 | 8.5.3.4.3 | 8.5.3.4.4 |
| 8.5.3.5.1 | 8.5.3.5.2 | 8.5.3.5.3 | 8.5.3.5.4 | 8.5.3.6.1 | 8.5.3.6.2 | 8.5.3.6.3 | 8.5.3.6.4 |
| 8.5.3.7.1 | 8.5.3.7.2 | 8.5.3.7.3 | 8.5.3.7.4 | 8.5.3.8.1 | 8.5.3.8.2 | 8.5.3.8.3 | 8.5.3.8.4 |
| 8.5.4.1.1 | 8.5.4.1.2 | 8.5.4.1.3 | 8.5.4.1.4 | 8.5.4.2.1 | 8.5.4.2.2 | 8.5.4.2.3 | 8.5.4.2.4 |
| 8.5.4.3.1 | 8.5.4.3.2 | 8.5.4.3.3 | 8.5.4.3.4 | 8.5.4.4.1 | 8.5.4.4.2 | 8.5.4.4.3 | 8.5.4.4.4 |
| 8.5.4.5.1 | 8.5.4.5.2 | 8.5.4.5.3 | 8.5.4.5.4 | 8.5.4.6.1 | 8.5.4.6.2 | 8.5.4.6.3 | 8.5.4.6.4 |
| 8.5.4.7.1 | 8.5.4.7.2 | 8.5.4.7.3 | 8.5.4.7.4 | 8.5.4.8.1 | 8.5.4.8.2 | 8.5.4.8.3 | 8.5.4.8.4 |
| 8.6.1.1.1 | 8.6.1.1.2 | 8.6.1.1.3 | 8.6.1.1.4 | 8.6.1.2.1 | 8.6.1.2.2 | 8.6.1.2.3 | 8.6.1.2.4 |
| 8.6.1.3.1 | 8.6.1.3.2 | 8.6.1.3.3 | 8.6.1.3.4 | 8.6.1.4.1 | 8.6.1.4.2 | 8.6.1.4.3 | 8.6.1.4.4 |
| 8.6.1.5.1 | 8.6.1.5.2 | 8.6.1.5.3 | 8.6.1.5.4 | 8.6.1.6.1 | 8.6.1.6.2 | 8.6.1.6.3 | 8.6.1.6.4 |
| 8.6.1.7.1 | 8.6.1.7.2 | 8.6.1.7.3 | 8.6.1.7.4 | 8.6.1.8.1 | 8.6.1.8.2 | 8.6.1.8.3 | 8.6.1.8.4 |
| 8.6.2.1.1 | 8.6.2.1.2 | 8.6.2.1.3 | 8.6.2.1.4 | 8.6.2.2.1 | 8.6.2.2.2 | 8.6.2.2.3 | 8.6.2.2.4 |
| 8.6.2.3.1 | 8.6.2.3.2 | 8.6.2.3.3 | 8.6.2.3.4 | 8.6.2.4.1 | 8.6.2.4.2 | 8.6.2.4.3 | 8.6.2.4.4 |
| 8.6.2.5.1 | 8.6.2.5.2 | 8.6.2.5.3 | 8.6.2.5.4 | 8.6.2.6.1 | 8.6.2.6.2 | 8.6.2.6.3 | 8.6.2.6.4 |
| 8.6.2.7.1 | 8.6.2.7.2 | 8.6.2.7.3 | 8.6.2.7.4 | 8.6.2.8.1 | 8.6.2.8.2 | 8.6.2.8.3 | 8.6.2.8.4 |
| 8..6.3.1.1 | 8.6.3.1.2 | 8.6.3.1.3 | 8.6.3.1.4 | 8.6.3.2.1 | 8.6.3.2.2 | 8.6.3.2.3 | 8.6.3.2.4 |
| 8.6.3.3.1 | 8.6.3.3.2 | 8.6.3.3.3 | 8.6.3.3.4 | 8.6.3.4.1 | 8.6.3.4.2 | 8.6.3.4.3 | 8.6.3.4.4 |
| 8.6.3.5.1 | 8.6.3.5.2 | 8.6.3.5.3 | 8.6.3.5.4 | 8.6.3.6.1 | 8.6.3.6.2 | 8.6.3.6.3 | 8.6.3.6.4 |
| 8.6.3.7.1 | 8.6.3.7.2 | 8.6.3.7.3 | 8.6.3.7.4 | 8.6.3.8.1 | 8.6.3.8.2 | 8.6.3.8.3 | 8.6.3.8.4 |
| 8.6.4.1.1 | 8.6.4.1.2 | 8.6.4.1.3 | 8.6.4.1.4 | 8.6.4.2.1 | 8.6.4.2.2 | 8.6.4.2.3 | 8.6.4.2.4 |
| 8.6.4.3.1 | 8.6.4.3.2 | 8.6.4.3.3 | 8.6.4.3.4 | 8.6.4.4.1 | 8.6.4.4.2 | 8.6.4.4.3 | 8.6.4.4.4 |
| 8.6.4.5.1 | 8.6.4.5.2 | 8.6.4.5.3 | 8.6.4.5.4 | 8.6.4.6.1 | 8.6.4.6.2 | 8.6.4.6.3 | 8.6.4.6.4 |
| 8.6.4.7.1 | 8.6.4.7.2 | 8.6.4.7.3 | 8.6.4.7.4 | 8.6.4.8.1 | 8.6.4.8.2 | 8.6.4.8.3 | 8.6.4.8.4 |
| 8.7.1.1.1 | 8.7.1.1.2 | 8.7.1.1.3 | 8.7.1.1.4 | 8.7.1.2.1 | 8.7.1.2.2 | 8.7.1.2.3 | 8.7.1.2.4 |
| 8.7.1.3.1 | 8.7.1.3.2 | 8.7.1.3.3 | 8.7.1.3.4 | 8.7.1.4.1 | 8.7.1.4.2 | 8.7.1.4.3 | 8.7.1.4.4 |
| 8.7.1.5.1 | 8.7.1.5.2 | 8.7.1.5.3 | 8.7.1.5.4 | 8.7.1.6.1 | 8.7.1.6.2 | 8.7.1.6.3 | 8.7.1.6.4 |
| 8.7.1.7.1 | 8.7.1.7.2 | 8.7.1.7.3 | 8.7.1.7.4 | 8.7.1.8.1 | 8.7.1.8.2 | 8.7.1.8.3 | 8.7.1.8.4 |
| 8.7.2.1.1 | 8.7.2.1.2 | 8.7.2.1.3 | 8.7.2.1.4 | 8.7.2.2.1 | 8.7.2.2.2 | 8.7.2.2.3 | 8.7.2.2.4 |

TABLE 3-continued

| | | | | | | | |
|---|---|---|---|---|---|---|---|
| 8.7.2.3.1 | 8.7.2.3.2 | 8.7.2.3.3 | 8.7.2.3.4 | 8.7.2.4.1 | 8.7.2.4.2 | 8.7.2.4.3 | 8.7.2.4.4 |
| 8.7.2.5.1 | 8.7.2.5.2 | 8.7.2.5.3 | 8.7.2.5.4 | 8.7.2.6.1 | 8.7.2.6.2 | 8.7.2.6.3 | 8.7.2.6.4 |
| 8.7.2.7.1 | 8.7.2.7.2 | 8.7.2.7.3 | 8.7.2.7.4 | 8.7.2.8.1 | 8.7.2.8.2 | 8.7.2.8.3 | 8.7.2.8.4 |
| 8.7.3.1.1 | 8.7.3.1.2 | 8.7.3.1.3 | 8.7.3.1.4 | 8.7.3.2.1 | 8.7.3.2.2 | 8.7.3.2.3 | 8.7.3.2.4 |
| 8.7.3.3.1 | 8.7.3.3.2 | 8.7.3.3.3 | 8.7.3.3.4 | 8.7.3.4.1 | 8.7.3.4.2 | 8.7.3.4.3 | 8.7.3.4.4 |
| 8.7.3.5.1 | 8.7.3.5.2 | 8.7.3.5.3 | 8.7.3.5.4 | 8.7.3.6.1 | 8.7.3.6.2 | 8.7.3.6.3 | 8.7.3.6.4 |
| 8.7.3.7.1 | 8.7.3.7.2 | 8.7.3.7.3 | 8.7.3.7.4 | 8.7.3.8.1 | 8.7.3.8.2 | 8.7.3.8.3 | 8.7.3.8.4 |
| 8.7.4.1.1 | 8.7.4.1.2 | 8.7.4.1.3 | 8.7.4.1.4 | 8.7.4.2.1 | 8.7.4.2.2 | 8.7.4.2.3 | 8.7.4.2.4 |
| 8.7.4.3.1 | 8.7.4.3.2 | 8.7.4.3.3 | 8.7.4.3.4 | 8.7.4.4.1 | 8.7.4.4.2 | 8.7.4.4.3 | 8.7.4.4.4 |
| 8.7.4.5.1 | 8.7.4.5.2 | 8.7.4.5.3 | 8.7.4.5.4 | 8.7.4.6.1 | 8.7.4.6.2 | 8.7.4.6.3 | 8.7.4.6.4 |
| 8.7.4.7.1 | 8.7.4.7.2 | 8.7.4.7.3 | 8.7.4.7.4 | 8.7.4.8.1 | 8.7.4.8.2 | 8.7.4.8.3 | 8.7.4.8.4 |
| 8.8.1.1.1 | 8.8.1.1.2 | 8.8.1.1.3 | 8.8.1.1.4 | 8.8.1.2.1 | 8.8.1.2.2 | 8.8.1.2.3 | 8.8.1.2.4 |
| 8.9.1.3.1 | 8.8.1.3.2 | 8.8.1.3.3 | 8.8.1.3.4 | 8.8.1.4.1 | 8.8.1.4.2 | 8.8.1.4.3 | 8.8.1.4.4 |
| 8.8.1.5.1 | 8.8.1.5.2 | 8.8.1.5.3 | 8.8.1.5.4 | 8.8.1.6.1 | 8.8.1.6.2 | 8.8.1.6.3 | 8.8.1.6.4 |
| 8.8.1.7.1 | 8.8.1.7.2 | 8.8.1.7.3 | 8.8.1.7.4 | 8.8.1.8.1 | 8.8.1.8.2 | 8.8.1.8.3 | 8.8.1.8.4 |
| 8.8.2.1.1 | 8.8.2.1.2 | 8.8.2.1.3 | 8.8.2.1.4 | 8.8.2.2.1 | 8.8.2.2.2 | 8.8.2.2.3 | 8.8.2.2.4 |
| 8.8.2.3.1 | 8.8.2.3.2 | 8.8.2.3.3 | 8.8.2.3.4 | 8.8.2.4.1 | 8.8.2.4.2 | 8.8.2.4.3 | 8.8.2.4.4 |
| 8.8.2.5.1 | 8.8.2.5.2 | 8.8.2.5.3 | 8.8.2.5.4 | 8.8.2.6.1 | 8.8.2.6.2 | 8.8.2.6.3 | 8.8.2.6.4 |
| 8.8.2.7.1 | 8.8.2.7.2 | 8.8.2.7.3 | 8.8.2.7.4 | 8.8.2.8.1 | 8.8.2.8.2 | 8.8.2.8.3 | 8.8.2.8.4 |
| 8.8.3.1.1 | 8.8.3.1.2 | $.8.3.1.3 | 8.8.3.1.4 | 8.8.3.2.1 | 8.8.3.2.2 | 8.8.3.2.3 | 8.8.3.2.4 |
| 8.8.3.3.1 | 8.8.3.3.2 | 8.8.3.3.3 | 8.8.3.3.4 | 8.8.3.4.1 | 8.8.3.4.2 | 8.8.3.4.3 | 8.8.3.4.4 |
| 8.8.3.5.1 | 8.8.3.5.2 | 8.8.3.5.3 | 8.8.3.5.4 | 8.8.3.6.1 | 8.8.3.6.2 | 8.8.3.6.3 | 8.8.3.6.4 |
| 8.8.3.7.1 | 8.8.3.7.2 | 8.8.3.7.3 | 8.8.3.7.4 | 8.8.3.8.1 | 8.8.3.8.2 | 8.8.3.8.3 | 8.8.3.8.4 |
| 8.8.4.1.1 | 8.8.4.1.2 | 8.8.4.1.3 | 8.8.4.1.4 | 8.8.4.2.1 | 8.8.4.2.2 | 8.8.4.2.3 | 8.8.4.2.4 |
| 8.8.4.3.1 | 8.8.4.3.2 | 8.8.4.3.3 | 8.8.4.3.4 | 8.8.4.4.1 | 8.8.4.4.2 | 8.8.4.4.3 | 8.8.4.4.4 |
| 8.8.4.5.1 | 8.8.4.5.2 | 8.8.4.5.3 | 8.8.4.5.4 | 8.8.4.6.1 | 8.8.4.6.2 | 8.8.4.6.3 | 8.8.4.6.4 |
| 8.8.4.7.1 | 8.8.4.7.2 | 8.8.4.7.3 | 8.8.4.7.4 | 8.8.4.8.1 | 8.8.4.8.2 | 8.8.4.8.3 | 8.8.4.8.4 |

Thus, the compound named in Table 3 of formula (v) having substituents from Group 1 of each variable B, X, D, and E named 2.4.1.1.1 specifies —$NH_2$ as A, -Pr-n as B, furan-2,5-diyl as X, —H as D and —H as E, and this compound is 2-amino-5-propyl-6-[2-(5-phosphono)furanyl]pyridine prepared in Example 15 as compound 15.14. Compounds named in Table 3 of formula (v) are compounds with a pyridinyl as $R^5$ in formula I. Analogously, the compound named 2.1.1.1.3 in Table 3 of formula (v) using substituents of Group 1 of each variable B, X, D, and E has the structure of 2-amino-3-ethyl-6-[2-(5-phosphono)furanyl]pyridine and was prepared in Example 15 as compound 15.12.

Compounds named in Table 3 of formula (vi) are compounds with a pyrazinyl as $R^1$ in formula I. One preferred pyrazinyl compound named in Table 3 of formula (vi) is 2.1.1.0.4. Using Group 1 of each variable, 2.1.1.0.4 has the structure of 2-amino-3-propyl-6-[2-(phosphono)furanyl]pyrazine and was prepared in Example 17 as compound 17.3. Similarly, compounds named in Table 3 of formula (vii) are compounds with a pyrimidinyl as $R^5$ in formula I. The formula (vii) compound named 2.4.1.1.0 in Table 3 using all Group 1 variables has the structure of 2-amino-5-propyl-6-[2-(phosphono)furanyl]pyrimidine and was prepared in Example 16 as compound 16.1. Similarly, compounds named in Table 3 of formula (viii) are compounds with a pyrimidinyl as $R^5$ in formula I. Thus, using Group 1 variable, the compound named 1.0.1.1.1 in Table 3 has the structure of 2-[2-(5-phosphono)furanyl]pyrimidine and was prepared in Example 16 as compound 16.5.

Some of the exemplary embodiments of the compounds named in Table 3 using Groups 1–4 for variable B, Groups 1–2 for variable X, Groups 1–2 for variable D, and Groups 1–3 for variable E in the compound of formulae (v), (vi), (vii), (viii) and (ix) are listed in Table 4.

TABLE 4

| Compound No. as A.B.X.D.E | Synthetic Example No. | Formula | A | group No.* | B | group No.* | X** | group No.* | D | group No.* | E |
|---|---|---|---|---|---|---|---|---|---|---|---|
| 1.1.1.1.1 | 15.6 | (v) | H | 1 | H | 1 | furan-2,5-diyl | 1 | H | 1 | H |
| 1.1.2.1.1. | 12.1 | (v) | H | 1 | H | 1 | pyridin-2,6-diyl | 1 | H | 1 | H |
| 6.1.4.2.1 | 13.1 | (v) | Me | 1 | H | 5 | CH2OCH2 | 2 | Me | 1 | H |
| 6.1.1.2.1 | 15.15 | (v) | Me | 1 | H | 1 | furan-2,5-diyl | 1 | Me | 2 | Br |
| 4.1.1.1.1 | 15.9 | (v) | Cl | 1 | H | 1 | furan-2,5-diyl | 1 | H | 1 | H |
| 1.8.1.1.2 | 15.10 | (v) | H | 1 | Cl | 1 | furan-2,5-diyl | 1 | H | 2 | Cl |
| 6.7.1.1.1 | 15.5 | (v) | Me | 1 | Br | 1 | furan-2,5-diyl | 1 | H | 1 | H |
| 2.1.1.1.1 | 15.1 | (v) | NH2 | 1 | H | 1 | furan-2,5-diyl | 1 | H | 1 | H |
| 2.7.1.1.1 | 15.2 | (v) | NH2 | 1 | Br | 1 | furan-2,5-diyl | 1 | H | 1 | H |
| 2.7.1.1.1 | 15.3 | (v) | NH2 | 1 | Br | 1 | furan-2,5-diyl | 1 | H | 2 | Br |
| 2.3.1.1.3 | 15.4 | (v) | NH2 | 1 | Et | 1 | furan-2,5-diyl | 1 | H | 1 | Et |
| 2.3.1.1.1 | 15.12 | (v) | NH2 | 1 | H | 1 | furan-2,5-diyl | 1 | H | 1 | Et |
| 2.3.1.1.1 | 15.13 | (v) | NH2 | 1 | Et | 1 | furan-2,5-diyl | 1 | H | 1 | H |
| 2.4.1.1.1 | 15.14 | (v) | NH2 | 1 | Pr-n | 1 | furan-2,5-diyl | 1 | H | 1 | H |
| 2.4.1.1.0 | 16.1 | (vii) | NH2 | 1 | Pr-n | 1 | furan-2,5-diyl | 1 | H | | null |
| 2.4.1.1.0 | 16.2 | (vii) | NH2 | 2 | Bu-i | 1 | furan-2,5-diyl | 1 | H | | null |
| 2.4.4.2.0 | 13.2 | (vii) | NH2 | 1 | Pr-n | 2 | CH2OCH2 | 1 | Me | | null |
| 2.1.1.2.0 | 16.6 | (vii) | NH2 | 1 | H | 1 | furan-2,5-diyl | 1 | Me | | null |
| 6.1.1.1.0 | 16.8 | (vii) | Me | 1 | H | 1 | furan-2,5-diyl | 1 | H | | null |

TABLE 4-continued

| Compound No. as A.B.X.D.E | Synthetic Example No. | Formula | A | group No.* | B | group No.* | X** | group No.* | D | group No.* | E |
|---|---|---|---|---|---|---|---|---|---|---|---|
| 2.1.1.1.0 | 16.3 | (vii) | NH2 | 1 | H | 1 | furan-2,5-diyl | 1 | H | | null |
| 2.3.1.1.0 | 16.4 | (vii) | NH2 | 1 | Et | 1 | furan-2,5-diyl | 1 | H | | null |
| 1.0.1.7.2 | 16.5 | (viii) | H | | null | 1 | furan-2,5-diyl | 1 | H | 1 | H |
| 6.0.1.7.2 | 16.9 | (viii) | Me | | null | 1 | furan-2,5-diyl | 1 | Br | 1 | Me |
| 6.2.1.0.1 | 17.1 | (vi) | Me | 1 | Me | 1 | furan-2,5-diyl | | null | 1 | H |
| 4.1.1.0.1 | 17.2 | (vi) | Cl | 1 | H | 1 | furan-2,5-diyl | | null | 1 | H |
| 2.1.1.0.4 | 17.3 | (vi) | NH2 | 1 | H | 1 | furan-2,5-diyl | | null | 1 | Pr-n |
| 2.8.1.0.1 | 15.19 | (vii) | NH2 | 1 | Cl | 1 | furan-2,5-diyl | 1 | H | | null |
| 2.1.1.5.0 | 16.11 | (vii) | NH2 | 1 | H | 1 | furan-2,5-diyl | 1 | SMe | | null |
| 1.8.1.0.1 | 17.6 | (vi) | H | 2 | SMe | 1 | furan-2,5-diyl | | null | 1 | H |
| 2.7.1.5.0 | 16.12 | (vii) | NH2 | 1 | Br | 1 | furan-2,5-diyl | 1 | SMe | | null |
| 2.8.1.0.1 | 17.7 | (vi) | NH2 | 2 | SMe | 1 | furan-2,5-diyl | | null | 1 | H |
| 2.1.1.0.3 | 17.8 | (vi) | NH2 | 1 | H | 1 | furan-2,5-diyl | | null | 3 | SMe |
| 2.8.1.0.1 | 17.9 | (vi) | NH2 | 1 | Cl | 1 | furan-2,5-diyl | | null | 3 | CO2Me |
| 1.1.3.1.1 | 18.8 | (v) | H | 1 | H | 1 | C(O)NHCH2 | 1 | H | 1 | H |
| 1.1.1.1.1 | 18.9 | (v) | H | 1 | H | 2 | NHC(O)CH2 | 1 | H | 1 | H |
| 2.1.1.1.2 | 15.19 | (v) | NH2 | 1 | H | 1 | furan-2,5-diyl | 1 | H | 3 | Pr-c |
| 2.6.1.1.1 | 15.20 | (v) | NH2 | 1 | Pr-c | 1 | furan-2,5-diyl | 1 | H | 1 | H |
| 2.8.1.0.1 | 17.10 | (vi) | NH2 | 2 | SMe | 1 | furan-2,5-diyl | | null | 1 | H |
| 6.2.1.1.1 | 15.22 | (v) | Me | 2 | CN | 1 | furan-2,5-diyl | 1 | H | 1 | H |
| 2.2.1.2.4 | 15.23 | (v) | NH2 | 2 | CN | 1 | furan-2,5-diyl | 1 | Me | 2 | CN |
| 1.1.3.1.1 | 30.1 | (v) | H | 1 | H | 2 | ethyn-1,2-diyl | 1 | H | 1 | H |
| 2.1.1.1.1 | 18.23 | (v) | NH2 | 1 | H | 2 | NHC(O)CH2 | 1 | H | 1 | H |
| 4.1.1.3.1 | 15.24 | (v) | Cl | 1 | H | 1 | furan-2,5-diyl | 2 | CN | 1 | H |
| 2.0.1.8.1 | 16.14 | (viii) | NH2 | | null | 1 | furan-2,5-diyl | 1 | Cl | 1 | H |
| 2.1.1.1.1 | 18.25 | (v) | NH2 | 1 | H | 2 | NHC(O)CH2 | 1 | H | 2 | Br |
| 2.7.1.1.1 | 18.26 | (v) | NH2 | 1 | Br | 2 | NHC(O)CH2 | 1 | H | 2 | Br |
| 2.3.1.1.3 | 18.28 | (v) | NH2 | 1 | Et | 2 | NHC(O)CH2 | 1 | H | 1 | Et |
| 2.8.1.2.0 | 33.1 | (vii) | NH2 | 1 | Cl | 1 | furan-2,5-diyl | 1 | Me | | null |
| 2.0.1.7.1 | 33.13 | (viii) | NH2 | | null | 1 | furan-2,5-diyl | 2 | OMe | 1 | H |
| 1.7.1.0.1 | 33.14 | (vi) | H | 4 | OMe | 1 | furan-2,5-diyl | | null | 1 | H |
| 1.7.1.0.1 | 33.27 | (vi) | H | 2 | OEt | 1 | furan-2,5-diyl | | null | 1 | H |
| 4.1.1.3.1 | 33.36 | (v) | Cl | 1 | H | 1 | furan-2,5-diyl | 2 | CN | 1 | H |
| 4.1.1.6.1 | 33.38 | (v) | Cl | 1 | H | 1 | furan-2,5-diyl | 2 | C(O)NH2 | 1 | H |
| 4.1.1.4.1 | 33.39 | (v) | Cl | 1 | H | 1 | furan-2,5-diyl | 1 | CO2Et | 1 | H |
| 4.1.1.2.4 | 33.41 | (v) | Cl | 1 | H | 1 | furan-2,5-diyl | 1 | Me | 2 | CN |
| 4.1.1.8.4 | 33.43 | (v) | Cl | 1 | H | 1 | furan-2,5-diyl | 2 | CF3 | 2 | CN |
| 0.2.1.2.1 | 33.44 | (ix) | null | 1 | Me | 1 | furan-2,5-diyl | 1 | Me | 2 | Br |
| 0.2.1.2.2 | 33.45 | (ix) | null | 1 | Me | 1 | furan-2,5-diyl | 1 | Me | 2 | Cl |
| 3.2.1.1.0 | 33.46 | (vii) | Br | 1 | Me | 1 | furan-2,5-diyl | 1 | H | | null |
| 3.7.1.1.0 | 33.47 | (vii) | Br | 1 | Br | 1 | furan-2,5-diyl | 1 | H | | null |
| 3.1.1.2.0 | 33.48 | (vii) | Br | 1 | H | 1 | furan-2,5-diyl | 1 | Me | | null |
| 3.8.1.7.0 | 33.50 | (vii) | Br | 1 | Cl | 1 | furan-2,5-diyl | 1 | Br | | null |
| 2.1.1.7.0 | 33.52 | (vii) | NH2 | 1 | H | 1 | furan-2,5-diyl | 1 | Br | | null |
| 3.1.1.7.0 | 33.54 | (vii) | Br | 1 | H | 1 | furan-2,5-diyl | 1 | Br | | null |
| 3.1.1.8.0 | 33.55 | (vii) | Br | 1 | H | 1 | furan-2,5-diyl | 1 | Cl | | null |
| 1.7.1.0.1 | 33.56 | (vi) | H | 1 | Br | 1 | furan-2,5-diyl | | null | 1 | H |
| 2.8.1.0.1 | 33.57 | (vi) | NH2 | 1 | Cl | 1 | furan-2,5-diyl | | null | 3 | CO2Me |
| 1.8.1.0.1 | 33.59 | (vi) | H | 3 | OPr-n | 1 | furan-2,5-diyl | | null | 1 | H |
| 6.1.1.1.1 | 33.97 | (v) | Me | 1 | H | 2 | NHC(O)CH2 | 1 | H | 1 | H |
| 1.2.1.1.1 | 33.98 | (v) | H | 1 | Me | 2 | NHC(O)CH2 | 1 | H | 1 | H |
| 2.1.1.1.2 | 33.99 | (v) | NH2 | 1 | H | 2 | NHC(O)CH2 | 1 | H | 2 | Cl |
| 2.8.1.1.1 | 33.100 | (v) | NH2 | 1 | Cl | 2 | NHC(O)CH2 | 1 | H | 1 | H |
| 6.1.1.2.1 | 33.102 | (v) | Me | 1 | H | 2 | NHC(O)CH2 | 1 | Me | 1 | H |
| 1.1.1.1.2 | 33.103 | (v) | H | 1 | H | 2 | NHC(O)CH2 | 1 | H | 2 | Cl |
| 1.1.1.1.1 | 33.104 | (v) | H | 1 | H | 2 | NHC(O)CH2 | 1 | H | 2 | Br |
| 5.1.1.1.1 | 33.105 | (v) | Me | 1 | H | 2 | NHC(O)CH2 | 1 | H | 2 | Br |
| 1.1.1.1.1 | 33.106 | (v) | H | 1 | H | 2 | NHC(O)CH2 | 1 | H | 1 | H |
| 1.1.1.1.2 | 33.107 | (v) | H | 1 | H | 2 | NHC(O)CH2 | 1 | H | 1 | Me |
| 1.1.1.2.1 | 33.108 | (v) | H | 1 | H | 2 | NHC(O)CH2 | 1 | Me | 1 | H |
| 6.8.1.2.0 | 33.109 | (vii) | Me | 1 | Cl | 2 | NHC(O)CH2 | 1 | Me | | null |
| 4.1.1.0.1 | 33.100 | (vi) | Cl | 1 | H | 2 | NHC(O)CH2 | | null | 1 | H |
| 1.7.1.1.2 | 33.111 | (v) | H | 1 | Br | 2 | NHC(O)CH2 | 1 | H | 1 | Me |
| 1.1.1.3.1 | 33.114 | (v) | H | 1 | H | 2 | NHC(O)CH2 | 1 | Et | 1 | H |
| 6.3.1.1.1 | 33.115 | (v) | Me | 1 | Et | 2 | NHC(O)CH2 | 1 | H | 1 | H |
| 6.1.1.1.1 | 33.116 | (v) | Me | 1 | H | 2 | NHC(O)CH2 | 1 | H | 2 | Br |
| 1.7.1.1.2 | 33.117 | (v) | H | 1 | Br | 2 | NHC(O)CH2 | 1 | H | 1 | Me |
| 1.2.1.1.1 | 33.118 | (v) | H | 1 | Me | 2 | NHC(O)CH2 | 1 | H | 2 | Br |
| 6.7.1.1.1 | 33.199 | (v) | Me | 1 | Br | 2 | NHC(O)CH2 | 1 | H | 2 | Br |
| 1.1.3.1.1 | 33.120 | (v) | H | 1 | H | 1 | C(O)NHCH2 | 1 | H | 1 | H |
| 6.1.3.1.1 | 33.121 | (v) | Me | 1 | H | 1 | C(O)NHCH2 | 1 | H | 1 | H |
| 3.1.3.1.1 | 33.123 | (v) | Br | 1 | H | 1 | C(O)NHCH2 | 1 | H | 1 | H |
| 4.1.3.1.1 | 33.124 | (v) | Cl | 1 | H | 1 | C(O)NHCH2 | 1 | H | 1 | H |
| 1.1.3.8.1 | 33.125 | (v) | H | 1 | H | 1 | C(O)NHCH2 | 1 | Cl | 1 | H |
| 1.1.3.0.1 | 33.127 | (vi) | H | 1 | H | 1 | C(O)NHCH2 | | null | 1 | H |

TABLE 4-continued

| Compound No. as A.B.X.D.E | Synthetic Example No. | Formula | A | group No.* | B | group No.* | X** | group No.* | D | group No.* | E |
|---|---|---|---|---|---|---|---|---|---|---|---|
| 1.8.3.1.1 | 33.130 | (v) | H | 3 | OPr-n | 1 | C(O)NHCH2 | 1 | H | 1 | H |
| 4.8.3.1.1 | 33.131 | (v) | Cl | 1 | Cl | 1 | C(O)NHCH2 | 1 | H | 1 | H |
| 4.7.3.1.1 | 33.132 | (v) | Cl | 3 | CF3 | 1 | C(O)NHCH2 | 1 | H | 1 | H |
| 1.8.3.1.1 | 33.132 | (v) | Cl | 3 | CF3 | 1 | C(O)NHCH2 | 1 | H | 1 | H |
| 1.1.3.0.2 | 33.140 | (vi) | H | 1 | H | 1 | C(O)NHCH2 |  | null | 1 | Me |
| 1.2.3.1.1 | 33.141 | (v) | H | 1 | Me | 1 | C(O)NHCH2 | 1 | H | 1 | H |
| 4.8.3.8.2 | 33.142 | (v) | Cl | 1 | Cl | 1 | C(O)NHCH2 | 1 | Cl | 2 | Cl |

*The group number in front of B, X, D or E indicates the compound group in which the corresponding B, X, D or E is selected.
**The direction of X groups is defined as going from R5 to the phosphorus atom The numbers designated in Table 3 also refer to preferred benzothiazole and benzoxazole compounds of formula X. These preferred compounds are shown in structures (x) and (xi), below:

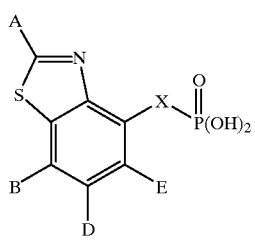

(x)

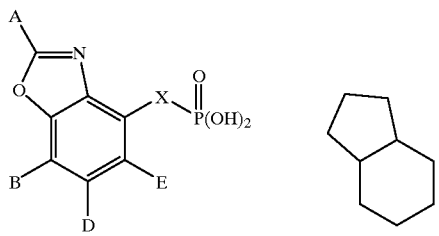

(xi)

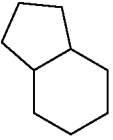

The preferred compounds of formula (x) and formula (xi) are listed in Table 3 by designated numbers assigned to B, X, A, D and E in the above formulae (x) and (xi) according to the following convention: B.X.A.D.E. For each moiety, structures are assigned to a number shown in the following tables for B, X, A, D, and E.

Variable B is divided into two Groups, each listing eight different substituents.

The substituents for variable B of formula (x) and formula (xi) in Table 3 are assigned the following numbers:

The Group 1 substituents for variable B in Table 3 for formulae (x) and (xi) are assigned the following numbers:

| | 1 | 2 | 3 | 4 | 5 | 6 | 7 | 8 |
|---|---|---|---|---|---|---|---|---|
| B = | H | Me | Et | Pr-n | Pr-c | Pr-i | Br | Cl |

The Group 2 substituents for variable B are assigned the following numbers:

| | 1 | 2 | 3 | 4 | 5 | 6 | 7 | 8 |
|---|---|---|---|---|---|---|---|---|
| B = | CN | F | OMe | OEt | SMe | SEt | $CH_2OH$ | C(O)OEt |

Variable X is selected from eight different substituents, assigned with the following numbers:

TABLE X

| | 1 | 2 | 3 | 4 | 5 | 6 | 7 | 8 |
|---|---|---|---|---|---|---|---|---|
| X = | $OCH_2$ | $SCH_2$ | $CH_2CH_2$ | $CH_2CH_2CH_2$ | $CH_2CF_2$ | $NHCH_2$ | OC(O) | SC(O) |

The direction of X groups is defined as going from the heterocycle to the phosphorus atom as shown in formula (x) and formula (xi).

Variable A is selected from four different substituents assigned with the following numbers:

TABLE A

| | 1 | 2 | 3 | 4 |
|---|---|---|---|---|
| A = | H | $NH_2$ | Br | Cl |

Variable D is selected from eight different substituents, assigned with the following numbers:

TABLE D

| 1 | 2 | 3 | 4 | 5 | 6 | 7 | 8 |
|---|---|---|---|---|---|---|---|
| D = | H | Me | Et | C(O)OMe | CH$_2$OMe | SMe | SEt | OMe |

Variable E is selected from four different substituents assigned with the following numbers:

TABLE E

| 1 | 2 | 3 | 4 |
|---|---|---|---|
| E = | H | Me | Et | F |

Thus, using Group 1 for variable B, the compound of formula (x) named in Table 3 as 1.1.2.1.1 specifies —H as B, —OCH$_2$— as X, —NH$_2$ as A, —H as D and —H as E, and this compound is 2-amino-4-phosphonomethoxybenzothiazole prepared in Example 34 as compound 34.2. Similarly, using group 1 for variable B, the compound named in Table 3 of formula (x) as 1.2.2.1.1 specifies —H as B, —SCH$_2$— as X, —NH$_2$ as A, —H as D and —H as E, and this compound is 2-amino-4-phosphonomethylthiobenzothiazole in Example 46 as compound 46.1.

Likewise, using Group 2 for variable B, the compound named 8.1.2.1.1 in Table 3 of formula (x) is 2-amino-7-ethoxycarbonyl-4-phosphonomethoxybenzothiazole in Example 37 prepared as compound 37.4.

Examples of preferred compounds of formula X also include, but not limited to the pharmaceutically acceptable salts and prodrugs of the compounds named in Table 5:

TABLE 5

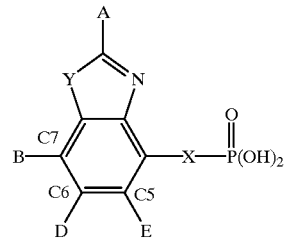

| Synthetic Example No. | A | Y | B | D | E | X |
|---|---|---|---|---|---|---|
| 36.1 | NH2 | S | C7(CH2)4C6 | C7(CH2)4C6 | H | OCH2 |
|  | NH2 | S | C7(CH2)4C6 | C7(CH2)4C6 | Me | OCH2 |
|  | NH2 | S | C7(CH2)4C6 | C7(CH2)4C6 | Et | OCH2 |
|  | NH2 | S | C7(CH2)4C6 | C7(CH2)4C6 | Pr-n | OCH2 |
|  | NH2 | S | C7(CH2)4C6 | C7(CH2)4C6 | Pr-c | OCH2 |
|  | NH2 | S | C7(CH2)4C6 | C7(CH2)4C6 | Ph | OCH2 |
|  | NH2 | S | C7(CH2)4C6 | C7(CH2)4C6 | C(O)OMe | OCH2 |
|  | NH2 | S | C7(CH2)4C6 | C7(CH2)4C6 | C(O)OEt | OCH2 |
|  | NH2 | S | C7(CH2)4C6 | C7(CH2)4C6 | C(O)NH2 | OCH2 |
|  | NH2 | S | C7(CH2)4C6 | C7(CH2)4C6 | OMe | OCH2 |
|  | NH2 | S | C7(CH2)4C6 | C7(CH2)4C6 | Br | OCH2 |
|  | NH2 | S | C7(CH2)4C6 | C7(CH2)4C6 | Cl | OCH2 |
|  | NH2 | S | C7(CH2)4C6 | C7(CH2)4C6 | I | OCH2 |
|  | NH2 | S | C7(CH2)4C6 | C7(CH2)4C6 | F | OCH2 |
|  | NH2 | S | C7(CH2)4C6 | C7(CH2)4C6 | CF3 | OCH2 |
|  | NH2 | S | C7(CH2)4C6 | C7(CH2)4C6 | CN | OCH2 |
|  | NH2 | S | C7(CH2)4C6 | C7(CH2)4C6 | SMe | OCH2 |
|  | NH2 | S | C7(CH2)4C6 | C7(CH2)4C6 | SEt | OCH2 |
|  | NH2 | S | C7(CH2)4C6 | C7(CH2)4C6 | NEt2 | OCH2 |
|  | NH2 | S | C7(CH2)4C6 | C7(CH2)4C6 | NMe2 | OCH2 |
|  | NH2 | O | C7(CH2)4C6 | C7(CH2)4C6 | H | OCH2 |
|  | NH2 | O | C7(CH2)4C6 | C7(CH2)4C6 | Me | OCH2 |
|  | NH2 | O | C7(CH2)4C6 | C7(CH2)4C6 | Et | OCH2 |
|  | NH2 | O | C7(CH2)4C6 | C7(CH2)4C6 | Pr-n | OCH2 |
|  | NH2 | O | C7(CH2)4C6 | C7(CH2)4C6 | Br | OCH2 |
|  | NH2 | O | C7(CH2)4C6 | C7(CH2)4C6 | Cl | OCH2 |
|  | NH2 | O | C7(CH2)4C6 | C7(CH2)4C6 | I | OCH2 |
|  | NH2 | O | C7(CH2)4C6 | C7(CH2)4C6 | Ph | OCH2 |
|  | NH2 | O | C7(CH2)4C6 | C7(CH2)4C6 | F | OCH2 |
|  | NH2 | O | C7(CH2)4C6 | C7(CH2)4C6 | NMe2 | OCH2 |
|  | NH2 | O | C7(CH2)4C6 | C7(CH2)4C6 | OH | OCH2 |
| 45.1 | H | S | C7(CH2)4C6 | C7(CH2)4C6 | H | OCH2 |
|  | H | S | C7(CH2)4C6 | C7(CH2)4C6 | Me | OCH2 |
|  | H | S | C7(CH2)4C6 | C7(CH2)4C6 | Et | OCH2 |

TABLE 5-continued

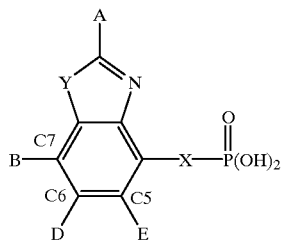

| Synthetic Example No. | A | Y | B | D | E | X |
|---|---|---|---|---|---|---|
| | H | S | C7(CH2)4C6 | C7(CH2)4C6 | Pr-n | OCH2 |
| | H | S | C7(CH2)4C6 | C7(CH2)4C6 | Br | OCH2 |
| | H | S | C7(CH2)4C6 | C7(CH2)4C6 | Cl | OCH2 |
| | H | S | C7(CH2)4C6 | C7(CH2)4C6 | I | OCH2 |
| | H | S | C7(CH2)4C6 | C7(CH2)4C6 | F | OCH2 |
| | H | S | C7(CH2)4C6 | C7(CH2)4C6 | Ph | OCH2 |
| | H | S | C7(CH2)4C6 | C7(CH2)4C6 | NMe2 | OCH2 |
| | H | O | C7(CH2)4C6 | C7(CH2)4C6 | H | OCH2 |
| | NH2 | S | C7(CH2)3C6 | C7(CH2)3C6 | H | OCH2 |
| | NH2 | S | C7(CH2)3C6 | C7(CH2)3C6 | Me | OCH2 |
| | NH2 | S | C7(CH2)3C6 | C7(CH2)3C6 | Et | OCH2 |
| | NH2 | S | C7(CH2)3C6 | C7(CH2)3C6 | Ph | OCH2 |
| | NH2 | S | C7(CH2)3C6 | C7(CH2)3C6 | Pr-i | OCH2 |
| | NH2 | S | C7(CH2)3C6 | C7(CH2)3C6 | Pr-c | OCH2 |
| | NH2 | S | C7(CH2)3C6 | C7(CH2)3C6 | Br | OCH2 |
| | NH2 | S | C7(CH2)3C6 | C7(CH2)3C6 | Cl | OCH2 |
| | NH2 | S | C7(CH2)3C6 | C7(CH2)3C6 | F | OCH2 |
| | NH2 | S | C7(CH2)3C6 | C7(CH2)3C6 | I | OCH2 |
| | NH2 | S | C7(CH2)3C6 | C7(CH2)3C6 | NMe2 | OCH2 |
| | NH2 | S | C7(CH2)3C6 | C7(CH2)3C6 | C(O)OEt | OCH2 |
| | NH2 | S | C7(CH2)3C6 | C7(CH2)3C6 | C(O)NH2 | OCH2 |
| | NH2 | S | C7(CH2)3C6 | C7(CH2)3C6 | OMe | OCH2 |
| | NH2 | S | C7(CH2)3C6 | C7(CH2)3C6 | OH | OCH2 |
| | H | S | C7(CH2)3C6 | C7(CH2)3C6 | H | OCH2 |
| | H | S | C7(CH2)3C6 | C7(CH2)3C6 | Me | OCH2 |
| | H | S | C7(CH2)3C6 | C7(CH2)3C6 | Et | OCH2 |
| | H | S | C7(CH2)3C6 | C7(CH2)3C6 | Ph | OCH2 |
| | H | S | C7(CH2)3C6 | C7(CH2)3C6 | OMe | OCH2 |
| | H | S | C7(CH2)3C6 | C7(CH2)3C6 | C(O)OMe | OCH2 |
| | H | S | C7(CH2)3C6 | C7(CH2)3C6 | Br | OCH2 |
| | H | S | C7(CH2)3C6 | C7(CH2)3C6 | OH | OCH2 |
| 36.2 | NH2 | S | C7(CH=CH=CH=CH)C6 | C7(CH=CH=CH=CH)C6 | H | OCH2 |
| | NH2 | S | C7(CH=CH=CH=CH)C6 | C7(CH=CH=CH=CH)C6 | Me | OCH2 |
| | NH2 | S | C7(CH=CH=CH=CH)C6 | C7(CH=CH=CH=CH)C6 | Et | OCH2 |
| | NH2 | S | C7(CH=CH=CH=CH)C6 | C7(CH=CH=CH=CH)C6 | Pr-i | OCH2 |
| | NH2 | S | C7(CH=CH=CH=CH)C6 | C7(CH=CH=CH=CH)C6 | Pr-c | OCH2 |
| | NH2 | S | C7(CH=CH=CH=CH)C6 | C7(CH=CH=CH=CH)C6 | OMe | OCH2 |
| | NH2 | S | C7(CH=CH=CH=CH)C6 | C7(CH=CH=CH=CH)C6 | Br | OCH2 |
| | NH2 | S | C7(CH=CH=CH=CH)C6 | C7(CH=CH=CH=CH)C6 | I | OCH2 |
| | NH2 | S | C7(CH=CH=CH=CH)C6 | C7(CH=CH=CH=CH)C6 | Cl | OCH2 |
| | NH2 | S | C7(CH=CH=CH=CH)C6 | C7(CH=CH=CH=CH)C6 | F | OCH2 |
| | NH2 | S | C7(CH=CH=CH=CH)C6 | C7(CH=CH=CH=CH)C6 | NMe2 | OCH2 |
| | NH2 | S | C7(CH=CH=CH=CH)C6 | C7(CH=CH=CH=CH)C6 | C(O)OMe | OCH2 |
| | NH2 | S | C7(CH=CH=CH=CH)C6 | C7(CH=CH=CH=CH)C6 | C(O)OEt | OCH2 |
| | NH2 | S | C7(CH=CH=CH=CH)C6 | C7(CH=CH=CH=CH)C6 | Ph | OCH2 |
| | NH2 | S | C7(CH=CH=CH=CH)C6 | C7(CH=CH=CH=CH)C6 | CF3 | OCH2 |
| | NH2 | S | C7(CH=CH=CH=CH)C6 | C7(CH=CH=CH=CH)C6 | CN | OCH2 |
| | NH2 | S | C7(CH=CH=CH=CH)C6 | C7(CH=CH=CH=CH)C6 | C(O)NH2 | OCH2 |
| | NH2 | S | C7(CH=CH=CH=CH)C6 | C7(CH=CH=CH=CH)C6 | SMe | OCH2 |
| | NH2 | S | C7(CH=CH=CH=CH)C6 | C7(CH=CH=CH=CH)C6 | SEt | OCH2 |
| | NH2 | S | C7(CH=CH=CH=CH)C6 | C7(CH=CH=CH=CH)C6 | CO2H | OCH2 |
| | NH2 | S | C7(CH=CH=CH=CH)C6 | C7(CH=CH=CH=CH)C6 | OH | OCH2 |
| | H | S | C7(CH=CH=CH=CH)C6 | C7(CH=CH=CH=CH)C6 | H | OCH2 |
| | H | S | C7(CH=CH=CH=CH)C6 | C7(CH=CH=CH=CH)C6 | Me | OCH2 |
| | H | S | C7(CH=CH=CH=CH)C6 | C7(CH=CH=CH=CH)C6 | H | OCH2 |
| | H | S | C7(CH=CH=CH=CH)C6 | C7(CH=CH=CH=CH)C6 | Me | OCH2 |
| | H | S | C7(CH=CH=CH=CH)C6 | C7(CH=CH=CH=CH)C6 | Et | OCH2 |
| | H | S | C7(CH=CH=CH=CH)C6 | C7(CH=CH=CH=CH)C6 | OMe | OCH2 |
| | H | S | C7(CH=CH=CH=CH)C6 | C7(CH=CH=CH=CH)C6 | Ph | OCH2 |
| | H | S | C7(CH=CH=CH=CH)C6 | C7(CH=CH=CH=CH)C6 | Br | OCH2 |
| | H | S | C7(CH=CH=CH=CH)C6 | C7(CH=CH=CH=CH)C6 | Cl | OCH2 |
| | H | S | C7(CH=CH=CH=CH)C6 | C7(CH=CH=CH=CH)C6 | OH | OCH2 |

TABLE 5-continued

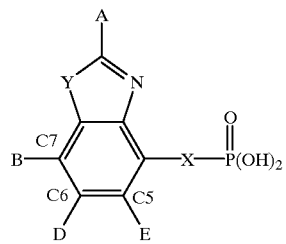

| Synthetic Example No. | A | Y | B | D | E | X |
|---|---|---|---|---|---|---|
| | NH2 | S | C7OCH=CHC6 | C7OCH=CHC6 | H | OCH2 |
| | NH2 | S | C7O—CH=CHC6 | C7O—CH=CHC6 | Me | OCH2 |
| | NH2 | S | C7O—CH=CHC6 | C7O—CH=CHC6 | Ph | OCH2 |
| | NH2 | S | C7O—CH=CHC6 | C7O—CH=CHC6 | Br | OCH2 |
| | NH2 | S | C7O—CH=CHC6 | C7O—CH=CHC6 | OH | OCH2 |
| | NH2 | S | C7O—CH=CHC6 | C7O—CH=CHC6 | OMe | OCH2 |
| | NH2 | S | C7CH=CH—OC6 | C7CH=CH—OC6 | H | OCH2 |
| | NH2 | S | C7CH=CH—OC6 | C7CH=CH—OC6 | Me | OCH2 |
| | NH2 | S | C7CH=CH—OC6 | C7CH=CH—OC6 | Br | OCH2 |
| | NH2 | S | C7CH=CH—OC6 | C7CH=CH—OC6 | Ph | OCH2 |
| | NH2 | S | C7CH=CH—OC6 | C7CH=CH—OC6 | OH | OCH2 |
| | NH2 | S | C7CH=CH—OC6 | C7CH=CH—OC6 | OMe | OCH2 |
| | NH2 | S | C7S—CH=CHC6 | C7S—CH=CHC6 | H | OCH2 |
| | NH2 | S | C7S—CH=CHC6 | C7S—CH=CHC6 | Me | OCH2 |
| | NH2 | S | C7S—CH=CHC6 | C7S—CH=CHC6 | Ph | OCH2 |
| | NH2 | S | C7S—CH=CHC6 | C7S—CH=CHC6 | OH | OCH2 |
| | NH2 | S | C7S—CH=CHC6 | C7S—CH=CHC6 | OMe | OCH2 |
| | NH2 | S | C7S—CH=CHC6 | C7S—CH=CHC6 | isobutyl | OCH2 |
| | NH2 | S | Me | C6(CH=CH—CH=CH)C5 | C6(CH=CH—CH=CH)C5 | OCH2 |
| | NH2 | S | Et | C6(CH=CH—CH=CH)C5 | C6(CH=CH—CH=CH)C5 | OCH2 |
| | NH2 | S | Pr-n | C6(CH=CH—CH=CH)C5 | C6(CH=CH—CH=CH)C5 | OCH2 |
| | NH2 | S | OMe | C6(CH=CH—CH=CH)C5 | C6(CH=CH—CH=CH)C5 | OCH2 |
| | NH2 | S | OH | C6(CH=CH—CH=CH)C5 | C6(CH=CH—CH=CH)C5 | OCH2 |
| | NH2 | S | OCH3 | C6(CH=CH—CH=CH)C5 | C6(CH=CH—CH=CH)C5 | OCH2 |
| | NH2 | S | Cl | C6(CH=CH—CH=CH)C5 | C6(CH=CH—CH=CH)C5 | OCH2 |
| | NH2 | S | Br | C6(CH=CH—CH=CH)C5 | C6(CH=CH—CH=CH)C5 | OCH2 |
| | NH2 | S | F | C6(CH=CH—CH=CH)C5 | C6(CH=CH—CH=CH)C5 | OCH2 |
| | NH2 | S | CH2OH | C6(CH=CH—CH=CH)C5 | C6(CH=CH—CH=CH)C5 | OCH2 |
| | NH2 | S | H | C6(CH=CH—CH=CH)C5 | C6(CH=CH—CH=CH)C5 | OCH2 |
| | NH2 | S | C(O)OMe | C6(CH=CH—CH=CH)C5 | C6(CH=CH—CH=CH)C5 | OCH2 |
| | NH2 | S | H | C6(CH2)4C5 | C6(CH2)4C5 | OCH2 |
| | NH2 | S | Me | C6(CH2)4C5 | C6(CH2)4C5 | OCH2 |
| | NH2 | S | Et | C6(CH2)4C5 | C6(CH2)4C5 | OCH2 |
| | NH2 | S | OH | C6(CH2)4C5 | C6(CH2)4C5 | OCH2 |
| | NH2 | S | OMe | C6(CH2)4C5 | C6(CH2)4C5 | OCH2 |
| | NH2 | S | CH2OH | C6(CH2)4C5 | C6(CH2)4C5 | OCH2 |
| | NH2 | S | Br | C6(CH2)4C5 | C6(CH2)4C5 | OCH2 |
| | NH2 | S | Cl | C6(CH2)4C5 | C6(CH2)4C5 | OCH2 |
| | NH2 | S | C(O)OMe | C6(CH2)4C5 | C6(CH2)4C5 | OCH2 |
| | NH2 | S | H | C6O—CH=CHC5 | C6O—CH=CHC5 | OCH2 |
| | NH2 | S | Me | C6O—CH=CHC5 | C6O—CH=CHC5 | OCH2 |
| | NH2 | S | Et | C6O—CH=CHC5 | C6O—CH=CHC5 | OCH2 |
| | NH2 | S | CH2OH | C6O—CH=CHC5 | C6O—CH=CHC5 | OCH2 |
| | NH2 | S | Br | C6O—CH=CHC5 | C6O—CH=CHC5 | OCH2 |
| | NH2 | S | Cl | C6O—CH=CHC5 | C6O—CH=CHC5 | OCH2 |
| | NH2 | S | Ph | C6O—CH=CHC5 | C6O—CH=CHC5 | OCH2 |
| | NH2 | S | OMe | C6O—CH=CHC5 | C6O—CH=CHC5 | OCH2 |
| | NH2 | S | Pr-n | C6O—CH=CHC5 | C6O—CH=CHC5 | OCH2 |
| | NH2 | S | C(O)OMe | C6O—CH=CHC5 | C6O—CH=CHC5 | OCH2 |
| | NH2 | S | H | C6S—CH=CHC5 | C6S—CH=CHC5 | OCH2 |
| | NH2 | S | Me | C6S—CH=CHC5 | C6S—CH=CHC5 | OCH2 |
| | NH2 | S | Et | C6S—CH=CHC5 | C6S—CH=CHC5 | OCH2 |
| | NH2 | S | OH | C6S—CH=CHC5 | C6S—CH=CHC5 | OCH2 |
| | NH2 | S | OMe | C6S—CH=CHC5 | C6S—CH=CHC5 | OCH2 |
| | NH2 | S | CH2OH | C6S—CH=CHC5 | C6S—CH=CHC5 | OCH2 |
| | NH2 | S | Br | C6S—CH=CHC5 | C6S—CH=CHC5 | OCH2 |

TABLE 5-continued

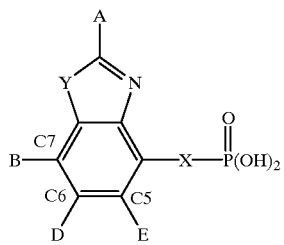

| Synthetic Example No. | A | Y | B | D | E | X |
|---|---|---|---|---|---|---|
| | NH2 | S | Cl | C6S—CH=CHC5 | C6S—CH=CHC5 | OCH2 |
| | NH2 | S | C(O)OMe | C6S—CH=CHC5 | C6S—CH=CHC5 | OCH2 |
| | NH2 | S | Ph | C6S—CH=CHC5 | C6S—CH=CHC5 | OCH2 |
| | H | S | Me | C6O—CH=CHC5 | C6O—CH=CHC5 | OCH2 |
| | H | S | Br | C6O—CH=CHC5 | C6O—CH=CHC5 | OCH2 |
| | H | S | Me | C6S—CH=CHC5 | C6S—CH=CHC5 | OCH2 |
| | H | S | Br | C6S—CH=CHC5 | C6S—CH=CHC5 | OCH2 |
| | H | S | H | C6O—CH=CHC5 | C6O—CH=CHC5 | OCH2 |
| | Cl | S | C7(CH2)4C6 | C7(CH2)4C6 | H | OCH2 |
| | Cl | S | C7(CH2)4C6 | C7(CH2)4C6 | Me | OCH2 |
| | Cl | S | C7(CH2)4C6 | C7(CH2)4C6 | Et | OCH2 |
| | Cl | S | C7(CH2)4C6 | C7(CH2)4C6 | Pr-n | OCH2 |
| | Cl | S | C7(CH2)4C6 | C7(CH2)4C6 | Ph | OCH2 |
| | Cl | S | C7(CH2)4C6 | C7(CH2)4C6 | Br | OCH2 |
| | Cl | S | C7(CH2)4C6 | C7(CH2)4C6 | Cl | OCH2 |
| | Cl | S | C7(CH2)4C6 | C7(CH2)4C6 | C(O)OMe | OCH2 |
| | Cl | S | C7(CH2)4C6 | C7(CH2)4C6 | OH | OCH2 |
| | Me | S | C7(CH2)4C6 | C7(CH2)4C6 | H | OCH2 |
| | Me | S | C7(CH2)4C6 | C7(CH2)4C6 | Me | OCH2 |
| | Me | S | C7(CH2)4C6 | C7(CH2)4C6 | Et | OCH2 |
| | Me | S | C7(CH2)4C6 | C7(CH2)4C6 | Pr-n | OCH2 |
| | Me | S | C7(CH2)4C6 | C7(CH2)4C6 | Ph | OCH2 |
| | Me | S | C7(CH2)4C6 | C7(CH2)4C6 | OH | OCH2 |
| | Me | S | C7(CH2)4C6 | C7(CH2)4C6 | Br | OCH2 |
| | Me | S | C7(CH2)4C6 | C7(CH2)4C6 | Cl | OCH2 |
| | Me | S | C7(CH2)4C6 | C7(CH2)4C6 | C(O)OMe | OCH2 |
| | Me | S | C7(CH2)4C6 | C7(CH2)4C6 | NMe2 | OCH2 |
| | NH2 | S | H | C6(CH2)4C5 | C6(CH2)4C5 | OCH2 |
| | NH2 | S | Me | C6(CH2)4C5 | C6(CH2)4C5 | OCH2 |
| | NH2 | S | Et | C6(CH2)4C5 | C6(CH2)4C5 | OCH2 |
| | NH2 | S | Pr-n | C6(CH2)4C5 | C6(CH2)4C5 | OCH2 |
| | NH2 | S | Br | C6(CH2)4C5 | C6(CH2)4C5 | OCH2 |
| | NH2 | S | Cl | C6(CH2)4C5 | C6(CH2)4C5 | OCH2 |
| | NH2 | S | OH | C6(CH2)4C5 | C6(CH2)4C5 | OCH2 |
| | NH2 | S | CF3 | C6(CH2)4C5 | C6(CH2)4C5 | OCH2 |
| | NH2 | S | C(O)OMe | C6(CH2)4C5 | C6(CH2)4C5 | OCH2 |
| | NH2 | S | Ph | C6(CH2)4C5 | C6(CH2)4C5 | OCH2 |
| | NH2 | S | NMe2 | C6(CH2)4C5 | C6(CH2)4C5 | OCH2 |
| 44.1 | Br | S | C7(CH2)4C6 | C7(CH2)4C6 | H | OCH2 |

The numbers designated in Table 1 also represent preferred prodrugs of compounds of formula I as shown in formula (xii) and (xiii), below:

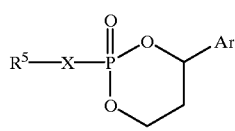

(xii)

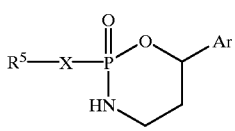

(xiii)

In the above formulae (xii) and (xiii), Ar stands for aryl including heteroaryl and is substituted by $R^{25}$. The preferred compounds of formula (xii) and formula (xiii) are listed in Table 1 designated by numbers assigned to X, $R^5$, $R^{25}$, and Ar in the above formulae (xii) and (xiii) according to the following convention: $X.R^5.R^{25}.Ar$.

Variable X is selected from seven different substituents, assigned the following numbers:

TABLE X

| | 1 | 2 | 3 | 4 | 5 | 6 | 7 |
|---|---|---|---|---|---|---|---|
| X = | Furan-2,5-diyl | $C(O)OCH_2$ | $C(O)NHCH_2$ | $NHC(O)CH_2$ | Pyridin-2,6-diyl | $CH_2OCH_2$ | $C(O)SCH_2$ |

Variable $R^5$ is selected from nine different substituents assigned the following numbers:

TABLE $R^5$

| | 1 | 2 | 3 | 4 |
|---|---|---|---|---|
| $R^5 =$ | H₂N-thiazolyl-SMe | H₂N-thiazolyl-isobutyl | H₂N-thiazolyl-cyclopropyl | H₂N-thiazolyl-SPr-n |

| | 5 | 6 | 7 | 8 | 9 |
|---|---|---|---|---|---|
| $R^5 =$ | H₂N-thiazolyl-SEt | H₂N-thiazolyl-isopropyl | H₂N-oxazolyl-SPr-n | H₂N-thiazolyl-CH₂-cyclopropyl | H₂N-oxazolyl-CH₂-cyclopropyl |

Variable $R^{25}$ is selected from nine different substituents assigned the following numbers:

TABLE $R^{25}$

| | 1 | 2 | 3 | 4 | 5 | 6 | 7 | 8 | 9 |
|---|---|---|---|---|---|---|---|---|---|
| $R^{25} =$ | F | Cl | Br | CN | $CF_3$ | Me | Et | OMe | NHAc |

Variable Ar is selected from six different substituents assigned the following numbers:

TABLE Ar

| | 1 | 2 | 3 | 4 | 5 | 6 |
|---|---|---|---|---|---|---|
| Ar = | 2-$R^{25}$-phenyl | 3-$R^{25}$-phenyl | 4-$R^{25}$-phenyl | 2-$R^{25}$-pyridin-5-yl | 3-$R^{25}$-pyridin-4-yl | 2-$R^{25}$-pyridin-4-yl |

The compounds named in Table 1 of formula (xii) or formula (xiii) each number listed in Table 1 of formula (xii) or formula (xiii) are shown without depictions of stereochemistry since the compounds are biologically active as the diastereomeric mixture or as a single stereoisomer.

Using the variable for X, $R^5$, $R^{25}$, and Ar, the compound of formula (xii) named 1.2.2.2 in Table 1 specifies furan-2, 5-diyl as X, 4-(2-amino-5-isobutyl)thiazolyl as $R^5$, chloro as $R^{25}$, and 3-chlorophenyl as Ar, and this compound is the diastereomers of 2-amino-5-isobutyl-4-{2-[5-(1-(3-chlorophenyl)-1,3-propyl)phosphono]furanyl}thiazole prepared in Example 19 as compound 19.46 (major isomer) and 19.45 (minor isomer).

The numbers designated in Table 3 also represent preferred prodrugs of compounds of formula I as shown in the following formulae (xiv) and (xv):

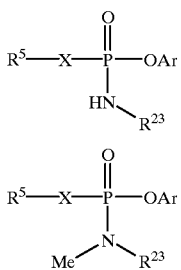

(xiv)

(xv)

In the compounds of formulae (xiv) and (xv), Ar represents aryl and heteroaryl and is substituted by $R^{25}$. The preferred compounds of formula (xiv) and formula (xv) are listed named in Table 3 by designated numbers assigned to $R^5$, $R^{23}$, Ar, $R^{25}$ and X in the above formulae (xiv) and (xv) according to the following convention: $R^5.R^{23}.Ar.R^{25}.X$. For each moiety, structures are assigned to a number shown in the following tables for $R^5$, $R^{23}$, Ar, $R^{25}$ and X.

The Variable $R^5$ is selected from eight different substituents assigned the following numbers:

TABLE $R^5$

The variable $R^{23}$ is selected from eight different substituents assigned the following numbers:

TABLE $R^{23}$

The variable Ar is selected from four different substituents assigned the following numbers:

TABLE Ar

The variable $R^{25}$ is selected from eight different substituents assigned the following numbers:

TABLE $R^{25}$

| 1 | 2 | 3 | 4 | 5 | 6 | 7 | 8 |
|---|---|---|---|---|---|---|---|
| $R^{25}$ = F | Cl | Br | NHAc | $CF_3$ | Me | $CO_2Et$ | OMe |

The variable X is selected from four different substituents assigned the following numbers:

TABLE X

| 1 | 2 | 3 | 4 |
|---|---|---|---|
| X = Furan-2,5-diyl | $C(O)OCH_2$ | $C(O)NHCH_2$ | $NHC(O)CH_2$ |

Thus, using the variables for $R^5$, $R^{23}$, Ar, $R^{25}$, and X, the compound of formula (viv) named in Table 3 as 2.7.2.2.1 specifies 4-(2-amino-5-isobutyl)thiazolyl as $R^5$, —CH(Me)$CO_2Me$ as $R^{23}$, 3-chlorophenyl as Ar, chloro as $R^{25}$, and furan-2,5-diyl as X, and this compound is 2-amino-5-isobutyl-4-{2-[5-(O-phenyl-N-(1-(1-methoxycarbonyl)ethyl)phosphono]furanyl}thiazole prepared in Example 31 as compound 31.6.

The numbers designated in Table 3 also represent preferred prodrugs of compounds of formula I as shown in the following formulae (xvi) and (xvii):

(xvi)
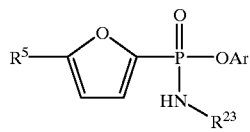

(xvii)
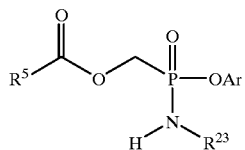

In the above formuale (xvi) and (xvii), Ar stands for aryl including heteroaryl, and is substituted by $R^{24}$ and $R^{25}$. The preferred compounds of formula (xvi) and formula (xvii) are listed in Table 3 by designated numbers assigned to $R^{24}$, $R^{25}$, Ar, $R^5$, and $R^{23}$ in the above formula according to the following convention, $R^{24}.R^{25}.Ar.R^5.R^{23}$. For each moiety, structures are assigned to a number shown in the following tables for $R^{24}$, $R^{25}$, Ar, $R^5$ and $R^{23}$.

Variable $R^{24}$ is selected from eight different substituents assigned the following numbers:

TABLE $R^{24}$

| 1 | 2 | 3 | 4 | 5 | 6 | 7 | 8 |
|---|---|---|---|---|---|---|---|
| $R^{24}$ = F | Cl | Br | NHAc | $CF_3$ | Me | $CO_2Et$ | OMe |

Variable $R^{25}$ is selected from eight different substituents assigned the following numbers:

TABLE $R^{25}$

| 1 | 2 | 3 | 4 | 5 | 6 | 7 | 8 |
|---|---|---|---|---|---|---|---|
| $R^{25}$ = F | Cl | Br | NHAc | $CF_3$ | Me | $CO_2Et$ | OMe |

Variable Ar is divided into two Groups, each listing four different subsituents. The Group 1 substituents for variable Ar are assigned the following numbers:

| 1 | 2 | 3 | 4 |
|---|---|---|---|

Ar =
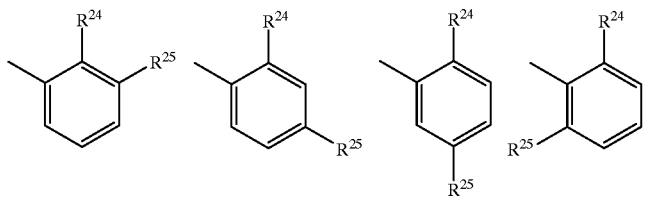

The Group 2 substituents for variable Ar are assigned the following numbers:

| | 1 | 2 | 3 | 4 |
|---|---|---|---|---|

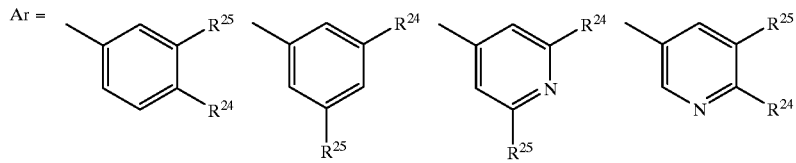

Variable $R^5$ is selected from eight different substituents assigned the following numbers:

TABLE $R^5$

| | 1 | 2 | 3 | 4 |
|---|---|---|---|---|

$R^5 =$ (structures 1–4: 2-amino-4-methylthiazole with 5-SMe; 5-isobutyl; 5-cyclopropyl; 5-SPr-n)

| | 5 | 6 | 7 | 8 |
|---|---|---|---|---|

$R^5 =$ (structures 5–8: 2-amino-4-methylthiazole with 5-SEt; 5-isopropyl; 2-amino-4-methyloxazole with 5-SPr-n; 2-amino-4-methylthiazole with 5-CH$_2$-cyclopropyl)

Variable $R^{23}$ is divided into two Groups, each listing four different substituents. The Group 1 substituents for variable $R^{23}$ are assigned the following numbers:

| | 1 | 2 | 3 | 4 |
|---|---|---|---|---|

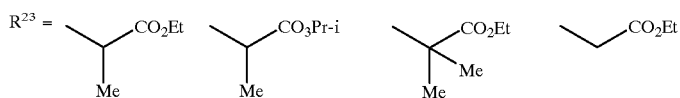

The Group 2 substituents for variable $R^{23}$ are assigned the following numbers:

| | 5 | 6 | 7 | 8 |
|---|---|---|---|---|
| $R^{23} =$ | $\sim\sim\text{CO}_2\text{Et}$ | $\text{CH(CO}_2\text{Et)}_2$ | $\text{CH(Me)CO}_2\text{Me}$ | cyclopropyl-$\text{CO}_3\text{Et}$ |

Variable $R^5$ is selected from eight different substituents assigned the following numbers,

TABLE $R^5$

| | 1 | 2 | 3 | 4 |
|---|---|---|---|---|
| $R^5 =$ | 2-amino-4-methyl-5-(SMe)thiazole | 2-amino-4-methyl-5-isobutylthiazole | 2-amino-4-methyl-5-cyclopropylthiazole | 2-amino-4-methyl-5-(SPr-n)thiazole |

| | 5 | 6 | 7 | 8 |
|---|---|---|---|---|
| $R^5 =$ | 2-amino-4-methyl-5-(SEt)thiazole | 2-amino-4-methyl-5-isopropylthiazole | 2-amino-4-methyl-5-(SPr-n)oxazole | 2-amino-4-methyl-5-(cyclopropylmethyl)thiazole |

Variable X is selected from four different substituents assigned the following numbers:

TABLE X

| | 1 | 2 | 3 | 4 |
|---|---|---|---|---|
| X = | Furan-2,5-diyl | C(O)OCH$_2$ | C(O)NHCH$_2$ | NHC(O)CH$_2$ |

Examples of preferred prodrugs of compounds of formula I are named in Table 6 as shown in the following prodrug formula (xi):

$$R^5\text{—X—P'} \quad (xix)$$

The preferred compounds of formula (xix) are listed in Table 6 by designated numbers assigned to P', $R^5$, and X in the above formula (xix) according to the following convention, P'.$R^5$.X. For each moiety, structures are assigned to a number in the following tables for P', $R^5$ and X.

Variable P' is divided into two Groups, each listing seven different substituents. The Group 1 substituents for variable P' are assigned the following numbers:

TABLE P'

| | 1 | 2 | 3 |
|---|---|---|---|
| P' = | 2-Ph-1,3,2-dioxaphosphorinane 2-oxide | 2-(pyridin-4-yl)-1,3,2-dioxaphosphorinane 2-oxide | P(O)(OPh)(NH-C(Me)$_2$-CO$_2$Et) |

TABLE P'-continued

| 4 | 5 | 6 | 7 |
|---|---|---|---|
| P' = P(=O)(-OPh)(-NH-CH(CH₃)-CO₂Et) | P(=O)(-O-CH₂-OCO₂Et)(-O-CH₂-OCO₂Et) | P(=O)(-O-CH(CH₃)-OCO₂Et)(-O-CH(CH₃)-OCO₂Et) | P(=O)(-OPh)(-NH-CH₂-CO₂Et) |

The Group 2 substituents for variable P' are assigned the following numbers:

| 1 | 2 | 3 | 4 |
|---|---|---|---|
| P' = cyclic phosphonate with CH₂OH | P(=O)(-O-CH₂-OC(O)Bu-t)(-O-CH₂-OC(O)Bu-t) | P(=O)(-OPh)(-NH-C(cyclopropyl)-CO₂Et) | P(=O)(-OPh)(-NH-CH₂CH₂-CO₂Et) |

| 5 | 6 | 7 |
|---|---|---|
| P(=O)(-O-CH₂-OC(O)Pr-)(-O-CH₂-OC(O)PR-i) | P(=O)(-NH-CH₂CH₂-CO₂Et)(-O-CH₂CH₂-SC(O)Bu-t) | bicyclic phosphonate with OH |

Variable $R^5$ is selected from nine different substituents assigned the following numbers:

TABLE $R^5$

| 1 | 2 | 3 | 4 |
|---|---|---|---|
| $R^5$ = 2-amino-4-methyl-5-(SMe)-thiazole | 2-amino-4-methyl-5-isobutyl-thiazole | 2-amino-4-methyl-5-cyclopropyl-thiazole | 2-amino-4-methyl-5-(SPr-n)-thiazole |

TABLE R⁵-continued

|   | 5 | 6 | 7 | 8 | 9 |
|---|---|---|---|---|---|
| R⁵ = | H₂N-[thiazole]-SEt | H₂N-[thiazole]-iPr | H₂N-[oxazole]-SPr-n | H₂N-[thiazole]-CH₂-cyclopropyl | H₂N-[oxazole]-CH₂-cyclopropyl |

Variable X is selected from six different substituents assigned the following numbers:

TABLE X

|   | 1 | 2 | 3 | 4 | 5 | 6 |
|---|---|---|---|---|---|---|
| X = | Furan-2,5-diyl | C(O)OCH₂ | C(O)NHCH₂ | NHC(O)CH₂ | Pyridin-2,6-diyl | CH₂OCH₂ |

TABLE 6

| | | | | | | | | | | | |
|---|---|---|---|---|---|---|---|---|---|---|---|
| 1.1.1 | 1.1.2 | 1.1.3 | 1.1.4 | 1.1.5 | 1.1.6 | 1.2.1 | 1.2.2 | 1.2.3 | 1.2.4 | 1.2.5 | 1.2.6 |
| 1.3.1 | 1.3.2 | 1.3.3 | 1.3.4 | 1.3.5 | 1.3.6 | 1.4.1 | 1.4.2 | 1.4.3 | 1.4.4 | 1.4.5 | 1.4.6 |
| 1.5.1 | 1.5.2 | 1.5.3 | 1.5.4 | 1.5.5 | 1.5.6 | 1.6.1 | 1.6.2 | 1.6.3 | 1.6.4 | 1.6.5 | 1.6.6 |
| 1.7.1 | 1.7.2 | 1.7.3 | 1.7.4 | 1.7.5 | 1.7.6 | 1.8.1 | 1.8.2 | 1.8.3 | 1.8.4 | 1.8.5 | 1.8.6 |
| 1.9.1 | 1.9.2 | 1.9.3 | 1.9.4 | 1.9.5 | 1.9.6 | 2.1.1 | 2.1.2 | 2.1.3 | 2.1.4 | 2.1.5 | 2.1.6 |
| 2.2.1 | 2.2.2 | 2.2.3 | 2.2.4 | 2.2.5 | 2.2.6 | 2.3.1 | 2.3.2 | 2.3.3 | 2.3.4 | 2.3.5 | 2.3.6 |
| 2.4.1 | 2.4.2 | 2.4.3 | 2.4.4 | 2.4.5 | 2.4.6 | 2.5.1 | 2.5.2 | 2.5.3 | 2.5.4 | 2.5.5 | 2.5.6 |
| 2.6.1 | 2.6.2 | 2.6.3 | 2.6.4 | 2.6.5 | 2.6.6 | 2.7.1 | 2.7.2 | 2.7.3 | 2.7.4 | 2.7.5 | 2.7.6 |
| 2.8.1 | 2.8.2 | 2.8.3 | 2.8.4 | 2.8.5 | 2.8.6 | 2.9.1 | 2.9.2 | 2.9.3 | 2.9.4 | 2.9.5 | 2.9.6 |
| 3.1.1 | 3.1.2 | 3.1.3 | 3.1.4 | 3.1.5 | 3.1.6 | 3.2.1 | 3.2.2 | 3.2.3 | 3.2.4 | 3.2.5 | 3.2.6 |
| 3.3.1 | 3.3.2 | 3.3.3 | 3.3.4 | 3.3.5 | 3.3.6 | 3.4.1 | 3.4.2 | 3.4.3 | 3.4.4 | 3.4.5 | 3.4.6. |
| 3.5.1 | 3.5.2 | 3.5.3 | 3.5.4 | 3.5.5 | 3.5.6 | 3.6.1 | 3.6.2 | 3.6.3 | 3.6.4 | 3.6.5 | 3.6.6 |
| 3.7.1 | 3.7.2 | 3.7.3 | 3.7.4 | 3.7.5 | 3.7.6 | 3.8.1 | 3.8.2 | 3.8.3 | 3.8.4 | 3.8.5 | 3.8.6 |
| 3.9.1 | 3.9.2 | 3.9.3 | 3.9.4 | 3.9.5 | 3.9.6 | 4.1.1 | 4.1.2 | 4.1.3 | 4.1.4 | 4.1.5 | 4.1.6 |
| 4.2.1 | 4.2.2 | 4.2.3 | 4.2.4 | 4.2.5 | 4.2.6 | 4.3.1 | 4.3.2 | 4.3.3 | 4.3.4 | 4.3.5 | 4.3.6 |
| 4.4.1 | 4.4.2 | 4.4.3 | 4.4.4 | 4.4.5 | 4.4.6 | 4.5.1 | 4.5.2 | 4.5.3 | 4.5.4 | 4.5.5 | 4.5.6 |
| 4.6.1 | 4.6.2 | 4.6.3 | 4.6.4 | 4.6.5 | 4.6.6 | 4.7.1 | 4.7.2 | 4.7.3 | 4.7.4 | 4.7.5 | 4.7.6 |
| 4.8.1 | 4.8.2 | 4.8.3 | 4.8.4 | 4.8.5 | 4.8.6 | 4.9.1 | 4.9.2 | 4.9.3 | 4.9.4 | 4.9.5 | 4.9.6 |
| 5.1.1 | 5.1.2 | 5.1.3 | 5.1.4 | 5.1.5 | 5.1.6 | 5.2.1 | 5.2.2 | 5.2.3 | 5.2.4 | 5.2.5 | 5.2.6 |
| 5.3.1 | 5.3.2 | 5.3.3 | 5.3.4 | 5.3.5 | 5.3.6 | 5.4.1 | 5.4.2 | 5.4.3 | 5.4.4 | 5.4.5 | 5.4.6 |
| 5.5.1 | 5.5.2 | 5.5.3 | 5.5.4 | 5.5.5 | 5.5.6 | 5.6.1 | 5.6.2 | 5.6.3 | 5.6.4 | 5.6.5 | 5.6.6 |
| 5.7.1 | 5.7.2 | 5.7.3 | 5.7.4 | 5.7.5 | 5.7.6 | 5.8.1 | 5.8.2 | 5.8.3 | 5.8.4 | 5.8.5 | 5.8.6 |
| 5.9.1 | 5.9.2 | 5.9.3 | 5.9.4 | 5.9.5 | 5.9.6 | 6.1.1 | 6.1.2 | 6.1.3 | 6.1.4 | 6.1.5 | 6.1.6 |
| 6.2.1 | 6.2.2 | 6.2.3 | 6.2.4 | 6.2.5 | 6.2.6 | 6.3.1 | 6.3.2 | 6.3.3 | 6.3.4 | 6.3.5 | 6.3.6 |
| 6.4.1 | 6.4.2 | 6.4.3 | 6.4.4 | 6.4.5 | 6.4.6 | 6.5.1 | 6.5.2 | 6.5.3 | 6.5.4 | 6.5.5 | 6.5.6 |
| 6.6.1 | 6.6.2 | 6.6.3 | 6.6.4 | 6.6.5 | 6.6.6 | 6.7.1 | 6.7.2 | 6.7.3 | 6.7.4 | 6.7.5 | 6.7.6 |
| 6.8.1 | 6.8.2 | 6.8.3 | 6.8.4 | 6.8.5 | 6.8.6 | 6.9.1 | 6.9.2 | 6.9.3 | 6.9.4 | 6.9.5 | 6.9.6 |
| 7.1.1 | 7.1.2 | 7.1.3 | 7.1.4 | 7.1.5 | 7.1.6 | 7.2.1 | 7.2.2 | 7.2.3 | 7.2.4 | 7.2.5 | 7.2.6 |
| 7.3.1 | 7.3.2 | 7.3.3 | 7.3.4 | 7.3.5 | 7.3.6 | 7.4.1 | 7.4.2 | 7.4.3 | 7.4.4 | 7.4.5 | 7.4.6 |
| 7.5.1 | 7.5.2 | 7.5.3 | 7.5.4 | 7.5.5 | 7.5.6 | 7.6.1 | 7.6.2 | 7.6.3 | 7.6.4 | 7.6.5 | 7.6.6 |
| 7.7.1 | 7.7.2 | 7.7.3 | 7.7.4 | 7.7.5 | 7.7.6 | 7.8.1 | 7.8.2 | 7.8.3 | 7.8.4 | 7.8.5 | 7.8.6 |
| 7.9.1 | 7.9.2 | 7.9.3 | 7.9.4 | 7.9.5 | 7.9.6 | | | | | | |

The numbers designated in Table 1 also represent preferred prodrugs of compounds of formula X as shown in the following formula (xx):

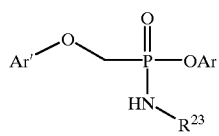

(xx)

In the above formula (xx), Ar stands for aryl including heteroaryl, and is substituted with $R^{25}$. The preferred compounds of formula (xx) are listed in Table 1 by designated numbers assigned to Ar', $R^{25}$, $R^{23}$, and Ar according to the following convention: Ar'.$R^{25}$.$R^{23}$.Ar. For each moiety, structures are assigned to a number in the following tables for Ar', $R^{25}$, $R^{23}$ and Ar, wherein $R^{25}$ is a substituent attached to Ar.

Variable Ar' is selected from seven different substituents assigned the following numbers:

TABLE Ar'

| 1 | 2 | 3 | 4 |
|---|---|---|---|
| Ar' (benzothiazole with H₂N-, Me, Br) | (benzothiazole with H₂N-, Me, Me) | (benzothiazole with H₂N-, Me, Br, Me) | (benzothiazole with H₂N-, Me, Et, SCN) |

| 5 | 6 | 7 |
|---|---|---|
| Ar' (benzothiazole with H₂N-, Me, Cl, Me) | (benzothiazole with H₂N-, Me, OMe, SCN) | (naphthothiazole with H₂N-, Me) |

Variable $R^{25}$ is selected from nine different substituents assigned the following numbers:

TABLE $R^{25}$

| | 1 | 2 | 3 | 4 | 5 | 6 | 7 | 8 | 9 |
|---|---|---|---|---|---|---|---|---|---|
| $R^{25}$ = | F | Cl | Br | NHAc | $CF_3$ | Me | Et | OMe | $CO_2Et$ |

Variable $R^{23}$ is selected from nine different substituents assigned the following numbers:

TABLE $R^{23}$

| | 1 | 2 | 3 | 4 |
|---|---|---|---|---|
| $R^{23}$ = | CH(Me)CO₂Et | CH(Me)CO₂Pr-i | C(Me)₂CO₂Et | CH₂CO₂Et |

| | 5 | 6 | 7 | 8 | 9 |
|---|---|---|---|---|---|
| $R^{23}$ = | CH₂CH₂CO₂Et | CH(CO₂Et)CO₂Et | CH(Me)CO₃Me | cyclopropyl-CO₂Et | CH(Pr-i)CO₂Et |

Variable Ar is selected from six different substituents assigned the following numbers:

The numbers designated in Table 6 also represented preferred prodrugs of compounds of formula X as shown in the following formula (xxi):

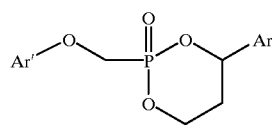
(xxi)

In the above formula (xxi), Ar stands for aryl including heteroaryl, and is substituted by $R^{25}$. The preferred compounds of formula (xxi) are listed in Table 6 by designated numbers assigned to Ar'.$R^2$, and Ar according to the follow TABLE Ar

| | 1 | 2 | 3 | 4 | 5 | 6 |
|---|---|---|---|---|---|---|
| Ar = | 2-Me-phenyl-$R^{25}$ | 3-Me-phenyl-$R^{25}$ | 4-Me-phenyl-$R^{25}$ | pyridyl-Me-$R^{25}$ | pyridyl-Me-$R^{25}$ | pyridyl-Me-$R^{25}$ | ing convention: Ar', $R^{25}$, Ar. For each moiety, structures are assigned to a number in the following tables for A', $R^{25}$, and Ar.

Variable Ar' is selected from seven different substituents assigned the following numbers:

TABLE Ar'

| | 1 | 2 | 3 | 4 |
|---|---|---|---|---|
| Ar' | 4-Me, 6-Br benzothiazol-2-amine | 4-Me, 7-Me benzothiazol-2-amine | 4-Me, 6-Br, 7-Me benzothiazol-2-amine | 4-Me, 7-Et, 6-SCN benzothiazol-2-amine |

| | 5 | 6 | 7 |
|---|---|---|---|
| Ar' | 4-Me, 7-Me, 6-Cl benzothiazol-2-amine | 4-Me, 7-OMe, 6-SCN benzothiazol-2-amine | 4-Me naphtho[2,1-d]thiazol-2-amine |

Variable $R^{25}$ is selected from nine different substituents assigned the following numbers:

TABLE $R^{25}$

| | 1 | 2 | 3 | 4 | 5 | 6 | 7 | 8 | 9 |
|---|---|---|---|---|---|---|---|---|---|
| $R^{25}$ = | F | Cl | Br | NHAc | $CF_3$ | Me | Et | OMe | CN |

Variable Ar is selected from six different substituents assigned the following numbers:

TABLE Ar

| | 1 | 2 | 3 | 4 | 5 | 6 |
|---|---|---|---|---|---|---|
| Ar = | 2-Me, $R^{25}$-phenyl | 3-Me, $R^{25}$-phenyl | 4-Me, $R^{25}$-phenyl | 5-Me, 2-$R^{25}$-pyridyl | $R^{25}$, Me-pyridyl | Me, $R^{25}$-pyridyl |

| | 1 | 2 | 3 |
|---|---|---|---|
| P' = | methyl 4-phenyl-1,3,2-dioxaphosphinane 2-oxide | methyl 4-(pyridin-4-yl)-1,3,2-dioxaphosphinane 2-oxide | ethyl 2-(methyl(phenoxy)phosphorylamino)-2-methylpropanoate |

TABLE Ar-continued

| 4 | 5 | 6 | 7 |
|---|---|---|---|

P' = (structures shown)

The numbers designated in Table 6 also represent preferred prodrugs of compounds of formula X as shown in the following formula (xxii):

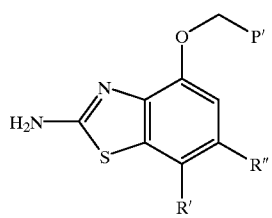

(xxii)

The preferred compounds of formula (xxii) are listed in Table 6 by designated numbers assigned to P', R' and R" according to the following convention, P'.R'.R". For each moiety, structures are assigned to a number in the following tables for P', R' and R".

Variable P' is divided into two Groups each listing seven different substituents. The Group 1 substituents for variable P' are assigned the following numbers: Table P'.

The Group 2 substituents for variable P' are assigned the following numbers:

Variable R' is selected from nine different substituents assigned the following numbers:

TABLE R'

| 1 | 2 | 3 | 4 | 5 | 6 | 7 | 8 | 9 |
|---|---|---|---|---|---|---|---|---|
| R' = H | Me | Et | OMe | Br | Cl | CO$_2$Et | Pr-i | Pr-c |

Variable R" is selected from six different substituents assigned the following numbers:

TABLE R"

| 1 | 2 | 3 | 4 | 5 | 6 |
|---|---|---|---|---|---|
| R" = H | Br | Cl | SCN | Me | OMe |

SECTION 1

Synthesis of Compounds of Formula I

Synthesis of compounds encompassed by the present invention typically includes some or all of the following general steps: (1) preparation of a phosphonate prodrug; (2) deprotection of a phosphonate ester; (3) modification of a

| 1 | 2 | 3 | 4 |
|---|---|---|---|

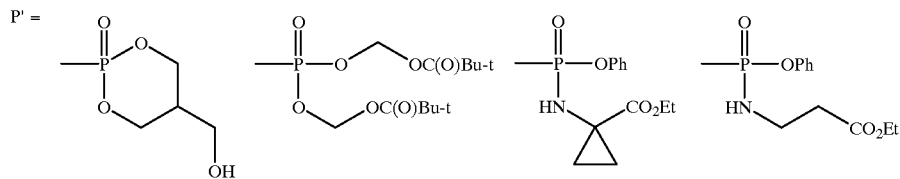

| 5 | 6 | 7 |
|---|---|---|

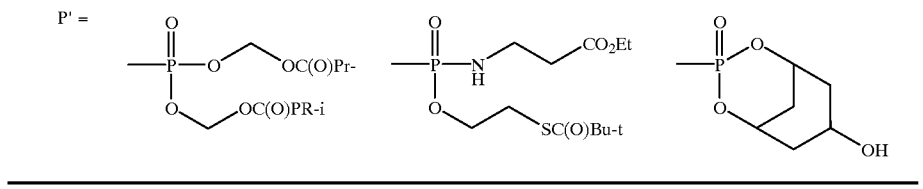

heterocycle; (4) coupling of a heterocycle with a phosphonate component; (5) construction of a heterocycle; (6) ring closure to construct a heterocycle with a phosphonate moiety present and (7) preparation of useful intermediates. These steps are illustrated in the following scheme for compounds of formula I wherein $R^5$ is a 5-membered heteroaromatic ring. Compounds of formula I wherein $R^5$ is a 6-member heteroaromatic ring or other heteroaromatic rings are prepared in an analogous manner. The procedures are also generally applicable to compounds of formula I where both Y groups are not —O.

(1) Preparation of a Phosphonate Prodrug

Prodrugs can be introduced at different stages of the synthesis. Most often these prodrugs are made from the phosphonic acids of formula 2, because of their liability. Advantageously, these prodrugs can be introduced at an earlier stage, provided that it can withstand the reaction conditions of the subsequent steps.

Compounds of formula 2, can be alkylated with electrophiles (such as alkyl halides, alkyl sulfonates, etc) under nucleophilic substitution reaction conditions to give phosphonate esters. For example, compounds of formula I,

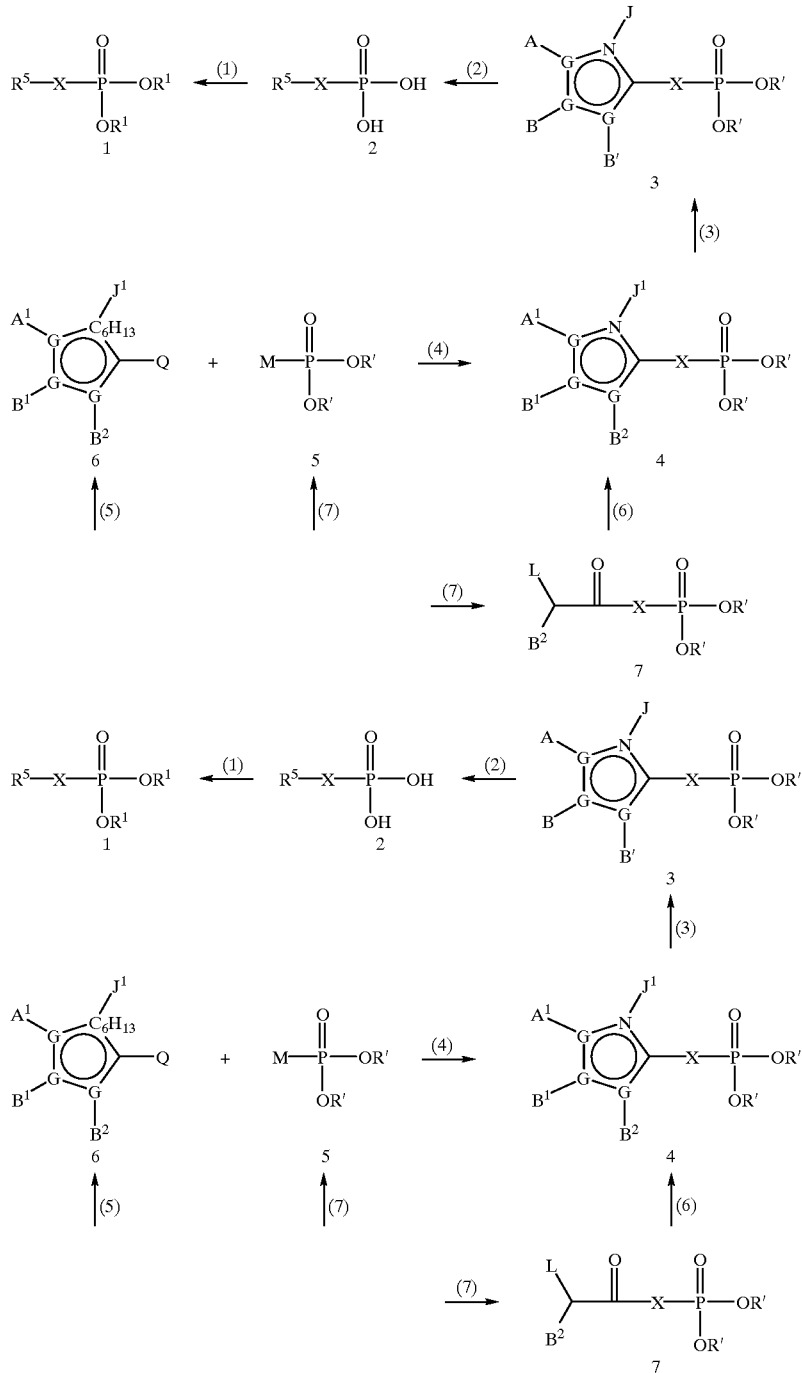

wherein $R^1$ is an acyloxyalkyl group can be synthesized through direct alkylation of compounds of formula 2 with an appropriate acyloxyalkyl halide (e.g. Cl, Br, I; Elhaddadi, et al *Phosphorus Sulfur*, 1990, 54(1–4): 143; Hoffmann, *Synthesis*, 1988, 62) in the presence of a suitable base (e.g. N,N'-dicyclohexyl-4-morpholinecarboxamidine, triethylamine, Hunig's base, etc.) in suitable solvents such as 1,1-dimethyl formamide ("DMF") (Starrett, et al, *J. Med. Chem.*, 1994, 1857). The carboxylate component of these acyloxyalkyl halides includes but is not limited to acetate, propionate, isobutyrate, pivalate, benzoate, and other carboxylates. When appropriate, further modification are envisioned after the formation of these acyloxyalkyl phosphonate esters such as reduction of a nitro group. For example, compounds of formula 3 wherein A is a $NO_2$ group can be converted to compounds of formula 3 wherein A is an $H_2N$— group under suitable reduction conditions (Dickson, et al, *J. Med. Chem.*, 1996, 39: 661; Iyer, et al, *Tetrahedron Lett.*, 1989, 30: 7141; Srivastva, et al, *Bioorg. Chem.*, 1984, 12: 118). These methods can be extended to the synthesis of other types of prodrugs, such as compounds of formula I where $R^1$ is a 3-phthalidyl, a 2-oxo-4,5-didehydro-1,3-dioxolanemethyl, or a 2-oxotetrahydrofuran-5-yl group (Biller et al., U.S. Pat. No. 5,157,027; Serafinowska et al., *J. Med. Chem.* 1995,38: 1372; Starrett et al., *J. Med. Chem.* 1994, 37: 1857; Martin et al., *J. Pharm. Sci.* 1987, 76: 180; Alexander et al., *Collect. Czech. Chem. Commun*, 1994, 59: 1853; EPO 0632048A1). N,N-Dimethylformamide dialkyl acetals can also be used to alkylate phosphonic acids (Alexander, P., et al *Collect. Czech. Chem. Commun.*, 1994, 59, 1853). Compounds of formula I wherein R1 is a cyclic carbonate, a lactone or a phthalidyl group can also be synthesized via direct alkylation of the free phosphonic acid with appropriate halides in the presence of a suitable base (e.g. NaH or diisopropylethylamine, Biller et al., U.S. Pat. No. 5,157,027; Serafinowska et al., J. Med. Chem. 1995, 38: 1372; Starrett et al., J. Med. Chem. 1994, 37: 1857; Martin et al., J. Pharm. Sci. 1987, 76: 180; Alexander et al., Collect. Czech. Chem. Commun, 1994, 59: 1853;EPO 0632048A1).

Alternatively, these phosphonate prodrugs can also be synthesized by reactions of the corresponding dichlorophosphonates with an alcohol (Alexander et al, *Collect. Czech. Chem. Commun.*, 1994, 59: 1853). For example, reactions of a dichlorophosphonate with substituted phenols and aralkyl alcohols in the presence of base (e.g. pyridine, triethylamine, etc) yield compounds of formula I where $R^1$ is an aryl group (Khamnei et al., *J. Med. Chem.*, 1996, 39: 4109; Serafinowska et al., *J. Med. Chem.*, 1995, 38: 1372; De Lombaert et al., *J. Med. Chem.*, 1994, 37: 498) or an arylalkyl group (Mitchell et al., *J. Chem. Soc. Perkin Trans.* 1, 1992, 38: 2345). The disulfide-containing prodrugs (Puech et al., *Antiviral Res.*, 1993, 22: 155) can also be prepared from a dichlorophosphonate and 2-hydroxyethyl disulfide under standard conditions. Dichlorophosphonates are also useful for the preparation of various phosphoramides as prodrugs. For example, treatment of a dichlorophosphonate with ammonia gives both a monophosphonamide and a diphosphonamide; treatment of a dichlorophosphonate with a 1-amino-3-propanol gives a cyclic 1,3-propylphosphonamide; treatment of a chlorophosphonate monophenyl ester with an aminoacid ester in the presence of a suitable base gives a substituted monophenyl monophosphonamidate.

Such reactive dichlorophosphonates can be generated from the corresponding phosphonic acids with a chlorinating agent (e.g. thionyl chloride: Starrett et al., *J. Med. Chem.*, 1994, 1857, oxalyl chloride: Stowell et al., *Tetrahedron Lett.*, 1990, 31: 3261, and phosphorus pentachloride: Quast et al., *Synthesis*, 1974, 490). Alternatively, a dichlorophosphonate can also be generated from its corresponding disilyl phosphonate esters (Bhongle et al., *Synth. Commun.*, 1987, 17: 1071) or dialkyl phosphonate esters (Still et al., *Tetrahedron Lett.*, 1983, 24: 4405; Patois et al., *Bull. Soc. Chim. Fr.*, 1993, 130: 485).

Chlorophosphonate monophenyl esters can be prepared from monophenyl phosphonate esters using the above described methods for dichlorophosphonate synthesis, and monophenyl phosphonate esters are easily made from their corresponding diphenyl phosphonate esters via base (e.g. sodium hydroxide) hydrolysis. Alternatively, treatment of a dichlorophosphonate with one equivalent of a phenol following by addition of an amine (e.g. alanine ethyl ester) in the presence of a suitable base (e.g. pyridine or triethylamine) will also give a monophenyl monophosphonamidate. When substituted phenols or other aryl-OH are used in place of phenol, then these methods are useful for the synthesis of various monoaryl monophosphonamidates as prodrugs for compounds of formula I.

Furthermore, these prodrugs can be prepared using Mitsunobu reactions (Mitsunobu, *Synthesis*, 1981, 1; Campbell, *J. Org. Chem.*, 1992, 52: 6331), and other coupling reactions (e.g. using carbodiimides: Alexander et al., *Collect. Czech. Chem. Commun.*, 1994, 59: 1853; Casara et al., *Bioorg. Med. Chem. Lett.*, 1992, 2: 145; Ohashi et al., *Tetrahedron Lett.*, 1988, 29: 1189, and benzotriazolyloxytris-(dimethylamino) phosphonium salts: Campagne et al., *Tetrahedron Lett.*, 1993, 34: 6743).

$R^1$ can also be introduced at an early stage of the synthesis provided that it is compatible with the subsequent reaction steps. For example, compounds of formula I where $R^1$ is an aryl group can be prepared by metalation of a 2-furanyl heterocycle (e.g. using LDA) followed by trapping the anion with a diaryl chlorophosphate.

It is envisioned that compounds of formula I can be mixed phosphonate esters (e.g. phenyl and benzyl esters, or phenyl and acyloxyalkyl esters) including the chemically combined mixed esters such as the phenyl and benzyl combined prodrugs reported by Meier, et al. *Bioorg. Med. Chem. Lett.*, 1997, 7: 99.

Cyclic propyl phosphonate esters can be synthesized by either reactions of the corresponding dichlorophosphonate with a substituted 1,3-propanediol or coupling reactions using suitable coupling reagents (e.g. DCC, EDCI, pyBOP: Hoffinan, *Synthesis*, 1988, 62). Some of these methods useful for the preparation of 1,3-propanediols are discussed below.

Synthesis of a 1,3-propanediol

Various methods can be used to prepare 1,3-propanediols such as (i) 1-substituted, (ii) 2-substituted, (iii) 1,2- or 1,3-annulated 1,3-propanediols. Substituents on the prodrug moiety of compounds of formula I (i.e. substituents on the 1,3-propanediol moiety) can be introduced or modified either during the synthesis of these diols or after the synthesis of compounds of formula 2.

(i) 1-Substituted 1,3-propanediols.

1,3-Propanediols useful in the synthesis of compounds in the present invention can be prepared using various synthetic methods. Additions of a aryl Grignard to a 1-hydroxy-propan-3-al give 1-aryl-substituted 1,3-propanediols (path a). This method is suitable for the conversion of various aryl halides to 1-arylsubstituted-1,3-propanediols (Coppi et. al., *J. Org. Chem.*, 1988, 53, 911). Conversions of aryl halides to 1-substituted 1,3-propanediols can also be achieved using Heck reactions (e.g. couplings with a 1,3-diox-4-ene) followed by reductions and subsequent hydrolysis reactions (Sakamoto et. al., *Tetrahedron Lett.*, 1992, 33, 6845). Various aromatic aldehydes can also be converted to 1-substituted-1,3-propanediols using alkenyl Grignard addition reactions followed by hydroboration-oxidation reactions (path b).

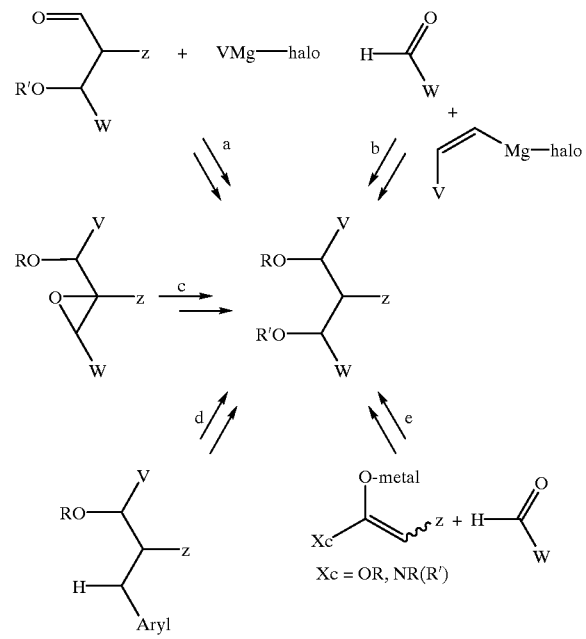

Aldol reactions between an enolate (e.g. lithium, boron, tin enolates) of a carboxylic acid derivative (e.g. tert-butyl acetate) and an aldehyde, and these reactions (e.g. the Evans's aldol reactions) are specially useful for the asymmetric synthesis of chiral 1,3-propanediols. For example, reaction of a metal enolate of t-butyl acetate with an aromatic aldehyde followed by reduction of the ester (path e) gives a 1,3-propanediol (Turner., *J. Org. Chem.*, 1990, 55 4744). Alternatively, epoxidation of cinnamyl alcohols using known methods (e.g. Sharpless epoxidations and other asymmetric epoxidation reactions) followed by reduction reactions (e.g. using Red-Al) give various 1,3-propanediols (path c). Enantiomerically pure 1,3-propanediols can be obtained via asymmetric reduction reactions (e.g. chiral borane reductions) of 3-hydroxy-ketones (Ramachandran et. al., *Tetrahedron Lett.*, 1997, 38 761). Alternatively, resolution of racemic 1,3-propanediols using various methods (e.g. enzymatic or chemical methods) can also give enantiomerically pure 1,3-propanediol. Propan-3-ols with a 1-heteroaryl substituent (e.g. a pyridyl, a quinolinyl or an isoquinolinyl) can be oxygenated to give 1-substituted 1,3-propanediols using N-oxide formation reactions followed by a rearrangement reaction in acetic anhydride conditions (path d) (Yamamoto et. al., *Tetrahedron*, 1981, 37, 1871).

(ii) 2-Substituted 1,3-propanediols:

A variety of 2-substituted 1,3-propanediols useful for the synthesis of compounds of formula I can be prepared from various other 1,3-propanediols (e.g. 2-(hydroxymethyl)-1,3-propanediols) using conventional chemistry (Larock, *Comprehensive Organic Transformations*, VCH, New York, 1989).

For example, reductions of a trialkoxycarbonylmethane under known conditions give a triol via complete reduction (path a) or a bis(hydroxymethyl)acetic acid via selective hydrolysis of one of the ester groups followed by reduction of the remaining two other ester groups. Nitrotriols are also known to give triols via reductive elimination (path b) (Latour et. al., *Synthesis*, 1987, 8, 742). Furthermore, a 2-(hydroxymethyl)-1,3-propanediol can be converted to a mono acylated derivative (e.g. acetyl, methoxycarbonyl) using an acyl chloride or an alkyl chloroformate (e.g. acetyl chloride or methyl chloroformate) (path d) using known chemistry (Greene et al., *Protective Groups In Organic Synthesis*; Wiley, New York, 1990). Other functional group manipulations can also be used to prepare 1,3-propanediols such as oxidation of one the hydroxylmethyl groups in a 2-(hydroxymethyl)-1,3-propanediol to an aldehyde followed by addition reactions with an aryl Grignard (path c). Aldehydes can also be converted to alkyl amines via reductive amination reactions (path e).

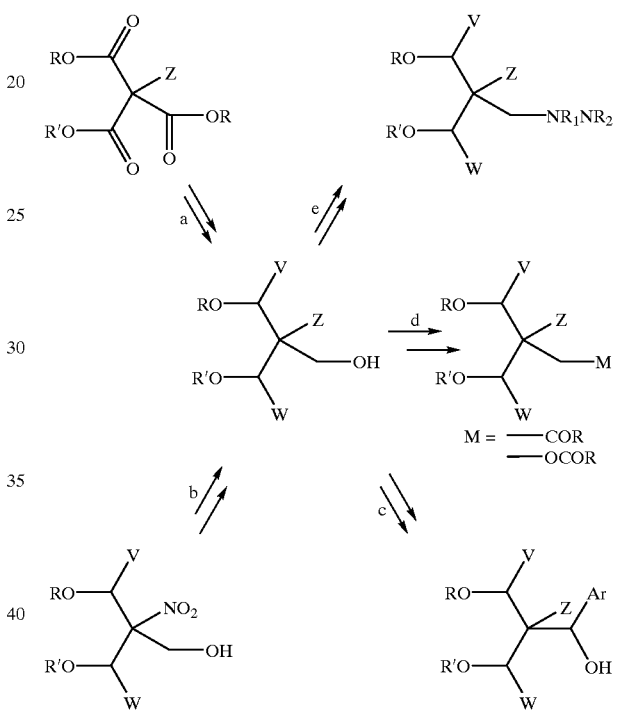

(iii) Annulated 1,3-propane Diols:

Compounds of formula I wherein V and Z or V and W are connected by four carbons to form a ring can be prepared from a 1,3-cyclohexanediol. For example, cis, cis-1,3,5-cyclohexanetriol can be modified (as described in section (ii)) to give various other 1,3,5-cyclohexanetriols which are useful for the preparations of compounds of formula I wherein $R^1$ and $R^1$ together are

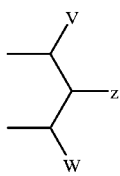

wherein together V and W are connected via 3 atoms to form a cyclic group containing 6 carbon atoms substituted with a hydroxy group. It is envisioned that these modifications can be performed either before or after formation of a cyclic phosphonate 1,3-propanediol ester. Various 1,3- cyclohexanediols can also be prepared using Diels-Alder reactions (e.g. using a pyrone as the diene: Posner et. al., *Tetrahedron Lett.*, 1991, 32, 5295). 2-Hydroxymethylcyclohexanols and 2-hydroxymethylcyclopentanols are useful for the preparations of compounds of formula I wherein $R^1$ and $R^1$ together are

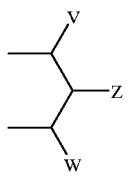

wherein together V and Z are connected via 2 or 3 atoms to form a cyclic group containing 5 or 6 carbon atoms. 1,3-Cyclohexanediol derivatives are also prepared via other cycloaddition reaction methodologies. For example, cycloadducts from the cycloadditon reactions of a nitrile oxide and an olefin can be converted to a 2-ketoethanol derivative which can be further converted to a 1,3-propanediol (including1,3-cyclohexanediol, 2-hydroxymethylcyclohexanol and 2-hydroxymethylcyclopentanol) using known chemistry (Curran, et. al., *J. Am. Chem. Soc.*, 1985, 107, 6023). Alternatively, precursors to 1,3-cyclohexanediol can be made from quinic acid (Rao, et. al., *Tetrahedron Lett.*, 1991, 32, 547.)

2) Deprotection of a Phosphonate Ester

Compounds of formula I wherein $R^1$ is H may be prepared from phosphonate esters using known phosphate and phosphonate ester cleavage conditions. Silyl halides are generally used to cleave various phosphonate esters, and subsequent mild hydrolysis of the resulting silyl phosphonate esters give the desired phosphonic acids. When required, acid scavengers (e.g. 1,1,1,3,3,3-hexamethyldisilazane, 2,6-lutidine, etc.) can be used for the synthesis of acid labile compounds. Such silyl halides include chlorotrimethylsilane (Rabinowitz, *J. Org. Chem.*, 1963, 28: 2975), and bromotrimethylsilane (McKenna, et al, *Tetrahedron Lett.*, 1977, 155), and iodotrimethylsilane (Blackburn, et al, *J. Chem. Soc., Chem. Commun.*, 1978, 870). Alternately, phosphonate esters can be cleaved under strong acidic conditions (e.g. HBr or HCl: Moffatt, et al, U.S. Pat. No. 3,524,846, 1970). These esters can also be cleaved via dichlorophosphonates, prepared by treating the esters with halogenating agents (e.g. phosphorus pentachloride, thionyl chloride, $BBr_3$: Pelchowicz et al, *J. Chem. Soc.*, 1961, 238) followed by aqueous hydrolysis to give phosphonic acids. Aryl and benzyl phosphonate esters can be cleaved under hydrogenolysis conditions (Lejczak, et al, *Synthesis*, 1982, 412; Elliott, et al, *J. Med. Chem.*, 1985, 28: 1208; Baddiley, et al, *Nature*, 1953, 171: 76) or metal reduction conditions (Shafer, et al, *J. Am. Chem. Soc.*, 1977, 99: 5118). Electrochemical (Shono, et al, *J. Org. Chem.*, 1979, 44: 4508) and pyrolysis (Gupta, et al, *Synth. Commun.*, 1980, 10: 299) conditions have also been used to cleave various phosphonate esters.

(3) Modification of an Existing Heterocycle

Syntheses of the heterocycles encompassed in the disclosed compounds have been well studied and described in numerous reviews (see section 4). Although it is advantageous to have the desired substituents present in these heterocycles before synthesis of compounds of formula 4, in some cases, the desired substituents are not compatible with subsequent reactions, and therefore modifications of an existing heterocycle are required late in the synthetic scheme using conventional chemistry (Larock, *Comprehensive organic transformations*, VCH, New York, 1989; Trost, *Comprehensive organic synthesis*; Pergamon press, New York, 1991). For example, compounds of formula I wherein A, A", or B is a halo or a cyano group can be prepared from the corresponding amine group by conversion to the diazonium group and reaction with various copper (I) salts (e.g. CuI, CuBr, CuCl, CuCN). Halogens can also be introduced by direct halogenations of various heterocycles. For example, 5-unsubstituted-2-aminothiazoles can be converted to 2-amino-5-halothiazoles using various reagents (e.g. NIS, NBS, NCS). Heteroaryl halides are also useful intermediates and are often readily converted to other substituents (such as A, A", B, B", C", D, D", E and E") via transition metal assisted coupling reactions such as Suzuki, Heck or Stille reactions (Farina et al, *Organic Reactions*, Vol. 50; Wiley, New York, 1997; Mitchell, *Synthesis*, 1992, 808; Suzuki, *Pure App. Chem.*, 1991, 63, 419; Heck *Palladium Reagents in Organic Synthesis*; Academic Press: San Diego, 1985). Compounds of formula I wherein A is a carbamoyl group can be made from their corresponding alkyl carboxylate esters via aminolysis with various amines, and conventional functional group modifications of the alkyl carboxylate esters are useful for syntheses of compounds of formula I wherein A is a —$CH_2OH$ group or a —$CH_2$-halo group. Substitution reactions of haloheterocycles (e.g. 2-bromothiazole, 5-bromothiazole) with various nucleophiles (e.g. HSMe, HOMe, etc.) represents still another method for introducing substituents such as A, A", B and B". For example, substitution of a 2-chlorothiazole with methanethiol gives the corresponding 2-methylthiothiazole.

It is envisioned that when necessary alkylation of nitrogen atoms in the heterocycles (e.g. imidazoles, 1,2,4-triazoles and 1,2,3,4-tetrazoles) can be readily performed using for example standard alkylation reactions (with an alkyl halide, an aralkyl halide, an alkyl sulfonate or an aralkyl sulfonate), or Mitsunobu reactions (with an alcohol).

(4) Coupling of a Heterocycle with a Phosphonate Component

When feasible compounds disclosed in the present invention are advantageously prepared via a convergent synthetic route entailing the coupling of a heterocycle with a phosphonate diester component.

Transition metal catalyzed coupling reactions such as Stille or Suzuki reactions are particularly suited for the synthesis of compounds of formula I. Coupling reactions between a heteroaryl halide or triflate (e.g. 2-bromopyridine) and a M—$PO_3R^1$ wherein M is a 2-(5-tributylstannyl)furanyl or a 2-(5-boronyl)furanyl group under palladium catalyzed reaction conditions (Farina et al, *Organic Reactions*, Vol. 50; Wiley, New York, 1997; Mitchell, *Synthesis*, 1992, 808; Suzuki, *Pure App. Chem.*, 1991, 63, 419) yield compounds of formula I wherein X is a furan-2, 5-diyl group. It is envisioned that the nature of the coupling partners for these reactions can also be reversed (e.g. coupling of trialkylstannyl or boronyl heterocycles with a halo-X—P(O)(O-alkyl)$_2$). Other coupling reactions between organostannes and an alkenyl halide or an alkenyl triflate are also reported which may be used to prepared compounds of formula I wherein X is an alkenyl group. The Heck reaction may be used to prepare compounds of formula I wherein X is an alkynyl group (Heck *Palladium Reagents in Organic Synthesis*; Academic Press: San Diego, 1985). These reactions are particularly suited for syntheses of various heteroaromatics as $R^5$ for compounds of formula I given the availability of numerous halogenated heterocycles, and these reactions are particularly suitable for parallel synthesis (e.g. combinatorial synthesis on solid phase(Bunin, B. A., *The Combinatorial Index*,; Academic press: San Diego, 1998) or in solution phase (Flynn, D. L. et al., *Curr. Op. Drug. Disc. Dev.*, 1998, 1, 1367)) to generate large combinatorial libraries. For example, ethyl 5-iodo-2-furanylphosphonate can be coupled to Wang's resin under suitable coupling reaction conditions. The resin-coupled 5-iodo-2-[5-(O-ethyl-O-Wang's resin)phosphono]furan can then be subjected to transition metal catalyzed Suzuki and Stille reactions (as described above) with organoboranes and organotins in a parallel manner to give libraries of compounds of formula 3 wherein X is furan-2,5-diyl.

Substitution reactions are useful for the coupling of a heterocycle with a phosphonate diester component. For example, cyanuric chloride can be substituted with dialkyl mercaptoalkylphosphonates or dialkyl aminoalkylphosphonates to give compounds of formula I wherein $R^5$ is a 1,3,5-triazine, X is an alkylthio or an alkylamino group. Alkylation reactions are also used for the coupling of a heterocycle with a phosphonate diester component. For example, a heteroaromatic thiol (e.g. a 1,3,4-thiadiazole-2-thiol) can be alkylated with a dialkyl methylphosphonate derivative (e.g. $ICH_2P(O)(OEt)_2$, $TsOCH_2P(O)(OEt)_2$, $TfOCH_2P(O)(OEt)_2$) to lead to compounds of formula I wherein X is an alkylthio group. In another aspect, alkylation reactions of a heteroaromatic carboxylic acid (e.g. a thiazole-4-carboxylic acid) with a dialkyl methylphosphonate derivative (e.g. $ICH_2P(O)(OEt)_2$, $TsOCH_2P(O)(OEt)_2$, $TfOCH_2P(O)(OEt)_2$) lead to compounds of formula I wherein X is an alkoxycarbonyl group, while alkylation reactions of a heteroaromatic thiocarboxylic acid (e.g. a thiazole-4-thiocarboxylic acid) with a dialkyl methylphosphonate derivative (e.g. $ICH_2P(O)(OEt)_2$, $TsOCH_2P(O)(OEt)_2$, $TfOCH_2P(O)(OEt)_2$) lead to compounds of formula I wherein X is an alkylthiocarbonyl group. Substitutions of haloalkyl heterocycles (e.g. 4-haloalkylthiazole) with nucleophiles containing the phosphonate group (diethyl hydroxymethylphosphonate) are useful for the preparation of compounds of formula I wherein X is an alkoxyalkyl or an alkylthioalkyl group. For example, compounds of formula I where X is a —$CH_2OCH_2$— group can be prepared from 2-chloromethylpyridine or 4-chloromethylthiazole using dialkyl hydroxymethylphosphonates and a suitable base (e.g. sodium hydride). It is possible to reverse the nature of the nucleophiles and electrophiles for the substitution reactions, i.e. haloalkyl- and/or sulfonylalkylphosphonate esters can be substituted with heterocycles containing a nucleophile (e.g. a 2-hydroxyalkylpyridine, a 2-mercaptoalkylpyridine, or a 4-hydroxyalkyloxazole).

Known amide bond formation reactions (e.g. the acyl halide method, the mixed anhydride method, the carbodiimide method) can also be used to couple a heteroaromatic carboxylic acid with a phosphonate diester component leading to compounds of formula I wherein X is an alkylaminocarbonyl or an alkoxycarbonyl group. For example, couplings of a thiazole-4-carboxylic acid with a dialkyl aminoalkylphosphonate or a dialkyl hydroxyalkylphosphonate give compounds of formula I wherein $R^5$ is a thiazole, and X is an alkylaminocarbonyl or an alkoxycarbonyl group. Alternatively, the nature of the coupling partners can be reversed to give compounds of formula I wherein X is an alkylcarbonylamino group. For example, 2-aminothiazoles can be coupled with $(RO)_2P(O)$-alkyl-$CO_2H$ (e.g. diethylphosphonoacetic acid) under these reaction conditions to give compounds of formula I wherein $R^5$ is a thiazole and X is an alkylcarbonylamino group. These reactions are also useful for parallel synthesis of compound libraries through combinatorial chemistry on solid phase or in solution phase. For example, $HOCH_2P(O)(OEt)(O\text{-resin})$, $H_2NCH_2P(O)(OEt)(O\text{-resin})$ and $HOOCCH_2P(O)(OEt)(O\text{-resin})$ (prepared using known methods) can be coupled to various heterocycles using the above described reactions to give libraries of compounds of formula 3 wherein X is a —C(O)$OCH_2$—, or a —C(O)$NHCH_2$—, or a —NHC(O)$CH_2$—.

Rearrangement reactions can also be used to prepare compounds covered in the present invention. For example, the Curtius's rearrangement of a thiazole-4-carboxylic acid in the presence of a dialkyl hydroxyalkylphosphonate or a dialkyl aminoalkylphosphonate lead to compounds of formula I wherein X is an alkylaminocarbonylamino or an alkoxycarbonylamino group. These reactions can also be adopted for combinatorial synthesis of various libraries of compounds of formula 3. For example, Curtius's rearrangement reactions between a heterocyclic carboxylic acid and $HOCH_2P(O)(OEt)(O\text{-resin})$, or $H_2NCH_2P(O)(OEt)(O\text{-resin})$ can lead to libraries of compounds of formula I wherein X is a —NHC(O)$OCH_2$—, or a —NHC(O)$NHCH_2$—.

For compounds of formula I wherein X is an alkyl group, the phosphonate group can be introduced using other common phosphonate formation methods such as Michaelis-Arbuzov reaction (Bhattacharya et al., *Chem. Rev.*, 1981, 81: 415), Michaelis-Becker reaction (Blackburn et al., *J. Organomet. Chem.*, 1988, 348: 55), and addition reactions of phosphorus to electrophiles (such as aldehydes, ketones, acyl halides, imines and other carbonyl derivatives).

Phosphonate component can also be introduced via lithiation reactions. For example, lithiation of an 2-ethynylpyridine using a suitable base followed by trapping the thus generated anion with a dialkyl chlorophosphonate lead to compounds of formula I wherein R5 is a pyridyl, X is a 1-(2-phosphono)ethynyl group.

(5) Construction of a Heterocycle

Although existing heterocycles are useful for the synthesis of compounds of formula I, when required, heterocycles can also be constructed leading to compounds in the current invention, and in some cases may be preferred for the preparations of certain compounds. The construction of heterocycles have been well described in the literature using a variety of reaction conditions (Joule et al., *Heterocyclic Chemistry*; Chapman hall, London, 1995; Boger, Weinreb, *Hetero Diels-Alder Methodology In Organic Synthesis*; Academic press, San Diego, 1987; Padwa, 1,3-*Dipolar Cycloaddition Chemistry*; Wiley, New York, 1984; Katritzsky et al., *Comprehensive Heterocyclic Chemistry*; Pergamon press, Oxford; Newkome et al., *Contemporary Heterocyclic Chemistry: Syntheses, Reaction and Applications*; Wiley, New York, 1982; *Syntheses of Heterocyclic Compounds*; Consultants Bureau, New York). Some of the methods which are useful to prepare compounds in the present invention are given as examples in the following discussion.

(i) Construction of a Thiazole Ring System

Thiazoles useful for the present invention can be readily prepared using a variety of well described ring-forming reactions (Metzger, *Thiazole and its derivatives*, part 1 and part 2; Wiley & Sons, New York, 1979). Cyclization reactions of thioamides (e.g. thioacetamide, thiourea) and alpha-halocarbonyl compounds (such as alpha-haloketones, alpha-haloaldehydes) are particularly useful for the construction of a thiazole ring system. For example, cyclization reactions between thiourea and 5-diethylphosphono-2-[(-2-bromo-1-oxo)alkyl]furans are useful for the synthesis of compounds of formula I wherein $R^5$ is a thiazole, A is an amino group and X is a furan-2,5-diyl group; cyclization reaction between thiourea and a bromopyruvate alkyl ester give a 2-amino-4-alkoxycarbonylthiazole which is useful for the preparations of compounds of formula I wherein R5 is a thiazole and X is an alkylaminocarbonyl, an alkoxycarbonyl, an alkylaminocarbonylamino, or an alkoxyacarbonylamino group. Thioamides can be prepared using reactions reported in the literature (Trost, *Comprehensive organic synthesis*, Vol. 6,; Pergamon press, New York, 1991, pages 419–434) and alpha-halocarbonyl compounds are readily accessible via conventional reactions (Larock, *Comprehensive organic transformations*, VCH, New York, 1989). For example, amides can be converted to thioamides using Lawesson's reagent or $P_2S_5$, and ketones can be halogenated using various halogenating reagents (e.g. NBS, $CuBr_2$).

(ii) Construction of an Oxazole Ring System

Oxazoles useful for the present invention can be prepared using various methods in the literature (Turchi, *Oxazoles*; Wiley & Sons, New York, 1986). Reactions between isocyanides (e.g. tosylmethylisocyanide) and carbonyl compounds (e.g. aldehydes and acyl chlorides) can be used to construct oxazole ring systems (van Leusen et al, *Tetrahedron Lett.*, 1972, 2369). Alternatively, cyclization reactions of amides (e.g. urea, carboxamides) and alpha-halocarbonyl compounds are commonly used for the construction of an oxazole ring system. For example, the reactions of urea and 5-diethylphosphono-2-[(-2-bromo-1-oxo)alkyl]furans are useful for the synthesis of compounds of formula I wherein $R^5$ is an oxazole, A is an amino group and X is a furan-2,5-diyl group. Reactions between amines and imidates are also used to construct the oxazole ring system (Meyers et al, *J. Org. Chem.*, 1986, 51(26), 5111).

(iii) Construction of a Pyridine Ring System

Pyridines useful for the synthesis of compounds of formula I can be prepared using various known synthetic methods (Klingsberg, Pyridine and Its Derivatives; Interscience Publishers, New York, 1960–1984). 1,5-Dicarbonyl compounds or their equivalents can be reacted with ammonia or compounds which can generate ammonia to produce 1,4-dihydropyridines which are easily dehydrogenated to pyridines. When unsaturated 1,5-dicarbonyl compounds, or their equivalents (e.g. pyrylium ions) are used to react with ammonia, pyridines can be generated directly. 1,5-Dicarbonyl compounds or their equivalents can be prepared using conventional chemistry. For example, 1,5-diketones are accessible via a number of routes, such as Michael addition of an enolate to an enone (or precursor Mannich base (Gill et al, *J. Am. Chem. Soc.*, 1952, 74, 4923)), ozonolysis of a cyclopentene precursor, or reaction of silyl enol ethers with 3-methoxyaliylic alcohols (Duhamel et al, *Tetrahedron*, 1986, 42, 4777). When one of the carbonyl carbons is at the acid oxidation state, then this type of reaction produces 2-pyridones which can be readily converted to 2-halopyridines (Isler et al, *Helv. Chim. Acta*, 1955, 38, 1033) or 2-aminopyridines (Vorbruggen et al, *Chem. Ber.*, 1984, 117, 1523). Alternatively, a pyridine can be prepared from an aldehyde, a 1,3-dicarbonyl compound and ammonia via the classical Hantzsch synthesis (Bossart et al, *Angew. Chem. Int. Ed. Engl.*, 1981, 20, 762). Reactions of 1,3-dicarbonyl compounds (or their equivalents) with 3-amino-enones or 3-amino-nitriles have also been used to produce pyridines (such as the Guareschi synthesis, Mariella, *Org. Synth., Coll. Vol. IV*, 1963, 210). 1,3-Dicarbonyl compounds can be made via oxidation reactions on corresponding 1,3-diols or aldol reaction products (Mukaiyama, *Org, Reactions*, 1982, 28, 203). Cycloaddition reactions have also been used for the synthesis of pyridines, for example cycloaddition reactions between oxazoles and alkenes (Naito et al., *Chem. Pharm. Bull.*, 1965, 13, 869), and Diels-Alder reactions between 1,2,4-triazines and enamines (Boger et al., *J. Org. Chem.*, 1981, 46, 2179).

(iv) Construction of a Pyrimidine Ring System

Pyrimidine ring systems useful for the synthesis of compounds of formula I are readily available (Brown, The pyrimidines; Wiley, New York, 1994). One method for pyrimidine synthesis involves the coupling of a 1,3-dicarbonyl component (or its equivalent) with an N—C—N fragment. The selection of the N—C—N component—urea (Sherman et al., *Org. Synth., Coll. Vol. IV*, 1963, 247), amidine (Kenner et al., *J. Chem. Soc.*, 1943, 125) or guanidine (Burgess, *J. Org. Chem.*, 1956, 21, 97; VanAllan, *Org. Synth., Coil. Vol. IV*, 1963, 245)—governs the substitution at C-2 in the pyrimidine products. This method is particular useful for the synthesis of compounds of formula I with various A groups. In another method, pyrimidines can be prepared via cycloaddition reactions such as aza-Diels-Alder reactions between a 1,3,5-triazine and an enamine or an ynamine (Boger et al., *J. Org. Chem.*, 1992, 57, 4331 and references cited therein).

(v) Construction of an Imidazole Ring System

Imidazoles useful for the synthesis of compounds of formula I are readily prepared using a variety of different synthetic methodologies. Various cyclization reactions are generally used to synthesize imidazoles such as reactions between amidines and alpha-haloketones (Mallick et al, *J. Am. Chem. Soc.*, 1984, 106(23), 7252) or alpha-hydroxyketones (Shi et al, *Synthetic Comm.*, 1993, 23(18), 2623), reactions between urea and alpha-haloketones, and reactions between aldehydes and 1,2-dicarbonyl compounds in the presence of amines.

(vi) Construction of an Isoxazole Ring System

Isoxazoles useful for the synthesis of compounds of formula I are readily synthesized using various methodologies (such as cycloaddition reactions between nitrile oxides and alkynes or active methylene compounds, oximation of 1,3-dicarbonyl compounds or alpha, beta-acetylenic carbonyl compounds or alpha,beta-dihalocarbonyl compounds, etc.) can be used to synthesize an isoxazole ring system (Grunanger et al., *Isoxazoles*; Wiley & Sons, New York, 1991). For example, reactions between alkynes and 5-diethylphosphono-2-chlorooximidofuran in the presence of base (e.g. triethylamine, Hunig's base, pyridine) are useful for the synthesis of compounds of formula I wherein $R^5$ is an isoxazole and X is a furan-2,5-diyl group.

(vii) Construction of a Pyrazole Ring System

Pyrazoles useful for the synthesis of compounds of formula I are readily prepared using a variety of methods (Wiley, *Pyrazoles, Pyrazolines, Pyrazolidines, Indazoles, and Condensed Rings*; Interscience Publishers, New York, 1967) such as reactions between hydrazines and 1,3-dicarbonyl compounds or 1,3-dicarbonyl equivalents (e.g. one of the carbonyl group is masked as an enamine or ketal or acetal), and additions of hydrazines to acrylonitriles followed by cyclization reactions (Dorn et al, *Org. Synth.*, 1973, *Coll. Vol. V*, 39). Reaction of 2-(2-alkyl-3-N,N-dimethylamino)acryloyl-5-diethylphosphonofurans with hydrazines are useful for the synthesis of compounds of formula I wherein $R^5$ is a pyrazole, X is a furan-2,5-diyl group and B" is an alkyl group.

(viii) Construction of a 1,2,4-triazole Ring System 1,2,4-Triazoles useful for the synthesis of compounds of formula I are readily available via various methodologies (Montgomery, 1,2,4-Triazoles; Wiley, New York, 1981). For example, reactions between hydrazides and imidates or thioimidates (Sui et al, *Bioorg. Med. Chem. Lett.*, 1998, 8, 1929; Catarzi et al, *J. Med. Chem.*, 1995, 38(2), 2196), reactions between 1,3,5-triazine and hydrazines (Grundmann et al, *J. Org. Chem.*, 1956, 21, 1037), and reactions between aminoguanidine and carboxylic esters (Ried et al, *Chem. Ber.*, 1968, 101, 2117) are used to synthesize 1,2,4-triazoles.

(6) Ring Closure to Construct a Heterocycle with a Phosphonate

Compounds of formula 4 can also be prepared using a ring closure reaction to construct the heterocycle from precursors that contain the phosphonate component. For example, cyclization reactions between thiourea and 5-diethylphosphono-2-[(-2-bromo-1-oxo)alkyl]furans are useful for the synthesis of compounds of formula I wherein $R^5$ is a thiazole, A is an amino group and X is a furan-2,5-diyl group. Oxazoles of the present invention can also be prepared using a ring closure reaction. In this case, reactions of urea and 5-diethylphosphono-2-[(-2-bromo-1-oxo)alkyl] furans are useful for the synthesis of compounds of formula I wherein $R^5$ is an oxazole, A is an amino group and X is a furan-2,5-diyl group. Reactions between 5-diethylphosphono-2-furaldehyde, an alkyl amine, a 1,2-diketone and ammonium acetate are useful to synthesize compounds of formula I wherein $R^5$ is an imidazole and X is a furan-2,5-diyl group. These types of ring closure reactions can also be used for the synthesis of pyridines or pyrimidines useful in the present invention. For example, reaction of 5-diethylphosphono-2-[3-dimethylamino-2-alkyl)acryloyl]furans and cyanoacetamide in the presence of base gives 5-alkyl-3-cyano-6-[2-(5-diethylphosphono) furanyl]-2-pyridones (Jain et al., *Tetrahedron Lett.*, 1995, 36, 3307). Subsequent conversion of these 2-pyridones to the corresponding 2-halopyridines (see references cited in section 3 for the modifications of heterocycles) will lead to compounds of formula I wherein $R^5$ is a pyridine, A is a halo group, X is a furan-2,5-diyl group, and B is an alkyl group. Reactions of 5-diethylphosphono-2-[3-dimethylamino-2-alkyl)acryloyl]furans and amidines in the presence of base give 5-alkyl-6-[2-(5-diethylphosphono)-furanyl] pyrimidines which will lead to compounds of formula I wherein $R^5$ is a pyrimidine, X is a furan-2,5-diyl group and B is an alkyl group.

(7) Preparation of Various Precursors Useful for Cyclization Reactions

Intermediates required for the synthesis of compounds in the present invention are generally prepared using either an existing method in the literature or a modification of an existing method. Syntheses of some of the intermediates useful for the synthesis of compounds in the present invention are described herein.

Various aryl phosphonate dialkyl esters are particularly useful for the synthesis of compounds of formula I. For example, compounds of formula I wherein X is a furan-2,5-diyl group can be prepared from a variety of furanyl precursors. It is envisioned that synthesis of other precursors may follow some or all of these reaction steps, and some modifications of these reactions may be required for different precursors. 5-Dialkylphosphono-2-furancarbonyl compounds (e.g. 5-diethylphosphono-2-furaldehyde, 5-diethylphosphono-2-acetylfuran) are well suited for the synthesis of compounds of formula I wherein X is a furan-2,5-diyl group. These intermediates are prepared from furan or furan derivatives using conventional chemistry such as lithiation reactions, protection of carbonyl groups and deprotection of carbonyl groups. For example, lithiation of furan using known methods (Gschwend *Org. React.* 1979, 26: 1) followed by addition of phosphorylating agents (e.g. $ClPO_3R_2$) gives 2-dialkylphosphono-furans (e.g. 2-diethylphosphonofuran). This method can also be applied to a 2-substituted furan (e.g. 2-furoic acid) to give a 5-dialkylphosphono-2-substituted furan (e.g. 5-diethylphosphono-2-furoic acid). It is envisioned that other aryl phosphonate esters can also be prepared using this approach or a modification of this approach. Alternatively, other methods such as transition metal catalyzed reactions of aryl halides or triflates (Balthazar et al. *J. Org. Chem.*, 1980, 45: 5425; Petrakis et al. *J. Am. Chem. Soc.*, 1987, 109: 2831; Lu et al. *Synthesis*, 1987, 726) are used to prepare aryl phosphonates. Aryl phosphonate esters can also be prepared from aryl phosphates under anionic rearrangement conditions (Melvin, *Tetrahedron Lett.*, 1981, 22: 3375; Casteel et al. *Synthesis*, 1991, 691). N-Alkoxy aryl salts with alkali metal derivatives of dialkyl phosphonate provide another general synthesis for heteroaryl-2-phosphonate esters (Redmore *J. Org. Chem.*, 1970, 35: 4114).

A second lithiation step can be used to incorporate a second group on the aryl phosphonate dialkyl ester such as an aldehyde group, a trialkylstannyl or a halo group, although other methods known to generate these functionalities (e.g. aldehydes) can be envisioned as well (e.g. Vilsmeier-Hack reaction or Reimar-Teimann reaction for aldehyde synthesis). In the second lithiation step, the lithiated aromatic ring is treated with reagents that either directly generate the desired functional group (e.g. for an aldehyde using DMF, $HCO_2R$, etc.) or with reagents that lead to a group that is subsequently transformed into the desired functional group using known chemistry (e.g. alcohols, esters, nitriles, alkenes can be transformed into aldehydes). For example, lithiation of a 2-dialkylphosphonofuran (e.g. 2-diethylphosphonofuran) under normal conditions (e.g. LDA in THF) followed by trapping of the thus generated anion with an electrophile (e.g. tributyltin chloride or iodine) produces a 5-functionalized-2-dialkylphosphonofuran (e.g. 5-tributylstannyl-2-diethylphosphonofuran or 5-iodo-2-diethylphosphonofuran). It is also envisioned that the sequence of these reactions can be reversed, i.e. the aldehyde moiety can be incorporated first followed by the phosphorylation reaction. The order of the reaction will be dependent on reaction conditions and protecting groups. Prior to the phosphorylation, it is also envisioned that it may be advantageous to protect some of these functional groups using a number of well-known methods (e.g. protection of aldehydes as acetals, aminals; protection of ketones as ketals). The protected functional group is then unmasked after phosphorylation. (*Protective groups in Organic Synthesis*, Greene, T. W., 1991, Wiley, New York). For example, protection of 2-furaldehyde as 1,3-propanediol acetal followed by a lithiation step (using for example LDA) and trapping the anion with a dialkyl chlorophosphate (e.g. diethyl chlorophosphate), and subsequent deprotection of the acetal functionality under normal deprotection conditions produces the 5-dialkylphosphono-2-furaldehyde (e.g. 5-diethylphosphono-2-furaldehyde). Another example is the preparation of 5-keto-2-dialkylphosphonofurans which encompass the following steps: acylations of furan under Friedel-Crafts reaction conditions give 2-ketofuran, subsequent protection of the ketone as ketals (e.g. 1,3-propanediol cyclic ketal) followed by a lithiation step as described above gives the 5-dialkylphosphono-2-furanketone with the ketone being protected as a 1,3-propanediol cyclic ketal, and final deprotection of the ketal under, for example, acidic conditions gives 2-keto-5-dialkylphosphonofurans (e.g. 2-acetyl-5-diethylphosphonofuran). Alternatively, 2-ketofurans can be synthesized via a palladium catalyzed reaction between 2-trialkylstannylfurans (e.g. 2-tributylstannylfuran) and an acyl chloride (e.g. acetyl chloride, isobutyryl chloride). It is advantageous to have the phosphonate moiety present in the 2-trialkylstannylfurans (e.g. 2-tributylstannyl-5-diethylphosphonofuran). 2-Keto-5-dialkylphosphonofurans can also be prepared from a 5-dialkylphosphono-2-furoic acid (e.g. 5-diethylphosphono-2-furoic acid) by conversion of the acid to the corresponding acyl chloride and followed by additions of a Grignard reagent.

Some of the above described intermediates can also be used for the synthesis of other useful intermediates. For example, a 2-keto-5-dialkylphosphonofuran can be further converted to a 1,3-dicarbonyl derivative which is useful for the preparation of pyrazoles, pyridines or pyrimidines. Reaction of a 2-keto-5-dialkylphosphonofuran (e.g. 2-acetyl-5-diethylphosphonofuran) with a dialkylformamide dialkyl acetal (e.g. dimethylformamide dimethyl acetal) gives a 1,3-dicarbonyl equivalent as a 2-(3-dialkylamino-2-alkyl-acryloyl)-5-dialkylphosphonofuran (e.g. 2-(3-dimethylaminoacryloyl)-5-diethylphosphonofuran).

It is envisioned that the above described methods for the synthesis of furan derivatives can be either directly or with some modifications applied to syntheses of various other useful intermediates such as aryl phosphonate esters (e.g. thienyl phosphonate esters, phenyl phosphonate esters or pyridyl phosphonate esters).

It is conceivable that when applicable the above described synthetic methods can be adopted for parallel synthesis either on solid phase or in solution to provide rapid SAR (structure activity relationship) exploration of FBPase inhibitors encompassed in the current invention, provided method development for these reactions are successful.

SECTION 2

Synthesis of Compounds of Formula X

Synthesis of the compounds encompassed by the present invention typically includes some or all of the following general steps: (1) preparation of a phosphonate prodrug; (2) deprotection of a phosphonate ester; (3) construction of a heterocycle; (4) introduction of a phosphonate component; (5) synthesis of an aniline derivative. Step (1) and step (2) were discussed in section 1, and discussions of step (3), step (4) and step (5) are given below. These methods are also generally applicable to compounds of Formula X, where both Y groups are not —O—.

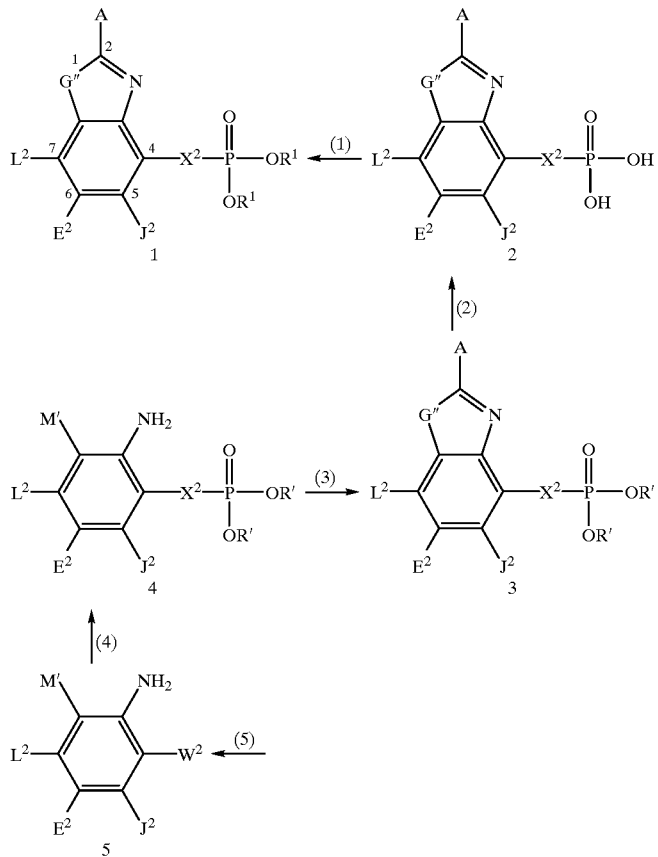

(3) Construction of a Heterocycle
  i. Benzothiazole ring system:
  Compounds of formula 3 wherein G"=S, i.e. benzothiazoles, can be prepared using various synthetic methods reported in the literature. Two of these methods are given as examples as discussed below. One method is the modification of commercially available benzothiazole derivatives to give the appropriate functionality on the benzothiazole ring. Another method is the annulation of various anilines (e.g. compounds of formula 4) to construct the thiazole portion of the benzothiazole ring. For example, compounds of formula 3 wherein G"=S, A=NH$_2$, L$^2$,E$^2$, J$^2$=H, X$^2$=CH$_2$O, and R'=Et can be prepared from the commercially available 4-methoxy-2-amino thiazole via a two-step sequence: conversion 4-methoxy-2-aminobenzothiazole to 4-hydroxy-2-aminobenzothiazole with reagents such as $BBr_3$ (Node, M.; et al *J. Org. Chem.* 45, 2243–2246, 1980) or $AlCl_3$ in presence of a thiol (e.g. EtSH) (McOmie, J. F. W.; et al. *Org. Synth., Collect. Vol. V*, 412, 1973) followed alkylation of the phenol group with diethylphosphonomethyl trifluoromethylsulfonate (Phillion, D. P.; et al. *Tetrahedron Lett.* 27, 1477–1484, 1986) in presence of a suitable base (e.g. NaH) in polar aprotic solvents (e.g. DMF) provide the required compound.

Several methods can be used to convert various anilines to benzothiazoles (Sprague, J. M.; Land, A. H. *Heterocycle. Compd.* 5, 506–13, 1957). For example, 2-aminobezothiazoles (formula 3 wherein $A=NH_2$) can be prepared by annulation of compounds of formula 4 wherein $W^2=H$, using various common methods. One method involves the treatment of a suitably substituted aniline with a mixture of KSCN and $CuSO_4$ in methanol to give a substituted 2-aminobezothiazole (Ismail, I. A.; Sharp, D. E; Chedekel, M. R. *J. Org. Chem.* 45, 2243–2246, 1980). Alternatively, a 2-aminobenzothiazole can also be prepared by the treatment of $Br_2$ in presence of KSCN in acetic acid (Patil, D. G.; Chedekel, M. R. *J. Org. Chem.* 49, 997–1000, 1984). This reaction can also be done in two step sequence. For example treatment of substituted phenylthioureas with $Br_2$ in $CHCl_3$ gives substituted 2-aminobenzothiazoles (Patil, D. G.; Chedekel, M. R. *J. Org. Chem.* 49, 997–1000, 1984). 2-Aminobenzothiazoles can also be made by condensation of ortho iodo anilines with thiourea in presence of Ni catalyst ($NiCl_2$ $(PPh_3)_2$) (Takagi, K.*Chem. Lett*. 265–266, 1986).

Benzothiazoles can undergo electrophilic aromatic substitution to give 6-substituted benzothiazoles (Sprague, J. M.; Land, A. H. *Heterocycle. Compd.* 5, 606–13, 1957). For example bromination of formula 3 wherein $G''=S$, $A=NH_2$, $L^2,E^2,J^2=H$, $X^2=CH_2O$ and $R'=Et$ with bromine in polar solvents such as AcOH gave compound of formula 3 wherein $E^2=Br$.

Furthermore, compounds of formula 3 wherein A is a halo, H, alkoxy, alkylthio or an alkyl can be prepared from the corresponding amino compound (Larock, *Comprehensive organic transformations*, VCH, New York, 1989; Trost, *Comprehensive organic synthesis*; Pergamon press, New York, 1991).

ii. Benzoxazoles:

Compounds of formula 3 wherein $G''=O$, i.e. benzoxazoles, can be prepared by the annulation of ortho aminophenols with suitable reagent (e.g. cyanogen halide ($A=NH_2$; Alt, K. O.; et al *J. Heterocyclic Chem.* 12, 775, 1975) or acetic acid ($A=CH_3$; Saa, J. M.; *J. Org. Chem.* 57, 589–594, 1992) or trialkyl orthoformate ($A=H$; *Org. Prep. Proced. Int.*, 22, 613, 1990)).

(4) Introduction of a Phosphonate Component:

Compounds of formula 4 (wherein $X^2=CH_2O$ and $R'=alkyl$) can made in different ways (e.g. using alkylation and nucleophilic substitution reactions). Typically, compounds of formula 5 wherein $M'=OH$ is treated with a suitable base (e.g. NaH) in polar aprotic solvent (e.g. DMF, DMSO) and the resulting phenoxide anion can be alkylated with a suitable electrophile preferably with a phosphonate component present (e.g. diethyl iodomethylphosphonate, diethyl trifluoromethylsulphonomethyl phosphonate, diethyl p-methyltoluenesulphonomethylphosphonate). The alkylation method can also be applied to the precursor compounds to compounds of formula 5 wherein a phenol moiety is present and it can be alkylated with a phosphonate containing component. Alternately, compounds of formula 4 can also be made from the nucleophilic substitution of the precursor compounds to compounds of formula 5 (wherein a halo group, preferably a fluoro or a chloro, is present ortho to a nitro group). For example, a compound of formula 4 (wherein $X^2=CH_2O$ and $R'=Et$) can be prepared from a 2-chloro-1-nitrobenzene derivative by treatment with $NaOCH_2P(O)(OEt)_2$ in DMF. Similarly, compounds of formula 4 where $X^2=$-alkyl-S— or -alkyl-N— can also be made.

(5) Synthesis of an Aniline Derivative:

Numerous synthetic methods have been reported for the synthesis of aniline derivatives, these methods can be applied to the synthesis of useful intermediates which can lead to compounds of formula X. For example, various alkenyl or aryl groups can be introduced on to a benzene ring via transition metal catalyzed reactions (Kasibhatla, S. R., et al. WO 98/39343 and the references cited in); anilines can be prepared from their corresponding nitro derivatives via reduction reactions (e.g. hydrogenation reactions in presence of 10% Pd/C, or reduction reactions using $SnCl_2$ in HCl (Patil, D. G.; Chedekel, M. R. *J. Org. Chem.* 49, 997–1000, 1984)).

SECTION 3

Synthesis of Substituted 1,3-hydroxyamines and 1,3-diamines

A large number of synthetic methods are available for the preparation of substituted 1,3-hydroxyamines and 1,3-diamines due to the ubiquitous nature of these functionalities in naturally occurring compounds. Following are some of these methods organised into: 1. synthesis of substituted 1,3-hydroxy amines; 2. synthesis of substituted 1,3-diamines and 3. Synthesis of chiral substituted 1,3-hydroxyamines and 1,3-diamines.

i. Synthesis of Substituted 1,3-hydroxy Amines:

1,3-Diols described in the earlier section can be converted selectively to either hydroxy amines or to corresponding diamines by converting hydroxy functionaliy to a leaving group and treating with anhydrous ammonia or required primary or secondary amines (Corey, et al., *Tetrahedron Lett.*, 1989, 30, 5207: Gao, et al., *J. Org. Chem.*, 1988, 53, 4081). A similar transformation may also be achieved directly from alcohols in Mitsunobu type of reaction conditions (Hughes, D. L., *Org. React.*, 1992, 42). A general synthetic procedure for 3-aryl-3-hydroxy-propan-1-amine type of prodrug moiety involves aldol type condensation of aryl esters with alkyl nitriles followed by reduction of resulting substituted benzoylacetonitrile (Shih et al., *Heterocycles*, 1986, 24, 1599). The procedure can also be adapted for formation 2-substitutedaminopropanols by using substituted alkylnitrile. In another approach, 3-aryl-3-amino-propan-1-ol type of prodrug groups are synthesized from aryl aldehydes by condensation of malonic acid in presence of ammonium acetate followed by reduction of resulting substituted aminoacids. Both these methods enable to introduce wide variety of substitution of aryl group (Shih, et al., *Heterocycles.*, 1978, 9, 1277). In an alternate approach, -substituted organolithium compounds of 1-amino-1-aryl ethyl dianion generated from styrene type of compounds undergo addition with carbonyl compounds to give variety of W, W' substitution by variation of the carbonyl componds (Barluenga, et al.,*J. Org. Chem.*, 1979, 44, 4798).

ii. Synthesis of Substituted 1,3-diamines:

Substituted 1,3-diamines are synthesized starting from variety of substrates. Arylglutaronitriles can be transformed to 1-substituted diamines by hydrolysis to amide and Hoffinan rearrangement conditions (Bertochio, et al., *Bull. Soc. Chim. Fr*, 1962, 1809). Whereas, malononitrile substitution will enable variety of Z substitution by electrophile introduction followed by hydride reduction to corresponding diamines. In another approach, cinnamaldehydes react with hydrazines or substituted hydrazines to give corresponding pyrazolines which upon catalytic hydrogenation result in substituted 1,3-diamines (Weinhardt, et al., *J. Med. Chem.*, 1985, 28, 694). High transdiastereoselectivity of 1,3-substitution is also attainable by aryl Grignard addition on to pyrazolines followed by reduction (Alexakis, et al., *J. Org. Chem.*, 1992, 576, 4563). 1-Aryl-1,3-diaminopropanes are also prepared by diborane reduction of 3-amino-3-arylacrylonitriles which intum are made from nitrile substituted aromatic compounds (Domow, et al., *Chem Ber.*, 1949, 82, 254). Reduction of 1,3-diimines obtained from corresponding 1,3-carbonyl compounds are another source of 1,3-diamine prodrug moiety which allows a wide variety of activating groups V and/or Z (Barluenga, et al., *J. Org. Chem.*, 1983, 48, 2255).

iii. Synthesis of Chiral Substituted 1,3-hydroxyamines and 1,3-diamines.

Enantiomerically pure 3-aryl-3-hydroxypropan-1-amines are synthesized by CBS enantioselective catalytic reaction of -chloropropiophenone followed by displacement of halo group to make secondary or primary amines as required (Corey, et al., Tetrahedron Lett., 1989, 30, 5207). Chiral 3-aryl-3-amino propan-1-ol type of prodrug moiety may be obtained by 1,3-dipolar addition of chirally pure olefin and substituted nitrone of arylaldehyde followed by reduction of resulting isoxazolidine (Koizumi, et al., *J. Org. Chem.*, 1982, 47, 4005). Chiral induction in 1,3-polar additions to form substituted isoxazolidines is also attained by chiral phosphine palladium complexes resulting in enatioselective formation of amino alcohols (Hori, et al., *J. Org. Chem.*, 1999, 64, 5017). Alternatively, optically pure 1-aryl substituted amino alcohols are obtained by selective ring opening of corresponding chiral epoxy alcohols with desired amines (Canas et al., *Tetrahedron Lett.*, 1991, 32, 6931).

Several methods are known for diastereoselective synthesis of 1,3-disubstituted aminoalcohols. For example, treatment of (E)-N-cinnamyltrichloroacetamide with hypochlorus acid results in trans-dihydrooxazine which is readily hydrolysed to erythro-chloro-hydroxy-phenylpropanamine in high diastereoselectivity (Commercon et al., *Tetrahedron Lett.*, 1990, 31, 3871). Diastereoselective formation of 1,3-aminoalcohols is also achieved by reductive amination of optically pure 3-hydroxy ketones (Haddad et al., *Tetrahedron Lett.*, 1997, 38, 5981). In an alternate approach, 3-aminoketones are transformed to 1,3-disubstituted aminoalcohols in high stereoslectivity by a selective hydride reduction (Barluenga et al., *J. Org. Chem.*, 1992, 57, 1219). All the above mentioned methods may also be applied to prepare corresponding V-Z or V-W annulated chiral aminoalcohols. Furthermore, such optically pure amino alcohols are also a source to obtain optically pure diamines by the procedures described earlier in the section.

Formulations

Compounds of the invention are administered orally in a total daily dose of about 0.01 mg/kg/dose to about 100 mg/kg/dose, preferably from about 0.1 mg/kg/dose to about 10 mg/kg/dose. The use of time-release preparations to control the rate of release of the active ingredient may be preferred. The dose may be administered in as many divided doses as is convenient. When other methods are used (e.g. intravenous administration), compounds are administered to the affected tissue at a rate from 0.05 to 10 mg/kg/hour, preferably from 0.1 to 1 mg/kg/hour. Such rates are easily maintained when these compounds are intravenously administered as discussed below.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Oral administration is generally preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions. It is preferred that the pharmaceutical composition be prepared which provides easily measurable amounts for administration. For example, an aqueous solution intended for intravenous infusion should contain from about 3 to 330 $\mu$g of the active ingredient per milliliter of solution in order that infusion of a suitable volume at a rate of about 30 mL/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of formulae I and X when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Preferred unit dosage formulations are those containing a daily dose or unit, daily sub-dose, or an appropriate fraction thereof, of a fructose 1,6-bisphosphatase inhibitor compound.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Utility

FBPase inhibitors may be used to treat diabetes mellitus, lower blood glucose levels, and inhibit gluconeogenesis.

FBPase inhibitors may also be used to treat excess glycogen storage diseases. Excessive hepatic glycogen stores are found in patients with some glycogen storage diseases. Since the indirect pathway contributes significantly to glycogen synthesis (Shulman, G. I. *Phys. Rev.* 72:1019–1035 (1992)), inhibition of the indirect pathway (gluconeogenesis flux) decreases glycogen overproduction.

FBPase inhibitors may also be used to treat or prevent diseases associated with increased insulin levels. Increased insulin levels are associated with an increased risk of cardiovascular complications and atherosclerosis (Folsom, et al., *Stroke*, 25:66–73 (1994); Howard, G. et al., *Circulation* 93:1809–1817 (1996)). FBPase inhibitors are expected to decrease postprandial glucose levels by enhancing hepatic glucose uptake. This effect is postulated to occur in individuals that are non-diabetic (or pre-diabetic, i.e. without elevated hepatic glucose output "hereinafter HGO" or fasting blood glucose levels). Increased hepatic glucose uptake will decrease insulin secretion and thereby decrease the risk of diseases or complications that arise from elevated insulin levels.

One aspect of the invention is directed to the use of new cyclic 1,3-propanyl ester methodology which results in efficient conversion of the cyclic phosph(oramid)ate. The phosphonate containing compounds by p450 enzymes found in large amounts in the liver and other tissues containing these specific enzymes.

In another aspect of the invention, this prodrug methodology can also be used to prolong the pharmacodynamic half-life because the cyclic phosph(oramid)ates of the invention can prevent the action of enzymes which degrade the parent drug.

In another aspect of the invention, this prodrug methodology can be used to achieve sustained delivery of the parent drug because various novel prodrugs are slowly oxidized in the liver at different rates.

The novel cyclic 1,3-propanylester methodology of the present invention may also be used to increase the distribution of a particular drug to the liver which contains abundant amounts of the p450 isozymes responsible for oxidizing the cylic 1,3-propanylester of the present invention so that the free phosph(oramid)ate is produced.

In another aspect of the invention, the cyclic phosph(oramid)ate prodrugs can increase the oral bioavailability of the drugs.

Theses aspects are described in greater detail below.

Evidence of the liver specificity can also be shown in vivo after both oral and i.v. administration of the prodrugs as described in Example E.

Drug is also detected in the liver following administration of drugs of formulae VI–VIII, shown below:

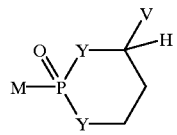
VI

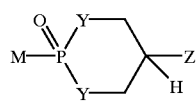
VII

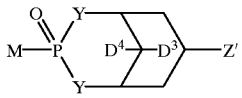
VIII

Prodrugs of formulae VI, VII, and VIII are particularly preferred.

The mechanism of cleavage could proceed by the following mechanisms. Further evidence for these mechanisms is indicated by analysis of the by-products of cleavage. Prodrugs of formula VI where Y is —O— generate phenyl vinyl ketone whereas prodrugs of formula VIII were shown to generate phenol (Example H).

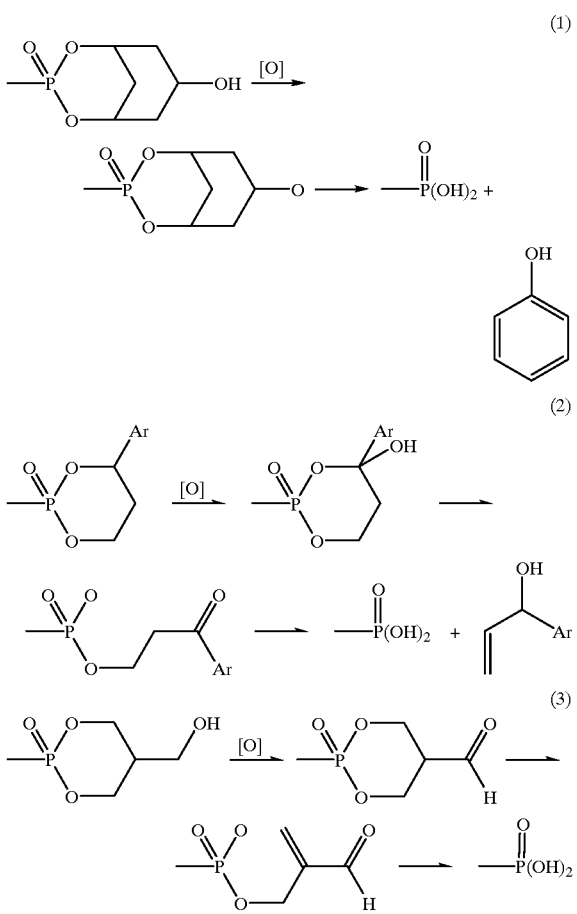

Although the esters in the invention are not limited by the above mechanisms, in general, each ester contains a group or atom susceptible to microsomal oxidation (e.g. alchohol, benzylic methine proton), which in turn generates an intermediate that breaks down to the parent compound in aqueous solution via β-elimination of the phosph(oramid)ate diacid.

EXAMPLES

1. Synthesis of Compounds of Formula I

Example 1

Preparation of 5-diethylphosphono-2-furaldehyde (1)

Step A.

A solution of 2-furaldehyde diethyl acetal (1 mmole) in THF (tetrahydrofuran) was treated with nBuLi (1 mmole) at –78° C. After 1 h, diethyl chlorophosphate (1.2 mmole) was added and the reaction was stirred for 40 min. Extraction and evaporation gave a brown oil.

Step B.

The resulting brown oil was treated with 80% acetic acid at 90° C. for 4 h. Extraction and chromatography gave compound 1 as a clear yellow oil. Alternatively this aldehyde can be prepared from fpuran as described below.

Step C.

A solution of furan (1 mmole) in diethyl ether was treated with TMEDA (N,N,N'N'-tetramethylethylenediamine) (1 mmole) and nBuLi (2 mmole) at –78° C. for 0.5 h. Diethyl chlorophosphate (1.2 mmole) was added to the reaction mixture and stirred for another hour. Extraction and distillation gave diethyl 2-furanphosphonate as a clear oil.

Step D.

A solution of diethyl 2-furanphosphonate (1 mmole) in THF was treated with LDA (1.12 mmole, lithium N,N-diisopropylamide) at –78° C. for 20 min. Methyl formate (1.5 mmole) was added and the reaction was stirred for 1 h. Extraction and chromatography gave compound 1 as a clear yellow oil. Preferably this aldehyde can be prepared from 2-furaldehyde as described below.

Step E.

A solution of 2-furaldehyde (1 mmole) and N,N'-dimethylethylene diamine (1 mmole) in toluene was refluxed while the resulting water being collected through a Dean-Stark trap. After 2 h the solvent was removed in vacuo and the residue was distilled to give furan-2-(N,N'-dimethylimidazolidine) as a clear colorless oil. bp 59–61° C. (3 mm Step F.

A solution of furan-2-(N,N'-dimethylimidazolidine) (1 mmole) and TMEDA (1 mmole) in THF was treated with nBuLi (1.3 mmole) at –40 to –48° C. The reaction was stirred at 0° C. for 1.5 h and then cooled to –55° C. and treated with a solution of diethylchlorophosphate (1.1 mmole) in THF. After stirring at 25° C. for 12 h the reaction mixture was evaporated and subjected to extraction to give 5-diethylphosphono-furan-2-(N,N'-dimethylimidazolidine) as a brown oil.

Step G.

A solution of 5-diethylphosphonofuran-2-(N,N'-dimethyl-imidazolidine) (1 mmole) in water was treated with concentrated sulfuric acid until pH=1. Extraction and chromatography gave compound 1 as a clear yellow oil.

Example 2

Preparation of 5-diethylphosphono-2-[(1-oxo)alkyl] furans and 6-diethylphosphono-2-[(1-oxo)alkyl] pyridines Step A.

A solution of furan (1.3 mmole) in toluene was treated with 4-methyl pentanoic acid (1 mmole), trifluoroacetic anhydride (1.2 mmole) and boron trifluoride etherate (0.1 mmole) at 56° C. for 3.5 h. The cooled reaction mixture was quenched with aqueous sodium bicarbonate (1.9 mmole), filtered through a celite pad. Extraction, evaporation and distillation gave 2-[(4-methyl-1-oxo)pentyl]furan as a brown oil (bp 65–77° C., 0.1 mmHg).

Step B.

A solution of 2-[(4-methyl-1-oxo)pentyl]furan (1 mmole) in benzene was treated with ethylene glycol (2.1 mmole) and p-toluenesulfonic acid (0.05 mmole) at reflux for 60 h while removing water via a Dean-Stark trap. Triethyl orthoformate (0.6 mmole) was added and resulting mixture was heated at reflux for an additional hour. Extraction and evaporation gave 2-(2-faranyl)-2-[(3-methyl)butyl]-1,3-dioxolane as an orange liquid.

Step C.

A solution of 2-(2-furanyl)-2-[(3-methyl)butyl]-1,3-dioxolane (1 mmole) in THF was treated with TMEDA (1 mmole) and nBuLi (1.1 mmole) at –45° C., and the resulting reaction mixture was stirred at –5 to 0° C. for 1 h. The resulting reaction mixture was cooled to –45° C., and cannulated into a solution of diethyl chlorophosphate in THF at –45° C. The reaction mixture was gradually warmed to ambient temperature over 1.25 h. Extraction and evaporation gave 2-[2-(5-diethylphosphono)furanyl]-2-[(3-methyl)butyl]-1,3-dioxolane as a dark oil.

Step D.

A solution of 2-[2-(5-diethylphosphono)furanyl]-2-[(3-methyl)butyl]-1,3-dioxolane (1 mmole) in methanol was treated with 1 N hydrochloric acid (0.2 mmole) at 60° C. for 18 h. Extraction and distillation gave 5-diethylphosphono-2-[(4-methyl-1-oxo)pentyl]furan (2.1) as a light orange oil (bp 152–156° C., 0.1 mmHg).

The following compounds were prepared according to this procedure:

(2.2) 5-diethylphosphono-2-acetylfuran: bp 125–136° C., 0.1 mmHg.

(2.3) 5-diethylphosphono-2-[(1-oxo)butyl]furan: bp 130–145° C., 0.08 mmHg.

Alternatively these compounds can be prepared using the following procedures:

Step E.

A solution of 2-[(4-methyl-1-oxo)pentyl]furan (1 mmole, prepared as in Step A) in benzene was treated with N,N-dimethyl hydrazine (2.1 mmole) and trifluoroacetic acid (0.05 mmole) at reflux for 6 h. Extraction and evaporation gave 2-[(4-methyl-1-oxo)pentyl]furan N,N-dimethyl hydrazone as a brown liquid.

Step F.

2-[(4-Methyl-1-oxo)pentyl]furan N,N-dimethyl hydrazone was subjected to the procedures of Step C to give 2-[(4-methyl-1-oxo)pentyl]-5-diethylphosphonofuran N,N-dimethyl hydrazone as a brown liquid which was treated with copper (II) chloride (1.1 equivalent) in ethanol-water at 25° C. for 6 h. Extraction and distillation gave compound 2.1 as a light orange oil.

Some of 5-diethylphosphono-2-[(1-oxo)alkyl]furans are prepared using the following procedures:

Step G.

A solution of compound 1 (1 mmole) and 1,3-propanedithiol (1.1 mmole) in chloroform was treated with borontrifluoride etherate (0.1 mmole) at 25° C. for 24 h. Evaporation and chromatography gave 2-(2-(5-diethylphosphono)furanyl)-1,3-dithiane as a light yellow oil.

A solution of 2-(2-(5-diethylphosphono)furanyl)-1,3-dithiane (1 mmole) in THF was cooled to –78° C. and treated with nBuLi (1.2 mmole). After 1 h. at –78° C. the reaction mixture was treated with cyclopropanemethyl bromide and reaction was stirred at –78° C. for another hour. Extraction and chromatography gave 2-(2-(5-diethylphosphono)furanyl)-2-cyclopropanemethyl-1,3-dithiane as an oil.

A solution of 2-(2-(5-diethylphosphono)furanyl)-2-cyclopropanemethyl-1,3-dithiane (1 mmole) in acetonitrile—water was treated with [bis(trifluoroacetoxy) iodo]benzene (2 mmole) at 25° C. for 24 h. Extraction and chromatography gave 5-diethylphosphono-2-(2-cyclopropylacetyl)furan as a light orange oil.

The following compounds were prepared according to this procedure:

(2.4) 5-Diethylphosphono-2-(2-ethoxycarbonylacetyl) furan (2.5) 5-Diethylphosphono-2-(2-methylthioacetyl)furan (2.6) 6-Diethylphosphono-2-acetylpyridine Example 3

Preparation of 4-[2-(5-phosphono)furanyllthiazoles, 4-[12-(6-phosphono)pyridylithiazoles and 4-[2-(5-phosphono)furanyl]selenazoles Step A.

A solution of compound 2.1 (1 mmole) in ethanol was treated with copper (II) bromide (2.2 mmole) at reflux for 3 h. The cooled reaction mixture was filtered and the filtrate was evaporated to dryness. The resulting dark oil was purified by chromatography to give 5-diethylphosphono-2-[(2-bromo-4-methyl-1-oxo)pentyl]furan as an orange oil.

Step B.

A solution of 5-diethylphosphono-2-[(2-bromo-4-methyl-1-oxo)pentyl]furan (1 mmole) and thiourea (2 mmole) in ethanol was heated at reflux for 2 h. The cooled reaction mixture was evaporated to dryness and the resulting yellow foam was suspended in saturated sodium bicarbonate and water (pH=8). The resulting yellow solid was collected through filtration to give 2-amino-5-isobutyl-4-[2-(5-diethylphosphono)furanyl]thiazole.

Step C.

A solution of 2-amino-5-isobutyl-4-[2-(5-diethylphosphono)furanyl]thiazole (1 mmole) in methylene chloride was treated with bromotrimethylsilane (10 mmole) at 25° C. for 8 h. The reaction mixture was evaporated to dryness and the residue was suspended in water. The resulting solid was collected through filtration to give 2-amino-5-isobutyl-4-[2-(5-phosphono)furanyl]thiazole (3.1) as an off-white solid. mp>250° C. Anal. calcd. for $C_{11}H_{15}N_2O_4PS+1.25HBr$: C: 32.75; H: 4.06; N: 6.94. Found: C: 32.39; H: 4.33; N: 7.18.

According to the above procedures or in some cases with minor modifications of these procedures using conventional chemistry the following compounds were prepared:

(3.2) 2-Methyl-5-isobutyl-4-[2-(5-phosphono)furanyl] thiazole. Anal. calcd. for $C_{12}H_{16}NO_4PS+HBr+0.1CH_2Cl_2$: C: 37.20; H: 4.44; N: 3.58. Found: C: 37.24; H: 4.56; N: 3.30.

(3.3) 4-[2-(5-Phosphono)furanyl]thiazole. Anal. calcd. for $C_7H_6NO_4PS+0.65$ HBr: C: 29.63; H: 2.36; N: 4.94. Found: C: 29.92; H: 2.66; N: 4.57.

(3.4) 2-Methyl-4-[2-(5-phosphono)furanyl]thiazole. mp 235–236° C. Anal. calcd. for $C_8H_8NO_4PS+0.25H_2O$: C: 38.48; H: 3.43; N: 5.61. Found: C: 38.68; H: 3.33; N: 5.36.

(3.5) 2-Phenyl-5-isobutyl-4-[2-(5-phosphono)furanyl] thiazole. Anal. calcd. for $C_{17}H_{18}NO_4PS+HBr$: C: 45.96; H: 4.31; N: 3.15. Found: C: 45.56; H: 4.26; N: 2.76.

(3.6) 2-Isopropyl-4-[2-(5-phosphono)furanyl]thiazole. mp 194–197° C. Anal. calcd. for $C_{10}H_{12}NO_4PS$: C: 43.96; H: 4.43; N: 5.13. Found: C: 43.70; H: 4.35; N: 4.75.

(3.7) 5-Isobutyl-4-[2-(5-phosphono)furanyl]thiazole. mp 164–166° C. Anal. calcd. for $C_{11}H_{14}NO_4PS$: C: 45.99; H: 4.91; N: 4.88. Found: C: 45.63; H: 5.01; N: 4.73.

(3.8) 2-Aminothiocarbonyl-4-[2-(5-phosphono)furanyl] thiazole. mp 189–191° C. Anal. calcd. for $C_8H_7N_2O_4PS_2$: C: 33.10; H: 2.43; N: 9.65. Found: C: 33.14; H: 2.50; N: 9.32.

(3.9) 2-(1-Piperidyl)-5-isobutyl-4-[2-(5-phosphono)furanyl] thiazole. Anal. calcd. for $C_{16}H_{23}N_2O_4PS+1.3HBr$: C: 40.41; H: 5.15; N: 5.89. Found: C: 40.46; H: 5.36; N: 5.53.

(3.10) 2-(2-Thienyl)-5-isobutyl-4-[2-(5-phosphono)furanyl] thiazole. Anal. calcd. for $C_{15}H_{16}NO_4PS_2+0.75H_2O$: C: 47.05; H: 4.61; N: 3.66. Found: C: 47.39; H: 4.36; N: 3.28.

(3.11) 2-(3-Pyridyl)-5-isobutyl-4-[2-(5-phosphono)furanyl] thiazole. Anal. calcd. for $C_{16}H_{17}N_2O_4PS+3.75HBr$: C: 28.78; H: 3.13; N: 4.20. Found: C: 28.73; H: 2.73; N: 4.53.

(3.12) 2-Acetamido-5-isobutyl-4-[2-(5-phosphono)furanyl] thiazole. mp 179–181° C. Anal. calcd. for $C_{13}H_{17}N_2O_5PS+0.25H_2O$: C: 44.76; H: 5.06; N: 8.03. Found: C: 44.73; H: 5.07; N: 7.89.

(3.13) 2-Amino-4-[2-(5-phosphono)furanyl]thiazole. Anal. calcd. for $C_7H_7N_2O_4PS$: C: 34.15; H: 2.87; N: 11.38. Found: C: 33.88; H: 2.83; N: 11.17.

(3.14) 2-Methylamino-5-isobutyl-4-[2-(5-phosphono) furanyl]thiazole. mp 202–205° C. Anal. calcd. for $C_{12}H_{17}N_2O_4PS+0.5H_2O$: C: 44.30; H: 5.58; N: 8.60. Found: C: 44.67; H: 5.27; N: 8.43.

(3.15) 2-(N-amino-N-methyl)amino-5-isobutyl-4-[2-(5-phosphono)furanyl]thiazole. mp 179–181° C. Anal. calcd. for $C_{12}H_{18}N_3O_4PS+1.25HBr$: C: 33.33; H: 4.49; N: 9.72. Found: C: 33.46; H: 4.81; N: 9.72.

(3.16) 2-Amino-5-methyl-4-[2-(5-phosphono)furanyl] thiazole. mp 200–220° C. Anal. calcd. for $C_8H_9N_2O_4PS+0.65HBr$: C: 30.72; H: 3.11; N: 8.96. Found: C: 30.86; H: 3.33; N: 8.85.

(3.17) 2,5-Dimethyl-4-[2-(5-phosphono)furanyl]thiazole. mp 195° C. (decomp). Anal. calcd. for $C_9H_{10}NO_4PS+0.7HBr$: C: 34.22; H: 3.41; N: 4.43. Found: C: 34.06; H: 3.54; N: 4.12.

(3.18) 2-Aminothiocarbonyl-5-isobutyl-4-[2-(5-phosphono) furanyl]thiazole. Anal. calcd. for $C_{12}H_{15}N_2O_4PS_2+0.1HBr+0.3EtOAc$: C: 41.62; H: 4.63; N: 7.35. Found: C: 41.72; H: 4.30; N: 7.17.

(3.19) 2-Ethoxycarbonyl-4-[2-(5-phosphono)furanyl] thiazole. mp 163–165° C. Anal. calcd. for $C_{10}H_{10}NO_6PS+0.5H_2O$: C: 38.47; H: 3.55; N: 4.49. Found: C: 38.35; H: 3.30; N: 4.42.

(3.20) 2-Amino-5-isopropyl-4-[2-(5-phosphono)furanyl] thiazole. Anal. calcd. for $C_{10}H_{13}N_2O_4PS+1HBr$: C: 32.53; H: 3.82; N: 7.59. Found: C: 32.90; H: 3.78; N: 7.65.

(3.21) 2-Amino-5-ethyl-4-[2-(5-phosphono)furanyl] thiazole. mp>250° C. Anal. calcd. for $C_9H_{11}N_2O_4PS$: C: 39.42; H: 4.04; N: 10.22. Found: C: 39.02; H: 4.15; N: 9.92.

(3.22) 2-Cyanomethyl-4-[2-(5-phosphono)furanyl]thiazole. mp 204–206° C. Anal. calcd. for $C_9H_7N_2O_4PS$: C: 40.01; H: 2.61; N: 10.37. Found: C: 39.69; H: 2.64; N: 10.03.

(3.23) 2-Aminothiocarbonylamino-5-isobutyl-4-[2-(5-phosphono)furanyl]thiazole. mp 177–182° C. Anal. calcd. for $C_{12}H_{16}N_3O_4PS_2+0.2hexane+0.3HBr$: C: 39.35; H: 4.78; N: 10.43. Found: C: 39.61; H: 4.48; N: 10.24.

(3.24) 2-Amino-5-propyl-4-[2-(5-phosphono)furanyl] thiazole. mp 235–237° C. Anal. calcd. for $C_{10}H_{13}N_2O_4PS+0.3H_2O$: C: 40.90; H: 4.67; N: 9.54. Found: C: 40.91; H: 4.44; N: 9.37.

(3.25) 2-Amino-5-ethoxycarbonyl-4-[2-(5-phosphono) furanyl]thiazole. mp 248–250° C. Anal. calcd. for $C_{10}H_{11}N_2O_6PS+0.1HBr$: C: 36.81; H: 3.43; N: 8.58. Found: C: 36.99; H: 3.35; N: 8.84.

(3.26) 2-Amino-5-methylthio-4-[2-(5-phosphono)furanyl] thiazole. mp 181–184° C. Anal. calcd. for $C_8H_9N_2O_4PS_2+0.4H_2O$: C: 32.08; H: 3.30; N: 9.35. Found: C:32.09; H: 3.31; N: 9.15.

(3.27) 2-Amino-5-cyclopropyl-4-[2-(5-phosphono)furanyl] thiazole. Anal. calcd. for $C_{10}H_{11}N_2O_4PS+1H_2O+0.75HBr$: C: 32.91; H: 3.80; N: 7.68. Found: C: 33.10; H: 3.80; N: 7.34.

(3.28) 2-Amino-5-methanesulfinyl-4-[2-(5-phosphono)furanyl]thiazole. mp>250° C. Anal. calcd. for $C_8H_9N_2OPS_2$+0.35NaCl: C: 29.23; H: 2.76; N: 8.52. Found: C: 29.37; H: 2.52; N: 8.44.

(3.29) 2-Amino-5-benzyloxycarbonyl-4-[2-(5-phosphono)furanyl]thiazole. Anal. calcd for $C_{15}H_{13}N_2O_6PS$+0.2$H_2O$: C: 46.93; H: 3.52; N: 7.30. Found: C: 46.64; H: 3.18; N: 7.20.

(3.30) 2-Amino-5-cyclobutyl-4-[2-(5-phosphono)furanyl]thiazole. Anal. calcd for $C_{11}H_{13}N_2O_4PS$+0.15 HBr+0.15$H_2O$: C: 41.93; H: 4.30; N: 8.89. Found: C: 42.18; H: 4.49; N: 8.53.

(3.31) 2-Amino-5-cyclopropyl-4-[2-(5-phosphono)furanyl]thiazole hydrobromide. Anal. calcd for $C_{10}H_{11}N_2O_4PSBr$+0.73HBr+0.15MeOH+0.5$H_2O$: C: 33.95; H: 3.74; N: 7.80; S: 8.93; Br: 16.24. Found: C: 33.72; H: 3.79; N: 7.65; S: 9.26; Br: 16.03.

(3.32) 2-Amino-5-[(N,N-dimethyl)aminomethyl]-4-[2-(5-phosphono)furanyl]thiazole dihydrobromide. Anal. calcd for $C_{10}H_{16}N_3O_4Br_2PS$+0.8$CH_2Cl_2$: C: 24.34; H: 3.33; N: 7.88. Found: C: 24.23; H: 3.35; N: 7.64.

(3.33) 2-Amino-5-methoxycarbonyl-4-[2-(5-phosphono)furanyl]thiazole. Mp 227° C. (decomp). Anal. calcd for $C_9H_9N_2O_6PS$+0.1$H_2O$+0.2HBr: C: 33.55; H: 2.94; N: 8.69. Found: C: 33.46; H: 3.02; N: 8.49.

(3.34) 2-Amino-5-ethylthiocarbonyl-4-[2-(5-phosphono)furanyl]thiazole. Mp 245° C. (decomp). Anal. calcd for $C_{10}H_{11}N_2O_5PS_2$: C: 35.93; H: 3.32; N: 8.38. Found: C: 35.98; H: 3.13; N: 8.17.

(3.35) 2-Amino-5-propyloxycarbonyl-4-[2-(5-phosphono)furanyl]thiazole. Mp 245° C. (decomp). Anal. calcd for $C_{11}H_{13}N_2O_6PS$: C: 39.76; H: 3.94; N: 8.43. Found: C: 39.77; H: 3.72; N: 8.19.

(3.36) 2-Amino-5-benzyl-4-[2-(5-phosphono)furanyl]thiazole. Anal. calcd for $C_{14}H_{13}N_2O_4PS$+$H_2O$: C: 47.46; H: 4.27; N: 7.91. Found: C: 47.24; H: 4.08; N: 7.85.

(3.37) 2-Amino-5-[(N,N-diethyl)aminomethyl]-4-[2-(5-phosphono)furanyl]thiazole dihydrobromide. Anal. calcd for $C_{12}H_{20}N_3O_4Br_2PS$+0.1HBr+1.4 MeOH: C: 29.47; H: 4.74; N: 7.69. Found: C: 29.41; H: 4.60; N: 7.32.

(3.38) 2-Amino-5-[(N,N-dimethyl)carbamoyl]-4-[2-(5-phosphono)furanyl]thiazole. Anal. calcd for $C_{10}H_{12}N_3O_5PS$+1.3HBr+1.0$H_2O$+0.3 Acetone: C: 28.59; H: 3.76; N: 9.18. Found: C: 28.40; H: 3.88; N: 9.01.

(3.39) 2-Amino-5-carboxyl-4-[2-(5-phosphono)furanyl]thiazole. Anal. calcd for $C_8H_7N_2O_6PS$+0.2HBr+0.1 $H_2O$: C: 31.18; H: 2.42; N: 9.09. Found: C: 31.11; H: 2.42; N: 8.83.

(3.40) 2-Amino-5-isopropyloxycarbonyl-4-[2-(5-phosphono)furanyl]thiazole. Mp 240° C. (decomp). Anal. calcd for $C_{11}H_{13}N_2O_6PS$: C: 39.76; H: 3.94; N: 8.43. Found: C: 39.42; H: 3.67; N: 8.09.

(3.41) 2-Methyl-5-ethyl-4-[2-(5-phosphono)furanyl]thiazole. Anal. calcd for $C_{10}H_{12}O_4PNS$+0.75HBr+0.35$H_2O$: C: 36.02; H: 4.13; N: 4.06. Found: C: 36.34; H: 3.86; N: 3.69.

(3.42) 2-Methyl-5-cyclopropyl-4-[2-(5-phosphono)furanyl]thiazole. Anal. calcd for $C_{11}H_{12}NO_4PS$+0.3HBr+0.5$CHCl_3$: C: 37.41; H: 3.49; N: 3.79. Found: C: 37.61; H: 3.29; N: 3.41.

(3.43) 2-Methyl-5-ethoxycarbonyl-4-[2-(5-phosphono)furanyl]thiazole. Anal. calcd for $C_{11}H_{12}NO_6PS$: C: 41.64; H: 3.81; N: 4.40. Found: C: 41.61; H: 3.78; N: 4.39.

(3.44) 2-[(N-acetyl)amino]-5-methoxymethyl-4-[2-(5-phosphono)furanyl]thiazole. Anal. calcd for $C_{11}H_{13}N_2O_6PS$+0.15HBr: C: 38.36; H: 3.85; N: 8.13. Found: C: 38.74; H: 3.44; N: 8.13.

(3.45) 2-Amino-5-(4-morpholinyl)methyl-4-[2-(5-phosphono)furanyl]thiazole dihydrobromide. Anal. calcd for $C_{12}H_{18}Br_2N_3O_5PS$+0.25HBr: C: 27.33; H: 3.49; N: 7.97. Found: C: 27.55; H: 3.75; N: 7.62.

(3.46) 2-Amino-5-cyclopropylmethoxycarbonyl-4-[2-(5-phosphono)furanyl]thiazole. Mp 238° C. (decomp). Anal. calcd for $C_{12}H_{13}N_2O_6PS$: C: 41.86; H: 3.81; N: 8.14. Found: C: 41.69; H: 3.70; N: 8.01.

(3.47) 2-Amino-5-methylthio-4-[2-(5-phosphono)furanyl]thiazole N,N-dicyclohexylammonium salt. Mp>250° C. Anal. calcd for $C_8H_9N_2O_4PS_2$+1.15 $C_{12}H_{23}N$: C: 52.28; H: 7.13; N: 8.81. Found: C: 52.12; H: 7.17; N: 8.81.

(3.48) 2-[(N-Dansyl)amino]-5-isobutyl-4-[2-(5-phosphono)furanyl]thiazole. Anal. calcd for $C_{23}H_{26}N_3O_6PS_2$+0.5HBr: C: 47.96; H: 4.64; N: 7.29. Found: C: 48.23; H: 4.67; N: 7.22.

(3.49) 2-Amino-5-(2,2,2-trifluoroethyl)-4-[2-(5-phosphono)furanyl]thiazole. Anal. calcd for $C_9H_8N_2F_3O_4PS$: C:32.94, H:2.46, N:8.54. Found: C:32.57, H:2.64, N:8.14.

(3.50) 2-Methyl-5-methylthio-4-[2-(5-phosphono)furanyl]thiazole. Anal. calcd for $C_9H_{10}NO_4PS_2$: C: 37.11; H: 3.46; N: 4.81. Found: C: 36.72; H: 3.23; N: 4.60.

(3.51) 2-Amino-5-methylthio-4-[2-(5-phosphono)furanyl]thiazole ammonium salt. Anal. calcd for $C_8H_{12}N_3O_4PS_2$: C: 31.07; H: 3.91; N: 13.59. Found: C: 31.28; H: 3.75; N: 13.60.

(3.52) 2-Cyano-5-ethyl-4-[2-(5-phosphono)furanyl]thiazole. Anal. calcd for $C_{10}H_9N_2O_4PS$: C: 42.26; H: 3.19; N: 9.86. Found: C: 41.96; H: 2.95; N: 9.76.

(3.53) 2-Amino-5-hydroxymethyl-4-[2-(5-phosphono)furanyl]thiazole. Anal. calcd for $C_8H_9N_2O_5PS$: C: 34.79; H: 3.28; N: 10.14. Found: C: 34.57; H: 3.00; N: 10.04.

(3.54) 2-Cyano-5-isobutyl-4-[2-(5-phosphono)furanyl]thiazole. Anal. calcd for $C_{12}H_{13}N_2O_4SP$+0.09HBr: C: 46.15; H: 4.20; N: 8.97. Found: C: 44.81; H: 3.91; N: 8.51.

(3.55) 2-Amino-5-isopropylthio-4-[2-(5-phosphono)furanyl]thiazole hydrobromide. Anal. calcd for $C_{10}H_{14}BrN_2O_4PS_2$: C: 29.94; H: 3.52; N: 6.98. Found: C: 30.10; H: 3.20; N: 6.70.

(3.56) 2-Amino-5-phenylthio-4-[2-(5-phosphono)furanyl]thiazole. Anal. calcd for $C_{13}H_{11}N_2O_4PS_2$: C: 44.07; H: 3.13; N: .91. Found: C: 43.83; H: 3.07; N: 7.74.

(3.57) 2-Amino-5-tert-butylthio-4-[2-(5-phosphono)furanyl]thiazole. Anal. calcd for $C_{11}H_{15}N_2O_4PS_2$+0.6$CH_2Cl_2$: C: 36.16; H: 4.24; N: 7.27. Found: C: 36.39; H: 3.86; N: 7.21.

(3.58) 2-Amino-5-propylthio-4-[2-(5-phosphono)furanyl]thiazole hydrobromide. Anal. calcd for $C_{11}H_{14}BrN_2O_4PS_2$: C: 29.94; H: 3.52; N: 6.98. Found: C: 29.58; H: 3.50; N: 6.84.

(3.59) 2-Amino-5-ethylthio-4-[2-(5-phosphono)furanyl]thiazole. Anal. calcd for $C_9H_{11}N_2O_4PS_2$+0.25HBr: C: 33.11; H: 3.47; N: 8.58. Found: C: 33.30; H: 3.42; N: 8.60.

(3.60) 2-[(N-tert-butyloxycarbonyl)amino]-5-methoxymethyl-4-[2-(5-phosphono)furanyl]thiazole. Anal. calcd for $C_{14}H_{19}N_2O_7PS$: C: 43.08; H: 4.91; N: 7.18. Found: C: 42.69; H: 4.58; N: 7.39.

(3.61) 2-Hydroxyl-4-[2-(5-phosphono)furanyl]thiazole. Anal. calcd for $C_7H_6NO_5PS$: C: 34.02; H: 2.45; N: 5.67. Found: C: 33.69; H: 2.42; N: 5.39.

(3.62) 2-Hydroxyl-5-ethyl-4-[2-(5-phosphono)furanyl]thiazole. Anal. calcd for $C_9H_{10}NO_5PS$: C: 39.28; H: 3.66; N: 5.09. Found: C: 39.04; H: 3.44; N: 4.93.

(3.63) 2-Hydroxyl-5-isopropyl-4-[2-(5-phosphono)furanyl]thiazole. Anal. calcd for $C_{10}H_{12}NO_5PS$+0.1HBr: C: 40.39; H: 4.10; N: 4.71. Found: C: 40.44; H: 4.11; N: 4.68.

(3.64) 2-Hydroxyl-5-isobutyl-4-[2-(5-phosphono)furanyl]thiazole. Anal. calcd for $C_{11}H_{14}NO_5PS$: C: 43.57; H: 4.65; N: 4.62. Found: C: 43.45; H: 4.66; N: 4.46.

(3.65) 5-Ethoxycarbonyl-4-[2-(5-phosphono)furanyl]thiazole. Anal. calcd for $C_{10}H_{10}NO_6PS$: C: 39.61; H: 3.32; N: 4.62. Found: C: 39.60; H: 3.24; N: 4.47.

(3.66) 2-Amino-5-vinyl-4-[2-(5-phosphono)furanyl]thiazole. Anal. calcd for $C_9H_9N_2O_4PS+0.28HCl$: C: 37.66; H: 3.26; N: 9.46. Found: C: 37.96; H: 3.37; N: 9.10.

(3.67) 2-Amino-4-[2-(6-phosphono)pyridyl]thiazole hydrobromide.

(3.68) 2-Methylthio-5-isobutyl-4-[2-(5-phosphono)furanyl]thiazole. Anal. calcd for $C_{12}H_{16}NO_4PS_2$: C: 43.24; H: 4.84; N: 4.20. Found: C: 43.55; H: 4.63; N: 4.46.

(3.69) 2-Amino-5-isobutyl-4-[2-(3-phosphono)furanyl]thiazole. Anal. calcd for $C_{11}H_{15}N_2O_4PS+0.1\ H_2O$: C: 43.45; H: 5.04; N: 9.21. Found: C: 43.68; H: 5.38; N: 8.98.

(3.70) 2-Amino-5-isobutyl-4-[2-(5-phosphono)furanyl]selenazole. Anal. calcd for $C_{11}H_{15}N_2O_4PSe+0.14\ HBr+0.6\ EtOAc$: C: 38.93; H: 4.86; N: 6.78. Found: C: 39.18; H: 4.53; N: 6.61.

(3.71) 2-Amino-5-methylthio-4-[2-(5-phosphono)furanyl]selenazole. Anal. calcd for $C_8H_9N_2O_4PSSe+0.7\ HBr+0.2\ EtOAc$: C: 25.57; H: 2.75; N: 6.78. Found: C: 25.46; H: 2.49; N: 6.74.

(3.72) 2-Amino-5-ethyl-4-[2-(5-phosphono)furanyl]selenazole. Anal. calcd for $C_9H_{11}N_2O_4PSe+HBr$: C: 26.89; H: 3.01; N: 6.97. Found: C: 26.60; H: 3.16; N: 6.81.

Example 4

Preparation of 5-halo-4-[2-(5-phosphono)furanyl]thiazoles

Step A.

A solution of 2-amino-4-[2-(5-diethylphosphono)furanyl]thiazole (prepared as in Step B of Example 3) (1 mmole) in chloroform was treated with N-bromo succinimide (NBS) (1.5 mmole) at 25° C. for 1 h. Extraction and chromatography gave 2-amino-5-bromo-4-[2-(5-diethylphosphono)furanyl]-thiazole as a brown solid.

Step B.

2-Amino-5-bromo-4-[2-(5-diethylphosphono)furanyl]thiazole was subjected to Step C of Example 3 to give 2-amino-5-bromo-4-[2-(5-phosphono)-furanyl]thiazole (4.1) as a yellow solid. mp>230° C. Anal. calcd. for $C_7H_6N_2O_4PSBr$: C: 25.86; H: 1.86; N: 8.62. Found: C: 25.93; H: 1.64; N: 8.53.

The following compounds were prepared according to this procedure:

(4.2) 2-Amino-5-chloro-4-[2-(5-phosphono)furanyl]thiazole. Anal. calcd. for $C_7H_6N_2O_4PSCl$: C: 29.96; H: 2.16; N: 9.98. Found: C: 29.99; H: 1.97; N: 9.75.

(4.3) 2-Amino-5-iodo-4-[2-(5-phosphono)furanyl]thiazole. Anal. calcd. for $C_7H_6N_2O_4PSI$: C: 22.42; H: 2.28; N: 6.70. Found: C: 22.32; H: 2.10; N: 6.31.

(4.4) 2,5-Dibromo-4-[2-(5-phosphono)furanyl]thiazole. Anal. calcd. for $C_7H_4NO_4PSBr_2$: C: 21.62; H: 1.04; N: 3.60. Found: C: 21.88; H: 0.83; N: 3.66.

Examples 5

Preparation of 2-halo-4-[2-(5-phosphono)furanyl]thiazoles

Step A.

A solution of 2-amino-5-isobutyl-4-[2-(5-diethylphosphono)-furanyl]thiazole (prepared as in Step B of Example 3) (1 mmole) in acetonitrile was treated with copper (II) bromide (1.2 mmole) and isoamyl nitrite (1.2 mmole) at 0° C. for 1 h. Extraction and chromatography gave 2-bromo-5-isobutyl-4-[2-(5-diethylphosphono)furanyl]thiazole as a brown solid.

Step B.

2-Bromo-5-isobutyl-4-[2-(5-diethylphosphono)furanyl]thiazole was subjected to Step C of Example 3 to give 2-bromo-5-isobutyl-4-[2-(5-phosphono)furanyl]thiazole (5.1) as a yellow hygroscopic solid. Anal. calcd. for $C_{11}H_{13}NO_4PSBr$: C: 36.08; H: 3.58; N: 3.83. Found: C: 36.47; H: 3.66; N: 3.69.

The following compound was prepared according to this procedure:

(5.2) 2-Chloro-5-isobutyl-4-[2-(5-phosphono)furanyl]thiazole: Anal. calcd. for $C_{11}H_{13}NO_4PSCl$: C: 41.07; H: 4.07; N: 4.35. Found: C: 40.77; H: 4.31; N: 4.05.

(5.3) 2-Bromo-5-methylthio-4-[2-(5-phosphono)furanyl]thiazole: Anal. calcd. for $C_8H_7NO_4PS_2Br$: C: 26.98; H: 1.98; N: 3.93. Found: C: 27.21; H: 1.82; N: 3.84.

Example 6

Preparation of Various 2- and 5-substituted 4-[2-(5-phosphono)furanyl]thiazoles

Step A.

A solution of 2-bromo-5-isobutyl-4-[2-(5-diethylphosphono)-furanyl]thiazole (1 mmole, prepared as in the Step A of Example 5) in DMF was treated with tributyl(vinyl)tin (5 mmole) and palladium bis(triphenylphosphine) dichloride (0.05 mmole) at 100° C. under nitrogen. After 5 h the cooled reaction mixture was evaporated and the residue was subjected to chromatography to give 2-vinyl-5-isobutyl-4-[2-(5-diethylphosphono)furanyl]thiazole as a yellow solid.

Step B.

2-Vinyl-5-isobutyl-4-[2-(5-diethylphosphono)furanyl]thiazole was subjected to Step C of Example 3 to give 2-vinyl-5-isobutyl-4-[2-(5-phosphono)-furanyl]thiazole (6.1) as a yellow solid. Anal. calcd. for $C_{13}H_{16}NO_4PS+1HBr+0.1H_2O$: C: 39.43; H: 4.38; N: 3.54. Found: C: 39.18; H: 4.38; N: 3.56.

This method can also be used to prepare various 5-substituted 4-[2-(5-phosphono)furanyl]thiazoles from their corresponding halides.

Step C.

2-Amino-5-bromo-4-[2-(5-diethylphosphono)furanyl]thiazole was subjected to Step A using 2-tributylstannylfuran as the coupling partner to give 2-amino-5-(2-furanyl)-4-[2-(5-diethylphosphono)furanyl]thiazole.

Step D.

2-Amino-5-(2-furanyl)-4-[2-(5-diethylphosphono)furanyl]thiazole was subjected to Step C of Example 3 to give 2-amino-5-(2-furanyl)-4-[2-(5-phosphono)furanyl]thiazole (6.2). mp 190–210° C. Anal. calcd. for $C_{11}H_9N_2O_5PS+0.25HBr$: C: 39.74; H: 2.80; N: 8.43. Found: C: 39.83; H: 2.92; N: 8.46.

The following compound was prepared according to this procedure:

(6.3) 2-Amino-5-(2-thienyl)-4-[2-(5-diethylphosphono)furanyl]thiazole. Anal. calcd. for $C_{11}H_9N_2O_4PS_2+0.3EtOAc+0.11HBr$: C: 40.77; H: 3.40; N: 7.79. Found: C: 40.87; H: 3.04; N: 7.45.

Example 7

Preparation of 2-ethyl-4-[12-(5-phosphono)furanyl]thiazoles

Step A.

A solution of 2-vinyl-5-isobutyl-4-[2-(5-diethylphosphono)furanyl]-thiazole (1 mmole, prepared as in the Step A of Example 6) in ethanol was treated with palladium on carbon (0.05 mmole) under 1 atmosphere of hydrogen for 12 h. The reaction mixture was filtered, the filtrate was evaporated and the residue was purified by chromatography to give 2-ethyl-5-isobutyl-4-[2-(5-diethylphosphono)furanyl]thiazole as a yellow foam.
Step B.

2-Ethyl-5-isobutyl-4-[2-(5-diethylphosphono)furanyl]thiazole was subjected to Step C of Example 3 to give 2-ethyl-5-isobutyl-4-[2-(5-phosphono)-furanyl]thiazole (7.1) as a yellow solid. Anal. calcd. for $C_{13}H_{18}NO_4PS+1HBr$: C: 39.41; H: 4.83; N: 3.53. Found: C: 39.65; H: 4.79; N: 3.61.

Example 8

Preparation of 4-phosphonomethoxymethylthiazoles
Step A.

A solution of diethyl hydroxymethylphosphonate (1 mmole) in DMF was treated with sodium hydride (1.2 mmole) followed by 2-methyl-4-chloromethylthiazole (1 mmole) at 0° C. and stirred at 25° C. for 12 h. Extraction and chromatography gave 2-methyl-4-(diethylphosphonomethoxymethyl)thiazole.
Step B.

2-Methyl-4-diethylphosphonomethoxymethylthiazole was subjected to Step C of Example 3 to give 2-methyl-4-phosphonomethoxymethylthiazole (8.1). Anal. calcd. for $C_6H_{10}NO_4PS+0.5HBr+0.5H_2O$: C: 26.43; H: 4.25; N: 5.14. Found: C: 26.52; H: 4.22; N: 4.84.
Step C.

2-Methyl-4-diethylphosphonomethoxymethylthiazole was subjected to Step A of Example 4 and followed by Step C of Example 3 to give 5-bromo-2-methyl-4-phosphonomethoxymethylthiazole (8.2). Anal. calcd. for $C_6H_9NO_4PSBr+0.5HBr$: C: 21.04; H: 2.80; N: 4.09. Found: C: 21.13; H: 2.69; N: 4.01.
Step D.

A solution of ethyl 2-[(N-Boc)amino]-4-thiazolecarboxylate (1 mmole) in $CH_2Cl_2$ (10 mL) was cooled to -78° C., and treated with DIBAL-H (1M, 5 mL). The reaction was stirred at -60° C. for 3 h, and quenched with a suspension of $NaF/H_2O$ (1 g/1 mL). The resulting mixture was filtered and the filtrate was concentrated to give 2-[(N-Boc)amino]-4-hydroxymethylthiazole as a solid.
Step E.

A solution of 2-[(N-Boc)amino]-4-hydroxymethylthiazole (1 mmole) in DMF (10 mL) was cooled to 0° C., and treated with NaH (1.1 mmole). The mixture was stirred at room temperature for 30 min, then phosphonomethyl trifluoromethanesulfonate (1.1 mmole) was added. After stirring at room temperature for 4 h, the reaction was evaporated to dryness. Chromatography of the residue gave 2-[(N-Boc)amino]-4-diethylphosphonomethoxylmethylthiazole as a solid.
Step F.

2-[(N-Boc)amino]-4-diethylphosphonomethoxylmethylthiazole was subjected to Step C of Example 3 to give 2-amino-4-phosphonomethoxymethylthiazole (8.3) as a solid. Anal. calcd. for $C_5H_9N_2O_4PS+0.16$ HBr+0.1 MeOH: C: 25.49; H: 4.01; N: 11.66. Found: C: 25.68; H: 3.84; N: 11.33.

Example 9

Preparation of 2-carbamoyl-4-[2-(5-phosphono)furanyl]thiazoles
Step A.

A solution of 2-ethoxycarbonyl-5-isobutyl-4-[2-(5-diethylphosphono)furanyl]thiazole (1 mmole) in saturated methanolic ammonia solution at 25° C. for 12 h. Evaporation and chromatography gave 2-carbamoyl-5-isobutyl-4-[2-(5-diethylphosphono)furanyl]thiazole as a white solid.
Step B.

2-Carbamoyl-5-isobutyl-4-[2-(5-diethylphosphono)furanyl]thiazole was subjected to Step C of Example 3 to give 2-carbamoyl-5-isobutyl-4-[2-(5-phosphono)furanyl]thiazole (9.1) as a solid. mp 185–186° C. Anal. calcd. for $C_{12}H_{15}N_2O_5PS$: C: 43.64; H: 4.58; N: 8.48. Found: C: 43.88; H: 4.70; N: 8.17.

The following compound was prepared according to this procedure:

(9.2) 2-Carbamoyl-4-[2-(5-phosphono)furanyl]thiazole. mp 195–200° C. Anal. calcd. for $C_8H_7N_2O_5PS+0.25H_2O$: C: 34.48; H: 2.71; N: 10.05. Found: C: 34.67; H: 2.44; N: 9.84.

2-Ethoxycarbonyl-4-[2-(5-diethylphosphono)furanyl]thiazoles can also be converted to other 2-substituted 4-[2-(5-phosphono)furanyl]thiazoles.
Step C.

A solution of 2-ethoxycarbonyl-4-[2-(5-diethylphosphono)furanyl]thiazole (1 mmole) in methanol was treated with sodium borohydride (1.2 mmole) at 25° C. for 12 h. Extraction and chromatography gave 2-hydroxymethyl-4-[2-(5-diethylphosphono)furanyl]thiazole.
Step D.

2-Hydroxymethyl-4-[2-(5-diethylphosphono)furanyl]-thiazole was subjected to Step C of Example 3 to give 2-hydroxymethyl-4-[2-(5-phosphono)furanyl]thiazole (9.3). mp 205–207° C. Anal. calcd. for $C_8H_8NO_5PS+0.25H_2O$: C: 36.16; H: 3.22; N: 5.27. Found: C: 35.98; H: 2.84; N: 5.15.

The following compound was prepared according to this procedure:

(9.4) 2-Hydroxymethyl-5-isobutyl-4-[2-(5-phosphono)furanyl]thiazole. mp 160–170° C. Anal. calcd. for $C_{12}H_{16}NO_5PS+0.75HBr$: C: 38.13; H: 4.47; N: 3.71. Found: C: 37.90; H: 4.08; N: 3.60.
Step E A solution of 2-hydroxymethyl-5-isobutyl-4-[2-(5-diethylphosphono)furanyl]thiazole (1 mmole) in methylene chloride was treated with phosphorus tribromide (1.2 mmole) at 25° C. for 2 h. Extraction and chromatography gave 2-bromomethyl-5-isobutyl-4-[2-(5-diethylphosphono)furanyl]thiazole.
Step F.

2-Bromomethyl-5-isobutyl-4-[2-(5-diethylphosphono)furanyl]-thiazole was subjected to Step C of Example 3 to give 2-bromomethyl-5-isobutyl-4-[2-(5-phosphono)furanyl]thiazole (9.5). mp 161–163° C. Anal. calcd. for $C_{12}H_{15}BrNO_4PS+0.25HBr$: C: 35.99; H: 3.84; N: 3.50. Found: C: 36.01; H: 3.52; N: 3.37.

The following compound was prepared according to this procedure:

(9.6) 2-Bromomethyl-4-[2-(5-phosphono)furanyl]thiazole. mp>250° C. Anal. calcd. for $C_8H_7BrNO_4PS$: C: 29.65; H: 2.18; N: 4.32. Found: C: 29.47; H: 1.99; N: 4.16.
Step G.

A solution of 2-hydroxymethyl-5-isobutyl-4-[2-(5-diethylphosphono)furanyl]thiazole (1 mmole) in methylene chloride was treated with thionyl chloride (1.2 mmole) at 25° C. for 2 h. Extraction and chromatography gave 2-chloromethyl-5-isobutyl-4-[2-(5-diethylphosphono)furanyl]thiazole.
Step H.

2-Chloromethyl-5-isobutyl-4-[2-(5-diethylphosphono)furanyl]-thiazole was subjected to Step C of Example 3 to give 2-chloromethyl-5-isobutyl-4-[2-(5-phosphono)furanyl] thiazole (9.7). mp 160–162° C. Anal. calcd. for $C_{12}H_{15}ClNO_4PS+0.45HBr$: C: 38.73; H: 4.18; N: 3.76. Found: C: 38.78; H: 4.14; N: 3.73.

Step I.

A solution of 2-bromomethyl-5-isobutyl-4-[2-(5-diethylphosphono)furanyl]thiazole (1 mmole) in DMF was treated with potassium phthalimide (1.2 mmole) at 25° C. for 12 h. Extraction and chromatography gave 2-phthalimidomethyl-5-isobutyl-4-[2-(5-diethylphosphono)furanyl]thiazole.

Step J.

2-Phthalimidomethyl-5-isobutyl-4-[2-(5-diethylphosphono)furanyl]-thiazole (1 mmole) in ethanol was treated with hydrazine (1.5 mmole) at 25° C. for 12 h. Filtration, evaporation and chromatography gave 2-aminomethyl-5-isobutyl-4-[2-(5-diethylphosphono)furanyl]thiazole.

Step K.

2-Aminomethyl-5-isobutyl-4-[2-(5-diethylphosphono)furanyl]-thiazole was subjected to Step C of Example 3 to give 2-aminomethyl-5-isobutyl-4-[2-(5-phosphono)furanyl]thiazole (9.8). mp 235–237° C. Anal. calcd. for $C_{12}H_{17}N_2O_4PS+0.205HBr$: C: 43.30; H: 5.21; N: 8.41. Found: C: 43.66; H: 4.83; N: 8.02.

According to the above procedures or in some cases with some minor modifications of the above procedures, the following compounds were prepared:

(9.9) 2-Carbamoyl-5-cyclopropyl-4-[2-(5-phosphono)furanyl]thiazole. Anal. calcd for $C_{11}H_{11}N_2O_5PS+0.15HBr$: C: 40.48; H: 3.44; N: 8.58. Found: C: 40.28; H: 3.83; N: 8.34.

(9.10) 2-Carbamoyl-5-ethyl-4-[2-(5-phosphono)furanyl]thiazole. Anal. calcd for $C_{10}H_{11}N_2O_5PS+0.75H_2O$: C: 38.04; H: 3.99; N: 8.87. Found: C: 37.65; H: 3.93; N: 8.76.

Example 10

Preparation of 4-[2-(5-phosphono)furanyl]oxazoles and 4-[2-(5-phosphono)furanyl]imidazoles Step A.

A solution of 5-diethylphosphono-2-[(2-bromo-4-methyl-1-oxo)pentyl]furan (1 mmole) in t-BuOH was treated with urea (10 mmole) at reflux for 72 h. Filtration, evaporation and chromatography gave 2-amino-5-isobutyl-4-[2-(5-diethylphosphono)furanyl]oxazole, and 2-hydroxy-5-isobutyl-4-[2-(5-diethylphosphono)furanyl]imidazole.

Step B.

2-Amino-5-isobutyl-4-[2-(5-diethylphosphono)furanyl]oxazole was subjected to Step C of Example 3 to give 2-amino-5-isobutyl-4-[2-(5-phosphono)furanyl]oxazole (10.1). mp 250° C. (decomp.). Anal. Calcd. for $C_{11}H_{15}N_2O_5P$: C: 46.16; H: 5.28; N: 9.79. Found: C: 45.80; H: 5.15; N: 9.55.

Step C.

2-Hydroxy-5-isobutyl-4-[2-(5-diethylphosphono)furanyl]imidazole was subjected to Step C of Example 3 to give 2-hydroxy-5-isobutyl-4-[2-(5-phosphono)furanyl]imidazole (10.14). mp 205° C. (decomp). Anal. Calcd. for $C_{11}H_{15}N_2O_5P$: C: 46.16; H: 5.28; N: 9.79. Found: C: 45.80; H: 4.90; N: 9.73.

Alternatively 4-[2-(5-phosphono)furanyl]oxazoles and 4-[2-(5-phosphono)furanyl]imidazoles can be prepared as following:

Step D.

A solution of 5-diethylphosphono-2-[(2-bromo-4-methyl-1-oxo)pentyl]furan (1 mmole) in acetic acid was treated with sodium acetate (2 mmole) and ammonium acetate (2 mmole) at 100° C. for 4 h. Evaporation and chromatography gave 2-methyl-5-isobutyl-4-[2-(5-diethylphosphono)furanyl]-oxazole, 2-methyl-4-isobutyl-5-[2-(5-diethylphosphono)furanyl]oxazole and 2-methyl-5-isobutyl-4-[2-(5-diethylphosphono)furanyl]imidazole.

Step E.

2-Methyl-5-isobutyl-4-[2-(5-diethylphosphono)furanyl]oxazole, 2-methyl-4-isobutyl-5-[2-(5-diethylphosphono)furanyl]oxazole and 2-methyl-5-isobutyl-4-[2-(5-diethylphosphono)furanyl]imidazole were subjected to Step C of Example 3 to give the following compounds:

(10.18) 2-Methyl-4-isobutyl-5-[2-(5-phosphono)furanyl]oxazole hydrogen bromide. mp>230° C.; Anal. Calcd. for $C_{12}H_{17}BrNO_5P+0.4H_2O$: C: 38.60; H: 4.81; N: 3.75. Found: C: 38.29; H: 4.61; N: 3.67.

(10.19) 2-Methyl-5-isobutyl-4-[2-(5-phosphono)furanyl]oxazole hydrogen bromide. Anal. Calcd. for $C_{12}H_{17}BrNO_5P$: C: 39.36; H: 4.68; N: 3.83. Found: C: 39.33; H: 4.56; N: 3.85.

(10.21) 2-Methyl-5-isobutyl-4-[2-(5-phosphono)furanyl]imidazole hydrogen bromide. Anal. Calcd. for $C_{12}H_{18}BrN_2O_4P+0.2NH_4Br$: C: 37.46; H: 4.93; N: 8.01. Found: C: 37.12; H: 5.11; N: 8.28.

Alternatively 4-[2-(5-phosphono)furanyl]imidazoles can be prepared as following:

Step F.

A solution of 5-diethylphosphono-2-(bromoacetyl)furan (1 mmole) in ethanol was treated with trifluoroacetamidine (2 mmole) at 80° C. for 4 h. Evaporation and chromatography gave 2-trifluoromethyl-4-[2-(5-diethylphosphono)furanyl]imidazole as an oil.

Step G.

2-Trifluoromethyl-4-[2-(5-diethylphosphono)furanyl]imidazole was subjected to Step C of Example 3 to give 2-trifluoromethyl-4-[2-(5-phosphono)-furanyl]imidazole (10.22). mp 188° C. (dec.); Anal. Calcd. for $C_8H_6F_3N_2O_4P+0.5HBr$: C: 29.79; H: 2.03; N: 8.68. Found: C: 29.93; H: 2.27; N: 8.30.

Alternatively 4,5-dimethyl-1-isobutyl-2-[2-(5-phosphono)furanyl]-imidazole can be prepared as following:

Step H.

A solution of 5-diethylphosphono-2-furaldehyde (1 mmole), ammonium acetate (1.4 mmole), 3,4-butanedione (3 mmole) and isobutylamine (3 mmole) in glacial acetic acid was heated at 100° C. for 24 h. Evaporation and chromatography gave 4,5-dimethyl-1-isobutyl-2-[2-(5-diethylphosphono)furanyl]imidazole as an yellow solid.

Step I. 4,5-Dimethyl-1-isobutyl-2-[2-(5-diethylphosphono)furanyl]-imidazole was subjected to Step C of Example 3 to give 4,5-dimethyl-1-isobutyl-2-[2-(5-phosphono)furanyl]imidazole (10.23); Anal. Calcd. for $C_{13}H_{19}N_2O_4P+1.35HBr$: C: 38.32; H: 5.03; N: 6.87. Found: C: 38.09; H: 5.04; N: 7.20.

According to the above procedures or in some cases with some minor modifications of the above procedures, the following compounds were prepared:

(10.2) 2-Amino-5-propyl-4-[2-(5-phosphono)furanyl]oxazole. mp 250° C. (decomp.); Anal. Calcd. for $C_{10}H_{13}N_2O_5P$: C: 44.13; H: 4.81; N: 10.29. Found: C: 43.74; H: 4.69; N: 9.92.

(10.3) 2-Amino-5-ethyl-4-[2-(5-phosphono)furanyl]oxazole. Anal. Calcd. for $C_9H_{11}N_2O_5P+0.4H_2O$: C: 40.73; H: 4.48; N: 10.56. Found: C: 40.85; H: 4.10; N: 10.21.

(10.4) 2-Amino-5-methyl-4-[2-(5-phosphono)furanyl]oxazole. Anal. Calcd. for $C_8H_9N_2O_5P+0.1H_2O$: C: 39.07; H: 3.77; N: 11.39. Found: C: 38.96; H: 3.59; N: 11.18.

(10.5) 2-Amino-4-[2-(5-phosphono)furanyl]oxazole. Anal. Calcd. for $C_7H_7N_2O_5P+0.6H_2O$: C: 34.90; H: 3.43; N: 11.63. Found: C: 34.72; H: 3.08; N: 11.35.

(10.6) 2-Amino-5-isobutyl-4-[2-(5-phosphono)furanyl]oxazole hydrogen bromide. Anal. Calcd. for $C_{11}H_{16}N_2O_5BrP+0.4H_2O$: C: 35.29; H: 4.52; N: 7.48. Found: C: 35.09; H: 4.21; N: 7.34.

(10.7) 2-Amino-5-phenyl-4-[2-(5-phosphono)furanyl]oxazole. Anal. Calcd. for $C_{13}H_{11}N_2O_5P$: C: 50.99; H: 3.62; N: 9.15. Found: C: 50.70; H: 3.43; N: 8.96.

(10.8) 2-Amino-5-benzyl-4-[2-(5-phosphono)furanyl]oxazole. Anal. Calcd. for $C_{14}H_{13}N_2O_5P+1.1H_2O$: C: 49.45; H: 4.51; N: 8.24. Found: C: 49.35; H: 4.32; N: 8.04.

(10.9) 2-Amino-5-cyclohexylmethyl-4-[2-(5-phosphono)furanyl]oxazole. Anal. Calcd. for $C_{14}H_{19}N_2O_5P+0.3H_2O$: C: 50.70; H: 5.96; N: 8.45. Found: C: 50.60; H: 5.93; N: 8.38.

(10.10) 2-Amino-5-allyl-4-[2-(5-phosphono)furanyl]oxazole. Anal. Calcd. for $C_{10}H_{11}N_2O_5P+0.4HBr+0.3H_2O$: C: 39.00; H: 3.93; N: 9.10. Found: C: 39.31; H: 3.83; N: 8.76.

(10.11) 5-Isobutyl-4-[2-(5-phosphono)furanyl]oxazole. Anal. Calcd. for $C_{11}H_{14}NO_5P$: C: 48.72; H: 5.20; N: 5.16. Found: C: 48.67; H: 5.02; N: 5.10.

(10.12) 2-Amino-5-butyl-4-[2-(5-phosphono)furanyl]oxazole. Anal. Calcd. for $C_{11}H_{15}N_2O_5P+0.2H_2O$: C: 45.59; H: 5.36; N: 9.67. Found: C: 45.32; H: 5.29; N: 9.50.

(10.13) 5-Isobutyl-4-[2-(5-phosphono)furanyl]oxazole-2-one. Anal. Calcd. for $C_{11}H_{14}NO_6P+0.39HBr$: C: 41.45; H: 4.55; N: 4.39. Found: C: 41.79; H: 4.22; N: 4.04.

(10.15) 5-Cyclohexylmethyl-2-hydroxy-4-[2-(5-phosphono)furanyl]imidazole. Anal. Calcd. for $C_{14}H_{19}N_2O_5P+0.05HBr$: C: 50.90; H:5.81; N:8.48. Found: C: 51.06; H: 5.83; N: 8.25.

(10.16) 5-Butyl-2-hydroxy-4-[2-(5-phosphono)furanyl]. Anal. Calcd. for $C_{11}H_{15}N_2O_5P+0.2H_2O$: C: 45.59; H: 5.36; N: 9.67. Found: C: 45.77; H: 5.34; N: 9.39.

(10.17) 5-Benzyl-2-hydroxy-4-[2-(5-phosphono)furanyl]imidazole. Anal. Calcd. for $C_{14}H_{13}N_2O_5P$: C: 52.51; H: 4.09; N: 8.75. Found: C: 52.29; H: 4.15; N: 8.36.

(10.20) 2-Methyl-5-propyl-4-[2-(5-phosphono)furanyl]imidazole hydrogen bromide. Anal. Calcd. for $C_{11}H_{16}BrN_2O_4P+0.5H_2O$: C: 36.69; H: 4.76; N: 7.78. Found: C: 36.81; H: 4.99; N: 7.42.

(10.24) 2-Amino-5-(2-thienylmethyl)-4-[2-(5-phosphono)furanyl]oxazole. Anal. calcd for $C_{12}H_{11}N_2O_5PS+0.9HBr$: C: 36.12; H: 3.01; N: 7.02. Found: C: 36.37; H: 2.72; N: 7.01.

(10.25) 2-Dimethylamino-5-isobutyl-4-[2-(5-phosphono)furanyl]oxazole hydrogen bromide. Anal. Calcd for $C_{13}H_{20}BrN_2O_5P+0.05HBr$: C: 39.11; H: 5.06; N: 7.02. Found: C: 39.17; H: 4.83; N: 6.66.

(10.26) 2-Isopropyl-5-isobutyl-4-[2-(5-phosphono)furanyl]oxazole. Anal. Calcd for $C_{14}H_{20}NO_5P+0.8HBr$: C: 44.48; H: 5.55; N: 3.71. Found: C: 44.45; H: 5.57; N: 3.73.

(10.27) 2-Amino-5-ethoxycarbonyl-4-[2-(5-phosphono)furanyl]oxazole. mp 245° C. (decomp.). Anal. Calcd for $C_{10}H_{11}N_2O_7P$: C: 39.75; H: 3.67; N: 9.27. Found: C: 39.45; H: 3.71; N: 8.87.

(10.28) 2-Methylamino-5-isobutyl-4-[2-(5-phosphono)furanyl]oxazole hydrogen bromide. Anal. Calcd for $C_{12}H_{18}BrN_2O_5P+0.7H_2O$: C: 36.60; H: 4.97; N: 7.11. Found: C: 36.50; H: 5.09; N: 7.04.

(10.29) 2-Ethyl-5-isobutyl-4-[2-(5-phosphono)furanyl]oxazole hydrogen bromide. Anal. Calcd for $C_{13}H_{19}BrNO_5P$: C: 41.07; H: 5.04; N: 3.68. Found: C: 41.12; H: 4.84; N: 3.62.

(10.30) 2-Ethylamino-5-isobutyl-4-[2-(5-phosphono)furanyl]oxazole hydrogen bromide. Anal. Calcd for $C_{13}H_{20}BrN_2O_5P$: C: 39.51; H: 5.10; N: 7.09. Found: C: 39.03; H: 5.48; N: 8.90.

(10.31) 2-Vinyl-5-isobutyl-4-[2-(5-phosphono)furanyl]oxazole. Anal. Calcd for $C_{13}H_{16}NO_5P+0.25HBr$: C: 49.18; H: 5.16; N: 4.41. Found: C: 48.94; H: 5.15; N: 4.40.

(10.32) 2-Amino-5-pentyl-4-[2-(5-phosphono)furanyl]oxazole. Anal. Calcd for $C_{12}H_{17}N_2O_5P+0.5H_2O$: C: 46.61; H: 5.87; N: 9.06. Found: C: 46.38; H: 5.79; N: 9.07.

(10.33) 5-Pentyl-2-hydroxy-4-[2-(5-phosphono)furanyl]imidazole. Anal. Calcd. for $C_{12}H_{17}N_2O_5P$: C: 48.00; H: 5.71; N: 9.33. Found: C: 48.04; H: 5.58; N: 9.26.

(10.45) 2-Amino-5-methylthio-4-[2-(5-phosphono)furanyl]oxazole. mp 196° C. (decomp). Anal. calcd. for $C_8H_9N_2O_5PS$: C:34.79; H:3.28; N: 10.14. Found: C: 34.60; H: 2.97; N: 10.00.

(10.35) 2-Amino-5-benzyloxycarbonyl-4-[2-(5-phosphono)furanyl]oxazole. mp 230° C. (decomp). Anal. calcd for $C_{15}H_{13}N_2O_7P+0.7H_2O$: C: 47.81; H: 3.85; N: 7.43. Found: C: 47.85; H: 3.88; N: 7.21.

(10.36) 2-Amino-5-isopropyloxycarbonyl-4-[2-(5-phosphono)furanyl]oxazole. mp 221° C. (decomp). Anal. calcd for $C_{11}H_{13}N_2O_7P+0.9H_2O$: C: 39.75; H: 4.49; N: 8.43. Found: C: 39.72; H: 4.25; N: 8.20.

(10.37) 2-Amino-5-methoxycarbonyl-4-[2-(5-phosphono)furanyl]oxazole. mp 240° C. (decomp). Anal. calcd for $C_9H_9N_2O_7P+0.3H_2O+0.1Acetone$: C: 37.31; H: 3.43; N: 9.36. Found: C: 37.37; H: 3.19; N: 9.01.

(10.38) 2-Amino-5-[(N-methyl)carbamoyl]-4-[2-(5-phosphono)furanyl]oxazole. mp 235° C. (decomp). Anal. calcd for $C_9H_{10}N_3O_6P$: C: 37.64; H: 3.51; N: 14.63. Found: C: 37.37; H: 3.22; N: 14.44.

(10.39) 2-Amino-5-ethylthiocarbonyl-4-[2-(5-phosphono)furanyl]oxazole. mp 225° C. (decomp). Anal. calcd for $C_{10}H_{11}N_2O_6PS$: C: 37.74; H: 3.48; N: 8.80. Found: C: 37.67; H: 3.27; N: 8.46.

(10.40) 2-Amino-5-isopropylthio-4-[2-(5-phosphono)furanyl]oxazole. Anal. calcd for $C_{10}H_{13}N_2O_5PS+0.2HBr$: C: 37.48; H: 4.15; N: 8.74. Found: C: 37.39; H: 4.11; N: 8.56.

(10.41) 2-Amino-5-phenylthio-4-[2-(5-phosphono)furanyl]oxazole. Anal. calcd for $C_{13}H_{11}N_2O_5PS+0.25$ HBr: C: 43.55; H: 3.16; N: 7.81. Found: C: 43.82 H: 3.28; N: 7.59.

(10.42) 2-Amino-5-ethylthio-4-[2-(5-phosphono)furanyl]oxazole. Anal. calcd for $C_9H_{11}N_2O_5PS+0.85HBr$: C: 30.11; H: 3.33; N: 7.80. Found: C: 30.18; H: 3.44; N: 7.60.

(10.43) 2-Amino-5-propylthio-4-[2-(5-phosphono)furanyl]oxazole. Anal. calcd for $C_{10}H_{13}N_2O_5+H_2O$: C: 37.27; H: 4.69; N: 8.69; $H_2O$; 5.59. Found: C: 37.27; H: 4.67; N: 8.60; $H_2O$; 5.66.

(10.44) 2-Amino-5-tert-butylthio-4-[2-(5-phosphono)furanyl]oxazole. Anal. calcd for $C_{11}H_{15}N_2O_5PS+0.25HBr$: C: 39.03; H: 4.54; N: 8.28. Found: C: 39.04; H: 4.62; N: 8.06.

(10.34) 4,5-Dimethyl-2-[2-(5-phosphono)furanyl]imidazole. Anal. Calcd. for $C_9H_{11}N_2O_4P+1.25 H_2O$: C: 40.84; H:5.14; N: 10.58. Found: C: 41.02; H: 5.09; N: 10.27.

Example 11

Preparation of N-alkylated 4-[2-(5-phosphono)furanyl]imidazoles and 4-[2-(5-phosphono)furanyl]oxazoles Step A.

A suspension of cesium carbonate (1.5 mmole) and 2-methyl-5-isobutyl-4-[2-(5-diethylphosphono)furanyl]

imidazole (1 mmole) in DMF was treated with iodomethane (1.5 mmole) at 25° C. for 16 h. Extraction and chromatography gave 1,2-dimethyl-4-isobutyl-5-[2-(5-diethylphosphono)-furanyl]imidazole and 1,2-dimethyl-5-isobutyl-4-[2-(5-diethylphosphono)-furanyl]imidazole.

Step B.

1,2-Dimethyl-4-isobutyl-5-[2-(5-diethylphosphono) furanyl]-imidazole and 1,2-dimethyl-5-isobutyl-4-[2-(5-diethylphosphono)furanyl]-imidazole were subjected to Step C of Example 3 to give the following compounds:

(11.1) 1,2-Dimethyl-5-isobutyl-4-[2-(5-phosphono)furanyl] imidazole hydrogen bromide. Anal. Calcd. for $C_{13}H_{20}N_2O_4PBr+0.8H_2O$: C: 39.67; H: 5.53; N: 7.12. Found: C: 39.63; H: 5.48; N: 7.16.

Example 12

Preparation of 2-[2-(6phosphono)pyridyl]pyridine

Step A.

A solution of 2,2'-bipyridyl (1 mmole) in dichloromethane was treated with m-chloroperoxybenzoic acid (2 mmole) at 0° C., and the reaction mixture was stirred at 25° C. for 2 h. Extraction and chromatography gave 2,2'-bipyridyl-N-oxide.

Step B.

(Redmore, D., *J. Org. Chem.*, 1970, 35, 4114) A solution of 2,2'-bipyridyl-N-oxide methyl ether (1 mmole, prepared from dimethyl sulfate and 2,2'-bipyridyl-N-oxide in diethyl phosphite) was added slowly at −30° C. to a solution of n-butyl lithium (1 mmole) in diethyl phosphite at −30° C. The resulting reaction mixture was stirred at 25° C. for 12 h. Extraction and chromatography gave 2-[2-(6-diethylphosphono)pyridyl]pyridine.

Step C.

2-[2-(6-Diethylphosphono)pyridyl]pyridine was subjected to Step C of Example 3 to give 2-[2-(6-phosphono) pyridyl]pyridine (12.1). mp 158–162° C. Anal. Calcd. for $C_{10}H_9N_2O_3P+0.5H_2O+0.1HBr$: C: 47.42; H: 4.02; N: 11.06. Found: C: 47.03; H: 3.67; N: 10.95.

Example 13

Preparation of 4,6-dimethyl-2-(phosphonomethoxymethyl)pyridine

Step A.

A solution of 2,4,6-collidine (1 mmole) in carbon tetrachloride was treated with NBS (5 mmole) and dibenzoyl peroxide (0.25 mmole) at 80° C. for 12 h. The reaction mixture was cooled to 0° C. and the precipitate was filtered. The filtrate was concentrated under vacuum. Chromatography gave 2-bromomethyl-4,6-dimethylpyridine.

Step B.

A solution of diethyl hydroxymethylphosphonate (1 mmole) in toluene was treated with sodium hydride (1.1 mmole) at 0° C., and after 15 min 2-bromomethyl-4,6-dimethylpyridine (1 mmole) was added. After 3 h the reaction mixture was subjected to extraction and chromatography to give 2-diethylphosphonomethyl-4,6-dimethylpyridine.

Step C.

2-Diethylphosphonomethyl-4,6-dimethylpyridine was subjected to Step C of Example 3 to give 4,6-dimethyl-2-(phosphonomethoxymethyl)pyridine (13.1). mp 109–112° C. Anal. Calcd. for $C_9H_{14}NO_4P+1.0H_2O+0.5HBr$: C: 37.32; H: 5.74; N: 4.84. Found: C: 37.18; H: 5.38; N: 4.67.

The following compound was prepared similarly:

(13.2) 2-Amino-4-methyl-5-propyl-6-phosphonomethoxymethylpyrimidine. mp 153–156° C. Anal. Calcd. for $C_{10}H_{18}N_3O_4P+1.25H_2O+1.6HBr$: C: 28.11; H: 5.21; N: 9.84. Found: C: 28.25; H: 4.75; N: 9.74.

Example 14

Preparation of diethyl 5-tributylstannyl-2-furanphosphonate (14)

A solution of diethyl 2-furanphosphonate (1 mmole, prepared as in Step C of Example 1) in THF was cooled at −78° C. and cannulated to a solution of lithium N-isopropyl-N-cyclohexylamine in THF at −78° C. over 15 min. The resulting mixture was stirred at −78° C. for 2 h and cannulated into a solution of tributyltin chloride (1 mmole) in THF at −78° C. over 20 min. The mixture was then stirred at −78° C. for 1 h, and at 25° C. for 12 h. Extraction and chromatography gave compound (14) as a light yellow oil.

Example 15

Preparation of 6-[2-(5-phosphono)furanyl]pyridines

Step A.

A solution of 2,6-dichloropyridine (120 mmol) in ethanol was treated with aqueous ammonia solution (28%, excess) at 160–165° C. for 60 h in a sealed tube. Extraction and chromatography gave 2-amino-6-chloropyridine as a white solid.

Step B.

A solution of 2-amino-6-chloropyridine (1 mmole) and compound 14 (1 mmole) in p-xylene was treated with tetrakis(triphenylohosphine) palladium (0.05 mmole) at reflux for 12 h. Extraction and chromatography gave 2-amino-6-[2-(5-diethylphosphono)furanyl]pyridine as a light yellow solid.

Step C.

2-Amino-6-[2-(5-diethylphosphono)furanyl]pyridine was subjected to Step C of Example 3 to give 2-amino-6-[2-(5-phosphono)furanyl]pyridine (15.1). mp 186–187° C. Anal. Calcd. for $C_9H_9N_2O_4P+0.4HBr$: C: 39.67; H: 3.48; N: 10.28. Found: C: 39.95; H: 3.36; N: 10.04.

Step D.

A solution of 2-amino-6-[2-(5-diethylphosphono)furanyl] pyridine (1 mmole) in acetic acid was treated with a solution of bromine in acetic acid (1N, 1 mmole) at 25° C. for 0.5 h. Evaporation and chromatography gave 2-amino-5-bromo-6-[2-(5-diethylphosphono)furanyl]pyridine and 2-amino-3,5-dibromo-6-[2-(5-diethylphosphono)furanyl]pyridine.

Step E.

2-Amino-5-bromo-6-[2-(5-diethylphosphono)furanyl] pyridine and 2-amino-3,5-dibromo-6-[2-(5-diethylphosphono)furanyl]pyridine were subjected to Step C of Example 3 to give the following compounds:

(15.2) 6-Amino-3-bromo-2-[2-(5-phosphono)furanyl] pyridine. Anal. Calcd. for $C_9H_8BrN_2O_4P+0.7H_2O+0.9HBr+0.12PhCH_3$: C: 28.44; H: 2.73; N: 6.74. Found: C: 28.64; H: 2.79; N: 6.31.

(15.3) 6-Amino-3,5-dibromo-2-[2-(5-phosphono)furanyl] pyridine. mp 233–235° C. Anal. Calcd. for $C_9H_7Br_2N_2O_4P+1.2HBr$: C: 21.84; H: 1.67; N: 5.66. Found: C: 21.90; H: 1.52; N: 5.30.

Step F.

A solution of 2-amino-3,5-dibromo-6-[2-(5-diethylphosphono)-furanyl]pyridine (1 mmole) in DMF was treated with tributyl(vinyl)tin (1.2 mmole) and tetrakis (triphenylphosphine) palladium (0.2 mmole) at 85° C. for 4 h. Evaporation and chromatography gave 2-amino-3,5-bis (vinyl)-6-[2-(5-diethylphosphono)furanyl]pyridine.

Step G.

A solution of 2-amino-3,5-bis(vinyl)-6-[2-(5-diethylphosphono)-furanyl]pyridine (1 mmole) in ethyl acetate was treated with palladium on carbon (10%) at 25° C. under 1 atmosphere of hydrogen for 12 h. Filtration, evaporation and chromatography gave 2-amino-3,5-diethyl-6-[2-(5-diethylphosphono)furanyl]pyridine.

Step H.

2-Amino-3,5-diethyl-6-[2-(5-diethylphosphono)furanyl]pyridine was subjected to Step C of Example 3 to give 2-amino-3,5-diethyl-6-[2-(5-phosphono)furanyl]pyridine (15.4). mp 217–218° C. Anal. Calcd. for $C_{13}H_{17}N_2O_4P+0.7H_2O+1.0HBr$: C: 40.06; H: 5.02; N: 7.19. Found: C: 40.14; H: 4.70; N: 6.87.

Step I.

A solution of 2-amino-6-picoline (1 mmole) in 48% hydrobromic acid (4.4 mmole) was treated with bromine (3 mmole) at 0° C. for 1 h. An aqueous solution of sodium nitrite (2.5 mmole) was then added and the reaction mixture was stirred at 0° C. for 0.5 h. An aqueous solution of sodium hydroxide (9.4 mmole) was then added and the reaction mixture was stirred at 25° C. for 1 h. Extraction and chromatography gave 2,3-dibromo-6-picoline and 2,3,5-tribromo-6-picoline.

Step J.

2,3-Dibromo-6-picoline was subjected to Step B of Example 15 and followed by Step C of Example 3 to give 5-bromo-2-methyl-6-[2-(5-phosphono)furanyl]pyridine (15.5). mp 207–208° C. Anal. Calcd. for $C_{10}H_9BrNO_4P+0.6HBr$: C: 32.76; H: 2.64; N: 3.88. Found: C: 32.62; H: 2.95; N: 3.55.

Following compounds were prepared according to the above described procedures or with some minor modifications of these procedures using conventional chemistry.

(15.6) 2-[2-(5-Phosphono)furanyl]pyridine. mp 220–221° C. Anal. Calcd. for $C_9H_8NO_4P+0.1H_2O+0.45HBr$: C: 41.05; H: 3.31; N: 5.32. Found: C: 41.06; H: 3.10; N: 5.10.

(15.7) 2-Amino-3-nitro-6-[2-(5-phosphono)furanyl]pyridine. mp 221–222° C. Anal. Calcd. for $C_9H_8N_3O_6P+0.55HBr+0.02PhCH_3$: C: 33.12; H: 2.65; N: 12.68. Found: C: 33.22; H: 2.43; N: 12.26.

(15.8) 2,3-Diamino-6-[2-(5-phosphono)furanyl]pyridine. mp 150–153° C. Anal. Calcd. for $C_9H_{10}N_3O_4P+1.5HBr+0.05PhCH_3$: C: 29.46; H: 3.15; N: 11.02. Found: C: 29.50; H: 3.29; N: 10.60.

(15.9) 2-Chloro-6-[2-(5-phosphono)furanyl]pyridine. mp 94–96° C. Anal. Calcd. for $C_9H_7ClNO_4P+0.25HBr$: C: 38.63; H: 2.61; N: 5.01. Found: C: 38.91; H: 3.00; N: 5.07.

(15.10) 3,5-Dichloro-2-[2-(5-phosphono)furanyl]pyridine. mp 180–181° C. Anal. Calcd. for $C_9H_6Cl_2NO_4P+0.7HBr$: C: 31.61; H: 2.01; N: 3.94. Found: C: 31.69; H: 2.09; N: 3.89.

(15.11) 3-Chloro-5-trifluoromethyl-2-[2-(5-phosphono)furanyl]pyridine. mp 253–254° C. Anal. Calcd. for $C_{10}H_6ClF_3NO_4P$: C: 36.67; H: 1.85; N: 4.28. Found: C: 36.69; H: 1.89; N: 4.30.

(15.12) 2-Amino-3-ethyl-6-[2-(5-phosphono)furanyl]pyridine. mp 220–221° C. Anal. Calcd. for $C_{11}H_{13}N_2O_4P+0.6HBr+0.2H_2O$: C: 41.24; H: 4.40; N: 8.74. Found: C: 41.02; H: 4.57; N: 8.68.

(15.13) 6-Amino-3-ethyl-2-[2-(5-phosphono)furanyl]pyridine. Anal. Calcd. for $C_{11}H_{13}N_2O_4P+1.0HBr+0.3H_2O$: C: 37.27; H: 4.15; N: 7.90. Found: C: 37.27; H: 4.19; N: 7.51.

(15.14) 6-Amino-3-propyl-2-[2-(5-phosphono)furanyl]pyridine. mp 252–253° C. Anal. Calcd. for $C_{12}H_{15}N_2O_4P+1.0HBr+1.0H_2O+0.32PhCH_3$: C: 41.65; H: 5.05; N: 6.82. Found: C: 41.97; H: 5.19; N: 6.83.

(15.15) 2,4-Dimethyl-3-bromo-6-[2-(5-phosphono)furanyl]pyridine. mp 232–233° C. Anal. Calcd. for $C_{11}H_{11}BrNO_4P+0.45HBr$: C: 35.85; H: 3.13; N: 3.80. Found: C: 35.98; H: 3.10; N: 3.71.

(15.16) 2-Chloro-4-amino-6-[2-(5-phosphono)furanyl]pyridine. Anal. Calcd. for $C_9H_8N_2O_4PCl+HBr+0.5 H_2O+MeOH$: C: 30.99; H: 3.38; N: 7.23. Found: C: 31.09; H: 3.21; N: 6.96.

(15.17) 3-Hydroxyl-2-[2-(5-phosphono)furanyl]pyridine. Anal. Calcd. for $C_9H_8NO_5P+1.1HBr+0.3\ CH_3Ph$: C: 37.26; H: 3.24; N: 3.91. Found: C: 37.66; H: 3.55; N: 3.84.

(15.19) 2-Amino-3-cyclopropyl-6-[2-(5-phosphono)furanyl]pyridine. Anal. Calcd. for $C_{12}H_{13}N_2O_4PCl+HBr+0.4\ H_2O$: C: 39.13; H: 4.05; N: 7.61. Found: C: 39.06; H: 3.85; N: 7.37.

(15.20) 2-Amino-5-cyclopropyl-6-[2-(5-phosphono)furanyl]pyridine. Anal. Calcd. for $C_{12}H_{13}N_2O_4P+HBr+0.7\ CH_3Ph$: C: 47.69; H: 4.64; N: 6.58. Found: C: 47.99; H: 4.62; N: 6.91.

(15.21) 5-Amino-2-methoxy-6-[2-(5-phosphono)furanyl]pyridine. Anal. Calcd. for $C_{10}H_{11}N_2O_5P+0.2\ H_2O$: C: 43.87; H: 4.20; N: 10.23. Found: C: 43.71; H: 3.77; N: 9.77.

(15.22) 2-Methyl-5-cyano-6-[2-(5-phosphono)furanyl]pyridine. Anal. Calcd. for $C_{11}H_9N_2O_4P+0.75\ HBr+0.5\ H_2O+0.5\ MePh$: C: 45.84; H: 3.91; N: 7.37. Found: C: 45.93; H: 3.56; N: 7.36.

(15.23) 2-Amino-3,5-bis(cyano)-4-methyl-6-[2-(5-phosphono)furanyl]pyridine. Anal. Calcd. for $C_{12}H_9N_4O_4P+0.7\ H_2O$: C: 45.49; H: 3.31; N: 17.68. Found: C: 45.48; H: 3.06; N: 17.51.

(15.24) 2-Chloro-4-cyano-6-[2-(5-phosphono)furanyl]pyridine. Anal. Calcd. for $C_{10}H_6N_2O_4PCl$: C: 42.20; H: 2.13; N: 9.84. Found: C: 41.95; H: 2.10; N: 9.47.

Example 16

Preparation of 2-[2-(5-phosphono)furanyl]pyrimidines and 4-[2-(5-phosphono)furanyl]pyrimidines Step A.

A solution of 5-diethylphosphono-2-[(1-oxo)pentyl]furan in N,N-dimethylformamide dimethyl acetal was heated at reflux for 12 h. Evaporation and chromatography gave diethyl 5-(2-propyl-3-N,N-dimethylamino)acryloyl-2-furanphosphonate.

Step B.

A solution of diethyl 5-(2-propyl-3-N,N-dimethylamino)acryloyl-2-furanphosphonate (1 mmole) in ethanol was treated with guanidine hydrogen chloride (1.2 mmole) and sodium ethoxide (1 mmole) at 80° C. for 12 h. The reaction mixture was evaporated, and residue was dissolved in water. The aqueous solution was neutralized with HCl (2 N), and concentrated under reduced pressure. The residue was co-evaporated with toluene to give 2-amino-5-propyl-4-[2-(5-ethylphosphono)-furanyl]pyrimidine as a yellow solid.

Step C.

2-Amino-5-propyl-4-[2-(5-ethylphosphono)furanyl]pyrimidine (1 mmole) and thionyl chloride was heated at reflux for 2 h. The reaction mixture was evaporated to dryness and the residue was dissolved in methylene chloride, and treated with excess pyridine and ethanol at 25° C. for 12 h. Evaporation and chromatography gave 2-amino-5-propyl-4-[2-(5-diethylphosphono)furanyl]pyrimidine.

Step D.

2-Amino-5-propyl-4-[2-(5-diethylphosphono)furanyl]pyrimidine was subjected to Step C of Example 3 to give 2-amino-5-propyl-4-[2-(5-phosphono)furanyl]pyrimidine (16.1). mp 258–259° C. Anal. Calcd. for $C_{11}H_{14}N_3O_4P+1.33H_2O$: C: 43.01; H: 5.47; N: 13.68. Found: C: 43.18; H: 5.31; N: 13.30.

The following compound was prepared according to this procedure:

(16.2) 2-Amino-5-isobutyl-4-[2-(5-phosphono)furanyl]pyrimidine. mp 218–220° C. Anal. Calcd. for $C_{12}H_{16}N_3O_4P+0.75HBr+0.3PhCH_3$: C: 43.92; H: 5.01; N: 10.90. Found: C: 44.02; H: 4.62; N: 10.69.

Alternatively other 4-[2-(5-phosphono)furanyl]pyrimidines can be prepared according to the following procedures:

Step E.

Compound 2.2 was subjected to Step A of Example 16 to give diethyl 5-(3-N,N-dimethylamino)acryloyl-2-furanphosphonate as an orange solid.

Step F.

A solution of diethyl 5-(3-N,N-dimethylamino)acryloyl-2-furanphosphonate (1 mmole), sodium ethoxide ethanol solution (2 mmole) and guanidine hydrochloride (1.1 mmole) was heated at 55° C. for 2 h. The reaction mixture was cooled in an ice bath and was neutralized with 1N HCl. Evaporation and chromatography gave 2-amino-4-[2-(5-diethylphosphono)-furanyl]pyrimidine as a yellow solid.

Step G.

2-Amino-4-[2-(5-diethylphosphono)furanyl]pyrimidine was subjected to Step C of Example 3 to give 2-amino-4-[2-(5-phosphono)furanyl]-pyrimidine (16.3). mp>230° C. Anal. Calcd. for $C_8H_8N_3O_4P+0.75H_2O+0.2HBr$: C: 35.48; H: 3.61; N: 15.51. Found: C: 35.42; H: 3.80; N: 15.30.

Step H.

A solution of 2-amino-4-[2-(5-diethylphosphono)furanyl]pyrimidine (1 mmole) in methanol and chloroform was treated with NBS (1.5 mmole) at 25° C. for 1 h. Extraction and chromatography gave 2-amino-5-bromo-4-[2-(5-diethylphosphono)furanyl]pyrimidine as a yellow solid.

Step I.

2-Amino-5-bromo-4-[2-(5-diethylphosphono)furanyl]pyrimidine was subjected to Steps F and G of Example 15 followed by Step C of Example 3 to give 2-amino-5-ethyl-4-[2-(5-phosphono)furanyl]pyrimidine (16.4). mp>225° C. Anal. Calcd. for $C_{10}H_{12}N_3O_4P+1.4H_2O+0.2HBr+0.25PhCH_3$: C: 42.30; H: 5.14; N: 12.59. Found: C: 42.74; H: 4.94; N: 12.13.

The following compounds were prepared according to the above described procedures or with some minor modifications using conventional chemistry:

(16.5) 2-[2-(5-Phosphono)furanyl]pyrimidine. mp 194–196° C. Anal. Calcd. for $C_8H_7N_2O_4P+0.1H_2O+0.55HBr$: C: 35.27; H: 2.87; N: 10.28. Found: C: 35.26; H: 2.83; N: 9.89.

(16.6) 2-Amino-6-methyl-4-[2-(5-phosphono)furanyl]pyrimidine. mp 238–239° C. Anal. Calcd. for $C_9H_{10}N_3O_4P+0.9HBr$: C: 32.96; H: 3.35; N: 12.81. Found: C: 33.25; H: 3.34; N: 12.46.

(16.7) 2-Methylthio-4-[2-(5-phosphono)furanyl]pyrimidine. mp 228–229° C. Anal. Calcd. for $C_9H_9N_2O_4PS+0.5H_2O$: C: 38.44; H: 3.58; N: 9.96. Found: C: 38.19; H: 3.25; N: 9.66.

(16.8) 2-Methyl-4-[2-(5-phosphono)furanyl]pyrimidine. mp 206–212° C. Anal. Calcd. for $C_9H_9N_2O_4P+0.9H_2O+0.25HBr$: C: 34.05; H: 3.30; N: 8.82. Found: C: 34.02; H: 3.06; N: 8.75.

(16.9) 4,6-Dimethyl-5-bromo-2-[2-(5-phosphono)furanyl]pyrimidine. mp 251–252° C. Anal. Calcd. for $C_{10}H_{10}BrN_2O_4P$: C: 36.06; H: 3.03; N: 8.41. Found: C: 35.89; H: 2.82; N: 8.11.

(16.10) 2-Amino-5-chloro-4-[2-(5-phosphono)furanyl]pyrimidine. Anal. Calcd. for $C_8H_7ClN_3O_4P+0.5H_2O$: C: 33.76; H: 2.83; N: 14.76. Found: C: 33.91; H: 2.86; N: 14.20.

(16.11) 2-Amino-6-methylthio-4-[2-(5-phosphono)furanyl]pyrimidine. Anal. Calcd. for $C_9H_{10}N_3O_4PS+HBr$: C: 29.36; H: 3.01; N: 11.41. Found: C: 29.63; H: 3.02; N: 11.27.

(16.12) 2-Amino-5-bromo-6-methylthio-4-[2-(5-phosphono)furanyl]pyrimidine. Anal. Calcd. for $C_9H_9N_3O_4PSBr+0.8$ HBr+0.2 MePh: C: 27.80; H: 2.56; N: 9.35. Found: C: 27.74; H: 2.40; N: 8.94.

(16.13) 2-Amino-(4-morpholino)-4-[2-(5-phosphono)furanyl]pyrimidine. Mp>230° C. Anal. Calcd. for $C_{12}H_{15}N_4O_5P+HBr+0.05$ MePh: C: 36.02; H: 4.01; N: 13.61. Found: C: 35.98; H: 4.04; N: 13.33.

(16.14) 6-Amino-4-chloro-2-[2-(5-phosphono)furanyl]pyrimidine. Mp>230° C. Anal. Calcd. for $C_8H_7N_3O_4PCl+0.5 H_2O$: C: 33.76; H: 2.83; N: 14.76. Found: C: 33.83; H: 2.54; N: 14.48.

Example 17

Preparation of 2-[2-(5-phosphono)furanyl]pyrazines and 2-[2-(5-phosphono)furanyl]triazines Step A.

The procedures described in Example 16 can also be applied to the synthesis of 2-[2-(5-phosphono)furanyl]pyrazine and 2-[2-(5-phosphono)furanyl]triazine analogs and in some cases with minor modifications of these procedures using conventional chemistry methods. The following compounds were prepared accordingly:

(17.1) 2,5-Dimethyl-3-[2-(5-phosphono)furanyl]pyrazine. mp 212–213° C. Anal. Calcd. for $C_{10}H_{11}N_2O_4P+0.75HBr$: C: 38.15; H: 3.76; N: 8.90. Found: C: 38.41; H: 3.93; N: 8.76.

(17.2) 2-Chloro-6-[2-(5-phosphono)furanyl]pyrazine. mp 204–205° C. Anal. Calcd. for $C_8H_6ClN_2O_4P+0.3HBr+0.02PhCH_3$: C: 34.10; H: 2.27; N: 9.77. Found: C: 34.36; H: 2.07; N: 9.39.

(17.3) 2-Amino-3-propyl-6-[2-(5-phosphono)furanyl]pyrazine. mp 227–228° C. Anal. Calcd. for $C_{11}H_{14}N_3O_4P+0.7HBr$: C: 38.87; H: 4.36; N: 12.36. Found: C: 39.19; H: 4.36; N: 11.92.

(17.4) 2-Amino-6-[2-(5-phosphono)furanyl]pyrazine. mp 235–236° C. Anal. calcd. for $C_8H_8N_3O_4P+1.15H_2O+0.03PhCH_3$; C: 37.26; H: 4.01; N: 15.88. Found C: 37.09; H: 3.67; N: 15.51.

(17.5) 2-Amino-3-bromo-6-[2-(5-phosphono)furanyl]pyrazine. Anal. calcd. for $C_8H_7N_3O_4PBr+1HBr$: C: 23.97; H: 2.01; N: 10.48. Found: C: 24.00; H: 2.00; N: 10.13.

(17.6) 3-Methylthio-2-[2-(5-phosphono)furanyl]pyrazine. Anal. calcd. for $C_9H_9N_2O_4PS+0.3$ $H_2O$: C: 38.94; H: 3.49; N: 10.09. Found: C: 38.99; H: 3.11; N: 9.67.

(17.7) 6-Amino-3-methylthio-2-[2-(5-phosphono)furanyl]pyrazine. Anal. calcd. for $C_9H_{10}N_3O_4PS+1.5$ $H_2O+1.7$ HBr+0.25 MePh: C: 27.19; H: 3.54; N: 8.85. Found: C: 27.10; H: 3.85; N: 8.49.

(17.8) 6-Amino-5-methylthio-2-[2-(5-phosphono)furanyl]pyrazine. Anal. calcd. for $C_9H_{10}N_3O_4PS+1.1$ HBr+0.05 MePh: C: 29.49; H: 3.04; N: 11.03. Found: C: 29.23; H: 2.79; N: 10.87.

(17.9) 6-Amino-5-methoxycarbonyl-3-chloro-2-[2-(5-phosphono)furanyl]pyrazine. Anal. calcd. for $C_{10}H_9N_3O_6PCl+0.3$ HBr+0.04 MePh: C: 34.15; H: 2.68; N: 11.62. Found C: 34.20; H: 2.90; N: 11.21.

(17.10) 6-Amino-3-methylthio-2-[2-(5-phosphono)furanyl]pyrazine ammonium salt. Anal. calcd. for $C_9H_{13}N_4O_4PS+0.8$ HBr: C: 29.30; H: 3.77; N: 15.18. Found: C: 29.03; H: 3.88; N: 15.08.

(17.11) 2-Amino-4-phenyl-6-[2-(5-phosphono)furanyl]triazine. Anal. calcd. for $C_{13}H_{11}N_4O_4P+HBr+0.1$ EtOAc: C: 39.45; H: 3.16; N: 13.73. Found: C: 39.77; H: 3.26; N: 13.48.

Example 18

Preparation of Analogs with X being Methoxycarbonyl, Methylthiocarbonyl, Methylaminocarbonyl and Methylcarbonylamino Preparations of 4-phosphonomethoxycarbonylthiazoles and 4-phosphonomethoxycarbonyloxazoles Step A.

A solution of 2-amino-4-ethoxycarbonylthiazole (1 mmole) in 1,4-dioxane (5 mL) was treated with di-tert-butyl dicarbonate (1.2 mmole), TMEDA (0.1 mmole) and DMAP (0.1 mmole) at room temperature. After the reaction was stirred for 20 h, it was evaporated to dryness. The residue was subjected to extraction to give 2-[N-Boc(amino)]-4-ethoxycarbonyl thiazole as a yellow solid.

Step B.

A solution of 2-[N-Boc(amino)]-4-ethoxycarbonylthiazole (1 mmole) in a 2:1 mixture of EtOH:$H_2O$ (10 mL) was treated with NaOH (3N, 3 mmole) and the reaction was stirred at 60° C. for 4 h. The reaction was cooled to 0° C. and neutralized to pH 5 with 3 N HCl, and the resulting solid was collected via filtration to give 2-[N-Boc(amino)]-4-carboxylthiazole as a white solid.

Step C.

A suspension of 2-[N-Boc(amino)]-4-carboxylthiazole (1 mmole) in $CH_2Cl_2$ (5 mL) was treated with thionyl chloride (4 mmole) at room temperature. After stirring for 4 h the reaction was evaporated to dryness. The residue was dissolved in $CH_2Cl_2$ (5 mL) and added to a solution of diethyl (hydroxymethyl)phosphonate (1.5 mmole) and pyridine (2 mmole) in $CH_2Cl_2$ (5 mL) at 0° C. The reaction was warmed to room temperature and stirred for 4 h. The reaction was quenched with water and the mixture was subjected to extraction to give 2-[N-Boc(amino)]-4-diethylphosphonomethoxycarbonylthiazole as a thick yellow oil.

Alternatively the ester linkage can be formed using a mixed anhydride method as exemplified in the following procedures:

A solution of 2-[N-Boc(amino)]-4-carboxylthiazole (1 mmole) in pyridine (5 mL) was treated with para-toluenesulfonyl chloride (2 mmole) followed by diethyl (hydroxymethyl)phosphonate (2 mmole) at room temperature for 4 h. Evaporation, extraction and chromatography gave 2-[N-Boc(amino)]-4-diethylphosphonomethoxycarbonylthiazole as a thick yellow oil.

Step D.

A solution of 2-[N-Boc(amino)]-4-diethylphosphonomethoxycarbonylthiazole (1 mmole) and anisole (0.1 mmole) in methylene chloride (5 mL) and trifluoroacetic acid (5 mL) was stirred at 0° C. for 1 h, and at room temperature for 1 h. Evaporation, extraction and chromatography gave 2-amino-4-diethyllphosphonomethoxycarbonylthiazole as a solid.

Step E.

2-Amino-4-diethyllphosphonomethoxycarbonylthiazole was subjected to Step C of Example 3 to give 2-amino-4-phosphonomethoxycarbonylthiazole (18.1) as a solid. Mp>240° C. (decomp). Anal. Calcd. for $C_5H_7N_2O_5PS$: C: 25.22; H: 2.96; N: 11.76. Found: C: 25.30; H: 2.86; N: 11.77.

Step F. A solution of 2-[N-Boc(amino)]-4-diethylphosphonomethoxycarbonylthiazole (1 mmole) in $CH_2Cl_2$ (5 mL) was treated with bromine (2 mmole) at room temperature for 4 h. Evaporation and extraction gave 2-[N-Boc(amino)]-5-bromo-4-diethylphosphonomethoxy carbonylthiazole as an orange oil which was subjected to Step D of Example 18 followed by Step C of Example 3 to give 2-amino-5-bromo-4-phosphonomethoxycarbonylthiazole (18.2) as a solid. Mp>230° C. (decomp). Anal. Calcd. for $C_5H_6N_2O_5PSBr$: C: 18.94; H: 1.91; N: 8.84. Found: C: 19.08; H: 1.76; N: 8.67.

Step G.

A solution of 2-[N-Boc(amino)]-5-bromo-4-diethylphosphonomethoxycarbonylthiazole (1 mmole) and dichlorobis(triphenylphosphine)palladium(II) (0.1 mmole) in DMF (5 mL) was treated with tributyl(vinyl)tin (2.5 mmole) and the reaction was stirred at 60° C. for 2 h. The solvent was removed and the residue taken up in EtOAc and stirred with 2 mmol NaF in 5 ml water for 1 h. Extraction and chromatography gave 2-[N-Boc(amino)]-5-vinyl-4-diethylphosphonomethoxycarbonylthiazole as a yellow solid.

Step H.

A suspension of 2-[N-Boc(amino)]-5-vinyl-4-diethylphosphonomethoxycarbonyl thiazole (1 mmole) and 10% Pd/C (0.5 mmole) in MeOH (5 mL) was stirred under an atmosphere of $H_2$ (balloon) at room temperature for 15 h. Filtration and evaporation gave 2-[N-Boc(amino)]-5-ethyl-4-diethylphosphonomethoxycarbonylthiazole as a yellow solid, which was subjected to Step D of Example 18 followed by Step C of Example 3 to give 2-amino-5-ethyl-4-phosphonomethoxycarbonylthiazole (18.3) as a solid. Mp>230° C. (decomp). Anal. Calcd. for $C_7H_{11}N_2O_5PS$: 31.58; H: 4.16; N: 10.52. Found: C: 31.80; H: 4.04; N: 10.18.

Step I.

A solution of N-[Bis(methylthio)methylene]glycine methyl ester (1 mmole) in anhydrous THF (2 mL) was added to a solution of t-BuOK (1.4 mmole) in anhydrous THF (10 mL) at −78° C. and the mixture was stirred for 30 min. Then a solution of ethyl isothiocyanate (1 mmole) in anhydrous THF (2 mL) was added and the reaction was stirred at −78° C. for 30 min and at room temperature for 2 h. The reaction was quenched with water. Extraction and chromatography gave 2-methylthio-5-(N-ethylamino)-4-methoxycarbonylthiazole as a yellow solid, which was subjected to Step B and C of Example 18 followed by Step C of Example 3 to give 2-methylthio-5-(N-ethylamino)-4-phosphonomethoxycarbonylthiazole (18.4) as a solid. Mp>200° C. (decomp). Anal. Calcd. for $C_8H_{13}N_2O_5PS_2$+0.1 HBr: C: 29.99; H: 4.12; N: 8.74. Found: C: 29.71; H: 4.10; N: 8.60.

II. Preparation of 4-phosphonomethylthiocarbonylthiazole

Step J.

A solution of 1 mmol of 2-[N-Boc(amino)]-4-thiazolecarboxylate acid chloride (1 mmole) and pyridine (2 mmole) in $CH_2Cl_2$ (5 mL) was cooled to −78° C. and $H_2S(g)$ was bubbled through the solution for 10 min. The reaction was stirred at −78° C. for 30 min and then warmed to room temperature. The mixture was washed with 3 N HCl. The organic phase was separated, dried and concentrated to give 2-[N-Boc(amino)]-4-thiazolethiocarboxylic acid as a yellow solid.

Step K.

A solution of give 2-[N-Boc(amino)]-4-thiazolethiocarboxylic acid (1 mmole) in THF (5 mL) was cooled to −78° C. and treated with NaH (2 mmole) in small portions. After 10 min the reaction was treated with a solution of diethylphosphonomethyl triflate in THF (5 mL). The reaction was stirred at −78° C. for 1 h, and then quenched with $H_2O$. Extraction and chromatography gave 2-[N-Boc(amino)]-4-diethylphosphonomethylthiocarbonylthiazole as a thick oil, which was subjected to Step D of Example 18 followed by Step C of Example 3 to give 2-amino-4-phosphonomethylthiocarbonylthiazole (18.5) as a solid. Mp>230° C. (decomp). Anal. Calcd. for $C_5H_7N_2O_4PS_2$: C: 23.62; H: 2.78; N: 11.02. Found: C: 23.77; H: 2.61; N: 10.73.

Preparation of 4-[(N-phosphonomethyl)carbamoyl]thiazole, 3-[N-phosphonomethyl)-carbamoyl]isothiazole and 2-[N-phosphonomethyl)carbamoyl]pyridine Step L.

A solution of 2-[N-Boc(amino)]-4-thiazolecarboxylic acid (1 mmole) in DMF (5 mL) was treated with 1-(3-dimethylaminopropyl)-3-ethylcarbodiimide hydrochloride (EDCI, 1.5 mmole) and 1-hydroxylbenzotriazole hydrate (HOBt, 1.5 mmole) followed by addition of diethyl aminomethylphosphonate (1.5 mmole) at room temperature for 24 h. The reaction was subjected to evaporation, extraction and chromatography to give 2-[N-Boc(amino)]-4-[(N-diethylphosphonomethyl)carbamoyl]thiazole as a white solid, which was subjected to Step D of Example 18 followed by Step C of Example 3 to give 2-amino-4-[(N-phosphonomethyl)carbamoyl]thiazole (18.6) as a light brown solid. Mp>245° C. (decomp). Anal. Calcd. for $C_5H_8N_3O_4PS$+1.05 HBr: C: 18.64; H: 2.83; N: 13.04. Found: C: 18.78; H: 2.43; N: 12.97.

Preparation of 2-[(N-phosphonoacetyl)amino]thiazole and 2-[(N-phosphonoacetyl)amino]pyridine Step M.

A solution of 2-amino-4,5-dimethylthiazole hydrochloride (2 mmole) and diethyl phosphonoacetica acid (1 mmole) in DMF (5 mL) was treated with EDCI (1.5 mmole), HOBt (1.5 mmole) and triethylamine (2 mmole) at room temperature for 24 h. The reaction was subjected to evaporation, extraction and chromatography to give 2-[(N-diethylphosphonoacetyl)amino]-4,5-dimethylthiazole as a yellow solid, which was subjected to Step D of Example 18 followed by Step C of Example 3 to give 4,5-dimethyl-2-[(N-phosphonoacetyl)amino]thiazole (18.7) as a light brown solid. Mp>250° C. Anal. Calcd. for $C_7H_{11}N_2O_4PS$: C: 33.60; H: 4.43; N: 11.20. Found: C: 33.62; H: 4.29; N: 10.99.

The following compounds were prepared using some of the above described procedures or some of the above procedures with some minor modifications using conventional chemistry:

(18.8) 2-[(N-phosphonomethyl)carbamoyl]pyridine . Anal. Calcd. for $C_7H_9N_2O_4P$+HBr+0.67 $H_2O$: C: 27.20; H: 3.70; N: 9.06. Found: C: 27.02; H: 3.71; N: 8.92.

(18.9) 2-[(N-phosphonoacetyl)amino]pyridine . Anal. Calcd. for $C_7H_9N_2O_4P$+HBr+0.67 $H_2O$: C: 27.20; H: 3.70; N: 9.06. Found: C: 27.05; H: 3.59; N: 8.86.

(18.10) 4-Ethoxycarbonyl-2-[(N-phosphonoacetyl)amino]thiazole. Anal. Calcd. for $C_8H_{11}N_2O_6PS$: C: 32.66; H: 3.77; N: 9.52. Found: C: 32.83; H: 3.58; N: 9.20.

(18.11) 2-Amino-5-bromo-4-[(N-phosphonomethyl)carbamoyl]thiazole. Mp 232° C. (decomp). Anal. Calcd. for $C_5H_7N_3O_4PSBr$+0.15HBr+0.1 hexane: C: 19.97; H: 2.56; N: 12.48. Found: C: 19.90; H: 2.29; N: 12.33.

(18.12) 2-Amino-5-(2-thienyl)-4-[(N-phosphonomethyl)carbamoyl]thiazole. Mp 245° C. (decomp). Anal. Calcd. for $C_9H_{10}N_3O_4PS_2$+0.1 EtOAc: C: 27.60; H: 2.91; N: 10.27. Found: C: 27.20; H: 2.67; N: 9.98.

(18.13) 4,5-Dichloro-3-[(N-phosphonomethyl)carbamoyl]isothiazole. Mp 189–191° C. Anal. Calcd. for $C_5H_5N_2O_4PSCl_2$: C: 20.63; H: 1.73; N: 9.62. Found: C: 20.43; H: 1.54; N: 9.51.

(18.14) 2-Amino-5-bromo-4-{[N-(1-phosphono-1-phenyl)methyl]carbamoyl}thiazole. Mp>250° C. Anal. Calcd. for $C_{11}H_{11}N_3O_4PSBr$: C: 33.69; H: 2.83; N: 10.71. Found: C: 33.85; H: 2.63; N: 10.85.

(18.15) 2-Amino-5-(2-thienyl)-4-phosphonomethoxycarbonylthiazole. Mp>230° C. (decomp). Anal. Calcd. for $C_9H_9N_2O_5PS_2$: C: 33.75; H: 2.83; N: 8.75. Found: C: 33.40; H: 2.74; N: 8.51.

(18.16) 2-Amino-5-benzyl-4-phosphonomethoxycarbonylthiazole. Mp>230° C. (decomp). Anal. Calcd. for $C_{12}H_{13}N_2O_5PS$: C: 43.91; H: 3.99; N: 8.53. Found: C: 43.77; H: 4.03; N: 8.25.

(18.17) 2-Methylthio-5-methylamino-4-phosphonomethoxycarbonylthiazole. Anal. Calcd. for $C_7H_{11}N_2O_5PS_2$+0.2 HBr: C: 26.74; H: 3.59; N: 8.91. Found: C: 26.79; H: 3.89; N: 8.89.

(18.18) 2-Amino-5-ethyl-4-[(N-phosphonomethyl)carbamoyl]thiazole. Mp 180° C. (decomp). Anal. Calcd. for $C_7H_{12}N_3O_4PS$+HBr+0.4 $CH_2Cl_2$: C: 23.49; H: 3.67; N: 11.18. Found: C: 23.73; H: 3.29; N: 11.42.

(18.19) 2-Amino-5-isopropyl-4-[(N-phosphonomethyl)carbarnoyl]thiazole. Mp 247–250° C. Anal. Calcd. for $C_8H_{14}N_3O_4PS$: C: 34.41; H: 5.05; N: 15.05. Found: C: 34.46; H: 4.80; N: 14.68.

(18.20) 2-Amino-5-isopropyl-4-phosphonomethoxycarbonylthiazole . Mp>230° C. Anal. Calcd. for $C_8H_{13}N_2O_5PS$: C: 34.29; H: 4.68; N: 10.00. Found: C: 33.97; H: 4.49; N: 9.70.

(18.21) 2-Amino-5-phenyl-4-phosphonomethoxycarbonylthiazole. Mp>230° C. Anal. Calcd. for $C_{11}H_{11}N_2O_5PS$: C: 42.04; H: 3.53; N: 8.91. Found: C: 42.04; H: 3.40; N: 8.72.

(18.22) 2-Amino-4-phosphonomethoxycarbonyloxazole. Anal. Calcd. for $C_5H_7N_2O_6P$+0.09 HBr: C: 26.18; H: 3.12; N: 12.21. Found: C: 26.29; H: 3.04; N: 11.90.

(18.23) 2-Amino-6-[(N-phosphonoacetyl)amino]pyridine. Anal. Calcd. for $C_7H_{10}N_3O_4P$+1.1 HBr+0.25 MeOH: C: 26.54; H: 3.72; N: 12.80. Found: C: 26.79; H: 3.63; N: 12.44.

(18.24) 2-Amino-5-methyl-4-[(N-phosphonomethyl)carbamoyl]thiazole. Mp>250° C. Anal. Calcd. for $C_6H_{10}N_3O_4PS$+0.06 EtOAc: C: 29.22; H: 4.12; N: 16.38. Found: C: 29.03; H: 3.84; N: 16.01.

(18.25) 2-Amino-3-bromo-6-[(N-phosphonoacetyl)amino]pyridine. Anal. Calcd. for $C_7H_9N_3O_4PBr$+1.25 HBr+0.8 EtOAc: C: 25.43; H: 3.48; N: 8.72. Found: C: 25.58; H: 3.71; N: 8.56.

(18.26) 2-Amino-3,5-dibromo-6-[(N-phosphonoacetyl)amino]pyridine. Anal. Calcd. for $C_7H_8N_3O_4PBr_2$+HBr+0.5 EtOAc: C: 21.03; H: 2.55; N: 8.18. Found: C: 21.28; H: 2.55; N: 7.91.

(18.27) 2-Amino-5-methyl-4-phosphonomethoxycarbonylthiazole. Mp 230° C. (decomp). Anal. Calcd. for $C_6H_9N_2O_5PS$: C: 28.58; H: 3.60; N: 11.11. Found: C: 28.38; H: 3.49; N: 11.10.

(18.28) 2-Amino-3,5-diethyl-6-[(N-phosphonoacetyl)amino]pyridine. MS calcd. for $C_{11}H_{18}N_3O_4P$+H: 288, found 288.

(18.29) 2-Amino-3,5-dibromo-6-{[N-(2,2-dibromo-2-phosphono)acetyl]amino}pyridine. Anal. Calcd. for $C_7H_6N_3O_4PBr_4$+0.5 HBr+EtOAc: C: 19.56; H: 2.16; N: 6.22. Found: C: 19.26; H: 2.29; N: 5.91.

(18.30) 2-Amino-5-isopropyl-4-phosphonomethoxycarbonyloxazole. Anal. Calcd. for $C_8H_{13}N_2O_6P$+0.2 HBr: C: 34.27; H: 4.75; N: 9.99. Found: C: 34.47; H: 4.84; N: 9.83

(18.31) 2-Amino-5-[1-(2-cyclohexylmethyl)ethynyl]-4-phosphonomethoxycarbonylthiazole. Mp 230° C. (decomp). Anal. Calcd. for $C_{14}H_{19}N_2O_5PS$+0.1 HBr:C: 45.89; H: 5.25; N: 7.64. Found: C: 45.85; H: 4.96; N: 7.44.

(18.32) 2-Amino-5-[1-(4-cyano)butynyl]-4-phosphonomethoxycarbonylthiazole. Mp 230° C. (decomp). Anal. Calcd. for $C_{10}H_{10}N_3O_5PS+0.25$ HBr: C: 35.80; H: 3.08; N: 12.53. Found: C: 35.92; H: 2.99; N: 12.20.

(18.33) 2-Amino-5-methyl-4-phosphonomethoxycarbonyloxazole. Anal. Calcd. for $C_6H_9N_2O_6P+0.15$ HBr: C: 29.03; H: 3.71; N: 11.28. Found: C: 28.98; H: 3.66; N: 11.21.

(18.34) 2-Amino-5-[1-(4-cyano)butyl]-4-phosphonomethoxycarbonylthiazole. Mp 230° C. (decomp). Anal. Calcd. for $C_{10}H_{14}N_3O_5PS$: C: 37.62; H: 4.42; N: 13.16. Found: C: 37.23; H: 4.18; N: 12.79.

(18.35) 2-Amino-5-pentyl-4-phosphonomethoxycarbonyloxazole. Anal. Calcd. for $C_{11}H_{17}N_2O_6P$: C: 41.10; H: 5.86; N: 9.59. Found: C: 41.16; H: 5.75; N: 9.50.

(18.36) 2-[N-Boc(amino)]-4-[(2-phosphono)ethoxycarbonyl]thiazole. Anal. Calcd. for $C_{11}H_{17}N_2O_7PS$: C: 37.50; H: 4.86; N: 7.95. Found: C: 37.10; H: 4.59; N: 7.84.

(18.37) 2-Amino-4-[(2-phosphono)ethoxycarbonyl]thiazole hydrobromide. Anal. Calcd. for $C_6H_9N_2O_5PS+HBr$: C: 21.63; H: 3.03; N: 8.41. Found: C: 22.01; H: 2.99; N: 8.15.

(18.38) 2-Amino-5-butyl-4-phosphonomethoxycarbonyloxazole. Anal. Calcd. for $C_9H_{15}N_2O_6P$: C: 38.86; H: 5.43; N: 10.07. Found: C: 38.59; H: 5.43; N: 9.96.

(18.39) 2-Amino-5-[1-(1-oxo-2,2-dimethyl)propyl]-4-phosphonomethoxycarbonylthiazole. Anal. Calcd. for $C_{10}H_{15}N_2O_6PS$: C: 37.27; H: 4.69; N: 8.69. Found: C: 37.03; H: 4.69; N: 8.39.

(18.40) 2-Amino-5-propyl-4-phosphonomethoxycarbonyloxazole. Anal. Calcd. for $C_8H_{13}N_2O_6P+0.35$ EtOAc+0.05 HBr: C: 37.75; H: 5.34; N: 9.37. Found: C: 37.69; H: 5.21; N: 9.03.

(18.41) 2-Amino-5-propyl-4-phosphonomethoxycarbonylthiazole. Mp 134° C. (decomp). Anal. Calcd. for $C_8H_{13}N_2O_5PS$: C: 34.29; H: 4.68; N: 10.00. Found: C: 33.90; H: 4.30; N: 9.61.

(18.42) 2-Amino-5-pentyl-4-phosphonomethoxycarbonylthiazole. Mp 130° C. (decomp). Anal. Calcd. for $C_{10}H_{17}N_2O_5PS$: C: 38.96; H: 5.56; N: 9.09. Found: C: 38.69; H: 5.25; N: 8.85.

(18.43) 2-Amino-5-bromo-4-phosphonomethylthiocarbonylthiazole. Mp 230° C. (decomp). Anal. Calcd. for $C_5H_6N_2O_5PS_2Br$: C: 18.03; H: 1.82; N: 8.41. Found: C: 18.40; H: 1.93; N: 8.18.

(18.44) 2-Amino-5-(2-furanyl)-4-phosphonomethoxycarbonylthiazole. Mp 230° C. (decomp). Anal. Calcd. for $C_9H_9N_2O_6PS$: C: 35.53; H: 2.98; N: 9.21. Found: C: 35.78; H: 3.05; N: 8.11.

(18.45) 2-Amino-5-ethyl-4-phosphonomethoxycarbonyloxazole. Mp 141° C. (decomp). Anal. Calcd. for $C_7H_{11}N_2O_6P$: C: 33.61; H: 4.43; N: 11.20. Found: C: 33.79; H: 4.47; N: 11.09.

(18.46) 5-Methyl-4-[(N-phosphonomethyl)carbamoyl]imidazole. Anal. calcd. for $C_6H_{10}N_3O_4P$: C: 32.89; H: 4.60; N: 19.18. Found: C: 33.04; H: 4.65; N: 18.84.

Example 19

Preparation of Various Phosphonate Diesters as Prodrugs

A suspension of 2-methyl-5-isobutyl-4-[2-(5-phosphono)furanyl]thiazole (1 mmole) in thionyl chloride (5 mL) was warmed at reflux for 4 h. The cooled reaction mixture was evaporated to dryness and the resulting yellow residue was dissolved in methylene chloride and treated with a solution of the corresponding benzyl alcohol (4 mmole) and pyridine (2.5 mmole) in methylene chloride. After stirring at 25° C. for 24 h the reaction mixture was subjected to extraction and chromatography to give the titled compounds. The following compounds were prepared according to this procedure:

(19.1) 2-Methyl-5-isobutyl-4-{2-[5-bis(4-pivaloyloxybenzyl)phosphono]furanyl}thiazole. Anal. Calcd. for $C_{36}H_{44}NO_8PS+0.4H_2O$: C: 62.76; H: 6.55; N: 2.03. Found: C: 62.45; H: 6.44; N: 2.04.

(19.2) 2-Methyl-5-isobutyl-4-{2-[5-bis(3,4-diacetoxybenzyl)phosphono]furanyl}thiazole. Anal. Calcd. for $C_{34}H_{36}NO_{12}PS+0.8H_2O$: C: 56.09; H: 5.21; N: 1.92. Found: C: 55.90; H: 4.98; N: 1.94.

(19.3) 2-Methyl-5-isobutyl-4-{2-[5-bis(4-acetoxy-3-methoxybenzyl)phosphono]furanyl}thiazole. Anal. Calcd. for $C_{32}H_{36}NO_{10}PS$: C: 58.44; H: 5.52; N: 2.13. Found: C: 58.16; H: 5.34; N: 2.13.

(19.4) 2-Methyl-5-isobutyl-4-{2-[5-bis(4-acetoxy-3-methylbenzyl)phosphono]furanyl}thiazole. Anal. Calcd. for $C_{32}H_{36}NO_8PS$: C: 61.43; H: 5.80; N: 2.24. Found: C: 61.34; H: 5.89; N: 2.25.

(19.5) 2-Amino-5-isobutyl-4-{2-[5-bis(3,4-diacetoxybenzyl)phosphono]furanyl}thiazole. Anal. Calcd. for $C_{33}H_{35}N_2O_{12}PS$: C: 55.46; H: 4.94; N: 3.92. Found: C: 55.06; H: 4.96; N: 3.79.

(19.6) 2-Amino-5-isobutyl-4-{2-[5-bis(4-acetoxybenzyl)phosphono]furanyl}thiazole. Anal. Calcd. for $C_{29}H_{31}N_2O_8PS$: C: 58.19; H: 5.22; N: 4.68. Found: C: 57.82; H: 4.83; N; 4.50.

This method is also useful for the preparation of phenyl phosphonate esters as prodrugs, and the following compound was prepared:

(19.7) 2-Methyl-5-isobutyl-4-[2-(5-diphenylphosphono)furanyl]thiazole. Anal. Calcd. for $C_{24}H_{24}NO_4PS+0.1H_2O$: C: 63.31; H: 5.36; N: 3.08. Found: C: 63.22; H: 5.34; N: 3.14.

(19.63) 2-Amino-5-isobutyl-4-[2-(5-diphenylphosphono)furanyl]thiazole. Mp 128–129 0° C. Anal. Calcd. for $C_{23}H_{23}N_2O_4PS$: C: 60.78; H: 5.10; N: 6.16. Found: C: 60.68; H: 4.83; N: 6.17.

(19.64) 2-Amino-5-isobutyl-4-[2-(5-phenylphosphono)furanyl]thiazole. Mp>250 0° C. Anal. Calcd. for $C_{17}H_{19}N_2O_4PS$: C: 53.96; H: 5.06; N: 7.40. Found: C: 53.81; H: 4.87; N: 7.41.

(19.65) 2-Amino-5-isobutyl-4-[2-(5-bis(3-chlorophenyl)phosphono)furanyl]thiazole. Anal. Calcd. for $C_{23}H_{21}N_2O_4PSCl_2+0.5$ $H_2O$: C: 51.89; H: 4.17; N: 5.26. Found C: 51.55; H: 3.99; N: 5.22.

(19.67) 2-Amino-5-isobutyl-4-[2-(5-bis(4-methoxyphenyl)phosphono)furanyl]thiazole. Anal. Calc. for $C_{25}H_{27}N_2O_6PS+0.5$ $H_2O$: C: 57.35; H: 5.39; N: 5.35. Found C: 57.11; H: 5.36; N: 5.75.

This method is also useful for the preparation of some thio-containing phosphonate esters as prodrugs, and the following compounds were prepared:

(19.8) 2-Methyl-5-isobutyl-4-{2-[5-bis(2-methylcarbonylthioethyl)phosphono]furanyl}thiazole. Anal. Calcd. for $C_{20}H_{28}NO_6PS_3$: C: 47.51; H: 5.58; N: 2.77. Found: C: 47.32; H: 5.56; N: 2.77.

(19.9) 2-Methyl-5-isobutyl-4-{2-[5-bis(thiobenzoylmethyl)phosphono]furanyl}thiazole. Anal. Calcd. for $C_{28}H_{28}NO_6PS_3$: C: 55.89; H: 4.69; N: 2.33. Found: C: 55.73; H: 4.72; N: 2.28.

This method is also useful for the preparation of cyclic phosphonate esters (e.g. cyclic 1,3-propanediol phosphonate esters) as prodrugs by coupling of phosphonic acids with various diols (e.g. 1,3-propanediols see Example 21 for the synthesis of some 1,3-propanediols), and the following compounds were made:

(19.10) 5-Isobutyl-2-methyl-4-{2-[5-(1-hydroxy-3,5-cyclohexyl)phosphono]furanyl}thiazole (minor isomer). Anal. Calcd. for $C_{18}H_{24}NO_5PS+0.33H_2O$: C: 53.60; H: 6.16; N: 3.47. Found: C: 53.75; H: 6.53; N: 3.45.

(19.11) 5-Isobutyl-2-methyl-4-{2-[5-(1-hydroxy-3,5-cyclohexyl)phosphono]furanyl}thiazole (major isomer). Anal. Calcd. for $C_{18}H_{24}NO_5PS$: C: 54.40; H: 6.09; N: 3.52. Found: C: 54.44; H: 6.11; N: 3.63.

(19.12) 5-Isobutyl-2-methyl-4-{2-[5-(2-hydroxymethyl-1,3-propyl)phosphono]furanyl}thiazole. Anal. Calcd. for $C_{16}H_{22}NO_5PS+0.3CH_2C_{12}+0.5H_2O$: C: 48.24; H: 5.86; N: 3.45. Found: C: 47.94; H: 5.59; N: 3.57.

(19.13) 5-Isobutyl-2-methyl-4-{2-[5-(1-phenyl-1,3-propyl)phosphono]furanyl}thiazole, (minor isomer). Anal. Calcd. for $C_{21}H_{24}NO_4PS+0.25H_2O$: C: 59.77; H: 5.85; N: 3.32. Found: C: 59.76; H: 5.69; N: 3.38.

(19.14) 5-Isobutyl-2-methyl-4-{2-[5-(1-phenyl-1,3-propyl)phosphono]furanyl}thiazole, (major isomer). Anal. Calcd. for $C_{21}H_{24}NO_4PS+0.5\ H_2O$: C: 59.14; H: 5.91; N: 3.28. Found: C: 59.27; H: 5.85; N: 3.38.

(19.15) 2-Amino-5-isobutyl-4-[2-(5-[2-(methoxycarbonyloxymethyl)-propan-1,3-yl]phosphono)furanyl]thiazole (minor isomer). mp 170–173° C. Anal. Calcd. for $C_{17}H_{23}N_2O_7PS$: C: 47.44; H: 5.39; N: 6.51. Found: C: 47.28; H: 5.27; N: 6.47.

(19.16) 2-Amino-5-isobutyl-4-[2-(5-[2-(methoxycarbonyloxymethyl)-propan-1,3-yl]phosphono)furanyl]thiazole (major isomer). Anal. Calcd. for $C_{17}H_{23}N_2O_7PS+0.5\ H_2O$: C: 46.47; H: 5.51; N: 6.38. Found: C: 46.38; H: 5.29; N: 6.20.

(19.17) 5-Isobutyl-2-methyl-4-{2-[5-(1-(4-pyridyl)-1,3-propyl)phosphono]furanyl}-thiazole. Anal. Calcd. for $C_{20}H_{23}N_2O_4PS+2H_2O+0.4CH_2Cl_2$: C: 50.16; H: 5.74; N: 5.74. Found: C: 50.36; H: 5.36; N: 5.80.

(19.18) 2-Amino-5-isobutyl-4-(2-{5-[1-(4-pyridyl)-propan-1,3-yl]phosphono}thiazole. mp 101–106° C. Anal. Calcd. for $C_{19}H_{22}N_3O_4PS+0.75H_2O$: C: 52.71; H: 5.47; N: 9.71. Found: C: 52.59; H: 5.49; N: 9.65.

(19.20) 2-Amino-5-isobutyl-4-{2-[5-(1-phenyl-1,3-propyl)phosphono]furanyl}thiazole (minor isomer). Anal. Calcd. for $C_{20}H_{23}N_2O_4PS+0.33HCl$: C: 55.80; H: 5.46; N: 6.51. Found: C: 55.95; H: 5.36; N: 6.46.

(19.21) 2-Amino-5-isobutyl-4-{2-[5-(1-phenyl-1,3-propyl)phosphono]furanyl}thiazol (major isomer). Anal. Calcd. for $C_{20}H_{23}N_2O_4PS+0.33HCl$: C:55.80; H: 5.46; N: 6.51. Found: C: 55.77; H: 5.19; N: 6.44.

(19.22) 2-Amino-5-ethyl-4-{2-[5-(1-phenyl-1,3-propyl)phosphono]furanyl}thiazole (less polar isomer). Anal. Calcd. for $C_{18}H_{19}N_2O_4PS+0.2HCl+0.25\ H_2O$: C: 53.75; H: 4.94; N: 6.97. Found: C: 53.86; H: 4.70; N: 6.87.

(19.23) 2-Amino-5-ethyl-4-{2-[5-(1-phenyl-1,3-propyl)phosphono]furanyl}-thiazol (more polar isomer). Anal. Calcd. for $C_{18}H_{19}N_2O_4PS+0.2HCl+0.25\ H_2O$: C: 53.75; H: 4.94; N: 6.97. Found: C: 53.92; H: 4.82; N: 6.92.

(19.24) 2-Amino-5-ethyl-4-{2-[5-(1-{4-pyridyl}-1,3-propyl)phosphono]furanyl}thiazole Anal. Calcd. for $C_{17}H_{18}N_3O_4PS+0.1HCl+0.5\ H_2O$: C: 50.54; H: 4.76; N: 10.40. Found: C: 50.38; H: 4.53; N: 10.25.

(19.25) 2-Methyl-4-{2-[5-(2-acetoxymethylpropan-1,3-diyl)phosphono]furanyl}thiazole. Anal. calcd. for $C_{14}H_{16}NO_6PS+0.5H_2O$: C: 45.90; H: 4.68; N: 3.82. Found C: 45.50; H: 4.55; N: 3.45.

(19.26) 2-Methyl-4-(2-{5-[1-(4-pyridyl)propan-1,3-diyl]phosphono}furanyl)thiazole. Anal. calcd. for $C_{16}H_{15}N_2O_4PS+0.75H_2O$: C: 51.13; H: 4.42; N: 7.45. Found: C: 50.86; H: 4.72; N: 7.11.

(19.27) 2-Amino-5-methylthio-4-(2-{5-[1-(4-pyridyl)propan-1,3-diyl]phosphono}furanyl)thiazole. Anal. calcd. for $C_{16}H_{16}N_3O_4PS_2+0.4\ HCl$: C: 45.32; H: 3.90; N: 9.91. Found: C: 45.29; H: 3.80; N: 9.83.

(19.28) 2-Amino-5-isobutyl-4-{2-[5-(1-(3-bromophenyl)propan-1,3-diyl)phosphono]furanyl}thiazole, major isomer. Anal. calcd. for $C_{20}H_{22}N_2O_4PBrS$: C: 48.30; H: 4.46; N: 5.63. Found: C: 48.51; H: 4.21; N: 5.33.

(19.29) 2-Amino-5-methylthio-4-{2-[5-(1-(R)-phenyl-1,3-propyl)phosphono]furanyl}thiazole. Anal. Calcd. for $C_{17}H_{17}N_2O_4PS+HCl$: C: 49.46; H: 4.39; N: 6.79. Found: C: 49.77; H: 4.13; N: 6.54.

(19.30) 2-Amino-5-isobutyl-4-{2-[5-(1-(3-bromophenyl)-1,3-propyl)phosphono]furanyl}thiazole, minor isomer. Anal. Calcd. for $C_{20}H_{22}N_2O_4PSBr+0.25HCl$: C: 47.43; H: 4.43; N: 5.53. Found: C: 47.58; H: 4.16; N: 5.31.

(19.31) 2-Amino-5-isobutyl-4-{2-[5-(2-benzyl-1,3-propyl)phosphono]furanyl}thiazole. Anal. Calcd. for $C_{21}H_{25}N_2O_4PS$: C: 58.32; H: 5.83; N: 6.48. Found: C: 57.98; H: 5.65; N: 6.47.

(19.32) 2-Amino-5-cycloproyl-4-{2-[5-(1-(4-pyridyl)-1,3-propyl)phosphono]furanyl}thiazole. Anal. Calcd. for $C_{18}H_{18}N_3O_4PS+0.5H_2O$: C: 52.42; H: 4.64; N: 10.19. Found: C: 52.62; H: 4.51; N: 9.89.

(19.33) 2-Methyl-5-isobutyl-4-{2-[5-(1-(S)-phenyl-1,3-propyl)phosphono]furanyl}thiazole, minor isomer. Anal. Calcd. for $C_{21}H_{24}NO_4PS$: C: 60.42; H: 5.79; N: 3.36. Found: C: 60.10; H: 5.58; N: 3.32.

(19.34) 2-Methyl-5-isobutyl-4-{2-[5-(1-(S)-phenyl-1,3-propyl)phosphono]furanyl}thiazole, major isomer. Anal. Calcd. for $C_{21}H_{24}NO_4PS+0.33\ H_2O$: C: 59.57; H: 5.87; N: 3.31. Found: C: 59.45; H: 5.83; N: 3.30.

(19.35) 2-Azido-5-ethyl-4-{2-[5-(1-phenyl-1,3-propyl)phosphono]furanyl}thiazole, major isomer. Anal. Calcd. for $C_{18}H_{17}N_4O_4PS+0.25H_2O+0.1$ isoamyl alcohol $(C_5H_{12}O)$: C: 51.71; H: 4.39; N: 13.04. Found: C: 51.80; H: 4.20; N: 12.78.

(19.36) 2-Azido-5-ethyl-4-{2-[5-(1-phenyl-1,3-propyl)phosphono]furanyl}thiazole, minor isomer. Anal. Calcd. for $C_{18}H_{17}N_4O_4PS+0.15$ isoamyl alcohol $(C_5H_{12}O)$: C: 52.42; H: 4.41; N: 13.04. Found: C: 52.27; H: 4.47; N: 12.76.

(19.37) 2-Amino-5-isobutyl-4-{2-[5-(1-(1-naphthyl)-1,3-propyl)phosphono]furanyl}thiazole. Anal. Calcd. for $C_{24}H_{25}N_2O_4PS$: C: 61.53; H: 5.38; N: 5.98. Found: C: 61.40; H: 5.12; N: 6.11.

(19.38) 2-Amino-5-isobutyl-4-{2-[5-(1-(2-bromophenyl)-1,3-propyl)phosphono]furanyl}thiazole. Anal. Calcd. for $C_{20}H_{22}N_2O_4PSBr+0.1\ C_5H_5N$: C: 48.73; H: 4.49; N: 5.82. Found: C: 48.63; H: 4.26; N: 5.70.

(19.39) 2-Amino-5-isobutyl-4-{2-[5-(1-(4-bromophenyl)-1,3-propyl)phosphono]furanyl}thiazole, minor isomer. Anal. Calcd. for $C_{20}H_{22}N_2O_4PSBr$: C: 48.30; H: 4.46; N: 5.63. Found: C: 48.23; H: 4.30; N: 5.77.

(19.40) 2-Amino-5-isobutyl-4-{2-[5-(1-(4-bromophenyl)-1,3-propyl)phosphono]furanyl}thiazole, major isomer. Anal. Calcd. for $C_{20}H_{22}N_2O_4PSBr$: C: 48.30; H: 4.46; N: 5.63. Found: C: 48.20; H: 4.63; N: 5.41.

(19.41) 2-Amino-5-isobutyl-4-{2-[5-(1-(4-fluoro-3-bromophenyl)-1,3-propyl)phosphono]furanyl}thiazole, minor isomer. Anal. Calcd. for $C_{20}H_{21}N_2O_4PSBrF+0.1\ C_5H_5N$: C: 47.06; H: 4.14; N: 5.62. Found: C: 47.00; H: 3.84; N: 5.48.

(19.42) 2-Amino-5-isobutyl-4-{2-[5-(1-(4-fluoro-3-bromophenyl)-1,3-propyl)phosphono]furanyl}thiazole, major isomer. Anal. Calcd. for $C_{20}H_{21}N_2O_4PSBrF$: C: 46.61; H: 4.11; N: 5.44; P: 6.01. Found: C: 46.81; H: 4.23; N: 5.65; P: 5.65.

(19.43) 2-Amino-5-isobutyl-4-{2-[5-(1-(4-trifluoromethylphenyl)-1,3-propyl)phosphono]furanyl}thiazole, minor isomer. Anal. Calcd. for $C_{21}H_{22}N_2O_4PSF_3+0.1\ H_2O$: C: 51.66; H: 4.58; N: 5.74. Found: C: 51.54; H: 4.28; N: 5.46.

(19.44) 2-Amino-5-isobutyl-4-{2-[5-(1-(4-trifluoromethylphenyl)-1,3-propyl)phosphono]furanyl}thiazole, major isomer. Anal. Calcd. for $C_{21}H_{22}N_2O_4PSF_3+0.1\ H_2O$: C: 51.66; H: 4.58; N: 5.74. Found: C: 51.48; H: 4.62; N: 5.81.

(19.45) 2-Amino-5-isobutyl-4-{2-[5-(1-(3-chlorophenyl)-1,3-propyl)phosphono]furanyl}thiazole, minor isomer. Anal. Calcd. for $C_{20}H_{22}N_2O_4PSCl+0.5\ H_2O$: C: 52.01; H: 5.02; N: 6.06. Found: C: 52.10; H: 4.92; N: 5.82.

(19.46) 2-Amino-5-isobutyl-4-{2-[5-(1-(3-chlorophenyl)-1,3-propyl)phosphono]furanyl}thiazole, major isomer. Anal. Calcd. for $C_{20}H_{22}N_2O_4PSCl+0.25\ H_2O$: C: 52.52; H: 4.96; N: 6.12. Found: C: 52.70; H: 4.79; N: 5.91.

(19.47) 2-Amino-5-isobutyl-4-{2-[5-(1-(3,5-dichlorophenyl)-1,3-propyl)phosphono]furanyl}thiazole, minor isomer. Anal. Calcd. for $C_{20}H_{21}N_2O_4PSCl_2$: C: 49.29; H: 4.34; N: 5.75. Found: C: 49.47; H: 4.60; N: 5.89.

(19.48) 2-Amino-5-isobutyl-4-{2-[5-(1-(3,5-dichlorophenyl)-1,3-propyl)phosphono]furanyl}thiazole, major isomer. Anal. Calcd. for $C_{20}H_{21}N_2O_4PSCl_2$: C: 49.29; H: 4.34; N: 5.75; Cl: 14.55. Found: C: 49.26; H: 4.36; N: 5.71; Cl: 14.66.

(19.49) 2-Amino-5-isobutyl-4-{2-[5-(2-(4-methoxybenzyl)-1,3-propyl)phosphono]furanyl}thiazole. Mp 185–188° C. Anal. Calcd. for $C_{22}H_{27}N_2O_5PS$: C: 57.13; H: 5.88; N: 6.06. Found: C: 56.86; H: 5.71; N: 5.73.

(19.50) 2-Amino-5-isobutyl-4-{2-[5-(2-methanesulfonyloxymethyl-1,3-propyl)phosphono]furanyl}thiazole. Anal. Calcd. for $C_{16}H_{23}N_2O_7PS_2+0.2\ H_2O$: C: 42.32; H: 5.19; N: 6.17. Found: C: 42.15; H: 4.94; N: 5.95.

(19.51) 2-Amino-5-isobutyl-4-{2-[5-(2-azidomethyl-1,3-propyl)phosphono]furanyl}thiazole. Mp 187–189° C. Anal. Calcd. for $C_{15}H_{20}N_5O_4PS$: C: 45.34; H: 5.07; N: 17.62. Found: C: 45.09; H: 4.82; N: 17.72.

(19.52) 2-Amino-5-isobutyl-4-{2-[5-(2-aminomethyl-1,3-propyl)phosphono]furanyl}thiazole. Anal. Calcd. for $C_{15}H_{22}N_3O_4PS+0.3\ H_2O+0.1\ HCl$: C: 47.36; H: 6.01; N: 11.04. Found: C: 47.55; H: 5.62; N: 10.64.

(19.53) 2-Amino-5-isobutyl-4-{2-[5-(1-(4-tert-butylphenyl)-1,3-propyl)phosphono]furanyl}thiazole, minor isomer. Mp 141–143° C. Anal. Calcd. for $C_{24}H_{31}N_2O_4PS+1.5\ HCl$: C: 54.47; H: 6.19; N: 5.29. Found: C: 54.44; H: 5.85; N: 4.92.

(19.54) 2-Amino-5-isobutyl-4-{2-[5-(1-(4-tert-butylphenyl)-1,3-propyl)phosphono]furanyl}thiazole, major isomer. Mp 178° C. (decomp). Anal. Calcd. for $C_{24}H_{31}N_2O_4PS+H_2O$: C: 58.52; H: 6.75; N: 5.69. Found: C: 58.20; H: 6.31; N: 5.29.

(19.55) 2-Amino-5-isobutyl-4-{2-[5-(1-(4-chlorophenyl)-1,3-propyl)phosphono]furanyl}thiazole, major isomer. Mp 102–104° C. Anal. Calcd. for $C_{20}H_{22}N_2O_4PSCl+H_2O+0.2EtOAc$: C: 51.14; H: 5.28; N: 5.73. Found: C: 50.86; H: 5.09; N: 5.34.

(19.56) 2-Amino-5-isobutyl-4-{2-[5-(1-(2,4-dichlorophenyl)-1,3-propyl)phosphono]furanyl}thiazole, major isomer. Mp 173–174° C. Anal. Calcd. for $C_{20}H_{21}N_2O_4PSCl_2$: C: 49.29; H: 4.34; N: 5.75. Found: C: 49.55; H: 4.32; N: 5.46.

(19.57) 2-Amino-5-isobutyl-4-{2-[5-(1,3-(S,S)-diphenyl)-1,3-propyl)phosphono]furanyl}thiazole. Mp 105–107° C. Anal. Calcd. for $C_{26}H_{27}N_2O_4PS+0.5H_2O+0.5HCl$: C: 59.85; H: 5.51; N: 5.37. Found: C: 59.83; H: 5.18; N: 5.27.

(19.58) 2-Amino-5-isobutyl-4-{2-[5-(1-(4-chlorophenyl)-1,3-propyl)phosphono]furanyl}thiazole, minor isomer. Mp 102–104° C. Anal. Calcd. for $C_{20}H_{22}N_2O_4PSCl$: C: 53.04; H: 4.90; N: 6.19. Found: C: 52.80; H: 4.70; N: 6.07.

(19.59) 2-Amino-5-isobutyl-4-{2-[5-(1-(3,5-difluorophenyl)-1,3-propyl)phosphono]furanyl}thiazole, minor isomer. Mp 152–154° C. Anal. Calcd. for $C_{20}H_{21}N_2O_4PSF_2+0.5\ H_2O+0.3\ EtOAc$: C: 51.98; H: 5.02; N: 5.72. Found: C: 51.67; H: 4.77; N: 5.42.

(19.60) 2-Amino-5-isobutyl-4-{2-[5-(1-(3,5-difluorophenyl)-1,3-propyl)phosphono]furanyl}thiazole, major isomer. Mp 94–95° C. Anal. Calcd. for $C_{20}H_{21}N_2O_4PSF_2$: C: 52.86; H: 4.66; N: 6.16. Found: C: 52.68; H: 4.73; N: 5.90.

(19.61) 2-Amino-5-isobutyl-4-{2-[5-(1-(3,5-dibromophenyl)-1,3-propyl)phosphono]furanyl}thiazole, major isomer. Mp 113–115° C. Anal. Calcd. for $C_{20}H_{21}N_2O_4PSBr_2+0.3\ EtOAc$: C: 42.25; H: 3.91; N: 4.65. Found: C: 42.52; H: 3.91; N: 4.96.

(19.62) 2-Amino-5-isobutyl-4-{2-[5-(1-(3,5-dibromophenyl)-1,3-propyl)phosphono]furanyl}thiazole, minor isomer. Mp 209–210° C. Anal. Calcd. for $C_{20}H_{21}N_2O_4PSBr_2$: C: 41.69; H: 3.67; N: 4.86. Found: C: 41.93; H: 3.71; N: 4.74.

(19.66) 2-Amino-5-isobutyl-4-{2-[5-(1-(3-pyridyl)-1,3-propyl)phosphono]furanyl}thiazole dihydrochloride. Anal. Calcd. for $C_{19}H_{22}N_3O_4PS+2HCl+2H_2O$: C: 43.19; H: 5.34; N: 7.95. Found: C: 43.10; H: 5.25; N: 7.85.

(19.68) 2-Amino-5-isobutyl-4-{2-[5-(1-oxo-1-phospha-2,5,8-trioxa-3,4-benzo)cyclooctan-1-yl]furanyl}thiazole. Anal. Calcd. for $C_{19}H_{21}N_2O_5PS+0.75\ H_2O$: C: 52.59; H: 5.23; N: 6.46. Found: C: 52.38; H: 4.85; N: 6.08.

Preferably the cyclic 1,3-propanediol phosphonate esters were prepared using 1,3-dicyclohexylcarbodiimide (DCC) coupling reaction conditions as following.

A suspension of 2-amino-5-isobutyl-4-[2-(5-phosphono)furanyl]thiazole (1 mmole) in DMF:pyridine (5:1, 10 mL) was treated with DCC (2 mmole) followed by 3-(3,5-dichloro)phenyl-1,3-propanediol (1.1 mmole). The resulting mixture was heated at 80° C. for 8 h. Evaporation followed by column chromatography gave 2-amino-5-isobutyl-4-{2-[5-(1-(3,5-dichlorophenyl)-1,3-propyl)phosphono]furanyl}thiazole, major isomer. (19.48) as a solid.

This method is also useful for the preparation of (5-substituted 2-oxo-1,3-dioxolen-4-yl)methyl and (5-substituted 2-thiocarbonyl-1,3-dioxolen-4-yl)methyl phosphonate prodrugs by coupling of phosphonic acids with 5-methyl-4-hydroxymethyl-2-oxo-1,3-dioxolene and 5-methyl-4-hydroxymethyl-2-thiocarbonyl-1,3-dioxolene (prepared from 4,5-dimethyl-2-oxo-1,3-dioxolene as described in Example 23). The following compound was made using this method.

(19.19) 2-Methyl-5-isobutyl-4-{2-[5-(bis(5-methyl-2-thioxo-1,3-dioxolen-4-yl)methy)-phosphono]furanyl}thiazole. Anal. Calcd. for $C_{22}H_{24}NO_8PS_3$: C: 47.39; H: 4.34; N: 2.51. Found: C: 47.42; H: 4.30; N: 2.52.

Alternatively, these compounds can be prepared according to reported procedures (*Chem. Pharm. Bull.* 1984, 32(6), 2241) by reaction of phosphonic acids with 5-methyl-4-bromomethyl-2-oxo-1,3-dioxolene in DMF in the presence of sodium hydride at 25° C.

2-Amino-5-isobutyl-4-{2-[5-bis(3-phthalidyl-2-ethyl)phosphono]furanyl}-thiazole is also prepared following the above described procedures using 2-(3-phthalidyl)ethanol which was prepared from phthalide-3-acetic acid in Example 22.

Example 20

Preparation of Acyloxyalkyl and Alkyloxncarbonyloxyalkyl Phosphonate Diesters as Prodrugs A solution of 2-methyl-4-[2-(5-phosphono)furanyl]thiazole (1 mmole) in acetonitrile and N,N,N-diisopropylethylamine (5 mmole) was treated with pivaloyloxymethyl iodide (4 mmole) at 0° C. for 24 h. Extraction and chromatography gave 2-methyl-4-[2-(5-dipivaloyloxymethylphosphono)furanyl]-thiazole (20.1). Anal. Calcd. for $C_{20}H_{28}NO_8PS$: C: 50.59; H: 6.03; N: 2.65. Found: C: 50.73; H: 5.96; N: 2.96.

The following compounds were prepared according to this procedure:

(20.2) 2-Methyl-5-isobutyl-4-{2-[5-(O-isobutyryloxymethyl-O-pivaloyloxymethyl)-phosphono]furanyl}thiazole. Anal. Calcd. for $C_{23}H_{34}NO_8PS$: C: 53.58; H: 6.65; N: 2.72. Found: C: 53.81; H: 6.83; N: 2.60.

(20.3) 2-Methyl-5-isobutyl-4-{2-[5-(dipivaloyloxymethyl)phosphono]furanyl}thiazole. Anal. Calcd. for $C_{24}H_{36}NO_8PS$: C: 54.43; H: 6.85; N: 2.64. Found: C: 54.46; H: 7.04; N: 2.55.

(20.4) 2-Amino-5-isobutyl-4-{2-[5-(dipivaloyloxymethyl)phosphono]furanyl}thiazole. Anal. Calcd. for $C_{23}H_{35}N_2O_8PS$: C: 52.07; H: 6.65; N: 5.28. Found: C: 52.45; H: 6.78; N: 5.01.

(20.5) 2-Bromo-5-isobutyl-4-{2-[5-(dipivaloyloxymethyl)phosphono]furanyl}thiazole. Anal. Calcd. for $C_{23}H_{33}NO_8PSBr$: C: 47.00; H: 5.75; N: 2.32. Found: C: 47.18; H: 5.46; N: 2.30.

The cyclic acyloxyalkyl phosphonate esters can also be prepared in a similar manner according to Farquhar's procedure (Farquhar, D. et al, *Tetrahedron Lett*. 1995, 36, 655).

(20.13) 2-Amino-5-isobutyl-4-{2-[5-(1-benzoyloxypropane-1,3-diyl)phosphono]furanyl}thiazole, more polar isomer. MS calcd for $C_{21}H_{23}N_2O_6PS$+H:463, found 463.

(20.14) 2-Amino-5-isobutyl-4-{2-[5-(1-benzoyloxypropane-1,3-diyl)phosphono]furanyl}thiazole, less polar isomer. MS calcd for $C_{21}H_{23}N_2O_6PS$+H: 463, found 463.

Alkyloxycarbonyloxyalkyl phosphonate esters were also prepared according to the above procedures with slight modifications described below:

A solution of 2-methyl-5-isobutyl-4-[2-(5-phosphono)furanyl]thiazole (1 mmole) in DMF was treated with N,N'-dicyclohexyl-4-morpholinecarboxarnidine (5 mmole) and ethylpropyloxycarbonyloxymethyl iodide (5 mmole) which was prepared from chloromethyl chloroformate according to the reported procedure (Nishimura et al. *J. Antibiotics*, 1987, 40(1), 81–90). The reaction mixture was stirred at 25° C. for 24 h, and evaporation followed by chromatography gave 2-methyl-5-isobutyl-4-{-2-[5-bis(ethoxycarbonyloxymethyl)phosphono]furanyl}thiazole (20.6). Anal. Calcd. for $C_{20}H_{28}NO_{10}PS$: C: 47.52; H: 5.58; N: 2.77. Found: C: 47.52; H: 5.67; N: 2.80.

The following compounds were prepared according to this procedure:

(20.7) 2-Methyl-5-isobutyl-4-{-2-[5-bis(isopropyloxycarbonyloxymethyl)phosphono]-furanyl}thiazole. Anal. Calcd. for $C_{22}H_{32}NO_{10}PS$: C: 49.53; H: 6.05; N: 2.63. Found: C: 49.58; H: 6.14; N: 2.75.

(20.8) 2-Amino-5-isobutyl-4-{-2-[5-bis(phenoxycarbonyloxymethyl)phosphono]-furanyl}thiazole. Anal. Calcd. for $C_{27}H_{27}N_2O_{10}PS$: C: 53.82; H: 4.52; N: 4.65. Found: C: 54.03; H: 4.16; N: 4.30.

(20.9) 2-Amino-5-isobutyl-4-{-2-[5-bis(ethoxycarbonyloxymethyl)phosphono]-furanyl}thiazole. Anal. Calcd. for $C_{19}H_{27}N_2O_{10}PS$: C: 45.06; H: 5.37; N: 5.53. Found: C: 45.1 1; H: 5.30; N: 5.43.

(20.10) 2-Methyl-5-isobutyl-4-{-2-[5-bis(isopropylthiocarbonyloxymethyl)-phosphono]furanyl}thiazole. Anal. Calcd. for $C_{22}H_{32}NO_8PS_3$+0.2 EtOAc: C: 46.95; H: 5.81; N: 2.40. Found: C: 47.06; H: 5.86; N: 2.73.

(20.11) 2-Amino-5-isobutyl-4-{2-[5-bis(isopropyloxycarbonyloxymethyl)phosphono]furanyl}thiazole. Anal. calcd. for $C_{21}H_{31}N_2O_{10}PS$: C: 47.19; H: 5.85; N: 5.24. Found: C: 47.33; H: 5.66; N:5.57.

(20.12) 2-Methyl-5-isobutyl-4-{2-[5-bis(benzoyloxymethyl)phosphono]furanyl}thiazole. Anal. calcd. for $C_{28}H_{28}NO_8PS$+0.2$CH_2Cl_2$: C: 59.31; H: 5.40; N: 2.64. Found: C: 59.25; H: 5.27; N: 2.44.

(20.15) 2-Amino-5-isobutyl-4-{2-[5-bis(1-(1-ethoxycarbonyloxy)ethyl)phosphono]-furanyl}thiazole. Mp 76–78° C. Anal. calcd. for $C_{21}H_{31}N_2O_{10}PS$: C: 47.19; H: 5.85; N: 5.42. Found: C: 48.06; H: 5.80; N: 5.16. 2-Amino-5-isobutyl-4-{2-[5-bis(3-(5,6,7-trimethoxy)phthalidyl)-phosphono]furanyl}thiazole is also synthesized following this procedure using 3-bromo-5,6,7-trimethoxyphthalide as the alkylating reagent.

Example 21

Preparation of 3-(2-pyridyl)propan-1,3-diol

Step A.

(*J. Org. Chem.*, 1957, 22, 589) A solution of 3-(2-pyridyl)propanol in acetic acid was treated with 30% hydrogen peroxide at 80° C. for 16 h. The reaction was concentrated under vacuum and the residue was dissolved in acetic anhydride and heated at 110° C. for 12 h. Evaporation and chromatography gave 3-(2-pyridyl)-1,3-propanediol diacetate.

Step B.

A solution of 3-(2-pyridyl)-1,3-propanediol diacetate (1 mmole) in methanol-water (3:1) was treated with potassium carbonate (5 mmole) at 25° C. for 3 h. Evaporation and chromatography gave 3-(2-pyridyl)-1,3-propanediol as a solid.

Example 22

Preparation of 3-(2-hydroxyethyl)phthalide

A solution of phthalide-3-acetic acid (1 mmole) in THF was treated with borane dimethylsulfide (1.5 mmole) at 0° C. for 1 h, and at 25° C. for 24 h. Extraction and chromatography gave 2-(3-phthalidyl)ethanol as a light yellow oil: Rf=0.25, 50% EtOAc-hexane.

Example 23

Preparation of 5-methyl-4-hydroxymethyl-2-oxo-1,3-dioxolene

A solution of 4,5-dimethyl-2-oxo-1,3-dioxolene (1 mmole) and selenium dioxide (2.5 mmole) in dioxane was heated at reflux for 1 h. Evaporation, extraction and chromatography gave 5-methyl-4-hydroxymethyl-2-oxo-1,3-dioxolene as a yellow oil. TLC: Rf=0.5, 5% MeOH-dichloromethane.

A solution of 5-methyl-4-hydroxymethyl-2-oxo-1,3-dioxolene (1 mmole) in DMF was treated with tert-butyldimethylsilane (1.2 mmole) and imidazole (2.2 mmole) at 25° C. for 24 h. Extraction and chromatography gave 5-methyl-4-tert-butyldimethylsilyloxymethyl-2-oxo-1,3-dioxolene.

A solution of 5-methyl-4-tert-butyldimethylsilyloxymethyl-2-oxo-1,3-dioxolene (1 mmole) and Lawesson's reagent (1.2 mmole) in toluene was heated to 120° C. for 12 h. Extraction and chromatography gave 5-methyl-4-tert-butyldimethylsilyloxymethyl-2-thio-1,3-dioxolene.

A solution of 5-methyl-4-tert-butyldimethylsilyloxymethyl-2-thio-1,3-dioxolene in methanolic hydrogen chloride was stirred at 0° C. for 1 h and 25° C. for 12 h. Extraction and chromatography gave 5-methyl-4-hydroxymethyl-2-thio-1,3-dioxolene.

Example 24

Preparation of Hydroxyethyldisulfidylethylphosphonate Diester

A suspension of 2-methyl-5-isobutyl-4-[2-(5-phosphono) furanyl]thiazole (1 mmole) in thionyl chloride (5 mL) is warmed at reflux for 4 h. The cooled reaction mixture is evaporated to dryness and the resulting yellow residue is treated with a solution of 2-hydroxyethyl disulfide (4 mmole), pyridine (2.5 mmole) in methylene chloride. After stirring at 25° C. for 4 h. the reaction is subjected to extraction and chromatography to give two compounds: 2-methyl-5-isobutyl-4-{2-[5-bis(6'-hydroxy-3',4'-disulfide) hexylphosphono]furanyl}thiazole and 2-methyl-5-isobutyl-4-{2-[5-(3',4'-disulfide)nonacyclicphosphono]-furanyl}thiazole.

Example 25

Preparation of 3-[2-(5-phosphono)furanyl]pyrazoles

Step A.

A solution of diethyl 5-(2-isobutyl-3-N,N-dimethylamino)acryloyl-2-furanphosphonate (1 mmole, prepared according to Step A of Example 17) in ethanol was treated with hydrazine (1.2 mmole) 80° C. for 12 h. Evaporation and chromatography gave 4-isobutyl-3-[2-(5-diethylphosphono)furanyl]pyrazole.

Step B.

4-Isobutyl-3-[2-(5-diethylphosphono)furanyl]pyrazole was subjected to Step C of Example 3 to give 4-isobutyl-3-[2-(5-phosphono)furanyl]pyrazole (25.1). mp 210–215° C. Anal. Calcd. for $C_{11}H_{15}N_2O_4P$: C: 48.89; H: 5.60; N: 10.37. Found: C: 48.67; H: 5.55; N: 10.20.

Step C.

4-Isobutyl-3-[2-(5-diethylphosphono)furanyl]pyrazole was subjected to Step A of Example 11 to give 1-methyl-4-isobutyl-3-[2-(5-diethylphosphono)furanyl]pyrazole.

Step D.

1-Methyl-4-isobutyl-3-[2-(5-diethylphosphono)furanyl] pyrazole was subjected to Step C of Example 3 to give 1-methyl-4-isobutyl-3-[2-(5-phosphono)furanyl]pyrazole (25.2). Anal. Calcd. for $C_{12}H_{17}N_2O_4P+0.85HBr+0.75 H_2O$: C: 39.32; H: 5.32; N: 7.64. Found: C: 39.59; H: 5.30; N: 7.47.

Example 26

Preparation of 3-[2-(5-phosphono)furanyl] isoxazoles

Step A.

A solution of 5-diethylphosphono-2-furaldehyde (1 mmole) in ethanol was treated with hydroxylamine (1.1 mmole) and sodium acetate (2.2 mmole) at 25° C. for 12 h. Extraction and chromatography gave 5-diethylphosphono-2-furaldehyde oxime.

Step B.

A solution of 5-diethylphosphono-2-furaldehyde oxime (1 mmole) in DMF was treated with N-chlorosuccinimide (1.1 mmole) at 25° C. for 12 h. Extraction gave 5-diethylphosphono-2-chlorooximidofuran.

Step C.

A solution of 5-diethylphosphono-2-chlorooximidofuran (1 mmole) and ethyl propiolate (5 mmole) in diethyl ether was treated with triethylamine (2 mmole) at 25° C. for 12 h. Extraction and chromatography gave 5-ethoxycarbonyl-3-{2-(5-diethylphosphono)furanyl]isoxazole.

Step D.

5-Ethoxycarbonyl-3-{2-(5-diethylphosphono)furanyl] isoxazole was subjected to Step A of Example 9 followed by Step C of Example 3 to give 5-carbamoyl-3-[2-(5-phosphono)furanyl]isoxazole (26.1). mp 221–225° C. Anal. Calcd. for $C_8H_7N_2O_6P+0.25EtOH$: C: 37.86; H: 3.18; N: 10.39. Found: C: 37.90; H: 3.02; N: 10.05.

The following compound was prepared according to this procedure:

(26.2) 5-Ethoxycarbonyl-4-methyl-3-[2-(5-phosphono) furanyl]isoxazole. mp 150–152° C. Anal. Calcd. for $C_{11}H_{12}NO_7P+0.25H_2O+0.15HBr$: C: 41.57; H: 4.01; N: 4.41. Found: C: 41.57; H: 4.20; N: 4.54.

(26.3) 4,5-Bis(ethoxycarbonyl)-3-[2-(5-phosphono)furanyl] isoxazole. Anal. calcd for $C_{13}H_{14}NO_9P$: C: 43.47; H: 3.93; N: 3.90. Found: C: 43.26; H: 3.92; N: 3.97.

(26.4) 5-Amino-4-ethoxycarbonyl-3-[2-(5-phosphono) furanyl]isoxazole. mp 190° C. (decomp). Anal. calcd for $C_{10}H_{11}N_2O_7P+0.25HBr$: C: 37.25; H: 3.52; N: 8.69. Found: C: 37.56; H: 3.50; N: 8.85.

(26.5) 4,5-bis(carbamoyl)-3-[2-(5-phosphono)furanyl] isoxazole. mp>220° C. Anal. calcd for $C_9H_8N_3O_7P$: C: 35.90; H: 2.68; N: 13.95. Found: C: 35.67; H: 2.55; N: 13.62.

(26.6) 4-Ethoxycarbonyl-5-trifluoromethyl-3-[2-(5-phosphono)furanyl]isoxazole. Anal. calcd for $C_{11}H_9F_3NO_7P+0.25HBr$: C: 35.20; H: 2.48; N: 3.73. Found: C: 35.25; H: 2.34; N: 3.98.

(26.7) 5-Amino-4-(2-furanyl)-3-[2-(5-phosphono)furanyl] isoxazole. mp>220° C. Anal. calcd for $C_{12}H_9N_2O_7P+ 0.1AcOEt$: C: 44.73; H: 2.97; N: 8.41. Found: C: 45.10; H: 2.58; N: 8.73.

(26.8) 4-Amino-5-cyano-3-[2-(5-phosphono)furanyl] isoxazole. Anal. calcd for $C_8H_6N_3O_5P+0.1H_2O+0.2HBr$: C: 35.18; H: 2.36; N: 15.39. Found: C: 35.34; H: 2.50; N: 15.08.

(26.9) 4-Cyano-5-phenyl-3-[2-(5-phosphono)furanyl] isoxazole. Anal. calcd for $C_{14}H_9N_2O_5P+0.15HBr$: C: 51.21; H: 2.81; N: 8.53. Found: C: 51.24; H: 3.09; N: 8.33.

Example 27

Preparation of 2-[2-(5-phosphono)furanyl]thiazoles

Step A.

Diethyl 5-tributylstannyl-2-furanphosphonate (14) and 2-bromo-4-ethoxycarbonylthiazole was subjected to Step A of Example 6 to give 4-ethoxycarbonyl-2-[2-(5-diethylphosphono)furanyl]thiazole.

Step B.

4-Ethoxycarbonyl-2-[2-(5-diethylphosphono)furanyl] thiazole was subjected to Step A of Example 9 followed by Step C of Example 3 to give 4-carbamoyl-2-[2-(5-phosphono)furanyl]thiazole (27.1). mp 239–240° C. Anal. Calcd. for $C_8H_7N_2O_5PS+0.2H_2O$: C: 34.59; H: 2.68; N: 10.08. Found: C: 34.65; H: 2.69; N: 9.84.

Example 28

Preparation of 4-(3,3-difluoro-3-phosphono-1-propyl)thiazoles

Step A.

A solution of 3-(tert-butyl-diphenylsilyloxy)-1-propanol (1 mmole) in methylene chloride (7 mL) was treated with powder molecular sieves (4 A, 0.5 equiv. wt/wt) and pyridinium chlorochromate (1.5 mmole) at 0° C. The resulting mixture was stirred at room temperature for 2 h, and diluted with diethyl ether (7 mL) and stirred at room temperature for another 30 min. Filtration, evaporation and chromatography gave 3-(tert-butyldiphenylsilyloxy)-1-propanal as a clear oil.

Step B.

A solution of LDA (1.06 mmole) in THF was treated with a solution of diethyl difluoromethylphosphonate (1 mmole) at −78° C. for 45 min. The reaction was then treated with a THF solution of 3-(tert-butyldiphenylsilyloxy)-1-propanal (1.07 mmole) and the resulting solution was stirred at −78° C. for another 4 h. The reaction was quenched with phenyl chlorothioformate (2.14 mmole), and the reaction mixture was subjected to extraction and chromatography to give diethyl 4-(tert-butyldiphenylsilyloxy)-3-phenoxythiocarbonyloxy-2,2-difluorobutylphosphonate as a clear oil.

Step C.

A solution of diethyl 4-(tert-butyldiphenylsilyloxy)-3-phenoxythiocarbonyloxy-2,2-difluorobutylphosphonate (1 mmole) in toluene (1 mL) was treated with tri-n-butyltin hydride (1.5 mmole) and AIBN (0.1 mmole), and the resulting reaction mixture was heated to reflux for 2 h. Evaporation and chromatography gave diethyl 4-(tert-butyldiphenylsilyloxy)-2,2-difluorobutylphosphonate as a clear oil.

Step D.

A solution of diethyl 4-(tert-butyldiphenylsilyloxy)-2,2-difluorobutylphosphonate (1 mmole) in methanol (1 mL) was treated with hydrochloric acid (4 N, 4 mmole) at 0° C., and the resulting reaction was stirred at room temperature for 2 h. Evaporation and chromatography gave diethyl 4-hydroxy-2,2-difluorobutylphosphonate as a clear oil.

Step E.

A solution of gave diethyl 4-hydroxy-2,2-difluorobutylphosphonate (1 mmole) in acetone (10 mL) was treated with Jones's reagent (10 mmole) at 0° C. for 30 min. The reaction was quenched with 2-propanol (10 mL), and the resulting mixture was filtered through a Celite pad. Evaporation of the filtrate followed by extraction gave diethyl 3-carboxyl-2,3difluoropropylphosphonate as an oil.

Step F.

A solution of diethyl 3-carboxyl-2,3-difluoropropylphosphonate (1 mmole) in thionyl chloride (3 mL) was heated to reflux for 2 h. The reaction was evaporated to dryness, and the residue was dissolved in diethyl ether (1 mL) was treated with an etheral solution of diazomethane (10 mmole) at 0° C. for 30 min. A solution of HBr in acetic acid (30%, 1 mL) was added to the reaction, and the resulting solution was stirred at room temperature for 1 h. The reaction was evaporated to dryness and the residue was dissolved in THF-EtOH (1:1, 5 mL) and treated with thiourea (1 mmole). The resulting reaction mixture was heated to 75° C. for 1 h. Evaporation followed by extraction and chromatography gave 2-amino-4-[1-(3-diethylphosphono-3,3-difluoro)propyl]thiazole as a solid, which was subjected to Step C of Example 3 to give gave 2-amino-4-[1-(3-phosphono-3,3-difluoro)propyl]thiazole (28.1) as a solid. Anal. Calcd. for $C_6H_9N_2O_3PSF_2+HBr$: C: 21.25; H: 2.97; N: 8.26. Found: C: 21.24; H: 3.25; N: 8.21.

The following compound was prepared in a similar manner: 2-Amino-5-methylthio-4-[1-(3-phosphono-3,3-difluoro)propyl]thiazole (28.2). MS m/e 305 (M+H).

Example 29

Preparation of 2-methylthio-5-phosphonomethylthio-1,3,4-thiadiazole and 2-phosphonomethylthiopyridine Step A.

A solution of 2-methylthio-1,3,4-thiadiazole-5-thiol (1 mmole) in THF (5 mL) was treated with sodium hydride (60%, 1.1 mmole) at 0° C. and the resulting mixture was stirred at room temperature for 30 min. The reaction was then cooled to 0° C. and treated with diethylphosphonomethyl trifluoromethanesulfonate (1.1 mmole). After stirring at room temperature for 12 h, the reaction was quenched with saturated ammonium chloride. Extraction and chromatography gave 2-methylthio-5-diethylphosphonomethylthio-1,3,4-thiadiazole as an oil.

Step B.

2-Methylthio-5-diethylphosphonomethylthio-1,3,4-thiadiazole was subjected to Step C of Example 3 to give 2-methylthio-5-phosphonomethylthio-1,3,4-thiadiazole (29.1) as a yellow solid. Anal. Calcd. for $C_4H_7N_2O_3P_3+0.2$ HBr: C: 17.50; H: 2.64; N: 10.21. Found: C: 17.64; H: 2.56; N: 10.00.

Alternatively, phosphonomethylthio substituted heteroaromatics are made using the following method as exemplified by the synthesis of 2-phosphonomethylthiopyridine:

Step C.

A solution of 2,2'-dipyridyl disulfide (1 mmole) in THF was treated with tri-n-butylphosphine (1 mmole) and diethyl hydroxymethylphosphonate at 0° C. The resulting reaction solution was stirred at room temperature for 18 h. Extraction and chromatography gave 2-diethylphosphonomethylthiopyridine as a yellow oil.

Step D.

2-Diethylphosphonomethylthiopyridine was subjected to Step C of Example 3 to give 2-phosphonomethylthiopyridine (29.2) as a yellow solid. Anal. Calcd. for $C_6H_8NO_3PS+0.62$ HBr: C: 28.22; H: 3.40; N: 5.49. Found: C: 28.48; H: 3.75; N: 5.14.

Example 30

Preparation of 2-[(2-phosphono)ethynyl]pyridine

Step A.

A solution of 2-ethynylpyridine (1 mmole) in THF (5 mL) was treated with LDA (1.2 mmole) at 0° C. for 40 min. Diethyl chlorophosphate (1.2 mmole) was added to the reaction and the resulting reaction solution was stirred at room temperature for 16 h. The reaction was quenched with saturated ammonium chloride followed by extraction and chromatography to give 2-[(2-diethylphosphono)ethynyl]pyridine as a yellow oil.

Step B.

2-[(2-Diethylphosphono)ethynyl]pyridine was subjected to Step C of Example 3 to give 2-[1-(2-phosphono)ethynyl]pyridine (30.1) as a brown solid. Mp 160° C. (decomp). MS m/e 184 (M+H).

Example 31
A. Preparation of Various Phosphoramides as Prodrugs
Step A.

A solution of 2-methyl-5-isopropyl-4-[2-(5-phosphono)furanyl]thiazole dichloridate (generated as in Example 19) (1 mmole) in dichloromethane (5 mL) was cooled to 0° C. and treated with a solution of benzyl alcohol (0.9 mmole) in dichloromethane (0.5 mL) and pyridine (0.3 mL). The resulting reaction solution was stirred at 0° C. for 1 h, and then added a solution of ammonia (excess) in THF. After stirring at room temperature for 16 h, the reaction was evaporated to dryness and the residue was purified by chromatography to give 2-methyl-5-isopropyl-4-[2-(5-phosphonomonoamido)furanyl]thiazole (31.1) as a yellow hard gum and 2-methyl-5-isopropyl-4-[2-(5-phosphorodiamido)furanyl]thiazole (31.2) as a yellow hard gum.

(31.1) 2-Methyl-5-isopropyl-4-[2-(5-phosphonomonoamido)furanyl]thiazole: MS m/e 299 (M–H).

(31.2) 2-Methyl-5-isopropyl-4-[2-(5-phosphorodiamido)furanyl]thiazole: MS m/e 298 (M–H).

Alternatively, a different method was used to prepare other phosphoramides as exemplified in the following procedure:
Step B.

A suspension of 2-amino-5-methylthio-4-[2-(5-phosphono)furanyl]thiazole dichloridate (generated as in Example 19) (1 mmole) in dichloromethane (5 mL) was cooled to 0° C. and ammonia (excess) was bubbled through the reaction for 10 min. After stirring at room temperature for 16 h, the reaction was evaporated to dryness and the residue was purified by chromatography to give 2-amino-5-methylthio-4-[2-(5-phosphorodiamido)furanyl]thiazole (31.3) as a foam. Anal. Calcd for $C_8H_{11}N_4O_2PS_2$+1.5 HCl+ 0.2 EtOH: C: 28.48; H: 3.90; N: 15.82. Found: C: 28.32; H: 3.76; N: 14.21.

The following compounds were prepared according to the above described procedures or in some cases with minor modifications of these procedures:

(31.4) 2-Amino-5-isobutyl-4-[2-(5-phosphonomonoamido)furanyl]thiazole. Mp 77–81° C. Anal. Calcd for $C_{11}H_{16}N_3O_3PS+H_2O+0.8$ $Et_3N$: C: 47.41; H: 7.55; N: 13.30. Found: C: 47.04; H: 7.55; N: 13.67.

(31.5) 2-Amino-5-isobutyl-4-[2-(5-phosphorodiamido)furanyl]thiazole. Anal. Calcd for $C_{11}H_{17}N_4O_2PS$+ $0.5H_2O+0.75$ HCl: C: 39.24; H: 5.61; N: 16.64. Found: C: 39.05; H: 5.43; N: 15.82.

(31.28) 2-Amino-5-isobutyl-4-{2-[5-(N,N'-diisobutyl)phosphoroadiamido]furanyl}-thiazole. Mp 182–183° C. Anal. Calcd. for $C_{19}H_{33}N_4O_2PS$: C: 55.32; H: 8.06; N: 13.58. Found: C: 54.93; H: 7.75; N: 13.20.

(31.29) 2-Amino-5-isobutyl-4-{2-[5-(N,N'-(1,3-bis(ethoxycarbonyl)-1-propyl)phosphoro)diamido]furanyl}thiazole. Anal. Calcd for $C_{29}H_{45}N_4O_{10}PS$: C: 51.78: H: 6.74; N: 8.33. Found: C: 51.70; H: 6.64; N: 8.15.

(31.30) 2-Amino-5-isobutyl-4-{2-[5-(N,N'-(1-benzyloxycarbonyl)-1-ethyl)phosphorodiamido]furanyl}thiazole. Anal. Calcd for $C_{31}H_{37}N_4O_6PS$: C: 59.60; H: 5.97; N: 8.97. Found C: 59.27; H: 5.63; N: 8.74.

(31.31) 2-Amino-5-isobutyl-4-{2-[5-bis(2-methoxycarbonyl-1-azirdinyl)phosphorodiamido]furanyl}thiazole. Anal. Calcd for $C_{19}H_{25}N_4O_6PS$+ $0.3CH_2Cl_2$: C: 46.93; H: 5.22; N: 11.34. Found: C: 58.20; H: 5.26; N: 9.25.

(31.39) 2-Amino-5-isobutyl-4-{2-[5-(N,N'-2-(1-ethoxycarbonyl)propyl)phosphorodiamido]furanyl}thiazole. Anal. Calcd for $C_{23}H_{37}N_4O_6PS$+ $0.6EtOAc+0.1$ $CH_2Cl_2$: C: 51.91; H: 7.18; N: 9.50. Found: C: 51.78; H: 7.17; N: 9.26.

The monophenyl-monophosphonamide derivatives of compounds of formula I can also be prepared according to the above described procedures:
Step C.

A solution of 2-amino-5-isobutyl-4-[2-(5-diphenylphosphono)furanyl]thiazole (prepared according to the procedures of Example 19) (1 mmole) in acetonitrile (9 mL) and water (4 mL) was treated with lithium hydroxide (1N, 1.5 mmole) at room temperature for 4 h. The reaction solution was evaporated to dryness, and the residue was dissolved in water (10 mL), cooled to 0° C. and the pH of the solution was adjusted to 4 by addition of 6 N HCl. The resulting white solid was collected through filtration to give 2-amino-5-isobutyl-4-[2-(5-phenylphosphono)furanyl]thiazole (19.64).
Step D.

A suspension of 2-amino-5-isobutyl-4-[2-(5-phenylphosphono)furanyl]thiazole (1 mmole) in thionyl chloride (3 mL) was heated to reflux for 2 h. The reaction solution was evaporated to dryness, and the residue was dissolved in anhydrous dichloromethane (2 mL) and the resulting solution was added to a solution of L-alanine methyl ester hydrochloride (1.2 mmole) in pyridine (0.8 mL) and dichloromethane (3 mL) at 0° C. The resulting reaction solution was stirred at room temperature for 14 h. Evaporation and chromatography gave 2-amino-5-isobutyl-4-{2-[5-(O-phenyl-N-(1-methoxycarbonyl)ethyl)phosphonamido]furanyl}thiazole (31.6) as an oil. Anal. calcd. for $C_{21}H_{26}N_3O_5PS$: C: 54.42; H: 5.65; N: 9.07. Found: C: 54.40; H: 6.02; N: 8.87.

The following compounds were prepared according to the above described procedures:

(31.7) 2-amino-5-isobutyl-4-{2-[5-(O-phenylphosphonamido)]furanyl}thiazole. mp 205° C. (decomp). Anal. calcd. for $C_{17}H_{20}N_3O_3PS+0.3$ $H_2O+0.3$ HCl: C: 51.86; H: 5.35; N: 10.67. Found: C: 51.58; H: 4.93; N: 11.08.

(31.8) 2-amino-5-isobutyl-4-{2-[5-(O-phenyl-N-ethoxycarbonylmethyl)phosphonamido]furanyl}thiazole. Anal. calcd. for $C_{21}H_{26}N_3O_5PS$: C: 54.42; H: 5.65; N: 9.07. Found: C: 54.78; H: 5.83; N: 8.67.

(31.9) 2-amino-5-isobutyl-4-{2-[5-(O-phenyl-N-isobutyl)phosphonamido]furanyl}thiazole. mp 151–152° C. Anal. calcd. for $C_{21}H_{28}N_3O_3PS$: C: 58.18; H: 6.51; N: 9.69. Found: C: 58.12; H: 6.54; N: 9.59.

(31.18) 2-amino-5-isobutyl-4-{2-[5-(O-phenyl-N-(1-(1-ethoxycarbonyl-2-phenyl)ethyl)phosphonamido)]furanyl}thiazole. Anal. calcd. for $C_{28}H_{32}N_3O_5PS$: C: 60.75; H: 5.83; N: 7.59. Found: C: 60.35; H: 5.77; N: 7.37.

(31.19) 2-amino-5-isobutyl-4-{2-[5-(O-phenyl-N-(1-(1-ethoxycarbonyl-2-methyl)propyl)phosphonamido)]furanyl}thiazole. Anal. calcd. for $C_{23}H_{30}N_3O_5PS$: C: 56.20; H: 6.15; N: 8.55. Found: C: 55.95; H: 5.80; N: 8.35.

(31.20) 2-amino-5-isobutyl-4-{2-[5-(O-phenyl-N-(1-(1,3-bis(ethoxycarbonyl) propyl)phosphonamido)]furanyl}thiazole. Anal. calcd. for $C_{26}H_{34}N_3O_7PS+0.2$ $CH_2Cl_2$: C: 54.20; H: 5.97; N: 7.24. Found C: 54.06; H: 5.68; N: 7.05.

(31.21) 2-amino-5-isobutyl-4-{2-[5-(O-(3-chlorophenyl)-N-(1-(1-methoxycarbonyl)ethyl) propyl)phosphonamido)]furanyl}thiazole. Anal. calcd. for $C_{21}H_{25}N_3O_5PSCl$: C: 50.65; H: 5.06; N: 8.44. Found: C: 50.56; H: 4.78; N: 8.56.

(31.22) 2-amino-5-isobutyl-4-{2-[5-(O-(4-chlorophenyl)-N-(1-(1-methoxycarbonyl)ethyl)phosphonamido)]furanyl}thiazole. Anal. calcd. for $C_{21}H_{25}N_3O_5PSCl+1HCl+0.2\ H_2O$: C: 46.88; H: 4.95; N: 7.81. Found: C: 47.33; H: 4.71; N: 7.36.

(31.23) 2-amino-5-isobutyl-4-{2-[5-(O-phenyl-N-(1-(1-bis(ethoxycarbonyl)methyl)phosphonamido)]furanyl}thiazole. Anal. calcd. for $C_{24}H_{30}N_3O_7PS$: C: 53.83; H: 5.65; N: 7.85. Found: C: 53.54 H: 5.63; N: 7.77.

(31.24) 2-amino-5-isobutyl-4-{2-[5-(O-phenyl-N-(1-morpholinyl)phosphonamido)]furanyl}thiazole. Anal. calcd. for $C_{21}H_{26}N_3O_4PS$: C: 56.37; H: 5.86; N: 9.39. Found: C: 56.36; H: 5.80; N: 9.20.

(31.25) 2-amino-5-isobutyl-4-{2-[5-(O-phenyl-N-(1-(1-benzyloxycarbonyl)ethyl)phosphonamido)]furanyl}thiazole. Anal. calcd. for $C_{27}H_{30}N_3O_5PS$: C: 60.10; H: 5.60; N: 7.79. Found: C: 59.80; H: 5.23; N: 7.53.

(31.32) 2-amino-5-isobutyl-4-{2-[5-(O-phenyl-N-benzyloxycarbonylmethyl)phosphonamido)]furanyl}thiazole. Anal. calcd. for $C_{26}H_{28}N_3O_5PS$: C: 59.42; H: 5.37; N: 8.00. Found: C: 59.60; H: 5.05; N: 7.91.

(31.36) 2-amino-5-isobutyl-4-{2-[5-(O-(4-methyoxyphenyl)-N-(1-(1-methoxycarbonyl)ethyl)phosphonamido)]furanyl}thiazole. Anal. calcd. for $C_{22}H_{28}N_3O_6PS+0.1\ CHCl_3+0.1\ MeCN$: C: 52.56; H: 5.62; N: 8.52. Found: C: 52.77; H: 5.23; N: 8.87.

(31.37) 2-amino-5-isobutyl-4-{2-[5-(O-phenyl-N-2-methoxycarbonyl)propyl)phosphonamido)]furanyl}thiazole. Anal. calcd. for $C_{22}H_{28}N_3O_5PS+0.6\ H_2O$: C: 54.11; H: 6.03; N: 8.60. Found: C: 53.86; H: 5.97; N: 8.61.

(31.38) 2-amino-5-isobutyl-4-{2-[5-(O-phenyl-N-(2-(1-ethoxycarbonyl)propyl)phosphonamido)]furanyl}thiazole. Anal. calcd. for $C_{23}H_{30}N_3O_5PS$: C: 56.20; H: 6.15; N: 8.55. Found: C: 55.90; H: 6.29; N: 8.46.

The reaction of a dichlorophosphonate with a 1-amino-3-propanol in the presence of a suitable base (e.g. pyridine, triethylamine) can also be used to prepare cyclic phosphoramidates as prodrugs of phosphonates. The following compounds were prepared in this manner:

(31.10) 2-Methyl-5-isobutyl-4-{2-[5-(1-phenyl-1,3-propyl)phosphonamido]furanyl}thiazole minor isomer. Anal. calcd. for $C_{21}H_{25}N_2O_3PS+0.25\ H_2O+0.1\ HCl$: C: 59.40; H: 6.08; N: 6.60. Found: C: 59.42; H: 5.72; N: 6.44.

(31.11) 2-Methyl-5-isobutyl-4-{2-[5-(1-phenyl-1,3-propyl)phosphonamido]furanyl}thiazole major isomer. Anal. calcd. for $C_{21}H_{25}N_2O_3PS+0.25\ H_2O$: C: 59.91; H: 6.11; N: 6.65. Found: C: 60.17; H: 5.81; N: 6.52.

(31.12) 2-Amino-5-isobutyl-4-{2-[5-(1-phenyl-1,3-propyl)phosphonamido]furanyl}thiazole major isomer. Anal. calcd. for $C_{20}H_{24}N_3O_3PS+0.25\ H_2O+0.1\ CH_2Cl_2$: C: 55.27; H: 5.72; N: 9.57. Found: C: 55.03; H: 5.42; N: 9.37.

(31.13) 2-Amino-5-isobutyl-4-{2-[5-(1-phenyl-1,3-propyl)phosphonamido]furanyl}thiazole minor isomer. Anal. calcd. for $C_{20}H_{24}N_3O_3PS+0.15\ CH_2Cl_2$: C: 56.26; H: 5.69; N: 9.77. Found: C: 56.36; H: 5.46; N: 9.59.

(31.14) 2-Amino-5-methylthio-4-{2-[5-(1-phenyl-1,3-propyl)phosphonamido]furanyl}thiazole less polar isomer. Anal. calcd. for $C_{17}H_{18}N_3O_3PS_2+0.4\ HCl$: C: 48.38; H: 4.39; N: 9.96. Found: C: 48.47; H: 4.21; N: 9.96.

(31.15) 2-Amino-5-methylthio-4-{2-[5-(1-phenyl-1,3-propyl)phosphonarnido]furanyl}thiazole more polar isomer. Anal. calcd. for $C_{17}H_{18}N_3O_3PS_2$: C: 50.11; H: 4.45; N: 10.31. Found: C: 49.84; H: 4.19; N: 10.13.

(31.16) 2-Amino-5-methylthio-4-{2-[5-(N-methyl-1-phenyl-1,3-propyl)phosphonamido]furanyl}thiazole. Anal. calcd. for $C_{18}H_{20}N_3O_3PS_2+0.25\ HCl$: C: 50.21; H: 4.74; N: 9.76. Found: C: 50.31; H: 4.46; N: 9.79.

(31.17) 2-Amino-5-methylthio-4-{2-[5-(1-phenyl-1,3-propyl)-N-acetylphosphonamido]furanyl}thiazole. Anal. calcd. for $C_{22}H_{26}N_3O_4PS+1.25\ H_2O$: C: 54.82; H: 5.96; N: 8.72. Found: C: 55.09; H: 5.99; N: 8.39.

(31.26) 2-amino-5-isobutyl-4-{2-[5-(1-oxo-1-phospha-2-oxa-7-aza-3,4-benocycloheptan-1-yl)]furanyl}thiazole, major isomer. Mp 233–234° C. Anal. calcd. for $C_{21}H_{24}N_3O_5PS+0.2\ CHCl_3$: C: 52.46; H: 5.03; N: 8.66. Found C: 52.08; H: 4.65; N: 8.58.

(31.27) 2-amino-5-isobutyl-4-{2-[5-(1-oxo-1-phospha-2-oxa-7-aza-3,4-benocycloheptan-1-yl)]furanyl}thiazole, minor isomer. MS calcd. for $C_{21}H_{24}N_3O_5PS+H$: 462, found 462.

(31.34) 2-amino-5-isobutyl-4-{2-[5-(3-(3,5-dichlorophenyl)-1,3-propyl)phosphonamido]furanyl}thiazole. Anal. calcd. for $C_{20}H_{22}N_3O_3PSCl_2$: C: 49.39; H: 4.56; N: 8.64. Found: C: 49.04; H: 4.51; N: 8.37.

(31.35) 2-amino-5-isobutyl-4-{2-[5-(4,5-benzo-1-oxo-1-phospha-2-oxa-6aza)cyclohexan-1-yl]furanyl}thiazole. Anal. calcd. for $C_{18}H_{20}N_3O_3PS+0.7\ H_2O$: C; 53.78; H: 5.37; N: 10.45. Found C: 53.63; H: 5.13; N: 10.36.

Example 32

Preparation of 5-[2-(5-phosphono)furanyl]tetrazole

Step A.

To a mixture of tetrazole (1 mmole) and powdered $K_2CO_3$ (1.5 mmole) in 1 mL DMF cooled to 0° C. was added benzyl chloromethyl ether (1.2 mmole) and the resulting mixture stirred for 30 min at 0° C. and then for 16 h at rt. The mixture was diluted with water and ether. Extraction and chromatography provided 2-benzyloxymethyltetrazole as a colorless oil.

Step B.

To a solution of 2-benzyloxymethyltetrazole (1 mmole) and TMEDA (2 mmole) in 3 mL diethyl ether at −78° C. was added n-BuLi in hexanes (1 mmole). This was let stir for 5 min at −78° C. and then it was added to a precooled (−78° C.) solution of (n-Bu)$_3$SnCl (1 mmole) in 2 mL of diethyl ether. After stirring at −78° C. for 30 min it was diluted with water and diethyl ether. Extraction and chromatography provided 2-benzyloxymethyl-5-(tributylstannyl)tetrazole as a colorless oil.

Step C.

A mixture of 5-iodo-2-diethylphosphonofuran (1 mmole), 2-benzyloxymethyl-5-(tributylstannyl)tetrazole (1.05 mmole), tetrakis(triphenylphosphine) palladium(0) (0.03 mmole) and copper(I) iodide (0.07 mmole) in 3 mL of toluene was refluxed at 110° C. for 20 h. Evaporation and chromatography provided 2-benzyloxymethyl-5-[2-(5-diethylphosphono)furanyl]tetrazole as an oil.

Step D.

A mixture of 2-benzyloxymethyl-5-[2-(5-diethylphosphono)furanyl]tetrazole (1 mmole) and 6 M HCl (1 mL) in 10 mL ethanol was heated at 70° C. for 20 h and then the solvent concentrated by evaporation, made basic with 1 N NaOH and extracted with EtOAc. The aqueous layer was made acidic and extracted with EtOAc. This EtOAc extract was evaporated to provide 5-[2-(5-diethylphosphono)furanyl]tetrazole as a solid, which was subjected to Step C of Example 3 to give 5-[2-(5-phosphono)furanyl]tetrazole (32.1) as a solid: mp 186–188° C. Anal. calcd. for $C_5H_5N_4O_4P+1.5\ H_2O$: C, 24.70; H, 3.32; N, 23.05. Found: C, 24.57; H: 2.57; N: 23.05.

Step E.
Step 1.

A mixture of 5-[2-(5-diethylphosphono)furanyl]tetrazole (1 mmole), 1-iodo-2-methylpropane (2 mmole) and powdered $K_2CO_3$ (2 mmole) in 5 mL DMF was stirred at 80° C. for 48 h and then diluted with $CH_2Cl_2$ and water and the layers separated. The $CH_2Cl_2$ layer was evaporated and combined with the product of the following reaction for chromatography.

Step 2.

The aqueous layer of Step 1 was made acidic and extracted with EtOAc. This extract was evaporated and the residue heated at 80° C. in 2 mL of $SOCl_2$ for 3 h and then the solvent evaporated. The residue was dissolved in 5 mL $CH_2Cl_2$ and 0.3 mL $NEt_3$ and 0.5 mL of EtOH was added. After stirring for 1 h at rt the mixture was diluted with $CH_2Cl_2$ and water. This organic extract was combined with that kept from Step 1 and chromatography provided 1-isobutyl-5-[2-(5-diethylphosphono)furanyl]tetrazole and 2-isobutyl-5-[2-(5-diethylphosphono)furanyl]tetrazole each as an oil.

Step 3.

1-Isobutyl-5-[2-(5-diethylphosphono)furanyl]tetrazole was subjected to Step C of Example 3 to give 1-isobutyl-5-[2-(5-phosphono)furanyl]tetrazole (32.2) as a solid: mp 200–202° C. Anal. calcd. for $C_9H_{13}N_4O_4P$: C: 39.71; H: 4.81; N: 20.58. Found: C: 39.64; H: 4.63; N: 20.21.

Step F.

A mixture of 2-isobutyl-5-[2-(5-diethylphosphono)furanyl]tetrazole (1 mmole) and TMSBr (10 mmole) in 10 mL of $CH_2Cl_2$ was stirred at room temperature for 16 h. The solvent was evaporated and the residue dissolved in 10:1 $CH_3CN$:water, the solvent evaporated and the residue precipitated from acetone by addition of dicyclohexylamine (2 mmole) to provide 2-isobutyl-5-[2-(5-phosphono)furanyl] tetrazole N,N-dicyclohexyl ammonium salt.

(32.3) as a solid: mp 226–228° C. Anal. calcd. for $C_9H_{13}N_4O_4P+C_{12}H_{23}N$: C: 55.63; H: 8.00; N: 15.44. Found: C: 55.55; H: 8.03; N: 15.07.

Example 33

High Throughput Synthesis of Various 2-(5-phosphono)furanyl Substituted Heteroaromatic Compounds Step A.

Various 2-(5-diethylphosphono)furanyl substituted heteroaromatic compounds were prepared in a similar manner as Step B of Example 15, and some of these compounds were used for the high throughput synthesis of compounds listed in Table 33.1 and Table 33.2.

Step B.

A mixture of 2-chloro-6-[2-(5-diethylphosphono)furanyl]pyridine (0.01 mmole) and TMSBr (0.1 mL) in $CH_2Cl_2$ (0.5 mL) was stirred at room temperature for 16 h and then evaporated and diluted with 0.5 mL of 9:1 $CH_3CN$:water. Evaporation provided 2-chloro-6-[2-(5-phosphono)furnayl]pyridine.

Step C.

A mixture of 2-chloro-6-[2-(5-diethylphosphono)furanyl]pyridine (0.01 mmole) and a solution of freshly prepared sodium propoxide in propanol (0.25 M, 0.4 mL) was let sit at 85° C. for 14 h. The reaction mixture was evaporated and the residue was subjected to Step B of Example 33 to give 2-propyloxy-6-[2-(5-phosphono)furanyl]pyridine.

Step D.

A mixture of 2-chloro-6-[2-(5-diethylphosphono)furanyl]pyridine (0.01 mmol) and 1-methylpiperazine (0.2 mL) in ethylene glycol (0.2 mL) was heated at 145° C. for 24 h. The mixture was further diluted with 0.5 mL of $CH_3CN$ and 0.1 mL of water and then 150 mg of Dowex 12-100 formate resin was added. After stirring this mixture 30 min it was filtered and the resin washed with DMF (210 min), $CH_3CN$ (210 min) and then 9:1 $CH_3CN$:water (110 min). Finally the resin was stirred with 9:1 TFA:water for 30 min, filtered and the filtrate evaporated. The residue obtained subjected to Step B of example to give 2-[1-(4-methyl)piperazinyl]-6-[2-(5-phosphono)furanyl]pyridine.

Step E.

A mixture of 3-chloro-5-[2-(5-diethylphosphono)furanyl] pyrazine (0.01 mmole), 5-tributylstannylthiophene (0.04 mmole), $Pd(PPh_3)_4$ (0.001 mmole) and CuI (0.002 mmole) in dioxane (0.5 mL) was heated at 85° C. for 16 h then the solvent was evaporated. The resulting residue and TMSBr (0.1 mL) in 0.5 mL $CH_2Cl_2$ was stirred at rt for 16 h and then evaporated and diluted with 0.5 mL of 9:1 $CH_3CN$:water. To this solution 150 mg of Dowex 12–100 formate resin was added and after stirring 30 min it was filtered and the resin washed with DMF (210 min), $CH_3CN$ (210 min) and then 9:1 $CH_3CN$:water (110 min). Finally the resin was stirred with 9:1 TFA:water for 30 min, filtered and the filtrate evaporated to give 3-(2-thienyl)-5-[2-(5-phosphono) furnayl]pyrazine.

Step F.

A mixture of 3-chloro-5-[2-(5-diethylphosphono)furanyl] pyrazine (0.01 mmole), 1-hexyne (0.04 mmole), diisopropylethylamine (0.1 mmole), $Pd(PPh_3)_4$ (0.001 mmole) and CuI (0.002 mmole) in dioxane (0.5 mL) was heated at 85° C. for 16 h then the solvent was evaporated. The resulting residue was subjected to Step B to give 3-(1-hexyn-1-yl)-5-[2-(5-phosphono)furanyl]pyrazine.

Preparation of the Carboxymethylphosphonate Resin

Step G.

A solution of trimethylphosphonoacetate (30.9 mmol), 2-(trimethylsiyl) ethanol (10.4 mmol) and DMAP (3.1 mmol) in toluene (25 iL) was refluxed for 48 h under $N_2$. After cooling, the solution was diluted with EtOAc and washed with 1N HCl followed by water. The organic solution was dried over sodium sulfate and concentrated under vacuum to give an oil. The residue was treated with LiI (10.4 mmol) in 2-butanone (30 mL), and refluxed overnight under $N_2$. The solution was diluted with EtOAc, washed with 1N HCl, dried over $Na_2SO_4$ and concentrated under vacuum to afford the SEM protected carboxy monomethylphosphonate as a colorless oil.

Step H.

Hydroxymethylpolystyrene (2.35 mmol) was prepared for coupling by combining with anhyrous THF (40 mL), gently skaking for 20 min. and then removing the excess solvent by cannula. This procedure was repeated 3 times. The swollen resin was then suspended in THF (40 mL) and DIPEA (21.2 mmol). To this mixture was added, by cannula, a solution of the SEM protected carboxy monomethylphosphonate (prepared in Step G)

(7.1 mmol), DIAD (7.1 mmol) and tris(4-chlorophenyl) phosphine (7.1 mmol) in THF (15 mL) which had been stirred for 15 min. prior to addition. After shaking the mixture overnight under a blanket of $N_2$, the resin was filtered, rinsed with THF (3×40 mL), DMF (3×40 mL), and THF again (3×40 mL) before drying under vacuum to afford 3.8 g of the coupled phosphonate resin.

Step I.

To coupled phosphonate resin (2.41 mmol) in THF (100 mL) was added 1M TBAF in THF solution (12 mL). The mixture was shaken overnight before being filtered and the resin rinsed with THF (3×40 mL) to afford the desired carboxymethylphosphonate resin as the tetrabutylammonium salt.

Coupling of the Carboxyymehylphosphonate Resin to a Heteroaromatic Amine
Step J.

In a 2 mL well, a heteroaromatic amine (0.14 mmol), resin (0.014 mmol), PyBOP (0.14 mmol) and TEA (0.36 mmol) in DMF (1.45 mL) were combined and shaken for 48 h at room temperature. The treated resin was then filtered, washed with DMF (3×) and $CH_2Cl_2$ (3×). The isolated resin was resuspended in $CH_2Cl_2$ (900 L), combined with TMSBr (100 L) and mixed for 6 h. The mixture was filtered, the resin washed with anhydrous $CH_2Cl_2$ (500 L) and the filtrate concentrated under vacuum. To the isolated residue was added a solution of $CH_3CN/H_2O$ (9:1, 300 L). After shaking for 30 min. the solvents were removed to provide the desired [{N-(phosphono)acetyl]amino} substituted heteroaromatic analogs. Compounds 33.97–33.119 and 33.146–33.164 were synthesized according to these procedures and they are listed in Table 33.1 and Table 33.2.

Preparation of the Aminomethylphosphonate Resin
Step K.

To a solution of dimethyl phthalimidomethylphosphonate (37 mmole) in 2-butanone (150 mL) was added LiI (38.9 mmol). After refluxing overnight under $N_2$, the solution was diluted with EtOAc, washed with 1N HCl, dried over $MgSO_4$ and concentrated under vacuum to afford monomethyl phthalimidomethylphosphonate as a white solid.
Step L.

As described above in Step H, monomethyl phthalimidomethylphosphonate was coupled to hydroxymethylpolystyrene to give the resin-coupled phthalimidomethylphosphonate monomethyl ester.
Step M.

To the resin-coupled phthalimidomethylphosphonate monomethyl ester (6.8 mmol) in DMF (7 mL) was added anhydrous hydrazine (3 mL). After shaking at room temperature for 24 h the resin was filtered, rinsed with DMF (3×10 mL), $CH_2Cl_2$ (3×10 mL) and then dried under vacuum to afford 832 mg the desired resin-coupled aminomethylphosphonate monomethyl ester.

Coupling of Various Heteroaromatic Carboxylic Acids to the Resin-coupled Aminomethylphosphonate Monomethyl Ester.
Step N.

In a 2 mL well, a heteroaromatic carboxylic acid (0.2 mmol), resin (0.02 mmol), EDC (0.2 mmol) and HOBT (0.2 mmol) in DMF (0.5 mL) were combined and shaken for 24 h at room temperature. The treated resin was then filtered, washed with DMF (3×) and $CH_2Cl_2$ (3×). The isolated resin was resuspended in $CH_2Cl_2$ (500 L), combined with TMSBr (50 L) and mixed for 6 h. The mixture was filtered, the resin washed with anhydrous $CH_2Cl_2$ (500 L) and the filtrate concentrated under vacuum. To the isolated residue was added a solution of $CH_3CN/H_2O$ (9:1, 300 L). After shaking for 30 min the solvents were evaporated to provide the desired (N-phosphonomethyl)carbamoyl substituted heteroaromatic analogs. Compounds 33.120–33.145 were synthesized according to these procedures and they are listed in Table 33.2.

The following compounds were prepared according to some or all of the above described procedures. These compounds were characterized by HPLC (as described below) and mass spectroscopy (APCI negative ion), and these characterization data are listed in Table 33.1 and Table 33.2.

HPLC was performed using a YMC ODS-Aq, Aq–303–5, 250 4.6 mm ID, S-5 μm, 120 A column with the UV detector set at 280 nm.

| HPLC Elution Program: 1.5 mL/min flow rate | | |
|---|---|---|
| Time (min) | % Acetonitrile (A) | % Buffer[a] (B) |
| 0 | 10 | 90 |
| 7.5 | 90 | 10 |
| 12.4 | 90 | 10 |
| 12.5 | 10 | 90 |
| 15 | 10 | 90 |

[a]Buffer = 95:5:0.1 water:methanol:acetic acid

TABLE 33.1

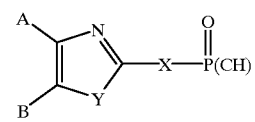

| synthetic example number | A | B | X | Y' | HPLC Rt (min.) | M-1 found |
|---|---|---|---|---|---|---|
| 33.146 | H | Br | NHC(O)CH2 | S | 6.58 | 299/301 |
| 33.147 | H | Ph | NHC(O)CH2 | S | 6.57 | 297 |
| 33.148 | Ph | H | NHC(O)CH2 | S | 6.06 | 297 |
| 33.149 | Ph | Et | NHC(O)CH2 | O | | 309 |
| 33.150 | H | H | NHC(O)CH2 | S | 4.22 | 221 |
| 33.151 | adamantyl | Me | NHC(O)CH2 | S | 6.59 | 369 |
| 33.152 | Bu-t | Br | NHC(O)CH2 | S | 6.62 | 355/357 |
| 33.153 | H | Ph(-4-Br) | NHC(O)CH2 | S | 6.62 | 375/377 |

TABLE 33.1-continued

| synthetic example number | A* | B* | X | Y' | HPLC Rt (min.) | M-1 found |
|---|---|---|---|---|---|---|
| 33.154 | H | H | NHC(O)CH2 | O | 6.68 | 205 |
| 33.155 | null | NH2 | NHC(O)CH2 | O | 6.6 | 221 |
| 33.156 | NHMe | null | NHC(O)CH2 | S | 3.82 | 251 |
| 33.157 | Me | H | NHC(O)CH2 | NH | | |
| 33.158 | H | H | NHC(O)CH2 | NH | | |
| 33.159 | OH | H | NHC(O)CH2 | NH | | |
| 33.160 | Bu-t | H | NHC(O)CH2 | O | 6.62 | 261 |
| 33.161 | null | 3-pyridyl | NHC(O)CH2 | O | 6.58 | 283 |
| 33.162 | CH2Ph(2,6-dichloro) | null | NHC(O)CH2 | O | | |
| 34.163 | Br | null | furan-2,5-diyl | NH | 4.46 | 292/294 |
| 34.164 | Br | null | furan-2,5-diyl | S | 5.96 | 309/311 |

*when A or B is null, then the corresponding G is N.

TABLE 33.2

| synthetic example number | A* | B* | X | D* | E* | HPLC Rt (min.) | M-1 found |
|---|---|---|---|---|---|---|---|
| 33.1 | NH2 | Cl | furan-2,5-diyl | Me | null | 11.06 | 288 |
| 33.2 | H | OC(O)(Ph-2,6-dichloro) | furan-2,5-diyl | H | H | 3.99 | 413 |
| 33.3 | OMe | H | furan-2,5-diyl | CH2OH | H | 8.34 | 284 |
| 33.4 | OMe | H | furan-2,5-diyl | C(O)NH2 | H | 8.23 | 297 |
| 33.5 | OMe | H | furan-2,5-diyl | CO2H | H | 9.54 | 298 |
| 33.6 | OH | H | furan-2,5-diyl | CF3 | C(O)NH2 | 3.91 | 351 |
| 33.7 | OMe | H | furan-2,5-diyl | CF3 | C(O)NH2 | 9.14 | 365 |
| 33.8 | null | H | furan-2,5-diyl | H | OMe | 9.72 | 255 |
| 33.9 | null | H | furan-2,5-diyl | H | OH | 4.52 | 241 |
| 33.10 | OH | H | furan-2,5-diyl | Me | null | 3.79 | 255 |
| 33.11 | OMe | H | furan-2,5-diyl | Me | null | 6.44 | 269 |
| 33.12 | NH2 | null | furan-2,5-diyl | OH | H | 3.96 | 256 |
| 33.13 | NH2 | null | furan-2,5-diyl | OMe | H | 8.02 | 270 |
| 33.14 | H | OMe | furan-2,5-diyl | null | H | 7.22 | 255 |
| 33.15 | H | OH | furan-2,5-diyl | null | H | 4.82 | 241 |
| 33.16 | OMe | H | furan-2,5-diyl | null | H | 7.48 | 255 |
| 33.17 | OEt | H | furan-2,5-diyl | H | H | 9.72 | 268 |
| 33.18 | OEt | H | furan-2,5-diyl | CH2OH | H | 5.26 | 298 |
| 33.19 | null | H | furan-2,5-diyl | Me | OEt | 7.80 | 283 |
| 33.20 | null | H | furan-2,5-diyl | Me | OH | 3.80 | 255 |
| 33.21 | OH | H | furan-2,5-diyl | Me | null | 3.77 | 255 |
| 33.22 | OEt | H | furan-2,5-diyl | Me | null | 7.33 | 283 |
| 33.23 | NH2 | null | furan-2,5-diyl | OH | H | 3.94 | 256 |
| 33.24 | NH2 | null | furan-2,5-diyl | OEt | H | 5.66 | 284 |
| 33.25 | NH2 | H | furan-2,5-diyl | OEt | null | 5.90 | 284 |
| 33.26 | NH2 | H | furan-2,5-diyl | OH | null | 3.78 | 256 |
| 33.27 | H | OEt | furan-2,5-diyl | null | H | 9.74 | 269 |
| 33.28 | H | OH | furan-2,5-diyl | null | H | 4.81 | 241 |
| 33.29 | OEt | H | furan-2,5-diyl | null | H | 9.78 | 269 |
| 33.30 | Br | H | furan-2,5-diyl | H | NO2 | 7.78 | 347/ |
| 33.31 | Cl | H | furan-2,5-diyl | H | C(O)OEt | 9.69 | 330 |
| 33.32 | Br | H | furan-2,5-diyl | H | C(O)OEt | 9.69 | 374/376 |
| 33.33 | Cl | H | furan-2,5-diyl | Me | C(O)NH2 | 3.72 | 315 |
| 33.34 | Cl | CF3 | furan-2,5-diyl | H | CF3 | 9.04 | 394 |
| 33.35 | Cl | H | furan-2,5-diyl | NH2 | H | 4.89 | 273 |

TABLE 33.2-continued

| synthetic example number | A* | B* | X | D* | E* | HPLC Rt (min.) | M-1 found |
|---|---|---|---|---|---|---|---|
| 33.36 | Cl | H | furan-2,5-diyl | CN | H | 7.93 | 283 |
| 33.37 | Cl | H | furan-2,5-diyl | CH2OH | H | 5.38 | 288 |
| 33.38 | Cl | H | furan-2,5-diyl | C(O)NH2 | H | 5.57 | 301 |
| 33.39 | Cl | H | furan-2,5-diyl | C(O)OEt | H | 8.54 | 330 |
| 33.40 | Cl | 1-triazinyl(3-amino-5-methylthio) | furan-2,5-diyl | H | H | 8.91 | 398 |
| 33.41 | Cl | H | furan-2,5-diyl | Me | CN | 8.22 | 297 |
| 33.42 | Cl | H | furan-2,5-diyl | CF3 | NH2 | 8.60 | 341 |
| 33.43 | Cl | H | furan-2,5-diyl | CF3 | CN | 8.66 | 351 |
| 33.44 | null | CH3 | furan-2,5-diyl | Me | Br | 9.25 | 331/333 |
| 33.45 | null | CH3 | furan-2,5-diyl | Me | Cl | 9.25 | 287 |
| 33.46 | Br | CH3 | furan-2,5-diyl | H | null | 5.62 | 317/319 |
| 33.47 | Br | Br | furan-2,5-diyl | H | null | 3.54 | 381/383/385 |
| 33.48 | Br | H | furan-2,5-diyl | Me | null | 5.55 | 317/319 |
| 33.49 | H | NH2 | furan-2,5-diyl | Br | null | 4.78 | 318/320 |
| 33.50 | Br | Cl | furan-2,5-diyl | Br | null | 8.38 | 417/419 |
| 33.51 | SMe | Ph | furan-2,5-diyl | Br | null | 9.26 | 425/427 |
| 33.52 | NH2 | H | furan-2,5-diyl | Br | null | 4.87 | 318/320 |
| 33.53 | NH2 | H | furan-2,5-diyl | OH | null | 3.70 | 256 |
| 33.54 | Br | H | furan-2,5-diyl | Br | null | 9.64 | 381/383/385 |
| 33.55 | Br | H | furan-2,5-diyl | Cl | null | 9.64 | 337/339 |
| 33.56 | H | Br | furan-2,5-diyl | null | H | 5.08 | 303/305 |
| 33.57 | NH2 | Cl | furan-2,5-diyl | null | C(O)OMe | 3.34 | 332 |
| 33.58 | OPr-n | H | furan-2,5-diyl | Me | null | 8.14 | 297 |
| 33.59 | H | OPr-n | furan-2,5-diyl | null | H | 8.45 | 283 |
| 33.60 | H | O(CH2)2OEt | furan-2,5-diyl | null | H | 7.82 | 313 |
| 33.61 | NH2 | null | furan-2,5-diyl | OH | H | 3.97 | 256 |
| 33.62 | NH2 | null | furan-2,5-diyl | OPr-n | H | 7.84 | 298 |
| 33.63 | OPr-n | H | furan-2,5-diyl | CH2OH | H | 4.36 | 312 |
| 33.64 | OBu-n | H | furan-2,5-diyl | CH2OH | H | 8.58 | 326 |
| 33.65 | O(CH2)2OEt | H | furan-2,5-diyl | CH2OH | H | 4.13 | 342 |
| 33.66 | NH2 | H | furan-2,5-diyl | OPr-n | null | 7.96 | 298 |
| 33.67 | NH2 | H | furan-2,5-diyl | OBu-n | null | 3.86 | 312 |
| 33.68 | H | OBu-i | furan-2,5-diyl | null | H | 8.80 | 297 |
| 33.69 | H | O(CH2)2OEt | furan-2,5-diyl | null | H | 7.14 | 299 |
| 33.70 | H | O(CH2)2NMe2 | furan-2,5-diyl | null | H | 4.57 | 312 |
| 33.71 | NH2 | null | furan-2,5-diyl | OBu-i | H | 8.06 | 312 |
| 33.72 | NH2 | null | furan-2,5-diyl | O(CH2)2OMe | H | 4.84 | 314 |
| 33.73 | NH2 | H | furan-2,5-diyl | OBu-i | null | 8.70 | 312 |
| 33.74 | Br | H | furan-2,5-diyl | C(O)NH2 | H | 7.68 | 346/348 |
| 33.75 | NH2 | null | furan-2,5-diyl | Cl | H | 4.77 | 274 |
| 33.76 | NH(CH2)2OH | H | furan-2,5-diyl | Me | null | 4.56 | 298 |
| 33.77 | H | NH(CH2)2OH | furan-2,5-diyl | null | H | 4.55 | 284 |
| 33.78 | NH2 | null | furan-2,5-diyl | NH(CH2)2OH | H | 4.58 | 299 |
| 33.79 | NH(CH2)2OH | H | furan-2,5-diyl | NH2 | null | 4.58 | 299 |
| 33.80 | NH(CH2)2OH | H | furan-2,5-diyl | CH2OH | H | 4.44 | 313 |
| 33.81 | NH2 | H | furan-2,5-diyl | NH(CH2)2OH | null | 4.33 | 299 |
| 33.82 | NHCH2—CH(OH)Me | H | furan-2,5-diyl | CH3 | null | 4.65 | 312 |
| 33.83 | NH2 | null | furan-2,5-diyl | NHCH2—CH(OH)Me | H | 4.63 | 313 |
| 33.84 | NHCH2—CH(OH)Me | H | furan-2,5-diyl | NH2 | null | 4.63 | 313 |
| 33.85 | NHCH2—CH(OH)Me | H | furan-2,5-diyl | CH2OH | H | 4.52 | 327 |
| 33.86 | NH2 | H | furan-2,5-diyl | NHCH2—CH(OH)Me | null | 4.65 | 313 |
| 33.87 | NH(CH2)3OH | H | furan-2,5-diyl | NH2 | null | 4.48 | 313 |
| 33.88 | NH2 | null | furan-2,5-diyl | NH(CH2)3OH | H | 4.48 | 313 |
| 33.89 | NH(CH2)3OH | H | furan-2,5-diyl | NH2 | null | 4.48 | 313 |
| 33.90 | NH2 | NH(CH2)3OH | furan-2,5-diyl | null | C(O)NH—(CH2)3OH | 4.76 | 414 |
| 33.91 | H | 4-morpholinyl | furan-2,5-diyl | null | H | 6.46 | 310 |

TABLE 33.2-continued

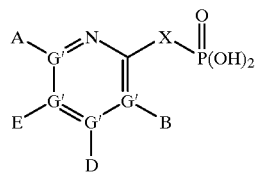

| synthetic example number | A* | B* | X | D* | E* | HPLC Rt (min.) | M-1 found |
|---|---|---|---|---|---|---|---|
| 33.92 | 4-morpholinyl | H | furan-2,5-diyl | Me | null | 6.53 | 324 |
| 33.93 | NH2 | null | furan-2,5-diyl | 4-morpholinyl | H | 6.15 | 325 |
| 33.94 | 4-morpholinyl | H | furan-2,5-diyl | NH2 | null | 4.84 | 325 |
| 33.95 | NH2 | 4-morpholinyl | furan-2,5-diyl | null | C(O)(4-morpholinyl) | 7.47 | 438 |
| 33.96 | NH2 | H | furan-2,5-diyl | 4-morpholinyl | null | 5.30 | 325 |
| 33.97 | Me | H | NHC(O)CH2 | H | H | 6.58 | 229 |
| 33.98 | H | Me | NHC(O)CH2 | H | H | 6.60 | 229 |
| 33.99 | NH2 | H | NHC(O)CH2 | H | Cl | 6.63 | 264 |
| 33.100 | NH2 | Cl | NHC(O)CH2 | H | H | 6.63 | 264 |
| 33.101 | H | OH | NHC(O)CH2 | H | H | 6.54 | 231 |
| 33.102 | Me | H | NHC(O)CH2 | Me | H | 6.59 | 243 |
| 33.103 | H | H | NHC(O)CH2 | H | Cl | 7.02 | 249 |
| 33.104 | H | H | NHC(O)CH2 | H | Br | 8.01 | 293/295 |
| 33.105 | Me | H | NHC(O)CH2 | H | Br | 6.64 | 307/309 |
| 33.106 | H | H | NHC(O)CH2 | H | H | 6.72 | 215 |
| 33.107 | H | H | NHC(O)CH2 | H | Me | 6.54 | 229 |
| 33.108 | H | H | NHC(O)CH2 | Me | H | 6.53 | 229 |
| 33.109 | Me | Cl | NHC(O)CH2 | Me | null | 3.93 | 279 |
| 33.110 | Cl | H | NHC(O)CH2 | null | H | 4.20 | 251 |
| 33.111 | H | Br | NHC(O)CH2 | H | Me | 6.44 | 307/309 |
| 33.112 | NH2 | H | NHC(O)CH2 | NH(Ph-4-Br) | null | 4.42 | 401/403 |
| 33.113 | NH2 | Bn | NHC(O)CH2 | H | Bn | 6.49 | 410 |
| 33.114 | H | H | NHC(O)CH2 | Et | H | 6.57 | 243 |
| 33.115 | Me | Et | NHC(O)CH2 | H | H | 6.54 | 257 |
| 33.116 | Me | H | NHC(O)CH2 | H | Br | 6.55 | 307/309 |
| 33.117 | H | Br | NHC(O)CH2 | H | Me | 6.51 | 307/309 |
| 33.118 | H | Me | NHC(O)CH2 | H | Br | 6.52 | 307/309 |
| 33.119 | Me | Br | NHC(O)CH2 | H | Br | 6.19 | 385/387/389 |
| 33.120 | H | H | C(O)NHCH2 | H | H | 3.74 | 215 |
| 33.121 | Me | H | C(O)NHCH2 | H | H | | 229 |
| 33.122 | OH | H | C(O)NHCH2 | H | H | 3.72 | 231 |
| 33.123 | Br | H | C(O)NHCH2 | H | H | 5.02 | 293/295 |
| 33.124 | Cl | H | C(O)NHCH2 | H | H | 4.60 | 249/251 |
| 33.125 | H | H | C(O)NHCH2 | Cl | H | 5.18 | |
| 33.126 | H | Br | C(O)NHCH2 | OH | H | 3.60 | 310/312 |
| 33.127 | H | H | C(O)NHCH2 | null | H | 3.70 | 216 |
| 33.128 | H | H | C(O)NHCH2 | NO2 | H | 5.00 | 260 |
| 33.129 | H | H | C(O)NHCH2 | H | Bu-n | 8.35 | 271 |
| 33.130 | H | OPr-n | C(O)NHCH2 | H | H | 7.46 | 273 |
| 33.131 | Cl | Cl | C(O)NHCH2 | H | H | 4.23 | 283/285/287 |
| 33.132 | Cl | CF3 | C(O)NHCH2 | H | H | 8.05 | 317/319 |
| 33.133 | H | Cl | C(O)NHCH2 | H | CF3 | 6.49 | 317/319 |
| 33.134 | H | Cl | C(O)NHCH2 | Cl | Cl | 7.20 | 318/320/322 |
| 33.135 | H | C(O)Ph | C(O)NHCH2 | H | H | 7.00 | 319 |
| 33.136 | H | OEt | C(O)NHCH2 | H | CF3 | 6.65 | 327 |
| 33.137 | SMe | Cl | C(O)NHCH2 | H | null | 5.82 | 296/298 |
| 33.138 | SMe | Br | C(O)NHCH2 | H | null | 5.40 | 340/342 |
| 33.139 | H | O(Ph-3-CF3) | C(O)NHCH2 | null | H | | 376 |
| 33.140 | H | H | C(O)NHCH2 | null | Me | 3.75 | 230 |
| 33.141 | H | Me | C(O)NHCH2 | H | H | 4.96 | 229 |
| 33.142 | Cl | Cl | C(O)NHCH2 | Cl | Cl | 9.18 | 351/353/355/357 |
| 33.143 | H | F | C(O)NHCH2 | OH | null | | 250 |
| 33.144 | Me | F | C(O)NHCH2 | OH | null | | 264 |
| 33.145 | OH | F | C(O)NHCH2 | OH | null | 3.93 | 266 |

*When A, B, D or E is null, then the corressponding G' is N.

Section 2

Synthesis of Compounds of Formula X

Example 34

Preparation of 2-amino-4-phosphonomethyloxy-6-bromobenzothiazole

Step A.

A solution of $AlCl_3$ (5 mmole) in EtSH (10 mL) was cooled to 0° C. and treated with 2-amino-4-methoxybenzothiazole (1 mmole). The mixture was stirred at 0–5° C. for 2 h. Evaporation and extraction gave 2-amino-4-hydroxybenzothiazole as white solid.

Step B.

A mixture of 2-amino-4-hydroxybenzothiazole (1 mmole) and NaH (1.3 mmole) in DMF (5 mL) was stirred at 0° C. for 10 min, and then treated with diethylphosphonomethyl trifluoromethylsulfonate (1.2 mmole). After being stirred at room temperature for 8 h, the reaction was subjected to extraction and chromatography to give 2-amino-4-diethylphosphonomethyloxybenzothiazole as an oil.

Step C.

A solution of 2-amino-4-(diethylphosphonomethyloxy) benzothiazole (1 mmole) in AcOH (6 mL) was cooled to 10° C. and treated with bromine (1.5 mmole) in AcOH (2 mL). After 5 min the mixture was stirred at room temperature for 2.5 h. The yellow precipitate was collected via filtration and washed with $CH_2Cl_2$ to give 2-amino-4-diethylphosphonomethyloxy-6-bromobenzothiazole.

Step D.

A solution of 2-amino-4-diethylphosphonomethyloxy-6-bromobenzothiazole (1 mmole) in $CH_2Cl_2$ (4 mL) was treated with TMSBr (10 mmole) at 0° C. After stirred for 8 h at room temperature the reaction was evaporated to dryness and the residue was taken into water (5 mL). The resulting precipitate was collected via filtration and washed with water to give 2-amino-4-phosphonomethyloxy-6-bromobenzothiazole (34.1) as white solid. mp>220° C.(dec.). Anal. Calcd. for $C_8H_8N_2O_4PSBr$: C:28.34; H:2.38; N:8.26. Found: C:28.32; H:2.24; N:8.06.

Similarly, the following compounds were prepared according to the above described procedures:

(34.2) 2-Amino-4-phosphonomethyloxybenzothiozole. mp>250° C. Anal. Calcd. for $C_8H_9N_2O_4PS+0.4\ H_2O$: C:35.93; H:3.69; N:10.48. Found: C:35.90; H:3.37; N:10.37.

Example 35

Preparation of 2-amino-4-phosphonomethyloxy-6-bromo-7-chlorobenzothiazole

Step A.

A solution of 1-(2-methoxy-5-chlorophenyl)-2-thiourea (1 mmole) in chloroform (10 mL) was cooled to 10° C. and treated with bromine (2.2 mmole) in chloroform (10 mL). The reaction was stirred at 10° C. for 20 min and at room temperature for 0.5 h. The resulting suspension was heated at reflux for 0.5 h. The precipitate was collected via filtration (washed with $CH_2Cl_2$) to give 2-amino-4-methoxy-7-chlorobenzothiazole which was subjected to Steps A, B, C and D of Example 34 to give 2-amino-4-phosphonomethoxy-6-bromo-7-chloro benzothiazole (35.1). mp>220° C.(dec.). Anal. Calcd. for $C_8H_7N_2O_4PSClBr$: C:25.72; H:1.89; N:7.50. Found: C:25.66; H:1.67; N:7.23.

Similarly, the following compounds were prepared according to the above described procedures:

(35.2) 2-Amino-4-phosphonomethoxy-6-bromo-7-methyl benzothiazole. mp>220° C. (dec.). Anal. Calcd. for $C_9H_{10}N_2O_4PSBr$: C:30.61; H:2.85; N:7.93 Found: C:30.25; H:2.50; N:7.77.

(35.3) 2-Amino-4-phosphonomethoxy-7-methylbenzothiazole. mp>220° C. (dec.). Anal. Calcd. for $C_9H_{11}N_2O_4PS+0.1\ H_2O$: C:36.99; H:4.48; N:9.59. Found: C:36.73; H:4.23; N:9.38.

(35.4) 2-Amino-4-phosphonomethoxy-7-chlorobenzothiazole. mp>220° C.(dec.). Anal. Calcd. for $C_8H_8N_2O_4PSCl+0.1H_2O$: C:32.41; H:2.79; N:9.45. Found: C:32.21; H:2.74; N:9.22.

Example 36

Preparation of 2-Amino-4-phosphonomethoxy-5,6,7,8-tetrahydronaphtho[1,2-d]thiazole Step A.

3-Amino-2-hydroxy-5,6,7,8-tetrahydronaphthalene was subjected to Step B of Example 34 to give 3-amino-2-diethylphosphonomethyloxy-5,6,7,8-tetrahydronaphthlene.

Step B. A solution of KSCN (16 mmole) and $CuSO_4$ (7.7 mmole) in MeOH (10 mL) was treated with a solution of 3-amino-2-diethylphosphonomethyloxy-5,6,7,8-tetrahydronaphthalene (1 mmole) in MeOH (5 mL) at room temperature. The mixture was heated at reflux for 2 h. Filtration, extraction and chromatography provided 2-amino-4-diethylphosphonomethyloxy-5,6,7,8-tetrahydronaphtho[1,2-d]thiazole as light brown solid.

Step C.

2-Amino-4-diethylphosphonomethyloxy-5,6,7,8-tetrahydronaphtho[1,2-d]thiazole was subjected to Step D of Example 34 to give 2-Amino-4-phosphonomethoxy-5,6,7,8-tetrahydronaphtho[1,2-d]thiazole (36.1). mp>220° C. (dec.). Anal. Calcd. for $C_{12}H_{15}N_2O_4PS+0.5\ H_2O$: C:45.86; H:4.81; N:8.91 Found: C:44.68; H:4.77; N:8.73.

The following compounds were also prepared according to above procedures:

(36.2) 2-Amino-4-phosphonomethoxy-[1,2-d] naphthothiazole. mp>240° C.(dec.). Anal. Calcd. for $C_{12}H_{11}N_2O_4PS+0.2HBr$: C:44.15; H:3.46; N:8.58. Found: C:44.13; H:3.46; N:8.59.

(36.3) 2-Amino-5,7-dimethyl-6-thiocyanato-4-phosphonomethoxybenzothiazole. mp>240° C.(dec.). Anal. Calcd. for $C_{11}H_{12}N_3O_4PS_2+0.2CH_2Cl_2$: C:37.13; H:3.45; N:11.60. Found: C:37.03; H:3.25; N:11.65.

Example 37

Preparation of 2-Amino-7-methoxy-6-thiocyanato-4-phosphonomethoxybenzothiazole

Step A.

2-Hydroxy-5-methoxynitrobenzene was subjected to Step B of Example 34 to give 2-diethylphosphonomethyloxy-5-methoxynitrobenzene.

Step B.

A solution of $SnCl_2$ (4 mmole) in freshly prepared methonolic HCl (10 mL) was added to a cold (0° C.) solution of 2-diethylphosphonomethyloxy-5-methoxynitrobenzene (1 mmole) in MeOH (5 mL). The mixture was warmed to room temperature and stirred for 3 h. Evaporation, extraction and chromatography provided 2-diethylphosphonomethyloxy-5-methoxyaniline.

Step C.

2-Diethylphosphonomethyloxy-5-methoxyaniline was subjected to Step B of Example 36 to give 2-amino-4-diethylphosphonomethyloxy-6-thiocyano-7-methoxybenzothiazole, which was subjected to Step D of Example 34 to give 2-amino-7-methoxy-6-thiocyanato-4-phosphonomethoxybenzothiazole (37.1). mp>170° C.(dec.). Anal. Calcd. for $C_{10}H_{10}N_3O_5PS_2$: C:34.58; H:2.90; N:12.10. Found: C:34.23; H:2.68; N: 11.77.

Similarly, the following compounds were prepared according to above procedures:

(37.2) 2-Amino-5,6-difluoro-4-phosphonomethoxybenzothiazole. mp>240° C.(dec.). Anal. Calcd. for $C_8H_7N_2O_4PSF_2$: C:32.44; H:2.38; N:9.46. Found: C:32.30; H:2.26; N:9.17.

(37.3) 2-Amino-5-fluoro-7-bromo-4-phosphonomethoxybenzothiazole. mp>190° C.(dec.). Anal. Calcd. for $C_8H_7N_2O_4PSBrF$: C:26.91; H:1.98; N:7.84. Found: C:27.25; H:1.92; N:7.54.

(37.4) 2-Amino-7-ethoxycarbonyl-4-phosphonomethoxybenzothiazole. mp>240° C.(dec.). Anal. Calcd. for $C_{11}H_{13}N_2O_6PS+0.2HBr+0.1DMF$: C:38.15; H:3.94; N:8.27. Found: C:38.51; H:3.57; N:8.66.

Example 38

Preparation of 2-Amino-7-bromo-6-thiocyanato-4-phosphonomethoxy benzothiazole

Step A.

A solution of 2-fluoro-5-bromonitrobenzene (1 mmole) in DMF (5 mL) was cooled to 0° C., and treated with a solution of freshly prepared sodium salt of diethylhydroxymethylphosphonate (1.2 mmole) in DMF (5 mL). The mixture was stirred at room temperature for 16 h. Evaporation, extraction and chromatography provided 2-diethylphosphonomethyloxy-5-bromonitrobenzene.

Step B.

2-Diethylphosphonomethyloxy-5-bromonitrobenzene was subjected to Step B of Example 37, Step B of Example 36, and Step D of Example 34 to give 2-amino-7-bromo-6-thiocyanato-4-phosphonomethoxybenzothiazole (38.1). mp>250° C.(dec.). Anal. Calcd. for $C_9H_7N_3O_4PS_2$ Br: C:27.29; H:1.78; N:10.61. Found: C:26.90; H:1.58; N:10.54.

Similarly, the following compound was prepared according to above procedures:

(38.2) 2-Amino-7-fluoro-6-thiocyanato-4-phosphonomethoxybenzothiazole. mp>136° C.(dec.). Anal. Calcd. for $C_9H_7N_3O_4PFS_2+0.3HBr$: C:30.07; H:2.05; N:11.69. Found: C:30.27; H:2.01; N: 11.38.

Example 39

Preparation of 2-Amino-7-hydroxymethyl-6-thiocyano-4-phosphonomethoxy benzothiazole Step A.

2-Chloro-5-formylnitrobenzene was subjected to Step A of Example 38 to give 2-diethylphosphonomethyloxy-5-formylnitrobenzene.

Step B.

A solution of 2-diethylphosphonomethyloxy-5-formylnitrobenzene (1 mmole) in methanol (5 mL) was treated with 10% palladium on carbon (0.05 mmole) under 1 atmosphere of hydrogen at room temperature for 12 h. Filtration followed by evaporation gave 2-diethylphosphonomethyloxy-5-hydroxymethylaniline which was subjected to Step B of Example 36 followed by Step D of Example 34 to give 2-amino-7-hydroxymethyl-6-thiocyanato-4-phosphonomethoxybenzothiazole (39.1). mp 181–184° C. Anal. Calcd. for $C_{10}H_{10}N_3O_5PS_2+0.35H_2O$: C:33.97; H:3.05; N:11.88. Found: C:33.76; H:2.66; N:11.61.

Example 40

Preparation of 2-Amino-6-bromo-7-fluoro-4-phosphonomethoxybenzothiazole

Step A.

A solution of 2-diethylphosphonomethyloxy-4-bromo-5-fluoroaniline (1 mmole, prepared as in Example 4, Step B) and KSCN (2 mmole) in AcOH (8 mL) was cooled to 10° C., and treated with a solution of bromine (2 mmole) in AcOH (5 mL). After being stirred at room temperature for 0.5 h, the reaction mixture was evaporated to dryness and the residue was purified by chromatography to provide 2-amino-7-fluoro1-6-bromo-4-diethylphosphonomethyloxybenzothiazole which was subjected to Step D of Example 34 to give 2-amino-6-bromo-7-fluoro-4-phosphonomethoxybenzothiazole (40.1). Anal. Calcd. for $C_8H_7N_2O_4PSBrF+0.1HBr$: C:26.31; H:1.96; N:7.67. Found: C:25.96; H:1.94; N:7.37.

Example 41

Preparation of 2-Amino-7-ethyl-6-thiocyano-4-phosphonomethoxy benzothiazole

Step A.

A solution of 2-diethylphosphonomethyloxy-5-bromonitrobenzene (1 mmole, prepared as in Example 37, Step A) in DMF (5 mL) was treated with tributyl(vinyl)tin (1.2 mmole) and palladium bis(triphenylphosphine) dichloride (0.1 mmole), and the mixture was heated at 60° C. under nitrogen for 6 h. Evaporation and chromatography gave 2-diethylphosphonomethyloxy-5-vinylnitrobenzene as an oil which was subjected to Step B of Example 38, Step B of Example 36, and Step D of Example 34 to give 2-amino-7-ethyl-6-thiocyano-4-phosphonomethoxybenzothiazole (41.1). mp>167° C.(dec.). Anal. Calcd. for $C_{11}H_{12}N_3O_4PS_2$: C:38.26; H:3.50; N:12.17. Found: C:27.87; H:3.47; N: 11.93.

Example 42

Preparation of 2-Amino-7-cyclopropyl-6-thiocyanato-4-phosphonomethoxy benzothiazole Step A.

A suspension of 2-diethylphosphonomethyloxy-5-vinylnitrobenzene (1 mmole, prepared as in Step A of Example 40) and $Pd(OAc)_2$ (0.1 mmole) in ether (8 mL) was treated with a solution of diazomethane (generated from 3.0 g of 1-methyl-3-nitro-1-nitrosoguanidine) in ether at 0° C. After being stirred at room temperature for 20 h the reaction was evaporated to dryness and the residue was chromatographed to give 2-diethylphosphonomethyloxy-5-cyclopropylnitrobenzene which was subjected to Step B of Example 37, Step B of Example 36, and Step D of Example 34 to give 2-amino-7-cyclopropyl-6-thiocyanato-4-phosphonomethoxybenzothiazole hydrogen bromide (42.1). Anal. Calcd. for $C_{12}H_{13}N_3O_4PS_2Br+0.1HBr$: C:27.76; H:2.72; N:8.09. Found: C:27.54; H:3.05; N:7.83.

Example 43

Preparation of 2-Amino-4-phosphonomethoxy-6-chloro-7-methyl benzothiazole

Step A.

2-Methoxy-4-chloro-5-methylaniline was subjected to Steps A and B of Example 34, Step B of Example 36, and Step D of Example 34 to give 2-amino-4-phosphonomethoxy-6-chloro-7-methyl benzothiazole (43.1). mp>250° C.(dec.). Anal. Calcd. for $C_9H_{10}N_2O_4PS_2Cl+0.3H_2O+0.4$ HBr: C:31.20; H:3.20; N:8.09. Found: C:31.37; H:2.87; N:7.89.

Similarly, the following compounds were prepared according to above procedures:

(43.2) 2-Amino-7-phenyl-6-thiocyanato-4-phosphonomethoxybenzothiazole. mp>250° C.(dec.). Anal. Calcd. for $C_{15}H_{12}N_3O_4PS_2+0.2H_2O$: C:45.38; H:3.15; N:10.58. Found: C:45.25; H:3.21; N:10.53.

Example 44

Preparation of 2-bromo-4-diethylphosphonomethoxy-5,6,7,8-tetrahydronaphtho[1,2-d]thiazole Step A.

A solution of 2-amino-4-diethylphosphonomethoxy-5,6,7,8-tetrahydronaphtho[1,2-d]thiazole (1 mmole) in $CH_3CN$ (4 mL) was cooled to 0° C., and treated with $CuBr_2$ (1.2 mmole) followed by isoamylnitrite (1.5 mmole) dropwisely. The resulting dark mixture was stirred for 3.5 h. Evaporation and chromatography gave 2-bromo-4-diethylphosphonomethoxy-5,6,7,8-tetrahydronaphtho[1,2-d]thiazole as an oil.

Step B.

2-Bromo-4-diethylphosphonomethoxy-5,6,7,8-tetrahydronaphtho[1,2-d]thiazole was subjected to Step D of Example 34 to give 2-bromo-4-phosphonomethoxy-5,6,7,8-tetrahydronaphtho[1,2-d]thiazole (44.1) as a solid. Mp 220–230° C. Anal. Calcd. for $C_{12}H_{13}NO_4PSBr$: C:38.11; H:3.46; N:3.70. Found: C:37.75; H:3.26; N:3.69.

Example 45

Preparation of 4-diethylphosphonomethoxy-5,6,7,8-tetrahydronaphtho[1,2-d]thiazole Step A.

A solution of isoamylnitrite (1.5 mmole) in DMF (1 mL) at 65° C. was treated with 2-amino-4-diethylphosphonomethoxy-5,6,7,8-tetrahydronaphtho[1,2-d]thiazole (1 mmole) in DMF (3 mL). After 30 min, the cooled reaction solution was subjected to evaporation and chromatography to provide 4-diethylphosphonomethoxy-5,6,7,8-tetrahydronaphtho[1,2-d]thiazole as an oil, which was subjected to Step D of Example 34 to give 4-phosphonomethoxy-5,6,7,8-tetrahydronaphtho[1,2-d]thiazole (45.1) as a solid. Mp 215–220° C. Anal. Calcd. for $C_{12}H_{14}NO_4PS+1.3HBr$: C:35.63; H:3.81; N:3.46. Found: C:35.53; H:3.46; N:3.40.

Example 46

Preparation of 2-Amino-4-phosphonomethythio benzothiazole

Step A.

2-Diethylphosphonomethylthioaniline, prepared according to Step B of Example 34, was subjected to Step B of Example 36 to give 2-amino-4-diethylphosphonomethythiobenzothiazole.

Step B.

2-Amino-4-diethylphosphonomethythiobenzothiazole was subjected to Step D of Example 34 to give 2-amino-4-phosphonomethythiobenzothiazole (46.1) as a foam. Anal. Calcd. for $C_8H_{10}N_2O_3PS_2+0.4H_2O$: C:35.63; H:3.81; N:3.46. Found: C:35.53; H:3.46; N:3.40.

Example 47

Preparation of Various Prodrugs of benzothiazoles

Step A.

A suspension of 2-amino-4-phosphonomethoxy-5,6,7,8-tetrahydronaphtho[1,2-d]thiazole (1 mmole) in DMF (10 mL) was treated with DCC (3 mmole) followed by 3-(3,5-dichloro)phenyl-1,3-propanediol (1.1 mmole). The resulting mixture was heated at 80° C. for 8 h. Evaporation followed by column chromatography gave 2-amino-4-{[3-(3,5-dichlorophenyl)propane-1,3-diyl]phosphonomethoxy}-5,6,7,8-tetrahydronaphtho[1,2-d]thiazole (47.1) as solid. mp>230° C. Anal. Calcd. for $C_{21}H_{21}N_2O_4PSCl_2$: C:50.51; H:4.24; N:5.61. Found: C:50.83; H:4.34; N:5.25.

Step B.

A solution of 4-phosphonomethoxy-5,6,7,8-tetrahydronaphtho[1,2-d]thiazole dichloridate (generated as in Example 19) (1 mmole) in dichloromethane (5 mL) is cooled to 0° C. and treated with a solution of benzyl alcohol (0.9 mmole) in dichloromethane (0.5 mL) and pyridine (0.3 mL). The resulting reaction solution is stirred at 0° C. for 1 h, and then added a solution of ammonia (excess) in THF. After stirring at room temperature for 16 h, the reaction is evaporated to dryness and the residue is purified by chromatography to give of 4-phosphonomonoamidomethoxy-5,6,7,8-tetrahydronaphtho[1,2-d]thiazole.

Alternatively, a different method is used to prepare other phosphoramides as exemplified in the following procedure:

Step C.

A suspension of 4-phosphonomethoxy-5,6,7,8-tetrahydronaphtho[1,2-d]thiazole dichloridate (generated as in Example 19) (1 mmole) in dichloromethane (5 mL) is cooled to 0° C. and ammonia (excess) is bubbled through the reaction for 10 min. After stirring at room temperature for 16 h, the reaction is evaporated to dryness and the residue is purified by chromatography to give 4-(phosphorodiamido)methoxy-5,6,7,8-tetrahydronaphtho[1,2-d]thiazole.

The monophenyl-monophosphonamide derivatives of compounds of formula X can also be prepared according to the above described procedures:

Step D.

A solution of 4-diphenylphosphonomethoxy-5,6,7,8-tetrahydronaphtho[1,2-d]thiazole (prepared according to the procedures of Example 19) (1 mmole) in acetonitrile (9 mL) and water (4 mL) is treated with lithium hydroxide (1N, 1.5 mmole) at room temperature for 24 h. The reaction solution is evaporated to dryness, and the residue is dissolved in water (10 mL), cooled to 0° C. and the pH of the solution is adjusted to 4 by addition of 6 N HCl. The resulting white solid is collected through filtration to give 4-phenylphosphonomethoxy-5,6,7,8-tetrahydronaphtho[1,2-d]thiazole.

Step E.

A suspension of 4-phenylphosphonomethoxy-5,6,7,8-tetrahydronaphtho[1,2-d]thiazole (1 mmole) in thionyl chloride (3 mL) is heated to reflux for 2 h. The reaction solution is evaporated to dryness, and the residue is dissolved in anhydrous dichloromethane (2 mL) and the resulting solution is added to a solution of L-alanine ethyl ester hydrochloride (1.2 mmole) in pyridine (0.8 mL) and dichloromethane (3 mL) at 0° C. The resulting reaction solution is stirred at room temperature for 14 h. Evaporation and chromatography give 4-[O-phenyl-N-(1-ethoxycarbonyl)ethylphosphonamido]methoxy-5,6,7,8-tetrahydronaphtho[1,2-d]thiazole.

Step F.

A solution of 4-phosphonomethoxy-5,6,7,8-tetrahydronaphtho[1,2-d]thiazole (1 mmole) in DMF is treated with N,N'-dicyclohexyl-4-morpholinecarboxamidine (5 mmole) and ethylpropyloxycarbonyloxymethyl iodide (5 mmole) which was prepared from chloromethyl chloroformate according to the reported procedure (Nishimura et al. *J Antibiotics*, 1987, 40, 81). The reaction mixture is stirred at 25° C. for 24 h. Evaporation and chromatography give 4-bis(ethoxycarbonyloxymethyl)phosphonomethoxy-5,6,7,8-tetrahydronaphtho[1,2-d]thiazole.

4-(Dipivaloyloxymethyl)phosphonomethoxy-5,6,7,8-tetrahydronaphtho[1,2-d]thiazole and 4-bis(isobutyryloxymethyl)phosphonomethoxy-5,6,7,8-tetrahydronaphtho[1,2-d]thiazole are also prepared in a similar manner.

Examples of use of the method of the invention includes the following. It will be understood that these examples are exemplary and that the method of the invention is not limited solely to these examples.

For the purposes of clarity and brevity, chemical compounds are referred to by synthetic Example number in the biological examples below.

Besides the following Examples, assays that may be useful for identifying compounds which inhibit gluconeogenesis include the following animal models of diabetes:

i. Animals with pancreatic b-cells destroyed by specific chemical cytotoxins such as Alloxan or Streptozotocin (e.g. the Streptozotocin-treated mouse, rat, dog, and monkey). Kodama, H., Fujita, M., Yamaguchi, I., *Japanese Journal of Pharmacology* 66, 331–336 (1994) (mouse); Youn, J. H., Kim, J. K., Buchanan, T. A., *Diabetes* 43, 564–571 (1994) (rat); Le Marchand, Y., Loten, E. G., Assimacopoulos-Jannet, F., et al., *Diabetes* 27, 1182–88 (1978) (dog); and Pitkin, R. M., Reynolds, W. A., *Diabetes* 19, 70–85 (1970) (monkey).

ii. Mutant mice such as the C57BL/Ks db/db, C57BL/Ks ob/ob, and C57BL/6J ob/ob strains from Jackson Laboratory, Bar Harbor, and others such as Yellow Obese, T-KK, and New Zealand Obese. Coleman, D. L., Hummel, K. P., *Diabetologia* 3, 238–248 (1967) (C57BL/Ks db/db); Coleman, D. L., *Diabetologia* 14, 141–148 (1978) (C57BL/6J ob/ob); Wolff, G. L., Pitot, H. C., *Genetics* 73, 109–123 (1973) (Yellow Obese); Dulin, W. E., Wyse, B. M., *Diabetologia* 6, 317–323 (1970) (T-KK); and Bielschowsky, M., Bielschowsky, F. Proceedings of the University of Otago Medical School 31, 29–31 (1953) (New Zealand Obese).

iii. Mutant rats such as the Zucker fa/fa Rat rendered diabetic with Streptozotocin or Dexamethasone, the Zucker Diabetic Fatty Rat, and the Wistar Kyoto Fatty Rat. Stolz, K. J., Martin, R. J. *Journal of Nutrition* 112, 997–1002 (1982) (Streptozotocin); Ogawa, A., Johnson, J. H., Ohnbeda, M., McAllister, C. T., Inman, L., Alain, T., Unger, R. H., The *Journal of Clinical Investigation* 90, 497–504 (1992) (Dexamethasone); Clark, J. B., Palmer, C. J., Shaw, W. N., *Proceedings of the Society for Experimental Biology and Medicine* 173, 68–75 (1983) (Zucker Diabetic Fatty Rat); and Idida, H., Shino, A., Matsuo, T., et al., *Diabetes* 30, 1045–1050 (1981) (Wistar Kyoto Fatty Rat).

iv. Animals with spontaneous diabetes such as the Chinese Hamster, the Guinea Pig, the New Zealand White Rabbit, and non-human primates such as the Rhesus monkey and Squirrel monkey. Gerritsen, G. C., Connel, M. A., Blanks, M. C., *Proceedings of the Nutrition Society* 40, 237 245 (1981) (Chinese Hamster); Lang, C. M., Munger, B. L., *Diabetes* 25, 434–443 (1976) (Guinea Pig); Conaway, H. H., Brown, C. J., Sanders, L. L. etal., *Journal of Heredity* 71, 179–186 (1980) (New Zealand White Rabbit); Hansen, B. C., Bodkin, M. L., *Diabetologia* 29, 713–719 (1986) (Rhesus monkey); and Davidson, I. W., Lang, C. M., Blackwell, W. L., *Diabetes* 16,395–401 (1967) (Squirrel monkey).

v. Animals with nutritionally induced diabetes such as the Sand Rat, the Spiny Mouse, the Mongolian Gerbil, and the Cohen Sucrose-Induced Diabetic Rat. Schmidt-Nielsen, K., Hainess, H. B., Hackel, D. B., *Science* 143, 689–690 (1964) (Sand Rat); Gonet, A. E., Stauffacher, W., Pictet, R., et al., *Diabetologia* 1, 162–171 (1965) (Spiny Mouse); Boquist, L., *Diabetologia* 8, 274–282 (1972) (Mongolian Gerbil); and Cohen, A. M., Teitebaum, A., Saliternik, R., *Metabolism* 21, 235–240 (1972) (Cohen Sucrose-Induced Diabetic Rat).

vi. Any other animal with one of the following or a combination of the following characteristics resulting from a genetic predisposition, genetic engineering, selective breeding, or chemical or nutritional induction: impaired glucose tolerance, insulin resistance, hyperglycemia, obesity, accelerated gluconeogenesis, increased hepatic glucose output.

BIOLOGICAL EXAMPLES

Example A

Inhibition of Human Liver FBPase

*E. coli* strain BL21 transformed with a human liver FBPase-encoding plasmid was obtained from Dr. M. R. El-Maghrabi at the State University of New York at Stony Brook. The enzyme was typically purified from 10 liters of recombinant *E. coli* culture as described (M. Gidh-Jain et al. ,1994, *The Journal of Biological Chemistry* 269, pp 27732–27738). Enzymatic activity was measured spectrophotometrically in reactions that coupled the formation of product (fructose 6-phosphate) to the reduction of dimethylthiazoldiphenyltetrazolium bromide (MTT) via $NADP^+$ and phenazine methosulfate (PMS), using phosphoglucose isomerase and glucose 6-phosphate dehydrogenase as the coupling enzymes. Reaction mixtures (200 $\mu$l) were made up in 96-well microtitre plates, and consisted of 50 mM Tris-HCl, pH 7.4, 100 mM KCl, 5 mM EGTA, 2 mM $MgCl_2$, 0.2 mM NADP, 1 mg/ml BSA, 1 mM MTT, 0.6 mM PMS, 1 unit/ml phosphoglucose isomerase, 2 units/ml glucose 6-phosphate dehydrogenase, and 0.150 mM substrate (fructose 1,6-bisphosphate). Inhibitor concentrations were varied from 0.01 $\mu$M to 10 $\mu$M. Reactions were started by the addition of 0.002 units of pure hlFBPase, and were monitored for 7 minutes at 590 nm in a Molecular Devices Plate Reader (37° C.).

The table below provides the $IC_{50}$ values for several compounds prepared. The $IC_{50}$ for AMP is 1 $\mu$M.

| Compound # | $IC_{50}$ (h1FBPase), $\mu$M |
| --- | --- |
| 3.1 | 0.025 |
| 3.2 | 0.1 |
| 3.25 | 0.014 |
| 3.26 | 0.015 |
| 3.58 | 82 |
| 3.67 | 2 |
| 3.69 | 1 |
| 3.70 | 0.04 |
| 6.3 | 0.044 |
| 10.1 | 0.12 |
| 10.27 | 0.038 |
| 10.43 | 0.07 |
| 15.20 | 0.04 |
| 15.14 | 0.032 |
| 16.1 | 0.06 |
| 17.6 | 0.62 |
| 17.11 | 0.78 |
| 18.3 | 0.05 |
| 18.11 | 0.33 |
| 18.20 | 0.039 |

-continued

| Compound # | IC$_{50}$ (h1FBPase), $\mu$M |
|---|---|
| 18.25 | 2 |
| 25.2 | 0.4 |
| 28.2 | 2.8 |
| 41.1 | 0.022 |

Inhibition of Rat Liver FBPase

E. coli strain BL21 transformed with a rat liver FBPase-encoding plasmid was obtained from Dr. M. R. El-Maghrabi at the State University of New York at Stony Brook. Recombinant FBPase was purified as described (El-Maghrabi, M. R., and Pilkis, S. J. (1991) Biochem. Biophys. Res. Commun. 176, 137–144) The enzyme assay was identical to that described above for human liver FBPase.

The table below provides the IC$_{50}$ values for several compounds prepared. The IC$_{50}$ for AMP is 20 $\mu$M.

| Compound # | IC$_{50}$ (r1FBPase), $\mu$M |
|---|---|
| 3.1 | 0.18 |
| 3.2 | 2.5 |
| 3.25 | 0.5 |
| 3.26 | 0.25 |
| 3.70 | 0.15 |
| 6.3 | 0.5 |
| 10.1 | 2 |
| 10.2 | 2.5 |
| 10.27 | 2.9 |
| 10.43 | 0.8 |
| 15.2 | 1.3 |
| 15.4 | 4.1 |
| 15.6 | 7 |
| 15.20 | 0.6 |
| 15.14 | 0.68 |
| 16.1 | 1.8 |
| 18.20 | 0.28 |
| 18.3 | 0.49 |
| 41.1 | 0.16 |

Example B
AMP Site Binding

To assess whether compounds bind to the allosteric AMP binding site of h1FBPase, the enzyme is incubated with radiolabeled AMP in the presence of a range of test compound concentrations. The reaction mixtures consist of 25 mM $^3$H-AMP (54 mCi/mmole) and 0–1000 mM test compound in 25 mM Tris-HCl, pH 7.4, 100 mM KCl and 1 mM MgCl$_2$. 1.45 mg of homogeneous FBPase (±1 nmole) is added last. After a 1 minute incubation, AMP bound to FBPase is separated from unbound AMP by means of a centrifugal ultrafiltration unit ("Ultrafree-MC", Millipore) used according to the instructions of the manufacturer. The radioactivity in aliquots (100 $\mu$l) of the upper compartment of the unit (the retentate, which contains enzyme and label) and the lower compartment (the filtrate, which contains unbound label) is quantified using a Beckman liquid scintillation counter. The amount of AMP bound to the enzyme is estimated by comparing the counts in the filtrate (the unbound label) to the total counts in the retentate.

Example C
AMP Site/Enzyme Selectivity

To determine the selectivity of compounds towards FBPase, effects of FBPase inhibitors on 5 key AMP binding enzymes were measured using the assays described below:

Adenosine Kinase:

Human adenosine kinase was purified from an E. coli expression system as described by Spychala et al. (Spychala, J., Datta, N. S., Takabayashi, K., Datta, M., Fox, I. H., Gribbin, T., and Mitchell, B. S. (1996) Proc. Natl. Acad. Sci. USA 93, 1232–1237). Activity was measured essentially as described by Yamada et al. (Yamada, Y., Goto, H., Ogasawara, N. (1988) Biochim. Biophys. Acta 660, 36–43) with a few minor modifications. Assay mixtures contained 50 mM TRIS-maleate buffer, pH 7.0, 0.1% BSA, 1 mM ATP 1 mM MgCl$_2$, ~1.0 $\mu$M [U-$^{14}$C] adenosine (400–600 mCi/mmol) and varying duplicate concentrations of inhibitor. $^{14}$C-AMP was separated from unreacted $^{14}$C-adenosine by absorption to anion exchange paper (Whatman) and quantified by scintillation counting.

Adenosine Monophosphate Deaminase:

Porcine heart AMPDA was purified essentially as described by Smiley et al. (Smiley, K. L., Jr, Berry, A. J., and Suelter, C. H. (1967) J. Biol. Chem. 242, 2502–2506) through the phosphocellulose step. Inhibition of AMPDA activity was determined at 37° C. in a 0.1 ml assay mixture containing inhibitor, ~0.005U AMPDA, 0.1% bovine serum albumin, 10 mM ATP, 250 mM KCl, and 50 mM MOPS at pH 6.5. The concentration of the substrate AMP was varied from 0.125–10.0 mM. Catalysis was initiated by the addition of enzyme to the otherwise complete reaction mixture, and termninated after 5 minutes by injection into an HPLC system. Activities were determined from the amount of IMP formed during 5 minutes. IMP was separated from AMP by HPLC using a Beckman Ultrasil-SAX anion exchange column (4.6 mm×25 cm) with an isocratic buffer system (12.5 mM potassium phosphate, 30 mM KCl, pH 3.5) and detected spectrophotometrically by absorbance at 254 nm.

Phosphofructokinase:

Enzyme (rabbit liver) was purchased from Sigma. Activity was measured at 30° C. in reactions in which the formation of fructose 1,6-bisphosphate was coupled to the oxidation of NADH via the action of aldolase, triosephosphate isomerase, and a-glycerophosphate dehydrogenase. Reaction mixtures (200 $\mu$l) were made up in 96-well microtitre plates and were read at 340 nm in a Molecular Devices Microplate Reader. The mixtures consisted of 200 mM Tris-HCl pH 7.0, 2 mM DTT, 2 mM MgCl$_2$, 0.2 mM NADH, 0.2 MM ATP, 0.5 mM Fructose 6-phosphate, 1 unit aldolase/ml, 3 units/ml triosephosphate isomerase, and 4 units/ml a-glycerophosphate dehydrogenase. Test compound concentrations ranged from 1 to 500 $\mu$M. Reactions were started by the addition of 0.0025 units of phosphofructokinase and were monitored for 15 minutes.

Glycogen Phosphorylase:

Enzyme (rabbit muscle) was purchased from Sigma. Activity was measured at 37° C. in reactions in which the formation of glucose 1-phosphate was coupled to the reduction of NADP via phosphoglucomutase and glucose 6-phosphate dehydrogenase. Assays were performed on 96-well microtitre plates and were read at 340 nm on a Molecular Devices Microplate Reader. Reaction mixtures consisted of 20 mM imidazole, pH 7.4, 20 mM MgCl$_2$, 150 mM potassium acetate, 5 mM potassium phosphate, 1 mM DTT, 1 mg/ml BSA, 0.1 mM NADP, 1 unit/ml phosphoglucomutase, 1 unit/ml glucose 6-phosphate dehydrogenase, 0.5% glycogen. Test compound concentrations ranged from 1 to 500 $\mu$M. Reactions were started by the addition of 17 $\mu$g enzyme and were monitored for 20 minutes.

Adenylate Kinase:

Enzyme (rabbit muscle) was purchase from Sigma. Activity was measured at 37° C. in reaction mixtures (100 $\mu$l)

containing 100 mM Hepes, pH 7.4, 45 mM $MgCl_2$, 1 mM EGTA, 100 mM KCl, 2 mg/ml BSA, 1 mM AMP and 2 mM ATP. Reactions were started by addition of 4.4 ng enzyme and terminated after 5 minutes by addition of 17 µl perchloric acid. Precipitated protein was removed by centrifugation and the supernatant neutralized by addition of 33 µl 3 M KOH/3 M $KHCO_3$. The neutralized solution was clarified by centrifugation and filtration and analyzed for ADP content (enzyme activity) by HPLC using a YMC ODS AQ column (25×4.6 cm). A gradient was run from 0.1 M $KH_2PO_4$, pH 6, 8 mM tetrabutyl ammonium hydrogen sulfate to 75% acetonitrile. Absorbance was monitored at 254 nM.

The table below gives the selectivity data for compounds 10.1 and 3.1.

| | 10.1 (µM) | 3.1 (µM) |
|---|---|---|
| FBPase (inh.) | 0.1 | 0.025 |
| Adenosine Kinase (inh.) | >>10 | >>10 |
| AMP Deaminase (inh.) | >>10 | >>10 |
| Adenylate Kinase (inh.) | >500 | >500 |
| Glycogen Phosphorylase (act.) | >100 | >100 |
| Phosphofructokinase (act.) | >500 | >500 |

Example D
Inhibition of Gluconeogenesis in Rat Hepatocytes

Hepatocytes were prepared from overnight fasted Sprague-Dawley rats (250–300 g) according to the procedure of Berry and Friend (Berry, M. N., Friend, D. S., 1969, J. Cell. Biol. 43, 506–520) as modified by Groen (Groen, A. K., Sips, H. J., Vervoom, R. C., Tager, J. M., 1982, Eur. J. Biochem. 122, 87–93). Hepatocytes (75 mg wet weight/ml) were incubated in 1 ml Krebs-bicarbonate buffer containing 10 mM Lactate, 1 mM pyruvate, 1 mg/ml BSA, and test compound concentrations from 1 to 500 µM. Incubations were carried out in a 95% oxygen, 5% carbon dioxide atmosphere in closed, 50-ml Falcon tubes submerged in a rapidly shaking water bath (37° C.). After 1 hour, an aliquot (0.25 ml) was removed, transferred to an Eppendorf tube and centrifuged. 50 µl of supernatant was then assayed for glucose content using a Sigma Glucose Oxidase kit as per the manufacturer's instructions.

$IC_{50}$'s for select compounds in this assay are shown in the table below.

| Compound | $IC_{50}$ Glucose Production, µM |
|---|---|
| 3.1 | 2.5 |
| 3.2 | 26 |
| 3.26 | 10 |
| 3.58 | 1.2 |
| 10.1 | 15 |
| 10.2 | 16 |
| 16.1 | 10 |
| 19.18 | 10 |
| 19.48 | 6.5 |
| 20.9 | 2.2 |
| 31.6 | 2.3 |
| 31.8 | 3 |

Example E
Glucose Production Inhibition and Fructose 1,6-bisphosphate Accumulation in Rat Hepatocytes Isolated rat hepatocytes are prepared as described in Example D and incubated under the identical conditions described. Reactions are terminated by removing an aliquot (250 µl) of cell suspension and spinning it through a layer of oil (0.8 ml silicone/mineral oil, 4/1) into a 10% perchloric acid layer (100 µl). After removal of the oil layer, the acidic cell extract layer is neutralized by addition of ⅓rd volume of 3 M KOH/3 M $KHCO_3$. After thorough mixing and centrifugation, the supernatant is analyzed for glucose content as described in Example D, and also for fructose 1,6-bisphosphate. Fructose 1,6-bisphosphate is assayed spectrophotometrically by coupling its enzymatic conversion to glycerol 3-phosphate to the oxidation of NADH, which is monitored at 340 nm. Reaction mixtures (1 ml) consist of 200 mM Tris-HCl, pH 7.4, 0.3 mM NADH, 2 units/ml glycerol 3-phosphate dehydrogenase, 2 units/ml triosephosphate isomerase, and 50–100 µl cell extract. After a 30 minute preincubation at 37° C., 1 unit/ml of aldolase is added and the change in absorbance measured until a stable value is obtained. 2 moles of NADH are oxidized in this reaction per mole of fructose 1,6-bisphosphate present in the cell extract.

A dose-dependent inhibition of glucose production accompanied by a dose-dependent accumulation of fructose 1,6 bisphosphate (the substrate of FBPase) is an indication that the target enzyme in the gluconeogenic pathway, FBPase, is inhibited.

Example F
Blood Glucose Lowering Following Intravenous Administration to Fasted Rats Sprague Dawley rats (250–300 g) were fasted for 18 hours and then dosed intravenously either with saline or 10 mg/kg of an FBPase inhibitor. Inhibitors were disolved in water and the solution adjusted to neutrality with NaOH. Blood samples were obtained from the tail vein of conscious animals just prior to injection and after 1 hour. Blood glucose was measured using a HemoCue Inc. glucose analyzer according to the instructions of the manufacturer.

The table below shows the % glucose lowering elicited by the compounds relative to saline-treated control animals.

| Compound # | i.v. Glucose Lowering, % |
|---|---|
| 3.1 | 65 |
| 3.2 | 55 (30 mg/kg) |
| 3.25 | 76 |
| 3.26 | 73 |
| 3.58 | 82 |
| 3.71 | 72 |
| 6.3 | 24 |
| 10.1 | 51 |
| 10.43 | 61 |
| 15.20 | 24 |
| 18.2 | 80 |
| 18.3 | 75 |
| 35.3 | 65 |
| 41.1 | 80 |

Several compounds were also tested at doses <10 mg/kg. Compound 3.26, for instance, was tested at 3 mg/kg and found to lower blood glucose by 52%.

Example G
Analysis of Drug Levels and Liver Accumulation in Rats

Sprague-Dawley rats (250–300 g) were fasted for 18 hours and then dosed intravenously either with saline (n=3) or 10 mgs/kg of either 10.1 or 3.1 (n=3/group). The compound was dissolved in water and the solution adjusted to neutrality with NaOH. One hour post injection rats were anesthetized with halothane and a liver biopsy (approx. 1 g)

was taken as well as a blood sample (2 ml) from the posterior vena cava. A heparin flushed syringe and needle were used for blood collection. The liver sample was immediately homogenized in ice-cold 10% perchloric acid (3 ml), centrifuged, and the supernatant neutralized with ⅓rd volume of 3 M KOH/3 M KHCO$_3$. Following centrifugation and filtration, 50 µl of the neutralized extract was analyzed for 10.1 content by HPLC. A YMC ODS AQ column (250×4.6 cm) was used and eluted with a gradient from 10 mM sodium phosphate pH 5.5 to 75% acetonitrile. Absorbance was monitored at 310–325 nm. Plasma was prepared from the blood sample by centrifugation and extracted by addition of methanol to 60% (v/v). The methanolic extract was clarified by centrifugation and filtration and then analyzed by HPLC as described above. Results are shown in the table below.

| Compound # | Plasma Conc. µM | Liver Conc., nmoles/g |
|---|---|---|
| 10.1 | 18 ± 2.8 | 35.6 ± 4.2 |
| 10.2 | 22 ± 1.5 | |
| 5.1 | 100 ± 5.7 | 6.7 ± 0.7 |
| 3.21 | 25 ± 1 | |
| 15.20 | 66.3 ± 3.9 | 13.1 ± 2.3 |
| 3.26 | 56 ± 2 | |

Example H
Glucose Lowering Following Oral Administration to the Fasted Rat

Compounds were administered by oral gavage to 18-hour fasted, Sprague Dawley rats (250–300g, n=¾/group). Phosphonic acids were prepared in deionized water, and the solution adjusted to neutrality with solidum hydroxide. Prodrugs were dissolved in polyethylene glycol (mw 400). Blood glucose was measured immediately prior to dosing and at 1 hour intervals thereafter by means of a HemoCue glucose analyzer (HemoCue Inc., Mission Viejo, Calif.). The table below indicates the maximum glucose lowering achieved relative to control animals dosed with saline.

| Compound # | % Glucose Lowering | Dose, mg/kg | Time point, h |
|---|---|---|---|
| 3.26 | 70 | 30 | 2 |
| 3.27 | 61 | 60 | 3 |
| 10.1 | 55 | 90 | 3 |
| 10.2 | 36 | 90 | 3 |
| 19.42 | 26 | 30 | 3 |
| 19.48 | 63 | 30 | 2 |
| 19.46 | 53 | 30 | 2 |
| 20.9 | 67 | 90 | 3 |
| 31.6 | 60 | 10 | 3 |

Example I
Estimation of the Oral Bioavailability of Phosphonic Acids and Their Prodrugs Phosphonic acids were dissolved in water, and the solution adjusted to neutrality with sodium hydroxide. Prodrugs were dissolved in 10% ethanol/90% polyethlene glycol (mw 400). Compound was administered by oral gavage to 18-hour fasted Sprague-Dawley rats (220–250 g) at doses ranging from 10–50 mg/kg. The rats were subsequently placed in metabolic cages and urine was collected for 24 hours. The quantity of phosphonic acid excreted into urine was determined by HPLC analysis as described in Example G. In a separate study, urinary recovery was determined following intravenous (tail vein) administration of compound (in the case of the prodrugs, the appropriate parent phosphonic acid was administered i.v.). The percentage oral bioavailability was estimated by comparison of the recovery of compound in urine 24 hours folowing oral administration, to that recovered in urine 24 hours after intravenous administration.

The oral bioavailabilities of select phosphonic acids, and prodrugs of phosphonic acids are shown in the table below.

| Compound # | % Oral bioavailability |
|---|---|
| 3.26 | 18 |
| 3.27 | 32 |
| 10.1 | 21 |
| 10.2 | 22 |
| 19.42 | 10 |
| 19.9 | 18.5 |
| 19.17 | 16.2 |
| 19.48 | 12 |
| 20.1 | 46 |
| 20.3 | 17.5 |
| 20.4 | 11 |
| 20.9 | 17.4 |
| 31.6 | 19 |
| 31.8 | 14 |

Example J
Blood Glucose Lowering in Zucker Diabetic Fatty Rats, Oral

Zucker Diabetic Fatty rats were purchased from Genetics Models Inc. (Indiannapolis, Ind.) at 8 weeks of age and fed the recommended Purina 5008 diet. At the age of 12 weeks, 16 animals with fed blood glucose levels between 500 and 700 mg/dl were selected and divided into two groups (n=8) with statistically equivalent average blood glucose levels. Compound 3.26 was administered at a dose of 100 mg/kg by oral gavage to one group of animals at 1 pm. The drug solution for this treatment was prepared at 25 mg/ml in deionized water and adjusted to neutrality by dropwise addition of 5 N NaOH. A second group of rats (n=8) was dosed orally with saline, in parallel. Blood glucose was measured in each rat just prior to drug or saline administration and 6 hours post administration. A HemoCue blood glucose analyzer (HemoCue Inc., Mission Viejo, Calif.) was used for these measurements according to the manufacturer's instructions. As shown in the table below, compound 3.26 treatment resulted in a 15.4% lowering of blood glucose relative to saline treated controls (p=0.01).

| | Blood Glucose, mg/dl | |
|---|---|---|
| Treatment Group | 1 pm | 7 pm |
| Saline | 575 ± 28 | 587 ± 26 |
| 3.26 | 573 ± 26 | 497 ± 14 |

The data indicate that Compound 3.26 is an effective oral glucose lowering agent in the Zucker Diabetic Fatty rat model of type II diabetes.

Example K
Blood Glucose Lowering in Zucker Diabetic Fatty Rats, Intravenous 12-week old Zucker Diabetic Fatty rats (Genetics Models Inc., Indianapolis, Ind.) aintained on Purina 5008 diet were instrumented with tail artery and tail vein catethers at 8 am on the day of the study. Food was removed for the remainder of the day. Starting at 12 pm, animals were infused for 6 hours via the tail vein catheter either with saline or compound 3.26 at 1, 3 or 30 mg/kg/h. Blood samples were obtained from the tail artery catheter at the start of the infusions, and at hourly intervals thereafter. Glucose was measured in the samples by means of a HemoCue analyzer (HemoCue Inc., Mission Viejo, Calif.) according to the manufacturer's instructions.

At the six hour time point, infusion of 3.26 at 3 and 30 mg/kg/h resulted in significant decreases in blood glucose of 29% and 39% respectively, relative to saline-infused controls. The study shows that 3.26 is an effective glucose lowering agent when administered intravenously to the Zucker Diabetic Fatty rat, a key rodent model of type II diabetes.

Example L
Inhibition of Gluconeogenesis by FBPase Inhibitor in Zucker Diabetic Fatty Rats Following a 6-hour infusion of 3.26 at 3 mg/kg/h or saline to Zucker Diabetic Fatty rats (n=3/group) as described in Example K, a bolus of $^{14}$C-bicarbonate (40 µCi/100 g body weight) was administered via the tail vein catheter. 20 minutes later, a blood sample (0.6 mL) was taken via the tail artery. Blood (0.5 ml) was diluted into 6 mL deionized water and protein precipitated by addition of 1 mL zinc sulfate (0.3 N) and 1 mL barium hydroxide (0.3 N). The mixture was centrifuged (20 minutes, 1000×g) and 5 mL of the resulting supernatant was then combined with 1 g of a mixed bed ion exchange resin (1 part AG 50W-X8, 100–200 mesh, hydrogen form, and 2 parts AG 1-X8, 100–200 mesh, acetate form) to separate $^{14}$-C-bicabonate from $^{14}$C-glucose. The slurry was shaken at room temperature for four hours and then allowed to settle. An aliquot of the supernatant (0.5 mL) was then counted in 5 mL scintillation cocktail. The percentage inhibition of gluconeogenesis in drug-treated rats was calculated by dividing the average cpm of $^{14}$C-glucose in samples from drug-treated animals by those from saline-injected animals.

$^{14}$C-Glucose production was found to be inhibited by 75% in the 3.26-infused rats. This result provides evidence that the glucose lowering activity of 3.26 in the Zucker Diabetic Fatty rat (Example K) is due to the inhibition of gluconeogenesis.

Example M
Blood Glucose Lowering in the Streptozotocin-Treated Rat

Diabetes is induced in male Sprague-Dawley rats (250–300 g) by intraperitoneal injection of 55 mg/kg streptozotocin (Sigma Chemical Co.). Six days later, blood glucose is measured as described in Example F. Animals are selected with fed blood glucose values (8 am) between 350 and 600 mg/dl, and divided into two groups. One group is dosed orally with compound (10–100 mg/kg) and the second with an equivalent volume of saline. Food is removed from the animals. Blood glucose is measured again after 2 and 4 hours of drug/saline administration.

Example N
Oral Absorption Determinations of Prodrugs in the Rat

Prodrugs 19.42, 19.48, 31.6, and 31.8 were administered to normal, fed rats at 30 mg/kg both by intraperitoneal injection and by oral gavage (n=3 rats/compound/route of aministration). Rats were subsequently placed in metabolic cages and urine collected for 24 hours. Parent compound, 3.1, was quantitated in urine by reverse phase HPLC as described in Example G. By comparison of the amount of parent compound excreted in urine following oral administration to that following intraperitoneal administration, the % oral absorption was calculated for each prodrug. Results are shown below:

| Compound | % excreted p.o. | % excreted i.p. | % absorption |
|---|---|---|---|
| 19.42 | 8.1 | 15.4 | 52 |
| 19.48 | 11.6 | 11.3 | 100 |
| 31.6 | 16.5 | 38.9 | 43 |
| 31.8 | 12.3 | 28.4 | 43 |

All four prodrugs tested were readily absorbed (43–100%) following oral administration Example O
Treatment With an FBPase Inhibitor Results in the Normalization of Hepatic Glycogen Levels in the db/db Mouse Db/db mice and their nondiabetic db/+littermates were obtained at 8 weeks of age (Jackson Labs., Bar Harbor, Me.) and enrolled in the study at 11 weeks of age. Db/db mice were treated orally either with saline or compound 3.26 (100 mg/kg) at 8 am and at 2 pm on the day of the study. Db/+mice were treated with saline according to the same schedule. At 6 pm, mice were anesthetized with halothane and a small section of liver (0.5 g) was removed by the freeze-clamping technique. The liver samples were fully frozen by subsequent immersion in liquid nitrogen and then homogenized in 5 volumes of cold 0.6 N perchloric acid. Glycogen content was determined enzymatically in the homogenates by the method of Keppler and Decker (Keppler D and Decker K in *Methods of Enzymatic Analysis*, Bergmeyer, HU, Ed., Verlag Chemie International, Deerfield Beach, Fla., 1974). Results relative to pretreatment (8 am) values determined in separate groups of mice, are shown in the table below:

| | Liver Glycogen, µmol glucose/g | |
|---|---|---|
| Treatment Group | Morning, 8 am | Evening, 6 pm |
| db/db, control | 102.9 ± 1.9 (n = 3) | 83.2 ± 22.5 (n = 7) |
| db/db, 3.26 | — | 34.4 ± 7.1 (n = 3) |
| db/+, control | 120.2 ± 6.7 (n = 3) | 15.7 ± 7.2 (n = 3) |

The data indicate that liver glycogen stores were not significantly reduced during the day in control (saline-treated) diabetic db/db mice, whereas there was significant glycogen mobilization in control, nondiabetic db/+mice. Acute treatment of db/db mice with 3.26 resulted in the reduction of glycogen stores to levels that approached those of nondiabetic db/+mice.

We claim:
1. A compound of formula (I):

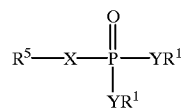

211 wherein $R^5$ is selected from the group consisting of:

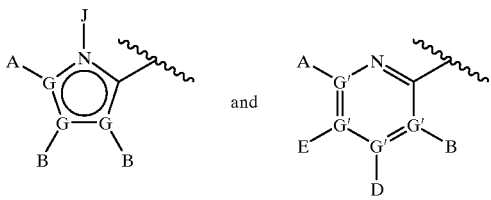

and wherein:
each G is independently selected from the group consisting of C, N, O, S, and Se, and wherein no more than one G is O, S, or Se, and at most one G is N;

each G' is independently selected from the group consisting of C and N and wherein no more than two G' groups are N;

A is selected from the group consisting of —H, —NR$^4_2$, —CONR$^4_2$, —CO$_2$R$^3$, halo, —S(O)R$^3$, —SO$_2$R$^3$, alkyl, alkenyl, alkynyl, perhaloalkyl, haloalkyl, aryl, —CH$_2$OH, —CH$_2$NR$^4_2$, —CH$_2$CN, —CN, —C(S)NH$_2$, —OR$^3$—SR$^3$, —N$_3$, —NHC(S)NR$^4_2$, —NHAc, and nothing;

each B and D are independently selected from the group consisting of —H, alkyl, alkenyl, alkynyl, aryl, alicyclic, aralkyl, alkoxyalkyl, —C(O)R$^{11}$—C(O)SR$^3$, —SO$_2$R$^{11}$—S(O)R$^3$, —CN, —NR$^9_2$, —OR$^3$, —SR$^3$, perhaloalkyl, halo, —NO$_2$, and nothing, all except —H, —CN, perhaloalkyl, —NO$_2$, and halo are substituted or unsubstituted;

E is selected from the group consisting of —H, alkyl, alkenyl, alkynyl, aryl, alicyclic, alkoxyalkyl, —C(O)OR$^3$, —CONR$^4_2$, —CN, —NR$^9_2$, —NO$_2$, —OR$^3$, —SR$^3$, perhaloalkyl, halo, and nothing, all except —H, —CN, perhaloalkyl, and halo are substituted or unsubstituted;

J is selected from the group consisting of —H and nothing;

X is a substituted or unsubstituted linking group that links $R^5$ to the phosphorus atom via 2–4 atoms, wherein 0–1 atoms are heteroatoms selected from N, O, and S, and the remaining atoms are carbon, except that if X is urea or carbamate there are 2 heteroatoms, measured by the shortest path between $R^5$ and the phosphorus atom, and wherein the atom attached to the phosphorus is a carbon atom, and wherein there is no N in the linking group unless it is connected directly to a carbonyl or in the ring of a heterocycle; and wherein X is not a 2 carbon atom -alkyl- or -alkenyl- group; with the proviso that X is not substituted with —COOR$^2$, —SO$_3$R$^1$, or —PO$_3$R$^1_2$;

Y is independently selected from the group consisting of —O—, and —NR6—;

when Y is —O—, then $R^1$ attached to —O— is independently selected from the group consisting of —H, alkyl, substituted or unsubstituted aryl, substituted or unsubstituted alicyclic where the cyclic moiety contains a carbonate or thiocarbonate, substituted or unsubstituted -alkylaryl, —C(R$^2$)$_2$OC(O)NR$^2_2$, —NR$^2$—C(O)—R$^3$, —C(R$^2$)$_2$—OC(O)R$^3$, —C(R$^2$)$_2$—O—C(O)OR$^3$, —C(R$^2$)$_2$OC(O)SR$^3$, -alkyl-S—C(O)R$^3$, -alkyl-S—S-alkylhydroxy, and -alkyl-S—S—S-alkylhydroxy, when Y is —NR$^6$—, then $R^1$ attached to —NR$^6$— is independently selected from the group consisting of

212

—H, —[C(R$^2$)$_2$]$_q$—COOR$^3$, —C(R$^4$)$_2$COOR$^3$, —[C(R$^2$)$_2$]$_q$—C(O)SR$^3$, and -cycloalkylene-COOR$^3$;

or when either Y is independently selected from —O— and —NR$^6$—, then together $R^1$ and $R^1$ are -alkyl-S—S-alkyl- to form a cyclic group, or together $R^1$ and $R^1$ are

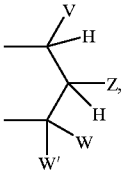

wherein
V, W, and W' are independently selected from the group consisting of —H, alkyl, aralkyl, alicyclic, aryl, substituted aryl, heteroaryl, substituted heteroaryl, 1-alkenyl, and 1-alkynyl; or together V and Z are connected via an additional 3–5 atoms to form a cyclic group containing 5–7 atoms, wherein 0–1 atoms are heteroatoms and the remaining atoms are carbon, substituted with hydroxy, acyloxy, alkoxycarbonyloxy, or aryloxycarbonyloxy attached to a carbon atom that is three atoms from both Y groups attached to the phosphorus; or together V and Z are connected via an additional 3–5 atoms to form a cyclic group, wherein 0–1 atoms are heteroatoms and the remaining atoms are carbon, that is fused to an aryl group at the beta and gamma position to the Y attached to the phosphorus;

together V and W are connected via an additional 3 carbon atoms to form a substituted or unsubstituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, wherein 0–1 atoms are heteroatoms and the remaining atoms are carbon, and V must be aryl, substituted aryl, heteroaryl, or substituted heteroaryl;

together W and W' are connected via an additional 2–5 atoms to form a cyclic group, wherein 0–2 atoms are heteroatoms and the remaining atoms are carbon, and V must be aryl, substituted aryl, heteroaryl, or substituted heteroaryl;

Z is selected from the group consisting of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH═CR$^2_2$)OH, —CH(C≡CR$^2$)OH, —R$^2$, —NR$^2_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^2$, and —(CH$_2$)$_p$—SR$^2$;

p is an integer 2 or 3;

q is an integer 1 or 2;

with the provisos that:
a) V, Z, W, W' are not all —H; and
b) when Z is —R$^2$, then at least one of V, W, and W' is not —H, alkyl, aralkyl, or alicyclic;

$R^2$ is selected from the group consisting of $R^3$ and —H;

$R^3$ is selected from the group consisting of alkyl, aryl, alicyclic, and aralkyl;

each $R^4$ is independently selected from the group consisting of —H, and alkyl, or together $R^4$ and $R^4$ form a cyclic alkyl group;

$R^6$ is selected from the group consisting of —H, lower alkyl, acyloxyalkyl, alkoxycarbonyloxyalkyl, and lower acyl;

each $R^9$ is independently selected from the group consisting of —H, alkyl, aralkyl, and alicyclic, or together $R^9$ and $R^9$ form a cyclic alkyl group;

$R^{11}$ is selected from the group consisting of alkyl, aryl, —$NR^2_2$, and —$OR^2$; and with the provisos that:
1) when G' is N, then the respective A, B, D, or E is nothing;
2) at least one of A and B, or A, B, D, and E is not selected from the group consisting of —H or nothing;
3) when $R^5$ is a six-membered ring, then X is not any 2 atom linker, a substituted or unsubstituted -alkyl-, a substituted or unsubstituted -alkenyl-, a substituted or unsubstituted -alkyloxy-, or a substituted or unsubstituted -alkylthio-;
4) when G is N, then the respective A or B is not halogen or a group directly bonded to G via a heteroatom;
5) $R^1$ is not unsubstituted C1–C10 alkyl;
6) when X is not an -aryl- group, then $R^5$ is not substituted with two or more aryl groups;

or pharmaceutically acceptable prodrugs or salts thereof.

2. The compound of claim 1 wherein $R^5$ is selected from the group consisting of pyrrolyl, imidazolyl, oxazolyl, thiazolyl, isothiazolyl, 1,2,4-thiadiazolyl, pyrazolyl, isoxazolyl, 1,2,3-oxadiazolyl, 1,2,4-oxadiazolyl, 1,2,5-oxadiazolyl, 1,3,4-oxadiazolyl, 1,2,4-thiadiazolyl, 1,3,4-thiadiazolyl, pyridinyl, pyrimidinyl, pyrazinyl, pyridazinyl, 1,3,5-triazinyl, 1,2,4-triazinyl, and 1,3-selenazolyl, all of which contain at least one substituent.

3. The compound of claim 1 wherein A is selected from the group consisting of —H, —$NR^4_2$, —$CONR^4_2$, —$CO_2R^3$, halo, C1–C6 alkyl, C2–C6 alkenyl, C2–C6 alkynyl, C1–C6 perhaloalkyl, C1–C6 haloalkyl, aryl, —$CH_2OH$, —$CH_2NR^4_2$, —$CH_2CN$, —CN, —$C(S)NH_2$, —$R^4$, —$SR^4$, —$N_3$, —$NHC(S)NR^4_2$, —NHAc, and nothing;

each B and D are independently selected from the group consisting of —H, alkyl, alkenyl, alkynyl, aryl, alicyclic, aralkyl, alkoxyalkyl, —$C(O)R^{11}$, —$C(O)SR^3$, —$SO_2R^{11}$, —$S(O)R^3$, —CN, —$NR^2_2$, —$OR^3$, —$SR^3$, perhaloalkyl, halo, and nothing, all except —H, —CN, perhaloalkyl, and halo are substituted or unsubstituted;

E is selected from the group consisting of —H, C1–C6 alkyl, C2–C6 alkenyl, C2–C6 alkynyl, aryl, C4–C6 alicyclic, alkoxyalkyl, —$C(O)OR^3$, —$CONR^4_2$, —CN, —$NR^9_2$, —$OR^3$, —$SR^3$, C1–C6 perhaloalkyl, halo, and nothing, all except —H, —CN, perhaloalkyl, and halo are substituted or unsubstituted; and each $R^4$ is independently selected from the group consisting of —H, and C1–C2 alkyl.

4. The compound of claim 1 wherein $R^5$ is:

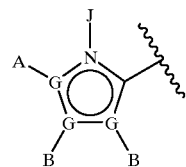

5. The compound of claim 1 wherein $R^5$ is:

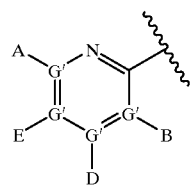

6. The compound of claim 1 wherein $R^5$ is selected from the group consisting of:

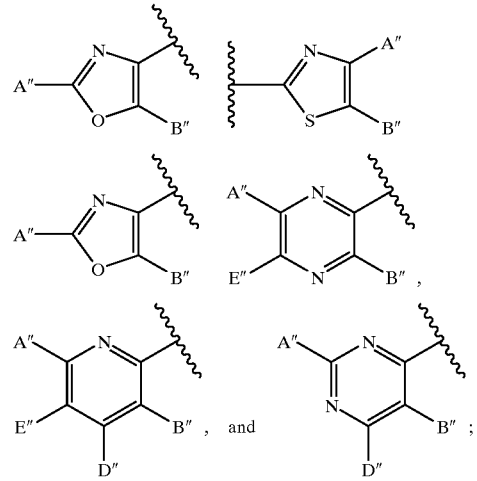

wherein
A" is selected from the group consisting of —H, —$NR^4_2$, —$CONR^4_2$, —$CO_2R^3$, halo, C1–C6 alkyl, C2–C6 alkenyl, C2–C6 alkynyl, C1–C6 perhaloalkyl, C1–C6 haloalkyl, aryl, —$CH_2OH$, —$CH_2NR^4_2$, —$CH_2CN$, —CN, —$C(S)NH_2$, —$OR^3$, —$SR^3$, —$N_3$, —$NHC(S)NR^4_2$, and —NHAc;

B" and D" are independently selected from the group consisting of —H, alkyl, alkenyl, alkynyl, aryl, alicyclic, aralkyl, alkoxyalkyl, —$C(O)R^{11}$, —$C(O)SR^3$, —$SO_2R^{11}$, —$S(O)R^3$, —CN, —$NR^9_2$, —$R^3$, —$SR^3$, perhaloalkyl, and halo, all except —H, —CN, perhaloalkyl, and halo are substituted or unsubstituted;

E" is selected from the group consisting of —H, C1–C6 alkyl, C2–C6 alkenyl, C2–C6 alkynyl, C4–C6 alicyclic, alkoxyalkyl, —$C(O)OR^3$, —$CONR^4_2$, —CN, —$NR^9_2$, —$OR^3$, —$SR^3$, C1–C6 perhaloalkyl, and halo, all except H, —CN, perhaloalkyl, and halo are substituted or unsubstituted; and each $R^4$ is independently selected from the group consisting of —H and C1–C2 alkyl.

7. The compound of claim 6 wherein $R^5$ is selected from the group consisting of:

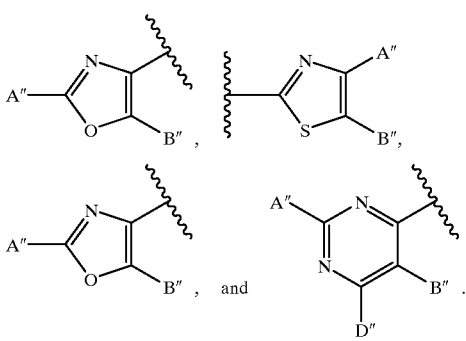

8. The compound of claim 6 wherein $R^5$ is selected from the group consisting of:

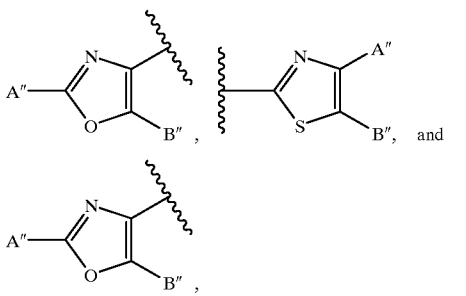

9. The compound of claim 6 wherein $R^5$ is selected from the group consisting of:

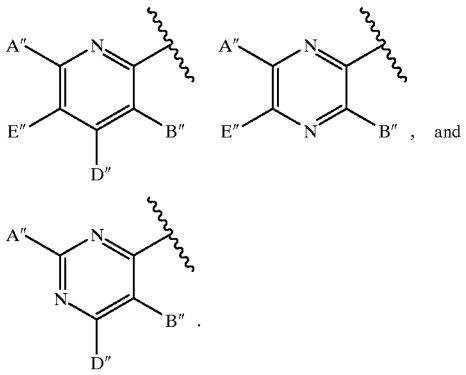

10. The compound of claim 1 wherein X is selected from the group consisting of-alkyl(hydroxy)-, -alkyl-, -alkynyl-, -aryl-, -carbonylalkyl-, -1,1-dihaloalkyl-, —alkoxyalkyl-, -alkyloxy-, -alkylthioalkyl-, -alkylthio-, -alkylaminocarbonyl-, —alkylcarbonylamino-, -alicyclic-, -aralkyl-, -alkylaryl-, -alkoxycarbonyl-, -carbonyloxyalkyl-, —alkoxycarbonylamino-, and -alkylaminocarbonylamino-, all substituted or unsubstituted.

11. The compound of claim 4 wherein X is selected from the group consisting of -alkyl(hydroxy)-, -alkyl-, -alkynyl-, -aryl-, -carbonylalkyl-, -1,1-dihaloalkyl-, —alkoxyalkyl-, -alkyloxy-, -alkylthioalkyl-, -alkylthio-, -alkylaminocarbonyl-, —alkylcarbonylamino-, -alicyclic-, -aralkyl-, -alkylaryl-, -alkoxycarbonyl-, -carbonyloxyalkyl-, —alkoxycarbonylamino-, and -alkylaminocarbonylamino-, all substituted or unsubstituted.

12. The compound of claim 5 wherein X is selected from the group consisting of-alkyl(hydroxy)-, -alkyl-, -alkynyl-, -aryl-, -carbonylalkyl-, -1,1-dihaloalkyl-, —alkoxyalkyl-, -alkyloxy-, -alkylthioalkyl-, -alkylthio-, -alkylaminocarbonyl-, —alkylcarbonylamino-, -alicyclic-, -aralkyl-, -alkylaryl-, -alkoxycarbonyl-, -carbonyloxyalkyl-, —alkoxycarbonylamino-, and -alkylaminocarbonylamino-, all substituted or unsubstituted.

13. The compound of claim 3 wherein X is selected from the group consisting of -heteroaryl-, -alkylcarbonylamino-, -alkylaminocarbonyl- -alkoxycarbonyl-, and -alkoxyalkyl-.

14. The compound of claim 13 wherein X is selected from the group consisting of -heteroaryl- and -alkoxycarbonyl-.

15. The compound of claim 3 wherein said compound is a compound of formulae II, III, or IV

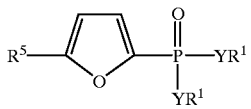 (II)

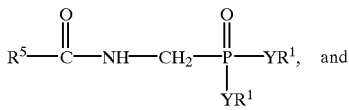 (III)

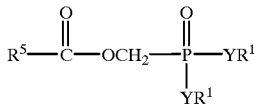 (IV)

16. The compound of claim 6 wherein X is selected from the group consisting of -alkyl(hydroxy)-, -alkyl-, -alkynyl-, -aryl-, -carbonylalkyl-, -1,1-dihaloalkyl-, —alkoxyalkyl-, -alkyloxy-, -alkylthioalkyl-, -alkylthio-, -alkylaminocarbonyl-, —alkylcarbonylamino-, -alicyclic-, -aralkyl-, -alkylaryl-, -alkoxycarbonyl-, -carbonyloxyalkyl-, —alkoxycarbonylamino-, and -alkylaminocarbonylamino-, all substituted or unsubstituted.

17. The compound of claim 16 wherein X is selected from the group consisting of -heteroaryl-, -alkylcarbonylamino-, -alkylaminocarbonyl-, -alkoxycarbonyl-, and -alkoxyalkyl-.

18. The compound of claim 17 wherein said compound is a compound of formulae II or IV:

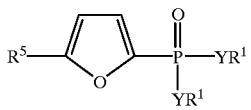 (II)

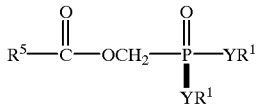 (IV)

19. The compound of claim 17 wherein A" is selected from the group consisting of —$NH_2$, —$CONH_2$, halo, —$CH_3$, —$CF_3$, —$CH_2$-halo, —CN, —$OCH_3$, —$SCH_3$, and —H.

20. The compound of claim 19 wherein A" is selected from the group consisting of —Cl, —$NH_2$, —Br, and —$CH_3$.

21. The compound of claim 17 wherein each B" is selected from the group consisting of —H, —C(O)$R^{11}$, —C(O)$SR^3$, alkyl, aryl, alicyclic, halo, —CN, —$SR^3$, —$NR^9_2$ and —$OR^3$.

22. The compound of claim 21 wherein each B" is selected from the group consisting of —H, —C(O)OR$^3$, —C(O)SR$^3$, C1–C6 alkyl, alicyclic, halo, heteroaryl, and —SR$^3$.

23. The compound of claim 17 wherein D" is selected from the group consisting of —H, —C(O)R$^{11}$, —C(O)SR$^3$, alkyl, aryl, alicyclic, halo, —NR$^9{}_2$, and —SR$^3$.

24. The compound of claim 23 wherein D" is selected from the group consisting of —H, —C(O)OR$^3$, lower alkyl, alicyclic, and halo.

25. The compound of claim 17 wherein E" is selected from the group consisting of —H, C1–C6 alkyl, lower alicyclic, halogen, —CN, —C(O)OR$^3$, —SR$^3$, and —CONR$^4{}_2$.

26. The compound of claim 25 wherein E" is selected from the group consisting of —H, —Br, and —Cl.

27. The compound of claim 1, where both Y groups are —O—.

28. The compound of claim 4, where both Y groups are —O—.

29. The compound of claim 5, where both Y groups are —O—.

30. The compound of claim 1, where one Y is —NR$^6$—, and one Y is —O—.

31. The compound of claim 4, where one Y is —NR—, and one Y is —O—.

32. The compound of claim 5, where one Y is —NR$^6$—, and one Y is —O—.

33. The compound of claim 1 wherein when Y is —O—, then R$^1$ attached to —O— is independently selected from the group consisting of —H, substituted or unsubstituted aryl, substituted or unsubstituted alicyclic where the cyclic moiety contains a carbonate or thiocarbonate, substituted or unsubstituted -alkylaryl, —C(R$^2$)$_2$OC(O)R$^3$, —C(R$^2$)$_2$—O—C(O)OR$^3$, —C(R$^2$)$_2$OC(O)SR$^3$, -alkyl-S—C(O)R$^3$, and -alkyl-S—S-alkylhydroxy;

when Y is —NR$^6$—, then R$^1$ attached to —NR$^6$— is independently selected from the group consisting of —H, —[C(R$^2$)$_2$]$_q$—COOR$^3$, —[C(R$^2$)$_2$]$_q$—C(O)SR$^3$, —C(R$^4$)$_2$COOR$^3$, and -cycloalkylene-COOR$^3$;

or when either Y is independently selected from —O— and —NR$^6$— then together R$^1$ and R$^1$ are

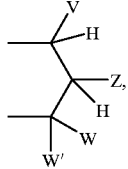

wherein

V, W, and W' are independently selected from the group consisting of —H, alkyl, aralkyl, alicyclic, aryl, substituted aryl, heteroaryl, substituted heteroaryl, 1-alkenyl, and 1-alkynyl, or together V and W are connected via an additional 3 carbon atoms to form a substituted or unsubstituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, wherein 0–1 atoms are heteroatoms and the remaining atoms are carbon, and V must be aryl, substituted aryl, heteroaryl, or substituted heteroaryl;

together W and W' are connected via an additional 2–5 atoms to form a cyclic group, wherein 0–2 atoms are heteroatoms and the remaining atoms are carbon, and V must be aryl, substituted aryl, heteroaryl, or substituted heteroaryl;

Z is selected from the group consisting of —CHR$^2$OH, —CHR$^2$OC(O)R$^3$, —CHR$^2$OC(S)R$^3$, —CHR$^2$OC(S) OR$^3$, —CHR$^2$OC(O)SR$^3$ —CHR$^2$OCO$_2$R$^3$, —OR$^2$, —SR$^2$—R$^2$, —NHCOR$^2$, —NHCO$_2$R$^3$, —(CH$_2$)$_p$—OR$^2$, and —(CH$_2$)$_p$—SR$^2$;

p is an integer 2 or 3;

q is an integer 1 or 2;

with the provisos that:
a) V, Z, W, W' are not all —H;
b) when Z is —R$^2$, then at least one of V, W, and W' is not —H, alkyl, aralkyl, or alicyclic; and
c) both Y groups are not —NR$^6$—;

R$^2$ is selected from the group consisting of R$^3$ and —H;

R$^3$ is selected from the group consisting of alkyl, aryl, alicyclic, and aralkyl;

R$^6$ is selected from the group consisting of —H, and lower alkyl.

34. The compound of claim 33 wherein when both Y groups are —O—, then R$^1$ is independently selected from the group consisting of substituted or unsubstituted aryl, substituted or unsubstituted benzyl, —C(R$^2$)$_2$OC(O)R$^3$, —C(R$^2$)$_2$OC(O)OR$^3$, and —H; and when Y is —NR$^6$—, then the R$^1$ attached to said —NR$^6$— group is selected from the group consisting of —C(R$^4$)$_2$—COOR$^3$ and —C(R$^2$)$_2$COOR$^3$; and the other Y group is —O— and then R$^1$ attached to said —O— is selected from the group consisting of substituted or unsubstituted aryl, —C(R$^2$)$_2$OC(O)R$^3$, and —C(R$^2$)$_2$OC(O)OR$^3$.

35. The compound of claim 34 wherein both Y groups are —O—, and R$^1$ is H.

36. The compound of claim 17 wherein both Y groups are —O—, and R$^1$ is aryl or —C(R$^2$)$_2$-aryl.

37. The compound of claim 17 wherein both Y groups are O—, and at least one R$^1$ is selected from the group consisting of —C(R$^2$)$_2$—C(O)R$^3$ and —C(R$^2$)$_2$—C(o)OR$^3$.

38. The compound of claim 17 wherein both Y groups are —O— and at least one R$^1$ is -alkyl-S—S-alkylhydroxyl, -alkyl-S—C(O)R$^3$, and -alkyl-S—S—S-alkylhydroxy, or together R$^1$ and R$^1$ are -alkyl-S—S-alkyl- to form a cyclic group.

39. The compound of claim 17 wherein at least one Y is —O—, and together R$^1$ and R$^1$ are

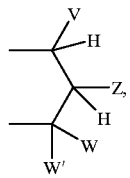

wherein

V, W, and W' are independently selected from the group consisting of —H, alkyl, aralkyl, alicyclic, aryl, substituted aryl, heteroaryl, substituted heteroaryl, 1-alkenyl, and 1-alkynyl, or together V and W are connected via an additional 3 carbon atoms to form a substituted or unsubstituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, wherein 0–1 atoms are heteroatoms and the remaining atoms are carbon, and V must be aryl, substituted aryl, heteroaryl, or substituted heteroaryl;

together W and W' are connected via an additional 2–5 atoms to form a cyclic group, wherein 0–2 atoms are heteroatoms and the remaining atoms are carbon, and V must be aryl, substituted aryl, heteroaryl, or substituted heteroaryl;

Z is selected from the group consisting of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —R$^2$, —NHCOR$^2$, —NHCO$_2$R$^3$, —(CH$_2$)$_p$—OR$^2$, and —(CH$_2$)$_p$—SR$^2$;

p is an integer 2 or 3;

with the provisos that:
a) V, Z, W, W' are not all —H;
b) when Z is —R$^2$, then at least one of V, W, and W' is not —H, alkyl, aralkyl or alicyclic; and
c) both Y groups are not —NR$^6$—;

R$^2$ is selected from the group consisting of R$^3$ and —H;

R$^3$ is selected from the group consisting of alkyl, aryl, alicyclic, and aralkyl;

R$^6$ is selected from the group consisting of —H, and lower alkyl.

40. The compound of claim 34 wherein one Y is —O—, and R$^1$ is substituted or unsubstituted aryl; and the other Y is —NR$^6$—, where R$^1$ attached to said —NR$^6$— is selected from the group consisting of —C(R$^4$)$_2$COOR$^3$, and —C(R$^2$)$_2$C(O)OR$^3$.

41. The compound of claim 40 wherein R$^1$ attached to —O— is selected from the group consisting of phenyl, and phenyl substituted with 1–2 substituents selected from the group consisting of —NHC(O)CH$_3$, —F, —Cl, —Br, —C(O)OCH$_2$CH$_3$, and —CH$_3$; and wherein R$^1$ attached to —NR$^6$— is —C(R$^2$)$_2$COOR$^3$; each R$^2$ is independently selected from the group consisting of —CH$_3$, —CH$_2$CH$_3$, and —H.

42. The compound of claim 41 wherein the substituents of said substituted phenyl are selected from the group consisting of 4—NHC(O)CH$_3$, —Cl, —Br, 2—C(O)OCH$_2$CH$_3$, and —CH$_3$.

43. The compound of claim 6 wherein
A" is selected from the group consisting of —NH$_2$, —CONH$_2$, halo, —CH$_3$, —CF$_3$, —CH$_2$-halo, —CN, —OCH$_3$, —SCH$_3$, and —H;
B" is selected from the group consisting of —H, —C(O)R$^{11}$, —C(O)SR$^3$, alkyl, aryl, alicyclic, halo, —CN, —SR$^3$, OR$^3$ and —NR$^9$$_2$;
D" is selected from the group consisting of —H, —C(O)R$^{11}$, —C(O)SR$^3$, NR$^9$$_2$, alky, aryl, alicyclic, halo, and —SR$^3$;
E" is selected from the group consisting of —H, C1–C6 alkyl, lower alicyclic, halo, —CN, —C(O)OR$^3$, and —SR$^3$;
X is selected from the group consisting of -alkyl (hydroxy)-, -alkyl-, -alkynyl-, —aryl-, -carbonylalkyl-, -1,1-dihaloalkyl-, -alkoxyalkyl-, -alkyloxy-, -alkylthioalkyl-, -alkylthio-, —alkylaminocarbonyl-, -alkylcarbonylamino-, -alicyclic-, -aralkyl-, -alkylaryl-, -alkoxycarbonyl-, —carbonyloxyalkyl-, -alkoxycarbonylamino-, and -alkylaminocarbonylamino-, all substituted or unsubstituted;

when both Y groups are —O—, then R$^1$ is independently selected from the group consisting of substituted or unsubstituted aryl, substituted or unsubstituted benzyl, —C(R$^2$)$_2$OC(O)R$^3$, —C(R$^2$)$_2$OC(O)OR$^3$, and —H; or when one Y is —O—, then R$^1$ attached to —O— is substituted or unsubstituted aryl; and the other Y is —NR$^6$—, then R$^1$ attached to —NR$^6$— is selected from the group consisting of —C(R$^4$)$_2$, COOR$^3$, and —C(R$^2$)$_2$C(O)OR$^3$; or when Y is —O— or —NR$^6$—, then together R$^1$ and R$^1$ are

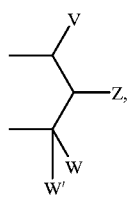

wherein

V, W, and W' are independently selected from the group consisting of —H, alkyl, aralkyl, alicyclic, aryl, substituted aryl, heteroaryl, substituted heteroaryl, 1-alkenyl, and 1-alkynyl, or together V and W are connected via an additional 3 carbon atoms to form a substituted or unsubstituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, wherein 0–1 atoms are heteroatoms and the remaining atoms are carbon, and V must be aryl, substituted aryl, heteroaryl, or substituted heteroaryl;

together W and W' are connected via an additional 2–5 atoms to form a cyclic group, wherein 0–2 atoms are heteroatoms and the remaining atoms are carbon, and V must be aryl, substituted aryl, heteroaryl, or substituted heteroaryl;

Z is selected from the group consisting of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —R$^2$, —NHCOR$^2$, —NHCO$_2$R$^3$, —(CH$_2$)$_p$—OR$^2$, and —(CH$_2$)$_p$—SR$^2$;

p is an integer 2 or 3;

with the provisos that:
a) V, Z, W, W' are not all —H;
b) when Z is —R$^2$, then at least one of V, W, and W' is not —H, alkyl, aralkyl, or alicyclic; and
c) both Y groups are not —NR$^6$—;

R$^2$ is selected from the group consisting of R$^3$ and —H;

R$^3$ is selected from the group consisting of alkyl, aryl, alicyclic, and aralkyl;

R[6] is selected from the group consisting of —H, and lower alkyl.

44. The compound of claim 6 wherein R[5] is

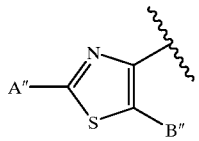

X is selected from the group consisting of methylenoxycarbonyl and furan-2,5-diyl; at least one Y group is —O—; or pharmaceutically acceptable salts or prodrugs thereof.

45. The compound of claim 44 wherein when Y is —O—, then R[1] attached to —O— is independently selected from the group consisting of —H, substituted or unsubstituted phenyl, —CH$_2$OC(O)-tBu, —CH$_2$OC(O)Et, and —CH$_2$OC(O)-iPr;

when Y is —NR[6]—, then R[1] is attached to —NR[6]— independently selected from the group consisting of —C(R[2])$_2$COOR[3], —C(R[4])$_2$COOR[3], or when Y is —O— or —NR[6]—, and at least one Y is —O—, then together R[1] and R[1] are

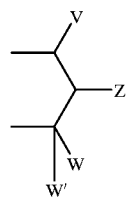

wherein
V is selected from the group consisting of substituted or unsubstituted aryl, and substituted or unsubstituted heteroaryl; and Z, W', and W are H; and
R[6] is selected from the group consisting of —H, and lower alkyl.

46. The compound of claim 45 wherein A" is —NH$_2$, X is furan-2,5-diyl, and B" is —CH$_2$—CH(CH$_3$)$_2$.

47. The compound of claim 45 wherein A" is —NH$_2$, X is furan-2,5-diyl, and B" is —COOEt.

48. The compound of claim 45 wherein A" is —NH$_2$, X is furan-2,5-diyl, and B" is —SMe.

49. The compound of claim 46 wherein A" is —NH$_2$, X is methyleneoxycarbonyl, and B" is —CH(CH$_3$)$_2$.

50. The compound of claim 46 wherein both Y groups are —O— and R[1] is —H.

51. The compound of claim 46 wherein both Y groups are —O—, and R[1] is —CH$_2$OC(O)OEt.

52. The compound of claim 46 wherein both Y groups are —O—, and R[1] and R[1] together are

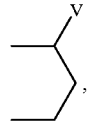

and V is phenyl substituted with 1–3 halogens.

53. The compound of claim 47 wherein both Y groups are —O—, and R[1] and R[1] together are

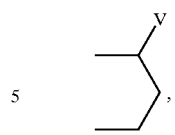

and V is phenyl substituted with 1–3 halogens.

54. The compound of claim 48 wherein both Y groups are —O—, and R[1] and R[1] together are

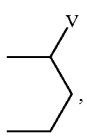

and V phenyl substituted with 1–3 halogens.

55. The compound of claim 49 wherein both Y groups are —O—, and R[1] and R[1] together are

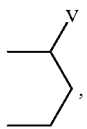

and V is phenyl substituted with 1–3 halogens.

56. The compound of claim 52 wherein V is selected from the group consisting of 3,5-dichlorophenyl, 3-bromo-4-fluorophenyl, 3-chlorophenyl, and 3-bromophenyl.

57. The compound of claim 46 wherein one Y is —O— and its corresponding R[1] is -phenyl while the other Y is —NH— and its corresponding R[1] is —CH(Me)CO$_2$Et and —NH—*CH(Me)CO$_2$Et is in the L-configuration.

58. The compound of claim 6 wherein R[5] is

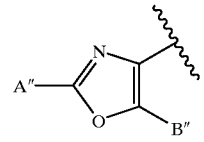

X is selected from the group consisting of furan-2,5-diyl and methyleneoxycarbonyl, and A" is —NH$_2$; at least one Y group is —O—; or pharmaceutically acceptable salts or prodrugs thereof.

59. The compound of claim 58 wherein
when Y is —O—, then each R[1] is independently selected from the group consisting of —H, substituted or unsubstituted phenyl, —CH$_2$OC(O)-tBu, —CH$_2$OC(O)Et, and —CH$_2$OC(O)-iPr;

or when Y is —NR[6]—, then each R[1] is independently selected from the group consisting of —C(R[2])$_2$C(O)OR[3], and —C(R[4])$_2$COOR[3];

or when Y is independently selected from —O— and —NR[6]—, then together R[1] and R[1] are

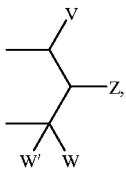

wherein

V selected from the group consisting of substituted or unsubstituted aryl and substituted or unsubstituted heteroaryl; and Z, W', and W are H.

60. The compound of claim 59 wherein B" is —SCH$_2$CH$_2$CH$_3$; and X is furan-2,5-diyl.

61. The compound of claim 60 wherein both Y groups are —O— and R$^1$ is —H.

62. The compound of claim 60 wherein one Y is —O— and its corresponding R$^1$ is -phenyl while the other Y is —NH—, and its corresponding R$^1$ is —CH(Me)CO$_2$Et, and —NH*CH(Me)CO$_2$Et is in the L-configuration.

63. The compound of claim 60 wherein both Y groups are —O— and R$^1$ is —CH$_2$OC(O)OEt.

64. The compound of claim 60 wherein both Y groups are —O—, R$^1$ and R$^1$ together are

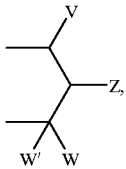

and V is phenyl substituted with 1–3 halogens.

65. The compound of claim 64 wherein V is selected from the group consisting of 3,5-dichlorophenyl, 3-bromo-4-fluorophenyl, 3-chlorophenyl, and 3-bromophenyl.

66. The compound of claim 6 wherein R$^5$ is

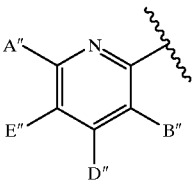

A" is —NH$_2$, E" and D" are —H, B" is selected from the group consisting of n-propyl and cyclopropyl, X is selected from the group consisting of furan-2,5-diyl and methyleneoxycarbonyl; at least one Y group is —O—; or pharmaceutically acceptable salts or prodrugs thereof.

67. The compound of claim 66 wherein when Y is —O—, then each R$^1$ is independently selected from the group consisting of —H, substituted or unsubstituted phenyl, —CH$_2$OC(O)-tBu, —CH$_2$OC(O)Et, and —CH$_2$OC(O)-iPr;

or when Y is —NR$^6$—, then each R$^1$ is independently selected from the group consisting of —C(R$^2$)$_2$C(O)OR$^3$, and —C(R$^4$)$_2$COOR$^3$;

or when Y is independently selected from —O— and —NR$^6$—, then together R$^1$ and R$^1$ are

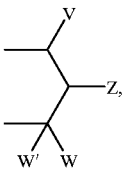

wherein

V selected from the group consisting of substituted or unsubstituted aryl and substituted or unsubstituted heteroaryl; and Z, W', and W are H.

68. The compound of claim 6 wherein R$^5$ is

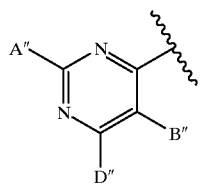

A" is —NH$_2$, D" is —H, B" is selected from the group consisting of n-propyl and cyclopropyl, X is selected from the group consisting of furan-2,5-diyl and methyleneoxycarbonyl; at least one Y group is —O—; or pharmaceutically acceptable salts or prodrugs thereof.

69. The compound of claim 68 wherein when Y is —O—, then each R$^1$ is independently selected from the group consisting of —H, substituted or unsubstituted phenyl, —CH$_2$OC(O)-tBu, —CH$_2$OC(O)Et, and —CH$_2$OC(O)-iPr;

or when Y is —NR$^6$—, then each R$^1$ is independently selected from the group consisting of —C(R$^2$)$_2$C(O)OR$^3$, and —C(R$^4$)$_2$COOR$^3$;

or when Y is independently selected from —O— and —NR$^6$—, then together R$^1$ and R$^1$ are

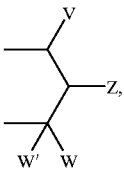

wherein

V is selected from the group consisting of substituted or unsubstituted aryl and substituted or unsubstituted heteroaryl; and Z, W', and W are H.

70. A method of treating a disease or condition responsive to inhibition of gluconeogenesis or responsive to lowered blood glucose levels in an animal which comprises administering to an animal suffering from a disease or condition responsive to inhibition of gluconeogenesis or responsive to lowered blood glucose levels a pharmaceutically effective amount of a FBPase inhibitor of formula (I):

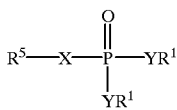

wherein R[5] is selected from the group consisting of:

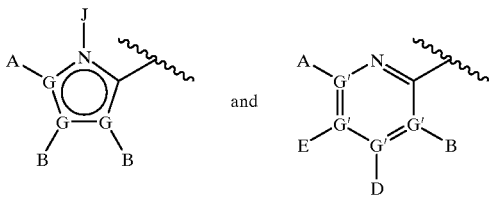

wherein:
- each G is independently selected from the group consisting of C, N, O, S and Se, and wherein no more than one G is O, S, or Se;
- each G' is independently selected from the group consisting of C and N and wherein no more than two G' groups are N;
- A is selected from the group consisting of —H, —NR[4], -CONR[4]$_2$, —CO$_2$R[3], halo, —S(O)R[3]—SO$_2$R[3], alkyl, alkenyl, alkynyl, perhaloalkyl, haloalkyl, aryl, —CH$_2$OH, —CH$_2$NR[4]$_2$, —CH$_2$CN, —CN, —C(S)NH$_2$, —OR[3], —SR[3], —N$_3$, —NHC(S)NR[4]$_2$, —NHAc, and nothing;
- each B and D are independently selected from the group consisting of —H, alkyl, alkenyl, alkynyl, aryl, alicyclic, aralkyl, alkoxyalkyl, —C(O)R[11], —C(O)SR[3], —SO$_2$R[11], —S(O)R[3], —CN, —NR[9]$_2$, —OR[3], —SR[3], perhaloalkyl, halo, —NO$_2$, and nothing, all except —H, —CN, perhaloalkyl, —NO$_2$, and halo are substituted or unsubstituted;
- E is selected from the group consisting of —H, alkyl, alkenyl, alkynyl, aryl, alicyclic, alkoxyalkyl, —C(O)OR[3], —CONR[4]$_2$, —CN, —NR[9]$_2$, —NO$_2$, —OR[3], —SR[3], perhaloalkyl, halo, and nothing, all except —H, —CN, perhaloalkyl, and halo are substituted or unsubstituted;
- J is selected from the group consisting of —H and nothing;
- X is a substituted or unsubstituted linking group that links R[5] to the phosphorus atom via 2–4 atoms, wherein 0–1 atoms are heteroatoms selected from N, O, and S and the remaining atoms are carbon, except that if X is urea or carbamate there are 2 heteroatoms, measured by the shortest path between R[5] and the phosphorus atom, and wherein the atom attached to the phosphorus is a carbon atom, and wherein there is no N in the linking group unless it is connected directly to a carbonyl or in the ring of a heterocycle; and wherein X is not a 2 carbon atom -alkyl- or -alkenyl group; with the proviso that X is not substituted with —COOR[2], —SO$_3$R[1], or —PO$_3$R[1]$_2$;
- Y is independently selected from the group consisting of —O—, and —NR[6]—;
- when Y is —O—, then R[1] attached to —O— is independently selected from the group consisting of —H, alkyl, substituted or unsubstituted aryl, substituted or unsubstituted alicyclic where the cyclic moiety contains a carbonate or thiocarbonate, substituted or unsubstituted-alkylaryl, —C(R[2])$_2$OC(O)NR[2]$_2$, —NR[2]—C(O)—R[3], —C(R[2])$_2$—OC(O)R[3], —C(R[2])$_2$—O—C(O)OR[3], —C(R[2])$_2$OC(O)SR[3], -alkyl-S—C(O)R[3], -alkyl-S—S-alkylhydroxy, and -alkyl-S—S—S-alkylhydroxy,
- when Y is —NR[6]—, then R[1] attached to —NR[6]— is independently selected from the group consisting of —H, —[C(R[2])$_2$]$_q$—COOR[3], —C(R[4])$_2$COOR[3], —[C(R[2])$_2$]$_q$—C(O)SR[3], and —cycloalkylene-COOR[3];
- or when either Y is independently selected from —O— and —NR[6]—, then together R[1] and R[1] are R[1] are -alkyl-S—S-alkyl- to form a cyclic group, or together R[1] and R[1] are

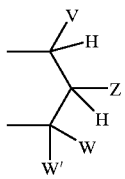

wherein
V, W, and W' are independently selected from the group consisting of —H, alkyl, aralkyl, alicyclic, aryl, substituted aryl, heteroaryl, substituted heteroaryl, 1-alkenyl, and 1-alkynyl; or
together V and Z are connected via an additional 3–5 atoms to form a cyclic group containing 5–7 atoms, wherein 0–1 atoms are heteroatoms and the remaining atoms are carbon, substituted with hydroxy, acyloxy, alkoxycarbonyloxy, or aryloxycarbonyloxy attached to a carbon atom that is three atoms from both Y groups attached to the phosphorus; or
together V and Z are connected via an additional 3–5 atoms to form a cyclic group, wherein 0–1 atoms are heteroatoms and the remaining atoms are carbon, that is fused to an aryl group at the beta and gamma position to the Y attached to the phosphorus;
together V and W are connected via an additional 3 carbon atoms to form a substituted or unsubstituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;
together Z and W are connected via an additional 3–5 atoms to form a cyclic group, wherein 0–1 atoms are heteroatoms and the remaining atoms are carbon, and V must be aryl, substituted aryl, heteroaryl, or substituted heteroaryl;
together W and W' are connected via an additional 2–5 atoms to form a cyclic group, wherein 0–2 atoms are heteroatoms and the remaining atoms are carbon, and V must be aryl, substituted aryl, heteroaryl, or substituted heteroaryl;
Z is selected from the group consisting of —CHR[2]OH, —CHR[2]OC(O)R[3], —CHR[2]OC(S)R[3], —CHR[2]OC(S)OR[3], —CHR[2]OC(O)SR[3], —CHR[2]OCO$_2$R[3], —OR[2], —SR[2], —CHR[2]N$_3$, —CH$_2$aryl, —CH(aryl)OH, —CH(CH=CR[2]$_2$)OH, —CH(C≡CR[2])OH, —R[2], NR[2]$_2$, —OCOR[3], —OCO$_2$R[3], —SCOR[3], —SCO$_2$R[3], —NHCOR[2], —NHCO$_2$R[3], —CH$_2$NHaryl, —(CH$_2$)$_p$—OR[2], and —(CH$_2$)$_p$—SR[2];

p is an integer 2 or 3;

q is an integer 1 or 2;

with the provisos that:
   a) V, Z, W, W' are not all —H; and
   b) when Z is —$R^2$, then at least one of V, W, and W' is not —H, alkyl, aralkyl, or alicyclic;

$R^2$ is selected from the group consisting of $R^1$ and —H;

$R^3$ is selected from the group consisting of alkyl, aryl, alicyclic, and aralkyl;

each $R^4$ is independently selected from the group consisting of —H, and alkyl, or together $R^4$ and $R^4$ form a cyclic alkyl group;

$R^6$ is selected from the group consisting of —H, lower alkyl, acyloxyalkyl, alkoxycarbonyloxyalkyl, and lower acyl;

each $R^9$ is independently selected from the group consisting of —H, alkyl, aralkyl, and alicyclic, or together $R^9$ and $R^9$ form a cyclic alkyl, group;

$R^{11}$ is selected from the group consisting of alkyl, aryl, —$NR^2_2$, and —$OR^2$; and with the provisos that:
   1) when G' is N, then the respective A, B, D, or E is nothing;
   2) at least one of A and B, or A, B, D, and E is not selected from the group consisting of —H or nothing;
   3) when $R^5$ is a six-membered ring, then X is not any 2 atom linker, a substituted or unsubstituted -alkyl-, a substituted or unsubstituted -alkenyl-, a substituted or unsubstituted -alkyloxy-, or a substituted or unsubstituted -alkylthio-;
   4) when G is N, then the respective A or B is not halogen or a group directly bonded to G via a heteroatom;
   5) $R^1$ is not unsubstituted C1–C10 alkyl;
   6) when X is not an -aryl- group, then $R^5$is not substituted with two or more aryl groups;

or pharmaceutically acceptable prodrugs or salts thereof.

71. The method of claim 70 wherein $R^5$ is selected from the group consisting of pyrrolyl, imidazolyl, oxazolyl, thiazolyl, isothiazolyl, 1,2,4-thiadiazolyl, pyrazolyl, isoxazolyl, 1,2,3-oxadiazolyl, 1,2,4-oxadiazolyl, 1,2,5-oxadiazolyl, 1,3,4-oxadiazolyl, 1,2,4-thiadiazolyl, 1,3,4-thiadiazolyl, 1,2,3-triazolyl, 1,2,4-triazolyl, 1,2,3,4-tetrazolyl, pyridinyl, pyrimidinyl, pyrazinyl, pyridazinyl, 1,3,5-triazinyl, 1,2,4-triazinyl, and 1,3-selenazolyl, all of which contain at least one substituent.

72. The method of claim 70 wherein $R^5$ is selected from the group consisting of:

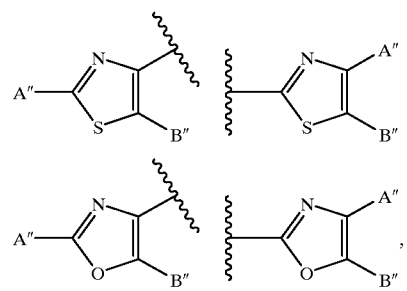

-continued

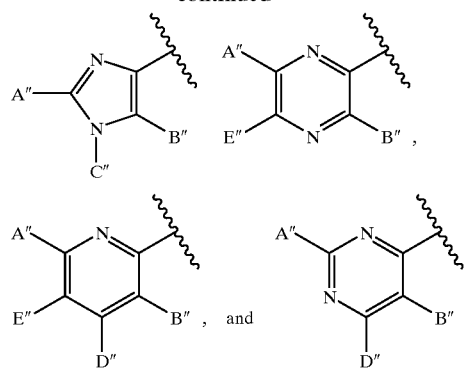

wherein

A" is selected from the group consisting of —H, —$NR^4_2$, —$CONR^4_2$, —$CO_2R^3$, halo, C1–C6 alkyl, C2–C6 alkenyl, C2–C6 alkynyl, C1–C6 perhaloalkyl, C1–C6 haloalkyl, aryl, —$CH_2OH$, —$CH_2NR^4_2$, —$CH_2CN$, —CN, —$C(S)NH_2$, —$R^3$, —$SR^3$, —$N_3$, —NHC(S)$NR^4_2$, and —NHAc;

B" and D" are independently selected from the group consisting of —H, alkyl, alkenyl, alkynyl, aryl, alicyclic, aralkyl, alkoxyalkyl, —$C(O)R^{11}$, —$C(O)SR^3$, —$SO_2R^{11}$, —$S(O)R^3$, —CN, —$NR^9_2$, —$OR^3$, —$SR^3$, perhaloalkyl, and halo, all except —H, —CN, perhaloalkyl, and halo are substituted or unsubstituted;

E" is selected from the group consisting of —H, C1–C6 alkyl, C2–C6 alkenyl, C2–C6 alkynyl, aryl, C4–C6 alicyclic, alkoxyalkyl, —C(O)OR, —$CONR^4_2$, —CN, —$NR^9_2$, —$OR^3$, —$SR^3$, C1–C6 perhaloalkyl, and halo, all except —H, —CN, perhaloalkyl, and halo are substituted or unsubstituted; and C" is selected from the group consisting of —H, alkyl, alkylalkenyl, alkylalkynyl, aryl, alicyclic, aralkyl, aryloxyalkyl, and alkoxyalkyl, all substituted or unsubstituted;

$R^4$ is selected from the group consisting of —H and C1–C2 alkyl; and $R^{11}$ is selected from the group consisting of alkyl, aryl, —$NR^2_2$, and —$OR^2$.

73. The method of claim 70 wherein $R^5$ is selected from the group consisting of:

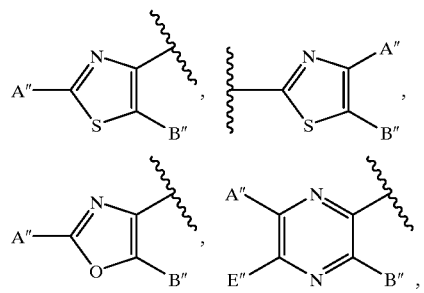

-continued

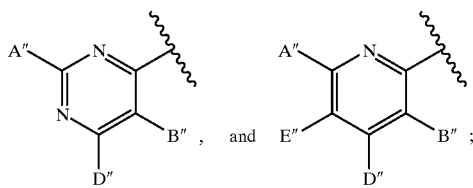

wherein
A" is selected from the group consisting of —H, —NR$^4_2$, —CONR$^4_2$, —CO$_2$R$^3$, halo, C1–C6 alkyl, C2–C6 alkenyl, C2–C6 alkynyl, C1–C6 perhaloalkyl, C1–C6 haloalkyl, aryl, —CH$_2$OH, —CH$_2$NR$^4_2$, —CH$_2$CN, —CN, —C(S)NH$_2$, —OR$^3$, —SR$^3$, —N$_3$, —NHC(S)NR$^4_2$, and —NHAc;

B" and D" are independently selected from the group consisting of —H, alkyl, alkenyl, alkynyl, aryl, alicyclic, aralkyl, alkoxyalkyl, —C(O)R$^{11}$, —C(O)SR$^3$, —SO$_2$R$^{11}$, —S(O)R$^3$, —CN, —NR$^9_2$, —OR$^3$, —SR$^3$, perhaloalkyl, and halo, all except —H, —CN, perhaloalkyl, and halo are substituted or unsubstituted;

E" is selected from the group consisting of —H, C1–C6 alkyl, C2–C6 alkenyl, C2–C6 alkynyl, C4–C6 alicyclic, alkoxyalkyl, —C(O)OR$^3$, —CONR$^4_2$, —CN, —NR$^9_2$, —R$^3$, —SR$^3$, C1–C6 perhaloalkyl, and halo, all except H, —CN, perhaloalkyl, and halo are substituted or unsubstituted; and each R$^4$ is independently selected from the group consisting of —H and C1–C2 alkyl.

74. The method of claim 73 wherein X is selected from the group consisting of -alkyl(hydroxy)-, -alkyl-, -alkynyl-, -aryl-, -carbonylalkyl-, -1,1-dihaloalkyl-, —alkoxyalkyl-, -alkyloxy-, -alkylthioalkyl-, -alkylthio-, -alkylaminocarbonyl-, —alkylcarbonylamino-, -alicyclic-, -aralkyl-, -alkylaryl-, -alkoxycarbonyl-, -carbonyloxyalkyl-, —alkoxycarbonylamino-, -alkylaminocarbonylamino-, -alkylamino-, and -alkenyl-, all substituted or unsubstituted.

75. The method of claim 74 wherein X is selected from the group consisting of -heteroaryl-, -alkylcarbonylamino-, -alkylaminocarbonyl-, -alkoxycarbonyl-, and -alkoxyalkyl-.

76. The method of claim 75 wherein R$^5$ is

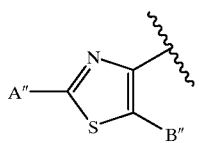

X is selected from the group consisting of methylenoxycarbonyl and furan-2,5-diyl; at least one Y group is —O—; or pharmaceutically acceptable salts or prodrugs thereof.

77. The method of claim 75 wherein R$^5$ is

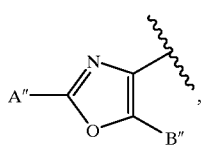

X is selected from the group consisting of furan-2,5-diyl and methyleneoxycarbonyl, and A" is —NH$_2$; at least one Y group is —O—; or pharmaceutically acceptable salts or prodrugs thereof.

78. The method of claim 75 wherein R$^5$ is

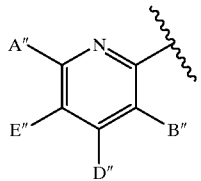

A" is —NH$_2$, E" and D" are —H, B" is selected from the group consisting of n-propyl and cyclopropyl, X is selected from the group consisting of furan-2,5-diyl and methyleneoxycarbonyl; at least one Y group is —O—; or pharmaceutically acceptable salts or prodrugs thereof.

79. The method of claim 75 wherein R$^5$ is

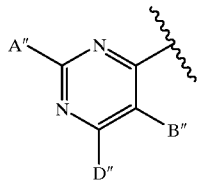

A" is —NH$_2$, D" is —H, B" is selected from the group consisting of n-propyl and cyclopropyl, X is selected from the group consisting of furan-2,5-diyl and methyleneoxycarbonyl; at least one Y group is —O—; or pharmaceutically acceptable salts or prodrugs thereof.

80. A method of treating diabetes, by administering to a patient in need thereof a pharmaceutically effective amount of an FBPase inhibitor of Formula I:

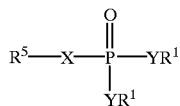

wherein R$^5$ is selected from the group consisting of:

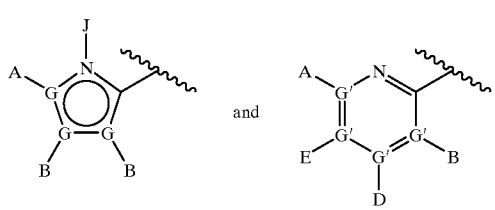

wherein:
each G is independently selected from the group consisting of C, N, O, S and Se, and wherein no more than one G is O, S, or Se;

each G' is independently selected from the group consisting of C and N and wherein no more than two G' groups are N;

A is selected from the group consisting of —H, —NR$^4_2$, —CONR$^4_2$, —CO$_2$R$^3$, halo, —S(O)R$^3$, —SO$_2$R$^3$, alkyl, alkenyl, alkynyl, perhaloalkyl, haloalkyl, aryl, —CH$_2$OH, —CH$_2$NR$^4_2$, —CH$_2$CN, —CN, —C(S)NH$_2$, —OR$^3$, —SR$^3$, —N$_3$, —NHC(S)NR$^4_2$, —NHAc, and nothing;

each B and D are independently selected from the group consisting of —H, alky, alkenyl, alkynyl, aryl, alicyclic, aralkyl, alkoxyalkyl, —C(O)R$^{11}$, —C(O)SR$^3$, —SO$_2$R$^{11}$, —S(O)R$^3$, —CN, —NR$^9{}_2$, —OR$^3$, —SR$^3$, perhaloalkyl, halo, —NO$_2$, and nothing, all except —H, —CN, perhaloalkyl, —NO$_2$, and halo are substituted or unsubstituted;

E is selected from the group consisting of —H, alkyl, alkenyl, alkynyl, aryl, alicyclic, alkoxyalkyl, —C(O)OR$^3$, —CONR$^4{}_2$, —CN, —NR$^9{}_2$, —NO$_2$, —OR$^3$, —SR$^3$, perhaloalkyl, halo, and nothing, all except —H, —CN, perhaloalkyl, and halo are substituted or unsubstituted;

J is selected from the group consisting of —H and nothing;

X is a substituted or unsubstituted linking group that links R$^5$ to the phosphorus atom via 2–4 atoms, wherein 0–1 atoms are heteroatoms selected from N, O, and S and the remaining atoms are carbon, except that if X is urea or carbamate there are 2 heteroatoms, measured by the shortest path between R$^5$ and the phosphorus atom, and wherein the atom attached to the phosphorus is a carbon atom, and wherein there is no N in the linking group unless it is connected directly to a carbonyl or in the ring of a heterocycle; and wherein X is not a 2 carbon atom -alkyl- or -alkenyl- group; with the proviso that X is not substituted with —COOR$^2$, —SO$_3$R$^1$, or —PO$_3$R$^1{}_2$;

Y is independently selected from the group consisting of —O—, and —NR$^6$—;

when Y is —O—, then R$^1$ attached to —O— is independently selected from the group consisting of —H, alkyl, substituted or unsubstituted aryl, substituted or unsubstituted alicyclic where the cyclic moiety contains a carbonate or thiocarbonate, substituted or unsubstituted-alkylaryl, —C(R$^2$)$_2$OC(O)NR$^2{}_2$, —NR$^2$—C(O)—R$^3$, —C(R$^2$)$_2$—C(O)R$^3$, —C(R$^2$)$_2$—O—C(O)OR$^3$, —C(R$^2$)$_2$OC(O)SR$^3$, -alkyl-S—C(O)R$^3$, -alkyl-S—S-alkylhydroxy, and -alkyl-S—S—S-alkylhydroxy, when Y is —NR$^6$—, then R$^1$ attached to —NR$^6$ is independently selected from the group consisting of —H, —[C(R$^2$)$_2$]$_q$, —COOR$^3$, —C(R$^4$)$_2$COOR$^3$, —[C(R$^2$)$_2$]$_q$—C(O)SR$^3$, and -cycloalkylene-COOR$^3$;

or when either Y is independently selected from —O— and —NR$^6$, then together R$^1$ and R$^1$ are -alkyl-S—S-alkyl- to form a cyclic group, or together R$^1$ and R$^1$ are

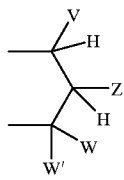

wherein

V, W, and W' are independently selected from the group consisting of —H, alkyl, aralkyl, alicyclic, aryl, substituted aryl, heteroaryl, substituted heteroaryl, 1-alkenyl, and 1-alkynyl; or together V and Z are connected via an additional 3–5 atoms to form a cyclic group containing 5–7 atoms, wherein 0–1 atoms are heteroatoms and the remaining atoms are carbon, substituted with hydroxy, acyloxy, alkoxycarbonyloxy, or aryloxycarbonyloxy attached to a carbon atom that is three atoms from both Y groups attached to the phosphorus; or together V and Z are connected via an additional 3–5 atoms to form a cyclic group, wherein 0–1 atoms are heteroatoms and the remaining atoms are carbon, that is fused to an aryl group at the beta and gamma position to the Y attached to the phosphorus;

together V and W are connected via an additional 3 carbon atoms to form a substituted or unsubstituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, wherein 0–1 atoms are heteroatoms and the remaining atoms are carbon, and V must be aryl, substituted aryl, heteroaryl, or substituted heteroaryl;

together W and W' are connected via an additional 2–5 atoms to form a cyclic group, wherein 0–2 atoms are heteroatoms and the remaining atoms are carbon, and V must be aryl, substituted aryl, heteroaryl, or substituted heteroaryl;

Z is selected from the group consisting of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=CR$^2{}_2$)OH, —CH(C≡CR$^2$)OH, —R$^2$, —NR$^2{}_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^2$, and —(CH$_2$)$_p$—SR$^2$;

p is an integer 2 or 3;

q is an integer 1 or 2;

with the provisos that:

a) V, Z, W, W' are not all —H; and b) when Z is —R$^2$, then at least one of V, W, and W' is not —H, alkyl aralkyl, or alicyclic;

R$^2$ is selected from the group consisting of R$^3$ and —H;

R$^3$ is selected from the group consisting of alky, aryl, alicyclic, and aralkyl;

each R$^4$ is independently selected from the group consisting of —H, and alkyl, or together R$^4$ and R$^4$ form a cyclic alkyl group;

R$^6$ is selected from the group consisting of —H, lower alkyl, acyloxyalkyl, alkoxycarbonyloxyalkyl, and lower acyl;

each R$^9$ is independently selected from the group consisting of —H, alkyl, aralkyl, and alicyclic, or together R$^9$ and R$^9$ form a cyclic alkyl group;

R$^{11}$ is selected from the group consisting of alkyl, aryl, —NR$^2{}_2$, and —OR$^2$; and with the provisos that:

1) when G' is N, then the respective A, B, D, or E is nothing;

2) at least one of A and B, or A, B, D, and E is not selected from the group consisting of —H or nothing;

3) when R$^5$ is a six-membered ring, then X is not any 2 atom linker, a substituted or unsubstituted -alkyl-, a substituted or unsubstituted -alkenyl-, a substituted or unsubstituted -alkyloxy-, or a substituted or unsubstituted -alkylthio-;

4) when G is N, then the respective A or B is not halogen or a group directly bonded to G via a heteroatom;

5) R¹ is not unsubstituted C1–C10 alkyl;
6) when X is not an -aryl- group, then R⁵ is not substituted with two or more aryl groups;

or pharmaceutically acceptable prodrugs or salts thereof.

81. The method of claim 80 wherein R⁵ is selected from the group consisting of pyrrolyl, imidazolyl, oxazolyl, thiazolyl, isothiazolyl, 1,2,4-thiadiazolyl, pyrazolyl, isoxazolyl, 1,2,3-oxadiazolyl, 1,2,4-oxadiazolyl, 1,2,5-oxadiazolyl, 1,3,4-oxadiazolyl, 1,2,4-thiadiazolyl, 1,3,4-thiadiazolyl, 1,2,3-triazolyl, 1,2,4-triazolyl, 1,2,3,4-tetrazolyl, pyridinyl, pyrimidinyl, pyrazinyl, pyridazinyl, 1,3,5-triazinyl, 1,2,4-triazinyl, and 1,3-selenazolyl, all of which contain at least one substituent.

82. The method of claim 80 wherein R⁵ is selected from the group consisting of:

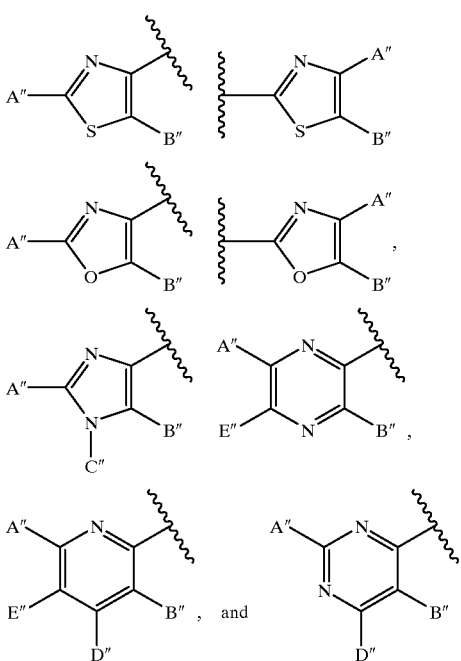

wherein
A" is selected from the group consisting of —H, —NR⁴₂, —CONR⁴₂, —CO₂R³, halo, C1–C6 alkyl, C2–C6 alkenyl, C2–C6 alkynyl, C1–C6 perhaloalkyl, C1–C6 haloalkyl, aryl, —CH₂OH, —CH₂NR⁴₂, —CH₂CN, —CN, —C(S)NH₂, —OR³, —SR³, —N₃, —NHC(S)NR⁴₂, and —NHAc;

B" and D" are independently selected from the group consisting of —H, alkyl, alkenyl, alkynyl, aryl, alicyclic, aralkyl, alkoxyalkyl, —C(O)R¹¹, —C(O)SR³, —SO₂R¹¹, —S(O)R³, —CN, —NR⁹₂, —OR³, —SR³, perhaloalkyl, and halo, all except —H, —CN, perhaloalkyl, and halo are substituted or unsubstituted;

E" is selected from the group consisting of —H, C1–C6 alkyl, C2–C6 alkenyl, C2–C6 alkynyl, aryl, C4–C6 alicyclic, alkoxyalkyl, —C(O)OR, —CONR⁴₂, —CN, —NR⁹₂, —OR³, —SR³, C1–C6 perhaloalkyl, and halo, all except —H, —CN, perhaloalkyl, and halo are substituted or unsubstituted;

C" is selected from the group consisting of —H, alkyl, alkylalkenyl, alkylalkynyl, aryl, alicyclic, aralkyl, aryloxyalkyl, and alkoxyalkyl, all substituted or unsubstituted;

R⁴ is selected from the group consisting of —H and C1–C2 alkyl; and

R¹¹ is selected from the group consisting of alkyl, aryl, —NR²₂, and —OR².

83. The method of claim 80 wherein R⁵ is selected from the group consisting of:

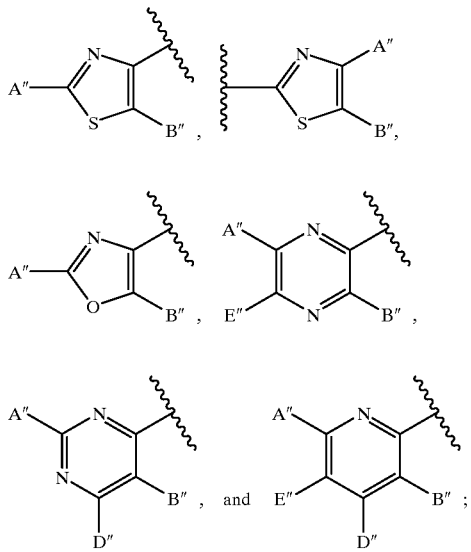

wherein

A" is selected from the group consisting of —H, —NR⁴₂, —CONR⁴₂, —CO₂R³, halo, C1–C6 alkyl, C2–C6 alkenyl, C2–C6 alkynyl, C1–C6 perhaloalkyl, C1–C6 haloalkyl, aryl, —CH₂OH, —CH₂NR⁴₂, —CH₂CN, —CN, —C(S)NH₂, —OR³, —SR³, —N₃, —NHC(S)NR⁴₂, and —NHAc;

B" and D" are independently selected from the group consisting of —H, alkyl, alkenyl, alkynyl, aryl, alicyclic, aralkyl, alkoxyalkyl, —C(O)R¹¹, —C(O)SR³—SO₂R¹¹, —S(O)R³, —CN, —NR⁹₂, —OR³, —SR³, perhaloalkyl, and halo, all except —H, —CN, perhaloalkyl, and halo are substituted or unsubstituted;

E" is selected from the group consisting of —H, C1–C6 alkyl, C2–C6 alkenyl, C2–C6 alkynyl, C4–C6 alicyclic, alkoxyalkyl, —C(O)OR³, —CONR⁴₂, —CN, —NR⁹₂, —R³, —SR³, C1–C6 perhaloalkyl, and halo, all except H, —CN, perhaloalkyl, and halo are substituted or unsubstituted; and each R⁴ is independently selected from the group consisting of —H and C1–C2 alkyl.

84. The method of claim 83 wherein X is selected from the group consisting of -alkyl(hydroxy)-, -alkyl-, -alkynyl-, -aryl-, -carbonylalkyl-, -1,1-dihaloalkyl-, —alkoxyalkyl-, -alkyloxy-, -alkylthioalkyl-, -alkylthio-, -alkylaminocarbonyl-, —alkylcarbonylamino-, -alicyclic-, -aralkyl-, -alkylaryl-, -alkoxycarbonyl-, -carbonyloxyalkyl-, —alkoxycarbonylamino-, -alkylaminocarbonylamino-, -alkylamino-, and -alkenyl-, all substituted or unsubstituted.

85. The method of claim 84 wherein X is selected from the group consisting of -heteroaryl-, -alkylcarbonylamino-, -alkylaminocarbonyl-, -alkoxycarbonyl-, and -alkoxyalkyl-.

86. The method of claim 85 wherein $R^5$ is

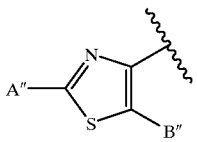

X is selected from the group consisting of methylenoxycarbonyl and furan-2,5-diyl; at least one Y group is —O—; or pharmaceutically acceptable salts or prodrugs thereof.

87. The method of claim 85 wherein $R^5$ is

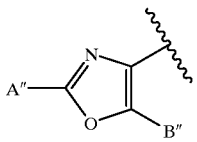

X is selected from the group consisting of furan-2,5-diyl and methyleneoxycarbonyl, and A″ is —NH₂; at least one Y group is —O—; or pharmaceutically acceptable salts or prodrugs thereof.

88. The method of claim 85 wherein $R^5$ is

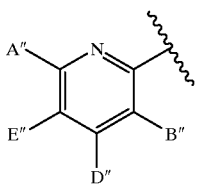

A″ is —NH₂, E″ and D″ are —H, B″ is selected from the group consisting of n-propyl and cyclopropyl, X is selected from the group consisting of furan-2,5-diyl and methyleneoxycarbonyl; at least one Y group is —O—; or pharmaceutically acceptable salts or prodrugs thereof.

89. The method of claim 85 wherein $R^5$ is

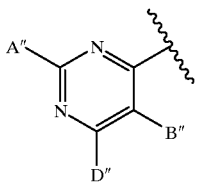

A″ is —NH₂, D″ is —H, B″ is selected from the group consisting of n-propyl and cyclopropyl, X is selected from the group consisting of furan-2,5-diyl and methyleneoxycarbonyl; at least one Y group is —O—; or pharmaceutically acceptable salts or prodrugs thereof.

90. The method of claim 85, where said patient has Type I diabetes.

91. The method of claim 85, where said patient has Type II diabetes.

92. A method of treating glycogen storage diseases, by administering to a patient in need thereof a pharmaceutically effective amount of an FBPase inhibitor of formula I:

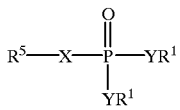

wherein $R^5$ is selected from the group consisting of:

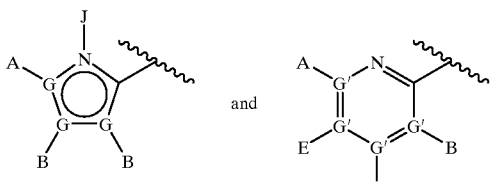

wherein:
each G is independently selected from the group consisting of C, N, O, S and Se, and wherein no more than one G is O, S, or Se;
each G' is independently selected from the group consisting of C and N and wherein no more than two G' groups are N;
A is selected from the group consisting of —H, —NR⁴₂, —CONR⁴₂, —CO₂R³, halo, —S(O)R³, —SO₂R³, alkyl, alkenyl, alkynyl, perhaloalkyl, haloalkyl, aryl, —CH₂OH, —CH₂NR⁴₂, —CH₂CN, —CN, —C(S)NH₂, —OR³, —SR³, —N₃, —NHC(S)NR⁴₂, —NHAc, and nothing;
each B and D are independently selected from the group consisting of —H, alkyl, alkenyl, alkynyl, aryl, alicyclic, aralkyl, alkoxyalkyl, —C(O)R¹¹, —C(O)SR³, —SO₂R¹¹, —S(O)R³, —CN, —NR⁹₂, —OR³, —SR³, perhaloalkyl, halo, -NO₂, and nothing, all except —H, —CN, perhaloalkyl, —NO₂, and halo are substituted or unsubstituted;
E is selected from the group consisting of —H, alkyl, alkenyl, alkynyl, aryl, alicyclic, alkoxyalkyl, —C(O)OR³, —CONR⁴₂, —CN, —NR⁹₂, —NO₂, —OR³, —SR³, perhaloalkyl, halo, and nothing, all except —H, —CN, perhaloalkyl, and halo are substituted or unsubstituted;
J is selected from the group consisting of —H and nothing;
X is a substituted or unsubstituted linking group that links $R^5$ to the phosphorus atom via 2–4 atoms, wherein 0–1 atoms are heteroatoms selected from N, O, and S and the remaining atoms are carbon, except that if X is urea or carbamate there are 2 heteroatoms, measured by the shortest path between $R^5$ and the phosphorus atom, and wherein the atom attached to the phosphorus is a carbon atom, and wherein there is no N in the linking group unless it is connected directly to a carbonyl or in the ring of a heterocycle; and wherein X is not a 2 carbon atom -alkyl- or -alkenyl- group; with the proviso that X is not substituted with —COOR², —SO₃R¹, or —PO₃R¹₂;
Y is independently selected from the group consisting of —O—, and —NR⁶—;
when Y is —O—, then R¹ attached to —O— is independently selected from the group consisting of —H, alkyl, substituted or unsubstituted aryl, substituted or unsubstituted alicyclic where the cyclic moiety contains a carbonate or thiocarbonate, substituted or unsubstituted-alkylaryl, —C(R$^2$)$_2$OC(O)NR$^2$$_2$, —NR$^2$—C(O)—R$^3$, —C(R$^2$)$_2$—OC(O)R$^3$, —C(R$^2$)$_2$—O—C(O)OR$^3$, —C(R$^2$)$_2$OC(O)SR$^3$, -alkyl-S—C(O)R$^3$, -alkyl-S—S-alkylhydroxy, and -alkyl-S—S—S-alkylhydroxy, when Y is —NR$^6$—, then R$^1$ attached to —NR$^6$— is independently selected from the group consisting of —H, —[C(R$^2$)$_2$]$_q$—COOR$^3$, —C(R$^4$)$_2$COOR$^3$, —[C(R$^2$)$_2$]$_q$—C(O)SR$^3$, and -cycloalkylene-COOR$^3$;

or when either Y is independently selected from —O— and —NR$^6$—, then together R$^1$ and R$^1$ are -alkyl-S—S-alkyl- to form a cyclic group, or together R$^1$ and R$^1$ are

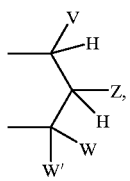

wherein

V, W, and W' are independently selected from the group consisting of —H, alkyl, aralkyl, alicyclic, aryl, substituted aryl, heteroaryl, substituted heteroaryl, 1-alkenyl, and 1-alkynyl; or together V and Z are connected via an additional 3–5 atoms to form a cyclic group containing 5–7 atoms, wherein 0–1 atoms are heteroatoms and the remaining atoms are carbon, substituted with hydroxy, acyloxy, alkoxycarbonyloxy, or aryloxycarbonyloxy attached to a carbon atom that is three atoms from both Y groups attached to the phosphorus; or together V and Z are connected via an additional 3–5 atoms to form a cyclic group, wherein 0–1 atoms are heteroatoms and the remaining atoms are carbon, that is fused to an aryl group at the beta and gamma position to the Y attached to the phosphorus;

together V and W are connected via an additional 3 carbon atoms to form a substituted or unsubstituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, wherein 0–1 atoms are heteroatoms and the remaining atoms are carbon, and V must be aryl, substituted aryl, heteroaryl, or substituted heteroaryl;

together W and W' are connected via an additional 2–5 atoms to form a cyclic group, wherein 0–2 atoms are heteroatoms and the remaining atoms are carbon, and V must be aryl, substituted aryl, heteroaryl, or substituted heteroaryl;

Z is selected from the group consisting of —CHR$^2$OH, —CHR$^2$OC(O)R$^3$, —CHR$^2$OC(S)R$^3$—CH$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=CR$^2$$_2$)OH, —CH(C≡CR$^2$)OH, —R$^2$, —NR$^2$$_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—R$^2$, and —(CH$_2$)$_p$—SR$^2$;

p is an integer 2 or 3;

q is an integer 1 or 2;

with the provisos that:
a) V, Z, W, W' are not all —H; and
b) when Z is —R$^2$, then at least one of V, W, and W' is not —H, alkyl aralkyl, or alicyclic;

R$^2$ is selected from the group consisting of R$^3$ and —H;

R$^3$ is selected from the group consisting of alkyl, aryl, alicyclic, and aralkyl;

each R$^4$ is independently selected from the group consisting of —H, and alkyl, or together R$^4$ and R$^4$ form a cyclic alkyl group;

R$^6$ is selected from the group consisting of —H, lower alkyl, acyloxyalkyl, alkoxycarbonyloxyalkyl, and lower acyl;

each R$^9$ is independently selected from the group consisting of —H, alkyl, aralkyl, and alicyclic, or together R$^9$ and R$^9$ form a cyclic alkyl group;

R$^{11}$ is selected from the group consisting of alkyl, aryl, —NR$^2$$_2$, and —OR$^2$; and with the provisos that:
1) when G' is N, then the respective A, B, D, or E is nothing;
2) at least one of A and B, or A, B, D, and E is not selected from the group consisting of —H or nothing;
3) when R$^5$ is a six-membered ring, then X is not any 2 atom linker, a substituted or unsubstituted -alkyl-, a substituted or unsubstituted-alkenyl-, a substituted or unsubstituted -alkyloxy-, or a substituted or unsubstituted -alkylthio-;
4) when G is N, then the respective A or B is not halogen or a group directly bonded to G via a heteroatom;
5) R$^1$ is not unsubstituted C1–C$_{10}$ alkyl;
6) when X is not an -aryl- group, then R$^5$ is not substituted with two or more aryl groups;

or pharmaceutically acceptable prodrugs or salts thereof.

93. The method of claim 92 wherein R$^5$ is selected from the group consisting of pyrrolyl, imidazolyl, oxazolyl, thiazolyl, isothiazolyl, 1,2,4-thiadiazolyl, pyrazolyl, isoxazolyl, 1,2,3-oxadiazolyl, 1,2,4-oxadiazolyl, 1,2,5-oxadiazolyl, 1,3,4-oxadiazolyl, 1,2,4-thiadiazolyl, 1,3,4-thiadiazolyl, 1,2,3-triazolyl, 1,2,4-triazolyl, 1,2,3,4-tetrazolyl, pyridinyl, pyrimidinyl, pyrazinyl, pyridazinyl, 1,3,5-triazinyl, 1,2,4-triazinyl, and 1,3-selenazolyl, all of which contain at least one substituent.

94. The method of claim 92 wherein R$^5$ is selected from the group consisting of:

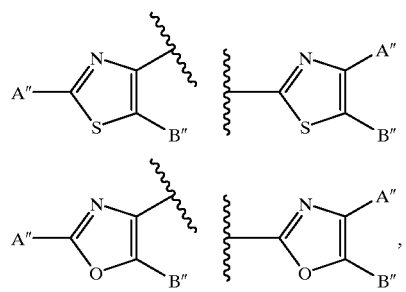

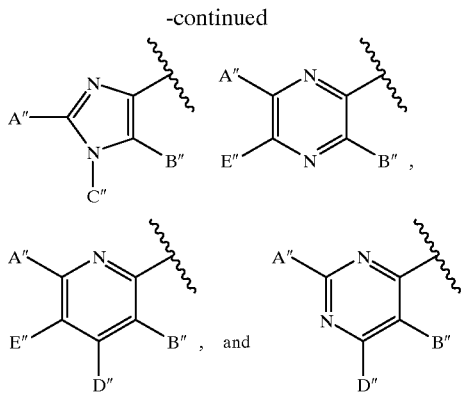

wherein

A" is selected from the group consisting of —H, —NR$^4_2$, —CONR$^4_2$, —CO$_2$R$^3$, halo, C1–C6 alkyl, C2–C6 alkenyl, C2–C6 alkynyl, C1–C6 perhaloalkyl, C1–C6 haloalkyl, aryl, —CH$_2$OH, —CH$_2$NR$^4_2$, —CH$_2$CN, —CN, —C(S)NH$_2$, —OR$^3$, —SR$^3$, —N$_3$, —NHC(S)NR$^4_2$, and —NHAc;

B" and D" are independently selected from the group consisting of —H, alkyl, alkenyl, alkynyl, aryl, alicyclic, aralkyl, alkoxyalkyl, —C(O)R$^{11}$—C(O)SR$^3$, —SO$_2$R$^{11}$—S(O)R$^3$, —CN, —NR$^9_2$, —OR$^3$, —SR$^3$, perhaloalkyl, and halo, all except —H, —CN, perhaloalkyl, and halo are substituted or unsubstituted;

E" is selected from the group consisting of —H, C1–C6 alkyl, C2–C6 alkenyl, C2–C6 alkynyl, aryl, C4–C6 alicyclic, alkoxyalkyl, —C(O)OR, —CONR$^4_2$, —CN, —NR$^9_2$, —OR$^3$, —SR$^3$, C1–C6 perhaloalkyl, and halo, all except —H, —CN, perhaloalkyl, and halo are substituted or unsubstituted; and C" is selected from the group consisting of —H, alkyl, alkylalkenyl, alkylalkynyl, aryl, alicyclic, aralkyl, aryloxyalkyl, and alkoxyalkyl, all substituted or unsubstituted;

R$^4$ is selected from the group consisting of —H and C1–C2 alkyl; and

R$^{11}$ is selected from the group consisting of alkyl, aryl, —NR$^2_2$, and —OR$^2$.

95. The method of claim 92 wherein R$^5$ is selected from the group consisting of:

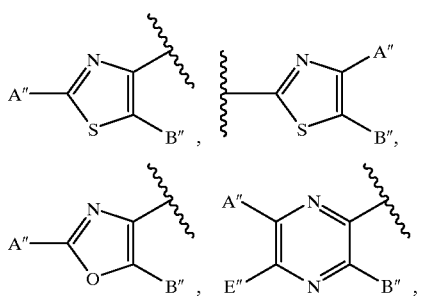

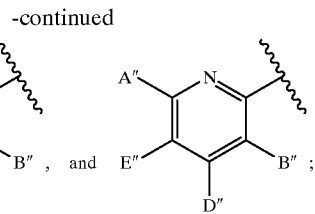

wherein

A" is selected from the group consisting of —H, —NR$^4_2$, —CONR$^4_2$, —CO$_2$R$^3$, halo, C1–C6 alkyl, C2–C6 alkenyl, C2–C6 alkynyl, C1–C6 perhaloalkyl, C1–C6 haloalkyl, aryl, —CH$_2$OH, —CH$_2$NR$^4_2$, —CH$_2$CN, —CN, —C(S)NH$_2$, —OR$^3$, —SR$^3$, —N$_3$, —NHC(S)NR$^4_2$, and —NHAc;

B" and D" are independently selected from the group consisting of —H, alkyl, alkenyl, alkynyl, aryl, alicyclic, aralkyl, alkoxyalkyl, —C(O)R$^{11}$, —C(O)SR$^3$, —SO$_2$R$^{11}$, —S(O)R$^3$, —CN, —NR$^9_2$, —OR$^3$, —SR$^3$, perhaloalkyl, and halo, all except —H, —CN, perhaloalkyl, and halo are substituted or unsubstituted;

E" is selected from the group consisting of —H, C1–C6 alkyl, C2–C6 alkenyl, C2–C6 alkynyl, C4–C6 alicyclic, alkoxyalkyl, —C(O)OR$^3$, —CONR$^4_2$, —CN, —NR$^9_2$, —OR$^3$, —SR$^3$, C1–C6 perhaloalkyl, and halo, all except H, —CN, perhaloalkyl, and halo are substituted or unsubstituted; and each R$^4$ is independently selected from the group consisting of —H and C1–C2 alkyl.

96. The method of claim 95 wherein X is selected from the group consisting of -alkyl(hydroxy)-, -alkyl-, -alkynyl-, -aryl-, -carbonylalkyl-, -1,1-dihaloalkyl-, —alkoxyalkyl-, -alkyloxy-, -alkylthioalkyl-, -alkylthio-, -alkylaminocarbonyl-, —alkylaminocarbonyl-, -alicyclic-, -aralkyl-, -alkylaryl-, -alkoxycarbonyl-, -carbonyloxyalkyl-, —alkoxycarbonylamino-, -alkylaminocarbonylamino-, -alkylamino-, and -alkenyl-, all substituted or unsubstituted.

97. The method of claim 96 wherein X is selected from the group consisting of -heteroaryl-, -alkylcarbonylamino-, -alkylaminocarbonyl-, -alkoxycarbonyl-, and -alkoxyalkyl-.

98. The method of claim 97 wherein R$^5$ is

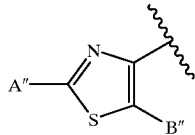

X is selected from the group consisting of methylenoxycarbonyl and furan-2,5-diyl; at least one Y group is —O—; or pharmaceutically acceptable salts or prodrugs thereof.

99. The method of claim 97 wherein R$^5$ is

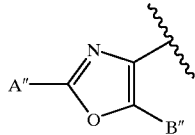

X is selected from the group consisting of furan-2,5-diyl and methyleneoxycarbonyl, and A" is —NH$_2$; at least one Y group is —O—; or pharmaceutically acceptable salts or prodrugs thereof.

100. The method of claim 97 wherein $R^5$ is

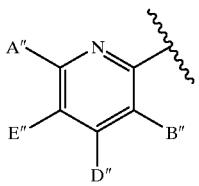

A" is —$NH_2$, E" and D" are —H, B" is selected from the group consisting of n-propyl and cyclopropyl, X is selected from the group consisting of furan-2,5-diyl and methyleneoxycarbonyl; at least one Y group is —O—; or pharmaceutically acceptable salts or prodrugs thereof.

101. The method of claim 97 wherein $R^5$ is

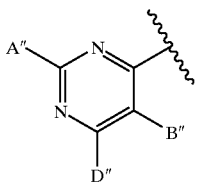

A" is —$NH_2$, D" is —H, B" is selected from the group consisting of n-propyl and cyclopropyl, X is selected from the group consisting of furan-2,5-diyl and methyleneoxycarbonyl; at least one Y group is —O—; or pharmaceutically acceptable salts or prodrugs thereof.

102. The method of claim 70 wherein said disease or condition is selected from the group consisting of atherosclerosis, hyperinsulinemia, hypercholesterolemia, and hyperlipidemia.

103. The method of claim 70 wherein said FBPase inhibitor is administered to prevent myocardial ischemic injury.

104. The compound of formula (X):

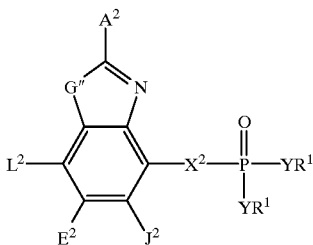

(X)

wherein:
G" is selected from the group consisting of —O— and —S—;

$A^2$, $L^2$, $E^2$, and $J^2$ are selected from the group consisting of —$NR^4_2$, —$NO_2$, —H, —$OR^2$, —$SR^2$, —C(O)$NR^4_2$, halo, —$COR^{11}$, —$SO_2R^3$, guanidinyl, amidinyl, aryl, aralkyl, alkoxyalkyl, —SCN, —$NHSO_2R^9$, —$SO_2NR^4_2$, —CN, —S(O)$R^3$, perhaloacyl, perhaloalkyl, perhaloalkoxy, C1–C5 alkyl, C2–C5 alkenyl, C2–C5 alkynyl, and lower alicyclic, or together $L^2$ and $E^2$ or $E^2$ and $J^2$ form an annulated cyclic group;

$X^2$ is a substituted or unsubstituted linking group that links $R^5$ to the phosphorus atom via 1–3 atoms, wherein 0–1 atoms are heteroatoms selected from N, O, and S and the remaining atoms are carbon, and wherein in the atom attached to the phosphorus is a carbon atom;

with the proviso that $X^2$ is not substituted with —$COOR^2$, —$SO_3R^1$, or —$PO_3R^1_2$;

Y is independently selected from the group consisting of—O—, and —$NR^6$—;

when Y is —O—, then $R^1$ attached to —O— is independently selected from the group consisting of —H, alkyl, substituted or unsubstituted aryl, substituted or unsubstituted alicyclic where the cyclic moiety contains a carbonate or thiocarbonate, substituted or unsubstituted-alkylaryl, —C($R^2$)$_2$OC(O)$NR^2_2$, —$NR^2$—C(O)—$R^3$, —C($R^2$)$_2$—C(O)$R^3$, —C($R^2$)$_2$—O—C(O)$OR^3$, —C($R^2$)$_2$OC(O)$SR^3$, -alkyl-S—C(O)R, -alkyl-S—S-alkylhydroxy, and -alkyl-S—S—S-alkylhydroxy, when Y is —$NR^6$—, then $R^1$ attached to —$NR^6$— is independently selected from the group consisting of —H, —[C($R^2$)$_2$]$_q$—$COOR^3$, —C($R^4$)$_2COOR^3$, —[C($R^2$)$_2$]$_q$—C(O)$SR^3$, and -cycloalkylene-$COOR^3$;

or when either Y is independently selected from —O— and $NR^6$—, then together $R^1$ and $R^1$ are -alkyl-S—S-alkyl- to form a cyclic group, or together $R^1$ and $R^1$ are

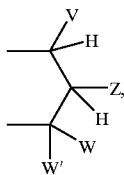

wherein
V, W, and W' are independently selected from the group consisting of —H, alkyl, aralkyl, alicyclic, aryl, substituted aryl, heteroaryl, substituted heteroaryl, 1-alkenyl, and 1-alkynyl; or together V and Z are connected via an additional 3–5 atoms to form a cyclic group containing 5–7 atoms, wherein 0–1 atoms are heteroatoms and the remaining atoms are carbon, substituted with hydroxy, acyloxy, alkoxycarbonyloxy, or aryloxycarbonyloxy attached to a carbon atom that is three atoms from both Y groups attached to the phosphorus; or together V and Z are connected via an additional 3–5 atoms to form a cyclic group, wherein 0–1 atoms are heteroatoms and the remaining atoms are carbon, that is fused to an aryl group at the beta and gamma position to the Y attached to the phosphorus;

together V and W are connected via an additional 3 carbon atoms to form a substituted or unsubstituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, wherein 0–1 atoms are heteroatoms and the remaining atoms are carbon, and V must be aryl, substituted aryl, heteroaryl, or substituted heteroaryl;

together W and W' are connected via an additional 2–5 atoms to form a cyclic group, wherein 0–2 atoms are heteroatoms and the remaining atoms are carbon, and V must be aryl, substituted aryl, heteroaryl, or substituted heteroaryl;

Z is selected from the group consisting of —CHR²OH, —CHR²OC(O)R³, —CHR²OC(S)R³, —CHR²OC(S)OR³, —CHR²OC(O)SR³—CHR²OCO₂R³—OR², —SR², —CHR²N₃, —CH₂aryl, —CH(aryl)OH, —CH(CH=CR²₂)OH, —CH(C≡CR²)OH, —R², —NR²₂—OCOR³, —OCO₂R³, —SCOR³, —SCO₂R³, —NHCOR², —NHCO₂R³, —CH₂NHaryl, —(CH₂)ₚ—OR², and —(CH₂)ₚ—SR²;

p is an integer 2 or 3;
q is an integer 1 or 2;
with the provisos that:
  a) V, Z, W, W' are not all —H; and
  b) when Z is —R², then at least one of V, W, and W' is not —H, alkyl aralkyl, or alicyclic;

R² is selected from the group consisting of R³ and —H;
R³ is selected from the group consisting of alkyl, aryl, alicyclic, and aralkyl;
each R⁴ is independently selected from the group consisting of —H, alkyl, or together R⁴ and R⁴ form a cyclic alkyl;
R⁶ is selected from the group consisting of —H, lower alkyl, acyloxyalkyl, alkoxycarbonyloxyalkyl, and lower acyl;
each R⁹ is independently selected from the group consisting of —H, alkyl, aralkyl, and alicyclic, or together R⁹ and R⁹ form a cyclic alkyl group;
R¹¹ is selected from the group consisting of alkyl, aryl, —NR²₂, and —OR²; or pharmaceutically acceptable prodrugs or salts thereof.

105. The compound of claim 104 wherein G" is —S—.

106. The compound of claim 104 wherein A², L², E², and J² are independently selected from the group consisting of —H, —NR⁴₂, —S—C≡N, halogen, —OR³, hydroxy, -alkyl(OH), aryl, alkyloxycarbonyl, —SR³, lower perhaloalkyl, and C1–C5 alkyl, or together L² and E² form an annulated cyclic group.

107. The compound of claim 106 wherein A², L², E² and J² are independently selected from the group consisting of —H, —NR⁴₂, —S—C≡N, halogen, lower alkoxy, hydroxy, lower alkyl(hydroxy), lower aryl, and C1–C5 alkyl, or together L² and E² form an annulated cyclic group.

108. The compound of claim 107 wherein A² is selected from the group consisting of —NH₂, —H, halo, and C1–C5 alkyl.

109. The compound of claim 107 wherein L² and E² are independently selected from the group consisting of —H, —S—C≡N, lower alkoxy, C1–C5 alkyl, lower alkyl (hydroxy), lower aryl, and halogen or together L² and E² form an annulated cyclic group containing an additional 4 carbon atoms.

110. The compound of claim 109 wherein J² is selected from the group consisting of —H, and C1–C5 alkyl.

111. The compound of claim 104 wherein X² is selected from the group consisting of -alkyl-, -alkenyl-, -alkynyl-, -alkylene-NR⁴—, -alkylene-O—, alkylene-S—, —C(O)-alkylene-, and -alkylene-C(O)—.

112. The compound of claim 111 wherein X² is selected from the group consisting of -alkylene-O—, alkylene-S—, and -alkyl-.

113. The compound of claim 112 wherein X² is -methyleneoxy-.

114. The compound of claim 104 where both Y groups are —O—.

115. The compound of claim 104, where one Y is —NR⁶—, and one Y is —O—.

116. The compound of claim 104 wherein when Y is —O—, then R¹ attached to —O— is independently selected from the group consisting of —H, substituted or unsubstituted aryl, substituted or unsubstituted alicyclic where the cyclic moiety contains a carbonate or thiocarbonate, substituted or unsubstituted -alkylaryl, —C(R²)₂OC(O)R³, —C(R²)₂, —O—C(O)OR³, —C(R²)₂OC(O)SR³, -alkyl-S—C(O)R³, and -alkyl-S—S-alkylhydroxy;

when Y is —NR⁶—, then R² attached to —NR⁶— is independently selected from the group consisting of —H, —[C(R²)₂]ᵩ—COOR³, —[C(R²)₂]ᵩ—C(O)SR³, —C(R⁴)₂COOR³, and -cycloalkylene-COOR³;

or when either Y is independently selected from —O— and —NR⁶—, then together R¹ and R¹ are

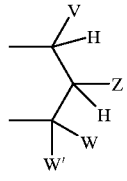

wherein
V, W, and W' are independently selected from the group consisting of —H, alkyl, aralkyl, alicyclic, aryl, substituted aryl, heteroaryl, substituted heteroaryl, 1-alkenyl, and 1-alkynyl, or
together V and W are connected via an additional 3 carbon atoms to form a substituted or unsubstituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;
together Z and W are connected via an additional 3–5 atoms to form a cyclic group, wherein 0–1 atoms are heteroatoms and the remaining atoms are carbon, and V must be aryl, substituted aryl, heteroaryl, or substituted heteroaryl;
together W and W' are connected via an additional 2–5 atoms to form a cyclic group, wherein 0–2 atoms are heteroatoms and the remaining atoms are carbon, and V must be aryl, substituted aryl, heteroaryl, or substituted heteroaryl;

Z is selected from the group consisting of —CHR²OH, —CHR²OC(O)R³, —CHR²OC(S)R³, —CHR²OC(S)OR³, —CHR²OC(O)SR³—CHR²OCO₂R³, —OR², —SR², —R², —NHCOR², —NHCO₂R³, —(CH₂)ₚ—OR², and —(CH₂)ₚ—SR²;

p is an integer 2 or 3;
q is an integer 1 or 2;
with the provisos that:
  a) V, Z, W, W' are not all —H;
  b) when Z is —R², then at least one of V, W, and W' is not —H, alkyl, aralkyl, or alicyclic; and
  c) both Y groups are not —NR⁶—;

R² is selected from the group consisting of R³ and —H;
R³ is selected from the group consisting of alkyl, aryl, alicyclic, and aralkyl;
R⁶ is selected from the group consisting of —H, and lower alkyl.

117. The compound of claim 116 wherein when both Y groups are —O—, then R¹ is independently selected from the group consisting of substituted or unsubstituted aryl, substituted or unsubstituted benzyl, —C(R²)₂OC(O)R³, —C(R²)₂OC(O)OR³, and —H; and when Y is —NR⁶—, then the R¹ attached to said —NR⁶— group is selected from the group consisting of —C(R⁴)₂—COOR³, —C(R²)₂COOR³, and —H; and the other Y group is —O— and the R¹ group attached to said —O— group is selected from the group consisting of substituted or unsubstituted aryl, —C(R²)₂OC(O)R³, and —C(R²)₂OC(O)OR³.

118. The compound of claim 116 wherein both Y groups are —O—, and R¹ is H.

119. The compound of claim 116 wherein both Y groups are —O—, and R¹ is aryl, or —C(R²)₂-aryl.

120. The compound of claim 116 wherein both Y groups are O—, and at least one R¹ is selected from the group consisting of —C(R²)₂—OC(O)R³, and —C(R²)₂—OC(O)OR³.

121. The compound of claim 116 wherein both Y groups are —O— and at least one R¹ is selected from the group consisting of -alkyl-S—S-alkylhydroxyl, -alkyl-S—C(O)R³, and -alkyl-S-S-S-alkylhydroxy, or together R¹ and R¹ are -alkyl-S-S-alkyl- to form a cyclic group.

122. The compound of claim 116 wherein at least one Y is —O—, and together R¹ and R¹ are

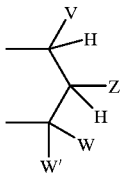

wherein

V, W, and W' are independently selected from the group consisting of —H, alkyl, aralkyl, alicyclic, aryl, substituted aryl, heteroaryl, substituted heteroaryl, 1-alkenyl, and 1-alkynyl, or together V and W are connected via an additional 3 carbon atoms to form a substituted or unsubstituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, wherein 0–1 atoms are heteroatoms and the remaining atoms are carbon, and V must be aryl, substituted aryl, heteroaryl, or substituted heteroaryl;

together W and W' are connected via an additional 2–5 atoms to form a cyclic group, wherein 0–2 atoms are heteroatoms and the remaining atoms are carbon, and V must be aryl, substituted aryl, heteroaryl, or substituted heteroaryl;

Z is selected from the group consisting of —CHR²OH, —CHR²OC(O)R³, CHR²OC(S)R³, —CHR²OC(S) OR³, —CHR²OC(O)SR³, —CHR²OCO₂R³, —OR², —SR², —R², —NHCOR², —NHCO₂R³, —(CH₂)ₚ—OR², and —(CH₂)ₚ—SR²;

p is an integer 2 or 3;

with the provisos that:
a) V, Z, W, W' are not all —H;
b) when Z is —R², then at least one of V, W, and W' is not —H, alkyl, aralkyl, or alicyclic; and
c) both Y groups are not —NR⁶—;

R² is selected from the group consisting of R³ and —H;

R³ is selected from the group consisting of alkyl, aryl, alicyclic, and aralkyl;

R⁶ is selected from the group consisting of —H, and lower alkyl.

123. The compound of claim 112 wherein R¹ is alicyclic where the cyclic moiety contains carbonate or thiocarbonate.

124. The compound of claim 117 wherein one Y is —O—, and R¹ is substituted or unsubstituted aryl; and the other Y is —NR⁶—, where R¹ attached to said —NR⁶— is selected from the group consisting of —C(R⁴)₂COOR³, and —C(R²)₂C(O)OR³.

125. The compound of claim 124 wherein R¹ attached to —O— is selected from the group consisting of phenyl, and phenyl substituted with 1–2 substituents selected from the group consisting of —NHC(O)CH₃, —Cl, —Br, —C(O)OCH₂CH₃, and —CH₃; and wherein R¹ attached to —NR⁶— is —C(R²)₂COOR³; each R² is independently selected from the group consisting of —CH₃, and —CH₂CH₃.

126. The compound of claim 125 wherein the substituents of said substituted phenyl are selected from the group consisting of 4—NHC(O)CH₃, —Cl, —Br, 2—C(O)OCH₂CH₃, and —CH₃.

127. The compound of claim 104 wherein A² is selected from the group consisting of —H, —NH₂, —CH₃, Cl, and Br;

L² is selected from the group consisting of —H, lower alkyl, halogen, lower alkyloxy, hydroxy, -alkenylene-OH, or together with E² forms a cyclic group selected from the group consisting of aryl, cyclic alkyl, heteroaryl, and heterocyclic alkyl;

E² is selected from the groups consisting of H, lower alkyl, halogen, SCN, lower alkyloxycarbonyl, lower alkyloxy, or together with L² forms a cyclic group selected from the group consisting of aryl, cyclic alkyl, heteroaryl, and heterocyclic alkyl;

J² is selected from the groups consisting of H, halogen, and lower alkyl;

G" is —S—;

X² is —CH₂O—; and at least one Y group is —O—; or pharmaceutically acceptable salts or prodrugs thereof.

128. The compound of claim 127 wherein one Y is —O— and its corresponding R¹ is substituted or unsubstituted phenyl, while the other Y is —NH—, and its corresponding R¹ is C(R²)₂—COOR³.

129. The compound of claim 128 wherein when the other Y is —NH—, then the corresponding R¹ is —CH²COOR³, and —NH—*CHR²COOR³ has L stereochemistry.

130. The compound of claim 127 where A² is NH₂, L² is -Et, E² is —SCN, and J² is —H.

131. The compound of claim 130 wherein both Y groups are —O—, then R¹ is —H.

132. The compound of claim 130 wherein both Y groups are —O—, and R¹ is —CH₂OC(O)OEt.

133. The compound of claim 130 wherein both Y groups are —O—, and R¹ and R¹ together are

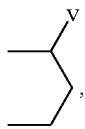, and V is phenyl substituted with 1–3 halogens.

134. The compound of claim 133 wherein V is selected from the group consisting of 3,5-dichlorophenyl, 3-bromo-4-fluorophenyl, 3-chlorophenyl, and 3-bromophenyl.

135. The compound of claim 130 wherein one Y is —O—, and its corresponding $R^1$ is -phenyl, while the other Y is —NH— and its corresponding $R^1$ is —CH(Me)CO$_2$Et, and —NH*CH(Me)CO$_2$Et, is in the L-configuration.

136. A method of treating a disease or condition responsive to inhibition of gluconeogenesis or responsive to lowered blood glucose levels in an animal which comprises administering to an animal suffering from a disease or condition responsive to inhibition of gluconeogenesis or responsive to lowered blood glucose levels a pharmaceutically effective amount of a FBPase inhibitor of formula (X):

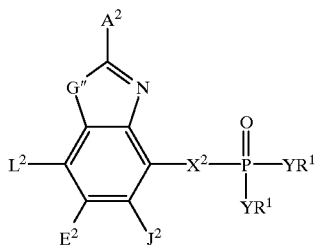

(X)

wherein:
G" is selected from the group consisting of —O— and —S—;
$A^2$, $L^2$, $E^2$, and $J^2$ are selected from the group consisting of —NR$^4_2$, —NO$_2$—H, —OR$^2$, —SR$^2$, —C(O)NR$^4_2$, halo, —COR$^{11}$, —SO$_2$R$^3$, guanidinyl, amidinyl, aryl, aralkyl, alkoxyalkyl, —SCN, —NHSO$_2$R$^9$, —SO$_2$NR$^4_2$, —CN, —S(O)R$^3$, perhaloacyl, perhaloalkyl, perhaloalkoxy, C1–C5 alkyl, C2–C5 alkenyl, C2–C5 alkynyl, and lower alicyclic, or together $L^2$ and $E^2$ or $E^2$ and $J^2$ form an annulated cyclic group;
$X^2$ is a substituted or unsubstituted linking group that links $R^5$ to the phosphorus atom via 1–3 atoms, wherein 0–1 atoms are heteroatoms selected from N, O, and S and the remaining atoms are carbon, and wherein in the atom attached to the phosphorus is a carbon atom;
with the proviso that $X^2$ is not substituted with —COOR$^2$, —SO$_3$R$^1$, or —PO$_3$R$^1_2$;
Y is independently selected from the group consisting of —O—, and —NR$^6$—;
when Y is —O—, then $R^1$ attached to —O— is independently selected from the group consisting of —H, alkyl, substituted or unsubstituted aryl, substituted or unsubstituted alicyclic where the cyclic moiety contains a carbonate or thiocarbonate, substituted or unsubstituted-alkylaryl, —C(R$^2$)$_2$OC(O)NR$^2_2$, —NR$^2$—C(O)—R$^3$, —C(R$^2$)$_2$—C(O)R$^3$, —C(R$^2$)$_2$—O—C(O)OR$^3$, —C(R$^2$)$_2$OC(O)SR$^3$, -alkyl-S—C(O)R$^3$, -alkyl-S—S-alkylhydroxy, and -alkyl-S—S-alkylhydroxy, when Y is —NR$^6$—, then $R^1$ attached to —NR$^6$— is independently selected from the group consisting of —H, —[C(R$^2$)$_2$]$_q$—COOR$^3$, —C(R$^4$)$_2$COOR$^3$, —[C(R$^2$)$_2$]$_q$—C(O)SR$^3$, and -cycloalkylene-COOR$^3$;
or when either Y is independently selected from —O— and NR$^6$, then together $R^1$ and $R^1$ are -alkyl-S—S-alkyl- to form a cyclic group, or together $R^1$ and $R^1$ are

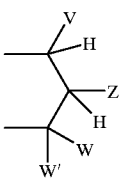

wherein
V, W, and W' are independently selected from the group consisting of —H, alkyl, aralkyl, alicyclic, aryl, substituted aryl, heteroaryl, substituted heteroaryl, 1-alkenyl, and 1-alkynyl; or
together V and Z are connected via an additional 3–5 atoms to form a cyclic group containing 5–7 atoms, wherein 0–1 atoms are heteroatoms and the remaining atoms are carbon, substituted with hydroxy, acyloxy, alkoxycarbonyloxy, or aryloxycarbonyloxy attached to a carbon atom that is three atoms from both Y groups attached to the phosphorus; or
together V and Z are connected via an additional 3–5 atoms to form a cyclic group, wherein 0–1 atoms are heteroatoms and the remaining atoms are carbon, that is fused to an aryl group at the beta and gamma position to the Y attached to the phosphorus;
together V and W are connected via an additional 3 carbon atoms to form a substituted or unsubstituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;
together Z and W are connected via an additional 3–5 atoms to form a cyclic group, wherein 0–1 atoms are heteroatoms and the remaining atoms are carbon, and V must be aryl, substituted aryl, heteroaryl, or substituted heteroaryl;
together W and W' are connected via an additional 2–5 atoms to form a cyclic group, wherein 0–2 atoms are heteroatoms and the remaining atoms are carbon, and V must be aryl, substituted aryl, heteroaryl, or substituted heteroaryl;
Z is selected from the group consisting of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=CR$^2_2$)OH, —CH(C≡CR$^2$)OH, —R$^2$, —NR$^2_2$, —COR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^2$, and —(CH$_2$)$_p$—SR$^2$;
p is an integer 2 or 3;
q is an integer 1 or 2;
with the provisos that:
a) V, Z, W, W' are not all —H; and
b) when Z is —R$^2$, then at least one of V, W, and W' is not —H, alkyl, aralkyl, or alicyclic;

249

$R^2$ is selected from the group consisting of $R^3$ and —H;
$R^3$ is selected from the group consisting of alkyl, aryl, alicyclic, and aralkyl;
each $R^4$ is independently selected from the group consisting of —H, alkyl, or together $R^4$ and $R^4$ form a cyclic alkyl;
$R^6$ is selected from the group consisting of —H, lower alkyl, acyloxyalkyl, alkoxycarbonyloxyalkyl, and lower acyl;
each $R^9$ is independently selected from the group consisting of —H, alkyl, aralkyl, and alicyclic, or together $R^9$ and $R^9$ form a cyclic alkyl group;
$R^{11}$ is selected from the group consisting of alkyl, aryl, —$NR^2_2$, and —$OR^2$; or pharmaceutically acceptable prodrugs or salts thereof.

137. A method of treating diabetes, by administering to a patient in need thereof a pharmaceutically effective amount of an FBPase inhibitor of formula (X):

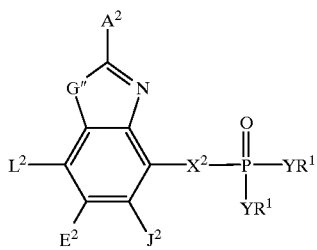

(X)

wherein:
G" is selected from the group consisting of —O— and —S—.
$A^2$, $L^2$, $E^2$, and $J^2$ are selected from the group consisting of—$NR^4_2$, —$NO_2$, —H, —$OR^2$, —$SR^2$, —$C(O)NR^4_2$, halo, —$COR^{11}$, —$SO_2R^3$, guanidinyl, amidinyl, aryl, aralkyl, alkoxyalkyl, —SCN, —$NHSO_2R^9$, —$SO_2NR^4_2$, —CN, —$S(O)R^3$, perhaloacyl, perhaloalkyl, perhaloalkoxy, C1–C5 alkyl, C2–C5 alkenyl, C2–C5 alkynyl, and lower alicyclic, or together L2 and E2 or $E^2$ and $J^2$ form an annulated cyclic group;
$X^2$ is a substituted or unsubstituted linking group that links $R^5$ to the phosphorus atom via 1–3 atoms, wherein 0–1 atoms are heteroatoms selected from N, O, and S and the remaining atoms are carbon, and wherein in the atom attached to the phosphorus is a carbon atom;
with the proviso that $X^2$ is not substituted with —$COOR^2$, —$SO_3R^1$, or —$PO_3R^1_2$;
Y is independently selected from the group consisting of —O—, and —$NR^6$—;
when Y is —O—, then $R^1$ attached to —O— is independently selected from the group consisting of —H, alkyl, substituted or unsubstituted aryl, substituted or unsubstituted alicyclic where the cyclic moiety contains a carbonate or thiocarbonate, substituted or unsubstituted-alkylaryl, —$C(R^2)_2OC(O)NR^2_2$, —$NR^2$—$C(O)$—$R^3$, —$C(R^2)_2$—$C(O)R^3$, —$C(R^2)_2$—O—$C(O)OR^3$, —$C(R^2)_2OC(O)SR^3$, -alkyl-S—C(O)$R^3$, -alkyl-S—S-alkylhydroxy, and -alkyl-S—S-S-alkylhydroxy,
when Y is —$NR^6$—, then $R^1$ attached to —$NR^6$— is independently selected from the group consisting of —H, —$[C(R^2)_2]_q$—$COOR^3$, —$C(R^4)_2COOR^3$, —$[C(R^2)_2]_q$—$C(O)SR^3$, and -cycloalkylene-$COOR^3$;

250 or when either Y is independently selected from —O— and —$NR^6$—, then together $R^1$ and $R^1$ are -alkyl-S—S-alkyl- to form a cyclic group, or together $R^1$ and $R^1$ are

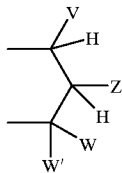

wherein
V, W, and W' are independently selected from the group consisting of —H, alkyl, aralkyl, alicyclic, aryl, substituted aryl, heteroaryl, substituted heteroaryl, 1-alkenyl, and 1-alkynyl; or
together V and Z are connected via an additional 3–5 atoms to form a cyclic group containing 5–7 atoms, wherein 0–1 atoms are heteroatoms and the remaining atoms are carbon, substituted with hydroxy, acyloxy, alkoxycarbonyloxy, or aryloxycarbonyloxy attached to a carbon atom that is three atoms from both Y groups attached to the phosphorus; or
together V and Z are connected via an additional 3–5 atoms to form a cyclic group, wherein 0–1 atoms are heteroatoms and the remaining atoms are carbon, that is fused to an aryl group at the beta and gamma position to the Y attached to the phosphorus;
together V and W are connected via an additional 3 carbon atoms to form a substituted or unsubstituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;
together Z and W are connected via an additional 3–5 atoms to form a cyclic group wherein 0–1 atoms are heteroatoms and the remaining atoms are carbon, and V must be aryl, substituted aryl, heteroaryl, or substituted heteroaryl;
together W and W' are connected via an additional 2–5 atoms to form a cyclic group, wherein 0–2 atoms are heteroatoms and the remaining atoms are carbon, and V must be aryl, substituted aryl, heteroaryl, or substituted heteroaryl;
Z is selected from the group consisting of —$CHR^2OH$, —$CHR^2OC(O)R^3$, —$CHR^2OC(S)R^3$, —$CHR^2OC(S)OR^3$, —$CHR^2OC(O)SR^3$, —$CHR^2OCO_2R^3$, —$OR^2$, —$SR^2$, —$CHR^2N_3$, —$CH_2aryl$, —$CH(aryl)OH$, —$CH(CH=CR^2_2)OH$, —$CH(C\equiv CR^2)OH$, —$R^2$, —$NR^2_2$, —$OCOR^3$, —$OCO_2R^3$, —$SCOR^3$, —$SCO_2R^3$, —$NHCOR^2$, —$NHCO_2R^3$—$CH_2NHaryl$, —$(CH_2)_p$—$OR^2$, and —$(CH_2)_p$—$SR^2$;
p is an integer 2 or 3;
q is an integer 1 or 2;
with the provisos that:
 a) V, Z, W, W' are not all —H; and
 b) when Z is —$R^2$, then at least one of V, W, and W' is not —H, alkyl, aralkyl, or alicyclic;
$R^2$ is selected from the group consisting of $R^3$ and —H;
$R^3$ is selected from the group consisting of alkyl, aryl, alicyclic, and aralkyl;

each $R^4$ is independently selected from the group consisting of —H, alkyl, or together $R^4$ and $R^4$ form a cyclic alkyl;

$R^6$ is selected from the group consisting of —H, lower alkyl, acyloxyalkyl, alkoxycarbonyloxyalkyl, and lower acyl;

each $R^9$ is independently selected from the group consisting of —H, alkyl, aralkyl, and alicyclic, or together $R^9$ and $R^9$ form a cyclic alkyl group;

$R^{11}$ is selected from the group consisting of alkyl, aryl, —$NR^2_2$, and —$OR^2$; or pharmaceutically acceptable prodrugs or salts thereof.

138. A method of treating glycogen storage diseases, by administering to a patient in need thereof a pharmaceutically effective amount of an FBPase inhibitor of formula (X):

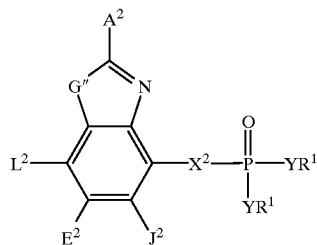

(X)

wherein:
G″ is selected from the group consisting of —O— and —S—;

$A^2$, $L^2$, $E^2$, and $J^2$ are selected from the group consisting of —$NR^4_2$, —$NO_2$, —H, —$OR^2$, —$SR^2$, —C(O)$NR^4_2$, halo, —$COR^{11}$, —$SO_2R^3$, guanidinyl, amidinyl, aryl, aralkyl, alkoxyalkyl, —SCN, —$NHSO_2R^9$, —$SO_2NR^4_2$, —CN, —S(O)$R^3$, perhaloacyl, perhaloalkyl, perhaloalkoxy, C1–C5 alkyl, C2–C5 alkenyl, C2–C5 alkynyl, and lower alicyclic, or together $L^2$ and $E^2$ or $E^2$ and $J^2$ form an annulated cyclic group;

$X^2$ is a substituted or unsubstituted linking group that links $R^5$ to the phosphorus atom via 1–3 atoms, wherein 0–1 atoms are heteroatoms selected from N, O, and S and the remaining atoms are carbon, and wherein in the atom attached to the phosphorus is a carbon atom;

with the proviso that $X^2$ is not substituted with —$COOR^2$, —$SO_3R^1$, or —$PO_3R^1_2$;

Y is independently selected from the group consisting of —O—, and —$NR^6$—;

when Y is —O—, then $R^1$ attached to —O— is independently selected from the group consisting of —H, alkyl, substituted or unsubstituted aryl, substituted or unsubstituted alicyclic where the cyclic moiety contains a carbonate or thiocarbonate, substituted or unsubstituted-alkylaryl, —C($R^2$)$_2$OC(O)$NR^2_2$, —$NR^2$—C(O)—$R^3$, —C($R^2$)$_2$—OC(O)—$R^3$, —C($R^2$)$_2$—O—C(O)$OR^3$, —C($R^2$)$_2$OC(O)$SR^3$, -alkyl-S—C(O)$R^3$, -alkyl-S—S-alkylhydroxy, and -alkyl-S—S—S-alkylhydroxy, when Y is —$NR^6$—, then $R^1$ attached to —$NR^6$— is independently selected from the group consisting of —H, —[C($R^2$)$_2$]$_q$—$COOR^3$, —C($R^4$)$_2$$COOR^3$, —[C($R^2$)$_2$]$_q$—C(O)$SR^3$, and -cycloalkylene-$COOR^3$;

or when either Y is independently selected from —O— and —$NR^6$—, then together $R^1$ and $R^1$ are -alkyl-S— S-alkyl- to form a cyclic group, or together $R^1$ and $R^1$ are

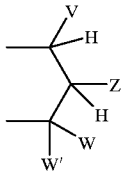

wherein
V, W, and W' are independently selected from the group consisting of —H, alkyl, aralkyl, alicyclic, aryl, substituted aryl, heteroaryl, substituted heteroaryl, 1-alkenyl, and 1-alkynyl; or together V and Z are connected via an additional 3–5 atoms to form a cyclic group containing 5–7 atoms, wherein 0–1 atoms are heteroatoms and the remaining atoms are carbon, substituted with hydroxy, acyloxy, alkoxycarbonyloxy, or aryloxycarbonyloxy attached to a carbon atom that is three atoms from both Y groups attached to the phosphorus; or together V and Z are connected via an additional 3–5 atoms to form a cyclic group, wherein 0–1 atoms are heteroatoms and the remaining atoms are carbon, that is fused to an aryl group at the beta and gamma position to the Y attached to the phosphorus;

together V and W are connected via an additional 3 carbon atoms to form a substituted or unsubstituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, wherein 0–1 atoms are heteroatoms and the remaining atoms are carbon, and V must be aryl, substituted aryl, heteroaryl, or substituted heteroaryl;

together W and W' are connected via an additional 2–5 atoms to form a cyclic group, wherein 0–2 atoms are heteroatoms and the remaining atoms are carbon, and V must be aryl, substituted aryl, heteroaryl, or substituted heteroaryl;

Z is selected from the group consisting of —$CHR^2OH$, —$CHR^2OC(O)R^3$, —$CHR^2OC(S)R^3$, —$CHR^2OC(S)OR^3$, —$CHR^2OC(O)SR^3$, —$CHR^2OCO_2R^3$, —$OR^2$, —$SR^2$, —$CHR^2N_3$, —$CH_2$aryl, —CH(aryl)OH, —CH(CH=$CR^2_2$)OH, —CH(C≡$CR^2$)OH, —$OR^2$, —$NR^2_2$, —$OCOR^3$, —$OCO_2R^3$, —$SCOR^3$, —$SCO_2R^3$, —$NHCOR^2$, —$NHCO_2R^3$, —$CH_2NHaryl$, —(CH$_2$)$_p$—$OR^2$, and —(CH$_2$)$_p$—$SR^2$;

p is an integer 2 or 3;
q is an integer 1 or 2;
with the provisos that:
a) V, Z, W, W' are not all —H; and
b) when Z is —$R^2$, then at least one of V, W, and W' is not —H, alkyl, aralkyl, or alicyclic;

$R^2$ is selected from the group consisting of $R^3$ and —H;
$R^3$ is selected from the group consisting of alkyl, aryl, alicyclic, and aralkyl;

each $R^4$ is independently selected from the group consisting of —H, alkyl, or together $R^4$ and $R^4$ form a cyclic alkyl;

R⁶ is selected from the group consisting of —H, lower alkyl, acyloxyalkyl, alkoxycarbonyloxyalkyl, and lower acyl;

each R⁹ is independently selected from the group consisting of —H, alkyl, aralkyl, and alicyclic, or together R⁹ and R⁹ form a cyclic alkyl group;

R¹¹ is selected from the group consisting of alkyl, aryl, —NR²₂, and —OR²; or pharmaceutically acceptable prodrugs or salts thereof.

139. The compound of claim 45 wherein A" is —NH₂, X is furan-2,5-diyl, and B" is —SCH₂CH₂CH₃.

140. The compound of claim 45 wherein one Y is —O— and its corresponding R¹ is -phenyl, and the other Y is —NH— and its corresponding R¹ is —CH₂CO₂Et.

141. The compound of claim 45 wherein one Y is —O— and its corresponding R¹ is -phenyl, and the other Y is —NH— and its corresponding R¹ is —C(Me)₂CO₂Et.

142. The compound of claims 45 wherein one Y is —O— and its corresponding R¹ is -(phenyl-4—NHC(O)CH₃), and the other Y is —NH— and its corresponding R¹ is —CH₂CO₂Et.

143. The compound of claim 45 wherein one Y is —O— and its corresponding R¹ is -(phenyl-4—NHC(O)CH₃), and the other Y is —NH— and its corresponding R¹ is —C(Me)₂CO₂Et.

144. The compound of claim 45 wherein one Y is —O— and its corresponding R¹ is -(phenyl-2—CO₂Et), and the other Y is —NH— and its corresponding R¹ is —CH₂CO₂Et.

145. The compound of claim 45 wherein one Y is —O— and its corresponding R¹ is -(phenyl-2—CH₃), and the other Y is —NH— and its corresponding R¹ is —CH₂CO₂Et.

146. The compound of claim 46 wherein one Y is —O— and its corresponding R¹ is -phenyl, and the other Y is —NH— and its corresponding R¹ is —CH₂CO₂Et.

147. The compound of claim 46 wherein one Y is —O— and its corresponding R¹ is -phenyl, and the other Y is —NH— and its corresponding R¹ is —C(Me)₂CO₂Et.

148. The compound of claim 46 wherein one Y is —O— and its corresponding R¹ is -(phenyl-4—NHC(O)CH₃), and the other Y is —NH— and its corresponding R¹ is —CH₂CO₂Et.

149. The compound of claim 46 wherein one Y is —O— and its corresponding R¹ is -(phenyl-4—NHC(O)CH₃), and the other Y is —NH— and its corresponding R¹ is —C(Me)₂CO₂Et.

150. The compound of claim 46 wherein one Y is —O— and its corresponding R¹ is -(phenyl-2—CO₂Et), and the other Y is —NH— and its corresponding R¹ is —CH₂CO₂Et.

151. The compound of claim 46 wherein one Y is —O— and its corresponding R¹ is -(phenyl-2—CH₃), and the other Y is —NH— and its corresponding R¹ is —CH₂CO₂Et.

152. The compound of claim 47 wherein both Y groups are —O— and R¹ is —H.

153. The compound of claim 47 wherein both Y groups are —O—, and R¹ is —CH₂OC(O)OEt.

154. The compound of claim 48 wherein both Y groups are —O— and R¹ is H—.

155. The compound of claim 48 wherein both Y groups are —O—, and R¹ is —CH₂OC(O)OEt.

156. The compound of claim 49 wherein both Y groups are —O— and R¹ is H—.

157. The compound of claim 49 wherein both Y groups are —O—, and R¹ is —CH₂OC(O)OEt.

158. The compound of claim 53 wherein V is selected from the group consisting of 3,5-dichlorophenyl, 3-bromo-4-fluorophenyl, 3-chlorophenyl, and 3-bromophenyl.

159. The compound of claim 47 wherein one Y is —O— and its corresponding R¹ is -phenyl while the other Y is —NH— and its corresponding R¹ is —CH(Me)CO₂Et and —NH*CH(Me)CO₂Et is in the L-configuration.

160. The compound of claim 54 wherein V is selected from the group consisting of 3,5-dichlorophenyl, 3-bromo-4-fluorophenyl, 3-chlorophenyl, and 3-bromophenyl.

161. The compound of claim 48 wherein one Y is —O— and its corresponding R¹ is -phenyl while the other Y is —NH—and its corresponding R¹ is —CH(Me) CO₂Et and —NH*CH(Me)CO₂Et is in the L-configuration.

162. The compound of claim 55 wherein V is selected from the group consisting of 3,5-dichlorophenyl, 3-bromo-4-fluorophenyl, 3-chlorophenyl, and 3-bromophenyl.

163. The compound of claim 49 wherein one Y is —O— and its corresponding R¹ is -phenyl while the other Y is —NH— and its corresponding R¹ is —CH(Me)CO₂Et and —NH*CH(Me)CO₂Et is in the L-configuration.

164. The compound of claim 60 wherein one Y is —O— and its corresponding R¹ is -phenyl, while the other Y is —NH, and its corresponding R1 is —CH₂CO₂Et.

165. The compound of claim 130 wherein one Y is —O—, and its corresponding R¹ is phenyl, while the other Y is —NH, and its corresponding R¹ is —CH₂CO₂Et.

* * * * *

UNITED STATES PATENT AND TRADEMARK OFFICE
CERTIFICATE OF CORRECTION

PATENT NO. : 6,489,476 B1
APPLICATION NO. : 09/389698
DATED : December 3, 2002
INVENTOR(S) : Qun Dang et al.

It is certified that error appears in the above-identified patent and that said Letters Patent is hereby corrected as shown below:

Column 211,
Line 56, "—NR6—" should read -- —NR$^6$— --.

Column 213,
Line 32, "R$^5$is" shoud read --R$^5$ is--.
Line 49, "—R$^4$" should read -- —OR$^4$ --.

Column 214,
Line 27, first structure,

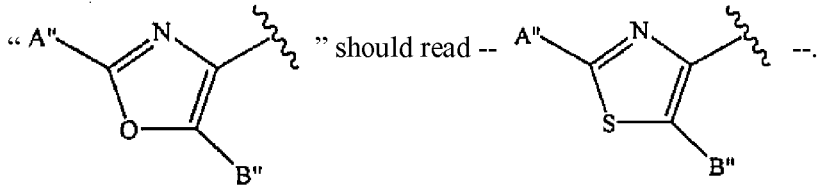 should read -- .

Line 55, "—R$^3$" should read -- —OR$^3$ --.

Column 215,
Lines 5 and 23, first structure,

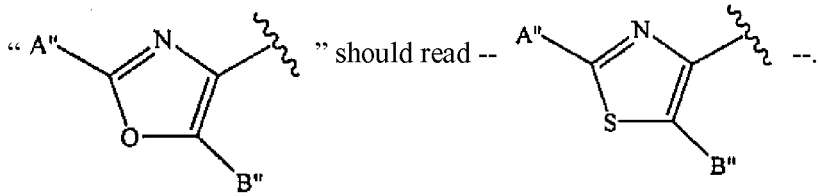 should read -- .

Column 218,
Line 46, "—C(R$^2$)$_2$—C(O)R$^3$ and —C(R$^2$)$_2$—C(o)OR$^3$" should read
    -- —C(R$^2$)$_2$—OC(O)R$^3$ and —C(R$^2$)$_2$—C(O)OR$^3$--.

Column 228,
Line 26, "—R$^3$" should read -- —OR$^3$--.

Column 229,
Line 26, "—R$^3$" should read -- —OR$^3$--.

Column 231,
Line 42, "—NR$^6$" should read -- —NR$^6$— --.
Line 47, "—NR$^6$" should read -- —NR$^6$— --.

UNITED STATES PATENT AND TRADEMARK OFFICE
CERTIFICATE OF CORRECTION

PATENT NO. : 6,489,476 B1
APPLICATION NO. : 09/389698
DATED : December 3, 2002
INVENTOR(S) : Qun Dang et al.

It is certified that error appears in the above-identified patent and that said Letters Patent is hereby corrected as shown below:

Column 232,
Line 32, "$R^3$and" should read -- "$R^3$ and"--.

Column 234,
Line 50, "—$R^3$" should read -- —$OR^3$ --.

Column 237,
Line 67, "—$(CH_2)_p$—$R^2$" should read -- —$(CH_2)_p$—$OR^2$--.

Column 240,
Lines 51-52, "methylenoxycarbonyl" should read --methyleneoxycarbonyl--.

Column 242,
Line 14, "unsubstituted-alkylaryl" should read --unsubstituted —alkylaryl--.
Line 15, "—$C(R^2)_2$—$C(O)R^3$" should read -- —$C(R^2)_2$—$OC(O)R^3$ --.
Line 16, "-alkyl-S—$C(O)R$" should read -- -alkyl-S—$C(O)R^3$ --.

Column 243,
Lines 8-9, "—$CH(CH=CR^2_2)OH$" should read -- —$CH(CH=CR^2_2)OH$--.

Column 247,
Line 64, "—$C(R^2)_2$—$C(O)R^3$" should read -- —$C(R^2)_2$—$OC(O)R^3$--.

Column 248,
Line 59, "—$COR^3$" should read -- —$OCOR^3$--.

Column 249,
Line 43, "L2 and E2" should read --$L^2$ and $E^2$--.
Line 60, "—$C(R^2)_2$—$C(O)R^3$" should read -- —$C(R^2)_2$—$OC(O)R^3$--.

Column 251,
Line 58, "—$C(R^2)_2$—$OC(O)$—$R^3$" should read -- —$C(R^2)_2$—$OC(O)R^3$ --.

Column 252,
Line 51, "—$OR^2$" should read -- —$R^2$--.

UNITED STATES PATENT AND TRADEMARK OFFICE
CERTIFICATE OF CORRECTION

PATENT NO. : 6,489,476 B1
APPLICATION NO. : 09/389698
DATED : December 3, 2002
INVENTOR(S) : Qun Dang et al.

It is certified that error appears in the above-identified patent and that said Letters Patent is hereby corrected as shown below:

Column 254,
Line 31, "—CH(Me) CO$_2$Et" should read -- —CH(Me)CO$_2$Et--.

Signed and Sealed this

Twenty-sixth Day of June, 2007

JON W. DUDAS
*Director of the United States Patent and Trademark Office*